(12) United States Patent
Sprecher et al.

US009212213B2

(10) Patent No.: US 9,212,213 B2
(45) Date of Patent: Dec. 15, 2015

(54) ZCYTOR17 HETERODIMERIC CYTOKINE RECEPTOR

(71) Applicant: ZymoGenetics, Inc., Princeton, NJ (US)

(72) Inventors: Cindy A. Sprecher, Sierra Vista, AZ (US); Joseph L. Kuijper, Kenmore, WA (US); Maria M. Dasovich, Seattle, WA (US); Francis J. Grant, Seattle, WA (US); Theodore E. Whitmore, Redmond, WA (US); Angela K. Hammond, Maple Valley, WA (US); Julia E. Novak, Bainbridge Island, WA (US); Jane A. Gross, Seattle, WA (US); Stacey R. Dillon, Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 67 days.

(21) Appl. No.: 14/138,199

(22) Filed: Dec. 23, 2013

(65) Prior Publication Data

US 2014/0141485 A1 May 22, 2014

Related U.S. Application Data

(60) Division of application No. 13/741,036, filed on Jan. 14, 2013, now Pat. No. 8,647,866, which is a division of application No. 13/405,916, filed on Feb. 27, 2012, now abandoned, which is a division of application No. 13/085,645, filed on Apr. 13, 2011, now abandoned, which is a division of application No. 12/545,770, filed on Aug. 21, 2009, now abandoned, which is a continuation of application No. 11/552,647, filed on Oct. 25, 2006, now abandoned, and a continuation of application No. 11/552,653, filed on Oct. 25, 2006, now abandoned, which is a division of application No. 10/351,157, filed on Jan. 21, 2003, now Pat. No. 7,494,804.

(60) Provisional application No. 60/435,361, filed on Dec. 19, 2002, provisional application No. 60/389,108, filed on Jun. 14, 2002, provisional application No. 60/350,325, filed on Jan. 18, 2002.

(51) Int. Cl.
*C07K 14/715* (2006.01)
*C07K 14/52* (2006.01)
*A61K 38/00* (2006.01)

(52) U.S. Cl.
CPC .............. *C07K 14/715* (2013.01); *C07K 14/52* (2013.01); *A01K 2217/05* (2013.01); *A61K 38/00* (2013.01)

(58) Field of Classification Search
CPC .................................................... C07K 14/715
USPC ....................................................... 530/350
See application file for complete search history.

(56) References Cited

U.S. PATENT DOCUMENTS

| 5,891,997 | A | 4/1999 | Mosley et al. |
| 6,518,399 | B1 | 2/2003 | Barnes et al. |
| 7,064,186 | B2 | 6/2006 | Sprecher et al. |
| 7,303,896 | B2 | 12/2007 | Ghilardi et al. |
| 7,495,080 | B2 | 2/2009 | Sprecher et al. |
| 7,521,537 | B2 | 4/2009 | Sprecher et al. |
| 2003/0224487 | A1 | 12/2003 | Sprecher et al. ............. 435/69.5 |
| 2004/0142422 | A1 | 7/2004 | Sprecher et al. ............. 435/69.1 |
| 2004/0152161 | A1 | 8/2004 | Cosman et al. ............. 435/69.1 |
| 2006/0182743 | A1 | 8/2006 | Bilsborough |

FOREIGN PATENT DOCUMENTS

| EP | 1188830 | 3/2002 |
| WO | 97/44455 | 11/1997 |
| WO | 00/75314 | 12/2000 |
| WO | 01/29070 | 4/2001 |
| WO | 01/93983 | 12/2001 |
| WO | 02/00690 | 1/2002 |
| WO | 02/00721 | 1/2002 |
| WO | 02/29060 | 4/2002 |
| WO | 02/77230 | 10/2002 |
| WO | 03/060090 | 7/2003 |
| WO | 03/072740 | 9/2003 |
| WO | 2004/003140 | 1/2004 |

OTHER PUBLICATIONS

Aioi, A. et al., *Br. J. Dermatol* 144(1):12-18, 2001.
Akdis, C.A., et al., *J. Invest. Dermatol.* 113(4) 628-34, 1999.
Aleksza, M., et al., *Br. J. Dermatol.* 147(6):1135-41, 2002.
Antunez, C., et al., *Clin. Exp. Allergy* 34(4) 559-66, 2004.
Asadullah, K. et al., *Arch. Dermatol* 138(9):1189-96, 2002.
Askenase, P.W., *Chem. Immunol.* 78:112-23, 2000.
Barnes, K.C., et al., *Genomics* 37(1):41-50, 1996.
Berger, C.L., et al., *Blood* 105(4):1640-7, 2005.
Bilsborough, J. et al., *J. Allergy Clin. Immunol.* 117(2):418-25, 2006.
Bonecchi, R., et al., *J. Exp. Med.* 187(1):129-34, 1998.
Dillon S.R., et al., *Nat. Immunol.* 5(7):752-60, 2004.
Dillon, S.R., et al., *Nat. Immunol.* 6(1):114, 2005.
Diveu, C., et al., *Eur. Cytokine Netw.* 15(4):291-302, 2004.
Diveu, C., et al., *J. Biol. Chem.* 278(50):49850, 2003.
Dreuw, A., et al., *Immunobiology* 210(6-8), 454, 2005.
Dreuw, A., et al., Keystone Symposia "Cytokines, Disease and Therapeutic Intervention," Feb. 12-17, 2005.
Dreuw, A., et al., *J. Biol. Chem.* 279(34):36112-20, 2004.
Fang, D., et al., *Nat. Immunol.* 3(3):281-7, 2002.

(Continued)

*Primary Examiner* — Prema Mertz
(74) *Attorney, Agent, or Firm* — Brian J. Walsh

(57) ABSTRACT

Novel polypeptide combinations, polynucleotides encoding the polypeptides, and related compositions and methods are disclosed for zcytor17-containing multimeric or heterodimer cytokine receptors that may be used as novel cytokine antagonists, and within methods for detecting ligands that stimulate the proliferation and/or development of hematopoietic, lymphoid and myeloid cells in vitro and in vivo. The present invention also includes methods for producing the multimeric or heterodimeric cytokine receptor, uses therefor and antibodies thereto.

6 Claims, 12 Drawing Sheets

(56) References Cited

OTHER PUBLICATIONS

Ghilardi, N. et al., *J. Biol. Chem.* 277(19):16831, 2002.
Gutermuth, J. et al., *Int. Arch. Allergy Immunol.* 135(3):262-76, 2004.
Hammond, A., et al., Orphan class I cytokine receptor Zcytor17 is upregulated in activated monocytes and T cells. (W-2-4) S48.
Hashimoto, Y., et al., *Life Sci.* 76(7):783-94, 2004.
Hashimoto, Y., et al., *J. Dermatol. Sci.* 35(2):143-50, 2004.
Hermanns, H.M., et al., *Experimental Dermatology* 15(N3):219-20, 2006.
Hijnen, D., et al., *J. Allergy Clin. Immunol.* 113(2):334-40, 2004.
Hwang, S.T., *Adv. Dermatol.* 17:211-41, 2001.
Leung, D.Y., et al., *Lancet* 361(9352): 151-60, 2003.
Lin, L., et al., *J. Med. Dent. Sci.* 50(1):27-33, 2003.
Nagao, M., et al., *J. Allergy Clin. Immunol.* 15(2):s272, 2005.
Matsuda, H., et al., *Int. Immunol.* 9(3):461-6, 1997.
Matsushima, H., et al., *J. Dermatol. Sci.* 32(3):223-30, 2003.
Parrish-Novak, J.E., et al., Interleukin 31 is a novel four-helical-bundle cytokine that signals through a heterodimeric receptor complex expressed in epithelial cells of lung and skin, (1023) Annual Meeting of the American Society of Human Genetics, 2003.
Robert, C., et al., *N. Engl. J. Med.* 341(24):1817-28, 1999.
Shimada, Y., et al., *J. Dermatol. Sci.* 34(3):201-8, 2004.
Sonkoly, E., et al., *J. Allergy Clin. Immunol.* 117(2):411-7, 2006.
Song, T., et al., *J. Allergy Clin. Immunol.* 15(2):s100, 2005.
Takano, N., et al., *Eur. J. Pharmacol.* 495(2-3):159-65, 2004.
Takano, N., et al., *Eur. J. Pharmacol.* 471(3):223-8, 2003.
Takaoka, A., et al., *Exp. Dermatol.* 15(3):161-7, 2006.
Takaoka, A., *Eur. J. Pharmacol,* PMID:15925362, 2005.
Vestergaard, C., et al., *J. Invest. Dermatol.* 115(4):640-6, 2000.
GenBank Accession No. AI123586, National Cancer Institute, Cancer Genome Anatomy Project (1997).
Gen Bank Accession No. A1799583, National Cancer Institute, Cancer Genome Anatomy Project (1997).
Sato et al.,*Current Opinion on Cell Biology* 174-179, 1994.

```
                  1              15 16             30 31             45
1 zcytor17lig  ---ASHTLPVRLLRP SDDVQKIVEELQSLS KMLLKD--VEEEKGV   40
2 mzcytor17lig ---ATCSLSFGAPIS KEDLRTTIDLLKQES QDLYNNYSIKQASGM   42
3 mIL-3        ASISGRDTHRLTRTL NCS-SIVKEIIGKL- --PEP----ELKT--   35
4 hIL-3        APMTQTTPLKTSW-V NCS-NMIDEIITHLK QPPLP--LLDFNNLN   41

46            60 61             75 76             90
1 zcytor17lig  LVSQNYTLPCLSPDA QPPNNIHSPAIRAYL KTIRQLDNKSVIDEI   85
2 mzcytor17lig SADESIQLPCFSLDR EALTNISVIIAHLEK VKVLSE-NTVDTSWV   86
3 mIL-3        DDEGPSLRNKS---- -----FRRVNLSKFV ESQGEVDPEDRYVIK   71
4 hIL-3        GEDQDILMENN---- -----LRRPNLEAFN RAVKSL--QNASAIE   75

91           105 106            120 121            135
1 zcytor17lig  IEHLDKLIFQDAPET NISVPTDTHE---CK RFILTISQQFSECMD   127
2 mzcytor17lig IRWLTNISCFNPLNL NISVPGNTDESYDCK VFVLTVLKQFSNCMA   131
3 mIL-3        SNLQKLNCCLPTSAN DSALPGVFIRDLD-- DFRKKLRFYMVH-LN   113
4 hIL-3        SILKNLLPCLPLATA APTRHPIHIKDGDWN EFRRKLTFY----LK   116

136            150 151            165 166            180
1 zcytor17lig  LALKSLTSGAQQATT                                   142
2 mzcytor17lig ELQAKDNTTC                                        141
3 mIL-3        DLETVLTSRPPQPAS GSVSPNRGTVEC                      140
4 hIL-3        TLENA----QAQQTT LSLAIF                            133
```

FIG. 1

```
            10        20        30        40        50
ZCYTOR  MASHSGPSTSVLFLFCCLGGWLASHTLPVRLLRPSDDVQKIVEELQSLSKMLLKD--VEE
          :  :.:......:  :::::.:.:::. .:.         .............:.   .:. :..  ...
M17RL-  MIFHTGTTKPTLVLLCCIGTWLATCSLSFGAPISKEDLRTTIDLLKQESQDLYNNYSIKQ
            10        20        30        40        50        60

60        70        80        90       100       110
ZCYTOR  EKGVLVSQNYTLPCLSPDAQPPNNIHSPAIRAYLKTIRQLDNKSVIDE-IIEHLDKLIFQ
         ...:  ....    :::.:  :  ..  .::    ...:  :.:......  :......:  ..  .:   :...
M17RL-  ASGMSADESIQLPCFSLDREALTNI--SVIIAHLEKVKVLSENTVDTSWVIRWLTNISCF
            70        80        90       100       110

120       130       140       150       160
ZCYTOR  DAPETNISVPTDTHE---CKRFILTISQQFSECM-DLALKSLTSGAQQATT
         ... . ::::::::..:    X:  :.::.  .:::.:X  .:.  :.   :.
M17RL-  NPLNLNISVPGNTDESYDCKVFVLTVLKQFSNCMAELQAKDNTTC
            120       130       140       150       160
```

```
                          1                                                      50
SEQ ID NO:109  MMWTWALWML PSLCKFSLAA LPAKPENISC VYYYRKNLTC TWSPGKETSY
SEQ ID NO:113  MMWTWALWML PSLCKFSLAA LPAKPENISC VYYYRKNLTC TWSPGKETSY
SEQ ID NO:111  MMWTWALWML PSLCKFSLAA LPAKPENISC VYYYRKNLTC TWSPGKETSY
SEQ ID NO:115  MMWTWALWML PSLCKFSLAA LPAKPENISC VYYYRKNLTC TWSPGKETSY 51                                                     100
SEQ ID NO:109  TQYTVKRTYA FGEKHDNCTT NSSTSENRAS CSFFLPRITI PDNYTIEVEA
SEQ ID NO:113  TQYTVKRTYA FGEKHDNCTT NSSTSENRAS CSFFLPRITI PDNYTIEVEA
SEQ ID NO:111  TQYTVKRTYA FGEKHDNCTT NSSTSENRAS CSFFLPRITI PDNYTIEVEA
SEQ ID NO:115  TQYTVKRTYA FGEKHDNCTT NSSTSENRAS CSFFLPRITI PDNYTIEVEA 101                                                    150
SEQ ID NO:109  ENGDGVIKSH MTYWRLENIA KTEPPKIFRV KPVLGIKRMI QIEWIKPELA
SEQ ID NO:113  ENGDGVIKSH MTYWRLENIA KTEPPKIFRV KPVLGIKRMI QIEWIKPELA
SEQ ID NO:111  ENGDGVIKSH MTYWRLENIA KTEPPKIFRV KPVLGIKRMI QIEWIKPELA
SEQ ID NO:115  ENGDGVIKSH MTYWRLENIA KTEPPKIFRV KPVLGIKRMI QIEWIKPELA 151                                                    200
SEQ ID NO:109  PVSSDLKYTL RFRTVNSTSW MEVNFAKNRK DKNQTYNLTG LQPFTEYVIA
SEQ ID NO:113  PVSSDLKYTL RFRTVNSTSW MEVNFAKNRK DKNQTYNLTG LQPFTEYVIA
SEQ ID NO:111  PVSSDLKYTL RFRTVNSTSW MEVNFAKNRK DKNQTYNLTG LQPFTEYVIA
SEQ ID NO:115  PVSSDLKYTL RFRTVNSTSW MEVNFAKNRK DKNQTYNLTG LQPFTEYVIA 201                                                    250
SEQ ID NO:109  LRCAVKESKF WSDWSQEKMG MTEEEAPCGL ELWRVLKPAE ADGRRPVRLL
SEQ ID NO:113  LRCAVKESKF WSDWSQEKMG MTEEEAPCGL ELWRVLKPAE ADGRRPVRLL
SEQ ID NO:111  LRCAVKESKF WSDWSQEKMG MTEEEAPCGL ELWRVLKPAE ADGRRPVRLL
SEQ ID NO:115  LRCAVKESKF WSDWSQEKMG MTEEEGKL.L PAIPVLSALV ~~~~~~~~~~

251                                                    300
SEQ ID NO:109  WKKARGAPVL EKTLGYNIWY YPESNTNLTE TMNTTNQQLE LHLGGESFWV
SEQ ID NO:113  WKKARGAPVL EKTLGYNIWY YPESNTNLTE TMNTTNQQLE LHLGGESFWV
SEQ ID NO:111  WKKARGAPVL EKTLGYNIWY YPESNTNLTE TMNTTNQQLE LHLGGESFWV
SEQ ID NO:115  ~~~~~~~~~~ ~~~~~~~~~~ ~~~~~~~~~~ ~~~~~~~~~~ ~~~~~~~~~~

301                                                    350
SEQ ID NO:109  SMISYNSLGK SPVATLRIPA IQEKSFQCIE VMQACVAEDQ LVVKWQSSAL
SEQ ID NO:113  SMISYNSLGK SPVATLRIPA IQEK~~~~~~ ~~~~~~~~~~ ~~~~~~~~~~
SEQ ID NO:111  SMISYNSLGK SPVATLRIPA IQEKSFQCIE VMQACVAEDQ LVVKWQSSAL
SEQ ID NO:115  ~~~~~~~~~~ ~~~~~~~~~~ ~~~~~~~~~~ ~~~~~~~~~~ ~~~~~~~~~~
```

FIG. 4A

```
              351                                                           400
SEQ ID NO:109 DVNTWMIEWF PDVDSEPTTL SWESVSQATN WTIQQDKLKP FWCYNISVYP
SEQ ID NO:113 ~~~~~~~~~~ ~~~~~~~~~~ ~~~~~~~~~~ ~~~~~~~~~~ ~~~~~~~~~~
SEQ ID NO:111 DVNTWMIEWF PDVDSEPTTL SWESVSQATN WTIQQDKLKP FWCYNISVYP
SEQ ID NO:115 ~~~~~~~~~~ ~~~~~~~~~~ ~~~~~~~~~~ ~~~~~~~~~~ ~~~~~~~~~~

401                                                           450
SEQ ID NO:109 MLHDKVGEPY SIQAYAKEGV PSEGPETKVE NIGVKTVTIT WKEIPKSERK
SEQ ID NO:113 ~~~~~~~~~~ ~~~~~~~~~~ ~~~~~~~~~~ ~~~~~~~~~~ ~~~~~~~~~~
SEQ ID NO:111 MLHDKVGEPY SIQAYAKEGV PSEGPETKVE NIGVKTVTIT WKEIPKSERK
SEQ ID NO:115 ~~~~~~~~~~ ~~~~~~~~~~ ~~~~~~~~~~ ~~~~~~~~~~ ~~~~~~~~~~

451                                                           500
SEQ ID NO:109 GIICNYTIFY QAEGGKGFSK TVNSSILQYG LESLKRKTSY IVQVMASTSA
SEQ ID NO:113 ~~~~~~~~~~ ~~~~~~~~~~ ~~~~~~~~~~ ~~~~~~~~~~ ~~~~~~~~~~
SEQ ID NO:111 GIICNYTIFY QAEGGKGFSK TVNSSILQYG LESLKRKTSY IVQVMASTSA
SEQ ID NO:115 ~~~~~~~~~~ ~~~~~~~~~~ ~~~~~~~~~~ ~~~~~~~~~~ ~~~~~~~~~~

501                                                           550
SEQ ID NO:109 GGTNGTSINF KTLSFSVFEI ILITSLIGGG LLILIILTVA YGLKKPNKLT
SEQ ID NO:113 ~~~~~~~~~~ ~~~~~~~~~~ ~~~~~~~~~~ ~~~~~~~~~~ ~~~~~~~~~~
SEQ ID NO:111 GGTNGTSINF KTLSFSVFEI ILITSLIGGG LLILIILTVA YGLKKPNKLT
SEQ ID NO:115 ~~~~~~~~~~ ~~~~~~~~~~ ~~~~~~~~~~ ~~~~~~~~~~ ~~~~~~~~~~

551                                                           600
SEQ ID NO:109 HLCWPTVPNP AESSIATWHG DDFKDKLNLK ESDDSVNTED RILKPCSTPS
SEQ ID NO:113 ~~~~~~~~~~ ~~~~~~~~~~ ~~~~~~~~~~ ~~~~~~~~~~ ~~~~~~~~~~
SEQ ID NO:111 HLCWPTVPNP AESSIATWHG DDFKDKLNLK ESDDSVNTED RILKPCSTPS
SEQ ID NO:115 ~~~~~~~~~~ ~~~~~~~~~~ ~~~~~~~~~~ ~~~~~~~~~~ ~~~~~~~~~~

601                                                           650
SEQ ID NO:109 DKLVIDKLVV NFGNVLQEIF TDEARTGQEN NLGGEKNGTR ILSSCPTSI~
SEQ ID NO:113 ~~~~~~~~~~ ~~~~~~~~~~ ~~~~~~~~~~ ~~~~~~~~~~ ~~~~~~~~~~
SEQ ID NO:111 DKLVIDKLVV NFGNVLQEIF TDEARTGQEN NLGGEKNGYV TCPFRPDCPL
SEQ ID NO:115 ~~~~~~~~~~ ~~~~~~~~~~ ~~~~~~~~~~ ~~~~~~~~~~ ~~~~~~~~~~

651                                                           700
SEQ ID NO:109 ~~~~~~~~~~ ~~~~~~~~~~ ~~~~~~~~~~ ~~~~~~~~~~ ~~~~~~~~~~
SEQ ID NO:113 ~~~~~~~~~~ ~~~~~~~~~~ ~~~~~~~~~~ ~~~~~~~~~~ ~~~~~~~~~~
SEQ ID NO:111 GKSFEELPVS PEIPPRKSQY LRSRMPEGTR PEAKEQLLFS GQSLVPDHLC
SEQ ID NO:115 ~~~~~~~~~~ ~~~~~~~~~~ ~~~~~~~~~~ ~~~~~~~~~~ ~~~~~~~~~~
```

FIG. 4B

```
              701                          733
SEQ ID NO:109 ~~~~~~~~~~ ~~~~~~~~~~ ~~~~~~~~~~ ~~~
SEQ ID NO:113 ~~~~~~~~~~ ~~~~~~~~~~ ~~~~~~~~~~ ~~~
SEQ ID NO:111 EEGAPNPYLK NSVTAREFLV SEKLPEHTKG EV~
SEQ ID NO:115 ~~~~~~~~~~ ~~~~~~~~~~ ~~~~~~~~~~ ~~~
```

FIG. 4C

```
                        10        20        30        40
ZCYTOR               MKLSPQPSCVNLGMMWTWALWMLPSLCKFSLAALPAKPENISCVYYY
                     ::   ::  :.::: :::  .  :::::::..:.::::::::..:.
M17R-O  MLSSQKGSCSQEPGAAHVQPLGVNAGIMWTLALWAFSFLCKFSLAVLPTKPENISCVFYF
            10        20        30        40        50        60

50        60        70        80        90       100
ZCYTOR  RKNLTCTWSPGKETSYTQYTVKRTYAFGEKHDNCTTNSSTSENRASCSFFLPRITIPDNY
        .::::::: : :::. :.:  :   ::..:.        .: :  ..::  ::       ::
M17R-O  DRNLTCTWRPEKETNDTSYIVTLTYSYGK------SNYSDNATEASYSFPRSCAMPPDIC
            70        80              90        100       110

110       120       130       140       150       160
ZCYTOR  TIEVEAENGDGVIKSHMTYWRLENIAKTEPPKIFRVKPVLGIKRMIQIEWIKPELAPVSS
        ..::..::::  :::  .:::.:  .:::::::: ::  ..:.  :  ::::::. :::   .
M17R-O  SVEVQAQNGDGKVKSDITYWHLISIAKTEPPIILSVNPICN--RMFQIQW-KPREKTRGF
            120       130       140       150       160       170

170       180       190       200       210       220
ZCYTOR  DLKYTLRFRTVNSTSWMEVNFAKNRKDKNQTYNLTGLQPFTEYVIALRCAVKESKFWSDW
        :    :::::::::::.::::: ::::  .: :  .  ::::::::.::: :::: ::: :::
M17R-O  PLVCMLRFRTVNSSRWTEVNF-ENCK---QVCNLTGLQAFTEYVLALRFRFNDSRYWSKW
            180       190       200       210       220

230       240       250       260       270       280
ZCYTOR  SQEKMGMTEEEAPCGLELWRVLKPAEADGRRPVRLLWKKARGAPVLEKTLGYNIWYYPES
        :.: .: ::: :  :.:..: ::..:: :::   .. :.:::::::::::::::.. .  ::.. ::.
M17R-O  SKEETRVTMEEVPHVLDLWRILEPADMNGDRKVRLLWKKARGAPVLEKTFGYHIQYFAEN
            230       240       250       260       270       280

290       300       310       320       330       340
ZCYTOR  NTNLTETMNTTNQQLELHLGGESFWVSMISYNSLGKSPVATLRIPAIQEKSFQCIEVMQA
        .:::: :  : ....:: ::  . ...  :.::..::::.  .. :::::..  .: .:::
M17R-O  STNLTEINNITTQQYELLLMSQAHSVSVTSFNSLGKSQETILRIPDVHEKTFQYIKSMQA
            290       300       310       320       330       340

350       360       370       380       390       400
ZCYTOR  CVAEDQLVVKWQSSALDVNTWMIEWFPDVD-SEPTTLSWESVSQATNWTIQQDKLKPFWC
         .::  :::::::::.: .:...:.:::. :.   ::.::::::::::.::::.::::::::::.:
M17R-O  YIAEPLLVVNWQSSIPAVDTWIVEWLPEAAMSKFPALSWESVSQVTNWTIEQDKLKPFTC
            350       360       370       380       390       400
```

Fig. 5A

```
              410       420       430       440       450       460
ZCYTOR   YNISVYPMLHDKVGEPYSIQAYAKEGVPSEGPETKVENIGVKTVTITWKEIPKSERKGII
         :::::::::. .::::::::::::::::. ::::.:::::.:::::::::::::: ::.:
M17R-O   YNISVYPVLGHRVGEPYSIQAYAKEGTPLKGPETRVENIGLRTATITWKEIPKSARNGFI
              410       420       430       440       450       460

470       480       490       500       510       520
ZCYTOR   CNYTIFYQAEGGKGFSKTVNSSILQYGLESLKRKTSYIVQVMASTSAGGTNGTSINFKTL
         ::: ::::::::: :.:::::::. :: :    :::: :.:::: :::::::. ::.:::
M17R-O   NNYTVFYQAEGGKELSKTVNSHALQCDLESLTRRTSYTVWVMASTRAGGTNGVRINFKTL
              470       480       490       500       510       520

530       540       550       560       570       580
ZCYTOR   SFSVFEIILITSLIGGGLLILIILTVAYGLKKPNKLTHLCWPTVPNPAESSIATWHGDDF
         : ::::::.:::::.:::::::: ::.:  ::. :::::: :: :::::::::.: : :
M17R-O   SISVFEIVLLTSLVGGGLLLLSIKTVTFGLRKPNRLTPLCCPDVPNPAESSLATWLGDGF
              530       540       550       560       570       580

590       600       610       620       630       640
ZCYTOR   KDKLNLKESDDSVNTEDRILKPCSTPSDKLVIDKLVVNFGNVLQEIFTDEARTGQENNLG
         : : :  :. :. :::: ::::.: :::   ::.:::::::::.:.. ::::::. . ..
M17R-O   K-KSNMKETGNSGNTEDVVLKPCPVPAD--LIDKLVVNFENFLEVVLTEEAGKGQASILG
              590       600       610       620       630       640

650       660
ZCYTOR   GEKNGTRILSSCPTSI
         :: :  :::.  :.
M17R-O   GEAN-EYILSQEPSCPGHC
              650       660
```

Fig 5B

ZCYTOR17 HETERODIMERIC CYTOKINE RECEPTOR

The present application is a divisional of U.S. patent application Ser. No. 13/741,036, filed Jan. 14, 2013, which is a divisional of U.S. patent application Ser. No. 13/405,916, filed Feb. 27, 2012, now abandoned, which is a divisional of U.S. patent application Ser. No. 13/085,645, filed Apr. 13, 2011, now abandoned, which is a divisional of U.S. patent application Ser. No. 12/545,770, filed Aug. 21, 2009, now abandoned, which is a continuation of U.S. patent application Ser. No. 11/552,647, filed Oct. 25, 2006, now abandoned, which is a continuation of U.S. patent application Ser. No. 11/552,653, filed Oct. 25, 2006, now abandoned, which is a divisional of U.S. patent application Ser. No. 10/351,157, filed Jan. 21, 2003, now U.S. Pat. No. 7,494,804, which claims the benefit of U.S. Patent Application Ser. No. 60/435,361, filed Dec. 19, 2002, U.S. Patent Application Ser. No. 60/389,108, filed Jun. 14, 2002, and U.S. Patent Application Ser. No. 60/350,325, filed Jan. 18, 2002, all of which are herein incorporated by reference.

BACKGROUND OF THE INVENTION

Proliferation and differentiation of cells of multicellular organisms are controlled by hormones and polypeptide growth factors. These diffusable molecules allow cells to communicate with each other and act in concert to form cells, tissues and organs, and to repair damaged tissue. Examples of hormones and growth factors include the steroid hormones (e.g., estrogen, testosterone), parathyroid hormone, follicle stimulating hormone, the interleukins, platelet derived growth factor (PDGF), epidermal growth factor (EGF), granulocyte-macrophage colony stimulating factor (GM-CSF), erythropoietin (EPO) and calcitonin.

Hormones and growth factors influence cellular metabolism by binding to receptors. Receptors may be integral membrane proteins that are linked to signaling pathways within the cell, such as second messenger systems. Other classes of receptors are soluble molecules, such as the transcription factors.

Cytokines generally stimulate proliferation or differentiation of cells of the hematopoietic lineage or participate in the immune and inflammatory response mechanisms of the body. Examples of cytokines which affect hematopoiesis are erythropoietin (EPO), which stimulates the development of red blood cells; thrombopoietin (TPO), which stimulates development of cells of the megakaryocyte lineage; and granulocyte-colony stimulating factor (G-CSF), which stimulates development of neutrophils. These cytokines are useful in restoring normal blood cell levels in patients suffering from anemia, thrombocytopenia, and neutropenia or receiving chemotherapy for cancer.

The interleukins are a family of cytokines that mediate immunological responses, including inflammation. The interleukins mediate a variety of inflammatory pathologies. Central to an immune response are T cells, which produce many cytokines and adaptive immunity to antigens. Cytokines produced by T cells have been classified as type 1 and type 2 (Kelso, A. *Immun. Cell Biol.* 76:300-317, 1998). Type 1 cytokines include IL-2, IFN-γ, LT-α, and are involved in inflammatory responses, viral immunity, intracellular parasite immunity and allograft rejection. Type 2 cytokines include IL-4, IL-5, IL-6, IL-10 and IL-13, and are involved in humoral responses, helminth immunity and allergic response. Shared cytokines between Type 1 and 2 include IL-3, GM-CSF and TNF-α. There is some evidence to suggest that Type 1 and Type 2 producing T cell populations preferentially migrate into different types of inflamed tissue.

Mature T cells may be activated, i.e., by an antigen or other stimulus, to produce, for example, cytokines, biochemical signaling molecules, or receptors that further influence the fate of the T cell population.

B cells can be activated via receptors on their cell surface including B cell receptor and other accessory molecules to perform accessory cell functions, such as production of cytokines.

Monocytes/macrophages and T-cells can be activated by receptors on their cell surface and play a central role in the immune response by presenting antigen to lymphocytes and also act as accessory cells to lymphocytes by secreting numerous cytokines.

Natural killer (NK) cells have a common progenitor cell with T cells and B cells, and play a role in immune surveillance. NK cells, which comprise up to 15% of blood lymphocytes, do not express antigen receptors, and therefore do not use MHC recognition as requirement for binding to a target cell. NK cells are involved in the recognition and killing of certain tumor cells and virally infected cells. In vivo, NK cells are believed to require activation, however, in vitro, NK cells have been shown to kill some types of tumor cells without activation.

The demonstrated in vivo activities of these cytokines illustrate the enormous clinical potential of, and need for, other cytokines, cytokine agonists, and cytokine antagonists or binding partners. The present invention addresses these needs by providing a new hematopoietic multimeric cytokine receptor, as well as related compositions and methods.

The present invention provides such polypeptides for these and other uses that should be apparent to those skilled in the art from the teachings herein.

BRIEF DESCRIPTION OF THE DRAWINGS

FIG. 1 is an illustration of a multiple alignment of human zcytor17lig (SEQ ID NO:2) (zcytor17lig), and mouse zcytor17lig (SEQ ID NO:11) (mzcytor17lig), mouse IL-3 (mIL-3) (SEQ ID NO:100), and human IL-3 (hIL-3) (SEQ ID NO:102).

FIG. 2 is an illustration of a multiple alignment of human zcytor17lig (SEQ ID NO:2) (zcytor17lig), and mouse zcytor17lig (SEQ ID NO:11) (mzcytor17lig).

FIG. 3A-3E is a Hopp/Woods hydrophilicity plot of human zcytor17lig (SEQ ID NO:2).

FIG. 4A-4C is a multiple alignment of zcytor17 polynucleotide sequences SEQ ID NO:109, SEQ ID NO:113, SEQ ID NO:5, SEQ ID NO:111, and SEQ ID NO:115.

FIG. 5A-5B is an alignment of human zcytor17 (ZCYTOR) (SEQ ID NO:5) and mouse zcytor17 (M17R-O) (SEQ ID NO:117). Between the two sequences, identical residues (:), Conserved residues (.) and gaps (—) are indicated.

SUMMARY OF THE INVENTION

Figure 3A:
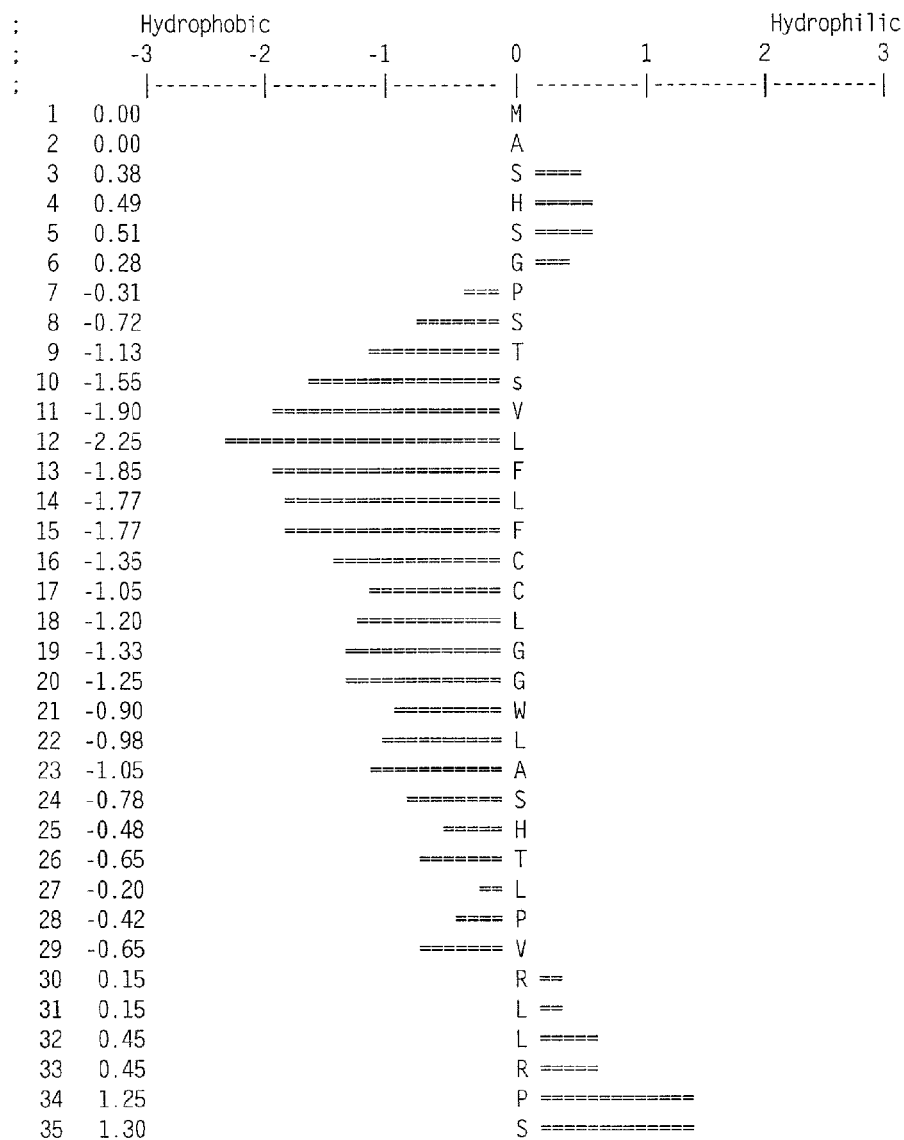
Figure 3E:
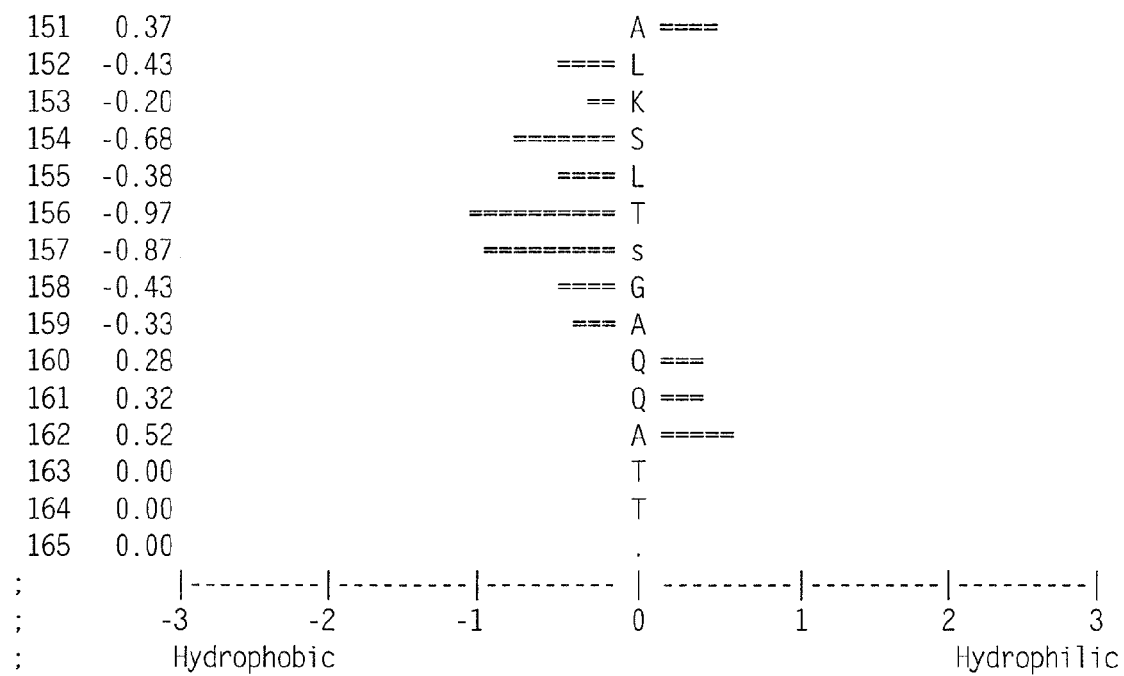

The present invention provides an isolated multimeric or heterodimeric cytokine receptor comprising at least one polypeptide having at least 90 percent sequence identity with SEQ ID NO:111 or SEQ ID NO:109; and wherein the multimeric or heterodimeric cytokine receptor binds a ligand comprising SEQ ID NO:2. Optionally, the isolated multimeric or heterodimeric cytokine receptor may further comprise a cytokine-binding domain of a class I cytokine receptor. The cytokine-binding domain of the class I cytokine receptor may comprise amino acid residue 28 to amino acid residue 429 of SEQ ID NO:7, amino acid residue 28 to amino acid residue 739 of SEQ ID NO:7, amino acid residue 1 to amino acid residue 429 of SEQ ID NO:7, amino acid residue 1 to amino acid residue 739 of SEQ ID NO:7, amino acid residue 1 to amino acid residue 761 of SEQ ID NO:7, amino acid residue 28 to amino acid residue 761 of SEQ ID NO:7, amino acid residue 28 to amino acid residue 979 of SEQ ID NO:7, or amino acid residue 1 to amino acid residue 979 of SEQ ID NO:7. The isolated multimeric or heterodimeric cytokine receptor may antagonize an activity of SEQ ID NO:2. The isolated multimeric or heterodimeric cytokine receptor may inhibit proliferation of hematopoietic cells, inhibit proliferation of immune cells, inhibit proliferation of inflammatory cells, inhibit an immune response, inhibit an inflammatory response, or inhibit proliferation of tumor cells of epithelial origin. The isolated multimeric or heterodimeric cytokine receptor may be soluble. The isolated multimeric or heterodimeric cytokine receptor may further comprises an affinity tag, such as, for instance, polyhistidine, protein A, glutathione S transferase, Glu-Glu, substance P, Flag™ peptide, streptavidin binding peptide, and immunoglobulin $F_c$ polypeptide, or cytotoxic molecule, such as, for instance, a toxin or radionuclide. The isolated multimeric or heterodimeric cytokine receptor wherein the polypeptide having at least 90 percent identity with SEQ ID NO:111 may comprise amino acid residue 20 to amino acid residue 227 of SEQ ID NO:111, amino acid residue 20 to amino acid residue 519 of SEQ ID NO:111, amino acid residue 20 to amino acid residue 543 of SEQ ID NO:111, amino acid residue 20 to amino acid residue 732 of SEQ ID NO:111, amino acid residue 1 to amino acid residue 227, amino acid residue 1 to amino acid residue 519, amino acid residue 1 to amino acid residue 543, or amino acid residue 1 to amino acid residue 732. The isolated multimeric or heterodimeric cytokine receptor wherein the polypeptide having at least 90 percent identity with SEQ ID NO:109 may comprise amino acid residue 1 to amino acid residue 649 of SEQ ID NO:109, or amino acid residue 20 to amino acid residue 649 of SEQ ID NO:109.

The present invention also provides an isolated multimeric or heterodimeric cytokine receptor comprising at least one polypeptide comprising amino acid residue 20 to amino acid residue 227 of SEQ ID NO:111. The at least one polypeptide may comprise amino acid residue 1 to amino acid residue 227 of SEQ ID NO:111, amino acid residue 20 to amino acid residue 519 of SEQ ID NO:111, amino acid residue 1 to amino acid residue 519 of SEQ ID NO:111, amino acid residue 1 to amino acid residue 543 of SEQ ID NO:111, amino acid residue 20 to amino acid residue 543 of SEQ ID NO:111, amino acid residue 1 to amino acid residue 732 of SEQ ID NO:111, or amino acid residue 20 to amino acid residue 732 of SEQ ID NO:111. The isolated multimeric or heterodimeric cytokine receptor may further comprise a cytokine-binding domain of a class I cytokine receptor, for instance, amino acid residue 28 to amino acid residue 429 of SEQ ID NO:7, amino acid residue 1 to amino acid residue 429 of SEQ ID NO:7, amino acid residue 28 to amino acid residue 739 of SEQ ID NO:7, amino acid residue 1 to amino acid residue 739 of SEQ ID NO:7, amino acid residue 28 to amino acid residue 761 of SEQ ID NO:7, amino acid residue 1 to amino acid residue 761 of SEQ ID NO:7, amino acid residue 28 to amino acid residue 979 of SEQ ID NO:7, or amino acid residue 1 to amino acid residue 979 of SEQ ID NO:7. The isolated multimeric or heterodimeric cytokine receptor may antagonize an activity of a ligand comprising SEQ ID NO:2. The isolated multimeric or heterodimeric cytokine receptor may inhibit proliferation of hematopoietic cells, inhibit proliferation of immune cells, inhibit proliferation of inflammatory cells, inhibit an immune response, inhibit an inflammatory response, or inhibit proliferation of tumor cells of epithelial origin. Optionally, the isolated multimeric or heterodimeric cytokine receptor may be soluble. The isolated multimeric or heterodimeric cytokine receptor may further comprise an affinity tag, such as, for instance, polyhistidine, protein A, glutathione S transferase, Glu-Glu, substance P, Flag™ peptide, streptavidin binding peptide, and immunoglobulin $F_c$ polypeptide, or cytotoxic molecule, such as, for instance, a toxin or radionuclide.

The present invention also provides a soluble multimeric or heterodimeric cytokine receptor comprising amino acid residue 20 to amino acid residue 227 of SEQ ID NO:111 and amino acid residue 28 to amino acid residue 429 of SEQ ID NO:7.

The present invention also provides an isolated polynucleotide that encodes a cytokine receptor polypeptide comprising an amino acid sequence having at least 90 percent sequence identity with SEQ ID NO:111 or SEQ ID NO:109, wherein the cytokine receptor polypeptide forms a multimeric or heterodimeric cytokine receptor, and wherein the multimeric or heterodimeric cytokine receptor binds a ligand comprising SEQ ID NO:2. The multimeric or heterodimeric cytokine receptor may further comprise a cytokine-binding domain of a class I cytokine receptor, such as, for instance, amino acid residue 28 to amino acid residue 429 of SEQ ID NO:7, amino acid residue 28 to amino acid residue 739 of SEQ ID NO:7, amino acid residue 1 to amino acid residue 429 of SEQ ID NO:7, amino acid residue 1 to amino acid residue 739 of SEQ ID NO:7, amino acid residue 1 to amino acid residue 761 of SEQ ID NO:7, amino acid residue 28 to amino acid residue 761 of SEQ ID NO:7, amino acid residue 28 to amino acid residue 979 of SEQ ID NO:7, or amino acid residue 1 to amino acid residue 979 of SEQ ID NO:7. The multimeric or heterodimeric cytokine receptor may antagonize an activity of SEQ ID NO:2. The multimeric or heterodimeric cytokine receptor may inhibit proliferation of hematopoietic cells, inhibit proliferation of immune cells, inhibit proliferation of inflammatory cells, inhibit an immune response, inhibit an inflammatory response, or inhibit proliferation of tumor cells of epithelial origin. Optionally, the multimeric or heterodimeric cytokine receptor may be soluble. The multimeric or heterodimeric cytokine receptor may further comprise an affinity tag, such as, for instance, polyhistidine, protein A, glutathione S transferase, Glu-Glu, substance P, Flag™ peptide, streptavidin binding peptide, and immunoglobulin $F_c$ polypeptide, or cytotoxic molecule, such as, for instance, a toxin or radionuclide. The encoded cytokine receptor polypeptide having at least 90 percent identity with SEQ ID NO:111 may comprise amino acid residue 20 to amino acid residue 227 of SEQ ID NO:111, amino acid residue 20 to amino acid residue 519 of SEQ ID NO:111, amino acid residue 20 to amino acid residue 543 of SEQ ID NO:111, amino acid residue 20 to amino acid residue 732 of SEQ ID NO:111, amino acid residue 1 to amino acid residue 227 of SEQ ID NO:111, amino acid residue 1 to amino acid residue 519 of SEQ ID NO:111, amino acid residue 1 to amino acid residue 543 of SEQ ID NO:111, or amino acid residue 1 to amino acid residue 732 of SEQ ID NO:111. The encoded cytokine receptor polypeptide having at least 90 percent identity with SEQ ID NO:109 may comprise amino acid residue 1 to amino acid residue 649 of SEQ ID NO:109, or amino acid residue 20 to amino acid residue 649 of SEQ ID NO:109.

The present invention also provides an isolated polynucleotide that encodes a cytokine receptor polypeptide comprising amino acid residue 20 to amino acid residue 227 of SEQ ID NO:111, wherein the cytokine receptor polypeptide forms a multimeric or heterodimeric cytokine receptor. The cytokine receptor polypeptide may comprise amino acid residue 1 to amino acid residue 227 of SEQ ID NO:111, amino acid residue 20 to amino acid residue 519 of SEQ ID NO:111, amino acid residue 1 to amino acid residue 519 of SEQ ID NO:111, amino acid residue 1 to amino acid residue 543 of SEQ ID NO:111, amino acid residue 20 to amino acid residue 543 of SEQ ID NO:111, amino acid residue 1 to amino acid residue 732 of SEQ ID NO:111, or amino acid residue 20 to amino acid residue 732 of SEQ ID NO:111. The multimeric or heterodimeric cytokine receptor may further comprise a cytokine-binding domain of a class I cytokine receptor, such as, for instance, amino acid residue 28 to amino acid residue 429 of SEQ ID NO:7, amino acid residue 1 to amino acid residue 429 of SEQ ID NO:7, amino acid residue 28 to amino acid residue 739 of SEQ ID NO:7, amino acid residue 1 to amino acid residue 739 of SEQ ID NO:7, amino acid residue 28 to amino acid residue 761 of SEQ ID NO:7, amino acid residue 1 to amino acid residue 761 of SEQ ID NO:7, amino acid residue 28 to amino acid residue 979 of SEQ ID NO:7, or amino acid residue 1 to amino acid residue 979 of SEQ ID NO:7. The multimeric or heterodimeric cytokine receptor may antagonize an activity of a ligand comprising SEQ ID NO:2. The multimeric or heterodimeric cytokine receptor may inhibit proliferation of hematopoietic cells, inhibit proliferation of immune cells, inhibit proliferation of inflammatory cells, inhibit an immune response, inhibit an inflammatory response, or inhibit proliferation of tumor cells of epithelial origin. Optionally, the multimeric or heterodimeric cytokine receptor may be soluble. The multimeric or heterodimeric cytokine receptor may further comprise an affinity tag or cytotoxic molecule as described herein.

The present invention also provides an expression vector that comprises the following operably linked elements: a transcription promoter; a DNA segment encoding a cytokine receptor polypeptide having at least 90 percent sequence identity with SEQ ID NO:111; and a transcription terminator; wherein the cytokine receptor polypeptide forms a multimeric or heterodimeric cytokine receptor, and wherein the multimeric or heterodimeric cytokine receptor binds a ligand comprising SEQ ID NO:2.

Alternatively, the present invention also provides an expression vector that comprises the following operably linked elements: a) a first transcription promoter; a first DNA segment encoding a cytokine receptor polypeptide having at least 90 percent sequence identity with SEQ ID NO:111; and a first transcription terminator; and b) a second transcription promoter; a second DNA segment encoding a cytokine-binding domain of a class I cytokine receptor; and a second transcription terminator; wherein the cytokine receptor polypeptide and the class I cytokine receptor form a multimeric or heterodimeric cytokine receptor; and wherein the multimeric or heterodimeric cytokine receptor binds to a ligand comprising SEQ ID NO:2.

Alternatively, the present invention also provides an expression vector that comprises the following operably linked elements: a) a first transcription promoter; a first DNA segment encoding a polypeptide having at least 90 percent sequence identity with SEQ ID NO:111; and a first transcription terminator; and b) a second transcription promoter; a second DNA segment encoding at least a portion of a class I cytokine receptor; and a second transcription terminator; wherein the polypeptide and the class I cytokine receptor form a multimeric cytokine receptor; and wherein the multimeric cytokine receptor binds to at least a portion of SEQ ID NO:2.

The expression vectors of the present invention may further include a secretory signal sequence linked to the first and second DNA segments. The multimeric or heterodimeric cytokine receptor may be soluble, membrane-bound, or attached to a solid support. The multimeric or heterodimeric cytokine receptor may antagonize an activity of a ligand comprising SEQ ID NO:2. The multimeric or heterodimeric cytokine receptor may inhibit proliferation of hematopoietic cells, inhibit proliferation of immune cells, inhibit proliferation of inflammatory cells, inhibit an immune response, inhibit an inflammatory response, or inhibit proliferation of tumor cells of epithelial origin. Optionally, the multimeric or heterodimeric cytokine receptor may be soluble. The multimeric or heterodimeric cytokine receptor may further comprise an affinity tag or cytotoxic molecule as described herein.

The present invention also provides a cultured cell including an expression vector as described herein, wherein the cell expresses the polypeptide or polypeptides encoded by the DNA segment or segments. The cell may secrete the multimeric or heterodimeric cytokine receptor. The multimeric cytokine receptor may bind and/or antagonize an activity of SEQ ID NO:2 as further described herein.

The present invention also provides a cultured cell which includes a first expression vector comprising: a) a transcription promoter; b) a DNA segment encoding a cytokine receptor polypeptide having at least 90 percent sequence identity with SEQ ID NO:111; and c) a transcription terminator; and a second expression vector comprising: a) a transcription promoter; b) a DNA segment encoding a cytokine-binding domain of a class I cytokine receptor; and c) a transcription terminator; wherein the cytokine receptor polypeptide and the class I cytokine receptor form a multimeric or heterodimeric cytokine receptor, and wherein the multimeric or heterodimeric cytokine receptor binds to a ligand that comprises SEQ ID NO:2. The first and second expression vectors may include a secretory signal sequence operably linked to the first and second DNA segments. The cultured cell may further comprise a third expression vector which includes a) a transcription promoter; b) a DNA segment encoding a cytokine-binding domain of a second class I cytokine receptor; and c) a transcription terminator; wherein the cytokine receptor polypeptide, the first class I cytokine receptor, and the second class I cytokine receptor form a multimeric cytokine receptor. The cytokine-binding domain of a class I cytokine receptor may be of SEQ ID NO:7 and/or SEQ ID NO:9. Optionally, the multimeric or heterodimeric cytokine receptor may be soluble. The multimeric or heterodimeric cytokine receptor may further include an affinity tag as described herein. The multimeric or heterodimeric cytokine receptor may bind to at least a portion of SEQ ID NO:2 and/or antagonize an activity of SEQ ID NO:2 as described herein.

The present invention also provides a method of producing an antibody to a multimeric or heterodimeric cytokine receptor comprising amino acid residue 20 to amino acid residue 227 of SEQ ID NO:111 and a cytokine-binding domain of a class I cytokine receptor. The method includes inoculating an animal with the multimeric or heterodimeric cytokine receptor, wherein the multimeric or heterodimeric cytokine receptor elicits an immune response in the animal to produce an antibody that specifically binds the multimeric or heterodimeric cytokine receptor; and isolating the antibody from the animal. The antibody may optionally be a monoclonal antibody. The antibody may optionally be a neutralizing antibody. The antibody may specifically bind to a multimeric or heterodimeric cytokine receptor as described herein.

The present invention also provides a composition which includes an effective amount of a soluble multimeric or heterodimeric cytokine receptor comprising amino acid residue 20 to amino acid residue 227 of SEQ ID NO:111 and a cytokine-binding domain of a class I cytokine receptor; and a pharmaceutically acceptable vehicle. The binding domain of the class I cytokine receptor may include amino acid residue 28 to amino acid residue 429 of SEQ ID NO:7. The soluble multimeric or heterodimeric cytokine receptor may bind to a ligand comprising SEQ ID NO:2. The soluble multimeric or heterodimeric cytokine receptor may further include an affinity tag or cytotoxic molecule as described herein. The composition may antagonize an activity of a ligand comprising SEQ ID NO:2. The composition may inhibit proliferation of hematopoietic cells, inhibit proliferation of immune cells, inhibit proliferation of inflammatory cells, inhibit an immune response, inhibit an inflammatory response, or inhibit proliferation of tumor cells of epithelial origin The present invention also provides a method of producing a multimeric or heterodimeric cytokine receptor comprising culturing a cell as described herein, and isolating the multimeric or heterodimeric cytokine receptor produced by the cell.

The present invention also provides an immune cell inhibiting composition which includes an effective amount of a soluble multimeric or heterodimeric cytokine receptor comprising amino acid residue 20 to amino acid residue 227 of SEQ ID NO:111 and a cytokine-binding domain of a class I cytokine receptor; and a pharmaceutically acceptable vehicle; wherein the soluble multimeric or heterodimeric cytokine receptor inhibits the proliferation of immune cells.

The present invention also provides an immune response inhibiting composition which includes an effective amount of a soluble multimeric or heterodimeric cytokine receptor comprising amino acid residue 20 to amino acid residue 227 of SEQ ID NO:111 and a cytokine-binding domain of a class I cytokine receptor; and a pharmaceutically acceptable vehicle; wherein the soluble multimeric or heterodimeric cytokine receptor inhibits an immune response.

The present invention also provides an inflammatory cell inhibiting composition which includes an effective amount of a soluble multimeric or heterodimeric cytokine receptor comprising amino acid residue 20 to amino acid residue 227 of SEQ ID NO:111 and a cytokine-binding domain of a class I cytokine receptor; and a pharmaceutically acceptable vehicle; wherein the soluble multimeric or heterodimeric cytokine receptor inhibits the proliferation of inflammatory cells.

The present invention also provides an inflammatory response inhibiting composition which includes an effective amount of a soluble multimeric or heterodimeric cytokine receptor comprising amino acid residue 20 to amino acid residue 227 of SEQ ID NO:111 and a cytokine-binding domain of a class I cytokine receptor; and a pharmaceutically acceptable vehicle; wherein the soluble multimeric or heterodimeric cytokine receptor inhibits an inflammatory response.

The present invention also provides a method of inhibiting an immune response in a mammal exposed to an antigen or pathogen. The method includes (a) determining directly or indirectly the level of antigen or pathogen present in the mammal; (b) administering a composition comprising a soluble multimeric or heterodimeric cytokine receptor in a pharmaceutically acceptable vehicle; (c) determining directly or indirectly the level of antigen or pathogen in the mammal; and (d) comparing the level of the antigen or pathogen in step (a) to the antigen or pathogen level in step (c), wherein a change in the level is indicative of inhibiting an immune response. The method may further comprise (e) re-administering a composition comprising a multimeric cytokine receptor in a pharmaceutically acceptable vehicle; (f) determining directly or indirectly the level of antigen or pathogen in the mammal; and (g) comparing the number of the antigen or pathogen level in step (a) to the antigen level in step (f), wherein a change in the level is indicative of inhibiting an immune response.

The present invention also provides a method for reducing hematopoietic cells and/or hematopoietic progenitors cells in a mammal. The method includes culturing bone marrow or peripheral blood cells with a composition comprising an effective amount of a soluble multimeric or heterodimeric cytokine receptor to produce a decrease in the number of lymphoid cells in the bone marrow or peripheral blood cells as compared to bone marrow or peripheral blood cells cultured in the absence of the multimeric cytokine receptor. The hematopoietic cells and hematopoietic cell progenitors may be lymphoid, which can be monocytic cells, macrophages, or T cells.

The present invention also provides a method of detecting the presence of a multimeric or heterodimeric cytokine receptor in a biological sample. The method includes contacting the biological sample with an antibody, or an antibody fragment, as described herein, wherein the contacting is performed under conditions that allow the binding of the antibody or antibody fragment to the biological sample; and detecting any of the bound antibody or bound antibody fragment.

The present invention also provides a method of a method of killing cancer cells. The method includes obtaining ex vivo a tissue or biological sample containing cancer cells from a patient, or identifying cancer cells in vivo; producing a multimeric or heterodimeric cytokine receptor by a method as described herein; formulating the multimeric or heterodimeric cytokine receptor in a pharmaceutically acceptable vehicle; and administering to the patient or exposing the cancer cells to the multimeric or heterodimeric cytokine receptor formulation; wherein the multimeric or heterodimeric cytokine receptor kills the cells. The multimeric or heterodimeric cytokine receptor may be further conjugated to a toxin.

The present invention also provides an antibody that specifically binds to a multimerc or heterodimeric cytokine receptor as described herein. The antibody may be a polyclonal antibody, a murine monoclonal antibody, a humanized antibody derived from a murine monoclonal antibody, an antibody fragment, a neutralizing antibody, or a human monoclonal antibody. The antibody or antibody fragment may specifically bind to a multimeric or heterodimeric cytokine receptor of the present invention which may comprise a cytokine receptor polypeptide comprising amino acid residue 20 to amino acid residue 227 of SEQ ID NO:111 and a cytokine-binding domain of a class I cytokine receptor. The antibody may further include a radionuclide, enzyme, substrate, cofactor, fluorescent marker, chemiluminescent marker, peptide tag, magnetic particle, drug, or toxin.

The present invention also provides a method for inhibiting zcytor17lig-induced proliferation or differentiation of hematopoietic cells and hematopoietic progenitor cells. The method includes culturing bone marrow or peripheral blood cells with a composition comprising an amount of a soluble multimeric or heterodimeric cytokine receptor comprising a cytokine receptor polypeptide comprising amino acid residue 20 to amino acid residue 227 of SEQ ID NO:111 and a cytokine-binding domain of a class I cytokine receptor sufficient to reduce proliferation or differentiation of the hematopoietic cells in the bone marrow or peripheral blood cells as compared to bone marrow or peripheral blood cells cultured in the absence of the soluble multimeric or heterodimeric cytokine receptor. The hematopoietic cells and hematopoietic progenitor cells may be lymphoid cells, such as macrophages or T cells.

The present invention also provides a method of reducing zcytor17lig-induced induced inflammation. The method includes administering to a mammal with inflammation an amount of a composition comprising amino acid residue 20 to amino acid residue 227 of SEQ ID NO:111 and a cytokine-binding domain of a class I cytokine receptor sufficient to reduce inflammation.

The present invention also provides a method of suppressing an inflammatory response in a mammal with inflammation. The method includes (1) determining a level of an inflammatory molecule; (2) administering a composition comprising amino acid residue 20 to amino acid residue 227 of SEQ ID NO:111 and a cytokine-binding domain of a class I cytokine receptor in a pharmaceutically acceptable vehicle; (3) determining a post administration level of the inflammatory molecule; (4) comparing the level of the inflammatory molecule in step (1) to the level of the inflammatory molecule in step (3), wherein a lack of increase or a decrease the inflammatory molecule level is indicative of suppressing an inflammatory response.

The present invention also provides a method for inhibiting zcytor17lig-induced proliferation or differentiation of hematopoietic cells and hematopoietic progenitor cells. The method includes culturing bone marrow or peripheral blood cells with a composition comprising amino acid residue 20 to amino acid residue 227 of SEQ ID NO:111 and a cytokine-binding domain of a class I cytokine receptor in a pharmaceutically acceptable vehicle sufficient to reduce proliferation or differentiation of the hematopoietic cells in the bone marrow or peripheral blood cells as compared to bone marrow or peripheral blood cells cultured in the absence of soluble multimeric or heterodimeric cytokine receptor. The hematopoietic cells and hematopoietic progenitor cells may be lymphoid cells, such as macrophages or T cells.

The present invention also provides a method of reducing zcytor17lig-induced induced inflammation. The method includes administering to a mammal with inflammation an amount of a composition comprising amino acid residue 20 to amino acid residue 227 of SEQ ID NO:111 and a cytokine-binding domain of a class I cytokine receptor in a pharmaceutically acceptable vehicle sufficient to reduce inflammation.

The present invention also provides a method of suppressing an inflammatory response in a mammal with inflammation. The method includes (1) determining a level of an inflammatory molecule; (2) administering a composition comprising a multimeric or heterodimeric cytokine receptor which comprises amino acid residue 20 to amino acid residue 227 of SEQ ID NO:111 in a pharmaceutically acceptable vehicle; (3) determining a post administration level of the inflammatory molecule; (4) comparing the level of the inflammatory molecule in step (1) to the level of the inflammatory molecule in step (3), wherein a lack of increase or a decrease in the inflammatory molecule level is indicative of suppressing an inflammatory response.

The present invention also provides a method of treating a mammal afflicted with an inflammatory disease in which zcytor17lig plays a role. The method includes administering an antagonist of zcytor17lig to the mammal such that the inflammation is reduced, wherein the antagonist is a soluble multimeric or heterodimeric cytokine receptor comprising amino acid residue 20 to amino acid residue 227 of SEQ ID NO:111 and a cytokine-binding domain of a class I cytokine receptor in a pharmaceutically acceptable vehicle. The inflammatory disease may be a chronic inflammatory disease, such as, for instance, inflammatory bowel disease, ulcerative colitis, Crohn's disease, atopic dermatitis, eczema, or psoriasis. The inflammatory disease may be an acute inflammatory disease, such as, for instance, endotoxemia, septicemia, toxic shock syndrome, or infectious disease. Optionally, the soluble multimeric or heterodimeric cytokine receptor may further comprise a radionuclide, enzyme, substrate, cofactor, fluorescent marker, chemiluminescent marker, peptide tag, magnetic particle, drug, or toxin.

The present invention also provides a method for detecting inflammation in a patient. The method includes obtaining a tissue or biological sample from a patient; incubating the tissue or biological sample with a soluble multimeric or heterodimeric cytokine receptor comprising amino acid residue 20 to amino acid residue 227 of SEQ ID NO:111 and a cytokine-binding domain of a class I cytokine receptor under conditions wherein the soluble multimeric or heterodimeric cytokine receptor binds to its complementary polypeptide in the tissue or biological sample; visualizing the soluble multimeric or heterodimeric cytokine receptor bound in the tissue or biological sample; and comparing levels of soluble multimeric or heterodimeric cytokine receptor bound in the tissue or biological sample from the patient to a normal control tissue or biological sample, wherein an increase in the level of soluble multimeric or heterodimeric cytokine receptor bound to the patient tissue or biological sample relative to the normal control tissue or biological sample is indicative of inflammation in the patient.

The present invention also provides a method for detecting a multiple cytokine receptor ligand from a test sample. The method includes contacting the test sample with a multimeric or heterodimeric cytokine receptor comprising a cytokine receptor polypeptide comprising amino acid residue 20 to amino acid residue 227 of SEQ ID NO:111 and a cytokine-binding domain of a class I cytokine receptor; and detecting the binding of the multimeric or heterodimeric cytokine receptor to the ligand in the test sample.

DETAILED DESCRIPTION OF THE INVENTION

Definitions

Prior to setting forth the invention in detail, it may be helpful to the understanding thereof to define the following terms:

Unless otherwise specified, "a," "an," "the," and "at least one" are used interchangeably and mean one or more than one.

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), Glu-Glu affinity tag (Grussenmeyer et al., *Proc. Natl. Acad. Sci. USA* 82:7952-4, 1985), substance P, Flag™ peptide (Hopp et al.,

*Biotechnology* 6:1204-10, 1988), streptavidin binding peptide, or other antigenic epitope or binding domain. See, in general, Ford et al., *Protein Expression and Purification* 2: 95-107, 1991. DNAs encoding affinity tags are available from commercial suppliers (e.g., Pharmacia Biotech, Piscataway, N.J.).

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of $<10^9$ M$^{-1}$.

The term "complements of a polynucleotide molecule" denotes a polynucleotide molecule having a complementary base sequence and reverse orientation as compared to a reference sequence. For example, the sequence 5' ATGCACGGG 3' is complementary to 5' CCCGTGCAT 3'.

The term "contig" denotes a polynucleotide that has a contiguous stretch of identical or complementary sequence to another polynucleotide. Contiguous sequences are said to "overlap" a given stretch of polynucleotide sequence either in their entirety or along a partial stretch of the polynucleotide. For example, representative contigs to the polynucleotide sequence 5'-ATGGCTTAGCTT-3' are 5'-TAGCTTgagtct-3' and 3'-gtcgacTACCGA-5'.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774-78, 1985).

An "isolated" polypeptide or protein is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. When used in this context, the term "isolated" does not exclude the presence of the same polypeptide in alternative physical forms, such as dimers or alternatively glycosylated or derivatized forms.

The term "neoplastic", when referring to cells, indicates cells undergoing new and abnormal proliferation, particularly in a tissue where in the proliferation is uncontrolled and progressive, resulting in a neoplasm. The neoplastic cells can be either malignant, i.e., invasive and metastatic, or benign.

The term "operably linked", when referring to DNA segments, indicates that the segments are arranged so that they function in concert for their intended purposes, e.g., transcription initiates in the promoter and proceeds through the coding segment to the terminator.

The term "ortholog" denotes a polypeptide or protein obtained from one species that is the functional counterpart of a polypeptide or protein from a different species. Sequence differences among orthologs are the result of speciation.

"Paralogs" are distinct but structurally related proteins made by an organism. Paralogs are believed to arise through gene duplication. For example, α-globin, β-globin, and myoglobin are paralogs of each other.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired.

A "polypeptide" is a polymer of amino acid residues joined by peptide bonds, whether produced naturally or synthetically. Polypeptides of less than about 10 amino acid residues are commonly referred to as "peptides".

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The term "receptor" denotes a cell-associated protein that binds to a bioactive molecule (i.e., a ligand) and mediates the effect of the ligand on the cell. Membrane-bound receptors are characterized by a multi-peptide structure comprising an extracellular ligand-binding domain and an intracellular effector domain that is typically involved in signal transduction. Binding of ligand to receptor results in a conformational change in the receptor that causes an interaction between the effector domain and other molecule(s) in the cell. This interaction in turn leads to an alteration in the metabolism of the cell. Metabolic events that are linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids. In general, receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor).

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

A "soluble receptor" is a receptor polypeptide that is not bound to a cell membrane. Soluble receptors are most commonly ligand-binding receptor polypeptides that lack transmembrane and cytoplasmic domains. Soluble receptors can comprise additional amino acid residues, such as affinity tags that provide for purification of the polypeptide or provide sites for attachment of the polypeptide to a substrate, or immunoglobulin constant region sequences. Many cell-surface receptors have naturally occurring, soluble counterparts that are produced by proteolysis. Soluble receptor polypeptides are said to be substantially free of transmembrane and intracellular polypeptide segments when they lack sufficient portions of these segments to provide membrane anchoring or signal transduction, respectively.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a protein encoded by a splice variant of an mRNA transcribed from a gene.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

The present invention is based in part upon the discovery of a novel multimeric cytokine receptor protein having the structure of a class I cytokine receptor, referred to herein as "multimeric cytokine receptor," or "zcytor17 multimeric cytokine receptor." The multimeric cytokine receptor includes at least a portion of a zcytor17 receptor subunit, disclosed in the commonly owned U.S. patent application Ser. No. 09/892, 949. Another receptor subunit polypeptide that may be included in the multimeric cytokine receptor of the present invention includes at least a portion of at least one polypeptide of a class I cytokine receptor, such as OSMRbeta and/or WSX-1. For example, the deduced amino acid sequence indicated that zcytor17 belongs to the receptor subfamily that includes gp130, LIF, IL-12, oncostatinM receptor beta (OSMRbeta) (SEQ ID NO:7), WSX-1 receptors (SEQ ID NO:9) (Sprecher, C A et al., *Biochem. Biophys. Res. Comm.,* 246: 81-90 (1998); and U.S. Pat. No. 5,925,735), DCRS2 (WIPO Publication No. WO 00/73451), the IL-2 receptor β-subunit and the β-common receptor (i.e., IL-3, IL-5, and GM-CSF receptor subunits). A further example of class I cytokine receptor subunit polypeptides that may be included in the multimeric cytokine receptor are the receptors for IL-2, IL-4, IL-7, Lif, IL-12, IL-15, EPO, TPO, GM-CSF and G-CSF (Cosman, *Cytokine,* 5(2):95-106 (1993)).

Cytokine receptor subunits are characterized by a multi-domain structure comprising an extracellular domain, a transmembrane domain that anchors the polypeptide in the cell membrane, and an intracellular domain. The extracellular domain may be a ligand-binding domain, and the intracellular domain may be an effector domain involved in signal transduction, although ligand-binding and effector functions may reside on separate subunits of a multimeric receptor. The ligand-binding domain may itself be a multi-domain structure. Multimeric receptors include homodimers (e.g., PDGF receptor αα and ββ isoforms, erythropoietin receptor, MPL, and G-CSF receptor), heterodimers whose subunits each have ligand-binding and effector domains (e.g., PDGF receptor αβ isoform), and multimers having component subunits with disparate functions (e.g., IL-2, IL-3, IL-4, IL-5, IL-6, IL-7, and GM-CSF receptors). Some receptor subunits are common to a plurality of receptors. For example, the AIC2B subunit, which cannot bind ligand on its own but includes an intracellular signal transduction domain, is a component of IL-3 and GM-CSF receptors. Many cytokine receptors can be placed into one of four related families on the basis of the structure and function. Hematopoietic receptors, for example, are characterized by the presence of a domain containing conserved cysteine residues and the WSXWS motif (SEQ ID NO:3). Cytokine receptor structure has been reviewed by Urdal, *Ann. Reports Med. Chem.* 26:221-228, 1991 and Cosman, *Cytokine* 5:95-106, 1993. Under selective pressure for organisms to acquire new biological functions, new receptor family members likely arise from duplication of existing receptor genes leading to the existence of multi-gene families. Family members thus contain vestiges of the ancestral gene, and these characteristic features can be exploited in the isolation and identification of additional family members. Thus, the cytokine receptor superfamily is subdivided into several families, for example, the immunoglobulin family (including CSF-1, MGF, IL-1, and PDGF receptors); the hematopoietin family (including IL-2 receptor β-subunit, GM-CSF receptor α-subunit, GM-CSF receptor β-subunit; and G-CSF, EPO, IL-3, IL-4, IL-5, IL-6, IL-7, and IL-9 receptors); TNF receptor family (including TNF (p80) TNF (p60) receptors, CD27, CD30, CD40, Fas, and NGF receptor).

Analysis of the zcytor17 sequence suggests that it is a member of the same receptor subfamily as the gp130, LIF, IL-12, WSX-1, IL-2 receptor β-subunit, IL-3, IL-4, and IL-6 receptors. Certain receptors in this subfamily (e.g., G-CSF) associate to form homodimers that transduce a signal. Other members of the subfamily (e.g., gp130, IL-6, IL-11, and LIF receptors) combine with a second subunit (termed a β-subunit) to bind ligand and transduce a signal. Specific β-subunits associate with a plurality of specific cytokine receptor subunits. For example, the β-subunit gp130 (Hibi et al., *Cell* 63:1149-1157, 1990) associates with receptor subunits specific for IL-6, IL-11, and LIF (Gearing et al., *EMBO J.* 10:2839-2848, 1991; Gearing et al., U.S. Pat. No. 5,284,755). Oncostatin M binds to a heterodimer of LIF receptor and gp130. CNTF binds to trimeric receptors comprising CNTF receptor, LIF receptor, and gp130 subunits.

A multimeric cytokine receptor of the present invention can be a heterodimer, trimer, tetramer, pentamer, and the like, comprising at least a portion of zcytor17 and at least a portion of a class I cytokine receptor. In addition, a multimeric cytokine receptor can be soluble, membrane-bound, or attached to a solid support. Analysis of the tissue distribution of the mRNA of the zcytor17 receptor revealed expression in activated CD4+ and CD8+ T-cell subsets, CD14+ monocytes, and weaker expression in CD19+ B-cells. Moreover, the mRNA was present in both resting or activated monocytic cell lines THP-1 (ATCC No. TIB-202), U937 (ATCC No. CRL-1593.2) and HL60 (ATCC No. CCL-240).

Nucleotide sequences of representative zcytor17-encoding DNA are described in SEQ ID NO:110 (from nucleotide 171 to 2366), with its deduced 732 amino acid sequence described in SEQ ID NO:111; SEQ ID NO:108 (from nucleotide 162 to 2108), with its deduced 649 amino acid sequence described in SEQ ID NO:109; and in SEQ ID NO:4 (from nucleotide 497 to 2482), with its deduced 662 amino acid sequence described in SEQ ID NO:5. In its entirety, the zcytor17 polypeptide (SEQ ID NO:111, SEQ ID NO:109 or SEQ ID NO:5) represents a full-length polypeptide segment (residue 1 (Met) to residue 732 (Val) of SEQ ID NO:111; residue 1 (Met) to residue 649 (Ile) of SEQ ID NO:109; residue 1 (Met) to residue 662 (Ile) of SEQ ID NO:5). The domains and structural features of the zcytor17 polypeptides are further described below.

Analysis of the zcytor17 polypeptide encoded by the DNA sequence of SEQ ID NO:110 revealed an open reading frame encoding 732 amino acids (SEQ ID NO:111) comprising a predicted secretory signal peptide of 19 amino acid residues (residue 1 (Met) to residue 19 (Ala) of SEQ ID NO:111), and a mature polypeptide of 713 amino acids (residue 20 (Ala) to residue 732 (Val) of SEQ ID NO:111). Analysis of the zcytor17 polypeptide encoded by the DNA sequence of SEQ ID NO:108 revealed an open reading frame encoding 649 amino acids (SEQ ID NO:109) comprising a predicted secretory signal peptide of 19 amino acid residues (residue 1 (Met) to residue 19 (Ala) of SEQ ID NO:109), and a mature polypeptide of 630 amino acids (residue 20 (Ala) to residue 649 (Ile) of SEQ ID NO:109). Analysis of the zcytor17 polypeptide encoded by the DNA sequence of SEQ ID NO:4 revealed an open reading frame encoding 662 amino acids (SEQ ID NO:5) comprising a predicted secretory signal peptide of 32 amino acid residues (residue 1 (Met) to residue 32 (Ala) of SEQ ID NO:5), and a mature polypeptide of 630 amino acids (residue 33 (Ala) to residue 662 (Ile) of SEQ ID NO:5). In addition to the WSXWS motif (SEQ ID NO:3) (corresponding to residues 211 to 215 of SEQ ID NO:111 and SEQ ID NO:109; and residues 224 to 228 of SEQ ID NO:5), the receptor comprises an extracellular domain (residues 20 (Ala) to 519 (Glu) of SEQ ID NO:111 and SEQ ID NO:109; residues 33 (Ala) to 532 (Glu) of SEQ ID NO:5) which includes a cytokine-binding domain of approximately 200 amino acid residues (residues 20 (Ala) to 227 (Pro) of SEQ ID NO:111 and SEQ ID NO:109; residues 33 (Ala) to 240 (Pro) of SEQ ID NO:5); a domain linker (residues 122 (Thr) to 125 (Pro) of SEQ ID NO:111 and SEQ ID NO:109; residues 135 (Thr) to 138 (Pro) of SEQ ID NO:111); a penultimate strand region (residues 194 (Phe) to 202 (Arg) of SEQ ID NO:111 and SEQ ID NO:109; residues 207 (Phe) to 215 (Arg) of SEQ ID NO:5); a fibronectin type III domain (residues 228 (Cys) to 519 (Glu) of SEQ ID NO:111 and SEQ ID NO:109; residues 241 (Cys) to 532 (Glu) of SEQ ID NO:5); a transmembrane domain (residues 520 (Ile) to 543 (Leu) of SEQ ID NO:111 and SEQ ID NO:109; residues 533 (Ile) to 556 (Leu) of SEQ ID NO:5); complete intracellular signaling domain (residues 544 (Lys) to 732 (Val) of SEQ ID NO:111; residues 544 (Lys) to 649 (Ile) of SEQ ID NO:109; and residues 557 (Lys) to 662 (Ile) of SEQ ID NO:5) which contains a "Box I" signaling site (residues 554 (Trp) to 560 (Pro) of SEQ ID NO:111 and SEQ ID NO:109; residues 567 (Trp) to 573 (Pro) of SEQ ID NO:5), and a "Box II" signaling site (residues 617 (Gln) to 620 (Phe) of SEQ ID NO:111 and SEQ ID NO:109; residues 630 (Gln) to 633 (Phe) of SEQ ID NO:5). Those skilled in the art will recognize that these domain boundaries are approximate, and are based on alignments with known proteins and predictions of protein folding. In addition to these domains, conserved receptor features in the encoded receptor include (as shown in SEQ ID NO:111 and SEQ ID NO:109) a conserved Cys residue at position 30 (position 43 as shown in SEQ ID NO:5), CXW motif (wherein X is any amino acid) at positions 40-42 (positions 53-55 as shown in SEQ ID NO:5), Trp residue at position 170 (position 183 as shown in SEQ ID NO:5), and a conserved Arg residue at position 202 (position 215 as shown in SEQ ID NO:5). The corresponding polynucleotides encoding the zcytor17 polypeptide regions, domains, motifs, residues and sequences described above are as shown in SEQ ID NO:110, SEQ ID NO:108, and SEQ ID NO:4.

Moreover, truncated forms of the zcytor17 polypeptide appear to be naturally expressed. Both forms encode soluble zcytor17 receptors. A polynucleotide encoding a "long-form" of the soluble zcytor17 receptor, truncated within the fibronectin type III domain, is shown in SEQ ID NO:112 and the corresponding polypeptide is shown in SEQ ID NO:113. This truncated form encodes residues 1 (Met) through 324 (Lys) of SEQ ID NO:111 and SEQ ID NO:109), and thus comprises an intact signal sequence, WSXWS (SEQ ID NO:3) motif, linker, cytokine binding domain, penultimate strand, and conserved, Cys, CXW motif, Trp and Arg residues as described above. A polynucleotide encoding a "short-form" of the soluble zcytor17 receptor, truncated at the end of the cytokine binding domain is shown in SEQ ID NO:114 and the corresponding polypeptide is shown in SEQ ID NO:115. This truncated form encodes a 239 residue polypeptide that is identical to residues 1 (Met) through 225 (Glu) of SEQ ID NO:111 and SEQ ID NO:109 and then diverges, and thus comprises an intact signal sequence, WSXWS (SEQ ID NO:3) motif, linker, cytokine binding domain, penultimate strand, and conserved, Cys, CXW motif, Trp and Arg residues as described above. A multiple alignment of the truncated forms compared to the full-length forms of zcytor17 is shown in FIG. 1.

Moreover, the zcytor17 cDNA of SEQ ID NO:110, SEQ ID NO:108, SEQ ID NO:112, and SEQ ID NO:114 encode polypeptides that may use an alternative initiating methionine (at nucleotide 75 of SEQ ID NO:110, at nucleotide 66 of SEQ ID NO:108, at nucleotide 66 of SEQ ID NO:112, and at nucleotide 66 of SEQ ID NO:114) that would encode a polypeptide in the same open reading frame (ORF) as the zcytor17 polypeptides of SEQ ID NO:111, SEQ ID NO:109, SEQ ID NO:113, and SEQ ID NO:115. Use of the alternative initiating methionine would add 32 amino acids (shown in SEQ ID NO:48) in-frame to the N-terminus of SEQ ID NO:111, SEQ ID NO:109, SEQ ID NO:113, and SEQ ID NO:111. In addition, nucleotide 536 of SEQ ID NO:4 may serve as an alternative initiating methionine, thus generating the same N-terminus (starting at amino acid 14 (Met) of SEQ ID NO:5) and signal polypeptide sequence, as SEQ ID NO:111, SEQ ID NO:109, SEQ ID NO:113, and SEQ ID NO:115. Moreover, the second Met at amino acid number 2 in the SEQ ID NO:111, SEQ ID NO:109, SEQ ID NO:113, and SEQ ID NO:115 sequences (similarly at amino acid number 15 (Met) in SEQ ID NO:5) may also serve as an alternative starting methionine for the polypeptides.

Nucleotide sequences of representative OSMRbeta-encoding DNA are described in SEQ ID NO:6 (from nucleotide 368 to 3304), with its deduced 979 amino acid sequence described in SEQ ID NO:7. In its entirety, the OSMRbeta polypeptide (SEQ ID NO:7) represents a full-length polypeptide segment (residue 1 (Met) to residue 979 (Cys) of SEQ ID NO:7. The domains and structural features of the OSMRbeta polypeptides are further described below.

Analysis of the OSMRbeta polypeptide encoded by the DNA sequence of SEQ ID NO:6 revealed an open reading frame encoding 979 amino acids (SEQ ID NO:7) comprising a predicted secretory signal peptide of 27 amino acid residues (residue 1 (Met) to residue 27 (Ala) of SEQ ID NO:7), and a mature polypeptide of 952 amino acids (residue 28 (Glu) to residue 979 (Cys) of SEQ ID NO:7. In addition to the two WSXWS motifs (SEQ ID NO:3) (corresponding to residues 129 to 133 and residues 415 to 419 of SEQ ID NO:7), the receptor comprises an extracellular domain (residues 28 (Glu) to 739 (Ser) of SEQ ID NO:7); which includes a cytokine-binding domain of approximately 400 amino acid residues (residues 28 (Glu) to 429 (Ala) of SEQ ID NO:7, which includes two linker domains (residues 31 (Pro) to 34 (Pro) and residues 343 (Asn) to 347 (Thr)), three regions of cytokine binding (residues 35 (Val) to 137 (Glu), residues 240 (Pro) to 342 (Glu), and residues 348 (Asn) to 429 (Ala), an immuoglobulin domain (residues 138 (Val) to 239 (Glu), two penultimate strand regions (residues 106 (His) to 115 (Lys) and residues 398 (Thr) to 405 (Arg) of SEQ ID NO:7), and a fibronectin type III domain (residues 430 (Pro) to 739 (Ser) of SEQ ID NO:7); a transmembrane domain (residues 740 (Met) to 761 (Leu) of SEQ ID NO:7); complete intracellular signaling domain (residues 762 (Lys) to 979 (Cys) of SEQ ID NO:7) which contains a "Box I" signaling site (residues 771 (Tyr) to 777 (Pro) of SEQ ID NO:7), and a "Box II" signaling site (residues 829 (Glu) to 832 (Leu) of SEQ ID NO:7). Those skilled in the art will recognize that these domain boundaries are approximate, and are based on alignments with known proteins and predictions of protein folding. In addition to these domains, conserved receptor features in the encoded receptor include (as shown in SEQ ID NO:7) conserved Trp residues at positions 52 and 353, a conserved Cys residue at position 288, CXW motif (wherein X is any amino acid) at positions 294-296, and a conserved Arg residue at position 405. The corresponding polynucleotides encoding the OSMRbeta polypeptide regions, domains, motifs, residues and sequences described above are as shown in SEQ ID NO:6.

The presence of transmembrane regions, and conserved and low variance motifs generally correlates with or defines important structural regions in proteins. Regions of low variance (e.g., hydrophobic clusters) are generally present in regions of structural importance (Sheppard, P. et al., supra.). Such regions of low variance often contain rare or infrequent amino acids, such as Tryptophan. The regions flanking and between such conserved and low variance motifs may be more variable, but are often functionally significant because they may relate to or define important structures and activities such as binding domains, biological and enzymatic activity, signal transduction, cell-cell interaction, tissue localization domains and the like.

The regions of conserved amino acid residues in zcytor17, described above, can be used as tools to identify new family members. For instance, reverse transcription-polymerase chain reaction (RT-PCR) can be used to amplify sequences encoding the conserved regions from RNA obtained from a variety of tissue sources or cell lines. In particular, highly degenerate primers designed from the zcytor17 sequences are useful for this purpose. Designing and using such degenerate primers may be readily performed by one of skill in the art.

The present invention also contemplates a multimeric zcytor17 receptor, as detailed herein, which is capable of intracellular signaling. Such receptors may include at least a portion of at least one extracellular domain of a zcytor17 receptor, and an intracellular domain from a zcytor17 receptor or another class I cytokine receptor. In addition to the extracellular domain of zcytor17, the multimeric cytokine receptor can also include the extracellular domain of at least a portion of class I cytokine receptor, for instance, the ligand binding domains of OSMRbeta receptor and/or WSX-1 receptor. Alternatively, the multimeric cytokine receptor may include the extracellular domain of another receptor, such as another class I cytokine receptor, and the intracellular domain of zcytor17 to effect intracellular signaling.

The present invention further contemplates a multimeric cytokine receptor that is soluble. For example, a multimeric cytokine receptor may be, for instance, a heterodimer which includes, for example, a portion of the extracellular domain of zcytor17 and a portion of the extracellular domain of a class I cytokine receptor, such as OSMRbeta (SEQ ID NO:7) and/or WSX-1 (SEQ ID NO:9). Additionally, a soluble multimeric cytokine receptor may also include an affinity tag, such as an immunoglobulin $F_c$ polypeptide. The soluble multimeric cytokine receptor can be expressed as a fusion with an immunoglobulin heavy chain constant region, such as an $F_c$ fragment, which contains two constant region domains and lacks the variable region. Such fusions are typically secreted as multimeric molecules wherein the $F_c$ portions are disulfide bonded to each other and two non-Ig polypeptides are arrayed in closed proximity to each other. Fusions of this type can be used for example, for dimerization, increasing stability and in vivo half-life, to affinity purify ligand, as in vitro assay tool or antagonist.

Through processes of cloning, and proliferation assays described in detail herein, a multimeric cytokine receptor of the present invention has been shown to bind a novel ligand polypeptide (zcytor17lig) (SEQ ID NO:2), disclosed in commonly owned U.S. Patent Application Ser. No. 60/350,325 and commonly owned U.S. Patent Application Ser. No. 60/375,323, with high specificity. Zcytor17lig was isolated from a cDNA library generated from activated human peripheral blood cells (hPBCs), which were selected for CD3. CD3 is a cell surface marker unique to cells of lymphoid origin, particularly T cells.

A zcytor17lig positive clone was isolated, and sequence analysis revealed that the polynucleotide sequence contained within the plasmid DNA was novel. The secretory signal sequence is comprised of amino acid residues 1 (Met) to 23 (Ala), and the mature polypeptide is comprised of amino acid residues 24 (Ser) to 164 (Thr) (as shown in SEQ ID NO:2).

Further, N-Terminal sequencing analysis of purified zcytor17lig from 293T cells showed an N-terminus at residue 27 (Leu) as shown in SEQ ID NO:2, with the mature polypeptide comprised of amino acid residues 27 (Leu) to 164 (Thr) (as shown in SEQ ID NO:2).

In general, cytokines are predicted to have a four-alpha helix structure, with helices A, C and D being most important in ligand-receptor interactions, and are more highly conserved among members of the family. Referring to the human zcytor17lig amino acid sequence shown in SEQ ID NO:2, alignment of human zcytor17lig, human IL-3, and human cytokine amino acid sequences it is predicted that zcytor17lig helix A is defined by amino acid residues 38-52; helix B by amino acid residues 83-98; helix C by amino acid residues 104-117; and helix D by amino acid residues 137-152; as shown in SEQ ID NO:2. Structural analysis suggests that the A/B loop is long, the B/C loop is short and the C/D loop is long. This loop structure results in an up-up-down-down helical organization. Based on 4-helix bundle structure, the cysteine residues within zcytor17lig that are conserved correspond to amino acid residues 72, 133, and 147 of SEQ ID NO:2; and 74, 137, and 151 of SEQ ID NO:11 described herein. Consistent cysteine placement is further confirmation of the four-helical-bundle structure. Also highly conserved in the zcytor17lig is the Glu residue as shown in SEQ ID NO:2 at residue 43.

Moreover, the predicted amino acid sequence of murine zcytor17lig shows 31% identity to the predicted human protein over the entire length of the sequences (SEQ ID NO:2 and SEQ ID NO:11). Based on comparison between sequences of human and murine zcytor17lig conserved residues were found in the regions predicted to encode alpha helices C and D. The corresponding polynucleotides encoding the human zcytor17lig polypeptide regions, domains, motifs, residues and sequences described herein are as shown in SEQ ID NO:1.

While helix D is relatively conserved between human and murine zcytor17lig, helix C is the most conserved. While both species have predominant acidic amino acids in this region, the differences may account for species specificity in interaction between zcytor17lig and its receptor, zcytor17, comprising monomeric, heterodimeric (e.g., zcytor17/OSMR-beta, WSX-1/OSMRbeta, zcytor17/WSX-1) or multimeric (e.g., zcytor17/OSMRbeta/WSX-1) receptors. Loop A/B and helix B of zcytor17lig are marginally conserved, and helix C through Loop C/D into helix D is most conserved between species; conservation through this region suggests that it is functionally significant. The D helices of human and murine zcytor17lig are also conserved. Zcytor17 receptor antagonists may be designed through mutations within zcytor17lig helix D. These may include truncation of the protein from residue Thr156 (SEQ ID NO:2), or conservation of residues that confer binding of the ligand to the receptor, but diminish signaling activity.

Four-helical bundle cytokines are also grouped by the length of their component helices. "Long-helix" form cytokines generally consist of between 24-30 residue helices, and include IL-6, ciliary neutrotrophic factor (CNTF), leukemia inhibitory factor (LIF) and human growth hormone (hGH). "Short-helix" form cytokines generally consist of between 18-21 residue helices and include IL-2, IL-4 and GM-CSF. Zcytor17lig is believed to be a new member of the short-helix form cytokine group. Studies using CNTF and IL-6 demonstrated that a CNTF helix can be exchanged for the equivalent helix in IL-6, conferring CTNF-binding properties to the chimera. Thus, it appears that functional domains of four-helical cytokines are determined on the basis of structural homology, irrespective of sequence identity, and can maintain functional integrity in a chimera (Kallen et al., *J. Biol. Chem.* 274:11859-11867, 1999). Therefore, the helical domains of zcytor17lig may be useful for preparing chimeric fusion molecules, particularly with other short-helix form cytokines to determine and modulate receptor binding specificity. The present invention also envisions fusion proteins engineered with helix A and/or helix D, and fusion proteins that combine helical and loop domains from other short-form cytokines such as IL-2, IL-4, IL-15, Lif, IL-12, IL-3 and GM-CSF.

The polynucleotide sequence for human IL-2 is shown in SEQ ID NO:176 and the corresponding amino acid sequence is shown in SEQ ID NO:177. The secretory signal sequence is comprised of amino acid residues 1 (Met) to 20 (Ser) of SEQ ID NO:177; nucleotides 48 to 107 of SEQ ID NO:176. The mature polypeptide is comprised of amino acid residues 21 (Ala) to 156 (Thr) of SEQ ID NO:177; nucleotides 108 to 515 of SEQ ID NO:176. Helix A of human IL-2 is comprised of amino acid residues 27 (Thr) to 48 (Leu) of SEQ ID NO:177; nucleotides 126 to 191 of SEQ ID NO:176. Helix B of human IL-2 comprises Helix B1 and Helix B2. Helix B1 of human IL-2 is comprised of amino acid residues 73 (Ala) to 80 (Gln) of SEQ ID NO:177; nucleotides 264 to 287 of SEQ ID NO:176. Helix B2 of human IL-2 is comprised of amino acid residues 83 (Glu) to 92 (Val) of SEQ ID NO:177; nucleotides 294 to 323 of SEQ ID NO:176. Thus, Helix B (comprising Helices B1 and B2) of IL-2 is represented by the amino acid sequence of SEQ ID NO:183 (nucleotide sequence of SEQ ID NO:182) wherein amino acid residues 9 and 10 can be any amino acid. SEQ ID NO:183 is identical to amino acids 73 (Ala) to 92 (Val) of SEQ ID NO:177 wherein amino acids 81 and 82 are any amino acid. In a preferred form, Helix B of IL-2 comprises amino acids 73 (Ala) to 92 (Val) of SEQ ID NO:177; nucleotides 264 to 323 of SEQ ID NO:176. Helix C of human IL-2 is comprised of amino acid residues 102 (His) to 116 (Val) of SEQ ID NO:177 nucleotides 351 to 395 of SEQ ID NO:176. Helix D of human IL-2 is comprised of amino acid residues 134 (Thr) to 149 (Gln) of SEQ ID NO:177; nucleotides 447 to 494 of SEQ ID NO:176.

The polynucleotide sequence for human IL-4 is shown in SEQ ID NO:178 and the corresponding amino acid sequence is shown in SEQ ID NO:179. The secretory signal sequence is comprised of amino acid residues 1 (Met) to 24 (Gly) of SEQ ID NO:179; nucleotides 64 to 135 of SEQ ID NO:178. The mature polypeptide is comprised of amino acid residues 25 (His) to 153 (Ser) of SEQ ID NO:179; nucleotides 136 to 522 of SEQ ID NO:178. Helix A of human IL-4 is comprised of amino acid residues 30 (Thr) to 42 (Thr) of SEQ ID NO:179; nucleotides 151 to 189 of SEQ ID NO:178. Helix B of human IL-4 is comprised of amino acid residues 65 (Glu) to 83 (His) of SEQ ID NO:179; nucleotides 256 to 312 of SEQ ID NO:178. Helix C of human IL-4 is comprised of amino acid residues 94 (Ala) to 118 (Ala) of SEQ ID NO:179; nucleotides 343 to 417 of SEQ ID NO:178. Helix D of human IL-4 is comprised of amino acid residues 133 (Leu) to 151 (Cys) of SEQ ID NO:179; nucleotides 460 to 516 of SEQ ID NO:178.

The polynucleotide sequence for human GM-CSF is shown in SEQ ID NO:180 and the corresponding amino acid sequence is shown in SEQ ID NO:181. The secretory signal sequence is comprised of amino acid residues 1 (Met) to 17 (Ser) of SEQ ID NO:181; nucleotides 9 to 59 of SEQ ID NO:180. The mature polypeptide is comprised of amino acid residues 18 (Ala) to 144 (Glu) of SEQ ID NO:181; nucleotides 60 to 440 of SEQ ID NO:180. Helix A of human GM-CSF is comprised of amino acid residues 30 (Trp) to 44 (Asn) of SEQ ID NO:181; nucleotides 96 to 140 of SEQ ID NO:180. Helix B of human GM-CSF is comprised of amino acid residues 72 (Leu) to 81 (Gln) of SEQ ID NO:181; nucleotides 222 to 251 of SEQ ID NO:180. Helix C of human GM-CSF is comprised of amino acid residues 85 (Gly) to 103 (Gln) of SEQ ID NO:181; nucleotides 261 to 317 of SEQ ID NO:180. Helix D of human GM-CSF is comprised of amino acid residues 120 (Phe) to 131 (Leu) of SEQ ID NO:181; nucleotides 366 to 401 of SEQ ID NO:180.

The amino acid residues comprising helices A, B, C, and D, for human zcytor17lig, IL-3, IL-2, IL-4, and GM-CSF are shown in Table 1.

TABLE 1

|  | Helix A | Helix B | Helix C | Helix D |
|---|---|---|---|---|
| zcytor17lig | 38-52 | 83-98 | 104-117 | 137-152 of SEQ ID NO: 2 |
| IL-3 | 35-45 | 73-86 | 91-103 | 123-141 of SEQ ID NO: 102 |
| IL-2 | 27-48 | 73-92 | 102-116 | 134-149 of SEQ ID NO: 177 or Helix B as described in SEQ ID NO: 183 |
| IL-4 | 30-42 | 65-83 | 94-118 | 133-151 of SEQ ID NO: 179 |
| GM-CSF | 30-44 | 72-81 | 85-103 | 120-131 of SEQ ID NO: 181 |

The present invention provides polynucleotide molecules, including DNA and RNA molecules that encode the zcytor17 polypeptides disclosed herein that can be included in the multimeric cytokine receptor. Those skilled in the art will recognize that, in view of the degeneracy of the genetic code, considerable sequence variation is possible among these polynucleotide molecules. SEQ ID NO:120, SEQ ID NO:121 and SEQ ID NO:122 are degenerate DNA sequences that encompass all DNAs that encode the zcytor17 polypeptide of SEQ ID NO:111, SEQ ID NO:109 and SEQ ID NO:5, respectively, and fragments thereof. Those skilled in the art will recognize that the degenerate sequences of SEQ ID NO:120, SEQ ID NO:121 and SEQ ID NO:122 also provide all RNA sequences encoding SEQ ID NO:111, SEQ ID NO:109 and SEQ ID NO:5 by substituting U for T. Thus, zcytor17 polypeptide-encoding polynucleotides comprising nucleotide 1 to nucleotide 2196 of SEQ ID NO:120, nucleotide 1 to nucleotide 1947 of SEQ ID NO:121, and nucleotide 1 to nucleotide 1986 of SEQ ID NO:122 and their RNA equivalents are contemplated by the present invention. Table 2 sets forth the one-letter codes used within SEQ ID NO:120, SEQ ID NO:121 and SEQ ID NO:122 to denote degenerate nucleotide positions. "Resolutions" are the nucleotides denoted by a code letter. "Complement" indicates the code for the complementary nucleotide(s). For example, the code Y denotes either C or T, and its complement R denotes A or G, A being complementary to T, and G being complementary to C.

TABLE 2

| Nucleotide | Resolution | Complement | Resolution |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |

TABLE 2-continued

| Nucleotide | Resolution | Complement | Resolution |
|---|---|---|---|
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NO:120, SEQ ID NO:121 and SEQ ID NO:122, encompassing all possible codons for a given amino acid, are set forth in Table 3.

TABLE 3

| Amino Acid | One Letter Code | Codons | Degenerate Codon |
|---|---|---|---|
| Cys | C | TGC TGT | TGY |
| Ser | S | AGC AGT TCA TCC TCG TCT | WSN |
| Thr | T | ACA ACC ACG ACT | ACN |
| Pro | P | CCA CCC CCG CCT | CCN |
| Ala | A | GCA GCC GCG GCT | GCN |
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Ter | . | TAA TAG TGA | TRR |
| Asn\|Asp | B |  | RAY |
| Glu\|Gln | Z |  | SAR |
| Any | X |  | NNN |

One of ordinary skill in the art will appreciate that some ambiguity is introduced in determining a degenerate codon, representative of all possible codons encoding each amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequences of SEQ ID NO:111, SEQ ID NO:109 and SEQ ID NO:5; or SEQ ID NO:117 and SEQ ID NO:119. Variant sequences can be readily tested for functionality as described herein.

One of ordinary skill in the art will also appreciate that different species can exhibit "preferential codon usage." In general, see, Grantham, et al., *Nuc. Acids Res.* 8:1893-912, 1980; Haas, et al. *Curr. Biol.* 6:315-24, 1996; Wain-Hobson et al., *Gene* 13:355-64, 1981; Grosjean and Fiers, *Gene* 18:199-209, 1982; Holm, *Nuc. Acids Res.* 14:3075-87, 1986; Ikemura, *J. Mol. Biol.* 158:573-97, 1982. As used herein, the term "preferential codon usage" or "preferential codons" is a term of art referring to protein translation codons that are most frequently used in cells of a certain species, thus favoring one or a few representatives of the possible codons encoding each amino acid (See Table 3). For example, the amino acid Threonine (Thr) may be encoded by ACA, ACC, ACG, or ACT, but in mammalian cells ACC is the most commonly used codon; in other species, for example, insect cells, yeast, viruses or bacteria, different Thr codons may be preferential. Preferential codons for a particular species can be introduced into the polynucleotides of the present invention by a variety of methods known in the art. Introduction of preferential codon sequences into recombinant DNA can, for example, enhance production of the protein by making protein translation more efficient within a particular cell type or species. Therefore, the degenerate codon sequences disclosed in SEQ ID NO:120, SEQ ID NO:121 and SEQ ID NO:122 serve as templates for optimizing expression of zcytor17 polynucleotides in various cell types and species commonly used in the art and disclosed herein. Sequences containing preferential codons can be tested and optimized for expression in various species, and tested for functionality as disclosed herein.

As previously noted, the isolated polynucleotides of the present invention include DNA and RNA. Methods for preparing DNA and RNA are well known in the art. In general, RNA is isolated from a tissue or cell that produces large amounts of zcytor17 RNA. Such tissues and cells are identified by Northern blotting (Thomas, *Proc. Natl. Acad. Sci. USA* 77:5201, 1980), and include PBLs, spleen, thymus, bone marrow, prostate, and lymph tissues, human erythroleukemia cell lines, acute monocytic leukemia cell lines, other lymphoid and hematopoietic cell lines, and the like. Total RNA can be prepared using guanidinium isothiocyanate extraction followed by isolation by centrifugation in a CsCl gradient (Chirgwin et al., *Biochemistry* 18:52-94, 1979). Poly (A)$^+$ RNA is prepared from total RNA using the method of Aviv and Leder (*Proc. Natl. Acad. Sci. USA* 69:1408-12, 1972). Complementary DNA (cDNA) is prepared from poly(A)$^+$ RNA using known methods. In the alternative, genomic DNA can be isolated. Polynucleotides encoding zcytor17 polypeptides are then identified and isolated by, for example, hybridization or polymerase chain reaction (PCR) (Mullis, U.S. Pat. No. 4,683,202).

A full-length clone encoding zcytor17 can be obtained by conventional cloning procedures. Complementary DNA (cDNA) clones are preferred, although for some applications (e.g., expression in transgenic animals) it may be preferable to use a genomic clone, or to modify a cDNA clone to include at least one genomic intron. Methods for preparing cDNA and genomic clones are well known and within the level of ordinary skill in the art, and include the use of the sequence disclosed herein, or parts thereof, for probing or priming a library. Expression libraries can be probed with antibodies to zcytor17, receptor fragments, or other specific binding partners.

The polynucleotides of the present invention can also be synthesized using DNA synthesis machines. Currently the method of choice is the phosphoramidite method. If chemically synthesized double stranded DNA is required for an application such as the synthesis of a gene or a gene fragment, then each complementary strand is made separately. The production of short polynucleotides (60 to 80 bp) is technically straightforward and can be accomplished by synthesizing the complementary strands and then annealing them. However, for producing longer polynucleotides (>300 bp), special strategies are usually employed, because the coupling efficiency of each cycle during chemical DNA synthesis is seldom 100%. To overcome this problem, synthetic genes (double-stranded) are assembled in modular form from single-stranded fragments that are from 20 to 100 nucleotides in length.

An alternative way to prepare a full-length gene is to synthesize a specified set of overlapping oligonucleotides (40 to 100 nucleotides). After the 3' and 5' short overlapping complementary regions (6 to 10 nucleotides) are annealed, large gaps still remain, but the short base-paired regions are both long enough and stable enough to hold the structure together. The gaps are filled and the DNA duplex is completed via enzymatic DNA synthesis by *E. coli* DNA polymerase I. After the enzymatic synthesis is completed, the nicks are sealed with T4 DNA ligase. Double-stranded constructs are sequentially linked to one another to form the entire gene sequence which is verified by DNA sequence analysis. See Glick and Pasternak, *Molecular Biotechnology, Principles & Applications of Recombinant DNA*, (ASM Press, Washington, D.C. 1994); Itakura et al., *Annu. Rev. Biochem.* 53: 323-56, 1984 and Climie et al., *Proc. Natl. Acad. Sci. USA* 87:633-7, 1990. Moreover, other sequences are generally added that contain signals for proper initiation and termination of transcription and translation.

The present invention also provides reagents which will find use in diagnostic applications. For example, the zcytor17lig gene, a probe comprising zcytor17lig DNA or RNA or a subsequence thereof, can be used to determine if the zcytor17lig gene is present on a human chromosome, such as chromosome 12, or if a gene mutation has occurred. Zcytor17lig is located at the 12q24.31 region of chromosome 12 (Example 13). Detectable chromosomal aberrations at the zcytor17lig gene locus include, but are not limited to, aneuploidy, gene copy number changes, loss of heterozygosity (LOH), translocations, insertions, deletions, restriction site changes and rearrangements. Such aberrations can be detected using polynucleotides of the present invention by employing molecular genetic techniques, such as restriction fragment length polymorphism (RFLP) analysis, short tandem repeat (STR) analysis employing PCR techniques, and other genetic linkage analysis techniques known in the art (Sambrook et al., ibid.; Ausubel et. al., ibid.; Marian, *Chest* 108:255-65, 1995).

The precise knowledge of a gene's position can be useful for a number of purposes, including: 1) determining if a sequence is part of an existing contig and obtaining additional surrounding genetic sequences in various forms, such as YACs, BACs or cDNA clones; 2) providing a possible candidate gene for an inheritable disease which shows linkage to the same chromosomal region; and 3) cross-referencing model organisms, such as mouse, which may aid in determining what function a particular gene might have.

One of skill in the art would recognize that the 12q24 region is frequently involved in gross genomic rearrangements, including translocations, deletions, inversions, and duplications, that are associated with various cancers. The Mitelman Database of Chromosomal Aberrations in Cancer, at the Cancer Genome Anatomy Project, National Institutes of Health, Bethesda, Md. located on the Internet lists 199 cases of cancers with genomic rearrangements involving 12q24. Of these, most are part of complex karyotypes with other rearrangements; however, in some cases the rearrangement involving 12q24 is the only genomic alteration. Given the expression of the receptor for zcytor17lig on cells of lymphoid and myeloid lineages, it is particularly significant to note that there are at least 4 cases of myeloid leukemia reported in the literature in which either translocation (2 cases: Yamagata et al, *Cancer Genet Cytogenet* 97:90-93, 1997; Dunphy and Batanian, *Cancer Genet Cytogenet* 114: 51-57, 1999) or duplication (2 cases: Bonomi et al, *Cancer Genet Cytogenet* 108:75-78, 1999) are the sole genomic alteration. This suggests that a gene or genes residing within 12q24 could be directly involved in the malignant transformation of these patients' cells. Inappropriate over expression of zcytor17lig could contribute to malignant transformation by promoting aberrant proliferation of receptor-bearing cells, through either autocrine or paracrine mechanisms Inhibition of zcytor17lig activity could thus inhibit growth of such cells. Alternatively, a genomic rearrangement resulting in inactivation of the zcytor17lig gene may promote malignant transformation and/or metastasis by removing zcytor17lig immunoregulatory functions. Indeed, a gene suppressing metastasis in prostate cancer has been mapped to 12q24-qter (Ichikawa et al, *Asian J Androl* 2:167-171, 2000). If zcytor17lig is the gene within this region responsible for the suppression of metastasis, then zcytor17lig itself may have therapeutic value in the treatment of cancer.

A diagnostic could assist physicians in determining the type of disease and appropriate associated therapy, or assistance in genetic counseling. As such, the inventive anti-zcytor17lig antibodies, polynucleotides, and polypeptides can be used for the detection of zcytor17lig polypeptide, mRNA or anti-zcytor17lig antibodies, thus serving as markers and be directly used for detecting or genetic diseases or cancers, as described herein, using methods known in the art and described herein. Further, zcytor17lig polynucleotide probes can be used to detect abnormalities or genotypes associated with chromosome 12q24.3 deletions and translocations associated with human diseases, or other translocations involved with malignant progression of tumors or other 12q24.3 mutations, which are expected to be involved in chromosome rearrangements in malignancy; or in other cancers. Similarly, zcytor17lig polynucleotide probes can be used to detect abnormalities or genotypes associated with chromosome 12 trisomy and chromosome loss associated with human diseases or spontaneous abortion. Thus, zcytor17lig polynucleotide probes can be used to detect abnormalities or genotypes associated with these defects.

One of skill in the art would recognize that zcytor17lig polynucleotide probes are particularly useful for diagnosis of gross chromosomal abnormalities associated with loss of heterogeneity (LOH), chromosome gain (e.g., trisomy), translocation, DNA amplification, and the like. Translocations within chromosomal locus 12q24.3 wherein the zcytor17lig gene is located are known to be associated with human disease. For example, 12q24 deletions and translocations, duplications and trisomy are associated with cancers as discussed above. Thus, since the zcytor17lig gene maps to this critical region, zcytor17lig polynucleotide probes of the present invention can be used to detect abnormalities or genotypes associated with 12q24 translocation, deletion and trisomy, and the like, described above.

As discussed above, defects in the zcytor17lig gene itself may result in a heritable human disease state. Molecules of the present invention, such as the polypeptides, antagonists, agonists, polynucleotides and antibodies of the present invention would aid in the detection, diagnosis prevention, and treatment associated with a zcytor17lig genetic defect. In addition, zcytor17lig polynucleotide probes can be used to detect allelic differences between diseased or non-diseased individuals at the zcytor17lig chromosomal locus. As such, the zcytor17lig sequences can be used as diagnostics in forensic DNA profiling.

In general, the diagnostic methods used in genetic linkage analysis, to detect a genetic abnormality or aberration in a patient, are known in the art. Analytical probes will be generally at least 20 nt in length, although somewhat shorter probes can be used (e.g., 14-17 nt). PCR primers are at least 5 nt in length, preferably 15 or more, more preferably 20-30 nt. For gross analysis of genes, or chromosomal DNA, a zcytor17lig polynucleotide probe may comprise an entire exon or more. Exons are readily determined by one of skill in the art by comparing zcytor17lig sequences (SEQ ID NO:1) with the genomic DNA for mouse zcytor17lig (SEQ ID NO:76). In general, the diagnostic methods used in genetic linkage analysis, to detect a genetic abnormality or aberration in a patient, are known in the art. Most diagnostic methods comprise the steps of (a) obtaining a genetic sample from a potentially diseased patient, diseased patient or potential non-diseased carrier of a recessive disease allele; (b) producing a first reaction product by incubating the genetic sample with a zcytor17lig polynucleotide probe wherein the polynucleotide will hybridize to complementary polynucleotide sequence, such as in RFLP analysis or by incubating the genetic sample with sense and antisense primers in a PCR reaction under appropriate PCR reaction conditions; (iii) visualizing the first reaction product by gel electrophoresis and/or other known methods such as visualizing the first reaction product with a zcytor17lig polynucleotide probe wherein the polynucleotide will hybridize to the complementary polynucleotide sequence of the first reaction; and (iv) comparing the visualized first reaction product to a second control reaction product of a genetic sample from wild type patient, or a normal or control individual. A difference between the first reaction product and the control reaction product is indicative of a genetic abnormality in the diseased or potentially diseased patient, or the presence of a heterozygous recessive carrier phenotype for a non-diseased patient, or the presence of a genetic defect in a tumor from a diseased patient, or the presence of a genetic abnormality in a fetus or pre-implantation embryo. For example, a difference in restriction fragment pattern, length of PCR products, length of repetitive sequences at the zcytor17lig genetic locus, and the like, are indicative of a genetic abnormality, genetic aberration, or allelic difference in comparison to the normal wild type control. Controls can be from unaffected family members, or unrelated individuals, depending on the test and availability of samples. Genetic samples for use within the present invention include genomic DNA, mRNA, and cDNA isolated from any tissue or other biological sample from a patient, which includes, but is not limited to, blood, saliva, semen, embryonic cells, amniotic fluid, and the like. The polynucleotide probe or primer can be RNA or DNA, and will comprise a portion of SEQ ID NO:1, the complement of SEQ ID NO:1, or an RNA equivalent thereof. Such methods of showing genetic linkage analysis to human disease phenotypes are well known in the art. For reference to PCR based methods in diagnostics see generally, Mathew (ed.), *Protocols in Human Molecular Genetics* (Humana Press, Inc. 1991), White (ed.), *PCR Protocols: Current Methods and Applications* (Humana Press, Inc. 1993), Cotter (ed.), *Molecular Diagnosis of Cancer* (Humana Press, Inc. 1996), Hanausek and Walaszek (eds.), *Tumor Marker Protocols* (Humana Press, Inc. 1998), Lo (ed.), *Clinical Applications of PCR* (Humana Press, Inc. 1998), and Meltzer (ed.), *PCR in Bioanalysis* (Humana Press, Inc. 1998).

Mutations associated with the zcytor17lig locus can be detected using nucleic acid molecules of the present invention by employing standard methods for direct mutation analysis, such as restriction fragment length polymorphism analysis, short tandem repeat analysis employing PCR techniques, amplification-refractory mutation system analysis, single-strand conformation polymorphism detection, RNase cleavage methods, denaturing gradient gel electrophoresis, fluorescence-assisted mismatch analysis, and other genetic analysis techniques known in the art (see, for example, Mathew (ed.), *Protocols in Human Molecular Genetics* (Humana Press, Inc. 1991), Marian, *Chest* 108:255 (1995), Coleman and Tsongalis, *Molecular Diagnostics* (Human Press, Inc. 1996), Elles (ed.) *Molecular Diagnosis of Genetic Diseases* (Humana Press, Inc. 1996), Landegren (ed.), *Laboratory Protocols for Mutation Detection* (Oxford University Press 1996), Birren et al. (eds.), *Genome Analysis, Vol. 2: Detecting Genes* (Cold Spring Harbor Laboratory Press 1998), Dracopoli et al. (eds.), *Current Protocols in Human Genetics* (John Wiley & Sons 1998), and Richards and Ward, "Molecular Diagnostic Testing," in *Principles of Molecular Medicine*, pages 83-88 (Humana Press, Inc. 1998). Direct analysis of an zcytor17lig gene for a mutation can be performed using a subject's genomic DNA. Methods for amplifying genomic DNA, obtained for example from peripheral blood lymphocytes, are well-known to those of skill in the art (see, for example, Dracopoli et al. (eds.), *Current Protocols in Human Genetics*, at pages 7.1.6 to 7.1.7 (John Wiley & Sons 1998)).

The present invention further provides counterpart polypeptides and polynucleotides from other species (orthologs). These species include, but are not limited to mammalian, avian, amphibian, reptile, fish, insect and other vertebrate and invertebrate species. Of particular interest are zcytor17 polypeptides from other mammalian species, including murine, porcine, ovine, bovine, canine, feline, equine, and other primate polypeptides. Orthologs of human zcytor17 can be cloned using information and compositions provided by the present invention in combination with conventional cloning techniques. For example, a cDNA can be cloned using mRNA obtained from a tissue or cell type that expresses zcytor17 as disclosed herein. Suitable sources of mRNA can be identified by probing Northern blots with probes designed from the sequences disclosed herein. A library is then prepared from mRNA of a positive tissue or cell line. A zcytor17-encoding cDNA can then be isolated by a variety of methods, such as by probing with a complete or partial human cDNA or with one or more sets of degenerate probes based on the disclosed sequences. A cDNA can also be cloned using PCR (Mullis, supra.), using primers designed from the representative human zcytor17 sequence disclosed herein. Within an additional method, the cDNA library can be used to transform or transfect host cells, and expression of the cDNA of interest can be detected with an antibody to zcytor17 polypeptide. Similar techniques can also be applied to the isolation of genomic clones.

A polynucleotide sequence for the mouse ortholog of human zcytor17 has been identified and is shown in SEQ ID NO:116 and the corresponding amino acid sequence shown in SEQ ID NO:117. Analysis of the mouse zcytor17 polypeptide encoded by the DNA sequence of SEQ ID NO:116 revealed an open reading frame encoding 662 amino acids (SEQ ID NO:117) comprising a predicted secretory signal peptide of 45 amino acid residues (residue 1 (Met) to residue 45 (Ala) of SEQ ID NO:117), and a mature polypeptide of 617 amino acids (residue 46 (Val) to residue 662 (Cys) of SEQ ID NO:117). Moreover, an additional Met residue, Met (28) can be used as a starting methionine; comprising a second predicted secretory signal peptide of 18 amino acid residues (residue 28 (Met) to residue 45 (Ala) of SEQ ID NO:117), and the same mature polypeptide of 617 amino acids (residue 46 (Val) to residue 662 (Cys) of SEQ ID NO:117. In addition to the WSXWS motif (SEQ ID NO:3) corresponding to residues 224-228 of SEQ ID NO:117, the receptor comprises an extracellular domain from residues 46 (Val) to 533 (Glu) of SEQ ID NO:117) that includes a cytokine-binding domain of approximately 200 amino acid residues (residues 46 (Val) to 240 (Pro) of SEQ ID NO:117) and a fibronectin III domain (residues 241 (His) to 533 (Glu) of SEQ ID NO:117); a CXW motif (residues 66 (Cys) to 68 (Trp) of SEQ ID NO:117); a domain linker (residues 142 (Thr) to 145 (Pro) of SEQ ID NO:117); a penultimate strand region (residues 207 (Phe) to 215 (Arg) of SEQ ID NO:117); a transmembrane domain (residues 534 (Ile) to 550 (Ile) of SEQ ID NO:117); complete intracellular signaling domain (residues 551 (Lys) to 662 (Cys) of SEQ ID NO:117) which contains a "Box I" signaling site (residues 568 (Cys) to 574 (Pro) of SEQ ID NO:117), and a "Box II" signaling site (residues 628 (Glu) to 631 (leu) of SEQ ID NO:117). Conserved residues common to class I cytokine receptors, are at residues 56 (Cys), 187 (Trp), and 215 (Arg). A comparison of the human and mouse amino acid sequences reveals that both the human and orthologous polypeptides contain corresponding structural features described above (and, see, FIG. 2). The mature sequence for the mouse zcytor17 begins at $Val_{46}$ (as shown in SEQ ID NO:117), which corresponds to $Ala_{33}$ (as shown in SEQ ID NO:5) in the human sequence. There is about 61% identity between the mouse and human sequences over the entire amino acid sequence corresponding to SEQ ID NO:5 and SEQ ID NO:117. The above percent identity was determined using a FASTA program with ktup=1, gap opening penalty=12, gap extension penalty=2, and substitution matrix=BLOSUM62, with other parameters set as default. The corresponding polynucleotides encoding the mouse zcytor17 polypeptide regions, domains, motifs, residues and sequences described above are as shown in SEQ ID NO:116.

Moreover, a truncated soluble form of the mouse zcytor17 receptor polypeptide appears to be naturally expressed. A polynucleotide sequence for a truncated soluble form of the mouse zcytor17 receptor has been identified and is shown in SEQ ID NO:118 and the corresponding amino acid sequence shown in SEQ ID NO:119. Analysis of the truncated soluble mouse zcytor17 polypeptide encoded by the DNA sequence of SEQ ID NO:118 revealed an open reading frame encoding 547 amino acids (SEQ ID NO:119) comprising a predicted secretory signal peptide of 45 amino acid residues (residue 1 (Met) to residue 45 (Ala) of SEQ ID NO:119), and a mature polypeptide of 502 amino acids (residue 46 (Val) to residue 547 (Val) of SEQ ID NO:119). Moreover, an additional Met residue, Met (28) can be used as a starting methionine; comprising a second predicted secretory signal peptide of 18 amino acid residues (residue 28 (Met) to residue 45 (Ala) of SEQ ID NO:119), and the same mature polypeptide of 502 amino acids (residue 46 (Val) to residue 547 (Val) of SEQ ID NO:119. In addition to the WSXWS motif (SEQ ID NO:3) corresponding to residues 224-228 of SEQ ID NO:119, the receptor comprises an extracellular domain from residues 46 (Val) to 533 (Trp) of SEQ ID NO:119) that includes a cytokine-binding domain of approximately 200 amino acid residues (residues 46 (Val) to 240 (Pro) of SEQ ID NO:119) and a fibronectin III domain (residues 241 (His) to 533 (Trp) of SEQ ID NO:119); a CXW motif (residues 66 (Cys) to 68 (Trp) of SEQ ID NO:119); a domain linker (residues 142 (Thr) to 145 (Pro) of SEQ ID NO:119); a penultimate strand region (residues 207 (Phe) to 215 (Arg) of SEQ ID NO:119); and a C-terminal tail region (residues 534 (Leu) to 547 (Val). Conserved residues common to class I cytokine receptors, are at residues 56 (Cys), 187 (Trp), and 215 (Arg). A comparison of the human and mouse amino acid sequences, including the truncated soluble mouse zcytor17, reveals that both the human and orthologous polypeptides contain corresponding structural features described above (and, see, FIG. 2). The corresponding polynucleotides encoding the truncated soluble mouse zcytor17 polypeptide regions, domains, motifs, residues and sequences described above are as shown in SEQ ID NO:118.

Those skilled in the art will recognize that the sequences disclosed in SEQ ID NO:110, SEQ ID NO:108 and SEQ ID NO:4 represent alleles of human zcytor17 and that allelic variation and alternative splicing are expected to occur. Allelic variants of this sequence can be cloned by probing cDNA or genomic libraries from different individuals according to standard procedures. Allelic variants of the DNA sequence shown in SEQ ID NO:110, SEQ ID NO:108 or SEQ ID NO:4, including those containing silent mutations and those in which mutations result in amino acid sequence changes, are within the scope of the present invention, as are proteins which are allelic variants of SEQ ID NO:111, SEQ ID NO:109, SEQ ID NO:5 SEQ ID NO:117 or SEQ ID NO:119. cDNAs generated from alternatively spliced mRNAs, which retain the properties of the zcytor17 polypeptide are included within the scope of the present invention, as are polypeptides encoded by such cDNAs and mRNAs. Allelic variants and splice variants of these sequences can be cloned by probing cDNA or genomic libraries from different individuals or tissues according to standard procedures known in the art. For example, the short-form and long-form soluble zcytor17 receptors described above, and in SEQ ID NO:112 and SEQ ID NO:113 or SEQ ID NO:114 and SEQ ID NO:115 can be considered allelic or splice variants of zcytor17.

The present invention also provides isolated zcytor17 polypeptides that are substantially similar to the polypeptides of SEQ ID NO:111, SEQ ID NO:109 or SEQ ID NO:5 and their orthologs, e.g., SEQ ID NO:117 and SEQ ID NO:119. The term "substantially similar" is used herein to denote polypeptides having at least 50%, at least 60%, at least 70%, at least 80%, at least 90%, at least 91%, at least 92%, at least 93%, at least 94%, at least 95%, at least 96%, at least 97%, at least 98%, at least 99%, or greater than 99% sequence identity to the sequences shown in SEQ ID NO:111, SEQ ID NO:109 or SEQ ID NO:5 or their orthologs, e.g., SEQ ID NO:117 and SEQ ID NO:119. Such polypeptides will more preferably be at least 90% identical, and most preferably 95% or more identical to SEQ ID NO:111, SEQ ID NO:109 and SEQ ID NO:5 or its orthologs.) Percent sequence identity is determined by conventional methods. See, for example, Altschul et al., *Bull. Math. Bio.* 48: 603-616, 1986 and Henikoff and Henikoff, *Proc. Natl. Acad. Sci. USA* 89:10915-10919, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown in Table 4 (amino acids are indicated by the standard one-letter codes). The percent identity is then calculated as:

$$\frac{\text{Total number of identical matches}}{[\text{length of the longer sequence plus the number of gaps introduced into the longer sequence in order to align the two sequences}]} \times 100$$

TABLE 4

| | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | -2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

Sequence identity of polynucleotide molecules is determined by similar methods using a ratio as disclosed above.

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of a putative variant zcytor17. The FASTA algorithm is described by Pearson and Lipman, *Proc. Nat'l Acad. Sci. USA* 85:2444 (1988), and by Pearson, *Meth. Enzymol.* 183:63 (1990).

Briefly, FASTA first characterizes sequence similarity by identifying regions shared by the query sequence (e.g., SEQ ID NO:111, SEQ ID NO:109, SEQ ID NO:5, SEQ ID NO:117 and SEQ ID NO:119) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, *J. Mol. Biol.* 48:444 (1970); Sellers, *SIAM J. Appl. Math.* 26:787 (1974)), which allows for amino acid insertions and deletions. Preferred parameters for FASTA analysis are: ktup=1, gap opening penalty=10, gap extension penalty=1, and substitution matrix=BLOSUM62, with other parameters set as default. These parameters can be introduced into a FASTA program by modifying the scoring matrix file ("SMATRIX"), as explained in Appendix 2 of Pearson, *Meth. Enzymol.* 183:63 (1990).

FASTA can also be used to determine the sequence identity of nucleic acid molecules using a ratio as disclosed above. For nucleotide sequence comparisons, the ktup value can range between one to six, preferably from three to six, most preferably three, with other FASTA program parameters set as default.

The BLOSUM62 table (Table 4) is an amino acid substitution matrix derived from about 2,000 local multiple alignments of protein sequence segments, representing highly conserved regions of more than 500 groups of related proteins (Henikoff and Henikoff, *Proc. Nat'l Acad. Sci. USA* 89:10915 (1992)). Accordingly, the BLOSUM62 substitution frequencies can be used to define conservative amino acid substitutions that may be introduced into the amino acid sequences of the present invention. Although it is possible to design amino acid substitutions based solely upon chemical properties (as discussed below), the language "conservative amino acid substitution" preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

Variant zcytor17 polypeptides or substantially homologous zcytor17 polypeptides are characterized as having one or more amino acid substitutions, deletions or additions. These changes are preferably of a minor nature, that is conservative amino acid substitutions (see Table 5) and other substitutions that do not significantly affect the folding or activity of the polypeptide; small deletions, typically of one to about 30 amino acids; and small amino- or carboxyl-terminal extensions, such as an amino-terminal methionine residue, a small linker peptide of up to about 20-25 residues, or an affinity tag. The present invention thus includes polypeptides that comprise a sequence that is at least 80%, preferably at least 90%, and more preferably 95% or more identical to the corresponding region of SEQ ID NO:111, SEQ ID NO:109, SEQ ID NO:5, SEQ ID NO:117 or SEQ ID NO:119 excluding the tags, extension, linker sequences and the like. Polypeptides comprising affinity tags can further comprise a proteolytic cleavage site between the zcytor17 polypeptide and the affinity tag. Suitable sites include thrombin cleavage sites and factor Xa cleavage sites.

TABLE 5

| Conservative amino acid substitutions | |
|---|---|
| Basic: | arginine |
|  | lysine |
|  | histidine |
| Acidic: | glutamic acid |
|  | aspartic acid |
| Polar: | glutamine |
|  | asparagine |
| Hydrophobic: | leucine |
|  | isoleucine |
|  | valine |
| Aromatic: | phenylalanine |
|  | tryptophan |
|  | tyrosine |
| Small: | glycine |
|  | alanine |
|  | serine |
|  | threonine |
|  | methionine |

The present invention provides an isolated an isolated multimeric cytokine receptor comprising a polypeptide having at least 90 percent sequence identity with SEQ ID NO:111, SEQ ID NO:109, or SEQ ID NO:5; and at least a portion of at least one class I cytokine receptor, wherein the multimeric cytokine receptor binds to at least a portion of SEQ ID NO:2. The polypeptide having at least 90 percent sequence identity with SEQ ID NO:111 may include, for instance, amino acid residue 20 to amino acid residue 227 of SEQ ID NO:111, amino acid residue 20 to amino acid residue 227 of SEQ ID NO:519, amino acid residue 20 to amino acid residue 543 of SEQ ID NO:111, amino acid residue 544 to amino acid residue 732 of SEQ ID NO:111, amino acid residue 544 to amino acid residue 649 of SEQ ID NO:109, amino acid residue 20 to amino acid residue 732 of SEQ ID NO:111, amino acid residue 20 to amino acid residue 649 of SEQ ID NO:109, and combinations thereof. The at least a portion of at least one class I cytokine receptor includes, for example, OSMRbeta (SEQ ID NO:7) and/or WSX-1 (SEQ ID NO:9). For example, the at least a portion of at least one class I cytokine receptor comprising at least a portion of SEQ ID NO:7 may comprise amino acid residue 28 to amino acid residue 429 of SEQ ID NO:7, amino acid residue 35 to amino acid residue 137 of SEQ ID NO:7, amino acid residue 240 to amino acid residue 342 of SEQ ID NO:7, amino acid residue 348 to amino acid residue 429 of SEQ ID NO:7, amino acid residue 28 to amino acid residue 739 of SEQ ID NO:7, amino acid residue 28 to amino acid residue 761 of SEQ ID NO:7, amino acid residue 762 to amino acid residue 979 of SEQ ID NO:7, and/or combinations thereof. The multimeric cytokine receptor may be a heterodimer, trimer, tetramer, pentamer, or the like. In addition, the multimeric cytokine receptor may be soluble, immobilized on a solid support, or membrane-bound. Optionally, the multimeric cytokine receptor may antagonize an activity of SEQ ID NO:2, such as inhibit or reduce the proliferation of hematopoietic, immune, and/or inflammatory cells, or inhibit or reduce the enhancement of the hematopoietic, immune, and/or inflammatory process, or inhibit or reduce the differentiation of hematopoietic cells, for instance lymphoid cells such as monocytic cells, macrophages and/or T cells. The multimeric cytokine receptor of the present invention may also comprise an affinity tag selected from the group of polyhistidine, protein A, glutathione S transferase, Glu-Glu, substance P, Flag™ peptide, streptavidin binding peptide, and an immunoglobulin $F_c$ polypeptide.

The present invention also provides for a ligand/receptor complex comprising a polypeptide which includes at least a portion of SEQ ID NO:2; and a soluble multimeric cytokine receptor comprising at least a portion of at least one polypeptide selected from the group of SEQ ID NO:111, SEQ ID NO:109, SEQ ID NO:7, and SEQ ID NO:9, wherein the polypeptide is attached to the soluble multimeric cytokine receptor. The soluble multimeric cytokine receptor may comprise the extracellular domain and/or transmembrane domain of zcytor17 (SEQ ID NO:111), OSMRbeta (SEQ ID NO:7), and/or WSX-1 (SEQ ID NO:9). For example, the soluble multimeric cytokine receptor may comprise amino acid residue 20 to 227 to SEQ ID NO:111, amino acid residue 20 to 519 to SEQ ID NO:111, amino acid residue 20 to 543 to SEQ ID NO:111, amino acid residue 28 to 739 to SEQ ID NO:7, amino acid residue 28 to 429 to SEQ ID NO:7, amino acid residue 35 to 137 to SEQ ID NO:7, amino acid residue 240 to 342 to SEQ ID NO:7, amino acid residue 348 to 429 to SEQ ID NO:7, or combinations thereof. The soluble multimeric cytokine receptor may be a heterodimer, trimer, tetramer, pentamer, or the like. The multimeric cytokine receptor of the present invention may also comprise an affinity tag as described herein. The polypeptide of the ligand/receptor complex may comprise amino acid residues of SEQ ID NO:2 selected from the group of 38 to 152, 27 to 164, 24 to 164, 1 to 164, 38 to 52, 83 to 98, 104 to 117, 137 to 152, and combinations thereof.

The ligand/receptor complex of the present may also comprise a fusion protein. The fusion protein may comprise at least four polypeptides, wherein the order of polypeptides from N-terminus to C-terminus are a first polypeptide comprising amino acid residues 38-52 of SEQ ID NO:2; a first spacer of 6-27 amino acid residues; a second polypeptide comprising amino acid residues selected from the group of (a) IL-2 helix B residues of SEQ ID NO:183; (b) IL-4 helix B residues 65-83 of SEQ ID NO:179; (c) IL-3 helix B residues 73-86 of SEQ ID NO:102; (d) GM-CSF helix B residues 72-81 of SEQ ID NO:181; and (e) amino acid residues 83-98 of SEQ ID NO:2; a second spacer of 5-11 amino acid residues; a third polypeptide comprising amino acid residues selected from the group of (a) IL-2 helix C residues 102-116 of SEQ ID NO:177; (b) IL-4 helix C residues 94-118 of SEQ ID NO:179; (c) IL-3 helix C residues 91-103 of SEQ ID NO:102; (d) GM-CSF helix C residues 85-103 of SEQ ID NO:181; and (e) amino acid residues 104-117 of SEQ ID NO:2; a third spacer of 3-29 amino acid residues; and a fourth polypeptide comprising amino acid residues selected from the group of (a) IL-2 helix D residues 134-149 of SEQ ID NO:177; (b) IL-3 helix D residues 123-141 of SEQ ID NO:102; (c) IL-4 helix D residues 133-151 of SEQ ID NO:179; (d) GM-CSF helix D residues 120-131 of SEQ ID NO:181; and (e) amino acid residues 137-152 of SEQ ID NO:2; and a multimeric cytokine receptor comprising at least a portion of at least one polypeptide selected from the group of SEQ ID NO:111, SEQ ID NO:109, SEQ ID NO:7, and SEQ ID NO:9; wherein the fusion protein is attached to the multimeric cytokine receptor.

Alternatively, the fusion protein may comprise at least four polypeptides, wherein the order of polypeptides from N-terminus to C-terminus are a first polypeptide comprising amino acid residues selected from a group of (a) IL-2 helix A residues 27-48 of SEQ ID NO:177; (b) IL-4 helix A residues 30-42 of SEQ ID NO:179; (c) IL-3 helix A residues 35-45 of SEQ ID NO:102; (d) GM-CSF helix A residues 30-44 of SEQ ID NO:181; and (e) amino acids residues 38-52 of SEQ ID NO:2; a first spacer of 6-27 amino acid residues; a second polypeptide comprising amino acid residues selected from the group of (a) IL-2 helix B residues of SEQ ID NO:183; (b); IL-4 helix B residues 65-83 of SEQ ID NO:179; (c) IL-3 helix B residues 73-86 of SEQ ID NO:102; (d) GM-CSF helix B residues 72-81 of SEQ ID NO:181; and (e) amino acid residues 83-98 of SEQ ID NO:2; a second spacer of 5-11 amino acid residues; a third polypeptide comprising amino acid residues selected from the group of (a) IL-2 helix C residues 102-116 of SEQ ID NO:177; (b) IL-4 helix C residues 94-118 of SEQ ID NO:179; (c) IL-3 helix C residues 91-103 of SEQ ID NO:102; (d) GM-CSF helix C residues 85-103 of SEQ ID NO:181; and (e) amino acid residues 104-117 of SEQ ID NO:2; a third spacer of 3-29 amino acid residues; and a fourth polypeptide comprising amino acid residues from 137-152 of SEQ ID NO:2; and a multimeric cytokine receptor comprising at least a portion of at least one polypeptide selected from the group of SEQ ID NO:111, SEQ ID NO:109, SEQ ID NO:7, and SEQ ID NO:9; wherein the fusion protein is attached to the multimeric cytokine receptor. A multimeric cytokine receptor may comprise at least one of the following polypeptides of SEQ ID NO:111, SEQ ID NO:109, SEQ ID NO:7, SEQ ID NO:9, or the extracellular domains thereof. The ligand/receptor complex can be soluble and may additionally include an affinity tag as described herein.

The present invention also provides an isolated and purified polynucleotide that encodes a polypeptide comprising an amino acid sequence having at least 90 percent sequence identity with SEQ ID NO:111, SEQ ID NO:109, or SEQ ID NO:5, wherein the polypeptide and at least a portion of at least one class I cytokine receptor form a multimeric cytokine receptor, and wherein the multimeric cytokine receptor binds to at least a portion of SEQ ID NO:2. The present invention also provides an isolated and purified polynucleotide that encodes a polypeptide comprising at least a portion of at least one of SEQ ID NO:111, SEQ ID NO:109, or SEQ ID NO:5, wherein the polypeptide and at least a portion of a class I cytokine receptor form a multimeric cytokine receptor, and wherein the multimeric cytokine receptor binds to at least a portion of SEQ ID NO:2. The polynucleotide may encode a polypeptide that is included in a soluble multimeric cytokine receptor and that may also include an affinity tag as described herein. The polypeptide may comprise, for example, amino acid residue 20 to 227 to SEQ ID NO:111, amino acid residue 20 to 519 to SEQ ID NO:111, amino acid residue 20 to 543 to SEQ ID NO:111, and/or combinations thereof. In addition, the at least a portion of at least one class I cytokine receptor may comprise, for example, amino acid residue 28 to 739 to SEQ ID NO:7, amino acid residue 28 to 429 to SEQ ID NO:7, amino acid residue 35 to 137 to SEQ ID NO:7, amino acid residue 240 to 342 to SEQ ID NO:7, amino acid residue 348 to 429 to SEQ ID NO:7, and/or combinations thereof. The soluble multimeric cytokine receptor may be a heterodimer, trimer, tetramer, pentamer, or the like. The at least a portion of SEQ ID NO:2 may include, for instance amino acid residues of SEQ ID NO:2 selected from the group of 38 to 152, 27 to 164, 24 to 164, 1 to 164, 38 to 52, 83 to 98, 104 to 117, 137 to 152, and combinations thereof. Optionally, the multimeric cytokine receptor may antagonize an activity of SEQ ID NO:2 as described herein.

The present invention further provides a variety of other polypeptide fusions and related multimeric proteins comprising one or more polypeptide fusions. For example, a zcytor17 polypeptide can be prepared as a fusion to a dimerizing protein as disclosed in U.S. Pat. Nos. 5,155,027 and 5,567,584. Preferred dimerizing proteins in this regard include immunoglobulin constant region domains. Immunoglobulin-zcytor17 polypeptide fusions can be expressed in genetically engineered cells to produce a variety of multimeric zcytor17 analogs. Auxiliary domains can be fused to zcytor17 polypeptides to target them to specific cells, tissues, or macromolecules (e.g., collagen). A zcytor17 polypeptide can be fused to two or more moieties, such as an affinity tag for purification and a targeting domain. Polypeptide fusions can also comprise one or more cleavage sites, particularly between domains. See, Tuan et al., *Connective Tissue Research* 34:1-9, 1996. For example, one or more domains from zcytor17 soluble receptor can be joined to a soluble cytokine receptor, such as OSMRbeta and/or WSX-1, which may enhance their biological properties or efficiency of production. Additionally, the soluble multimeric cytokine receptor may further include an affinity tag. An affinity tag can be, for example, a tag selected from the group of polyhistidine, protein A, glutathione S transferase, Glu-Glu, substance P, Flag™ peptide, streptavidin binding peptide, and an immunoglobulin $F_c$ polypeptide.

The proteins of the present invention can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents. Proteins are purified by chromatography. See, for example, Robertson et al., *J. Am. Chem. Soc.* 113:2722, 1991; Ellman et al., *Methods Enzymol.* 202:301, 1991; Chung et al., *Science* 259:806-9, 1993; and Chung et al., *Proc. Natl. Acad. Sci. USA* 90:10145-9, 1993). In a second method, translation is carried out in *Xenopus* oocytes by microinjection of mutated mRNA and chemically aminoacylated suppressor tRNAs (Turcatti et al., *J. Biol. Chem.* 271:19991-8, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470-7476, 1994. Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395-403, 1993).

A limited number of non-conservative amino acids, amino acids that are not encoded by the genetic code, non-naturally occurring amino acids, and unnatural amino acids may be substituted for zcytor17 amino acid residues.

Essential amino acids in the polypeptides of the present invention can be identified according to procedures known in the art, such as site-directed mutagenesis or alanine-scanning mutagenesis (Cunningham and Wells, *Science* 244: 1081-5, 1989; Bass et al., *Proc. Natl. Acad. Sci. USA* 88:4498-502, 1991). In the latter technique, single alanine mutations are introduced at every residue in the molecule, and the resultant mutant molecules are tested for biological activity (e.g. ligand binding and signal transduction) as disclosed below to identify amino acid residues that are critical to the activity of the molecule. See also, Hilton et al., *J. Biol. Chem.* 271:4699-4708, 1996. Sites of ligand-receptor, protein-protein or other biological interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., Science 255:306-312, 1992; Smith et al., *J. Mol. Biol.* 224:899-904, 1992; Wlodaver et al., *FEBS Lett.* 309:59-64, 1992. The identities of essential amino acids can also be inferred from analysis of homologies with related receptors.

Determination of amino acid residues that are within regions or domains that are critical to maintaining structural integrity can be determined. Within these regions one can determine specific residues that will be more or less tolerant of change and maintain the overall tertiary structure of the molecule. Methods for analyzing sequence structure include, but are not limited to, alignment of multiple sequences with high amino acid or nucleotide identity and computer analysis using available software (e.g., the Insight II® viewer and homology modeling tools; MSI, San Diego, Calif.), secondary structure propensities, binary patterns, complementary packing and buried polar interactions (Barton, *Current Opin. Struct. Biol.* 5:372-376, 1995 and Cordes et al., *Current Opin. Struct. Biol.* 6:3-10, 1996). In general, when designing modifications to molecules or identifying specific fragments determination of structure will be accompanied by evaluating activity of modified molecules.

Amino acid sequence changes are made in zcytor17 polypeptides so as to minimize disruption of higher order structure essential to biological activity. For example, when the zcytor17 polypeptide comprises one or more helices, changes in amino acid residues will be made so as not to disrupt the helix geometry and other components of the molecule where changes in conformation abate some critical function, for example, binding of the molecule to its binding partners. The effects of amino acid sequence changes can be predicted by, for example, computer modeling as disclosed above or determined by analysis of crystal structure (see, e.g., Lapthorn et al., *Nat. Struct. Biol.* 2:266-268, 1995). Other techniques that are well known in the art compare folding of a variant protein to a standard molecule (e.g., the native protein). For example, comparison of the cysteine pattern in a variant and standard molecules can be made. Mass spectrometry and chemical modification using reduction and alkylation provide methods for determining cysteine residues which are associated with disulfide bonds or are free of such associations (Bean et al., *Anal. Biochem.* 201:216-226, 1992; Gray, *Protein Sci.* 2:1732-1748, 1993; and Patterson et al., *Anal. Chem.* 66:3727-3732, 1994). It is generally believed that if a modified molecule does not have the same disulfide bonding pattern as the standard molecule folding would be affected. Another well known and accepted method for measuring folding is circular dichrosism (CD). Measuring and comparing the CD spectra generated by a modified molecule and standard molecule is routine (Johnson, *Proteins* 7:205-214, 1990). Crystallography is another well known method for analyzing folding and structure. Nuclear magnetic resonance (NMR), digestive peptide mapping and epitope mapping are also known methods for analyzing folding and structural similarities between proteins and polypeptides (Schaanan et al., *Science* 257:961-964, 1992).

A Hopp/Woods hydrophilicity profile of the zcytor17 protein sequence as shown in SEQ ID NO:2, SEQ ID NO:46, SEQ ID NO:54, SEQ ID NO:57 and SEQ ID NO:93 can be generated (Hopp et al., *Proc. Natl. Acad. Sci.* 78:3824-3828, 1981; Hopp, *J. Immun. Meth.* 88:1-18, 1986 and Triquier et al., *Protein Engineering* 11:153-169, 1998). See, FIG. 1. The profile is based on a sliding six-residue window. Buried G, S, and T residues and exposed H, Y, and W residues were ignored. For example, in zcytor17, hydrophilic regions include amino acid residues 43 through 48 of SEQ ID NO:2 and SEQ ID NO:46 (residues 56 through 61 of SEQ ID NO:54), amino acid residues 157 through 162 of SEQ ID NO:2 and SEQ ID NO:46 (residues 170 through 175 of SEQ ID NO:54), amino acid residues 158 through 163 of SEQ ID NO:2 and SEQ ID NO:46 (residues 171 through 176 of SEQ ID NO:54), amino acid residues 221 through 226 of SEQ ID NO:2 and SEQ ID NO:46 (residues 234 through 239 of SEQ ID NO:54), and amino acid residues 426 through 431 of SEQ ID NO:2 and SEQ ID NO:46 (residues 439 through 444 of SEQ ID NO:54).

Those skilled in the art will recognize that hydrophilicity or hydrophobicity will be taken into account when designing modifications in the amino acid sequence of a zcytor17 polypeptide, so as not to disrupt the overall structural and biological profile. Of particular interest for replacement are hydrophobic residues selected from the group consisting of Val, Leu and Ile or the group consisting of Met, Gly, Ser, Ala, Tyr and Trp. For example, residues tolerant of substitution could include such residues as shown in SEQ ID NO:2, SEQ ID NO:46, SEQ ID NO:54, SEQ ID NO:57 and SEQ ID NO:93. However, Cysteine residues would be relatively intolerant of substitution.

The identities of essential amino acids can also be inferred from analysis of sequence similarity between class I cytokine receptor family members with zcytor17. Using methods such as "FASTA" analysis described previously, regions of high similarity are identified within a family of proteins and used to analyze amino acid sequence for conserved regions. An alternative approach to identifying a variant zcytor17 polynucleotide on the basis of structure is to determine whether a nucleic acid molecule encoding a potential variant zcytor17 polynucleotide can hybridize to a nucleic acid molecule having the nucleotide sequence of SEQ ID NO:1, SEQ ID NO:45 or SEQ ID NO:53, as discussed above.

Other methods of identifying essential amino acids in the polypeptides of the present invention are procedures known in the art, such as site-directed mutagenesis or alanine-scanning mutagenesis (Cunningham and Wells, *Science* 244:1081 (1989), Bass et al., *Proc. Natl. Acad. Sci. USA* 88:4498 (1991), Coombs and Corey, "Site-Directed Mutagenesis and Protein Engineering," in *Proteins: Analysis and Design*, Angeletti (ed.), pages 259-311 (Academic Press, Inc. 1998)). In the latter technique, single alanine mutations are introduced at every residue in the molecule, and the resultant mutant molecules are tested for biological activity as disclosed below to identify amino acid residues that are critical to the activity of the molecule. See also, Hilton et al., *J. Biol. Chem.* 271:4699 (1996).

The present invention also includes a multimeric cytokine receptor which includes functional fragments of zcytor17 polypeptides and nucleic acid molecules encoding such functional fragments. A "functional" zcytor17 or fragment thereof defined herein is characterized by its ability to mediate proliferative or differentiating activity, by its ability to induce or inhibit specialized cell functions, or by its ability to bind specifically to an anti-zcytor17 antibody or zcytor17 ligand (either soluble or immobilized). Moreover, functional fragments also include the signal peptide, intracellular signaling domain, and the like. As previously described herein, zcytor17 is characterized by a class I cytokine receptor structure. Thus, the present invention further provides fusion proteins encompassing: (a) polypeptide molecules comprising an extracellular domain, cytokine-binding domain, or intracellular domain described herein; and (b) functional fragments comprising one or more of these domains. The other polypeptide portion of the fusion protein may comprise at least a portion of one or more of another class I cytokine receptor, for example, gp130, LIF, IL-12, WSX-1, IL-2 receptor β-subunit and the β-common receptor (i.e., IL3, IL-5, and GM-CSF receptor β-subunits), or by a non-native and/or an unrelated secretory signal peptide that facilitates secretion of the fusion protein.

Routine deletion analyses of nucleic acid molecules can be performed to obtain functional fragments of a nucleic acid molecule that encodes a zcytor17 polypeptide. As an illustration, DNA molecules having the nucleotide sequence of SEQ ID NO:1, SEQ ID NO:45 or SEQ ID NO:53 or fragments thereof, can be digested with Bal31 nuclease to obtain a series of nested deletions. These DNA fragments are then inserted into expression vectors in proper reading frame, and the expressed polypeptides are isolated and tested for zcytor17 activity, or for the ability to bind anti-zcytor17 antibodies or zcytor17 ligand. One alternative to exonuclease digestion is to use oligonucleotide-directed mutagenesis to introduce deletions or stop codons to specify production of a desired zcytor17 fragment. Alternatively, particular fragments of a zcytor17 polynucleotide can be synthesized using the polymerase chain reaction.

Standard methods for identifying functional domains are well-known to those of skill in the art. For example, studies on the truncation at either or both termini of interferons have been summarized by Horisberger and Di Marco, *Pharmac. Ther.* 66:507 (1995). Moreover, standard techniques for functional analysis of proteins are described by, for example, Treuter et al., *Molec. Gen. Genet.* 240:113 (1993); Content et al., "Expression and preliminary deletion analysis of the 42 kDa 2-5A synthetase induced by human interferon," in *Biological Interferon Systems, Proceedings of ISIR-TNO Meeting on Interferon Systems*, Cantell (ed.), pages 65-72 (Nijhoff 1987); Herschman, "The EGF Receptor," in *Control of Animal Cell Proliferation* 1, Boynton et al., (eds.) pages 169-199 (Academic Press 1985); Coumailleau et al., *J. Biol. Chem.* 270:29270 (1995); Fukunaga et al., *J. Biol. Chem.* 270:25291 (1995); Yamaguchi et al., *Biochem. Pharmacol.* 50:1295 (1995); and Meisel et al., *Plant Molec. Biol.* 30:1 (1996).

Multiple amino acid substitutions can be made and tested using known methods of mutagenesis and screening, such as those disclosed by Reidhaar-Olson and Sauer (*Science* 241: 53-57, 1988) or Bowie and Sauer (*Proc. Natl. Acad. Sci. USA* 86:2152-2156, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832-10837, 1991; Ladner et al., U.S. Pat. No. 5,223,409; Huse, WIPO Publication WO 92/062045) and region-directed mutagenesis (Derbyshire et al., *Gene* 46:145, 1986; Ner et al., *DNA* 7:127, 1988).

Variants of the disclosed zcytor17 DNA and polypeptide sequences can be generated through DNA shuffling as disclosed by Stemmer, *Nature* 370:389-91, 1994, Stemmer, *Proc. Natl. Acad. Sci. USA* 91:10747-51, 1994 and WIPO Publication WO 97/20078. Briefly, variant DNAs are generated by in vitro homologous recombination by random fragmentation of a parent DNA followed by reassembly using PCR, resulting in randomly introduced point mutations. This technique can be modified by using a family of parent DNAs, such as allelic variants or DNAs from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed herein can be combined with high-throughput, automated screening methods to detect activity of cloned, mutagenized zcytor17 receptor polypeptides in host cells. Preferred assays in this regard include cell proliferation assays and biosensor-based ligand-binding assays, which are described below. Mutagenized DNA molecules that encode active receptors or portions thereof (e.g., ligand-binding fragments, signaling domains, and the like) can be recovered from the host cells and rapidly sequenced using modern equipment. These methods allow the rapid determination of the importance of individual amino acid residues in a polypeptide of interest, and can be applied to polypeptides of unknown structure.

The present invention also provides a novel multimeric cytokine receptor in which a segment comprising at least a portion of one or more of the domains of zcytor17, for instance, secretory, extracellular, transmembrane, and intracellular, is fused to another polypeptide, for example, an extracellular domain of a class I cytokine receptor, such as OSMRbeta and/or WSX-1. Fusion is preferably done by splicing at the DNA level to allow expression of chimeric molecules in recombinant production systems. The resultant molecules are then assayed for such properties as improved solubility, improved stability, prolonged clearance half-life, improved expression and secretion levels, and pharmacodynamics. Such a multimeric cytokine receptor may further comprise additional amino acid residues (e.g., a polypeptide linker) between the component proteins or polypeptides. A domain linker may comprise a sequence of amino acids from about 3 to about 20 amino acids long, from about 5 to 15 about amino acids long, from about 8 to about 12 amino acids long, and about 10 amino acids long. One function of a linker is to separate the active protein regions to promote their independent bioactivity and permit each region to assume its bioactive conformation independent of interference from its neighboring structure.

'Using the methods discussed herein, one of ordinary skill in the art can identify and/or prepare a variety of polypeptide fragments or variants of SEQ ID NO:111, SEQ ID NO:109, SEQ ID NO:5, SEQ ID NO:117 and SEQ ID NO:119 that retain the signal transduction or ligand binding activity. For example, one can make a zcytor17 "soluble receptor" by preparing a variety of polypeptides that are substantially homologous to the cytokine-binding domain (residues 20 (Ala) to 227 (Pro) of SEQ ID NO:111 and SEQ ID NO:109; residues 33 (Ala) to 240 (Pro) of SEQ ID NO:5), the extracellular domain (residues 20 (Ala) to 519 (Glu) of SEQ ID NO:111 and SEQ ID NO:109; residues 33 (Ala) to 532 (Glu) of SEQ ID NO:5), or allelic variants or species orthologs thereof (e.g., see SEQ ID NO:117 and SEQ ID NO:119 and functional fragments thereof as described herein)) and retain ligand-binding activity of the wild-type zcytor17 protein. Moreover, variant zcytor17 soluble receptors such as those shown in SEQ ID NO:113 and SEQ ID NO:115 can be isolated. Such polypeptides may include additional amino acids from, for example, part or all of the transmembrane and intracellular domains. Such polypeptides may also include additional polypeptide segments as generally disclosed herein such as labels, affinity tags, and the like.

For any zcytor17 polypeptide, including variants, soluble receptors, and fusion polypeptides or proteins, one of ordinary skill in the art can readily generate a fully degenerate polynucleotide sequence encoding that variant using the information set forth in Tables 1 and 2 above.

The zcytor17 multimeric cytokine receptors of the present invention, including full-length polypeptides, biologically active fragments, and fusion polypeptides, can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., Molecular Cloning: *A Laboratory Manual*, 2nd ed., Cold Spring Harbor Laboratory Press, Cold Spring Harbor, N.Y., 1989, and Ausubel et al., eds., *Current Protocols in Molecular Biology*, John Wiley and Sons, Inc., NY, 1987.

The present invention also provides an expression vector comprising an isolated and purified DNA molecule including the following operably linked elements: a first transcription promoter, a first DNA segment encoding a polypeptide having at least 90 percent sequence identity with SEQ ID NO:111, and a first transcription terminator; and a second transcription promoter, a second DNA segment encoding at least a portion of a class I cytokine receptor, and a second transcription terminator; wherein the polypeptide and the class I cytokine receptor form a multimeric cytokine receptor; and wherein the multimeric cytokine receptor binds to at least a portion of SEQ ID NO:2. The DNA molecule may further comprise a secretory signal sequence operably linked to the first and second DNA segments. The multimeric cytokine receptor may be soluble and/or may further comprise an affinity tag as described herein. In addition, the multimeric cytokine receptor may antagonize an activity of SEQ ID NO:2 as described herein. The at least at portion of a class I cytokine receptor may comprise portions of SEQ ID NO:7 and/or SEQ ID NO:9, such as, for instance, amino acid residue 28 to amino acid residue 429 of SEQ ID NO:7, amino acid residue 35 to amino acid residue 137 of SEQ ID NO:7, amino acid residue 240 to amino acid residue 342 of SEQ ID NO:7, amino acid residue 348 to amino acid residue 429 of SEQ ID NO:7, amino acid residue 28 to amino acid residue 739 of SEQ ID NO:7, amino acid residue 28 to amino acid residue 761 of SEQ ID NO:7, amino acid residue 762 to amino acid residue 979 of SEQ ID NO:7, or combinations thereof. The present invention also provides a cultured cell containing the above-described expression vector.

In general, a DNA sequence, for example, encoding a zcytor17 polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct, for example, a zcytor17 polypeptide into the secretory pathway of a host cell, a secretory signal sequence (also known as a leader sequence, prepro sequence or pre sequence) is provided in the expression vector. The secretory signal sequence may be that of zcytor17, or may be derived from another secreted protein (e.g., t-PA) or synthesized de novo. The secretory signal sequence is operably linked to the zcytor17 DNA sequence, i.e., the two sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain secretory signal sequences may be positioned elsewhere in the DNA sequence of interest (see, e.g., Welch et al., U.S. Pat. No. 5,037,743; Holland et al., U.S. Pat. No. 5,143,830).

Alternatively, the secretory signal sequence contained in the polypeptides of the present invention is used to direct other polypeptides into the secretory pathway. The present invention provides for such fusion polypeptides. A signal fusion polypeptide can be made wherein a secretory signal sequence derived from amino acid 1 (Met) to amino acid 19 (Ala) of SEQ ID NO:111 and SEQ ID NO:109, or wherein a secretory signal sequence derived from amino acid 1 (Met) to amino acid 32 (Ala) of SEQ ID NO:5, or amino acid 1 (Met) to amino acid 45 (Ala) of SEQ ID NO:117 or SEQ ID NO:119), or amino acid 28 (Met) to residue 45 (Ala) of SEQ ID NO:117 or SEQ ID NO:119), is operably linked to another polypeptide using methods known in the art and disclosed herein. The secretory signal sequence contained in the fusion polypeptides of the present invention is preferably fused amino-terminally to an additional peptide to direct the additional peptide into the secretory pathway. Such constructs have numerous applications known in the art. For example, these novel secretory signal sequence fusion constructs can direct the secretion of an active component of a normally non-secreted protein. Such fusions may be used in vivo or in vitro to direct peptides through the secretory pathway.

The present invention also provides a cultured cell comprising a first expression vector comprising a DNA molecule containing the following operably linked elements: a transcription promoter, a DNA segment encoding a polypeptide having at least 90 percent sequence identity with SEQ ID NO:111, and a transcription terminator; and a second expression vector comprising a transcription promoter, a DNA segment encoding at least a portion of a class I cytokine receptor, and a transcription terminator; wherein the polypeptide and the class I cytokine receptor form a multimeric cytokine receptor. The first and second expression vectors may further comprise a secretory signal sequence operably linked to the first and second DNA segments. The multimeric cytokine receptor may be soluble, may be a heterodimer, and/or may further comprise an affinity tag as described herein. In addition, the multimeric cytokine receptor may antagonize an activity of SEQ ID NO:2 as described herein. The at least at portion of a class I cytokine receptor may comprise portions of SEQ ID NO:7 and/or SEQ ID NO:9, such as, for instance, amino acid residue 28 to amino acid residue 429 of SEQ ID NO:7, amino acid residue 35 to amino acid residue 137 of SEQ ID NO:7, amino acid residue 240 to amino acid residue 342 of SEQ ID NO:7, amino acid residue 348 to amino acid residue 429 of SEQ ID NO:7, amino acid residue 28 to amino acid residue 739 of SEQ ID NO:7, amino acid residue 28 to amino acid residue 761 of SEQ ID NO:7, amino acid residue 762 to amino acid residue 979 of SEQ ID NO:7, or combinations thereof.

Cultured mammalian cells are suitable hosts within the present invention. Methods for introducing exogenous DNA into mammalian host cells include calcium phosphate-mediated transfection (Wigler et al., Cell 14:725, 1978; Corsaro and Pearson, Somatic Cell Genetics 7:603, 1981: Graham and Van der Eb, Virology 52:456, 1973), electroporation (Neumann et al., EMBO J. 1:841-845, 1982), DEAE-dextran mediated transfection (Ausubel et al., ibid.), and liposome-mediated transfection (Hawley-Nelson et al., Focus 15:73, 1993; Ciccarone et al., Focus 15:80, 1993, and viral vectors (Miller and Rosman, BioTechniques 7:980-90, 1989; Wang and Finer, Nature Med. 2:714-716, 1996). The production of recombinant polypeptides in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., J. Gen. Virol. 36:59-72, 1977) and Chinese hamster ovary (e.g. CHO-K1; ATCC No. CCL 61) cell lines. Additional suitable cell lines are known in the art and available from public depositories such as the American Type Culture Collection, Rockville, Md. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g., hygromycin resistance, multi-drug resistance, puromycin acetyltransferase) can also be used. Alternative markers that introduce an altered phenotype, such as green fluorescent protein, or cell surface proteins such as CD4, CD8, Class I MHC, placental alkaline phosphatase may be used to sort transfected cells from untransfected cells by such means as FACS sorting or magnetic bead separation technology.

Other higher eukaryotic cells can also be used as hosts, including plant cells, insect cells and avian cells. The use of *Agrobacterium rhizogenes* as a vector for expressing genes in plant cells has been reviewed by Sinkar et al., *J. Biosci. (Bangalore)* 11:47-58, 1987. Transformation of insect cells and production of foreign polypeptides therein is disclosed by Guarino et al., U.S. Pat. No. 5,162,222 and WIPO publication WO 94/06463. Insect cells can be infected with recombinant baculovirus, commonly derived from *Autographa californica* nuclear polyhedrosis virus (AcNPV). See, King, L. A. and Possee, R. D., *The Baculovirus Expression System: A Laboratory Guide*, London, Chapman & Hall; O'Reilly, D. R. et al., *Baculovirus Expression Vectors: A Laboratory Manual*, New York, Oxford University Press., 1994; and, Richardson, C. D., Ed., *Baculovirus Expression Protocols. Methods in Molecular Biology*, Totowa, N.J., Humana Press, 1995. A second method of making recombinant zcytor17 baculovirus utilizes a transposon-based system described by Luckow (Luckow, V. A, et al., *J Virol* 67:4566-79, 1993). This system, which utilizes transfer vectors, is sold in the Bac-to-Bac™ kit (Life Technologies, Rockville, Md.). This system utilizes a transfer vector, pFastBac1™ (Life Technologies) containing a Tn7 transposon to move the DNA encoding the zcytor17 polypeptide into a baculovirus genome maintained in *E. coli* as a large plasmid called a "bacmid." See, Hill-Perkins, M. S. and Possee, R. D., *J Gen Virol* 71:971-6, 1990; Bonning, B. C. et al., *J Gen Virol* 75:1551-6, 1994; and, Chazenbalk, G. D., and Rapoport, B., *J Biol Chem* 270:1543-9, 1995. In addition, transfer vectors can include an in-frame fusion with DNA encoding an epitope tag at the C- or N-terminus of the expressed zcytor17 polypeptide, for example, a Glu-Glu epitope tag (Grussenmeyer, T. et al., *Proc. Natl. Acad. Sci.* 82:7952-4, 1985). Using a technique known in the art, a transfer vector containing zcytor17 is transformed into *E. coli*, and screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, e.g., Sf9 cells. Recombinant virus that expresses zcytor17 is subsequently produced. Recombinant viral stocks are made by methods commonly used in the art.

The recombinant virus is used to infect host cells, typically a cell line derived from the fall armyworm, *Spodoptera frugiperda*. See, in general, Glick and Pasternak, *Molecular Biotechnology: Principles and Applications of Recombinant DNA*, ASM Press, Washington, D.C., 1994. Another suitable cell line is the High FiveO™ cell line (Invitrogen) derived from *Trichoplusia ni* (U.S. Pat. No. 5,300,435). Commercially available serum-free media are used to grow and maintain the cells. Suitable media are Sf900 II™ (Life Technologies) or ESF 921™ (Expression Systems) for the Sf9 cells; and Ex-cellO405™ (JRH Biosciences, Lenexa, Kans.) or Express FiveO™ (Life Technologies) for the *T. ni* cells. Procedures used are generally described in available laboratory manuals (King, L. A. and Possee, R. D., ibid.; O'Reilly, D. R. et al., ibid.; Richardson, C. D., ibid.). Subsequent purification of the zcytor17 polypeptide from the supernatant can be achieved using methods described herein.

Fungal cells, including yeast cells, can also be used within the present invention. Yeast species of particular interest in this regard include *Saccharomyces cerevisiae, Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936 and 4,661,454. Transformation systems for other yeasts, including *Hansenula polymorpha, Schizosaccharomyces pornbe, Kluyveromyces lactis, Kluyveromyces fragilis, Ustilago maydis, Pichia pastoris, Pichia methanolica, Pichia guillermondii* and *Candida maltosa* are known in the art. See, for example, Gleeson et al., *J. Gen. Microbiol.* 132:3459-3465, 1986 and Cregg, U.S. Pat. No. 4,882,279. *Aspergillus* cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming *Neurospora* are disclosed by Lambowitz, U.S. Pat. No. 4,486,533.

The use of *Pichia methanolica* as host for the production of recombinant proteins is disclosed in WIPO Publications WO 97/17450, WO 97/17451, WO 98/02536, and WO 98/02565. DNA molecules for use in transforming *P. methanolica* will commonly be prepared as double-stranded, circular plasmids, which are preferably linearized prior to transformation. For polypeptide production in *P. methanolica*, it is preferred that the promoter and terminator in the plasmid be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. A preferred selectable marker for use in *Pichia methanolica* is a *P. methanolica* ADE2 gene, which encodes phosphoribosyl-5-aminoimidazole carboxylase (AIRC; EC 4.1.1.21), which allows ade2 host cells to grow in the absence of adenine. For large-scale, industrial processes where it is desirable to minimize the use of methanol, it is preferred to use host cells in which both methanol utilization genes (AUG1 and AUG2) are deleted. For production of secreted proteins, host cells deficient in vacuolar protease genes (PEP4 and PRB1) are preferred. Electroporation is used to facilitate the introduction of a plasmid containing DNA encoding a polypeptide of interest into *P. methanolica* cells. It is preferred to transform *P. methanolica* cells by electroporation using an exponentially decaying, pulsed electric field having a field strength of from 2.5 to 4.5 kV/cm, preferably about 3.75 kV/cm, and a time constant (t) of from 1 to 40 milliseconds, most preferably about 20 milliseconds.

Prokaryotic host cells, including strains of the bacteria *Escherichia coli, Bacillus* and other genera are also useful host cells within the present invention. Techniques for transforming these hosts and expressing foreign DNA sequences cloned therein are well known in the art (see, e.g., Sambrook et al., ibid.). When expressing a zcytor17 polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell. *P. methanolica* cells are cultured in a medium comprising adequate sources of carbon, nitrogen and trace nutrients at a temperature of about 25° C. to 35° C. Liquid cultures are provided with sufficient aeration by conventional means, such as shaking of small flasks or sparging of fermentors. A preferred culture medium for *P. methanolica* is YEPD (2% D-glucose, 2% Bacto™ Peptone (Difco Laboratories, Detroit, Mich.), 1% Bacto™ yeast extract (Difco Laboratories), 0.004% adenine and 0.006% L-leucine).

Within one aspect of the present invention, a zcytor17 multimeric cytokine receptor (including transmembrane and intracellular domains) is produced by a cultured cell, and the cell is used to screen for ligands for the receptor, including the natural ligand (SEQ ID NO:2), as well as agonists and antagonists of the natural ligand. To summarize this approach, a cDNA or gene encoding the receptor is combined with other genetic elements required for its expression (e.g., a transcription promoter), and the resulting expression vector is inserted into a host cell. Cells that express the DNA and produce functional receptor are selected and used within a variety of screening systems.

Mammalian cells suitable for use in expressing the novel receptors of the present invention and transducing a receptor-mediated signal include cells that express a β-subunit, such as gp130, and cells that co-express gp130 and LIF receptor (Gearing et al., *EMBO J.* 10:2839-2848, 1991; Gearing et al., U.S. Pat. No. 5,284,755). In this regard it is generally preferred to employ a cell that is responsive to other cytokines that bind to receptors in the same subfamily, such as IL-6 or LIF, because such cells will contain the requisite signal transduction pathway(s). Preferred cells of this type include BaF3 cells (Palacios and Steinmetz, *Cell* 41: 727-734, 1985; Mathey-Prevot et al., Mol. Cell. Biol. 6: 4133-4135, 1986), the human TF-1 cell line (ATCC number CRL-2003) and the DA-1 cell line (Branch et al., *Blood* 69:1782, 1987; Broudy et al., *Blood* 75:1622-1626, 1990). In the alternative, suitable host cells can be engineered to produce a β-subunit or other cellular component needed for the desired cellular response. For example, the murine cell line BaF3 (Palacios and Steinmetz, *Cell* 41:727-734, 1985; Mathey-Prevot et al., *Mol. Cell. Biol.* 6: 4133-4135, 1986), a baby hamster kidney (BHK) cell line, or the CTLL-2 cell line (ATCC TIB-214) can be transfected to express the mouse gp130 subunit, or mouse gp130 and LIF receptor, in addition to zcytor17. It is generally preferred to use a host cell and receptor(s) from the same species, however this approach allows cell lines to be engineered to express multiple receptor subunits from any species, thereby overcoming potential limitations arising from species specificity. In the alternative, species homologs of the human receptor cDNA can be cloned and used within cell lines from the same species, such as a mouse cDNA in the BaF3 cell line. Cell lines that are dependent upon one hematopoietic growth factor, such as IL-3, can thus be engineered to become dependent upon a zcytor17 ligand or anti-zcytor17 antibody.

Cells expressing functional zcytor17 are used within screening assays. A variety of suitable assays are known in the art. These assays are based on the detection of a biological response in the target cell. One such assay is a cell proliferation assay. Cells are cultured in the presence or absence of a test compound, and cell proliferation is detected by, for example, measuring incorporation of tritiated thymidine or by colorimetric assay based on the reduction or metabolic breakdown of Alymar Blue™ (AccuMed, Chicago, Ill.) or 3-(4,5-dimethylthiazol-2-yl)-2,5-diphenyl tetrazolium bromide (MTT) (Mosman, *J. Immunol. Meth.* 65:55-63, 1983). An alternative assay format uses cells that are further engineered to express a reporter gene. The reporter gene is linked to a promoter element that is responsive to the receptor-linked pathway, and the assay detects activation of transcription of the reporter gene. A preferred promoter element in this regard is a serum response element, STAT or SRE (see, for example, Shaw et al., *Cell* 56:563-572, 1989). A preferred such reporter gene is a luciferase gene (de Wet et al., *Mol. Cell. Biol.* 7:725, 1987). Expression of the luciferase gene is detected by luminescence using methods known in the art (e.g., Baumgartner et al., *J. Biol. Chem.* 269:19094-29101, 1994; Schenborn and Goiffin, *Promega Notes* 41:11, 1993). Luciferase assay kits are commercially available from, for example, Promega Corp., Madison, Wis. Target cell lines of this type can be used to screen libraries of chemicals, cell-conditioned culture media, fungal broths, soil samples, water samples, and the like. For example, a bank of cell- or tissue-conditioned media samples can be assayed on a target cell to identify cells that produce ligand. Positive cells are then used to produce a cDNA library in a mammalian cell expression vector, which is divided into pools, transfected into host cells, and expressed. Media samples from the transfected cells are then assayed, with subsequent division of pools, retransfection, subculturing, and re-assay of positive cells to isolate a clonal cell line expressing the ligand. Media samples conditioned by kidney, liver, spleen, thymus, other lymphoid tissues, or T-cells are preferred sources of ligand for use in screening procedures.

The present invention also provides a method of producing a multimeric cytokine receptor. The method includes culturing a cell as described herein, and isolating the multimeric cytokine receptor produced by the cell.

The present invention also provides a method for detecting a multiple cytokine receptor ligand in a test sample. The method includes contacting the test sample with a multimeric cytokine receptor comprising a polypeptide comprising amino acid residue 20 to amino acid residue 227 of SEQ ID NO:111 or SEQ ID NO:109 (amino acid residue 33 to amino acid residue 240 of SEQ ID NO:5), and at least a portion of at least one class I cytokine receptor; and detecting the binding of the multimer cytokine receptor to the ligand in the test sample. The at least a portion of at least one class I cytokine receptor can include, for example, a portion of SEQ ID NO:9 and/or a portion of SEQ ID NO:7, such as, for instance, amino acid residue 28 to amino acid residue 429 of SEQ ID NO:7, amino acid residue 35 to amino acid residue 137 of SEQ ID NO:7, amino acid residue 240 to amino acid residue 342 of SEQ ID NO:7, amino acid residue 348 to amino acid residue 429 of SEQ ID NO:7, amino acid residue 28 to amino acid residue 739 of SEQ ID NO:7, and/or combinations thereof.

A natural ligand for a zcytor17 multimeric cytokine receptor of the present invention can also be identified by mutagenizing a cytokine-dependent cell line expressing zcytor17 and culturing it under conditions that select for autocrine growth. See WIPO publication WO 95/21930. Within a typical procedure, cells expressing zcytor17 are mutagenized, such as with EMS. The cells are then allowed to recover in the presence of the required cytokine, then transferred to a culture medium lacking the cytokine. Surviving cells are screened for the production of a ligand for zcytor17 multimeric cytokine receptor, such as by adding soluble receptor polypeptide comprising the zcytor17 cytokine-binding domain and at least a portion of a class I cytokine receptor, such as the cytokine-binding domain of OSMRbeta (SEQ ID NO:7) and/or WSX-1 (SEQ ID NO:9), as described herein to the culture medium to compete against the ligand or by assaying conditioned media on wild-type cells compared to transfected cells expressing the zcytor17 multimeric cytokine receptor. Preferred cell lines for use within this method include cells that are transfected to express gp130 or gp130 in combination with LIF receptor. Preferred such host cell lines include transfected CTLL-2 cells (Gillis and Smith, *Nature* 268:154-156, 1977) and transfected BaF3 cells.

Moreover, a secretion trap method employing zcytor17 soluble multimeric cytokine receptor can be used to isolate a zcytor17 ligand, such as SEQ ID NO:2 (Aldrich, et al, *Cell* 87: 1161-1169, 1996). A cDNA expression library prepared from a known or suspected ligand source is transfected into COS-7 cells. The cDNA library vector generally has an SV40 origin for amplification in COS-7 cells, and a CMV promoter for high expression. The transfected COS-7 cells are grown in a monolayer and then fixed and permeabilized. Tagged or biotin-labeled zcytor17 soluble multimeric cytokine receptor, described herein, is then placed in contact with the cell layer and allowed to bind cells in the monolayer that express an anti-complementary molecule, i.e., a zcytor17 ligand. A cell expressing a ligand will thus be bound with receptor molecules. An anti-tag antibody (anti-Ig for Ig fusions, M2 or anti-FLAG for FLAG-tagged fusions, streptavidin, anti-Glu-Glu tag, and the like) which is conjugated with horseradish peroxidase (HRP) is used to visualize these cells to which the tagged or biotin-labeled zcytor17 soluble multimeric cytokine receptor has bound. The HRP catalyzes deposition of a tyramide reagent, for example, tyramide-FITC. A commercially-available kit can be used for this detection (for example, Renaissance TSA-Direct™ Kit; NEN Life Science Products, Boston, Mass.). Cells which express zcytor17 multimeric cytokine receptor ligand will be identified under fluorescence microscopy as green cells and picked for subsequent cloning of the ligand using procedures for plasmid rescue as outlined in Aldrich, et al, supra., followed by subsequent rounds of secretion trap assay, or conventional screening of cDNA library pools, until single clones are identified.

As a multimeric receptor complex, the activity of zcytor17 polypeptide can be measured by a silicon-based biosensor microphysiometer which measures the extracellular acidification rate or proton excretion associated with receptor binding and subsequent physiologic cellular responses. An exemplary device is the Cytosensor™ Microphysiometer manufactured by Molecular Devices, Sunnyvale, Calif. A variety of cellular responses, such as cell proliferation, ion transport, energy production, inflammatory response, regulatory and receptor activation, and the like, can be measured by this method. See, for example, McConnell, H. M. et al., *Science* 257:1906-1912, 1992; Pitchford, S. et al., *Meth. Enzymol.* 228:84-108, 1997; Arimilli, S. et al., *J. Immunol. Meth.* 212:49-59, 1998; Van Liefde, I. Et al., *Eur. J. Pharmacol.* 346:87-95, 1998. The microphysiometer can be used for assaying eukaryotic, prokaryotic, adherent or non-adherent cells. By measuring extracellular acidification changes in cell media over time, the microphysiometer directly measures cellular responses to various stimuli, including agonists, ligands, or antagonists of the zcytor17 polypeptide. Preferably, the microphysiometer is used to measure responses of a zcytor17-expressing eukaryotic cell, compared to a control eukaryotic cell that does not express zcytor17 polypeptide. Zcytor17-expressing eukaryotic cells comprise cells into which zcytor17 has been transfected or infected via adenovirus vector, and the like, as described herein, creating a cell that is responsive to zcytor17-modulating stimuli, or are cells naturally expressing zcytor17, such as zcytor17-expressing cells derived from lymphoid, spleen, thymus tissue or PBLs. Differences, measured by an increase or decrease in extracellular acidification, in the response of cells expressing zcytor17, relative to a control, are a direct measurement of zcytor17-modulated cellular responses. Moreover, such zcytor17-modulated responses can be assayed under a variety of stimuli. Also, using the microphysiometer, there is provided a method of identifying agonists and antagonists of zcytor17 multimeric cytokine receptor, comprising providing cells expressing a zcytor17 multimeric cytokine receptor, culturing a first portion of the cells in the absence of a test compound, culturing a second portion of the cells in the presence of a test compound, and detecting an increase or a decrease in a cellular response of the second portion of the cells as compared to the first portion of the cells. Antagonists and agonists, including the natural ligand for zcytor17 multimeric cytokine receptor, can be rapidly identified using this method.

A zcytor17 multimeric cytokine receptor can be expressed as a fusion with an immunoglobulin heavy chain constant region, typically an $F_c$ fragment, which contains two constant region domains and lacks the variable region. Methods for preparing such fusions are disclosed in U.S. Pat. Nos. 5,155,027 and 5,567,584. Such fusions are typically secreted as multimeric molecules wherein the $F_c$ portions are disulfide bonded to each other and two non-Ig polypeptides are arrayed in closed proximity to each other. Fusions of this type can be used for example, for dimerization, increasing stability and in vivo half-life, to affinity purify ligand, as in vitro assay tool or antagonist. For use in assays, the chimeras are bound to a support via the $F_c$ region and used in an ELISA format.

Additional assays provided by the present invention include the use of hybrid receptor polypeptides. These hybrid polypeptides fall into two general classes. Within the first class, the intracellular domain of zcytor17, comprising approximately residues 544 (Lys) to 732 (Val) of SEQ ID NO:111, residues 544 (Lys) to 649 (Ile) of SEQ ID NO:109, or residues 557 (Lys) to 662 (Ile) of SEQ ID NO:5, or residues 551 (Lys) to 662 (Cys) of SEQ ID NO:117 is joined to the ligand-binding domain of a second receptor. It is preferred that the second receptor be a hematopoietic cytokine receptor, such as, for instance, mpl receptor (Souyri et al., *Cell* 63:1137-1147, 1990). The hybrid receptor will further comprise a transmembrane domain, which may be derived from either receptor. A DNA construct encoding the hybrid receptor is then inserted into a host cell. Cells expressing the hybrid receptor are cultured in the presence of a ligand for the binding domain and assayed for a response. This system provides a means for analyzing signal transduction mediated by zcytor17 while using readily available ligands. This system can also be used to determine if particular cell lines are capable of responding to signals transduced by zcytor17. A second class of hybrid receptor polypeptides comprise the extracellular (ligand-binding) domain (approximately residues 20 (Ala) to 519 (Glu) of SEQ ID NO:111 and SEQ ID NO:109; approximately residues 33 (Ala) to 532 (Glu) of SEQ ID NO:5) or cytokine-binding domain of zcytor17 (approximately residues 20 (Ala) to 227 (Pro) of SEQ ID NO:111 and SEQ ID NO:109; or approximately residues 33 (Ala) to 240 (Pro) of SEQ ID NO:5; approximately residues 46 (Val) to 533 (Glu) of SEQ ID NO:117; or approximately residues 46 (Val) to 533 (Trp) of SEQ ID NO:119) with a cytoplasmic domain of a second receptor, preferably a cytokine receptor, and a transmembrane domain. The transmembrane domain may be derived from either receptor. Hybrid receptors of this second class are expressed in cells known to be capable of responding to signals transduced by the second receptor. Together, these two classes of hybrid receptors enable the use of a broad spectrum of cell types within receptor-based assay systems.

The expression of WSX-1 is strongest in thymus, spleen, PBL, and lymph node, as well as increased expression observed for activated T-cells. The tissue distribution for OSMRbeta is described as very broad. The tissue distribution of these three receptors suggests that a target for zcytor17lig is hematopoietic lineage cells, in particular T-cells, monocytes/macrophages and lymphoid progenitor cells and lymphoid cells. Other known four-helical-bundle cytokines that act on lymphoid cells include IL-2, IL-4, IL-7, and IL-15. For a review of four-helical-bundle cytokines, see, Nicola et al., *Advances in Protein Chemistry* 52:1-65, 1999 and Kelso, A., *Immunol. Cell Biol.* 76:300-317, 1998.

Conditioned media (CM) from CD3+ selected, PMA/Ionomycin-stimulated human peripheral blood cells supported the growth of BaF3 cells that expressed the zcytor17 receptor, OSMRbeta and WSX-1 receptor and were otherwise dependent on IL-3. Conditioned medias from cells that were not: 1) PMA/Ionomycin-stimulated; or were not: 2) CD3 selected (with or without PMA/Ionomycin stimulation) did not support the growth of Baf3 cells expressing zcytor17, OSMRbeta and WSX-1 (BaF3/zcytor17/WSX-1/OSMRbeta) receptor-expressing cells. Control experiments demonstrated that this proliferative activity was not attributable to other known growth factors, and that the ability of such conditioned media to stimulate proliferation of zcytor17/WSX-1/OSMRbeta receptor-expressing cells could be neutralized by a soluble form of the zcytor17 receptor.

Conditioned-media from CD3+ selected cells activated with PMA/Ionomycin also supported growth of BaF3 cells that expressed the zcytor17 receptor and OSMRbeta receptor (zcytor17/OSMRbeta), while BaF3 cells expressing only zcytor17 receptor and WSX-1 receptor (zcytor17/WSX-1), or containing only the OSMRbeta receptor, were not stimulated by this conditioned-media.

Proliferation of zcytor17/WSX-1/OSMRbeta receptor-expressing BaF3 cells exposed to CM from CD3+ selected, PMA/Ionomycin-stimulated human peripheral blood cells were identified by visual inspection of the cultures and/or by proliferation assay. Many suitable proliferation assays are known in the art, and include assays for reduction of a dye such as AlamarBlue™ (AccuMed International, Inc. Westlake, Ohio), 3-(4,5-dimethylthiazol-2-yl)-2,5-diphenyl tetrazolium bromide (Mosman, *J. Immunol. Meth.* 65: 55-63, 1983); 3,(4,5 dimethyl thiazol-2-yl)-5-3-carboxymethoxyphenyl-2H-tetrazolium; 2,3-bis(2-methoxy-4-nitro-5-sulfophenyl)-5-[(phenylamino)carbonyl]-2H-tetrazolium hydroxide; and cyanoditolyl-tetrazolium chloride (which are commercially available from Polysciences, Inc., Warrington, Pa.); mitogenesis assays, such as measurement of incorporation of $^3$H-thymidine; dye exclusion assays using, for example, naphthalene black or trypan blue; dye uptake using diacetyl fluorescein; and chromium release. See, in general, Freshney, *Culture of Animal Cells: A Manual of Basic Technique,* 3rd ed., Wiley-Liss, 1994, which is incorporated herein by reference.

A cDNA library was prepared from CD3+ selected, PMA- and Ionomycin-stimulated primary human peripheral blood cells. The CD3+ selected, PMA- and Ionomycin-stimulated human peripheral blood cells cDNA library was divided into pools containing multiple cDNA molecules and was transfected into a host cell line, for example, BHK 570 cells (ATCC accession no. 10314). The transfected host cells were cultured in a medium that did not contain exogenous growth factors (e.g., 5% FBS) and conditioned medium was collected. The conditioned media were assayed for the ability to stimulate proliferation of BaF3 cells transfected with the zcytor17, WSX-1, and OSMRbeta receptors. cDNA pools producing conditioned medium that stimulated BaF3/zcytor17/WSX-1/OSMRbeta receptor cells were identified. This pooled plasmid cDNA was electroporated into *E. coli.* cDNA was isolated from single colonies and transfected individually into BHK 570 cells. Positive clones were identified by a positive result in the BaF3/zcytor17/WSX-1/OSMRbeta receptor proliferation assay, and the activity was confirmed by neutralization of proliferation using the soluble zcytor17 receptor.

In view of the tissue distribution observed for zcytor17 receptor agonists (including the natural zcytor17lig/substrate/cofactor/etc.) and/or antagonists have enormous potential in both in vitro and in vivo applications. Compounds identified as zcytor17lig agonists are useful for expansion, proliferation, activation, differentiation, and/or induction or inhibition of specialized cell functions of cells involved in homeostasis of hematopoiesis and immune function. For example, zcytor17lig and agonist compounds are useful as components of defined cell culture media, and may be used alone or in combination with other cytokines and hormones to replace serum that is commonly used in cell culture. Agonists are thus useful in specifically promoting the growth and/or development of T-cells, B-cells, monocytes/macrophages, NK cells, cytotoxic lymphocytes, and other cells of the lymphoid and myeloid lineages in culture.

Antagonists are also useful as research reagents for characterizing sites of ligand-receptor interaction. Antagonists are useful to inhibit expansion, proliferation, activation, and/or differentiation of cells involved in regulating hematopoiesis. Inhibitors of zcytor17lig activity (zcytor17lig antagonists) include anti-zcytor17lig antibodies and soluble multimeric cytokine receptors, as well as other peptidic and non-peptidic agents (including ribozymes).

A zcytor17lig-binding protein, such as a multimeric cytokine receptor of the present invention, can also be used for purification of ligand. The multimeric cytokine receptor is immobilized on a solid support, such as beads of agarose, cross-linked agarose, glass, cellulosic resins, silica-based resins, polystyrene, cross-linked polyacrylamide, or like materials that are stable under the conditions of use. Methods for linking polypeptides to solid supports are known in the art, and include amine chemistry, cyanogen bromide activation, N-hydroxysuccinimide activation, epoxide activation, sulfhydryl activation, and hydrazide activation. The resulting medium will generally be configured in the form of a column, and fluids containing ligand are passed through the column one or more times to allow ligand to bind to the receptor polypeptide. The ligand is then eluted using changes in salt concentration, chaotropic agents (guanidine HCl), or pH to disrupt ligand-receptor binding.

An assay system that uses a ligand-binding receptor (or an antibody, one member of a complement/anti-complement pair) or a binding fragment thereof, and a commercially available biosensor instrument (BIAcore, Pharmacia Biosensor, Piscataway, N.J.) may be advantageously employed. Such receptor, antibody, member of a complement/anti-complement pair or fragment is immobilized onto the surface of a receptor chip. Use of this instrument is disclosed by Karlsson, *J. Immunol. Methods* 145:229-40 (1991) and Cunningham and Wells, *J. Mol. Biol.* 234:554-63 (1993). A receptor, antibody, member or fragment is covalently attached, using amine or sulfhydryl chemistry, to dextran fibers that are attached to gold film within the flow cell. A test sample is passed through the cell. If a ligand, epitope, or opposite member of the complement/anti-complement pair is present in the sample, it will bind to the immobilized receptor, antibody or member, respectively, causing a change in the refractive index of the medium, which is detected as a change in surface plasmon resonance of the gold film. This system allows the determination of on- and off-rates, from which binding affinity can be calculated, and assessment of stoichiometry of binding. Alternatively, ligand/receptor binding can be analyzed using SELDI™ technology (Ciphergen, Inc., Palo Alto, Calif.).

Ligand-binding receptor polypeptides can also be used within other assay systems known in the art. Such systems include Scatchard analysis for determination of binding affinity (see Scatchard, *Ann. NY Acad. Sci.* 51: 660-72 (1949)) and calorimetric assays (Cunningham et al., *Science* 253:545-48 (1991); and Cunningham et al., *Science* 245:821-25 (1991)).

The present invention also provides an antibody that specifically binds to a polypeptide or at least at portion of a multimeric cytokine receptor as described herein.

Zcytor17 multimeric cytokine receptors can also be used to prepare antibodies that bind to epitopes, peptides or polypeptides thereof. The multimeric cytokine receptor or a fragment thereof serves as an antigen (immunogen) to inoculate an animal and elicit an immune response. One of skill in the art would recognize that antigenic, epitope-bearing polypeptides may contain a sequence of at least 6, preferably at least 9, and more preferably at least 15 to about 30 contiguous amino acid residues of a polypeptide(s) of the multimeric cytokine receptor, such as zcytor17 (SEQ ID NO:111), OSMRbeta (SEQ ID NO:7), and/or WSX-1 (SEQ ID NO:9). Polypeptides comprising a larger portion of a multimeric cytokine receptor, i.e., from 30 to 100 residues up to the entire length of the amino acid sequence are included. Antigens or immunogenic epitopes can also include attached tags, adjuvants, carriers and vehicles, as described herein.

Antibodies from an immune response generated by inoculation of an animal with these antigens can be isolated and purified as described herein. Methods for preparing and isolating polyclonal and monoclonal antibodies are well known in the art. See, for example, *Current Protocols in Immunology*, Cooligan, et al. (eds.), National Institutes of Health, John Wiley and Sons, Inc., 1995; Sambrook et al., *Molecular Cloning: A Laboratory Manual*, Second Edition, Cold Spring Harbor, N.Y., 1989; and Hurrell, J. G. R., Ed., *Monoclonal Hybridoma Antibodies: Techniques and Applications*, CRC Press, Inc., Boca Raton, Fla., 1982.

As would be evident to one of ordinary skill in the art, polyclonal antibodies can be generated from inoculating a variety of warm-blooded animals such as horses, cows, goats, sheep, dogs, chickens, rabbits, mice, and rats with a multimeric cytokine receptor or a fragment thereof. The immunogenicity of a multimeric cytokine receptor may be increased through the use of an adjuvant, such as alum (aluminum hydroxide) or Freund's complete or incomplete adjuvant. Multimeric cytokine receptors useful for immunization also include fusion polypeptides, such as fusions of zcytor17, OSMRbeta, and/or WSX-1, or a portion thereof with an immunoglobulin polypeptide or with maltose binding protein. The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization.

As used herein, the term "antibodies" includes polyclonal antibodies, affinity-purified polyclonal antibodies, monoclonal antibodies, and antigen-binding fragments, such as $F(ab')_2$ and Fab proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced. Moreover, human antibodies can be produced in transgenic, non-human animals that have been engineered to contain human immunoglobulin genes as disclosed in WIPO Publication WO 98/24893. It is preferred that the endogenous immunoglobulin genes in these animals be inactivated or eliminated, such as by homologous recombination.

Antibodies are considered to be specifically binding if: 1) they exhibit a threshold level of binding activity, and 2) they do not significantly cross-react with related polypeptide molecules. A threshold level of binding is determined if anti-multimeric cytokine receptor antibodies herein bind to a multimeric cytokine receptor, peptide or epitope with an affinity at least 10-fold greater than the binding affinity to control (non-multimeric cytokine receptor) protein. It is preferred that the antibodies exhibit a binding affinity ($K_a$) of $10^6$ M$^{-1}$ or greater, preferably $10^7$ M$^{-1}$ or greater, more preferably $10^8$ M$^{-1}$ or greater, and most preferably $10^9$ M$^{-1}$ or greater. The binding affinity of an antibody can be readily determined by one of ordinary skill in the art, for example, by Scatchard analysis (Scatchard, G., *Ann. NY Acad. Sci.* 51: 660-672 (1949)).

Whether anti-multimeric cytokine receptor antibodies do not significantly cross-react with related polypeptide molecules is shown, for example, by the antibody detecting zcytor17 multimeric cytokine receptor but not known related polypeptides using a standard Western blot analysis (Ausubel et al., ibid.). Examples of known related polypeptides are those disclosed in the prior art, such as known orthologs, and paralogs, and similar known members of a protein family. Screening can also be done using non-human multimeric cytokine receptor, and multimeric cytokine receptor mutant polypeptides. Moreover, antibodies can be "screened against" known related polypeptides, to isolate a population that specifically binds to the multimeric cytokine receptor. For example, antibodies raised to multimeric cytokine receptor are adsorbed to related polypeptides adhered to insoluble matrix; antibodies specific to multimeric cytokine receptor will flow through the matrix under the proper buffer conditions. Screening allows isolation of polyclonal and monoclonal antibodies non-crossreactive to known closely related polypeptides (*Antibodies: A Laboratory Manual*, Harlow and Lane (eds.), Cold Spring Harbor Laboratory Press, 1988; *Current Protocols in Immunology*, Cooligan, et al. (eds.), National Institutes of Health, John Wiley and Sons, Inc., 1995). Screening and isolation of specific antibodies is well known in the art. See, *Fundamental Immunology*, Paul (eds.), Raven Press, 1993; Getzoff et al., *Adv. in Immunol.* 43: 1-98, 1988; *Monoclonal Antibodies: Principles and Practice*, Goding, J. W. (eds.), Academic Press Ltd., 1996; Benjamin et al., *Ann. Rev. Immunol.* 2: 67-101, 1984. Specifically binding anti-multimeric cytokine receptor antibodies can be detected by a number of methods in the art, and disclosed below.

A variety of assays known to those skilled in the art can be utilized to detect antibodies which bind to multimeric cytokine receptor proteins or polypeptides. Exemplary assays are described in detail in *Antibodies: A Laboratory Manual*, Harlow and Lane (Eds.), Cold Spring Harbor Laboratory Press, 1988. Representative examples of such assays include: concurrent immunoelectrophoresis, radioimmunoassay, radio-immuno-precipitation, enzyme-linked immunosorbent assay (ELISA), dot blot or Western blot assay, inhibition or competition assay, and sandwich assay. In addition, antibodies can be screened for binding to wild-type versus mutant multimeric cytokine receptor protein or polypeptide.

Within another aspect the present invention provides an antibody produced by the method as disclosed above, wherein the antibody binds to at least a portion of a multimer cytokine receptor comprising at least a portion of SEQ ID NO:111, SEQ ID NO:109, or SEQ ID NO:5. In one embodiment, the antibody disclosed above specifically binds to a polypeptide shown in SEQ ID NO:111, SEQ ID NO:109, or SEQ ID NO:5. In another embodiment, the antibody can be a monoclonal antibody or a polyclonal antibody.

Antibodies to multimeric cytokine receptor may be used for tagging cells that express multimeric cytokine receptor; for isolating multimeric cytokine receptor by affinity purification; for diagnostic assays for determining circulating levels of multimeric cytokine receptor; for detecting or quantitating soluble multimeric cytokine receptor as a marker of underlying pathology or disease; in analytical methods employing FACS; for screening expression libraries; for generating anti-idiotypic antibodies; and as neutralizing antibodies or as antagonists to block multimeric cytokine receptor activity in vitro and in vivo. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates. Antibodies herein may also be directly or indirectly conjugated to drugs, toxins, radionuclides and the like, and these conjugates used for in vivo diagnostic or therapeutic applications. Moreover, antibodies to multimeric cytokine receptor or fragments thereof may be used in vitro to detect denatured multimeric cytokine receptor or fragments thereof in assays, for example, Western Blots or other assays known in the art.

Suitable detectable molecules may be directly or indirectly attached to the multimeric cytokine receptor or antibody, and include radionuclides, enzymes, substrates, cofactors, inhibitors, fluorescent markers, chemiluminescent markers, magnetic particles and the like. Suitable cytotoxic molecules may be directly or indirectly attached to the polypeptide or antibody, and include bacterial or plant toxins (for instance, diphtheria, toxin, saporin, *Pseudomonas* exotoxin, ricin, abrin and the like), as well as therapeutic radionuclides, such as iodine-131, rhenium-188 or yttrium-90 (either directly attached to the polypeptide or antibody, or indirectly attached through means of a chelating moiety, for instance). Multimeric cytokine receptors or antibodies may also be conjugated to cytotoxic drugs, such as adriamycin. For indirect attachment of a detectable or cytotoxic molecule, the detectable or cytotoxic molecule can be conjugated with a member of a complementary/anticomplementary pair, where the other member is bound to the polypeptide or antibody portion. For these purposes, biotin/streptavidin is an exemplary complementary/anticomplementary pair.

A soluble multimeric cytokine receptor can also act as zcytor17lig "antagonists" to block zcytor17lig binding and signal transduction in vitro and in vivo. These anti-zcytor17lig binding proteins would be useful for inhibiting zcytor17lig activity or protein-binding.

Polypeptide-toxin fusion proteins or antibody-toxin fusion proteins can be used for targeted cell or tissue inhibition or ablation (for instance, to treat cancer cells or tissues). Alternatively, if the polypeptide has multiple functional domains (i.e., an activation domain or a receptor binding domain, plus a targeting domain), a fusion protein including only the targeting domain may be suitable for directing a detectable molecule, a cytotoxic molecule or a complementary molecule to a cell or tissue type of interest. In instances where the domain only fusion protein includes a complementary molecule, the anti-complementary molecule can be conjugated to a detectable or cytotoxic molecule. Such domain-complementary molecule fusion proteins thus represent a generic targeting vehicle for cell/tissue-specific delivery of generic anti-complementary-detectable/cytotoxic molecule conjugates.

Moreover, inflammation is a protective response by an organism to fend off an invading agent. Inflammation is a cascading event that involves many cellular and humoral mediators. On one hand, suppression of inflammatory responses can leave a host immunocompromised; however, if left unchecked, inflammation can lead to serious complications including chronic inflammatory diseases (e.g., rheumatoid arthritis, multiple sclerosis, inflammatory bowel disease and the like), septic shock and multiple organ failure. Importantly, these diverse disease states share common inflammatory mediators. The collective diseases that are characterized by inflammation have a large impact on human morbidity and mortality. Therefore it is clear that anti-inflammatory antibodies and binding polypeptides, such as anti-zcytor17lig antibodies and binding polypeptides described herein, could have crucial therapeutic potential for a vast number of human and animal diseases, from asthma and allergy to autoimmunity and septic shock. As such, use of anti-inflammatory anti zcytor17lig antibodies and binding polypeptides described herein can be used therapeutically as zcytor17lig antagonists described herein, particularly in diseases such as arthritis, endotoxemia, inflammatory bowel disease, psoriasis, related disease and the like.

Arthritis

Arthritis, including osteoarthritis, rheumatoid arthritis, arthritic joints as a result of injury, and the like, are common inflammatory conditions which would benefit from the therapeutic use of anti-inflammatory antibodies and binding polypeptides, such as anti-zcytor17lig antibodies and binding polypeptides of the present invention. For example, rheumatoid arthritis (RA) is a systemic disease that affects the entire body and is one of the most common forms of arthritis. It is characterized by the inflammation of the membrane lining the joint, which causes pain, stiffness, warmth, redness and swelling. Inflammatory cells release enzymes that may digest bone and cartilage. As a result of rheumatoid arthritis, the inflamed joint lining, the synovium, can invade and damage bone and cartilage leading to joint deterioration and severe pain amongst other physiologic effects. The involved joint can lose its shape and alignment, resulting in pain and loss of movement.

Rheumatoid arthritis (RA) is an immune-mediated disease particularly characterized by inflammation and subsequent tissue damage leading to severe disability and increased mortality. A variety of cytokines are produced locally in the rheumatoid joints. Numerous studies have demonstrated that IL-1 and TNF-alpha, two prototypic pro-inflammatory cytokines, play an important role in the mechanisms involved in synovial inflammation and in progressive joint destruction. Indeed, the administration of TNF-alpha and IL-1 inhibitors in patients with RA has led to a dramatic improvement of clinical and biological signs of inflammation and a reduction of radiological signs of bone erosion and cartilage destruction. However, despite these encouraging results, a significant percentage of patients do not respond to these agents, suggesting that other mediators are also involved in the pathophysiology of arthritis (Gabay, *Expert. Opin. Biol. Ther.* 2(2): 135-149, 2002). One of those mediators could be zcytor17lig, and as such a molecule that binds or inhibits zcytor17lig, such as anti zcytor17lig antibodies or binding partners, could serve as a valuable therapeutic to reduce inflammation in rheumatoid arthritis, and other arthritic diseases.

There are several animal models for rheumatoid arthritis known in the art. For example, in the collagen-induced arthritis (CIA) model, mice develop chronic inflammatory arthritis that closely resembles human rheumatoid arthritis. Since CIA shares similar immunological and pathological features with RA, this makes it an ideal model for screening potential human anti-inflammatory compounds. The CIA model is a well-known model in mice that depends on both an immune response, and an inflammatory response, in order to occur. The immune response comprises the interaction of B-cells and CD4+ T-cells in response to collagen, which is given as antigen, and leads to the production of anti-collagen antibodies. The inflammatory phase is the result of tissue responses from mediators of inflammation, as a consequence of some of these antibodies cross-reacting to the mouse's native collagen and activating the complement cascade. An advantage in using the CIA model is that the basic mechanisms of pathogenesis are known. The relevant T-cell and B-cell epitopes on type II collagen have been identified, and various immunological (e.g., delayed-type hypersensitivity and anti-collagen antibody) and inflammatory (e.g., cytokines, chemokines, and matrix-degrading enzymes) parameters relating to immune-mediated arthritis have been determined, and can thus be used to assess test compound efficacy in the CIA model (Wooley, *Curr. Opin. Rheum.* 3:407-20, 1999; Williams et al., *Immunol.* 89:9784-788, 1992; Myers et al., *Life Sci.* 61:1861-78, 1997; and Wang et al., *Immunol.* 92:8955-959, 1995).

The administration of soluble zcytor17 comprising polypeptides (including heterodimeric and multimeric receptors described herein), such as zcytor17-Fc4 or other zcytor17 soluble and fusion proteins to these CIA model mice was used to evaluate the use of zcytor17 to ameliorate symptoms and alter the course of disease. As a molecule that modulates immune and inflammatory response, zcytor17lig, may induce production of SAA, which is implicated in the pathogenesis of rheumatoid arthritis, zcytor17lig antagonists may reduce SAA activity in vitro and in vivo, the systemic or local administration of zcytor17lig antagonists such as anti-zcytor17lig antibodies or binding partners, zcytor17 comprising polypeptides (including heterodimeric and multimeric receptors described herein), such as zcytor17-Fc4 or other zcytor17 soluble and fusion proteins can potentially suppress the inflammatory response in RA. Other potential therapeutics include zcytor17 polypeptides, soluble heterodimeric and multimeric receptor polypeptides, or anti zcytor17lig antibodies or binding partners of the present invention, and the like.

Endotoxemia

Endotoxemia is a severe condition commonly resulting from infectious agents such as bacteria and other infectious disease agents, sepsis, toxic shock syndrome, or in immunocompromised patients subjected to opportunistic infections, and the like. Therapeutically useful of anti-inflammatory antibodies and binding polypeptides, such as anti-zcytor17lig antibodies and binding polypeptides of the present invention, could aid in preventing and treating endotoxemia in humans and animals. Other potential therapeutics include zcytor17 polypeptides, soluble heterodimeric and multimeric receptor polypeptides, or anti zcytor17lig antibodies or binding partners of the present invention, and the like, could serve as a valuable therapeutic to reduce inflammation and pathological effects in endotoxemia.

Lipopolysaccharide (LPS) induced endotoxemia engages many of the proinflammatory mediators that produce pathological effects in the infectious diseases and LPS induced endotoxemia in rodents is a widely used and acceptable model for studying the pharmacological effects of potential pro-inflammatory or immunomodulating agents. LPS, produced in gram-negative bacteria, is a major causative agent in the pathogenesis of septic shock (Glausner et al., *Lancet* 338:732, 1991). A shock-like state can indeed be induced experimentally by a single injection of LPS into animals. Molecules produced by cells responding to LPS can target pathogens directly or indirectly. Although these biological responses protect the host against invading pathogens, they may also cause harm. Thus, massive stimulation of innate immunity, occurring as a result of severe Gram-negative bacterial infection, leads to excess production of cytokines and other molecules, and the development of a fatal syndrome, septic shock syndrome, which is characterized by fever, hypotension, disseminated intravascular coagulation, and multiple organ failure (Dumitru et al. *Cell* 103:1071-1083, 2000).

These toxic effects of LPS are mostly related to macrophage activation leading to the release of multiple inflammatory mediators. Among these mediators, TNF appears to play a crucial role, as indicated by the prevention of LPS toxicity by the administration of neutralizing anti-TNF antibodies (Beutler et al., *Science* 229:869, 1985). It is well established that 1 ug injection of *E. coli* LPS into a C57Bl/6 mouse will result in significant increases in circulating IL-6, TNF-alpha, IL-1, and acute phase proteins (for example, SAA) approximately 2 hours post injection. The toxicity of LPS appears to be mediated by these cytokines as passive immunization against these mediators can result in decreased mortality (Beutler et al., *Science* 229:869, 1985). The potential immunointervention strategies for the prevention and/or treatment of septic shock include anti-TNF mAb, IL-1 receptor antagonist, LIF, IL-10, and G-CSF. Since LPS induces the production of pro-inflammatory factors possibly contributing to the pathology of endotoxemia, the neutralization of zcytor17lig activity, SAA or other pro-inflammatory factors by antagonizing zcytor17lig polypeptide can be used to reduce the symptoms of endotoxemia, such as seen in endotoxic shock. Other potential therapeutics include zcytor17 polypeptides, soluble heterodimeric and multimeric receptor polypeptides, or anti-zcytor17lig antibodies or binding partners of the present invention, and the like.

Inflammatory Bowel Disease. IBD

In the United States approximately 500,000 people suffer from Inflammatory Bowel Disease (IBD) which can affect either colon and rectum (Ulcerative colitis) or both, small and large intestine (Crohn's Disease). The pathogenesis of these diseases is unclear, but they involve chronic inflammation of the affected tissues. Potential therapeutics include zcytor17 polypeptides, soluble heterodimeric and multimeric receptor polypeptides, or anti-zcytor17lig antibodies or binding partners of the present invention, and the like, could serve as a valuable therapeutic to reduce inflammation and pathological effects in IBD and related diseases.

Ulcerative colitis (UC) is an inflammatory disease of the large intestine, commonly called the colon, characterized by inflammation and ulceration of the mucosa or innermost lining of the colon. This inflammation causes the colon to empty frequently, resulting in diarrhea. Symptoms include loosening of the stool and associated abdominal cramping, fever and weight loss. Although the exact cause of UC is unknown, recent research suggests that the body's natural defenses are operating against proteins in the body which the body thinks are foreign (an "autoimmune reaction"). Perhaps because they resemble bacterial proteins in the gut, these proteins may either instigate or stimulate the inflammatory process that begins to destroy the lining of the colon. As the lining of the colon is destroyed, ulcers form releasing mucus, pus and blood. The disease usually begins in the rectal area and may eventually extend through the entire large bowel. Repeated episodes of inflammation lead to thickening of the wall of the intestine and rectum with scar tissue. Death of colon tissue or sepsis may occur with severe disease. The symptoms of ulcerative colitis vary in severity and their onset may be gradual or sudden. Attacks may be provoked by many factors, including respiratory infections or stress.

Although there is currently no cure for UC available, treatments are focused on suppressing the abnormal inflammatory process in the colon lining. Treatments including corticosteroids immunosuppressives (eg. azathioprine, mercaptopurine, and methotrexate) and aminosalicytates are available to treat the disease. However, the long-term use of immunosuppressives such as corticosteroids and azathioprine can result in serious side effects including thinning of bones, cataracts, infection, and liver and bone marrow effects. In the patients in whom current therapies are not successful, surgery is an option. The surgery involves the removal of the entire colon and the rectum.

There are several animal models that can partially mimic chronic ulcerative colitis. The most widely used model is the 2,4,6-trinitrobenesulfonic acid/ethanol (TNBS) induced colitis model, which induces chronic inflammation and ulceration in the colon. When TNBS is introduced into the colon of susceptible mice via intra-rectal instillation, it induces T-cell mediated immune response in the colonic mucosa, in this case leading to a massive mucosal inflammation characterized by the dense infiltration of T-cells and macrophages throughout the entire wall of the large bowel. Moreover, this histopathologic picture is accompanies by the clinical picture of progressive weight loss (wasting), bloody diarrhea, rectal prolapse, and large bowel wall thickening (Neurath et al. *Intern. Rev. Immunol.* 19:51-62, 2000).

Another colitis model uses dextran sulfate sodium (DSS), which induces an acute colitis manifested by bloody diarrhea, weight loss, shortening of the colon and mucosal ulceration with neutrophil infiltration. DSS-induced colitis is characterized histologically by infiltration of inflammatory cells into the lamina propria, with lymphoid hyperplasia, focal crypt damage, and epithelial ulceration. These changes are thought to develop due to a toxic effect of DSS on the epithelium and by phagocytosis of lamina propria cells and production of TNF-alpha and IFN-gamma. Despite its common use, several issues regarding the mechanisms of DSS about the relevance to the human disease remain unresolved. DSS is regarded as a T cell-independent model because it is observed in T cell-deficient animals such as SCID mice.

The administration of anti-zcytor17lig antibodies or binding partners, soluble zcytor17 comprising polypeptides (including heterodimeric and multimeric receptors), such as zcytor17-Fc4 or other zcytor17 soluble and fusion proteins to these TNBS or DSS models can be used to evaluate the use of zcytor17lig antagonists to ameliorate symptoms and alter the course of gastrointestinal disease. Zcytor17lig may play a role in the inflammatory response in colitis, and the neutralization of zcytor17lig activity by administrating zcytor17lig antagonists is a potential therapeutic approach for IBD. Other potential therapeutics include zcytor17 polypeptides, soluble heterodimeric and multimeric receptor polypeptides, or anti-zcytor17lig antibodies or binding partners of the present invention, and the like.

Psoriasis

Psoriasis is a chronic skin condition that affects more than seven million Americans. Psoriasis occurs when new skin cells grow abnormally, resulting in inflamed, swollen, and scaly patches of skin where the old skin has not shed quickly enough. Plaque psoriasis, the most common form, is characterized by inflamed patches of skin ("lesions") topped with silvery white scales. Psoriasis may be limited to a few plaques or involve moderate to extensive areas of skin, appearing most commonly on the scalp, knees, elbows and trunk. Although it is highly visible, psoriasis is not a contagious disease. The pathogenesis of the diseases involves chronic inflammation of the affected tissues. Zcytor17 polypeptides, soluble heterodimeric and multimeric receptor polypeptides, or anti-zcytor17lig antibodies or binding partners of the present invention, and the like, could serve as a valuable therapeutic to reduce inflammation and pathological effects in psoriasis, other inflammatory skin diseases, skin and mucosal allergies, and related diseases.

Psoriasis is a T-cell mediated inflammatory disorder of the skin that can cause considerable discomfort. It is a disease for which there is no cure and affects people of all ages. Psoriasis affects approximately two percent of the populations of European and North America. Although individuals with mild psoriasis can often control their disease with topical agents, more than one million patients worldwide require ultraviolet or systemic immunosuppressive therapy. Unfortunately, the inconvenience and risks of ultraviolet radiation and the toxicities of many therapies limit their long-term use. Moreover, patients usually have recurrence of psoriasis, and in some cases rebound, shortly after stopping immunosuppressive therapy.

Differentiation is a progressive and dynamic process, beginning with pluripotent stem cells and ending with terminally differentiated cells. Pluripotent stem cells that can regenerate without commitment to a lineage express a set of differentiation markers that are lost when commitment to a cell lineage is made. Progenitor cells express a set of differentiation markers that may or may not continue to be expressed as the cells progress down the cell lineage pathway toward maturation. Differentiation markers that are expressed exclusively by mature cells are usually functional properties such as cell products, enzymes to produce cell products, and receptors. The stage of a cell population's differentiation is monitored by identification of markers present in the cell population.

There is evidence to suggest that factors that stimulate specific cell types down a pathway towards terminal differentiation or dedifferentiation affect the entire cell population originating from a common precursor or stem cell.

A multimeric cytokine receptor of the present invention can be useful for stimulating proliferation, activation, differentiation and/or induction or inhibition of specialized cell function of cells of the involved homeostasis of the hematopoiesis and immune function. In particular, multimeric cytokine receptors as described herein are useful for stimulating proliferation, activation, differentiation, induction or inhibition of specialized cell functions of cells of the hematopoietic lineages, including, but not limited to, T cells, B cells, monocytes/macrophages, NK cells, neutrophils, endothelial cells, fibroblasts, eosinophils, chondrocytes, mast cells, langerhan cells, monocytes, and macrophages, as well as epithelial cells. Epithelial cells include, for example, ameloblasts, chief cells, chromatophores, enterochramaffin cells, enterochromaffin-like cells, goblet cells, granulosa cells, keratinocytes, dendritic cells, labyrinth supporting cells, melanocytes, merkel cells, paneth cells, parietal cells, sertoli cells, and the like.

The present invention also provides a method for reducing hematopoietic cells and hematopoietic cell progenitors of a mammal. The method includes culturing bone marrow or peripheral blood cells with a composition comprising an effective amount of a soluble multimeric cytokine receptor to produce a decrease in the number of lymphoid cells in the bone marrow or peripheral blood cells as compared to bone marrow or peripheral blood cells cultured in the absence of the multimeric cytokine receptor. The hematopoietic cells and hematopoietic cell progenitors can be lymphoid cells, such as monocytic cells, macrophages, or T cells.

The present invention also provides a method of inhibiting an immune response in a mammal exposed to an antigen or pathogen. The method includes (a) determining directly or indirectly the level of antigen or pathogen present in the mammal; (b) administering a composition comprising a soluble multimeric cytokine receptor in an acceptable pharmaceutical vehicle; (c) determining directly or indirectly the level of antigen or pathogen in the mammal; and (d) comparing the level of the antigen or pathogen in step (a) to the antigen or pathogen level in step (c), wherein a change in the level is indicative of inhibiting an immune response. The method may further include (e) re-administering a composition comprising a multimeric cytokine receptor in an acceptable pharmaceutical vehicle; (f) determining directly or indirectly the level of antigen or pathogen in the mammal; and (g) comparing the number of the antigen or pathogen level in step (a) to the antigen level in step (f), wherein a change in the level is indicative of inhibiting an immune response.

Alternatively, the method can include (a) determining a level of an antigen- or pathogen-specific antibody; (b) administering a composition comprising a soluble multimeric cytokine receptor in an acceptable pharmaceutical vehicle; (c) determining a post administration level of antigen- or pathogen-specific antibody; (d) comparing the level of antibody in step (a) to the level of antibody in step (c), wherein a decrease in antibody level is indicative of inhibiting an immune response.

Zcytor17lig was isolated from tissue known to have important immunological function and which contain cells that play a role in the immune system. Zcytor17lig is expressed in CD3+ selected, activated peripheral blood cells, and it has been shown that zcytor17lig expression increases after T cell activation. Moreover, results of experiments described in the Examples section herein suggest that a multimeric or heterodimeric cytokine receptor of the present invention can have an effect on the growth/expansion of monocytes/macrophages, T-cells, B-cells, NK cells and/or differentiated state of monocytes/macrophages, T-cells, B-cells, NK cells or these cells' progenitors. Factors that both stimulate proliferation of hematopoietic progenitors and activate mature cells are generally known, however, proliferation and activation can also require additional growth factors. For example, it has been shown that IL-7 and Steel Factor (c-kit ligand) were required for colony formation of NK progenitors. IL-15 plus IL-2 in combination with IL-7 and Steel Factor was more effective (Mrozek et al., *Blood* 87:2632-2640, 1996). However, unidentified cytokines may be necessary for proliferation of specific subsets of NK cells and/or NK progenitors (Robertson et. al., *Blood* 76:2451-2438, 1990). Similarly, zcytor17lig may act alone or in concert or synergy with other cytokines to enhance growth, proliferation expansion and modification of differentiation of monocytes/macrophages, T-cells, B-cells or NK cells.

Assays measuring differentiation include, for example, measuring cell markers associated with stage-specific expression of a tissue, enzymatic activity, functional activity or morphological changes (Watt, *FASEB*, 5:281-284 (1991); Francis, *Differentiation* 57:63-75 (1994); and Raes, *Adv. Anim. Cell Biol. Technol. Bioprocesses*, 161-171 (1989)). Alternatively, zcytor17lig polypeptide itself can serve as an additional cell-surface or secreted marker associated with stage-specific expression of a tissue. As such, direct measurement of zcytor17lig polypeptide, or its loss of expression in a tissue as it differentiates, can serve as a marker for differentiation of tissues.

Similarly, direct measurement of zcytor17lig polypeptide, or its loss of expression in a tissue can be determined in a tissue or in cells as they undergo tumor progression. Increases in invasiveness and motility of cells, or the gain or loss of expression of zcytor17lig in a pre-cancerous or cancerous condition, in comparison to normal tissue, can serve as a diagnostic for transformation, invasion and metastasis in tumor progression. As such, knowledge of a tumor's stage of progression or metastasis will aid the physician in choosing the most proper therapy, or aggressiveness of treatment, for a given individual cancer patient. Methods of measuring gain and loss of expression (of either mRNA or protein) are well known in the art and described herein and can be applied to zcytor17lig expression. For example, appearance or disappearance of polypeptides that regulate cell motility can be used to aid diagnosis and prognosis of prostate cancer (Banyard, J. and Zetter, B. R., *Cancer and Metast. Rev.* 17:449-458, 1999). As an effector of cell motility, zcytor17lig gain or loss of expression may serve as a diagnostic for lymphoid, B-cell, epithelial, hematopoietic and other cancers.

Moreover, the activity and effect of zcytor17lig on tumor progression and metastasis can be measured in vivo. Several syngeneic mouse models have been developed to study the influence of polypeptides, compounds or other treatments on tumor progression. In these models, tumor cells passaged in culture are implanted into mice of the same strain as the tumor donor. The cells will develop into tumors having similar characteristics in the recipient mice, and metastasis will also occur in some of the models. Appropriate tumor models for our studies include the Lewis lung carcinoma (ATCC No. CRL-1642) and B16 melanoma (ATCC No. CRL-6323), amongst others. These are both commonly used tumor lines, syngeneic to the C57BL6/J mouse, that are readily cultured and manipulated in vitro. Tumors resulting from implantation of either of these cell lines are capable of metastasis to the lung in C57BL6/J mice. The Lewis lung carcinoma model has recently been used in mice to identify an inhibitor of angiogenesis (O'Reilly M S, et al. *Cell* 79: 315-328, 1994). C57BL6/J mice are treated with an experimental agent either through daily injection of recombinant protein, agonist or antagonist or a one time injection of recombinant adenovirus. Three days following this treatment, $10^5$ to $10^6$ cells are implanted under the dorsal skin. Alternatively, the cells themselves may be infected with recombinant adenovirus, such as one expressing zcytor17lig, before implantation so that the protein is synthesized at the tumor site or intracellularly, rather than systemically. The mice normally develop visible tumors within 5 days. The tumors are allowed to grow for a period of up to 3 weeks, during which time they may reach a size of 1500-1800 mm$^3$ in the control treated group. Tumor size and body weight are carefully monitored throughout the experiment. At the time of sacrifice, the tumor is removed and weighed along with the lungs and the liver. The lung weight has been shown to correlate well with metastatic tumor burden. As an additional measure, lung surface metastases are counted. The resected tumor, lungs and liver are prepared for histopathological examination, immunohistochemistry, and in situ hybridization, using methods known in the art and described herein. The influence of the expressed polypeptide in question, e.g., zcytor17lig, on the ability of the tumor to recruit vasculature and undergo metastasis can thus be assessed. In addition, aside from using adenovirus, the implanted cells can be transiently transfected with zcytor17lig. Use of stable zcytor17lig transfectants as well as use of induceable promoters to activate zcytor17lig expression in vivo are known in the art and can be used in this system to assess zcytor17lig induction of metastasis. Moreover, purified zcytor17lig or zcytor17lig conditioned media can be directly injected in to this mouse model, and hence be used in this system. For general reference see, O'Reilly M S, et al. *Cell* 79:315-328, 1994; and Rusciano D, et al. Murine Models of Liver Metastasis. *Invasion Metastasis* 14:349-361, 1995.

A soluble multimeric cytokine receptor of the present invention or antibodies thereto may be useful in treating tumorgenesis, and therefore would be useful in the treatment of cancer. Zcytor17lig is expressed in activated T-cells, monocytes and macrophages, and is linked to a region of the human chromosome wherein translocations are common in leukemias. Moreover, the zcytor17lig is shown to act through a cytokine receptor, zcytor17 multimeric cytokine receptor, which is also expressed in activated T-cells, monocytes and macrophages. Over stimulation of activated T-cells, monocytes and macrophages by zcytor17lig could result in a human disease state such as an immune cell cancer. As such, identifying zcytor17lig expression, polypeptides (e.g., by anti-zcytor17lig antibodies, zcytor17 soluble multimeric cytokine receptors (e.g., zcytor17 receptor, heterodimers (e.g., zcytor17/OSMRbeta, zcytor17/WSX-1), multimers (e.g., zcytor17/OSMRbeta/WSX-1)), or other zcytor17lig binding partners) can serve as a diagnostic, and can serve as antagonists of zcytor17lig proliferative activity. The ligand could be administered in combination with other agents already in use including both conventional chemotherapeutic agents as well as immune modulators such as interferon alpha. Alpha/beta interferons have been shown to be effective in treating some leukemias and animal disease models, and the growth inhibitory effects of interferon-alpha and zcytor17lig may be additive.

NK cells are thought to play a major role in elimination of metastatic tumor cells and patients with both metastases and solid tumors have decreased levels of NK cell activity (Whiteside et. al., *Curr. Top. Microbiol. Immunol.* 230:221-244, 1998). An agent that stimulates NK cells would be useful in the elimination of tumors.

The present invention provides a method of reducing proliferation of a neoplastic monocytes/macrophages comprising administering to a mammal with a monocyte/macrophage neoplasm an amount of a composition including a soluble multimeric cytokine receptor or antibody thereto sufficient to reduce proliferation of the neoplastic monocytes/macrophages.

The present invention provides a method for inhibiting activation or differentiation of monocytes/macrophages. Monocytes are incompletely differentiated cells that migrate to various tissues where they mature and become macrophages. Macrophages play a central role in the immune response by presenting antigen to lymphocytes and play a supportive role as accessory cells to lymphocytes by secreting numerous cytokines. Macrophages can internalize extracellular molecules and upon activation have an increased ability to kill intracellular microorganisms and tumor cells. Activated macrophages are also involved in stimulating acute or local inflammation.

In another aspect, the present invention provides a method of reducing proliferation of a neoplastic B or T-cells comprising administering to a mammal with a B or T cell neoplasm an amount of a composition including a soluble multimeric cytokine receptor sufficient to reducing proliferation of the neoplastic monocytes/macrophages. Furthermore, the zcytor17lig antagonist can be a ligand/toxin fusion protein.

A zcytor17 multimeric cytokine receptor-saporin fusion toxin may be employed against a similar set of leukemias and lymphomas, extending the range of leukemias that can be treated with a cytokine antagonist. For example, such leukemias can be those that over-express zcytor17 receptors (e.g., zcytor17 receptor, heterodimers (e.g., zcytor17/OSMRbeta, zcytor17/WSX-1), multimers (e.g., zcytor17/OSMRbeta/WSX)). Fusion toxin mediated activation of the zcytor17 receptor, zcytor17 receptor heterodimers or multimers (e.g., zcytor17/OSMRbeta, zcytor17/WSX-1 or zcytor17/WSX-1/OSMR) provides two independent means to inhibit the growth of the target cells, the first being identical to the effects seen by the ligand alone, and the second due to delivery of the toxin through receptor internalization. The lymphoid and monocyte restricted expression pattern of the zcytor17 receptor suggests that the ligand-saporin conjugate can be tolerated by patients.

The tissue distribution of receptors for a given cytokine offers a strong indication of the potential sites of action of that cytokine. Expression of zcytor17 was seen in monocytes and B-cells, with a dramatic increase of expression upon activation for CD3+, CD4+, and CD8+ T-cells. In addition, two monocytic cell lines, THP-1 (Tsuchiya et al., *Int. J. Cancer*

26:171-176, 1980) and U937 (Sundstrom et al., *Int. J. Cancer* 17:565-577, 1976), were also positive for zcytor17 expression.

Northern analysis of WSX-1 receptor revealed transcripts in all tissues examined, with increased levels of expression in human spleen, thymus, lymph node, bone marrow, and peripheral blood leukocytes. Also, expression levels of WSX-1 increased upon activation of T-cells.

Expression of OSMR is reported to be very broad (Mosley et al, *JBC* 271:32635-32643, 1996). This distribution of zcytor17, WSX-1, and OSMRbeta receptors supports a role for zcytor17lig in immune responses, especially expansion of T-cells upon activation or a role in the monocyte/macrophage arm of the immune system.

Thus, particular embodiments of the present invention are directed toward use of a soluble multimeric cytokine receptor, for instance zcytor17/WSX-1/OSMR, and zcytor17/OSMR heterodimers, as antagonists in inflammatory and immune diseases or conditions such as pancreatitis, type I diabetes (IDDM), pancreatic cancer, pancreatitis, Graves Disease, inflammatory bowel disease (IBD), Crohn's Disease, colon and intestinal cancer, diverticulosis, autoimmune disease, sepsis, organ or bone marrow transplant; inflammation due to trauma, surgery or infection; amyloidosis; splenomegaly; graft versus host disease; and where inhibition of inflammation, immune suppression, reduction of proliferation of hematopoietic, immune, inflammatory or lymphoid cells, macrophages, T-cells (including Th1 and Th2 cells, CD4+ and CD8+ cells), suppression of immune response to a pathogen or antigen. Moreover the presence of zcytor17 expression in activated immune cells such as activated CD4+ and CD19+ cells showed that zcytor17 receptor may be involved in the body's immune defensive reactions against foreign invaders: such as microorganisms and cell debris, and could play a role in immune responses during inflammation and cancer formation. As such, antibodies and binding partners of the present invention that are agonistic or antagonistic to zcytor17 receptor function, such as a soluble zcytor17 multimeric cytokine receptor, can be used to modify immune response and inflammation.

The zcytor17lig structure and tissue expression suggests a role in early hematopoietic or thymocyte development and immune response regulation or inflammation. These processes involve stimulation of cell proliferation and differentiation in response to the binding of one or more cytokines to their cognate receptors. In view of the tissue distribution observed for this zcytor17lig, agonists (including the natural receptor(s)) and antagonists have enormous potential in both in vitro and in vivo applications. Compounds identified as zcytor17lig agonists are useful for stimulating proliferation and development of target cells in vitro and in vivo. For example, agonist compounds, zcytor17lig, or anti-zcytor17lig antibodies, are useful as components of defined cell culture media, and may be used alone or in combination with other cytokines and hormones to replace serum that is commonly used in cell culture. Agonists are thus useful in specifically promoting the growth and/or development or activation of monocytes, T-cells, B-cells, and other cells of the lymphoid and myeloid lineages, and hematopoietic cells in culture.

The molecules of the present invention have particular use in the monocyte/macrophage arm of the immune system. Methods are known that can assess such activity. For example, interferon gamma (IFNγ) is a potent activator of mononuclear phagocytes. For example, an increase in expression of zcytor17 upon activation of THP-1 cells (ATCC No. TIB-202) with interferon gamma could suggest that this receptor is involved in monocyte activation. Monocytes are incompletely differentiated cells that migrate to various tissues where they mature and become macrophages. Macrophages play a central role in the immune response by presenting antigen to lymphocytes and play a supportive role as accessory cells to lymphocytes by secreting numerous cytokines. Macrophages can internalize extracellular molecules and upon activation have an increased ability to kill intracellular microorganisms and tumor cells. Activated macrophages are also involved in stimulating acute or local inflammation. Moreover, monocyte-macrophage function has been shown to be abnormal in a variety of diseased states. For example see, Johnston, R B, *New Eng. J. Med.* 318:747-752, 1998.

One of skill in the art would recognize that agonists of zcytor17 multimeric cytokine receptor, such as zcytor17lig, are useful. For example, depressed migration of monocytes has been reported in populations with a predisposition to infection, such as newborn infants, patients receiving corticosteroid or other immunosuppressive therapy, and patients with diabetes mellitus, burns, or AIDS. Agonists for zcytor17 multimeric cytokine receptor, such as zcytor17lig, could result in an increase in the ability of monocytes to migrate and possibly prevent infection in these populations. There is also a profound defect of phagocytic killing by mononuclear phagocytes from patients with chronic granulomatous disease. This results in the formation of subcutaneous abscesses, as well as abscesses in the liver, lungs, spleen, and lymph nodes. An agonist of zcytor17 multimeric cytokine receptor, such as zcytor17lig, could correct or improve this phagocytic defect. In addition, defective monocyte cytotoxicity has been reported in patients with cancer and Wiskott-Aldrich syndrome (eczema, thrombocytopenia, and recurrent infections). Activation of monocytes by agonists of zcytor17 multimeric cytokine receptor, such as zcytor17lig, could aid in treatment of these conditions. The monocyte-macrophage system is prominently involved in several lipid-storage diseases (sphingolipidoses) such as Gaucher's disease. Resistance to infection can be impaired because of a defect in macrophage function, which could be treated by agonists to zcytor17 multimeric cytokine receptor such as zcytor17lig.

Moreover, one of skill in the art would recognize that antagonists of a zcytor17 multimeric cytokine receptor are useful. For example, in atherosclerotic lesions, one of the first abnormalities is localization of monocyte/macrophages to endothelial cells. These lesions could be prevented by use of antagonists to zcytor17lig. Zcytor17 soluble multimeric cytokine receptors, such as, for instance, heterodimers and trimers, can also be used as antagonists to the zcytor17lig. Moreover, monoblastic leukemia is associated with a variety of clinical abnormalities that reflect the release of the biologic products of the macrophage, examples include high levels of lysozyme in the serum and urine and high fevers. Moreover, such leukemias exhibit an abnormal increase of monocytic cells. These effects could possibly be prevented by antagonists to zcytor17lig, such as described herein.

Using methods known in the art, and disclosed herein, one of skill could readily assess the activity of a zcytor17 multimeric cytokine receptor in the disease states disclosed herein, inflammation, cancer, or infection as well as other disease states involving monocytic cells. In addition, as zcytor17lig is expressed in a T-cell, macrophage and monocyte-specific manner, and these diseases involve abnormalities in monocytic cells, such as cell proliferation, function, localization, and activation, the polynucleotides, polypeptides, and antibodies of the present invention can be used to as diagnostics to detect such monocytic cell abnormalities, and indicate the presence of disease. Such methods involve taking a biological sample from a patient, such as blood, saliva, or biopsy, and comparing it to a normal control sample. Histological, cytological, flow cytometric, biochemical and other methods can be used to determine the relative levels or localization of zcytor17lig, or cells expressing zcytor17lig, i.e., monocytes, in the patient sample compared to the normal control. A change in the level (increase or decrease) of zcytor17lig expression, or a change in number or localization of monocytes (e.g., increase or infiltration of monocytic cells in tissues where they are not normally present) compared to a control would be indicative of disease. Such diagnostic methods can also include using radiometric, fluorescent, and colorimetric tags attached to polynucleotides, polypeptides or antibodies of the present invention. Such methods are well known in the art and disclosed herein.

Amino acid sequences having zcytor17lig activity can be used to modulate the immune system by binding soluble zcytor17 multimeric cytokine receptor, and thus, preventing the binding of zcytor17lig with endogenous zcytor17lig receptor. Zcytor17lig antagonists, such as a zcytor17 multimeric cytokine receptor, can also be used to modulate the immune system by inhibiting the binding of Zcytor17 ligand with the endogenous zcytor17lig receptor. Accordingly, the present invention includes the use of a multimeric cytokine receptor that can be also used to treat a subject which produces an excess of either zcytor17lig or Zcytor17 comprising receptor(s). Suitable subjects include mammals, such as humans or veterinary animals.

Zcytor17lig has been shown to be expressed in activated mononuclear cells, and may be involved in regulating inflammation. As such, polypeptides of the present invention can be assayed and used for their ability to modify inflammation, or can be used as a marker for inflammation. Methods to determine proinflammatory and antiinflammatory qualities of zcytor17lig are known in the art and discussed herein. Moreover, it may be involved in up-regulating the production of acute phase reactants, such as serum amyloid A (SAA), α1-antichymotrypsin, and haptoglobin, and that expression of zcytor17 receptor ligand may be increased upon injection of lipopolysaccharide (LPS) in vivo that are involved in inflammatory response (Dumoutier, L. et al., *Proc. Nat'l. Acad. Sci.* 97:10144-10149 (2000)). Production of acute phase proteins, such as SAA, is considered a short-term survival mechanism where inflammation is beneficial; however, maintenance of acute phase proteins for longer periods contributes to chronic inflammation and can be harmful to human health. For review, see Uhlar, C M and Whitehead, A S, *Eur. J. Biochem.* 265:501-523 (1999); and Baumann H. and Gauldie, *J. Immunology Today* 15:74-80 (1994). Moreover, the acute phase protein SAA is implicated in the pathogenesis of several chronic inflammatory diseases, is implicated in atherosclerosis and rheumatoid arthritis, and is the precursor to the amyloid A protein deposited in amyloidosis (Uhlar, C M and Whitehead, supra.). Thus, where a ligand such as zcytor17lig that acts as a pro-inflammatory molecule and induces production of SAA, antagonists would be useful in treating inflammatory disease and other diseases associated with acute phase response proteins induced by the ligand. Such antagonists are provided by the present invention. For example, a method of reducing inflammation comprises administering to a mammal with or at risk of developing inflammation an amount of a composition of a soluble multimeric cytokine receptor that is sufficient to reduce inflammation. Moreover, a method of suppressing an inflammatory response in a mammal with inflammation can comprise: (1) determining a level of serum amyloid A protein; (2) administering a composition comprising a soluble multimeric cytokine receptor polypeptide as described herein in an acceptable pharmaceutical vehicle; (3) determining a post administration level of serum amyloid A protein; (4) comparing the level of serum amyloid A protein in step (1) to the level of serum amyloid A protein in step (3), wherein a lack of increase or a decrease in serum amyloid A protein level is indicative of suppressing an inflammatory response.

Like zcytor17lig, analysis of the tissue distribution of the mRNA corresponding it's zcytor17 receptor cDNA showed that mRNA level was highest in monocytes and prostate cells, and is elevated in activated monocytes, and activated CD4+, activated CD8+, and activated CD3+ cells. Hence, zcytor17 receptor is also implicated in inducing inflammatory and immune response. Thus, particular embodiments of the present invention are directed toward use of zcytor17lig-antibodies, and zcytor17lig, as well as soluble zcytor17 receptor heterodimers as antagonists in inflammatory and immune diseases or conditions such as pancreatitis, type I diabetes (IDDM), pancreatic cancer, pancreatitis, Graves Disease, inflammatory bowel disease (IBD), Crohn's Disease, colon and intestinal cancer, diverticulosis, autoimmune disease, sepsis, organ or bone marrow transplant; inflammation due to trauma, sugery or infection; amyloidosis; splenomegaly; graft versus host disease; and where inhibition of inflammation, immune suppression, reduction of proliferation of hematopoietic, immune, inflammatory or lymphoid cells, macrophages, T-cells (including Th1 and Th2 cells, CD4+ and CD8+ cells), suppression of immune response to a pathogen or antigen. Moreover the presence of zcytor17 receptor and zcytor17lig expression in activated immune cells such as activated CD3+, monocytes, CD4+ and CD19+ cells showed that zcytor17 receptor may be involved in the body's immune defensive reactions against foreign invaders: such as microorganisms and cell debris, and could play a role in immune responses during inflammation and cancer formation. As such, zcytor17lig and zcytor17lig-antibodies of the present invention that are agonistic or antagonistic to zcytor17 receptor function, can be used to modify immune response and inflammation.

Moreover, zcytor17lig polypeptides that bind zcytor17 multimeric cytokine receptors and antibodies thereto are useful to:

Antagonize or block signaling via a zcytor17 multimeric cytokine receptor in the treatment of acute inflammation, inflammation as a result of trauma, tissue injury, surgery, sepsis or infection, and chronic inflammatory diseases such as asthma, inflammatory bowel disease (IBD), chronic colitis, splenomegaly, rheumatoid arthritis, recurrent acute inflammatory episodes (e.g., tuberculosis), and treatment of amyloidosis, and atherosclerosis, Castleman's Disease, asthma, and other diseases associated with the induction of acute-phase response.

Antagonize or block signaling via the zcytor17 multimeric cytokine receptor in the treatment of autoimmune diseases such as IDDM, multiple sclerosis (MS), systemic Lupus erythematosus (SLE), myasthenia gravis, rheumatoid arthritis, and IBD to prevent or inhibit signaling in immune cells (e.g. lymphocytes, monocytes, leukocytes) via zcytor17 receptor (Hughes C et al., *J. Immunol* 153: 3319-3325 (1994)). Asthma, allergy and other atopic disease may be treated with an MAb against, for example, soluble zcytor17 multimeric cytokine receptors or zcytor17/CRF2-4 heterodimers, to inhibit the immune response or to deplete offending cells. Blocking or inhibiting signaling via zcytor17 multimeric cytokine receptor, using the polypeptides and antibodies of the present invention, may also benefit diseases of the pancreas, kidney, pituitary and neuronal cells. IDDM, NIDDM, pancreatitis, and pancreatic carcinoma may benefit. Zcytor17 multimeric cytokine receptor may serve as a target for MAb therapy of cancer where an antagonizing MAb inhibits cancer growth and targets immune-mediated killing. (Holliger P, and Hoogenboom, H *Nature Biotech.* 16: 1015-1016 (1998)). Mabs to soluble zcytor17 receptor monomers, homodimers, heterodimers and multimers may also be useful to treat nephropathies such as glomerulosclerosis, membranous neuropathy, amyloidosis (which also affects the kidney among other tissues), renal arteriosclerosis, glomerulonephritis of various origins, fibroproliferative diseases of the kidney, as well as kidney dysfunction associated with SLE, IDDM, type II diabetes (NIDDM), renal tumors and other diseases.

Agonize or initiate signaling via the zcytor17 multimeric cytokine receptor in the treatment of autoimmune diseases such as IDDM, MS, SLE, myasthenia gravis, rheumatoid arthritis, and IBD. Zcytor17lig may signal lymphocytes or other immune cells to differentiate, alter proliferation, or change production of cytokines or cell surface proteins that ameliorate autoimmunity. Specifically, modulation of a T-helper cell response to an alternate pattern of cytokine secretion may deviate an autoimmune response to ameliorate disease (Smith J A et al., *J. Immunol.* 160:4841-4849 (1998)). Similarly, zcytor17lig may be used to signal, deplete and deviate immune cells involved in asthma, allergy and atopoic disease. Signaling via zcytor17 multimeric cytokine receptor may also benefit diseases of the pancreas, kidney, pituitary and neuronal cells. IDDM, NIDDM, pancreatitis, and pancreatic carcinoma may benefit. Zcytor17 multimeric cytokine receptor may serve as a target for MAb therapy of pancreatic cancer where a signaling MAb inhibits cancer growth and targets immune-mediated killing (Tutt, A L et al., *J Immunol.* 161: 3175-3185 (1998)). Similarly T-cell specific leukemias, lymphomas, plasma cell dyscrasia (e.g., multiple myeloma), and carcinoma may be treated with monoclonal antibodies (e.g., neutralizing antibody) to zcytor17-comprising soluble receptors of the present invention.

Soluble zcytor17 multimeric cytokine receptors as described herein can be used to neutralize/block zcytor17 receptor ligand activity in the treatment of autoimmune disease, atopic disease, NIDDM, pancreatitis and kidney dysfunction as described above. A soluble form of zcytor17 multimeric cytokine receptor may be used to promote an antibody response mediated by T cells and/or to promote the production of IL-4 or other cytokines by lymphocytes or other immune cells.

A soluble zcytor17 multimeric cytokine receptor may be useful as antagonists of zcytor17lig. Such antagonistic effects can be achieved by direct neutralization or binding of its natural ligand. In addition to antagonistic uses, the soluble receptors can bind zcytor17lig and act as carrier or vehicle proteins, in order to transport zcytor17lig to different tissues, organs, and cells within the body. As such, the soluble receptors can be fused or coupled to molecules, polypeptides or chemical moieties that direct the soluble-receptor-ligand complex to a specific site, such as a tissue, specific immune cell, monocytes, or tumor. For example, in acute infection or some cancers, benefit may result from induction of inflammation and local acute phase response proteins. Thus, the soluble receptors described herein or antibodies thereto can be used to specifically direct the action of a pro-inflammatory zcytor17lig ligand. See, Cosman, D. *Cytokine* 5: 95-106 (1993); and Fernandez-Botran, R. *Exp. Opin. Invest. Drugs* 9:497-513 (2000).

Moreover, the soluble zcytor17 multimeric cytokine receptors can be used to stabilize the zcytor17lig, to increase the bioavailability, therapeutic longevity, and/or efficacy of the ligand by stabilizing the ligand from degradation or clearance, or by targeting the ligand to a site of action within the body. For example, the naturally occurring IL-6/soluble IL-6R complex stabilizes IL-6 and can signal through the gp130 receptor. See, Cosman, D. supra., and Fernandez-Botran, R. supra. Moreover, Zcytor17 may be combined with a cognate ligand such as its ligand to comprise a ligand/soluble receptor complex. Such complexes may be used to stimulate responses from cells presenting a companion receptor subunit. The cell specificity of zcytor17 multimeric cytokine receptor/zcytor17lig complexes may differ from that seen for the ligand administered alone. Furthermore the complexes may have distinct pharmacokinetic properties such as affecting half-life, dose/response and organ or tissue specificity. Zcytor17 multimeric cytokine receptor/ligand complexes thus may have agonist activity to enhance an immune response or stimulate mesangial cells or to stimulate hepatic cells. Alternatively, only tissues expressing a signaling subunit the heterodimerizes with the complex may be affected analogous to the response to IL6/IL6R complexes (Hirota H. et al., *Proc. Nat'l. Acad. Sci.* 92:4862-4866 (1995); and Hirano, T. in Thomason, A. (Ed.) "The Cytokine Handbook", $3^{rd}$ Ed., p. 208-209). Soluble receptor/cytokine complexes for IL12 and CNTF display similar activities.

Zcytor17lig may also be used within diagnostic systems for the detection of circulating levels of ligand, and in the detection of acute phase inflammatory response. Within a related embodiment, antibodies or other agents that specifically bind to zcytor17lig can be used to detect circulating zcytor17lig polypeptides; conversely, zcytor17lig itself can be used to detect circulating or locally-acting receptor polypeptides. Elevated or depressed levels of ligand or receptor polypeptides may be indicative of pathological conditions, including inflammation or cancer. Moreover, detection of acute phase proteins or molecules such as zcytor17lig can be indicative of a chronic inflammatory condition in certain disease states (e.g., rheumatoid arthritis). Detection of such conditions serves to aid in disease diagnosis as well as help a physician in choosing proper therapy.

Polynucleotides encoding a zcytor17 multimeric cytokine receptor are useful within gene therapy applications where it is desired to increase or inhibit zcytor17lig activity. If a mammal has a mutated or absent zcytor17 gene, the zcytor17 gene of the present invention can be introduced into the cells of the mammal. In one embodiment, a gene encoding a zcytor17 multimeric cytokine receptor is introduced in vivo in a viral vector. Such vectors include an attenuated or defective DNA virus, such as, but not limited to, herpes simplex virus (HSV), papillomavirus, Epstein Barr virus (EBV), adenovirus, adeno-associated virus (AAV), and the like. Defective viruses, which entirely or almost entirely lack viral genes, are preferred. A defective virus is not infective after introduction into a cell. Use of defective viral vectors allows for administration to cells in a specific, localized area, without concern that the vector can infect other cells. Examples of particular vectors include, but are not limited to, a defective herpes simplex virus 1 (HSV1) vector (Kaplitt et al., *Molec. Cell. Neurosci.* 2:320-30 (1991)); an attenuated adenovirus vector, such as the vector described by Stratford-Perricaudet et al., *J. Clin. Invest.* 90:626-30 (1992); and a defective adeno-associated virus vector (Samulski et al., *J. Virol.* 61:3096-101 (1987); and Samulski et al., *J. Virol.* 63:3822-8 (1989)).

A zcytor17 gene of the present invention can be introduced in a retroviral vector, e.g., as described in Anderson et al., U.S. Pat. No. 5,399,346; Mann et al. *Cell* 33:153 (1983); Temin et al., U.S. Pat. No. 4,650,764; Temin et al., U.S. Pat. No. 4,980, 289; Markowitz et al., *J. Virol.* 62:1120 (1988); Temin et al., U.S. Pat. No. 5,124,263; International Patent Publication No. WO 95/07358, published Mar. 16, 1995 by Dougherty et al.; and Kuo et al., *Blood* 82:845 (1993). Alternatively, the vector can be introduced by lipofection in vivo using liposomes. Synthetic cationic lipids can be used to prepare liposomes for in vivo transfection of a gene encoding a marker (Feigner et al., *Proc. Natl. Acad. Sci. USA* 84:7413-7 (1987); Mackey et al., *Proc. Natl. Acad. Sci. USA* 85:8027-31 (1988)). The use of lipofection to introduce exogenous genes into specific organs in vivo has certain practical advantages. Molecular targeting of liposomes to specific cells represents one area of benefit. More particularly, directing transfection to particular cells represents one area of benefit. For instance, directing transfection to particular cell types would be particularly advantageous in a tissue with cellular heterogeneity, such as the immune system, pancreas, liver, kidney, and brain. Lipids may be chemically coupled to other molecules for the purpose of targeting. Targeted peptides (e.g., hormones or neurotransmitters), proteins such as antibodies, or non-peptide molecules can be coupled to liposomes chemically.

It is possible to remove the target cells from the body; to introduce the vector as a naked DNA plasmid; and then to re-implant the transformed cells into the body. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun or use of a DNA vector transporter. See, e.g., Wu et al., *J. Biol. Chem.* 267:963-7 (1992); and Wu et al., *J. Biol. Chem.* 263:14621-4 (1988).

Antisense methodology can be used to inhibit zcytor17 multimeric cytokine receptor gene transcription, such as to inhibit cell proliferation in vivo. Polynucleotides that are complementary to a segment of a zcytor17-encoding polynucleotide (e.g., a polynucleotide as set forth in SEQ ID NO:110. SEQ ID NO:108, or SEQ ID NO:4) are designed to bind to zcytor17lig-encoding mRNA and to inhibit translation of such mRNA. Such antisense polynucleotides are used to inhibit expression of zcytor17lig polypeptide-encoding genes in cell culture or in a subject.

Mice engineered to express the zcytor17lig gene, referred to as "transgenic mice," and mice that exhibit a complete absence of zcytor17lig gene function, referred to as "knockout mice," may also be generated (Snouwaert et al., *Science* 257:1083 (1992); Lowell et al., *Nature* 366:740-42 (1993); Capecchi, M. R., *Science* 244: 1288-1292 (1989); Palmiter, R. D. et al. *Annu Rev Genet.* 20: 465-499 (1986)). For example, transgenic mice that over-express zcytor17lig, either ubiquitously or under a tissue-specific or tissue-restricted promoter can be used to ask whether over-expression causes a phenotype. For example, over-expression of a wild-type zcytor17lig polypeptide, polypeptide fragment or a mutant thereof may alter normal cellular processes, resulting in a phenotype that identifies a tissue in which zcytor17lig expression is functionally relevant and may indicate a therapeutic target for the zcytor17lig, its agonists or antagonists. For example, a preferred transgenic mouse to engineer is one that over-expresses the zcytor17lig (amino acid residues 23-164 of SEQ ID NO:2; or 24-163 of SEQ ID NO:11). Moreover, such over-expression may result in a phenotype that shows similarity with human diseases. Similarly, knockout zcytor17lig mice can be used to determine where zcytor17lig is absolutely required in vivo. The phenotype of knockout mice is predictive of the in vivo effects of that a zcytor17lig antagonist, such as a soluble zcytor17 multimeric cytokine receptor, may have. The human or mouse zcytor17lig cDNA described herein can be used to generate knockout mice. These mice may be employed to study the zcytor17lig gene and the protein encoded thereby in an in vivo system, and can be used as in vivo models for corresponding human diseases. Moreover, transgenic mice expression of zcytor17lig antisense polynucleotides or ribozymes directed against zcytor17lig, described herein, can be used analogously to transgenic mice described above. Studies may be carried out by administration of purified zcytor17lig protein, as well.

The present invention also provides a composition which includes an effective amount of a soluble multimeric cytokine receptor comprising a polypeptide comprising amino acid residue 20 to amino acid residue 543 of SEQ ID NO:111 and at least a portion of at least one class I cytokine receptor; and a pharmaceutically acceptable vehicle. The polypeptide may be comprised of various fragment or portions of the extracellular domain of SEQ ID NO:111, SEQ ID NO:109, and/or SEQ ID NO:5, such as for instance, amino acid residue 20 to amino acid residue 227 of SEQ ID NO:111 and amino acid residue 20 to amino acid residue 519 of SEQ ID NO:111. The at least a portion of at least one class I cytokine receptor can include, for example, a portion of SEQ ID NO:9 and/or a portion of SEQ ID NO:7, such as, for instance, amino acid residue 28 to amino acid residue 429 of SEQ ID NO:7, amino acid residue 35 to amino acid residue 137 of SEQ ID NO:7, amino acid residue 240 to amino acid residue 342 of SEQ ID NO:7, amino acid residue 348 to amino acid residue 429 of SEQ ID NO:7, amino acid residue 28 to amino acid residue 739 of SEQ ID NO:7, and/or combinations thereof. The multimeric cytokine receptor may further include an affinity tag as described herein.

The present invention also provides an immune cell inhibiting composition which includes an effective amount of a soluble multimeric cytokine receptor comprising a polypeptide comprising amino acid residue 20 to amino acid residue 227 of SEQ ID NO:111 and at least a portion of at least one class I cytokine receptor; and a pharmaceutically acceptable vehicle, wherein the soluble multimeric cytokine receptor inhibits the proliferation of immune cells.

The present invention also provides an inflammatory cell inhibiting composition which includes an effective amount of a soluble multimeric cytokine receptor comprising a polypeptide comprising amino acid residue 20 to amino acid residue 227 of SEQ ID NO:111 and at least a portion of at least one class I cytokine receptor; and a pharmaceutically acceptable vehicle, wherein the soluble multimeric cytokine receptor inhibits the proliferation of inflammatory cells.

Experimental evidence suggests a role for zcytor17lig in the progression of diseases that involve the skin or epithelium of internal surfaces, such as, for instance, large intestine, small intestine, pancrease, lung, prostate, uterus, and the like. First, as disclosed herein, zcytor17 receptors, including both OSM receptor beta and zcytor17, are expressed in several cell types located in epithelial surfaces including cell lines derived from lung epithelium, lung fibroblast, prostate, colon, breast, liver epithelium, bone and skin epithelium, bone fibroblast, and the like. Moreover, as disclosed herein, examples from each of these cell types also responded to zcytor17lig activation of a STAT reporter construct. In addition, several cell lines responded to zcytor17lig stimulation by producing increased levels of IL-6, IL-8, MCP-1 (a chemotactic factor) as described herein. In whole, these data suggest a role for zcytor17lig in diseases that involve the epithelium such as, for instance, atopic dermatitis; dermatitis; psoriasis; psoriatic arthritis; eczema; gingivitis; peridontal disease; inflammatory bowel diseases (IBD) (e.g., ulcerative colitis, Crohn's disease); reproductive disorders, such as, for instance, cervical dysplasia, cervical cancer; other skin diseases like cancers: sarcomas; carcinomas; melanoma, etc. i.e, not just inflammatory diseases, since immune system is involved in activating/curing cancers; diseases involving barrier dysfunction, such as, for instance, graft-versus-host disease (GVHD) and irritable bowel syndrome (IBS); and diseases that involve lung epithelium, such as asthma, emphysema, and the like. In addition, the release of cytokines IL-6, IL-8, and MCP-1 by cells exposed to zcytor17lig suggests that zcytor17lig is involved in inflammation. Therefore, regulation of zcytor17lig can be useful in the treatment of autoimmune, inflammatory, or cancerous diseases associated with the tissues that express receptor. These diseases include, for example, prostatitis, hepatitis, osteoarthritis, and the like. Zcytor17lig may positively or negatively directly or indirectly regulate these diseases. Therefore, the administration of zcytor17lig can be used to treat diseases as described herein directly or with molecules that inhibit zcytor17lig activity including, for example, both monoclonal antibodies to zcytor17lig or monoclonal antibodies to zcytor17, or monoclonal antibodies that recognize the zcytor17 and OSM receptor beta complex.

Data also suggests that zcytor17lig may be involved in the regulation of TH2 T cell mediated diseases. First, zcytor17lig is made by the TH2 subset of activated T cells. TH2 cells express more zcytor17lig as compared to TH1 cells. In addition, at least two lung epithelial cell lines (SK-LU-1, A549) were stimulated to increase IL13 receptor alpha-2 mRNA in response to zcyto17 ligand stimulation as described herein. There is an association of IL-13 receptor alpha2 chain and tumorigenicity of human breast and pancreatic tumors. This suggests that zcytor17lig may play a role in regulating tumorigenicity of these types of cancers, as well as other cancers. Therefore, the administration of a zcytor17lig antagonist or direct use of zcytor17lig may be useful in treatment of these types of cancers, benign or malignant and at various grades (grades I-IV) and stages (e.g., TNM or AJC staging methods) of tumor development, in mammals, preferably humans.

It is well-known in the art that IL13 is involved in the generation of activated TH2 cells and in TH2 mediated diseases, such as asthma, atopic dermatitis, and the like. Zcytor17lig or zcytor17lig antagonists may be useful in the treatment of diseases that involved TH2 T cells. This would include diseases such as, for instance, atopic dermatitis, asthma, as well as other diseases that are exacerbated by activated TH2 cells. The involvement of zcytor17lig in diseases, such as, for instance, atopic dermatitis, is also supported by the phenotype of the transgenic mice that overexpress zcytor17lig and develop symptoms of atopic dermatitis as described herein.

Despite the preferential expression of zcytor17lig by TH2 cells, there is still some expression of zcytor17lig in TH1 cells and in CD8+ T cells. Therefore, zcytor17lig or its antagonists may be useful in treating diseases that involve immune modulation of activated T cells including, for example, viral infection, cancers, graft rejection, and the like.

Zcytor17lig may also be involved in the development of cancer. There is expression of the zcytor17 and OSM receptor beta receptors in human bone fibroblast osteosarcomas, human skin fibroblast melanoma, colon epithelial carcinoma, adenocarcinoma, breast epithelial adenocarcinoma, prostate epithelial adenosarcoma, and lung epithelial adenocarcinoma and carcinoma. Therefore, it may be useful to treat tumors of epithelial origin with either zcytor17lig, fragments thereof, or zcytor17lig antagonists which include, but are not limited to, carcinoma, adenocarcinoma, and melanoma. Notwithstanding, zcytor17lig or a zcytor17lig antagonist may be used to treat a cancer, or reduce one or more symptoms of a cancer, from a cancer including but not limited to, squamous cell or epidermoid carcinoma, basal cell carcinoma, adenocarcinoma, papillary carcinoma, cystadenocarcinoma, bronchogenic carcinoma, bronchial adenoma, melanoma, renal cell carcinoma, hepatocellular carcinoma, transitional cell carcinoma, choriocarcinoma, seminoma, embryonal carcinoma, malignant mixed tumor of salivary gland origin, Wilms' tumor, immature teratoma, teratocarcinoma, and other tumors comprising at least some cells of epithelial origin.

Generally, the dosage of administered zcytor17lig polypeptide (or Zcytor16 analog or fusion protein) will vary depending upon such factors as the patient's age, weight, height, sex, general medical condition and previous medical history. Typically, it is desirable to provide the recipient with a dosage of zcytor17lig polypeptide which is in the range of from about 1 pg/kg to 10 mg/kg (amount of agent/body weight of patient), although a lower or higher dosage also may be administered as circumstances dictate. One skilled in the art can readily determine such dosages, and adjustments thereto, using methods known in the art.

Administration of a zcytor17 multimeric receptor agonist or antagonist to a subject can be topical, inhalant, intravenous, intraarterial, intraperitoneal, intramuscular, subcutaneous, intrapleural, intrathecal, by perfusion through a regional catheter, or by direct intralesional injection. When administering therapeutic proteins by injection, the administration may be by continuous infusion or by single or multiple boluses.

Additional routes of administration include oral, mucosal-membrane, pulmonary, and transcutaneous. Oral delivery is suitable for polyester microspheres, zein microspheres, proteinoid microspheres, polycyanoacrylate microspheres, and lipid-based systems (see, for example, DiBase and Morrel, "Oral Delivery of Microencapsulated Proteins," in *Protein Delivery: Physical Systems*, Sanders and Hendren (eds.), pages 255-288 (Plenum Press 1997)). The feasibility of an intranasal delivery is exemplified by such a mode of insulin administration (see, for example, Hinchcliffe and Blum, *Adv. Drug Deliv. Rev.* 35:199 (1999)). Dry or liquid particles comprising Zcytor17 multimeric receptor agonist or antagonist can be prepared and inhaled with the aid of thy-powder dispersers, liquid aerosol generators, or nebulizers (e.g., Pettit and Gombotz, *TIBTECH* 16:343 (1998); Patton et al., *Adv. Drug Deliv. Rev.* 35:235 (1999)). This approach is illustrated by the AERX diabetes management system, which is a hand-held electronic inhaler that delivers aerosolized insulin into the lungs. Studies have shown that proteins as large as 48,000 kDa have been delivered across skin at therapeutic concentrations with the aid of low-frequency ultrasound, which illustrates the feasibility of transcutaneous administration (Mitragotri et al., *Science* 269:850 (1995)). Transdermal delivery using electroporation provides another means to administer a molecule having Zcytor17 multimeric receptor binding activity (Potts et al., *Pharm. Biotechnol.* 10:213 (1997)).

A pharmaceutical composition comprising a protein, polypeptide, or peptide having Zcytor17 multimeric receptor binding activity can be formulated according to known methods to prepare pharmaceutically useful compositions, whereby the therapeutic proteins are combined in a mixture with a pharmaceutically acceptable vehicle. A composition is said to be in a "pharmaceutically acceptable vehicle" if its administration can be tolerated by a recipient patient. Sterile phosphate-buffered saline is one example of a pharmaceutically acceptable vehicle. Other suitable vehicles are well-known to those in the art. See, for example, Gennaro (ed.), *Remington's Pharmaceutical Sciences*, 19th Edition (Mack Publishing Company 1995).

For purposes of therapy, molecules having Zcytor17 multimeric receptor binding activity and a pharmaceutically acceptable vehicle are administered to a patient in a therapeutically effective amount. A combination of a protein, polypeptide, or peptide having Zcytor17 multimeric receptor binding activity and a pharmaceutically acceptable vehicle is said to be administered in a "therapeutically effective amount" or "effective amount" if the amount administered is physiologically significant. An agent is physiologically significant if its presence results in a detectable change in the physiology of a recipient patient. For example, an agent used to treat inflammation is physiologically significant if its presence alleviates at least a portion of the inflammatory response.

A pharmaceutical composition comprising Zcytor17lig (or Zcytor17lig analog or fusion protein) can be furnished in liquid form, in an aerosol, or in solid form. Liquid forms, are illustrated by injectable solutions, aerosols, droplets, topological solutions and oral suspensions. Exemplary solid forms include capsules, tablets, and controlled-release forms. The latter form is illustrated by miniosmotic pumps and implants (Bremer et al., *Pharm. Biotechnol.* 10:239 (1997); Ranade, "Implants in Drug Delivery," in *Drug Delivery Systems*, Ranade and Hollinger (eds.), pages 95-123 (CRC Press 1995); Bremer et al., "Protein Delivery with Infusion Pumps," in *Protein Delivery: Physical Systems*, Sanders and Hendren (eds.), pages 239-254 (Plenum Press 1997); Yewey et al., "Delivery of Proteins from a Controlled Release Injectable Implant," in *Protein Delivery: Physical Systems*, Sanders and Hendren (eds.), pages 93-117 (Plenum Press 1997)). Other solid forms include creams, pastes, other topological applications, and the like.

Liposomes provide one means to deliver therapeutic polypeptides to a subject intravenously, intraperitoneally, intrathecally, intramuscularly, subcutaneously, or via oral administration, inhalation, or intranasal administration. Liposomes are microscopic vesicles that consist of one or more lipid bilayers surrounding aqueous compartments (see, generally, Bakker-Woudenberg et al., *Eur. J. Clin. Microbiol. Infect. Dis.* 12 (*Suppl.* 1):S61 (1993), Kim, *Drugs* 46:618 (1993), and Ranade, "Site-Specific Drug Delivery Using Liposomes as Carriers," in *Drug Delivery Systems*, Ranade and Hollinger (eds.), pages 3-24 (CRC Press 1995)). Liposomes are similar in composition to cellular membranes and as a result, liposomes can be administered safely and are biodegradable. Depending on the method of preparation, liposomes may be unilamellar or multilamellar, and liposomes can vary in size with diameters ranging from 0.02 μm to greater than 10 μm. A variety of agents can be encapsulated in liposomes: hydrophobic agents partition in the bilayers and hydrophilic agents partition within the inner aqueous space(s) (see, for example, Machy et al., *Liposomes In Cell Biology And Pharmacology* (John Libbey 1987), and Ostro et al., *American J. Hosp. Pharm.* 46:1576 (1989)). Moreover, it is possible to control the therapeutic availability of the encapsulated agent by varying liposome size, the number of bilayers, lipid composition, as well as the charge and surface characteristics of the liposomes.

Liposomes can adsorb to virtually any type of cell and then slowly release the encapsulated agent. Alternatively, an absorbed liposome may be endocytosed by cells that are phagocytic. Endocytosis is followed by intralysosomal degradation of liposomal lipids and release of the encapsulated agents (Scherphof et al., *Ann. N.Y. Acad. Sci.* 446:368 (1985)). After intravenous administration, small liposomes (0.1 to 1.0 μm) are typically taken up by cells of the reticuloendothelial system, located principally in the liver and spleen, whereas liposomes larger than 3.0 μm are deposited in the lung. This preferential uptake of smaller liposomes by the cells of the reticuloendothelial system has been used to deliver chemotherapeutic agents to macrophages and to tumors of the liver.

The reticuloendothelial system can be circumvented by several methods including saturation with large doses of liposome particles, or selective macrophage inactivation by pharmacological means (Claassen et al., *Biochim. Biophys. Acta* 802:428 (1984)). In addition, incorporation of glycolipid- or polyethelene glycol-derivatized phospholipids into liposome membranes has been shown to result in a significantly reduced uptake by the reticuloendothelial system (Allen et al., *Biochim. Biophys. Acta* 1068:133 (1991); Allen et al., *Biochim. Biophys. Acta* 1150:9 (1993)).

Liposomes can also be prepared to target particular cells or organs by varying phospholipid composition or by inserting receptors or ligands into the liposomes. For example, liposomes, prepared with a high content of a nonionic surfactant, have been used to target the liver (Hayakawa et al., Japanese Patent 04-244,018; Kato et al., *Biol. Pharm. Bull.* 16:960 (1993)). These formulations were prepared by mixing soybean phospatidylcholine, α-tocopherol, and ethoxylated hydrogenated castor oil (HCO-60) in methanol, concentrating the mixture under vacuum, and then reconstituting the mixture with water. A liposomal formulation of dipalmitoylphosphatidylcholine (DPPC) with a soybean-derived sterylglucoside mixture (SG) and cholesterol (Ch) has also been shown to target the liver (Shimizu et al., *Biol. Pharm. Bull.* 20:881 (1997)).

Alternatively, various targeting ligands can be bound to the surface of the liposome, such as antibodies, antibody fragments, carbohydrates, vitamins, and transport proteins. For example, liposomes can be modified with branched type galactosyllipid derivatives to target asialoglycoprotein (galactose) receptors, which are exclusively expressed on the surface of liver cells (Kato and Sugiyama, *Crit. Rev. Ther. Drug Carrier Syst.* 14:287 (1997); Murahashi et al., *Biol. Pharm. Bull.* 20:259 (1997)). Similarly, Wu et al., *Hepatology* 27:772 (1998), have shown that labeling liposomes with asialofetuin led to a shortened liposome plasma half-life and greatly enhanced uptake of asialofetuin-labeled liposome by hepatocytes. On the other hand, hepatic accumulation of liposomes comprising branched type galactosyllipid derivatives can be inhibited by preinjection of asialofetuin (Murahashi et al., *Biol. Pharm. Bull.* 20:259 (1997)). Polyaconitylated human serum albumin liposomes provide another approach for targeting liposomes to liver cells (Kamps et al., *Proc. Nat'l Acad. Sci. USA* 94:11681 (1997)). Moreover, Geho, et al. U.S. Pat. No. 4,603,044, describe a hepatocyte-directed liposome vesicle delivery system, which has specificity for hepatobiliary receptors associated with the specialized metabolic cells of the liver.

In a more general approach to tissue targeting, target cells are prelabeled with biotinylated antibodies specific for a ligand expressed by the target cell (Harasym et al., *Adv. Drug Deliv. Rev.* 32:99 (1998)). After plasma elimination of free antibody, streptavidin-conjugated liposomes are administered. In another approach, targeting antibodies are directly attached to liposomes (Harasym et al., *Adv. Drug Deliv. Rev.* 32:99 (1998)).

Polypeptides having Zcytor17 multimeric receptor binding activity can be encapsulated within liposomes using standard techniques of protein microencapsulation (see, for example, Anderson et al., *Infect. Immun.* 31:1099 (1981), Anderson et al., *Cancer Res.* 50:1853 (1990), and Cohen et al., *Biochim. Biophys. Acta* 1063:95 (1991), Alving et al. "Preparation and Use of Liposomes in Immunological Studies," in *Liposome Technology*, 2nd Edition, Vol. III, Gregoriadis (ed.), page 317 (CRC Press 1993), Wassef et al., *Meth. Enzymol.* 149:124 (1987)). As noted above, therapeutically useful liposomes may contain a variety of components. For example, liposomes may comprise lipid derivatives of poly(ethylene glycol) (Allen et al., *Biochim. Biophys. Acta* 1150:9 (1993)).

Degradable polymer microspheres have been designed to maintain high systemic levels of therapeutic proteins. Microspheres are prepared from degradable polymers such as poly (lactide-co-glycolide) (PLG), polyanhydrides, poly (ortho esters), nonbiodegradable ethylvinyl acetate polymers, in which proteins are entrapped in the polymer (Gombotz and Pettit, *Bioconjugate Chem.* 6:332 (1995); Ranade, "Role of Polymers in Drug Delivery," in *Drug Delivery Systems*, Ranade and Hollinger (eds.), pages 51-93 (CRC Press 1995); Roskos and Maskiewicz, "Degradable Controlled Release Systems Useful for Protein Delivery," in *Protein Delivery: Physical Systems*, Sanders and Hendren (eds.), pages 45-92 (Plenum Press 1997); Bartus et al., *Science* 281:1161 (1998); Putney and Burke, *Nature Biotechnology* 16:153 (1998); Putney, *Curr. Opin. Chem. Biol.* 2:548 (1998)). Polyethylene glycol (PEG)-coated nanospheres can also provide vehicles for intravenous administration of therapeutic proteins (see, for example, Gref et al., *Pharm. Biotechnol.* 10:167 (1997)).

The present invention also contemplates chemically modified polypeptides having binding Zcytor17 multimeric receptor activity such as zcytor17 multimeric receptor heterodimeric or multimeric soluble receptors, and Zcytor17 multimeric receptor antagonists, for example anti-zcytor17 multimeric receptor antibodies or binding polypeptides, which a polypeptide is linked with a polymer, as discussed above.

Other dosage forms can be devised by those skilled in the art, as shown, for example, by Ansel and Popovich, *Pharmaceutical Dosage Forms and Drug Delivery Systems,* $5^{th}$ Edition (Lea & Febiger 1990), Gennaro (ed.), *Remington's Pharmaceutical Sciences,* $19^{th}$ Edition (Mack Publishing Company 1995), and by Ranade and Hollinger, Drug Delivery Systems (CRC Press 1996).

As an illustration, pharmaceutical compositions may be supplied as a kit comprising a container that comprises a polypeptide with a Zcytor17 multimeric receptor extracellular domain, e.g., zcytor17 multimeric receptor heterodimeric or multimeric soluble receptors, or a Zcytor17 multimeric receptor antagonist (e.g., a neutralizing antibody or antibody fragment that binds a Zcytor17 multimeric receptor polypeptide). Therapeutic polypeptides can be provided in the form of an injectable solution for single or multiple doses, or as a sterile powder that will be reconstituted before injection. Alternatively, such a kit can include a dry-powder disperser, liquid aerosol generator, or nebulizer for administration of a therapeutic polypeptide. Such a kit may further comprise written information on indications and usage of the pharmaceutical composition. Moreover, such information may include a statement that the Zcytor17 multimeric receptor composition is contraindicated in patients with known hypersensitivity to Zcytor17 multimeric receptor.

The complete disclosure of all patents, patent applications, and publications, and electronically available material (e.g., GenBank amino acid and nucleotide sequence submissions) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

EXAMPLES

Example 1

Construction of MPL-Zcytor17 Polypeptide Chimera

MPL Extracellular and TM Domain Fused to the Zcytor17 Intracellular Signaling Domain The 5' extracellular domain of the murine MPL receptor was isolated from a plasmid containing the murine MPL receptor (PHZ1/MPL plasmid) by digestion with EcoRI and BamHI generating a 1164 bp fragment. The digestion was run on a 1% agarose gel and the fragment was isolated using the Qiaquick gel extraction kit (Qiagen) as per manufacturer's instructions. The rest of the MPL extracellular domain and transmembrane domain were generated using PCR with primers ZC6,673 (SEQ ID NO:13) and ZC29,082 (SEQ ID NO:14). The reaction conditions were as follows: 15 cycles at 94° C. for 1 min., 55° C. for 1 min., 72° C. for 2 min.; followed by 72° C. for 7 min.; then a 4° C. soak. The PCR product was run on a 1% agarose gel and the approximately 400 bp MPL receptor fragment was isolated using Qiaquick™ gel extraction kit (Qiagen) as per manufacturer's instructions.

The intracellular domain of human zcytor17 was isolated from a plasmid containing zcytor17 receptor cDNA (#23/pCAP) using PCR with primers ZC29,083 (SEQ ID NO:15) and ZC29,145 (SEQ ID NO:16). The polynucleotide sequence that corresponds to the zcytor17 receptor coding sequence is shown in SEQ ID NO:5. The reaction conditions were as per above. The PCR product was run on a 1% agarose gel and the approximately 320 bp zcytor17 fragment isolated using Qiaquick gel extraction kit as per manufacturer's instructions.

Each of the isolated PCR fragments described above were mixed at a 1:1 volumetric ratio and used in a PCR reaction using ZC6673 (SEQ ID NO:13) and ZC29145 (SEQ ID NO:16) to create all but the 5' MPL portion of the MPL-zcytor17 chimera. The reaction conditions were as follows: 15 cycles at 94° C. for 1 min., 55° C. for 1 min., 72° C. for 2 min.; followed by 72° C. for 7 min.; then a 4° C. soak. The entire PCR product was run on a 1% agarose gel and the approximately 700 bp MPL-zcytor17 chimera fragment isolated using Qiaquick gel extraction kit (Qiagen) as per manufacturer's instructions. The MPL-zcytor17 chimera fragment was digested with BamHI (BRL) and XbaI (Boerhinger Mannheim) as per manufacturer's instructions. The entire digest was run on a 1% agarose gel and the cleaved MPL-zcytor17 chimera isolated using Qiaquick™ gel extraction kit (Qiagen) as per manufacturer's instructions. The resultant cleaved MPL-zvytor17 chimera plus 5' MPL EcoRI/BamHI fragment described above were inserted into an expression vector to generate the full MPL-zcytor17 chimeric receptor as described below.

Recipient expression vector pZP-7 was digested with EcoRI (BRL) and Xba1 (BRL) as per manufacturer's instructions, and gel purified as described above. This vector fragment was combined with the EcoRI and XbaI cleaved MPL-zcytor17 PCR chimera isolated above and the EcoRI and BamHI 5' MPL fragment isolated above in a ligation reaction. The ligation was run using T4 Ligase (Epicentre Technologies), at room temperature for 1 hour as per manufacturer's instructions. A sample of the ligation was electroporated into DH10B ElectroMAX™ electrocompetent *E. coli* cells (25 μF, 200Ω, 1.8V). Transformants were plated on LB+Ampicillin plates and single colonies screened by miniprep (Qiagen) and digestion with EcoRI to check for the MPL-zcytor17 chimera. EcoRI digestion of correct clones yield about a 2 kb fragment. Confirmation of the MPL-zcytor17 chimera sequence was made by sequence analyses. The insert was approximately 3.1 kb, and was full-length.

Example 2

MPL-zcytor17 Chimera Based Proliferation in BAF3 Assay Using Alamar Blue

A. Construction of BaF3 Cells Expressing MPL-Zcytor17 Chimera

BaF3, an interleukin-3 (IL-3) dependent pre-lymphoid cell line derived from murine bone marrow (Palacios and Steinmetz, *Cell* 41: 727-734, 1985; Mathey-Prevot et al., *Mol. Cell. Biol.* 6: 4133-4135, 1986), was maintained in complete media (RPMI medium (JRH Bioscience Inc., Lenexa, Kans.) supplemented with 10% heat-inactivated fetal calf serum, 1-2 ng/ml murine IL-3 (mIL-3) (R & D, Minneapolis, Minn.), 2 mM L-glutaMax-1™ (Gibco BRL), 1 mM Sodium Pyruvate (Gibco BRL), and PSN antibiotics (GIBCO BRL)). Prior to electroporation, pZP-7/MPL-zcytor17 plasmid DNA was prepared and purified using a Qiagen Maxi Prep kit (Qiagen) as per manufacturer's instructions. BaF3 cells for electroporation were washed twice in RPMI media and then resuspended in RPMI media at a cell density of $10^7$ cells/ml. One ml of resuspended BaF3 cells was mixed with 30 μg of the pZP-7/MPL-zcytor17 plasmid DNA and transferred to separate disposable electroporation chambers (GIBCO BRL). At room temperature cells were given 5×0.1 msec shocks at 800 volts followed by 5×2 ms shocks at 600 volts delivered by an electroporation apparatus (Cyto-Pulse). Alternatively, cells were electroporated with two serial pulses (800 μFAD/300 V; followed by 1180 μFAD/300 V) delivered by a Cell-Porator (GibcoBRL) electroporation apparatus. The electroporated cells were transferred to 50 ml of complete media and placed in an incubator for 15-24 hours (37° C., 5% CO2). Then Geneticin™ (Gibco) selection (1 mg/ml G418) was added to the cells in a T-162 flask to isolate the G418-resistant pool. Pools of the transfected BaF3 cells, hereinafter called BaF3/MPL-zcytor17 cells, were assayed for signaling capability as described below.

B. Testing the Signaling Capability of the BaF3/MPL-Zcytor17 Cells Using an Alamar Blue Proliferation Assay BaF3/MPL-zcytor17 cells were spun down and washed in the complete media, described above, but without mIL-3 (hereinafter referred to as "mIL-3 free media"). The cells were spun and washed 3 times to ensure the removal of the mIL-3 Cells were then counted in a hemacytometer. Cells were plated in a 96-well format at 5000 cells per well in a volume of 100 μl per well using the mIL-3 free media.

Proliferation of the BaF3/MPL-zcytor17 cells was assessed using murine thrombopoietin (mTPO) diluted with mIL-3 free media to 200 ng/ml, 100 ng/ml, 50 ng/ml, 25 ng/ml, 12.5 ng/ml, 6.25 ng/ml, 3.1 ng/ml, 1.5 ng/ml concentrations. One hundred microliters of the diluted mTPO was added to the BaF3/MPL-zcytor17 cells. The total assay volume was 200 μl. Negative controls were run in parallel using mIL-3 free media only, without the addition of mTPO. The assay plates were incubated at 37° C., 5% $CO_2$ for 3 days at which time Alamar Blue (Accumed, Chicago, Ill.) was added at 20 μl/well. Alamar Blue gives a fluorometric readout based on the metabolic activity of cells, and is thus a direct measurement of cell proliferation in comparison to a negative control. Plates were again incubated at 37° C., 5% $CO_2$ for 24 hours. Plates were read on the Fmax™ plate reader (Molecular Devices Sunnyvale, Calif.) using the SoftMax™ Pro program, at wavelengths 544 (Excitation) and 590 (Emission), or a Wallac Victor 2 plate reader (PerkinElmer Life Sciences, Boston, Mass.).

Results confirmed the signaling capability of the intracellular portion of the zcytor17 receptor, as the thrombopoietin induced proliferation at approximately 9-13 fold over background at mTPO concentrations of 50 ng/ml and greater.

Example 3

Construction of Expression Vector Expressing Full-Length Zcytor17: pZp7pX/Zcytor17

A. Cloning of Full Length Zcytor17 cDNA for Expression:

To obtain a full-length zcytor17 cDNA, 5' and 3' PCR products were isolated and joined using an internal PstI site. The PCR primers were designed using the nucleotide sequence SEQ ID NO:4 and include BamHI and Xho I restriction sites for cloning purposes.

A 5' PCR product was generated using a WI-38 cDNA library as a template and oligonucleotides ZC29,359 (SEQ ID NO:18) and ZC27,899 (SEQ ID NO:19) as primers. WI-38 is an in-house cDNA library generated from a human embryonic lung cell line (ATCC CRL-2221). This 5' PCR reaction was run as follows: 30 cycles at 94° C. for 1 minute, 65° C. for 1 minute, 72° C. for 2 minutes, then 72° C. for 7 minutes; 10° C. soak. The PCR reaction used approximately 3 μg of plasmid prepared from the cDNA library, 20 pmoles of each oligonucleotide, and five units of PWO DNA polymerase (Roche). About 90% of the 5' PCR product was ethanol precipitated, digested with BamHI and PstI and gel purified on a 1.0% agarose gel. The approximately 600 bp band was excised and used for ligation to the cloning vector pUC18 digested with BamHI and PstI. The resulting transformants were sequenced to confirm the zcytor17 cDNA sequence. For one of these transformants, plasmid DNA was prepared and digested with BamHI and PstI. The resulting approximately 600 bp band was gel purified and used for a ligation below to form a full-length cDNA.

A 3' PCR product was generated using a human testes in-house cDNA library as a template and oligonucleotides ZC27,895 (SEQ ID NO:20) and ZC29,122 (SEQ ID NO:21) as primers. This 3' PCR reaction was run as follows: 30 cycles at 94° C. for 45 seconds, 65° C. for 45 seconds, 72° C. for 2 minutes, then 72° C. for 7 minutes; 10° C. soak. The entire 3' PCR reaction was gel purified on a 1.0% agarose gel and the major 1500 bp band excised. This band was cloned into the PCR Blunt II TOPO vector using the Zeroblunt TOPO kit (Invitrogen). The resulting transformants were sequenced to confirm the zcytor17 cDNA sequence. For one of these transformants, plasmid DNA was prepared and digested with PstI and XhoI. The resulting approximately 1500 bp band was gel purified. A three-part ligation was performed with the 5' BamHI to Pst I fragment above, the 3' PstI to XhoI fragment, and the expression vector pZp7pX digested with BamHI and XhoI. This generated a pZp7pX plasmid containing a full-length cDNA for zcytor17 (SEQ ID NO:4), designated pZp7p/zcytor17. The full length zcytor17 cDNA in pZp7p/zcytor17 has a silent mutation that changes the T to G at position 1888 of SEQ ID NO:4 (encoding a Gly residue at residue 464 of SEQ ID NO:5). As this mutation is silent, the zcytor17 cDNA in pZp7p/zcytor17 encodes the polypeptide as shown in SEQ ID NO:5. Plasmid pZp7pX is a mammalian expression vector containing an expression cassette having the CMV promoter, intron A, multiple restriction sites for insertion of coding sequences, and a human growth hormone terminator. The plasmid also has an *E. coli* origin of replication, a mammalian selectable marker expression unit having an SV40 promoter, enhancer and origin of replication, a puromycin resistance gene and the SV40 terminator.

B. Construction of Expression Vector Expressing Full-Length WSX-1

The entire WSX-1 receptor (SEQ ID NO:9) was isolated from a plasmid containing the WSX-1 receptor cDNA (SEQ ID NO:8) (U.S. Pat. No. 5,925,735). hWSX-1/pBluescript SK(+) plasmid DNA (Stratagene, La Jolla, Calif.) was digested with EcoRI and XhoI to generate a 1075 bp fragment, and also digested with XhoI and XbaI to generate a 900 bp fragment. Both digests were run on a 1% agarose gel and the cleaved WSX-1 fragments isolated.

Recipient expression vector pZp7Z was digested with EcoRI and XbaI and gel purified as described above. This vector fragment was combined with the two cleaved zcytor17 fragments isolated above in a ligation reaction using T4 Ligase (BRL). The ligation was incubated at room temperature overnight. A sample of the ligation was electroporated in to DH10B electroMAX™ electrocompetent *E. coli* cells (25 μF, 200Ω, 2.3V). Six colonies were grown in culture and miniprepped DNA was prepared and digested to confirm the correct WSX-1 full-length insert of 2.0 kb. The resulting plasmid is pZPZ7Z/WSX-1.

Example 4

Zcytor17 Based Proliferation in BAF3 Assay Using Alamar Blue

A. Construction of BaF3 Cells Expressing Zcytor17 Receptor, WSX-1 Receptor and OSMR BaF3 cells expressing the full-length zcytor17 receptor were constructed as per Example 2A above, using 30 μg of the zcytor17 expression vector, described in Example 3A. One exception is that in place of Geneticin selection, 2 μg/ml of Puromycin (ClonTech) was added to the transfected cells in a T-162 flask to isolate the puromycin-resistant pool. The BaF3 cells expressing the zcytor17 receptor mRNA were designated as BaF3/zcytor17. To obtain clones, pools of BaF3/zcytor17 cells were counted in a hemocytometer and plated at 1 cell/well, 0.5 cell/well, 0.1 cell/well, and 0.01 cell/well in 96-well dishes. Fifteen clones were scaled up to T75 flasks, and five clones were assayed for zcytor17 expression. Total RNA was isolated from cell pellets using a S.N.A.P.™ total RNA Isolation Kit (InVitrogen). First-strand cDNA was synthesized using the proSTAR™ First Strand RT-PCR kit, and then PCR with zcytor17 specific primers ZC29,180 (SEQ ID NO:22) and ZC29,122 (SEQ ID NO:23) was performed to screen the clones for expression of zcytor17. One clone, BaF3/zcytor17#15 was chosen to expand and transfect with the WSX-1 expression vector.

BaF3 cells expressing zcytor17 and full-length WSX-1 were constructed as per Example 2A above, using 30 μg of the WSX-1 expression vector WSX-1/pZp7Z (Example 3B) to electroporate the BaF3/zcytor17#15 cells. One exception is that in place of Geneticin selection, 200 μg/ml Zeocin (InVitrogen) was added to the transfected cells in a T-162 flask to isolate the zeocin-resistant pool. The BaF3 cells expressing zcytor17 and WSX-1 were designated BaF3/zcytor17/hWSX-1. To obtain clones, pools of Baf3/zcytor17/hWSX-1 cells were plated at limiting dilution in 96-well plates. The resulting clones were expanded and total RNA was isolated using a S.N.A.P.™ total RNA Isolation Kit (InVitrogen). First-strand cDNA was synthesized using the proSTAR™ First Strand RT-PCR kit, and then PCR with WSX-1 specific primers ZC9791 (SEQ ID NO:24) and ZC9793 (SEQ ID NO:25) was used to screen the clones for expression of WSX-1. One clone, BaF3/zcytor17/hWSX-1#5 was chosen to expand further and transfect with the OSMRbeta expression vector.

BaF3 cells expressing zcytor17, WSX-1 and full-length OSMRbeta were constructed as per Example 2A above, using 30 μg of the OSMRbeta expression vector OSMR/pZp7NX described in Example 29 to electroporate the BaF3/zcytor17/hWSX-1#5 cells. The BaF3 cells expressing zcytor17, WSX-1, and OSMRbeta mRNA were designated BaF3/zcytor17/WSX-1/OSMR. To obtain clones, pools of BaF3/zcytor17/WSX-1/OSMRbeta cells were plated at limiting dilution in 96-well plates. Individual clones were expanded and total RNA was isolated using a S.N.A.P.™ total RNA Isolation Kit (InVitrogen). First-strand cDNA was synthesized using the proSTAR™ First Strand RT-PCR kit, and then PCR with OSMRbeta specific primers ZC40109 (SEQ ID NO:26) and ZC40112 (SEQ ID NO:27) was used to screen the clones for expression of zcytor17, WSX-1, and OSMR. One clone, BaF3/zcytor17/WSX-1/OSMR#5 was selected and these cells were used to screen for zcytor17lig as described below in Examples 5 and 6.

B. Construction of BaF3 Cells Expressing Zcytor17 Receptor and OSMR

BaF3 cells expressing the full-length zcytor17 receptor were constructed as per Example 2A above, using 30 μg of the zcytor17 expression vector, described in Example 3A. One exception is that in place of Geneticin selection, 2 μg/ml of Puromycin (ClonTech) was added to the transfected cells in a T-162 flask to isolate the puromycin-resistant pool. The BaF3 cells expressing the zcytor17 receptor mRNA were designated as BaF3/zcytor17. To obtain clones, pools of Baf3/zcytor17 cells were plated at limiting dilution in 96-well plates. These clones were expanded in culture and total RNA was isolated using a S.N.A.P.™ total RNA Isolation Kit (InVitrogen). First-strand cDNA was synthesized using the proSTAR™ First Strand RT-PCR kit, and then PCR was used to screen the clones for expression of zcytor17. One clone, BaF3/zcytor17 #15 was chosen to expand and transfect with the OSMRbeta expression vector.

BaF3 cells expressing zcytor17 and full-length OSMRbeta were constructed as per Example 2A above, using 30 μg of the OSMRbeta expression vector OSMR/pZp7NX (example 29) to electroporate the BaF3/zcytor17#15 cells. The BaF3 cells expressing zcytor17 and OSMRbeta mRNA were designated BaF3/zcytor17/OSMR. These cells were used to screen for zcytor17lig as described below in Example 5.

Example 5

Screening for Zcytor17lig Using BaF3/Zcytor17/WSX-1/OSMRbeta Cells Using an Alamar Blue Proliferation Assay A. Activation of CCRF-CEM and CCRF-HSB2 Cells to Test for Presence of Zcytor17lig CCRF-CEM and CCRF-HSB2 cells were obtained from ATCC and stimulated in culture to produce conditioned media to test for the presence of zcytor17lig activity as described below. The suspension cells were seeded at $2 \times 10^5$ cells/ml or $5 \times 10^5$ cells/ml in RPMI-1640 media supplemented with 10% FBS, 2 mM L-glutamine (GibcoBRL), 1×PSN (GibcoBRL), and activated with 10 ng/ml Phorbol- 12-myristate-13-acetate (PMA) (Calbiochem, San Diego, Calif.) and 0.5 µg/ml Ionomycin™ (Calbiochem) for 24 or 48 hrs. The supernatant from the stimulated cells was used to assay proliferation of the BaF3/zcytor17/WSX-1/OSMRbeta cells or BaF3/zcytor17/OSMRbeta cells as described below.

B. Screening for Zcytor17lig Using BaF3/Zcytor17/WSX-1/OSMRbeta Cells or BaF3/Zcytor17/OSMRbeta Cells Using an Alamar Blue Proliferation Assay BaF3/zcytor17/WSX-1/OSMRbeta cells or BaF3/zcytor17/OSMRbeta cells were spun down and washed in mIL-3 free media. The cells were spun and washed 3 times to ensure the removal of the mIL-3. Cells were then counted in a hemacytometer. Cells were plated in a 96-well format at 5000 cells per well in a volume of 100 µl per well using the mIL-3 free media.

Proliferation of the BaF3/zcytor17/WSX-1/OSMRbeta cells or BaF3/zcytor17/OSMRbeta cells was assessed using conditioned media from activated CCRFCEM and CCRF-HSB2 cells (see Example 5A). Conditioned media was diluted with mIL-3 free media to 50%, 25%, 12.5%, 6.25%, 3.125%, 1.5%, 0.75%, and 0.375% concentrations. 100 µl of the diluted conditioned media was added to the BaF3/zcytor17/WSX-1/OSMRbeta cells or BaF3/zcytor17/OSMRbeta cells. The total assay volume is 200 µl. The assay plates were incubated at 37° C., 5% $CO_2$ for 3-5 days at which time Alamar Blue (Accumed, Chicago, Ill.) was added at 20 µl/well. Plates were again incubated at 37° C., 5% $CO_2$ for 24 hours. Plates were read on the Fmax™ plate reader (Molecular devices) as described above (Example 2).

Results confirmed the proliferative response of the BaF3/zcytor17/WSX-1/OSMRbeta cells or BaF3/zcytor17/OSMRbeta cells to a factor present in the activated CCRF-CEM and CCRF-HSB2 conditioned media. The response, as measured, was approximately 10-fold over background at the 25% concentration. The untransfected BaF3 cells did not proliferate in response to this factor, nor did BaF3 cells transfected with zcytor17 and WSX-1 (BaF3/zcytor17/WXS-1 cells), showing that this factor was specific for Zcytor17/OSMRbeta or zcytor17/OSMRbeta/WSX-1 receptors. Moreover soluble zcytor17 receptor diminished this proliferative activity of zcytor17lig in the BaF3/zcytor17/WSX-1/OSMRbeta cells (see, Example 11). Similar results are expected in BaF3/zcytor17/OSMRbeta cells.

C. Human Primary Source Used to Isolate Zcytor17lig

One hundred milliliters blood draws were taken from each of six donors. The blood was drawn using 10×10 ml vacutainer tubes containing heparin. Blood was pooled from six donors (600 ml), diluted 1:1 in PBS, and separated using a Ficoll-Paque® PLUS (Pharmacia Biotech). The isolated primary human cell yield after separation on the ficoll gradient was $1.2 \times 10^9$ cells.

Cells were suspended in 9.6 ml MACS buffer (PBS, 0.5% EDTA, 2 mM EDTA). 1.6 ml of cell suspension was removed and 0.4 ml CD3 microbeads (Miltenyi Biotec, Auburn, Calif.) added. The mixture was incubated for 15 min. at 4° C. These cells labeled with CD3 beads were washed with 30 ml MACS buffer, and then resuspended in 2 ml MACS buffer.

A VS+ column (Miltenyi) was prepared according to the manufacturer's instructions. The VS+ column was then placed in a VarioMACS™ magnetic field (Miltenyi). The column was equilibrated with 5 ml MACS buffer. The isolated primary human cells were then applied to the column. The CD3 negative cells were allowed to pass through. The column was rinsed with 9 ml (3×3 ml) MACS buffer. The column was then removed from the magnet and placed over a 15 ml falcon tube. CD3+ cells were eluted by adding 5 ml MACS buffer to the column and bound cells flushed out using the plunger provided by the manufacturer. The incubation of the cells with the CD3 magnetic beads, washes, and VS+ column steps (incubation through elution) above were repeated five more times. The resulting CD3+ fractions from the six column separations were pooled. The yield of CD3+ selected human cells were $3 \times 10^8$ total cells.

A sample of the pooled CD3+ selected human cells was removed for staining and sorting on a fluorescent antibody cell sorter (FACS) to assess their purity. The human CD3+ selected cells were 91% CD3+ cells.

The human CD3+ selected cells were activated by incubating in RPMI+5% FBS+PMA 10 ng/ml and Ionomycin 0.5 µg/ml (Calbiochem) for 13 hours 37° C. The supernatant from these activated CD3+ selected human cells was tested for zcytor17lig activity as described below. Moreover, the activated CD3+ selected human cells were used to prepare a cDNA library, as described in Example 6, below.

D. Testing Supernatant from Activated CD3+ Selected Human Cells for Zcytor17lig Using BaF3/Zcytor17/WSX-1/OSMRbeta Cells and an Alamar Blue Proliferation Assay BaF3/zcytor17/WSX-1/OSMRbeta cells or BaF3/zcytor17/OSMRbeta cells were spun down and washed in mIL-3 free media. The cells were spun and washed 3 times to ensure the removal of the mIL-3 Cells were then counted in a hemacytometer. Cells were plated in a 96-well format at 5000 cells per well in a volume of 100 µl per well using the mIL-3 free media.

Proliferation of the BaF3/zcytor17/WSX-1/OSMRbeta cells or BaF3/zcytor17/OSMRbeta cells were assessed using conditioned media from activated CD3+ selected human cells (see Example 5C) diluted with mIL-3 free media to 25%, 12.5%, 6.25%, 3.125%, 1.5%, 0.75%, 0.375% and 0.187% concentrations. 100 µl of the diluted conditioned media was added to the BaF3/zcytor17/WSX-1/OSMRbeta cells or BaF3/zcytor17/OSMRbeta cells. The total assay volume was 200 µl. The assay plates were incubated and assayed as described in Example 5B.

Results confirmed the proliferative response of the BaF3/zcytor17/WSX-1/OSMRbeta cells or BaF3/zcytor17/OSMRbeta cells to a factor present in the activated CD3+ selected human Cell conditioned media. The response, as measured, was approximately 15-fold over background at the 25% concentration. The untransfected BaF3 cells did not proliferate in response to this factor, nor did BaF3 cells transfected with zcytor17 and WSX-1 (BaF3/zcytor17/WXS-1 cells), showing that this factor is specific for Zcytor17/OSMRbeta or zcytor17/OSMRbeta/WSX-1 receptors.

Example 6

Cloning of Human Zcytor17lig from a Human CD3+ Selected Cell Library

Screening of a primary human activated CD3+ selected cell cDNA library revealed an isolated cDNA that is a novel member of the four-helix bundle cytokine family. This cDNA encoded the zcytor17lig. The cDNA was identified by screening for activity of the zcytor17lig using the zcytor17/WSX-1/OSM receptors.

A. The Vector for CD3+ Selected Library Construction

The vector for CD3+ selected library construction was pZP7NX. The pZP7NX vector was constructed as follows: The coding region for the DHFR selective marker in vector pZP7 was removed by DNA digestion with NcoI and PstI restriction enzymes (Boehringer Mannheim). The digested DNA was run on 1% agarose gel, cut out and gel purified using the Qiagen Gel Extraction Kit (Qiagen) as per manufacturer's instructions. A DNA fragment representing the coding region of Zeocin selective marker was amplified by PCR method with primers ZC13,946 (SEQ ID NO:28) and ZC13,945 (SEQ ID NO:29), and pZeoSV2(+) as a template. There are additional PstI and BclI restriction sites in primer ZC13,946 (SEQ ID NO:28), and additional NcoI and SfuI sites in primer ZC13,945 (SEQ ID NO:29). The PCR fragment was cut with PstI and NcoI restriction enzymes and cloned into pZP7 vector prepared by cleaving with the same two enzymes and subsequent gel purification. This vector was named pZP7Z. Then the Zeocin coding region was removed by DNA digestion of vector pZP7Z with BclI and SfuI restriction enzymes. The digested DNA was run on 1% agarose gel, cut out and gel purified, and then ligated with a DNA fragment of Neomycin coding region cut from pZem228 vector (deposited at the American Type Culture Collection (ATCC), Manassas, Va.; ATCC Deposit No. 69446) with the same restriction enzymes (BclI and SfuI).

This new vector was named pZP7N, in which the coding region for DHFR selective marker was replaced by the coding region for a Neomycin selective marker from vector pZem228. A stuffer fragment including an Xho1 site was added to pZP7N to create a vector suitable for high efficiency directional cloning of cDNA; this new vector was called pZP7NX. To prepare the vector for cDNA, 20 μg of pZP7NX was digested with 20 units of EcoR1 (Life Technologies Gaithersberg, Md.) and 20 units of Xho1 (Boehringer Mannheim Indianapolis, Ind.) for 5 hours at 37° C., then 68° C. for 15 minutes. The digest was then run on a 0.8% low melt agarose 1×TAE gel to separate the stuffer from the vector. The vector band was excised and digested with "beta-Agarase" (New England Biolabs, Beverly, Mass.) following the manufacturer's recommendations. After ethanol precipitation the digested vector was resuspended in water to 45 ng/ml in preparation for ligation of CD3+ selected cDNA library described below.

B. Preparation of Primary Human Activated CD3+ Selected Cell cDNA Library

Approximately $1.5 \times 10^8$ primary human CD3+ selected cells stimulated in ionomycin/PMA were isolated by centrifugation after culturing at 37° C. for 13 hours (Example 5C). Total RNA was isolated from the cell pellet using the "RNeasy Midi" kit from Qiagen, Inc. (Valencia, Calif.). mRNA was isolated from 225 micrograms of total RNA using the "MPG mRNA purification kit" from CPG Inc. (Lincoln Park, N.J.). 3.4 micrograms of mRNA was isolated and converted to double stranded cDNA using the following procedure.

First strand cDNA from stimulated human CD3+ selected cells was synthesized as follows. Nine lll Oligo d(T)-selected poly(A) CD3+ RNA at a concentration of 0.34 μg/μl and 1.0 μl of 1 μg/μl first strand primer ZC18,698 (SEQ ID NO:30) containing an XhoI restriction site were mixed and heated at 65° C. for 4 minutes and cooled by chilling on ice. First strand cDNA synthesis was initiated by the addition of 9 μl of first strand buffer (5× SUPERSCRIPT® buffer; (Life Technologies), 4 μl of 100 mM dithiothreitol and 2 μl of a deoxynucleotide triphosphate solution containing 10 mM each of dATP, dGTP, dTTP and 5-methyl-dCTP (Pharmacia Biotech Inc.) to the RNA-primer mixture. The reaction mixture was incubated at 45° C. for 4 minutes followed by the addition of 8 μl of 200 U/μl SuperscriptII®, RNase H-reverse transcriptase (Life technologies). The reaction was incubated at 45° C. for 45 minutes followed by an incubation ramp of 1° C. every 2 minutes to 50° C. where the reaction was held for 10 minutes. To denature any secondary structure and allow for additional extension of the cDNA the reaction was then heated to 70° C. for 2 minutes then dropped to 55° C. for 4 minutes after which 2 μl of SuperscriptII® RT was added and incubated an additional 15 minutes followed by a ramp up to 70° C. 1 minute/1° C. Unincorporated nucleotides were removed from the cDNA by twice precipitating in the presence of 2 μg of glycogen carrier, 2.0 M ammonium acetate and 2.5 volume ethanol, followed by a 100 μl wash with 70% ethanol. The cDNA was resuspended in 98 μl water for use in second strand synthesis.

Second strand synthesis was performed on the first strand cDNA under conditions that promoted first strand priming of second strand synthesis resulting in DNA hairpin formation. The second strand reaction contained 98 μl of the first strand cDNA, 30 μl of 5× polymerase I buffer (100 mM Tris: HCl, pH 7.5, 500 mM KCl, 25 mM $MgCl_2$, 50 mM $(NH_4)_2SO_4$), 2 μl of 100 mM dithiothreitol, 6 μl of a solution containing 10 mM of each deoxynucleotide triphosphate, 5 μl of 5 mM b-NAD, 1 μl of 3 U/μl E. coli DNA ligase (New England Biolabs Inc.) and 4 μl of 10 U/μl E. coli DNA polymerase I (New England Biolabs Inc.). The reaction was assembled at room temperature and was incubated at room temperature for 2 minutes followed by the addition of 4 μl of 3.8 U/μl RNase H (Life Technologies). The reaction was incubated at 15° C. for two hours followed by a 15 minute incubation at room temperature. 10 μl of 1M TRIS pH7.4 was added to the reaction and extracted twice with phenol/chloroform and once with chloroform, the organic phases were then back extracted with 50 μl of TE (10 mM TRIS pH 7.4, 1 mM EDTA), pooled with the other aqueous and ethanol precipitated in the presence of 0.3 M sodium acetate. The pellet was washed with 100 μl 70% ethanol air dried and resuspended in 40 μl water.

The single-stranded DNA of the hairpin structure was cleaved using mung bean nuclease. The reaction mixture contained 40 μl of second strand cDNA, 5 μl of 10× mung bean nuclease buffer (Life technologies), 5 μl of mung bean nuclease (Pharmacia Biotech Corp.) diluted to 1 U/μl in 1× mung bean nuclease buffer. The reaction was incubated at 37° C. for 45 minutes. The reaction was terminated by the addition of 10 μl of 1 M Tris: HCl, pH 7.4 followed by sequential phenol/chloroform and chloroform extractions as described above. Following the extractions, the cDNA was ethanol precipitated in the presence of 0.3 M sodium acetate. The pellet was washed with 100 μl 70% ethanol air dried and resuspended in 38 μl water.

The resuspended cDNA was blunt-ended with T4 DNA polymerase. The cDNA, which was resuspended in 38 μl of water, was mixed with 12 μl 5× T4 DNA polymerase buffer (250 mM Tris:HCl, pH 8.0, 250 mM KCl, 25 mM $MgCl_2$), 2 μl 0.1 M dithiothreitol, 6 μl of a solution containing 10 mM of each deoxynucleotide triphosphate and 2 μl of 1 U/μl T4 DNA polymerase (Boehringer Mannheim Corp.). After an incubation of 45 minutes at 15° C., the reaction was terminated by the addition of 30 μl TE followed by sequential phenol/chloroform and chloroform extractions and back extracted with 20 μl TE as described above. The DNA was ethanol precipitated in the presence of 2 μl Pellet Paint™ (Novagen) carrier and 0.3 M sodium acetate and was resuspended 11 μl of water.

EcoRI adapters were ligated onto the 5' ends of the cDNA described above to enable cloning into an expression vector. 11 μl of cDNA and 4 μl of 65 pmole/μl of Eco RI hemiphosphorylated adaptor (Pharmacia Biotech Corp) were mixed with 5 μl 5× ligase buffer (Life Technologies), 2 μl of 10 mM ATP and 3 μl of 1 U/μl T4 DNA ligase (Life Technologies), 1 μl 10× ligation buffer (Promega Corp), 9 μl water. The extra dilution with 1× buffer was to prevent the pellet paint from precipitating. The reaction was incubated 9 hours in a water bath temperature ramp from 10° C. to 22° C. over 9 hours, followed by 45 minutes at 25° C. The reaction was terminated by incubation at 68° C. for 15 minutes.

To facilitate the directional cloning of the cDNA into an expression vector, the cDNA was digested with XhoI, resulting in a cDNA having a 5' Eco RI cohesive end and a 3' XhoI cohesive end. The XhoI restriction site at the 3' end of the cDNA had been previously introduced using the ZC18698 (SEQ ID NO:31) primer. Restriction enzyme digestion was carried out in a reaction mixture containing 35 µl of the ligation mix described above, 6 µl of 10× H buffer (Boehringer Mannheim Corp.), 1 µl of 2 mg/ml BSA (Biolabs Corp.), 17 µl water and 1.0 µl of 40 U/µl XhoI (Boehringer Mannheim). Digestion was carried out at 37° C. for 1 hour. The reaction was terminated by incubation at 68° C. for 15 minutes followed by ethanol precipitation, washing drying as described above and resuspension in 30 µl water.

The resuspended cDNA was heated to 65° C. for 5 minutes and cooled on ice, 4 µl of 5× gel loading dye (Research Genetics Corp.) was added, the cDNA was loaded onto a 0.8% low melt agarose 1×TAE gel (SEA PLAQUE GTG™ low melt agarose; FMC Corp.) and electrophoresed. The contaminating adapters and cDNA below 0.6 Kb in length were excised from the gel. The electrodes were reversed, molten agarose was added to fill in the wells, the buffer was changed and the cDNA was electrophoresed until concentrated near the lane origin. The area of the gel containing the concentrated cDNA was excised and placed in a microfuge tube, and the agarose was melted by heating to 65° C. for 15 minutes. Following equilibration of the sample to 45° C., 2 µl of 1 U/µl Beta-agarase I (Biolabs, Inc.) was added, and the mixture was incubated for 90 min. at 45° C. to digest the agarose. After incubation, 1 tenth volume of 3 M Na acetate was added to the sample, and the mixture was incubated on ice for 15 minutes. The sample was centrifuged at 14,000×g for 15 minutes at room temperature to remove undigested agarose, the cDNA was ethanol precipitated, washed in 70% ethanol, air-dried and resuspended in 40 µl water.

To determine the optimum ratio of cDNA to vector several ligations were assembled and electroporated. Briefly, 2 µl of 5× T4 ligase buffer (Life Technologies), 1 µl of 10 mM ATP, 1 µl pZP7NX digested with EcoR1-Xho1, 1 µl T4 DNA ligase diluted to 0.25 u/µl (Life Technologies) water to 10 µl and 0.5, 1, 2 or 3 µl of cDNA were mixed in 4 separate ligations, incubated at 22° C. for 4 hours, 68° C. for 20 minutes, sodium acetate-ethanol precipitated, washed, dried and resuspended in 10 µl. A single microliter of each ligation was electroporated into 40 µl DH10b ElectroMax™ electrocompetent bacteria (Life Technologies) using a 0.1 cm cuvette (Biorad) and a Genepulser, pulse Controller™ (Biorad) set to 2.5 KV, 25 lF, 200 ohms. These cells were immediately resuspended in 1 ml SOC broth (Manniatis et al. supra.) followed by 500 µl of 50% glycerol-SOC as a preservative. These "glycerol stocks" were frozen in several aliquots at −70° C. An aliquot of each was thawed and plated serially on LB-agar plates supplemented with ampicillin at 100 µg/ml. Colony numbers indicated that the optimum ratio of CD3+ cDNA to pZP7NX vector was 1 µl to 45 ng; such a ligation yielded 4.5 million primary clones.

For the purpose of screening the library using a BaF3-based proliferation assay (Example 5) glycerol stocks from above were diluted into liquid cultures of 100 or 250 clones per pool in deep well microtiter plates, grown 24 hours at 37° C. with shaking and plasmid isolated using a Qiagen kit following the manufacturer's instructions. Such DNA was subsequently transfected into BHK cells, media conditioned 72 hours, harvested and stored at −80° C., and subsequently placed on 5K BaF3/zcytor17/WSX-1/OSMRbeta cells or BaF3/zcytor17/OSMRbeta cells for 72 hours after which proliferation was assessed using an "Alamar blue" fluorescence assay (Example 5B and Example 2B).

Example 7

Expression Cloning of Human Zcytor17lig

The glycerol stocks from the activated human CD3+ selected cell library (Example 6) were added to Super Broth II™ (Becton Dickinson, Cockeysville, Md.)+0.1 mg/ml ampicillin (amp) at a concentration of 250 cells per 800 microliters. The E. coli were allowed to equilibrate for 24 hours at room temperature. At the time of inoculation, 400 microliters was plated on LB+amp plates to determine the actual titer of the inoculation. After 24 hours the plates were counted and then the final concentration of the SuperBrothII™+E. coli was adjusted so that the final concentration was 250 cells per 1.2 ml. Three times 2 liters were inoculated for a total of 6 liters. The media were then plated into 96-well deep well blocks (Qiagen). Plating was done on the 8-channel Q-Fill2™ dispenser (Genetix, Christchurch, Dorset, UK). The E. coli were grown overnight at 37° C. shaking at 250 rotations/min. on a New Brunswick Scientific Innova 4900 multi-tier environment shaker. The E. coli were spun out of solution at 3000 rpm, using a Beckman GS-6KR centrifuge. These E. coli pellets were frozen at −20° C. or used fresh before miniprepping the plasmid DNA. Each pellet contains approximately 250 cDNA clones from the human CD3+ selected cell library.

These pools of 250 cDNA clones were then mini-prepped using QIAprep™ 96 Turbo Miniprep kit (Qiagen). Plasmid DNA was eluted using 125 µl of TE (10 mM Tris pH 8, 1 mM EDTA). This plasmid DNA was then used to transfect BHK cells.

BHK Transfection

BHK cells were plated in 96-well tissue culture plates at a density of 12,000 cells per well in a volume of 100 µl. per well. Culture media was DMEM (GibcoBRL), 5% heat-inactivated fetal bovine serum, 2 mM L-glutamine (GibcoBRL), 1×PSN (GibcoBRL), 1 mM NaPyruvate (GibcoBRL).

The following day, BHK cells were washed once with 100 µl SFA. SFA is serum-free media which is DMEM/F12 or DMEM (Gibco/BRL), 2 mM GlutaMax™ (Gibco/BRL), 1 mM NaPyruvate, 10 µg/ml transferrin, 5 µg/ml insulin, 10 µg/ml fetuin, 2 µg/ml selenium, 25 mM HEPES (Gibco/BRL), 100 µM non-essential amino acids (Gibco/BRL).

A DNA/Lipofectamine™ mix was made as follows: 2.2 µl Lipofectamine™ reagent (Gibco/BRL) was combined with 102.8 µl SFA at room temperature; approximately 5 µl of the plasmid DNA (200 ng/µl) was then added to the Lipofectamine™/SFA to form the DNA/Lipofectamine™ mixture, which was incubated at room temperature for 30 minutes. The SFA was removed from the BHK cells and the cells were incubated with 50 µl of the DNA/Lipofectamine™ mix for 5 hours at 37° C. with 5% CO₂. Fifty µl of the DNA/Lipofectamine™ mixture was added to each of two wells of the BHK cells, so that transfections were done in duplicate.

After BHK cells were incubated with DNA/Lipofectamine™ mix for 5 hours, the DNA/Lipofectamine™ mix was removed and 100 µl culture media was added. Cells were incubated overnight, the media was removed and replaced with 100 µl. culture media. After culturing cells for 48-72 hours, conditioned media was removed, frozen at −80° C. for a minimum of 20 minutes, thawed, and then 50 µl was assayed in the Baf3 proliferation assay, described in Example 5, to identify pools of 250 clones with ligand activity.

Twenty 96-well plates were screened in a single assay. This represented approximately 250 cDNAs/well or 480,000 cDNAs total. Of these, conditioned media from approximately 60 wells (representing 250 cDNAs per well) tested positive in the proliferation assay. One of these positive pools was chosen to break down and isolate a single cDNA that would encode the zcytor17lig. This was pool 62A12.

For pool 62A12, 1 μl. of DNA was used to transform ElectroMax™ DH10B cells (Gibco/BRL) by electroporation. The transformants were plated on LB+amp (100 μg/ml) plates to give single colonies. From the electroporated pool, 672 individual colonies were selected by toothpick into seven 96-well plates containing 1.2 ml of SuperBrothII™ per well. These plates were numbered #62.1 through #62.7. These were cultured overnight and the plasmid DNA miniprepped as above. For all seven plates, plasmid DNA from the breakdown plates was transfected into BHK cells and assayed by proliferation as above, except that transfections were not done in duplicate.

Two positive clones 62.6C7 and 62.6E9 were identified by activity from a total of 672 clones. Plasmid DNA miniprepped from clone 62.6E9 was sequenced and a tentative identification was obtained, but a mixed sequence was obtained from this positive clones. To further isolate the zcytor17lig cDNA to a single clone, 1 μl of DNA from pool 62.6E9 was used to electroporate DH10B cells and the transformants plated on LB+amp (100 μg/ml) plates to give single colonies. Plasmid DNA miniprepped from several colonies was sequenced to give the exact DNA sequence. The polynucleotide sequence of zcytor17lig was full-length (SEQ ID NO:1) and its corresponding amino acid sequence is shown (SEQ ID NO:2).

Example 8

Construction of Mammalian Expression Vectors that Express Zcytor17 Soluble Receptors Zcytor17CEE, Zcytor17CFLG, Zcytor17CHIS and Zcytor17-Fc4

A. Construction of Zcytor17 Mammalian Expression Vector Containing Zcytor17CEE, Zcytor17CFLG and Zcytor17CHIS An expression vector was prepared for the expression of the soluble, extracellular domain of the zcytor17 polypeptide, pZp9zcytor17CEE, where the construct is designed to express a zcytor17 polypeptide comprised of the predicted initiating methionine and truncated adjacent to the predicted transmembrane domain, and with a C-terminal Glu-Glu tag (SEQ ID NO:32).

An approximately 1500 bp PCR product was generated using ZC29,451 (SEQ ID NO:33) and ZC29,124 (SEQ ID NO:34) as PCR primers to add EcoRI and BamHI restriction sites. A human HPVS in-house cDNA library was used as a template and PCR amplification was performed as follows: 30 cycles at 94° C. for 1 minute, 65° C. for 1 minute, 72° C. for 1.5 minutes, then 72° C. for 7 minutes; 10° C. soak. The PCR reaction was ethanol precipitated and digested with EcoRI and BamHI restriction enzymes. The digested PCR product was gel purified on a 1.0% agarose gel and the approximately 1500 bp band excised. This band was then re-amplified using identical primers with the following cycling: 30 cycles at 94° C. for 1 minute, 65° C. for 1 minute, 72° C. for 3 minutes, then 72° C. for 7 minutes; 10° C. soak. The PCR reaction was ethanol precipitated and digested with EcoRI and BamHI restriction enzymes. The digested PCR product was gel purified on a 1.0% agarose gel and the approximately 1500 bp band excised. The excised DNA was subcloned into plasmid CEEpZp9 that had been cut with EcoRI and BamHI, to generate plasmid with a GLU-GLU C-terminally tagged soluble receptor for zcytor17, zcytor17CEEpZp9. The extracellular domain in the zcytor17CEE cDNA in zcytor17CEEpZp9 has a silent mutation that changes the T to C at position 1705 of SEQ ID NO:4 (encoding a Pro residue at residue 403 of SEQ ID NO:5). As this mutation is silent, the zcytor17 cDNA in zcytor17CEEpZp9 encodes the polypeptide as shown in SEQ ID NO:5. Moreover, because of the construct used, a Gly-Ser residue pair is inserted C-terminal to the end of the soluble, extracellular domain of zcytor17 and prior to the C-terminal Glu-Glu Tag (SEQ ID NO:32). As such, the tag at the C-terminus of the zcytor17 extracellular domain, was a Glu-Glu tag as shown in (SEQ ID NO:17). Plasmid CEEpZp9 is a mammalian expression vector containing an expression cassette having the mouse metallothionein-1 promoter, multiple restriction sites for insertion of coding sequences, and a human growth hormone terminator. The plasmid also has an *E. coli* origin of replication, a mammalian selectable marker expression unit having an SV40 promoter, enhancer and origin of replication, a DHFR gene and the SV40 terminator. Using standard molecular biological techniques zcytor17CEEpZp9 was electroporated into DH10B competent cells (GIBCO BRL, Gaithersburg, Md.) according to manufacturer's direction and plated onto LB plates containing 100 μg/ml ampicillin, and incubated overnight. Colonies were screened by restriction analysis, or PCR from DNA prepared from individual colonies. The insert sequence of positive clones was verified by sequence analysis. A large scale plasmid preparation was done using a QIAGEN® Maxi prep kit (Qiagen) according to manufacturer's instructions.

The same process is used to prepare the zcytor17 soluble receptors with a C-terminal his tag, composed of 6 His residues in a row; and a C-terminal FLAG® tag (SEQ ID NO:36), zcytor17CFLAG. To construct these constructs, the aforementioned vector has either the HIS or the FLAG® tag in place of the glu-glu tag (e.g., SEQ ID NO:17; SEQ ID NO:32 or SEQ ID NO:35).

B. Mammalian Expression Construction of Soluble Human Zcytor17 Receptor: Zcytor17-Fc4

An expression vector, pEZE-2 hzcytor17/Fc4, was prepared to express a C-terminally Fc4 tagged soluble version of hzcytor17 (human zcytor17-Fc4) in PF CHO cells. PF CHO cells are an in house CHO cell line adapted for growth in protein-free medium (ExCell 325 PF medium; JRH Biosciences). The in house CHO cell line was originally derived from CHO DG44 cells (G. Urlaub, J. Mitchell, E. Kas, L. A. Chasin, V. L. Funanage, T. T. Myoda and J. L. Hamlin, "The Effect Of Gamma Rays at the Dihydrofolate Reductase Locus: Deletions and Inversions," Somatic Cell and *Molec. Genet.*, 12: 555-566 (1986). A fragment of zcytor17 cDNA that includes the polynucleotide sequence from extracellular domain of the zcytor17 receptor was fused in frame to the Fc4 polynucleotide sequence (SEQ ID NO:37) to generate a zcytor17-Fc4 fusion (SEQ ID NO:38 and SEQ ID NO:39). The pEZE-2 vector is a mammalian expression vector that contains the Fc4 polynucleotide sequence and a cloning site that allows rapid construction of C-terminal Fc4 fusions using standard molecular biology techniques.

A 1566 base pair fragment was generated by PCR, containing the extracellular domain of human zcytor17 and the first two amino acids of Fc4 (Glu and Pro) with FseI and BglII sites coded on the 5' and 3' ends, respectively. This PCR fragment was generated using primers ZC29,157 (SEQ ID NO:40) and ZC29,150 (SEQ ID NO:41) by amplification from a plasmid containing the extracellular domain of human zcytor17 (pZp9zcytor17CEE) (Example 8). The PCR reaction conditions were as follows: 25 cycles of 94° C. for 1 minute, 60° C. for 1 minute, and 72° C. for 2 minutes; 1 cycle at 72° C. for 10 minutes; followed by a 4° C. soak. The fragment was digested with FseI and BglII restriction endonucleases and subsequently purified by 1% gel electrophoresis and band purification using QiaQuick gel extraction kit (Qiagen). The resulting purified DNA was ligated for 5 hours at room temperature into a pEZE-2 vector previously digested with FseI and BglII containing Fc4 3' of the FseI and BglII sites.

Two μl of the ligation mix was electroporated in 37 μl DH10B electrocompetent *E. coli* (Gibco) according to the manufacturer's directions. The transformed cells were diluted in 400 μl of LB media and plated onto LB plates containing 100 μg/ml ampicillin. Clones were analyzed by restriction digests and positive clones were sent for DNA sequencing to confirm the sequence of the fusion construct. 1 μl of a positive clone was transformed into 37 μl of DH10B electrocompetent *E. coli* and streaked on a LB/amp plate. A single colony was picked from this streaked plate to start a 250 ml LB/amp culture that was then grown overnight at 37° C. with shaking at 250 rpm. This culture was used to generate 750 μg of purified DNA using a Qiagen plasmid Maxi kit (Qiagen).

Example 9

Transfection and Expression of Zcytor17 Soluble Receptor Polypeptides

BHK 570 cells (ATCC No. CRL-10314), DG-44 CHO, or other mammalian cells are plated at about $1.2 \times 10^6$ cells/well (6-well plate) in 800 μl of appropriate serum free (SF) media (e.g., DMEM, Gibco/BRL High Glucose) (Gibco BRL, Gaithersburg, Md.). The cells are transfected with expression plasmids containing zcytor17CEE, zcytor17CFLG, zcytor17CHIS or zcytor17-Fc4 (Example 8), using Lipofectin™ (Gibco BRL), in serum free (SF) media according to manufacturer's instruction. Single clones expressing the soluble receptors are isolated, screened and grown up in cell culture media, and purified using standard techniques.
A. Mammalian Expression of Soluble Human Zcytor17CEE Receptor BHK 570 cells (ATCC NO: CRL-10314) were plated in T-75 tissue culture flasks and allowed to grow to approximately 50 to 70% confluence at 37° C., 5% $CO_2$, in DMEM/FBS media (DMEM, Gibco/BRL High Glucose, (Gibco BRL, Gaithersburg, Md.), 5% fetal bovine serum, 1 mM L-glutamine (JRH Biosciences, Lenea, Kans.), 1 mM sodium pyruvate (Gibco BRL)). The cells were then transfected with the plasmid containing zcytor17CEE (Example 8) using Lipofectamine (Gibco BRL), in serum free (SF) media formulation (DMEM, 10 mg/ml transferrin, 5 mg/ml insulin, 2 mg/ml fetuin, 1% L-glutamine and 1% sodium pyruvate). Ten μg of the plasmid DNA pZp9zcytor17CEE (Example 8) was diluted into a 15 ml tube to a total final volume of 500 μl with SF media. 50 μl of Lipofectamine was mixed with 450 μl of SF medium. The Lipofectamine mix was added to the DNA mix and allowed to incubate approximately 30 minutes at room temperature. Four ml of SF media was added to the DNA:Lipofectamine mixture. The cells were rinsed once with 5 ml of SF media, aspirated, and the DNA:Lipofectamine mixture was added. The cells were incubated at 37° C. for five hours, and then 5 ml of DMEM/10% FBS media was added. The flask was incubated at 37° C. overnight after which time the cells were split into the selection media (DMEM/FBS media from above with the addition of 1 μM methotrexate or 10 μM Methotrexate (Sigma Chemical Co., St. Louis, Mo.) in 150 mm plates at 1:2, 1:10, and 1:50. Approximately 10 days post-transfection, one 150 mm plate of 1 μM methotrexate resistant colonies was trypsinized, the cells were pooled, and one-half of the cells were replated in 10 μM methotrexate; to further amplify expression of the zcytor17CEE protein. A conditioned-media sample from this pool of amplified cells was tested for expression levels using SDS-PAGE and Western analysis.
B. Mammalian Expression of Soluble Human Zcytor17-Fc4 Receptor Five replicates of 200 μg of pEZE-2 hzcytor17Fc4 plasmid DNA (Example 8) were linearized by restriction digestion with FspI, a restriction enzyme that cuts once within the vector and does not disturb genes necessary for expression. 200 μg of CHO cell genomic DNA was added to each replicate as carrier DNA and then the DNA was precipitated by addition of 0.1 volumes of 3M Sodium Acetate pH 5.2 and 2.2 volumes ethanol followed by a 15 minute ice incubation and microcentrifugation at 4° C. The resulting DNA pellets were washed in 70% ethanol and air dried before being resuspended in 100 μl protein free (PF) CHO non-selection growth media (21 g/L PF CHO Ex Cell 325/200 mM L-glutamine (Gibco)/100 mM sodium pyruvate (Gibco)/1×HT Supplement (Gibco). Ten million PF CHO passage 61 cells were added to the DNA in 600 μl of PF CHO non-selection growth media and then electroporated in a Gene Pulser II Electroporation system (BioRad) using 950 μF capacitance and 300 Kv using a 0.4 cm gap Gene Pulser (BioRad) electroporation cuvette. All 5 replicates of the electroporated cells were pooled and directly selected in −HT media (21 g/L PF CHO Ex Cell 325/200 mM L-glutamine (Gibco)/100 mM sodium pyruvate (Gibco). Cells were selected for 15 days in −HT media before being passaged at $4 \times 10^5$ ml into 50 nm MTX selection. Eight days later cells were seeded at $3.5 \times 10^5$ cells/ml into 200 mM MTX selection. After one week, cells were seeded at $4 \times 10^5$ cells/ml into 1 μM MTX selection. After two weeks at 1 μM MTX, cells were seeded at $1 \times 10^6$ cells/ml into 50 ml to generate conditioned medium. The resulting 72 hour conditioned media was analyzed by probing western blots with an antibody generated against human Ig. The cells produced hzcytor17/Fc4 protein at approximately 1 mg/L.
C. Larger-Scale Mammalian Expression of Soluble Human Zcytor17-Fc4 Receptor Two hundred micrograms of pEZE-2 hzcytor17Fc4 plasmid DNA (Example 8) was linearized by restriction digestion with FspI, a restriction enzyme that cuts once within the pEZE-2 vector and does not disturb genes necessary for expression. 200 μg of CHO genomic DNA (prepared in-house) was added as carrier DNA and then the DNA was precipitated by addition of 0.1 volumes of 3M Sodium Acetate pH 5.2 and 2.5 volumes ethanol followed by microcentrifugation at Room temperature. Five replicate DNA pellets were made and transformed. The resulting DNA pellet was washed in 70% ethanol and air dried before being resuspended in 100 μl PF CHO non-selection growth media (21 g/L PF CHO Ex Cell 325/200 mM L-glutamine (Gibco)/100 mM sodium pyruvate (Gibco)/1×HT Supplement (Gibco). Ten million PF CHO cells were added to the DNA in 600 μl of PF CHO non-selection growth media and then electroporated in a Gene Pulser II Electroporation system (BioRad) using 950 μF capacitance and 300 volts using a 0.4 cm gap Gene Pulser (BioRad) electroporation cuvette. The electroporated cells were pooled and put directly into selection in −HT media (21 g/L PF CHO Ex Cell 325/200 mM L-glutamine (Gibco)/ 100 mM sodium pyruvate (Gibco). Cells were selected for 14 days in −HT media before being passaged at $4\times10^5$/ml into 50 nm MTX selection. Cells were amplified to 200 nM MTX and then to 1 uM MTX. The −HT, 50 nM, and 1 uM pools were seeded at $1\times10^6$ c/ml for 48 hours, and the resulting conditioned media was analyzed by probing western blots with an antibody generated against human Ig.

Example 10

Purification of Zcytor17 Soluble Receptors from BHK 570 and CHO Cells

A. Transient Mammalian Expression and Purification of Soluble Human Zcytor17-Fc4 Receptor pEZE-2 hzcytor17Fc4 plasmid DNA (Example 11B) was introduced into 40 maxi plates of BHK cells using Lipofectamine (Gibco BRL) as described herein and in manufacturer's instructions. Cells were allowed to recover overnight, then were rinsed and refed with serum-free medium (SL7V4, made in-house). After 72 hours, the media was collected and filtered, and cells were refed with serum-free medium. After 72 hours, the media was again collected and filtered.

The serum-free conditioned media (2×1.5 L batches) from transiently transfected BHK cells was pumped over a 1.5 ml Protein A-agarose column in 20 mM Tris, pH 7.5, 0.5 M NaCl. The column was washed extensively with this buffer and then the bound protein was eluted with 1 ml of 0.2 M glycine, pH 2.5, 0.5 M NaCl. The eluted protein was collected into 0.1 ml of 2 M Tris, pH 8.5.

Aliquots were collected for SDS-polyacrylamide gel electrophoresis and the bulk zcytor17-Fc was dialyzed overnight against PBS. The soluble receptor was sterile filtered and placed in aliquots at −80° C.

B. Purification of Zcytor17-Fc4

Recombinant carboxyl terminal Fc4 tagged zcytor17 (Example 8 and Example 9) was produced from transfected CHO cells. The CHO transfection was performed using methods known in the art. Approximately five-liters of conditioned media were harvested and sterile filtered using Nalgene 0.2 μm filters.

Protein was purified from the filtered media by a combination of Poros 50 protein A affinity chromatography (PerSeptive Biosystems, 1-5559-01, Framingham, Mass.) and Superdex 200 gel exclusion chromatography column (Amersham Pharmacia Biotech, Piscataway, N.J.). Culture medium was directly loaded onto a 10×70 mm (5.5-ml bed volume) protein A affinity column at a flow of about 3-10 ml/minute. Following column washing for ten column volumes of PBS, bound protein was eluted by five column volumes of 0.1 M glycine, pH 3.0 at 10 ml/minute). Fractions of 2 ml each were collected into tubes containing 100 μl of 2.0 M Tris, pH 8.0, in order to neutralize the eluted proteins. Samples from the affinity column were analyzed by SDS-PAGE with coomassie staining and Western blotting for the presence of zcytor17-Fc4 using human Ig-HRP. Zcytor17-Fc4-containing fractions were pooled and concentrated to 1-2 ml using Biomax-30 concentrator (Millipore), and loaded onto a 20×580 mm Superdex 200 gel filtration column. The fractions containing purified zcytor17-Fc4 were pooled, filtered through 0.2 μm filter, aliquoted into 100 μl each, and frozen at −80° C. The concentration of the final purified protein was determined by BCA assay (Pierce, Rockford, Ill.).

C. SDS-PAGE and Western Blotting Analysis of Zcytor17/Fc4

Recombinant zcytor17-Fc4 was analyzed by SDS-PAGE (Nupage 4-12%, Invitrogen, Carlsbad, Calif.) with coomassie staining method and Western blotting using human Ig-HRP. Either the conditioned media or purified protein was electrophoresed using an Invitrogen Novex's Xcell II mini-cell, and transferred to nitrocellulose (0.2 mm; Invitrogen, Carlsbad, Calif.) at room temperature using Novex's Xcell II blot module with stirring according to directions provided in the instrument manual. The transfer was run at 500 mA for one hour in a buffer containing 25 mM Tris base, 200 mM glycine, and 20% methanol. The filters were then blocked with 10% non-fat dry milk in PBS for 10 minutes at room temperature. The nitrocellulose was quickly rinsed, then the human Ig-HRP antibody (1:2000) was added in PBS containing 2.5% non-fat dry milk. The blots were incubated for two hours at room temperature, or overnight at 4° C., with gentle shaking. Following the incubation, the blots were washed three times for 10 minutes each in PBS, then quickly rinsed in $H_2O$. The blots were developed using commercially available chemiluminescent substrate reagents (SuperSignal® ULTRA reagents 1 and 2 mixed 1:1; reagents obtained from Pierce, Rockford, Ill.), and the signal was captured using Lumi-Imager's Lumi Analyst 3.0 software (Boehringer Mannheim GmbH, Germany) for exposure times ranging from 10 second to 5 minutes or as necessary.

The purified zcytor17-Fc4 appeared as a single band with either the coomassie or silver staining at about 220 kDa under non-reducing conditions, and at about 120 kDa under reducing conditions, suggesting the dimeric form of zcytor17-Fc4 under non-reducing conditions as expected.

Example 11

Assay Using Zcytor17 Soluble Receptor Zcytor17-Fc4 Soluble Receptor in Competitive Inhibition Assay BaF3/zcytor17/WSX-1/OSMRbeta cells or BaF3/zcytor17/OSMRbeta cells were spun down and washed in mIL-3 free media. The cells were spun and washed 3 times to ensure the removal of the mIL-3. Cells were then counted in a hemacytometer. Cells were plated in a 96-well format at 5000 cells per well in a volume of 100 μl per well using the mIL-3 free media.

Both conditioned media from the CCRF-CEM and CCRF-HSB2 cell activation and the human CD3+ selected cells, described in Example 5, were added in separate experiments at 25%, 12.5%, 6.25%, 3.125%, 1.5%, 0.75%, 0.375%, and 0.187% concentrations, with or without zcytor17 soluble receptors (Zcytor17-Fc4; See, Example 9 and Example 10) at 1-10 μg/ml. The total assay volume was 200 μl.

The assay plates were incubated at 37° C., 5% $CO_2$ for 3-5 days at which time Alamar Blue (Accumed) was added at 20 μl/well. Plates were again incubated at 37° C., 5% $CO_2$ for 16-24 hours. Plates were read on the Fmax™ plate reader (Molecular Devices) as described in Example 2. Results demonstrated partial inhibition of cell growth with zcytor17-Fc4 soluble receptor at 10 μg/ml, confirming that the factor in each sample was specific for the zcytor17 receptor.

Titration curves, diluting out the soluble receptor, or soluble receptor heterodimers and trimers comprising zcytor17 receptor (e.g., zcytor17/OSMR, zcytor17/WSX-1, or zcytor17/OSMR/WSX-1, or other Class I cytokine receptor subunits) are also run using the above stated assay to determine whether zcytor17 receptors are able to completely inhibit growth, for example, at low or physiologic concentrations.

Example 12

Secretion Trap Assay

A secretion trap assay is used to test the binding of the zcytor17lig to receptors comprising zcytor17 receptor, such as the zcytor17 receptor or receptor heterodimers and trimers comprising zcytor17 receptor (e.g., zcytor17/OSMR, zcytor17/WSX-1, or zcytor17/OSMR/WSX-1, or other Class I cytokine receptor subunits). Zcytor17lig plasmid DNA is transfected into COS cells, and used to assess binding of the zcytor17lig to receptors comprising zcytor17 receptor by secretion trap as described below.

A. COS Cell Transfections

The COS cell transfection is performed as follows: Mix about 800 ng of zcytor17lig cDNA and 5 µl Lipofectamine™ in 92 µl serum free DMEM media (55 mg sodium pyruvate, 146 mg L-glutamine, 5 mg transferrin, 2.5 mg insulin, 1 µg selenium and 5 mg fetuin in 500 ml DMEM), incubate at room temperature for 30 minutes and then add 400 µl serum free DMEM media. Add this 500 µl mixture onto $1.5 \times 10^5$ COS cells/well plated on 12-well tissue culture plate and incubate for 5 hours at 37° C. Add 500 µl 20% FBS DMEM media (100 ml FBS, 55 mg sodium pyruvate and 146 mg L-glutamine in 500 ml DMEM) and incubate overnight.

B. Secretion Trap Assay

The secretion trap is performed as follows: Media is rinsed off cells with PBS and then fixed for 15 minutes with 1.8% Formaldehyde in PBS. Cells are then washed with TNT (0.1M Tris-HCL, 0.15M NaCl, and 0.05% Tween-20 in $H_2O$), and permeated with 0.1% Triton-X in PBS for 15 minutes, and again washed with TNT. Cells are blocked for 1 hour with TNB (0.1M Tris-HCL, 0.15M NaCl and 0.5% Blocking Reagent (NEN Renaissance TSA-Direct Kit) in $H_2O$), and washed again with TNT. If using the biotinylated receptor protein, the cells are blocked for 15 minute incubations with Avidin and then Biotin (Vector Labs) washing in-between with TNT. Depending on which soluble receptor is used, the cells are incubated for 1 hour in TNB with: (A) 1-3 µg/ml zcytor17 soluble receptor zcytor17-Fc4 fusion protein (Example 10); (B) 1-3 µg/ml zcytor17/OSMRbeta soluble receptor protein; (C) 1-3 µg/ml zcytor17/WSX-1 soluble receptor protein; or (D) 1-3 µg/ml zcytor17/OSMR/WSX-1 soluble receptor protein. Cells are then washed with TNT. Depending on which soluble receptor is used (e.g., if labeled with an Fc4 tag (SEQ ID NO:37), C-terminal FLAG tag (SEQ ID NO:36), or CEE tag (SEQ ID NO:32; SEQ ID NO:35)), cells are incubated for another hour with: (A) 1:200 diluted goat-anti-human Ig-HRP (Fc specific); (B) 1:1000 diluted M2-HRP; (C) 1:1000 diluted anti-GluGlu antibody-HRP; or (D) 1:300 diluted streptavidin-HRP (NEN kit) in TNB, for example. Again cells are washed with TNT.

Positive binding is detected with fluorescein tyramide reagent diluted 1:50 in dilution buffer (NEN kit) and incubated for 4-6 minutes, and washed with TNT. Cells are preserved with Vectashield Mounting Media (Vector Labs Burlingame, Calif.) diluted 1:5 in TNT. Cells are visualized using a FITC filter on fluorescent microscope.

Example 13

Chromosomal Assignment and Placement of the Gene Sequence for the Zcytor17lig The zcytor17lig gene sequence was mapped to human chromosome 12 using the commercially available version of the "Stanford G3 Radiation Hybrid Mapping Panel" (Research Genetics, Inc., Huntsville, Ala.). The "Stanford G3 RH Panel" contains DNA from each of 83 radiation hybrid clones of the whole human genome, plus two control DNAs (the RM donor and the A3 recipient). A publicly available WWW server (e.g., Standford University) allows chromosomal localization of markers and genes.

For the mapping of the zcytor17lig gene sequence with the "Stanford G3 RH Panel", 20 µl reactions were set up in a 96-well microtiter plate compatible for PCR (Stratagene, La Jolla, Calif.) and used in a "RoboCycler Gradient 96" thermal cycler (Stratagene). Each of the 95 PCR reactions consisted of 2 µl 10×PCR reaction buffer (Qiagen, Inc., Valencia, Calif.), 1.6 µl dNTPs mix (2.5 mM each, PERKIN-ELMER, Foster City, Calif.), 1 µl sense primer, ZC41,458 (SEQ ID NO:42), 1 µl antisense primer, ZC41,457 (SEQ ID NO:43), 2 µl "RediLoad" (Research Genetics, Inc., Huntsville, Ala.), 0.1 µl Qiagen HotStarTaq DNA Polymerase (5 units/µl), 25 ng of DNA from an individual hybrid clone or control and distilled water for a total volume of 20 µl. The reactions were overlaid with an equal amount of mineral oil and sealed. The PCR cycler conditions were as follows: an initial 1 cycle 15 minute denaturation at 95° C., 35 cycles of a 45 second denaturation at 95° C., 1 minute annealing at 53° C. and 1 minute and 15 seconds extension at 72° C., followed by a final 1 cycle extension of 7 minutes at 72° C. The reactions were separated by electrophoresis on a 2% agarose gel (EM Science, Gibbstown, N.J.) and visualized by staining with ethidium bromide.

The results showed linkage of the zcytor17lig gene sequence to the chromosome 12 marker SHGC-83339 with a LOD score of >11 and at a distance of 17 cR__10000 from the marker. This marker positions zcytor17lig gene in the 12q24.31 chromosomal region.

Example 14

Identification and Cloning of Murine Zcytor17lig

A. Identification of Full Length Murine Zcytor17lig

Using the human zcytor17lig peptide sequence (SEQ ID NO:2) to query an in house DNA database, a murine cDNA, Genbank Accession No. AK005939, was identified as a potential partial sequence for the murine zcytor17lig. The AK005939 cDNA sequence was used to query a database containing murine genomic fragments. A genomic contig of the murine zcytor17lig was assembled (SEQ ID NO:76). Prediction of coding potential on this genomic fragment with the program Genscan revealed a likely cDNA sequence, with the same gene structure as the human zcytor17lig. A murine cDNA sequence is represented in SEQ ID NO:10, and corresponding polypeptide sequence is shown in SEQ ID NO:11.

B. Cloning of Mouse Zcytor17lig from a Mouse Testis cDNA Library by PCR

Based on the genomic sequence (SEQ ID NO:76), two PCR primers were designed and used to identify a cDNA source of mouse zcytor17lig by PCR. These Primers ZC41498 (SEQ ID NO:86) and ZC41496 (SEQ ID NO:87) were designed to the putative 5' and 3' untranslated regions of the mouse sequences (SEQ ID NO:76 and SEQ ID NO:10). Several cDNA sources were screened by PCR, including Marathon-ready cDNAs (Clontech) and aliquots of locally made cDNA libraries. Products were visualized on 1% agarose gels. Bands of the expected size were observed in reactions utilizing a mouse testis cDNA library template. These PCR reactions were successfully performed in approximately 50 µl volumes with or without 10% DMSO, using pfu turbo polymerase (Stratagene) according to the manufacturer's recommendations; with an additional application of a wax hot-start employing hot start 50s (Molecular Bioproducts, Inc. San Diego, Calif.). PCR thermocycling was performed with a single cycle of 94° C. for 4 min; followed by 40 cycles of 94° C.: 30 seconds, 48° C.: 30 seconds, 72° C.: 50 seconds; with additional final 72° C. extension for 7 minutes. The two PCR reactions were pooled and purified using low melt agarose and Gelase agarose digesting enzyme (Epicenter, Inc. Madison, Wis.) according to the manufacturer's recommendations.

DNA sequence determination of these PCR products revealed a murine zcytor17 cDNA sequence (SEQ ID NO:90) which comprised an ORF identical to SEQ ID NO:10, confirming that SEQ ID NO:10 encoded the mouse zcytor17lig polypeptide. PCR primers, ZC41583 (SEQ ID NO:88) and ZC41584 (SEQ ID NO:89), were then used to add FseI and AscI restriction sites and a partial Kozak sequence to the mcytor17lig open reading frame and termination codon (SEQ ID NO:92). A Robocycler 40 thermocycler (Stratagene) was used to run a temperature gradient of annealing temperatures and cycling as follows. Pfu turbo polymerase (Stratagene) was applied as described above, but only in 10% DMSO. Cycling was performed with a single cycle of 94° C. for 4 min; followed by 20 cycles of 94° C.: 30 seconds, 65° C. to 51° C. gradient: 30 seconds, 72° C.: 1 minute; and a single 72° C. extension for 7 minutes. The template for this second thermocycling reaction was 1 µl of the initial gel-purified mcytor17lig PCR product, above. Resulting PCR product from the three lowest temperature reactions were pooled and gel purified using the Gelase (Epicenter) method described above. This purified mzcytor17lig was digested with FseI and AscI and ligated into a pZP7X vector modified to have FseI and AscI sites in its cloning site. Plasmid pZP7X is a mammalian expression vector containing an expression cassette having the mouse metallothionein-1 (MT-1) promoter, multiple restriction sites for insertion of coding sequences, and a human growth hormone terminator. The plasmid also has an *E. coli* origin of replication, a mammalian selective marker expression unit having an SV40 promoter, enhancer and origin of replication, a DHFR gene, and the SV40 terminator. The cloned murine cDNA sequence is represented in SEQ ID NO:90, and corresponding polypeptide sequence is shown in SEQ ID NO:91 (which is identical to SEQ ID NO:11).

Example 15

Isolation of Mouse Zcytor17lig cDNA Clone from an Activated Mouse Spleen Library A. Murine Primary Source Used to Isolate Mouse Zcytor17lig Mouse spleens from Balb/C mice, are collected and mashed between frosted-end slides to create a cell suspension. The isolated primary mouse cell yield is expected to be about $6.4 \times 10^8$ cells prior to selection described below.

The spleen cells are suspended in 9.6 ml MACS buffer (PBS, 0.5% EDTA, 2 mM EDTA). 1.6 ml of cell suspension is removed and 0.4 ml CD90 (Thy1.2) microbeads (Miltenyi Biotec) added. The mixture is incubated for 15 min. at 4° C. These cells labeled with CD90 beads are washed with 30 ml MACS buffer, and then resuspended in 2 ml MACS buffer.

A VS+ column (Miltenyi) is prepared according to the manufacturer's instructions. The VS+ column is then placed in a VarioMACS™ magnetic field (Miltenyi). The column is equilibrated with 5 ml MACS buffer. The isolated primary mouse cells are then applied to the column. The CD90 negative cells are allowed to pass through. The column is rinsed with 9 ml (3×3 ml) MACS buffer. The column is then removed from the magnet and placed over a 15 ml falcon tube. CD90+ cells are eluted by adding 5 ml MACS buffer to the column and bound cells flushed out using the plunger provided by the manufacturer. The incubation of the cells with the CD90 magnetic beads, washes, and VS+ column steps (incubation through elution) above are repeated once more. The resulting CD90+ fractions from the 2 column separations are pooled. The yield of CD90+ selected mouse spleen cells are expected to be about $1 \times 10^8$ total cells.

A sample of the pooled CD90+ selected mouse cells is removed for staining and sorting on a fluorescent antibody cell sorter (FACS) to assess their purity. A PE-conjugated hamster anti-mouse CD3ε antibody (PharMingen) is used for staining and sorting the CD90+ selected cells. The mouse CD90+ selected cells should be about 93% CD3+ cells, suggesting the cells are 93% T-cells.

The murine CD90+ selected cells are activated by incubating $3 \times 10^6$ cells/ml in RPMI+5% FBS+PMA 10 ng/ml and Ionomycin 0.5 µg/ml (Calbiochem) for overnight at 37° C. The supernatant from these activated CD90+ selected mouse cells is tested for zcytor17lig activity as described below. Moreover, the activated CD90+ selected mouse cells are used to prepare a cDNA library, as described in Example 16, below.

Example 16

Cloning of Mouse Zcytor17lig from a Mouse CD90+ Selected Cell Library

Screening of a primary mouse activated CD90+ selected cell cDNA library can reveal isolated cDNA that is a novel member of the four-helix bundle cytokine family that would encode the mouse ortholog of the human zcytor17lig. The cDNA is identified by hybridization screening.

A. The Vector for CD90+ Selected Library Construction

The vector, pZP7N is used for CD3+ selected library construction (See Example 6A)

B. Preparation of Primary Mouse Activated CD90+ Selected Cell cDNA Library

Approximately $1.5 \times 10^8$ primary mouse CD90+ selected cells stimulated in ionomycin/PMA (Example 15) are isolated by centrifugation. Total RNA is isolated from the cell pellet, and converted to double stranded cDNA as described in Example 6B. This DNA is subsequently transfected into BHK cells, as described in Example 6B, and proliferation is assessed using an "Alamar blue" fluorescence assay (Example 2B).

For the purpose of screening the library by secretion trap cloning, a complex, amplified form of the library is needed to transfect COS-7 cells. 4.8 million clones are plated on 110 15 cm LB-agar plates supplemented with 100 µg/ml ampicillin, 10 µg/ml methicillin. After growing the plates overnight at 37° C. the bacteria are harvested by scraping and pelleted. Plasmid DNA is extracted from the pelleted bacteria using a Nucleobond-giga™ (Clonetech) following the manufacturer's instructions. This plasmid is then used to transfect COS-7 cells on slides and screened using the secretion trap technique described below (Example 17).

C. Screening the Activated Mouse cDNA Library

Approximately $5 \times 10^5$ clones are plated on 10 LB/Amp Maxi plates. The colonies are lifted, denatured, neutralized, and cross-linked using the standard procedure (Sambrook, J. et al. supra.). Fifty nanograms of the 300 bp 5' RACE PCR fragment (Example 14) is labeled with $^{32}$P using Prime-Itr RmT random primer labeling kit (Stratagene). The 10 filters are hybridized with this labeled probe at 65° C. overnight using ExpressHyb™ Hybridization Solution (Clontech). The filters are then washed sequentially at 60° C. for 1 hour three times with 0.2×SSC (30 mM NaCl, 3 mM sodium citrate, pH 7.0), 0.1% SDS; and then at 65° C. for 1 hour. The filters are exposed at −80° C. overnight, and the X-ray film are developed. Agar plugs containing the positive colonies are pulled, and the clones plated on 10-cm LB/Amp plates. The colonies are then filter-lifted and hybridized again following the same procedure described above. Single DNA clones are isolated and sequenced using standard methods, to identify the mouse cDNA.

Example 17

Mouse Zcytor17lig does not Bind to Human Zcytor17 Soluble Receptor in Secretion Trap Assay The DNA for mouse clone mzcytor17lig/pZP7 was transfected into COS cells, and the binding of zcytor17 comprising soluble receptors (human zcytor17 soluble receptor zcytor17-Fc4 (Example 10), or soluble receptor heterodimers (zcytor17/WSX-1 or BaF3/zcytor17/OSMRbeta), to the transfected COS cells were tested by a secretion trap assay (Example 12). The assay confirmed that the mouse zcytor17lig does not bind to human zcytor17 soluble receptor.

The COS cell transfection was performed as per Example 12 using about 0.7 μg mouse zcytor17lig cDNA (Example 16) in 3 μl.

The secretion trap was performed as per example 12 using, for example, 1 μg/ml zcytor17 soluble receptor Fc4 fusion protein (Example 10) (or zcytor17 comprising soluble receptor heterodimers as described herein) in TNB, and 1:200 diluted goat-anti-human Ig-HRP (Fc specific) in TNB for the detectable antibody. Positive binding of the soluble human zcytor17 receptor to the prepared fixed cells was not detected with fluorescein tyramide reagent as per Example 12. Cells were preserved and visualized according to Example 12.

Results indicated that the mouse zcytor17lig does not bind to human zcytor17 soluble receptor (or zcytor17 comprising soluble receptor heterodimers as described herein).

Example 18

Expression of Mouse Zcytor17lig in Mammalian Cells

Mammalian Expression of Mouse Zcytor17lig

BHK 570 cells (ATCC No: CRL-10314) were plated in 10 cm tissue culture dishes and allowed to grow to approximately 20% confluence overnight at 37° C., 5% $CO_2$, in DMEM/FBS media (DMEM, Gibco/BRL High Glucose media; Gibco BRL, Gaithersburg, Md.), 5% fetal bovine serum (Hyclone, Logan, Utah), 1 mM L-glutamine (JRH Biosciences, Lenexa, Kans.), 1 mM sodium pyruvate (Gibco BRL). The cells were then transfected with the plasmid mzcytor17lig/pZP7X (Example 14) using a mammalian stable Lipofectamine (GibcoBRL) transfection kit according to the manufacturer's instructions.

One day after transfection, the cells were split 1:10 and 1:20 into the selection media (DMEM/FBS media with the addition of 1 μM methotrexate (Sigma Chemical Co., St. Louis, Mo.)) in 150 mm plates. The media on the cells was replaced with fresh selection media at day 5 post-transfection. Approximately 10 days post-transfection, methotrexate resistant colonies were trypsinized and the cells pooled and plated into large-scale culture flasks. Once the cells were grown to approximately 90% confluence, they were rinsed with PBS three times, and cultured with serum-free ESTEP2 media (DMEM (Gibco BRL), 0.11 g/l Na Pyruvate, 3.7 g/l $NaHCO_3$, 2.5 mg/l insulin, 5 mg/l transferrin, pH7.0) conditioned media. The conditioned media was collected three days later, and put into a BaF3 proliferation assay using Alamar Blue, described in Example 19 below.

Example 19

Mouse Zcytor17lig does not Activate Human Zcytor17 Receptor in BaF3 Assay Using Alamar Blue Proliferation of BaF3/zcytor17, BaF3/zcytor17/OSMR-beta and BaF3/zcytor17/WSX-1 cells (Example 4, and 5B) was assessed using serum-free conditioned media from BHK cells expressing mouse zcytor17lig (Example 18). BaF3/Zcytor17, BaF3/zcytor17/OSMRbeta and BaF3/zcytor17/WSX-1 cells were spun down, washed and plated in mIL-3 free media as described in Example 5B. Conditioned media from BHK cells expressing mouse zcytor17lig (Example 18) was diluted with mIL-3 free media to 50%, 25%, 12.5%, 6.25%, 3.125%, 1.5%, 0.75% and 0.375% concentrations. The proliferation assay was performed as per Example 5B. The results of this assay were negative, indicating that mouse zcytor17lig does not activate human zcytor17, zcytor17/OSMRbeta, or zcytor17/WSX-1 receptor complexes.

Example 20

Human Zcytor17lig Activates Human, Zcytor17/OSMRbeta Receptor, in Luciferase Assay A. Construction of BaF3/KZ134/Zcytor17 Cell Line The KZ134 plasmid was constructed with complementary oligonucleotides ZC12,749 (SEQ ID NO:44) and ZC12,748 (SEQ ID NO:45) that contain STAT transcription factor binding elements from 4 genes, which includes a modified c-fos S is inducible element (m67SIE, or hSIE) (Sadowski, H. et al., Science 261:1739-1744, 1993), the p21 SIE1 from the p21 WAF1 gene (Chin, Y. et al., Science 272:719-722, 1996), the mammary gland response element of the β-casein gene (Schmitt-Ney, M. et al., Mol. Cell. Biol. 11:3745-3755, 1991), and a STAT inducible element of the Fcg RI gene, (Seidel, H. et al., Proc. Natl. Acad. Sci. 92:3041-3045, 1995). These oligonucleotides contain Asp718-XhoI compatible ends and were ligated, using standard methods, into a recipient firefly luciferase reporter vector with a c-fos promoter (Poulsen, L. K. et al., J. Biol. Chem. 273:6229-6232, 1998) digested with the same enzymes and containing a neomycin selectable marker. The KZ134 plasmid was used to stably transfect BaF3 cells, using standard transfection and selection methods, to make the BaF3/KZ134 cell line.

A stable BaF3/KZ134 indicator cell line, expressing the full-length zcytor17 receptor or zcytor17/OSMRbeta receptor was constructed as per Example 4. Clones were diluted, plated and selected using standard techniques. Clones were screened by luciferase assay (see Example 20B, below) using the human zcytor17lig conditioned media or purified zcytor17lig protein (see Example 35, below) as an inducer. Clones with the highest luciferase response (via STAT luciferase) and the lowest background were selected. Stable transfectant cell lines were selected. The cell lines were called BaF3/KZ134/zcytor17 or BaF3/KZ134/zcytor17/OSMRbeta depending on the receptors transfected into the cell line.

Similarly, BHK cell lines were also constructed using the method described herein, and were used in luciferase assays described herein. The cell lines were called BHK/KZ134/zcytor17 or BHK/KZ134/zcytor17/OSMRbeta depending on the receptors transfected into the cell line.

B. Human Zcytor17lig Activates Human Zcytor17 Receptor in BaF3/KZ134/Zcytor17/OSMRbeta or BHK/KZ134/zcytor17/OSMRbeta Luciferase Assay BaF3/KZ134/zcytor17 and BaF3/KZ134/zcytor17/OSMRbeta cells were spun down and washed in mIL-3 free media. The cells were spun and washed 3 times to ensure removal of mIL-3. Cells were then counted in a hemacytometer. Cells were plated in a 96-well format at about 30,000 cells per well in a volume of 100 µl per well using the mIL-3 free media. The same procedure was used for untransfected BaF3/KZ134 cells for use as a control in the subsequent assay. BHK/KZ134/zcytor17 or BHK/KZ134/zcytor17/OSMRbeta cells were plated in a 96-well format at 15,000 cells per well in 100 µl media. Parental BHK/KZ134 cells were used as a control.

STAT activation of the BaF3/KZ134/Zcytor17, BaF3/KZ134/zcytor17/OSMRbeta, BHK/KZ134/zcytor17, or BHK/KZ134/zcytor17/OSMRbeta cells was assessed using (1) conditioned media from BHK570 cells transfected with the human zcytor17lig (Example 7), (2) conditioned media from BHK570 cells transfected with the mouse zcytor17lig (Example 18), (3) purified human zcytor17lig (Example 35), or (4) mIL-3 free media to measure media-only control response. Conditioned media was diluted with RPMI mIL-3 free media to 50%, 25%, 12.5%, 6.25%, 3.125%, 1.5%, 0.75% and 0.375% concentrations. Purified human zcytor17lig was diluted to a concentration of 1200, 600, 300, 150, 75, 37.5, 18.75, or 9.4 pM. 100 µl of the diluted conditioned media or protein was added to the BaF3/KZ134/Zcytor17, BaF3/KZ134/zcytor17/OSMRbeta, BHK/KZ134/zcytor17, or BHK/KZ134/zcytor17/OSMRbeta cells. The assay using the conditioned media was done in parallel on untransfected BaF3/KZ134 or BHK/KZ134 cells as a control. The total assay volume was 200 µl. The assay plates were incubated at 37° C., 5% $CO_2$ for 24 hours at which time the BaF3 cells were pelleted by centrifugation at 2000 rpm for 10 min., and the media was aspirated and 25 µl of lysis buffer (Promega) was added. For the BHK cell lines, the centrifugation step was not necessary as the cells are adherant. After 10 minutes at room temperature, the plates were measured for activation of the STAT reporter construct by reading them on a luminometer (Labsystems Luminoskan, model RS) which added 40 µl of luciferase assay substrate (Promega) at a five second integration.

The results of this assay confirmed that the STAT reporter response of the BaF3/KZ134/zcytor17/OSMRbeta and BHK/KZ134/zcytor17/OSMRbeta cells to the human zcytor17lig when compared to either the BaF3/KZ134/zcytor17 cells, the BHK/KZ134/zcytor17 cells or the untransfected BaF3/KZ134 or BHK/KZ134 control cells, showed that the response was mediated through the zcytor17/OSMRbeta receptors. The results also showed that the mouse zcytor17lig does not activate the STAT reporter assay through the human receptor complex.

Example 21

Mouse Zcytor17lig is Active in Mouse Bone Marrow Assay

A. Isolation of Non-Adherent Low Density Marrow Cells:

Fresh mouse femur aspirate (marrow) is obtained from 6-10 week old male Balb/C or C57BL/6 mice. The marrow is then washed with RPMI+10% FBS (JRH, Lenexa Kans.; Hyclone, Logan Utah) and suspended in RPMI+10% FBS as a whole marrow cell suspension. The whole marrow cell suspension is then subjected to a density gradient (Nycoprep, 1.077, Animal; Gibco BRL) to enrich for low density, mostly mononuclear, cells as follows: The whole marrow cell suspension (About 8 ml) is carefully pipetted on top of about 5 ml Nycoprep gradient solution in a 15 ml conical tube, and then centrifuged at 600×g for 20 minutes. The interface layer, containing the low density mononuclear cells, is then removed, washed with excess RPMI+10% FBS, and pelleted by centrifugation at 400×g for 5-10 minutes. This pellet is resuspended in RPMI+10% FBS and plated in a T-75 flask at approximately $10^6$ cells/ml, and incubated at 37° C. 5% $CO_2$ for approximately 2 hours. The resulting cells in suspension are Non-Adherent Low Density (NA LD) Marrow Cells.

B. 96-Well Assay

NA LD Mouse Marrow Cells are plated at 25,000 to 45,000 cells/well in 96 well tissue culture plates in RPMI+10% FBS+1 ng/mL mouse Stem Cell Factor (mSCF) (R&D Systems, Minneapolis, Minn.), plus 5% conditioned medium from one of the following: (1) BHK 570 cells expressing mouse zcytor17lig (Example 18), (2) BHK 570 cells expressing human zcytor17lig (Example 7), or (3) control BHK 570 cells containing vector and not expressing either Ligand. These cells are then subjected to a variety of cytokine treatments to test for expansion or differentiation of hematopoietic cells from the marrow. For testing, the plated NA LD mouse marrow cells are subjected to human Interleukin-15 (hIL-15) (R&D Systems), or one of a panel of other cytokines (R&D Systems). Serial dilution of hIl-15, or the other cytokines, are tested, with 2-fold serial dilution from about 50 ng/ml down to about 0.5 ng/ml concentration. After 8 to 12 days the 96-well assays are scored for cell proliferation by Alamar blue assay as described in Example 5B.

C. Results from the 96-Well NA LD Mouse Marrow Assay

Conditioned media from the BHK cells expressing both mouse and human zcytor17lig can promote the expansion of a population of hematopoietic cells either alone or in synergy with other cytokines in the NA LD mouse marrow in comparison to control BHK conditioned medium. The population hematopoietic cells expanded by the mouse zcytor17lig with or without other cytokines, and those hematopoietic cells expanded by the human zcytor17lig with or without other cytokines, are further propagated in cell culture. These hematopoietic cells are stained with a Phycoerythrin labeled anti-Pan NK cell antibody (PharMingen) and subjected to flow cytometry analysis, which demonstrated that the expanded cells stained positively for this natural killer (NK) cell marker. Similarly, other specific hematopoietic cell markers can be used to determine expansion of, for example, CD4+ or CD8+ T-cells, other T-cell populations, B-cells, and other immune cell markers.

The same 96-well assay is run, using fresh human marrow cells bought from Poietic Technologies, Gaithersburg, Md. Again, a positive result shows that zcytor17lig alone or in synergy with other cytokines, the mouse and human zcytor17lig can expand a hematopoietic cell population that is stained positively for specific cell markers as disclosed above.

Example 22

Constructs for Generating Zcytor17lig Transgenic Mice

Construct for Expressing Human Zcytor17Lig from the MT-1 Promoter

Oligonucleotides are designed to generate a PCR fragment containing a consensus Kozak sequence and the human zcytor17lig coding region. These oligonucleotides are designed with an FseI site at the 5' end and an AscI site at the 3' end to facilitate cloning into (a) pMT12-8, our standard transgenic vector, or (b) pKFO51, a lymphoid-specific transgenic vector (Example 22B).

PCR reactions are carried out with about 200 ng human zcytor17lig template (SEQ ID NO:1) and oligonucleotides designed to amplify the full-length or active portion of the zcytor17lig. PCR reaction conditions are determined using methods known in the art. PCR products are separated by agarose gel electrophoresis and purified using a QiaQuick™ (Qiagen) gel extraction kit. The isolated, correct sized DNA fragment is digested with FseI and AscI (Boerhinger-Mannheim), ethanol precipitated and ligated into pMT12-8 previously digested with FseI and AscI. The pMT12-8 plasmid, designed for expressing a gene of interest in liver and other tissues in transgenic mice, contains an expression cassette flanked by 10 kb of MT-1 5' DNA and 7 kb of MT-1 3' DNA. The expression cassette comprises the MT-1 promoter, the rat insulin II intron, a polylinker for the insertion of the desired clone, and the human growth hormone (hGH) poly A sequence.

About one microliter of each ligation reaction is electroporated into DH10B ElectroMax™ competent cells (GIBCO BRL, Gaithersburg, Md.) according to manufacturer's direction and plated onto LB plates containing 100 µg/ml ampicillin, and incubated overnight. Colonies are picked and grown in LB media containing 100 µg/ml ampicillin. Miniprep DNA is prepared from the picked clones and screened for the human zcytor17lig insert by restriction digestion with EcoRI alone, or FseI and AscI combined, and subsequent agarose gel electrophoresis. Maxipreps of the correct pMT-human zcytor17lig are performed. A SalI fragment containing with 5' and 3' flanking sequences, the MT-1 promoter, the rat insulin II intron, human zcytor17lig cDNA and the hGH poly A sequence is prepared to be used for microinjection into fertilized murine oocytes. Microinjection and production of transgenic mice are produced as described in Hogan, B. et al. *Manipulating the Mouse Embryo*, 2$^{nd}$ ed., Cold Spring Harbor Laboratory Press, NY, 1994.

B. Construct for Expressing Human Zcytor17lig from the Lymphoid-Specific EµLCK Promoter Oligonucleotides are designed to generate a PCR fragment containing a consensus Kozak sequence and the human zcytor17lig coding region. These oligonucleotides are designed with an FseI site at the 5' end and an AscI site at the 3' end to facilitate cloning into pKFO51, a lymphoid-specific transgenic vector.

PCR reactions are carried out with about 200 ng human zcytor17lig template (SEQ ID NO:1) and oligonucleotides designed to amplify the full-length or active portion of the zcytor17lig. A PCR reaction is performed using methods known in the art. The isolated, correct sized DNA fragment is digested with FseI and AscI (Boerhinger-Mannheim), ethanol precipitated and ligated into pKFO51 previously digested with FseI and AscI. The pKFO51 transgenic vector is derived from p1026X (Iritani, B. M., et al., *EMBO J.* 16:7019-31, 1997) and contains the T cell-specific lck proximal promoter, the B/T cell-specific immunoglobulin µ heavy chain enhancer, a polylinker for the insertion of the desired clone, and a mutated hGH gene that encodes an inactive growth hormone protein (providing 3' introns and a polyadenylation signal).

About one microliter of each ligation reaction is electroporated, plated, clones picked and screened for the human zcytor17lig insert by restriction digestion as described above. A correct clone of pKFO51-zcytor17lig is verified by sequencing, and a maxiprep of this clone is performed. A NotI fragment, containing the lck proximal promoter and immunoglobulin µ enhancer (EµLCK), zcytor17lig cDNA, and the mutated hGH gene is prepared to be used for microinjection into fertilized murine oocytes.

C. Construct for Expressing Mouse Zcytor17lig from the EF1Alpha Promoter

Primers ZC41,498 (SEQ ID NO:86) and ZC41,496 (SEQ ID NO:87) were used to PCR a mouse testis cDNA library template. These PCR reactions were successfully performed in approximately 50 µl volumes with or without 10% DMSO, using pfu turbo polymerase (Stratagene) according to the manufacturer's recommendations; with an additional application of a wax hot-start employing hot start 50s (Molecular Bioproducts, Inc. San Diego, Calif.). PCR thermocycling was performed with a single cycle of 94° C. for 4 min; followed by 40 cycles of 94° C.: 30 seconds, 48° C.: 30 seconds, 72° C.: 50 seconds; with additional final 72° C. extension for 7 minutes. The two PCR reactions were pooled and purified using low melt agarose and Gelase agarose digesting enzyme (Epicenter, Inc. Madison, Wis.) according to the manufacturer's recommendations.

DNA sequenced PCR products revealed a murine zcytor17 cDNA sequence (SEQ ID NO:90) which comprised an ORF identical to SEQ ID NO:10, confirming that SEQ ID NO:10 encoded the mouse zcytor17lig polypeptide. PCR primers, ZC41583 (SEQ ID NO:88) and ZC41584 (SEQ ID NO:89), were then used to add FseI and AscI restriction sites and a partial Kozak sequence to the mcytor17lig open reading frame and termination codon (SEQ ID NO:92). A Robocycler 40 thermocycler (Stratagene) was used to run a temperature gradient of annealing temperatures and cycling as follows. Pfu turbo polymerase (Stratagene) was applied as described above, but only in 10% DMSO. Cycling was performed with a single cycle of 94° C. for 4 min; followed by 20 cycles of 94° C.: 30 seconds, 65° C. to 51° C. gradient: 30 seconds, 72° C.: 1 minute; and a single 72° C. extension for 7 minutes. The template for this second thermocycling reaction was 1 µl of the initial gel-purified mcytor17lig PCR product, above. Resulting PCR product from the three lowest temperature reactions were pooled and gel purified using the Gelase (Epicenter) method described above. This purified fragment was then digested with FseI and AscI and ligated into a pZP7X vector modified to have FseI and AscI sites in its cloning site. This was sent to sequencing to confirm the correct sequence. The cloned murine cDNA sequence is represented in SEQ ID NO:90, and corresponding polypeptide sequence is shown in SEQ ID NO:91 (which is identical to SEQ ID NO:11).

The isolated, correct sized DNA fragment digested with FseI and AscI (Boerhinger-Mannheim) was subcloned into a plasmid containing EF1alpha promoter previously digested with FseI and AscI. Maxipreps of the correct EF1alpha mouse zcytor17lig were performed. The expression cassette contains the EF1alpha promoter (with a deleted FseI site), the EF1alpha intron, SUR IRES like site to facilitate expression, a polylinker flanked with rat insulin II sites on the 5' end which adds FseI PmeI AscI sites for insertion of the desired clone, and the human growth hormone (hGH) poly A sequence. A 7.5 kb NotI fragment containing the EF1alpha promoter expression cassette and mouse zcytor17lig was prepared to be used for microinjection into fertilized murine oocytes. The EF1alpha plsdmid was obtained from Louis-Marie of the Laboratoire de Differenciation Cellulaire, as described in Taboit-Dameron et al., 1999, *Transgenic Research* 8:223-235.

D. Construct for Expressing Mouse Zcytor17lig from the Lymphoid-Specific EµLCK Promoter Oligonucleotides were designed to generate a PCR fragment containing a consensus Kozak sequence and the mouse zcytor17lig coding region. These oligonucleotides were designed with an FseI site at the 5' end and an AscI site at the 3' end to facilitate cloning into pKFO51 (see Example 22B, above).

The isolated, correct sized zcytor17lig DNA fragment used in EF1alpha constructs, digested with FseI and AscI (Boerhinger-Mannheim), was subcloned into a plasmid containing pKFO51, a lymphoid-specific transgenic vector. The pKFO51 transgenic vector is derived from p1026X (Iritani, B. M., et al., *EMBO J.* 16:7019-31, 1997) and contains the T cell-specific lck proximal promoter, the B/T cell-specific immunoglobulin µ heavy chain enhancer, a polylinker for the insertion of the desired clone, and a mutated hGH gene that encodes an inactive growth hormone protein (providing 3' introns and a polyadenylation signal). A 6.5 kb NotI fragment, containing the lck proximal promoter and immunoglobulin µ enhancer (EµLCK), mouse zcytor17lig cDNA, and the mutated hGH gene was prepared to be used for microinjection into fertilized murine oocytes (Example 41).

Example 23

Construction of Mammalian Expression Vectors that Express Zcytor17lig-CEE

A. Construction of ZCytor17lig-CEE/pZMP21

An expression plasmid containing all or part of a polynucleotide encoding human zCytor17lig was constructed via homologous recombination. The plasmid was called zCytor17Lig-CEE/pZMP21.

The construction of zCytor17Lig-CEE/pZMP21 was accomplished by generating a zCytor17Lig-CEE fragment (SEQ ID NO:95) using PCR amplification. The DNA template used for the production of the zCytor17Lig-CEE fragment was zCytor17Lig/pZP7nx. The primers used for the production of the zCytor17Lig-CEE fragment were: (1) ZC41607 (SEQ ID NO:97) (sense sequence), which includes from the 5' to the 3' end: 28 bp of the vector flanking sequence (5' of the insert) and 21 bp corresponding to the 5' sequence of zCytor17Lig; and (2) ZC41605 (SEQ ID NO:98) (anti-sense sequence), which includes from the 5' to the 3' end: 37 bp of the vector flanking sequence (3' of the insert), 3 bp of the stop codon, 21 bp encoding a C-terminal EE tag, and 21 bp corresponding to the 3' end of zCytor17Lig sequence. The fragment resulting from the above PCR amplification is a copy of the template zCytor17Lig with the addition of a C-terminal EE tag, yielding a final product zCytor17Lig-CEE.

PCR reactions were run as follows: To a 100 µl final volume was added: 10 µl of 10× Taq Polymerase Reaction Buffer with 15 mM MgCl (Gibco), 1 µl of Taq DNA Polymerase (5 units/µl, Gibco), 3 µl of 10 mM dNTPs, 78 µl dH2O, 3 µl of a 20 pmol/µl stock of primer ZC41607 (SEQ ID NO:97) 3 µl of a 20 pmol/µl stock of primer ZC41605 (SEQ ID NO:98), and 41 µl of a 0.13 µg/µl stock of zCytor17lig template DNA. A volume equal to 50 µl of mineral oil was added to the mixture. The reaction was heated to 94° C. for 5 minutes, followed by 35 cycles at 94° C. for 1 minute; 55° C. for 2 minutes; 72° C. for 3 minutes; followed by a 10 minute extension at 72° C. and held at 4° C. until the reaction was collected.

The plasmid pZMP21 was restriction digested with BglII enzyme, cleaned with a QiaQuick PCR Purification Kit (Qiagen) using a microcentrifuge protocol, and used for recombination with the PCR fragment. Plasmid pZMP21 was constructed from pZMP20 which was constructed from pZP9 (deposited at the American Type Culture Collection, 10801 University Boulevard, Manassas, Va. 20110-2209, and is designated No. 98668) with the yeast genetic elements taken from pRS316 (deposited at the American Type Culture Collection, 10801 University Boulevard, Manassas, Va. 20110-2209, and designated No. 77145), an IRES element from poliovirus, and the extracellular domain of CD8, truncated at the carboxyl terminal end of the transmembrane domain. PZMP21 is a mammalian expression vector containing an expression cassette having the MPSV promoter, immunoglobulin signal peptide intron, multiple restriction sites for insertion of coding sequences, a stop codon and a human growth hormone terminator. The plasmid also has an *E. coli* origin of replication, a mammalian selectable marker expression unit having an SV40 promoter, enhancer and origin of replication, a DHFR gene, the SV40 terminator, as well as the URA3 and CEN-ARS sequences required for selection and replication in *S. cerevisiae*.

Fifty microliters of competent yeast cells (*S. cerevisiae*) were independently combined with 100 ng of cut plasmid, 5 µl of previously described PCR mixture, and transferred to a 0.2 cm electroporation cuvette. The yeast/DNA mixture was electropulsed at 0.75 kV (5 kV/cm), ∞ ohms, 25 µF. Each cuvette had 600 µl of 1.2 M sorbitol added, and the yeast was plated in one 100 µl aliquot and one 300 µl aliquot onto two URA-D plates and incubated at 30° C. After about 72 hours, the Ura+ yeast transformants from a single plate were resuspended in 1 ml H$_2$O and spun briefly to pellet the yeast cells. The cell pellet was resuspended in 500 µl of lysis buffer (2% Triton X-100, 1% SDS, 100 mM NaCl, 10 mM Tris, pH 8.0, 1 mM EDTA). The 500 µl of the lysis mixture was added to an Eppendorf tube containing 300 µl acid washed 600 µm glass beads and 300 µl phenol-chloroform, vortexed for 1 minute intervals two or three times, followed by a 5 minute spin in a Eppendorf centrifuge at maximum speed. Three hundred microliters of the aqueous phase was transferred to a fresh tube, and the DNA precipitated with 600 µl 100% ethanol (EtOH), followed by centrifugation for 10 minutes at 4° C. The DNA pellet was then washed with 500 µl 70% EtOH, followed by centrifugation for 1 minute at 4° C. The DNA pellet was resuspended in 30 µl H$_2$O.

Transformation of electrocompetent *E. coli* cells (MC1061) was done with 5 µl of the yeast DNA prep and 50 µl of MC1061 cells. The cells were electropulsed at 2.0 kV, 25 µF and 400 ohms (Ω). Following electroporation, 600 µl SOC (2% Bacto' Tryptone (Difco, Detroit, Mich.), 0.5% yeast extract (Difco), 10 mM NaCl, 2.5 mM KCl, 10 mM MgCl$_2$, 10 mM MgSO$_4$, 20 mM glucose) was added. The electroporated *E. coli* cells were plated in a 200 µl and a 50 µl aliquot on two LB AMP plates (LB broth (Lennox), 1.8% Bacto Agar (Difco), 100 mg/L Ampicillin). The plates were incubated upside down for about 24 hours at 37° C. Three Ampicillin-resistant colonies were selected at random and submitted for sequence analysis of the insert. Large scale plasmid DNA was isolated from a sequence-confirmed clone using the Qiagen Maxi kit (Qiagen) according to manufacturer's instructions.

B. Mammalian Expression of Human Zcytor17lig

Full-length zCytor17Lig protein was produced in BHK cells transfected with zCytor17Lig-CEE/pZMP21 (Example 23A). BHK 570 cells (ATCC CRL-10314) were plated in T75 tissue culture flasks and allowed to grow to approximately 50 to 70% confluence at 37° C., 5% $CO_2$, in growth media (SL7V4, 5% FBS, 1% pen/strep). The cells were then transfected with zCytor17Lig-CEE/pZMP21 by liposome-mediated transfection (using Lipofectamine™; Life Technologies), in serum free (SF) media (SL7V4). The plasmid (16 µg) was diluted into 1.5 ml tubes to a total final volume of 640 µl with SF media. Thirty-five microliters of the lipid mixture was mixed with 605 µl of SF medium, and the resulting mixture was allowed to incubate approximately 15 minutes at room temperature. Five milliliters of SF media was then added to the DNA:lipid mixture. The cells were rinsed once with 10 ml of PBS, the PBS was decanted, and the DNA:lipid mixture was added. The cells are incubated at 37° C. for five hours, then 15 ml of media (SL7V4, 5% FBS, 1% pen/strep) was added to each plate. The plates were incubated at 37° C. overnight, and the DNA:lipid media mixture was replaced with selection media (SL7V4, 5% FBS, 1% pen/strep, 1 µM methotrexate) the next day. Approximately 10 days post-transfection, methotrexate-resistant colonies from the T75 transfection flask were trypsinized, and the cells were pooled and plated into a T-162 flask and transferred to large-scale culture.

Example 24

Expression of Zcytor17 Soluble Receptor in *E. coli*

A. Construction of Expression Vector pCMH01 that Expresses Huzcytor17/MBP-6H Fusion Polypeptide An expression plasmid containing a polynucleotide encoding a zcytor17 soluble receptor fused C-terminally to maltose binding protein (MBP) was constructed via homologous recombination. The fusion polypeptide contains an N-terminal approximately 388 amino acid MBP portion fused to any of the zcytor17 soluble receptors described herein. A fragment of zcytor17 cDNA (SEQ ID NO:4) was isolated using PCR as described herein. Two primers were used in the production of the zcytor17 fragment in a standard PCR reaction: (1) one containing about 40 bp of the vector flanking sequence and about 25 bp corresponding to the amino terminus of the zcytor17, and (2) another containing about 40 bp of the 3' end corresponding to the flanking vector sequence and about 25 bp corresponding to the carboxyl terminus of the zcytor17. Two µl of the 100 µl PCR reaction was run on a 1.0% agarose gel with 1×TBE buffer for analysis, and the expected approximately fragment was seen. The remaining PCR reaction was combined with the second PCR tube and precipitated with 400 µl of absolute ethanol. The precipitated DNA used for recombining into the Sma1 cut recipient vector pTAP170 to produce the construct encoding the MBP-zcytor17 fusion, as described below.

Plasmid pTAP170 was derived from the plasmids pRS316 and pMAL-c2. The plasmid pRS316 is a *Saccharomyces cerevisiae* shuttle vector (Hieter P. and Sikorski, R., *Genetics* 122:19-27, 1989). pMAL-C2 (NEB) is an *E. coli* expression plasmid. It carries the tac promoter driving MalE (gene encoding MBP) followed by a His tag, a thrombin cleavage site, a cloning site, and the rrnB terminator. The vector pTAP170 was constructed using yeast homologous recombination. 100 ng of EcoR1 cut pMAL-c2 was recombined with 1 µg Pvu1 cut pRS316, 1 µg linker, and 1 µg Sca1/EcoR1 cut pRS316. The linker consisted of oligos zc19,372 (SEQ ID NO:172) (100 pmole): zc19,351 (SEQ ID NO:173) (1 pmole): zc19,352 (SEQ ID NO:174) (1 pmole), and zc19,371 (SEQ ID NO:175) (100 pmole) combined in a PCR reaction. Conditions were as follows: 10 cycles of 94° C. for 30 seconds, 50° C. for 30 seconds, and 72° C. for 30 seconds; followed by 4° C. soak. PCR products were concentrated via 100% ethanol precipitation.

One hundred microliters of competent yeast cells (*S. cerevisiae*) were combined with 10 µl of a mixture containing approximately 1 µg of the human zcytor17 insert, and 100 ng of SmaI digested pTAP170 vector, and transferred to a 0.2 cm electroporation cuvette. The yeast/DNA mixture was electropulsed at 0.75 kV (5 kV/cm), infinite ohms, 25 µF. To each cuvette was added 600 µl of 1.2 M sorbitol. The yeast was then plated in two 300 µl aliquots onto two –URA D plates and incubated at 30° C.

After about 48 hours, the Ura+ yeast transformants from a single plate were picked, DNA was isolated, and transformed into electrocompetent *E. coli* cells (e.g., MC1061, Casadaban et. al. *J. Mol. Biol.* 138, 179-207), and plated on MM/CA+ KAN 25 µg/L plates (Pryor and Leiting, *Protein Expression and Purification* 10:309-319, 1997) using standard procedures. Cells were grown in MM/CA with 25 µg/ml Kanomyacin for two hours, shaking, at 37° C. One ml of the culture was induced with 1 mM IPTG. Two to four hours later the 250 µl of each culture was mixed with 250 µl acid washed glass beads and 250 µl Thorner buffer with 5% βME and dye (8M urea, 100 mM Tris pH7.0, 10% glycerol, 2 mM EDTA, 5% SDS). Samples were vortexed for one minute and heated to 65° C. for 10 minutes. 20 µl were loaded per lane on a 4%-12% PAGE gel (NOVEX). Gels were run in 1×MES buffer. The positive clones were designated pCMH01 and subjected to sequence analysis.

One microliter of sequencing DNA was used to transform strain BL21. The cells were electropulsed at 2.0 kV, 25 µF and 400 ohms. Following electroporation, 0.6 ml MM/CA with 25 µg/L Kanomyacin. Cells were grown in MM/CA and induced with ITPG as described above. The positive clones were used to grow up for protein purification of the huzcytor17/MBP-6H fusion protein using standard techniques.

B. Purification of Huzcytor17/MBP-6H Soluble Receptor from *E. coli* Fermentation Unless otherwise noted, all operations were carried out at 4° C. The following procedure was used for the purification of recombinant huzcytor17/MBP-6H soluble receptor polypeptide. *E. coli* cells containing the pCMH01 construct and expressing huzcytor17/MBP-6H soluble receptor polypeptide were constructed using standard molecular biology methods and cultured in SuperBroth II (12 g/L Casien, 24 g/L Yeast Extract, 11.4 g/L di-potassium phosphate, 1.7 g/L Mono-potassium phosphate; Becton Dickenson, Cockeysville, Md.). The resulting cells were harvested and frozen in 0.5% glycerol. Twenty grams of the frozen cells were used for protein purification.

Thawed cells were resuspended in 500 mL Amylose Equilibration buffer (20 mM Tris, 100 mM NaCl, pH 8.0). A French Press cell breaking system (Constant Systems Ltd., Warwick, UK) with a temperature setting of –7° C. to –10° C. and 30K PSI was used to lyse the cells. The resuspended cells were checked for breakage by $A_{600}$ readings before and after cycling through the French Press. The lysed cell suspension was pelleted at 10,000 G for 30 minutes. Supernatant was harvested from the debris pellet for protein purification.

Twenty-five milliliters of Amylose resin (New England Biolabs, Beverly, Mass.) was poured into a Bio-Rad, 2.5 cm D×10 cm H glass column. The column was packed and equilibrated by gravity with 10 column volumes (CVs) of Amylose Equilibration buffer. The harvested cell supernatant was batch loaded to the Amylose resin, overnight with rocking. The loaded resin was returned to the glass column, washed with 10 CVs Amylose Equilibration buffer, and eluted by gravity with ~2 CVs Amylose Elution buffer (Amylose Equilibration buffer, 10 mM Maltose, Fluka Biochemical, Switzerland). Ten 5 ml fractions were collected over the elution profile and assayed for absorbance at 280 and 320 nM. The Amylose resin was regenerated with 1 CV of distilled $H_2O$, 5 CVs of 0.1% (w/v) SDS (Sigma), 5 CVs of distilled $H_2O$, 5 CVs of Amylose Equilibration buffer, and finally 1 CV of Amylose Storage buffer (Amylose Equilibration buffer, 0.02% (w/v) Sodium Azide). The regenerated resin was stored at 4° C.

Elution profile fractions of interest were pooled and dialyzed in a 10K dialysis chamber (Slide-A-Lyzer, Pierce Immunochemical) against 4 changes of 4 L PBS pH 7.4 (Sigma) over an 8 hour time period. Following dialysis, the material harvested represented the purified huzcytor17/MBP-6H polypeptide. The purified huzcytor17/MBP-6H polypeptide was filter sterilized and analyzed via SDS-PAGE Coomassie staining for an appropriate molecular weight product. The concentration of the huzcytor17/MBP-6H polypeptide was determined by BCA analysis to be 0.76 mg/ml.

Purified huzcytor17/MBP-6H polypeptide was appropriately formulated for the immunization of rabbits and sent to R & R Research and Development (Stanwood, Wash.) for polyclonal antibody production (Example 25, below).

Example 25

Human Zcytor17 Receptor Polyclonal Antibody

A. Preparation and Purification

Polyclonal antibodies were prepared by immunizing 2 female New Zealand white rabbits with the purified recombinant protein huzcytor17/MBP-6H (Example 24). The rabbits were each given an initial intraperitoneal (IP) injection of 200 µg of purified protein in Complete Freund's Adjuvant followed by booster IP injections of 100 µg protein in Incomplete Freund's Adjuvant every three weeks. Seven to ten days after the administration of the second booster injection (3 total injections), the animals were bled and the serum was collected. The animals were then boosted and bled every three weeks.

The huzcytor17/MBP-6H specific rabbit serum was preadsorbed of anti-MBP antibodies using a CNBr-SEPHAROSE 4B protein column (Pharmacia LKB) that was prepared using 10 mg of non-specific purified recombinant MBP-fusion protein per gram of CNBr-SEPHAROSE. The huzcytor17/MBP-6H-specific polyclonal antibodies were affinity purified from the pre-adsorbed rabbit serum using a CNBr-SEPHAROSE 4B protein column (Pharmacia LKB) that was prepared using 10 mg of the specific antigen purified recombinant protein huzcytor17/MBP-6H. Following purification, the polyclonal antibodies were dialyzed with 4 changes of 20 times the antibody volume of PBS over a time period of at least 8 hours. Human zcytor17-specific antibodies were characterized by ELISA using 500 ng/ml of the purified recombinant protein huzcytor17/MBP-6H as antibody target. The lower limit of detection (LLD) of the rabbit anti-huzcytor17/MBP-6H affinity purified antibody is 500 pg/ml on its specific purified recombinant antigen huzcytor17/MBP-6H.

B. SDS-PAGE and Western Blotting Analysis of Rabbit Anti-Human ZcytoR17 MBP-6H Antibody Rabbit anti-human ZcytoR17 MBP-6H antibody was tested by SDS-PAGE (NuPage 4-12%, Invitrogen, Carlsbad, Calif.) with coomassie staining method and Western blotting using goat anti-rabbit IgG-HRP. Either purified protein (200-25 ng) or conditioned media containing zcytor17 was electrophoresed using an Invitrogen Novex's Xcell II mini-cell, and transferred to nitrocellulose (0.2 mm; Invitrogen, Carlsbad, Calif.) at room temperature using Novex's Xcell blot module with stirring according to directions provided in the instrument manual. The transfer was run at 300 mA for one hour in a buffer containing 25 mM Tris base, 200 mM glycine, and 20% methanol. The filter was then blocked with Western A buffer (in house, 50 mM Tris, pH 7.4, 5 mM EDTA, pH 8.0, 0.05% Igepal CA-630, 150 mM NaCl, and 0.25% gelatin) overnight with gentle rocking at 4° C. The nitrocellulose was quickly rinsed, then the rabbit anti-human zcytoR17 MBP-6H (1:1000) was added in Western A buffer. The blot was incubated for 1.5 hours at room temperature with gentle rocking. The blot was rinsed 3 times for 5 minutes each in Western A, then goat anti-rabbit IgG HRP antibody (1:1000) was added in Western A buffer. The blot was incubated for 1.25 hours at room temperature with gentle rocking. The blot was rinsed 3 times for 5 minutes each in Western A, then quickly rinsed in $H_2O$. The blot was developed using commercially available chemiluminescent substrate reagents (ECL Western blotting detection reagents 1 and 2 mixed 1:1; reagents obtained from Amersham Pharmacia Biotech, Buckinghamshire, England) and the blot was exposed to X-ray film for up to 15 minutes.

The rabbit anti-human zcytoR17 MBP-6H was able to detect human zcytor17 present in conditioned media as well as zcytoR17 purified protein as a band at 120 kDa under reducing conditions.

Example 26

Tissue Distribution of Mouse Zcytor17 in Tissue Panels Using PCR

A panel of cDNAs from murine tissues was screened for mouse zcytor17 expression using PCR. The panel was made in-house and contained 94 marathon cDNA and cDNA samples from various normal and cancerous murine tissues and cell lines are shown in Table 6, below. The cDNAs came from in-house libraries or marathon cDNAs from in-house RNA preps, Clontech RNA, or Invitrogen RNA. The mouse marathon cDNAs were made using the marathon-Ready™ kit (Clontech, Palo Alto, Calif.) and QC tested with mouse transferrin receptor primers ZC10,651 (SEQ ID NO:46) and ZC10,565 (SEQ ID NO:47) and then diluted based on the intensity of the transferrin band. To assure quality of the amplified library samples in the panel, three tests for quality control (QC) were run: (1) To assess the RNA quality used for the libraries, the in-house cDNAs were tested for average insert size by PCR with vector oligos that were specific for the vector sequences for an individual cDNA library; (2) Standardization of the concentration of the cDNA in panel samples was achieved using standard PCR methods to amplify full length alpha tubulin or G3PDH cDNA using a 5' vector oligo: ZC14,063 (SEQ ID NO:48) and 3' alpha tubulin specific oligo primer ZC17,574 (SEQ ID NO:49) or 3' G3PDH specific oligo primer ZC17,600 (SEQ ID NO:50); and (3) a sample was sent to sequencing to check for possible ribosomal or mitochondrial DNA contamination. The panel was set up in a 96-well format that included a mouse genomic DNA (Clontech, Palo Alto, Calif.) positive control sample. Each well contained approximately 0.2-100 pg/μl of cDNA. The PCR was set up using oligos ZC38,065 (SEQ ID NO:51) and ZC38,068 (SEQ ID NO:52), TaKaRa Ex Taq™ (TAKARA Shuzo Co LTD, Biomedicals Group, Japan), and Redioad dye (Research Genetics, Inc., Huntsville, Ala.). The amplification was carried out as follows: 1 cycle at 94° C. for 5 minutes; 5 cycles of 94° C. for 30 seconds, 68° C. for 30 seconds; 35 cycles of 94° C. for 30 seconds, 56° C. for 30 seconds and 72° C. for 30 seconds, followed by 1 cycle at 72° C. for 5 minutes. About 10 μl of the PCR reaction product was subjected to standard Agarose gel electrophoresis using a 4% agarose gel. The correct predicted DNA fragment size was observed in brain, CD90+ cells, dendritic, embryo, MEWt#2, Tuvak-prostate cell line, salivary gland, skin and testis.

The DNA fragment for skin and testis were excised and purified using a Gel Extraction Kit (Qiagen, Chatsworth, Calif.) according to manufacturer's instructions. Fragments were confirmed by sequencing to show that they were indeed mouse zcytor17.

TABLE 6

| Tissue/Cell line | #samples |
| --- | --- |
| 229 | 1 |
| 7F2 | 1 |
| Adipocytes-Amplified | 1 |
| aTC1.9 | 1 |
| Brain | 4 |
| CCC4 | 1 |
| CD90+ Amplified | 1 |
| OC10B | 1 |
| Dentritic | 1 |
| Embyro | 1 |
| Heart | 2 |
| Kidney | 3 |
| Liver | 2 |
| Lung | 2 |
| MEWt#2 | 1 |
| P388D1 | 1 |
| Pancreas | 1 |
| Placenta | 2 |
| Jakotay-Prostate Cell Line | 1 |
| Nelix-Prostate Cell Line | 1 |
| Paris-Prostate Cell Line | 1 |
| Torres-Prostate Cell Line | 1 |
| Tuvak-Prostate Cell Line | 1 |
| Salivary Gland | 2 |
| Skeletal Muscle | 1 |
| Skin | 2 |
| Small Intestine | 1 |
| Smooth Muscle | 2 |
| Spleen | 2 |
| Stomach | 1 |
| Testis | 3 |
| Thymus | 1 |

Example 27

Human Zcytor17 Expression in Various Tissues Using Real-Time Quantitative RT/PCR A. Primers and Probes for Human Zcytor17, OSMRbeta and Zcytor17Lig for Conventional and Quantitative RT-PCR Real-time quantitative RT-PCR using the ABI PRISM 7900 Sequence Detection System (PE Applied Biosystems, Inc., Foster City, Calif.) has been previously described (See, Heid, C. A. et al., *Genome Research* 6:986-994, 1996; Gibson, U. E. M. et al., *Genome Research* 6:995-1001, 1996; Sundaresan, S. et al., *Endocrinology* 139:4756-4764, 1998). This method incorporates use of a gene specific probe containing both reporter and quencher fluorescent dyes. When the probe is intact the reporter dye emission is negated due to the close proximity of the quencher dye. During PCR extension using additional gene-specific forward and reverse primers, the probe is cleaved by 5' nuclease activity of Taq polymerase which releases the reporter dye from the probe resulting in an increase in fluorescent emission.

The primers and probes used for real-time quantitative RT-PCR analyses of human Zcytor17, OSMRbeta and Zcytor17ligand expression were designed using the primer design software Primer Express™ (PE Applied Biosystems, Foster City, Calif.). Primers for human Zcytor17 were designed spanning an intron-exon junction to eliminate possible amplification of genomic DNA. The forward primer, ZC37,877 (SEQ ID NO:53) and the reverse primer, ZC37,876 (SEQ ID NO:54) were used in a PCR reaction at a 200 nM concentration to synthesize a 73 bp product. The corresponding Zcytor17 TaqMan® probe, designated ZC37,776 (SEQ ID NO:55) was synthesized and labeled by PE Applied Biosystems and used in each PCR reaction at a concentration of 200 nM. The ZC37,776 (SEQ ID NO:55) probe was labeled at the 5' end with a reporter fluorescent dye (6-carboxy-fluorescein) (FAM) (PE Applied Biosystems) and at the 3' end with a fluorescent quencher dye (6-carboxy-tetramethyl-rhodamine) (TAMRA) (Epoch Biosciences, Bothell, Wash.).

Primers for human OSMRbeta were designed spanning an intron-exon junction to eliminate possible amplification of genomic DNA. The forward primer, ZC43,891 (SEQ ID NO:137) and the reverse primer, ZC43,900 (SEQ ID NO:138) were used in a PCR reaction (below) at a 200 nM concentration. The corresponding OSMRbeta TaqMan® probe, designated ZC43,896 (SEQ ID NO:139) was synthesized and labeled by PE Applied Biosystems and used in each PCR reaction at a concentration of 200 nM. The ZC43,896 (SEQ ID NO:139) probe was labeled at the 5' end with a reporter fluorescent dye (6-carboxy-fluorescein) (FAM) (PE Applied Biosystems) and at the 3' end with a non-fluorescent quencher dye (ECLIPSE) (Epoch Biosciences).

Primers for human Zcytor17ligand were designed spanning an intron-exon junction to eliminate possible amplification of genomic DNA. The forward primer, ZC43,280 (SEQ ID NO:140) and the reverse primer, ZC43,281 (SEQ ID NO:141) were used in a PCR reaction (below) at about 200 nM concentration. The corresponding Zcytor17ligand TaqMan® probe, designated ZC43,275 (SEQ ID NO:142) was synthesized and labeled by PE Applied Biosystems and used in each PCR reaction at a concentration of 200 nM. The ZC43,275 (SEQ ID NO:142) probe was labeled at the 5' end with a reporter fluorescent dye (6-carboxy-fluorescein) (FAM) (PE Applied Biosystems) and at the 3' end with a non-fluorescent quencher dye (ECLIPSE) (Epoch Biosciences).

As a control to test the integrity and quality of RNA samples tested, all RNA samples were screened for either rRNA or GUS using primer and probe sets either ordered from PE Applied Biosystems (rRNA kit) or designed in-house (GUS). The rRNA kit contained the forward primer (SEQ ID NO:56), the rRNA reverse primer (SEQ ID NO:57), and the rRNA TaqMan® probe (SEQ ID NO:58). The rRNA probe was labeled at the 5' end with a reporter fluorescent dye VIC (PE Applied Biosystems) and at the 3' end with the quencher fluorescent dye TAMRA (PE Applied Biosystems). The GUS primers and probe were generated in-house and used in each PCR reaction at 200 nM and 100 nM, respectively. The forward primer was ZC40,574 (SEQ ID NO:143) and the reverse primer was ZC40,575 (SEQ ID NO:144). The GUS probe ZC43,017 (SEQ ID NO:145) was labeled at the 5' end with a reporter fluorescent dye (Yakima-Yellow) (Epoch Biosciences) and at the 3' end with a non-fluorescent quencher dye (ECLIPSE) (Epoch Biosciences). The rRNA and GUS results also serve as an endogenous control and allow for the normalization of the Zcytor17 mRNA expression results seen in the test samples.

For conventional non-quantitative RT-PCR, primers were designed using the primer design software Primer Express™ (PE Applied Biosystems, Foster City, Calif.). The human zcytor17 primers generate an approximately 1000 base pair product and are as follows: forward primer ZC28,917 (SEQ ID NO:83), and reverse primer ZC28,480 (SEQ ID NO:146). The human OSMRbeta primers generate a 202 base pair product and are as follows: forward primer ZC41,653 (SEQ ID NO:147) and reverse primer ZC41,655 (SEQ ID NO:148). The human Zcytor17ligand primers generate a 305 base pair product and are as follows: forward primer ZC41,703 (SEQ ID NO:149) and reverse primer ZC41,704 (SEQ ID NO:150).

B. Primers and Probes for Murine Zcytor17, OSMRbeta and Zcytor17Ligand for Conventional and Quantitative RT-PCR The primers and probes used for real-time quantitative RT-PCR analyses of murine Zcytor17, OSMRbeta and Zcytor17lig expression were designed using the primer design software Primer Express™ (PE Applied Biosystems, Foster City, Calif.). Primers for murine Zcytor17 were designed spanning an intron-exon junction to eliminate possible amplification of genomic DNA. The forward primer, ZC43,272 (SEQ ID NO:151) and the reverse primer, ZC43,273 (SEQ ID NO:152) were used in the PCR reactions (below) at 300 nM concentration. The corresponding Zcytor17 TaqMan® probe, designated ZC43,478 (SEQ ID NO:153) was synthesized and labeled by PE Applied Biosystems. The ZC43,478 (SEQ ID NO:153) probe was labeled at the 5' end with a reporter fluorescent dye (6-carboxy-fluorescein) (FAM) (PE Applied Biosystems) and at the 3' end with a quencher fluorescent dye (6-carboxy-tetramethyl-rhodamine) (TAMRA) (PE Applied Biosystems). The ZC43,478 (SEQ ID NO:153) probe was used in the PCR reactions at a concentration of 100 nM.

Primers for murine Zcytor17ligand were designed spanning an intron-exon junction to eliminate possible amplification of genomic DNA. The forward primer, ZC43,278 (SEQ ID NO:154) and the reverse primer, ZC43,279 (SEQ ID NO:155) were used in the PCR reactions at 500 nM concentration. The corresponding Zcytor17ligand TaqMan® probe, designated ZC43,276 (SEQ ID NO:156) was synthesized and labeled by PE Applied Biosystems. The ZC43,478 (SEQ ID NO:153) probe was labeled at the 5' end with a reporter fluorescent dye (6-carboxy-fluorescein) (FAM) (PE Applied Biosystems) and at the 3' end with a non-fluorescent quencher dye (ECLIPSE) (Epoch Biosciences). The ZC43,276 (SEQ ID NO:156) probe was used in the PCR reactions (below) at a concentration of 200 nM.

Primers for murine OSMRbeta were designed spanning an intron-exon junction to eliminate possible amplification of genomic DNA. The forward primer, ZC43,045 (SEQ ID NO:157) and the reverse primer, ZC43,046 (SEQ ID NO:158) were used in the PCR reactions at a 300 nM concentration. The corresponding OSMRbeta TaqMan® probe, designated ZC43,141(SEQ ID NO:159) was synthesized and labeled by Epoch Biosciences. The ZC43,141 (SEQ ID NO:159) probe was labeled at the 5' end with a reporter fluorescent dye (6-carboxy-fluorescein) (FAM) (PE Applied Biosystems) and at the 3' end with a non-fluorescent quencher dye (ECLIPSE) (Epoch Biosciences). The ZC43,141 (SEQ ID NO:159) probe was used in the PCR reactions (below) at a concentration of 100 nM.

As a control to test the integrity and quality of RNA samples tested, all RNA samples were screened for either murine GUS or transferrin receptor using primers and probes designed using the primer design program Primer Express™ (PE Applied Biosystems Inc., Foster City, Calif.). The murine GUS primers are as follows: forward primer, ZC43,004 (SEQ ID NO:160), reverse primer, ZC43,005 (SEQ ID NO:161), and TaqMan® probe ZC43,018 (SEQ ID NO:162). The murine GUS probe ZC43,018 (SEQ ID NO:162) was labeled at the 5' end with a reporter fluorescent dye Yakima-Yellow (Epoch Biosciences) and at the 3' end with the non-fluorescent quencher dye ECLIPSE (Epoch Biosciences). The murine GUS primers were used in the PCR reactions at 300 nM and the probe, ZC43,018 (SEQ ID NO:162), was used at 100 nM. In some cases murine Transferrin Receptor was used instead of GUS as the endogenous control. The transferrin receptor forward primer, ZC40,269 (SEQ ID NO:163) and the reverse primer, ZC40,268 (SEQ ID NO:164) were used at 300 nM. The transferrin receptor probe, ZC40,298 (SEQ ID NO:165) was used in PCR at 100 nM and was labeled at the 5' end with a reporter fluorescent dye VIC (PE Applied Biosystems) and at the 3' end with a fluorescent quencher dye (TAMRA) (PE Applied Biosystems). The murine GUS and transferrin receptor results also serve as an endogenous control and allow for the normalization of the Zcytor17, OSMRbeta and Zcytor17ligand mRNA expression results seen in the test samples.

For conventional semi-quantitative RT-PCR, primers were designed using the primer design software Primer Express™ (PE Applied Biosystems). The murine Zcytor17 primers generate a 276 base pair product and are as follows: forward primer ZC43,140 (SEQ ID NO:166), and reverse primer ZC43,139 (SEQ ID NO:167). The murine OSMRbeta primers generate a 575 base pair product and are as follows: forward primer ZC41,608 (SEQ ID NO:168) and reverse primer ZC41,609 (SEQ ID NO:169). The murine Zcytor17ligand primers generate a 657 bp product and are as follows: forward primer ZC41,502 (SEQ ID NO:170) and reverse primer ZC41,500 (SEQ ID NO:171).

C. Protocols for Realtime Quantitative RT-PCR and Conventional Semi-Quantitative RT-PCR Relative levels of Zcytor17, OSMRbeta and Zcytor17ligand mRNA were determined by analyzing total RNA samples using the one-step RT-PCR method (PE Applied Biosystems). Total RNA from Zcytor17- and OSMRbeta-transfected BAF cells (human) or BHK cells (murine) was isolated by standard methods and used to generate a standard curve used for quantitation of Zcytor17 and OSMRbeta. The curve consisted of 10-fold serial dilutions ranging from 100-0.01 ng/µl with each standard curve point analyzed in triplicate. Similarly, for Zcytor17ligand, activated CD4+ T cell RNA (previously shown to make Zcytor17ligand) was used to generate a standard curve in the same 100-0.01 ng/µl range. Total RNA from human or murine cells was analyzed in triplicate for either human or murine Zcytor17, OSMRbeta and Zcytor17ligand transcript levels and for one of the following endogenous control genes: rRNA, GUS or transferrin receptor. In a total volume of 10 µl, each RNA sample was subjected to a One-Step RT-PCR reaction containing: approximately 50-100 ng of total RNA in a preformulated 2× master mix containing an internal control dye (ROX)(carboxy-x-rhodamine) and Thermo-Start® DNA Polymerase (Abgene, Surrey, UK); appropriate primers for the gene of interest (see parts A and B of current example); the appropriate probe (see parts A and B for concentration); Superscript® reverse transcriptase (50 U/µl) (PE Applied Biosystems), and an appropriate volume of RNase-free water.

PCR thermal cycling conditions were as follows: an initial reverse transcription (RT) step of one cycle at 48° C. for 30 minutes; followed by a Thermo-Start® enzyme activation step of one cycle at 95° C. for 10 minutes; followed by 40 cycles of amplification at 95° C. for 15 seconds and 60° C. for 1 minute. Relative Zcytor17, OSMRbeta and Zcytor17ligand RNA levels were determined by using the Standard Curve Method as described by the manufacturer, PE Biosystems (User Bulletin #2: ABI Prism 7700 Sequence Detection System, Relative Quantitation of Gene Expression, Dec. 11, 1997). The rRNA, GUS or Transferrin Receptor measurements were used to normalize the levels of the gene of interest.

The semi-quantitative RT-PCR reactions used the 'Superscript One-Step RT-PCR System with Platinum Taq' (Invitrogen, Carlsbad, Calif.). Each 25 µl reaction consisted of the following: 12.5 µl of 2× Reaction Buffer, 0.5 µl (20 pmol/µl) of forward primer, 0.5 µl (20 pmol/µl) of reverse primer, 0.4 µl RT/Taq polymerase mix, 5.0 µl of Rediload Gel Loading Buffer (Invitrogen), 5.1 µl RNase-free water, and 1.0 µl total RNA (100 ng/µl). The amplification was carried out as follows: one cycle at 45° C. for 30 minutes followed by 35-38 cycles of 94° C., 20 seconds; Variable annealing temp (See Table 7 below), 20 seconds; 72° C., 45 seconds; then ended with a final extension at 72° C. for 5 minutes. Eight to ten microliters of the PCR reaction product was subjected to standard agarose gel electrophoresis using a 2% agarose gel.

TABLE 7

| | |
|---|---|
| Murine Zcytor17 | 58° C. anneal temp |
| Murine OSMRbeta | 60° C. anneal temp |
| Murine Zcytor17ligand | 52° C. anneal temp |
| Human Zcytor17 | 55° C. anneal temp |
| Human OSMRbeta | 59° C. anneal temp |
| Human Zcytor17ligand | 59° C. anneal temp |

D. Isolation of RNA from Human and Murine PBMC Subsets and Cell Lines

Blood was drawn from several anonymous donors and peripheral blood mononuclear cells (PBMC) isolated using standard Ficoll gradient methodology. Monocytes were then isolated using the Monocyte Isolation Kit and the Magnetic Cell Separation System (Miltenyi Biotec, Auburn, Calif.). The monocytes were then plated onto ultra-low adherence 24-well plates in endotoxin-free media. They were either unstimulated or treated with recombinant human IFNg (R&D Systems Inc.) at 10 ng/ml. Cells were collected at 24 and 48 hours. In similar manner, CD4+ and CD8+ T cells were isolated from PBMC's using the anti-CD4 or anti-CD8 magnetic beads from Miltenyi Biotec. Cells were then activated for 4 or 16 hours in tissue culture plates coated with 0.5 µg/ml anti-CD3 antibodies in media containing 5 µg/ml anti-CD28 antibodies. NK cells were also isolated from PBMC's using Miltenyi's anti-CD56 coated magnetic beads. Some of the NK cells were collected at time zero for RNA and the others were plated in media containing Phorbol Myristate Acetate (PMA) (5 ng/ml) and ionomycin (0.5 µg/ml) for 24 hours. Additionally, several human monocyte-like cell lines, U937, THP-1 and HL-60, were collected in either their resting or activated states. U937 cells were activated overnight with PMA (10 ng/ml). HL-60's were activated overnight with PMA (10 ng/ml) or for 72 and 96 hours with IFNg (10 ng/ml) to drive them down a monocytic pathway. THP-1 cells were activated overnight with a combination of LPS (10 ng/ml) and IFNg (10 ng/ml). RNA was prepared from all primary cells using the RNeasy Midiprep™ Kit (Qiagen, Valencia, Calif.) as per manufacturer's instructions. Carryover DNA was removed using the DNA-Free™ kit (Ambion, Inc., Austin, Tex.). RNA concentration was determined using standard spectrophotometry and RNA quality determined using the Bioanalyzer 2100 (Agilent Technologies, Palo Alto, Calif.).

Murine T Cell RNA was collected using a variety of methods well-known in the art. Primary splenic CD4+ and CD8+ T cells were isolated from the spleens of C57Bl/6 mice using antibody-coated magnetic beads and the Magnetic Cell Separation System from Miltenyi Biotec. The CD4+ and CD8+ T cells were then activated by culturing the cells in 24-well plates coated with anti-CD3 antibodies (500 ng/ml) in media containing anti-CD28 antibodies at 5 µg/ml. Cells were harvested for RNA at 0, 4 and 16 hours. Similarly, CD4+ T cells were isolated and then skewed towards a Th1 or Th2 phenotype using the following protocol. Since C57Bl/6 T cells are already skewed in the Th1 direction, all that was required was to activate for 6 hours with 0.5 µg/ml PMA and 10 ng/ml ionomycin. 'Th2' skewing was obtained by plating naïve CD4+ T cells with 2.5 µg/ml anti-CD28, 10 ng/ml mIL-2 (R&D Systems Inc.) and 25 ng/ml mIL-4 (R&D Systems) into plates coated with 0.5 µg/ml anti-CD3. After 2 days in culture, cells were resuspended in media containing 10 ng/ml mL-2 (R&D Systems) and 25 ng/ml mIL-4 Cells were cultured for an additional three days then activated with PMA and ionomycin for 6 hours.

One additional set of Th1 and Th2 skewed T cells was derived using the T Cell Receptor Transgenic DO11.10 T cell line. All cells were plated into anti-CD3 and anti-CD28 coated plates. The 'Th1' cells were plated in media containing mIL-12 (1 ng/ml) and anti-IL-4 (10 µg/ml). The 'Th2' cells were plated in media containing mIL-4 (10 ng/ml) and anti-IFNg (10 µg/ml). After 24 hours, all cultures were given mIL-2 (10 ng/ml). After two more days, the media on the cells was changed and new media containing the aforementioned cytokines was added and cells were cultured an additional 4 days before being harvested.

All of the murine T cell RNA was prepared using the RNeasy Midiprep™ Kit (Qiagen) and contaminating DNA was removed using the DNA-free™ kit from Ambion.

E. Isolation of RNA from the Murine Models of Pancreatitis and Irritable Bowel Disease To induce a condition similar to human Irritable Bowel Disease (IBD), the hybrid mouse strain C57Bl6/129S6F1 was used. Mice were divided into 4 groups with an average size of six mice per group. Group 1 was given no Dextran Sulfate Sodium (DSS) and was sacrificed on day 14. Group 2 received 2% DSS for two days prior to being sacrificed. Group 3 received 2% DSS for seven days prior to sacrifice. Group 4 received 2% DSS for seven days then allowed to recover for seven days and was sacrificed on day 14. On the day of sacrifice, the distal colon sections were removed and placed in RNAlater™ (Ambion). The colon sections were homogenized using standard techniques and RNA was isolated using the RNeasy Midiprep™ Kit (Qiagen). Contaminating DNA was removed by DNA-free™ (Ambion) treatment as per manufacturer's instructions.

In a different study, acute pancreatitis was induced in male CD-1 mice by caerulein injection. Mice were divided into three groups (n=8 mice/group). Group 1 animals were given seven i.p. injections (1 injection per hour) with Vehicle (saline), and then sacrificed at 12 and 24 hours following the first injection. Groups 2 and 3 were given seven i.p. injections of caerulein (Sigma) (Catalog#C-9026) at a dose of 50 µg/kg/hr for six hours (1 injection per hour). Group 2 was sacrificed at 12 hrs after the first injection and Group 3 was sacrificed at 24 hrs following the first injection. Pancreases were removed at the time of sacrifice and snap frozen for RNA isolation. Tissues were homogenized and RNA was isolated using the Qiagen RNeasy Midiprep™ Kit.

In yet another study, murine Zcytor17ligand transgenic mice were generated and observed for phenotypic changes (see Example 41). Piloerection and hair loss was observed in many of the transgenic mice. Four transgenic mice were sacrificed and skin samples from both normal and hairless areas were removed and snap frozen for later RNA isolation. Skin sections from two non-transgenic control mice were collected as well. Skin samples were homogenized and then digested with Proteinase K (Qiagen) (Catalog#19133) for 20 minutes at 60° C. RNA was then isolated using the Qiagen RNeasy Midiprep™ Kit following manufacturer's instructions. Carryover DNA was removed using DNA-free™ kit from Ambion.

F. Results of Quantitative and Semi-Quantitative RT-PCR for Human Zcytor17, OSMRbeta and Zcytor17ligand Zcytor17 and OSMRbeta expression was examined by quantitative RT-PCR in four sets of primary human monocytes that were either in their resting state or activated with IFNg for 24 or 48 hours. Zcytor17 expression was below detection in the unstimulated cells but increased dramatically after the 24-hour activation with IFNg, and was the highest after 48 hours of activation. In all cases OSMRbeta was below detection. Zcytor17ligand was not tested in these samples.

In the primary T cells, Zcytor17 was below detection in both the resting CD4+ and CD8+ subsets. After a four-hour activation, however, expression of Zcytor17 went up in both subsets and then decreased to a slightly lower level at the 16 hour time point. OSMRbeta was below detection in these samples. Zcytor17ligand expression was examined using semi-quantitative RT-PCR. No expression was detected in the unstimulated CD4+ and CD8+ T cells. However, after the four hour activation, high levels of Zcytor17ligand were detected. This level dropped somewhat at the 16 hour time point.

Expression of Zcytor17 was not examined in NK cells. OSMRb was below detection in these samples. Zcytor17ligand expression was below detection in the resting NK cells, however there was a faint signal generated by the activated NK cells suggesting that these cells may make Zcytor17ligand under certain conditions.

In the human monocyte-like cell lines, U937, THP-1 and HL-60, OSMRbeta expression was below detection in all of the resting and activated samples except for activated THP-1 samples where a faint signal was detected. Zcytor17 expression was high in both the U937 and THP-1 resting cell lines and showed a strong upregulation following activation. Expression in U937's was the highest of any cell type. In the HL-60's, Zcytor17 was expressed at moderate levels in the unstimulated cells and decreased upon stimulation with PMA. However, the expression of Zcytor17 was dramatically upregulated in the HL-60's when stimulated with IFNg for 72 and 96 hours. All of the human expression data is summarized in Table 8 below.

TABLE 8

| Primary Human Monocytes | Activation Status | Zcytor17 | OSMRbeta | Zcytor17Ligand |
|---|---|---|---|---|
| Human Monocytes | Unstim | − | − | |
| Human Monocytes | Act. 24 hr IFNg | + | − | |
| Human Monocytes | Act. 48 hr IFNg | ++ | − | |
| Human CD4+ | Unstim | − | − | − |
| Human CD4+ | Act 4 hr | ++ | − | ++ |
| Human CD4+ | Act. 16 hr | + | − | + |
| Human CD8+ | Unstim | − | − | − |
| Human CD8+ | Act 4 hr | ++ | − | ++ |
| Human CD8+ | Act. 16 hr | + | − | + |
| Human NK Cells | Unstim | | − | − |
| Human NK Cells | Act 24 hr | | − | + |
| U937 | Unstim | ++ | − | − |
| U937 | Act. 16 hr | +++ | − | − |
| THP-1 | Unstim | ++ | − | − |
| THP-1 | Act. 16 hr | +++ | + | − |
| HL-60 | Unstim | ++ | − | − |
| HL-60 | Act. 16 hr PMA | + | − | − |
| HL-60 | Act. 72 hr IFNg | +++ | − | − |
| HL-60 | Act. 96 hr IFNg | +++ | − | − |

G. Results of Quantitative and Semi-Quantitative RT-PCR for Murine Zcytor17, OSMRbeta and Zcytor17ligand Murine Zcytor17, OSMRbeta and Zcytor17ligand expression levels were examined in several murine T cells populations and the results are summarized in Table 9 below. Murine Zcytor17 expression was tested by semi-quantitative RT-PCR and shown to be at low levels on both resting and activated primary CD4+ T cells. Expression of Zcytor17 was detected on resting CD8+ T cells and then seemed to drop upon activation with anti-CD3 and anti-CD28 antibodies at both the 4- and 16-hour time points. OSMRbeta expression was measured by quantitative RT-PCR and shown to be expressed in resting and activated CD4+ and CD8+ T cells. The expression of OSMRbeta went up after a 4-hour activation and then returned to the unstimulated levels by 16 hours in both the CD4+ and CD8+ T cells. Zcytor17ligand was detected by quantitative RT-PCR and shown to be expressed at very low levels in unstimulated CD4+ T cells. However, following a 4-hour activation, Zcytor17ligand expression was dramatically upregulated and then dropped slightly by the 16-hour time point. In CD8+ T cells, no Zcytor17ligand was detected in the unstimulated cells. There was some Zcytor17ligand expression at the 4-hour time point, but by 16 hours expression levels had dropped back below detection.

In the DO11.10 T cells, Zcytor17 expression was detected in the naïve and Th2 skewed cells, but not in the Th1 skewed cells. OSMRbeta expression was at low levels in the naïve DO11.10 cells. There was a dramatic increase in OSMRbeta expression levels in the Th1 skewed cells and a moderate increase of expression in the Th2-skewed cells. The Zcytor17ligand expression in these cells was shown to be predominantly by the Th2 skewed subset. Low levels were detected in the Th1 subset and no expression was detected in the naïve cells. These results are summarized in the Table 9 below.

In the primary CD4+ T cells that were skewed in either the Th1 or Th2 direction, Zcyto17 wasn't examined. OSMRbeta expression was detected in all three samples with the highest levels found in the Th2 sample. Similar to the DO11.10 results, Zcytor17ligand expression was detected at high levels in the Th2 skewed subset, with a small amount detected in the Th1 subset and levels were below detection in the unstimulated cells. These results are summarized in the Table 9 below.

TABLE 9

| Murine T Cells | Zcytor17 | OSMRbeta | Zcytor17ligand |
|---|---|---|---|
| CD4+ T Cells Unstimulated | + | + | +/− |
| CD4+ T Cells 4 hr Activation | + | ++ | ++ |
| CD4+ T Cells 16 hr Activation | + | + | + |
| CD8+ T Cells Unstimulated | + | + | − |
| CD8+ T Cells 4 hr Activation | +/− | ++ | + |
| CD8+ T Cells 16 hr Activation | − | + | − |
| DO11.10 Naïve | + | + | − |
| DO11.10 Th1 | − | +++ | + |
| DO11.10 Th2 | + | ++ | ++ |
| CD4+ T Cells Unstimulated | | ++ | − |
| CD4+ T Cells - Th1 Skewed | | +++ | + |
| CD4+ T Cells - Th2 Skewed | | ++ | +++ |

In the Zcytor17ligand transgenic skin samples, Zcytor17, OSMRbeta and Zcytor17ligand expression levels were determined using quantitative RT-PCR. Zcytor17 was shown to be present in all samples at roughly equivalent levels. There were dramatically higher levels of OSMRbeta expression in the non-transgenic control animals than the transgenic samples. Zcytor17ligand expression was below detection in the non-transgenic control animals with moderate to high levels of expression in the transgenic animals. The results are summarized in Table 10 below.

TABLE 10

| Murine Zcytor17ligand Transgenic Skin | Skin Phenotype | Zcytor17 | OSMRbeta | Zcytor17ligand |
|---|---|---|---|---|
| Wild Type Mouse | Normal | + | +++ | − |
| Wild Type Mouse | Normal | + | +++ | − |
| Transgenic #1 | Normal | + | + | + |
| Transgenic #1 | Hair Loss | + | + | + |
| Transgenic #2 | Normal | + | + | + |
| Transgenic #2 | Hair Loss | + | + | + |
| Transgenic #3 | Normal | + | + | + |
| Transgenic #3 | Hair Loss | + | + | + |
| Transgenic #4 | Normal | + | + | +++ |
| Transgenic #4 | Hair Loss | + | + | +++ |

In a different experiment, Zcytor17, OSMRbeta and Zcytor17ligand expression levels were measured by quantitative RT-PCR in the pancreases of mice subjected to acute pancreatitis. Zcytor17 expression was below detection in all of the samples. OSMRbeta expression was seen at low levels in the normal control samples (Group 1), but showed a strong upregulation at the 12-hour time point (Group 2) and slightly lower levels at the 24-hour time point (Group 3). Zcytor17ligand expression was below detection in the control animals, but showed high levels in both of the caerulein injected groups. The data is summarized in Table 11 below.

TABLE 11

| Pancreatitis Model | Description | Zcytor17 | OSMRbeta | Zcytor17ligand |
|---|---|---|---|---|
| Group 1 | Normal Control | − | + | − |
| Group 2 | 12 hr Post Injection | − | +++ | ++ |
| Group 3 | 24 hr Post Injection | − | ++ | ++ |

In another experiment, Zcytor17 and OSMRbeta expression levels were examined in the distal colons of mice subjected to DSS treatment. In this murine model of Inflammatory Bowel Disease, expression levels of both genes were determined by quantitative RT-PCR and are summarized in Table 12 below. Zcytor17 expression levels increased with the severity of the disease, with low levels of expression in the Group 1 normal animals and increasing amounts seen Groups 2 and 3. In the Group 4 animals, the Zcytor17 levels had returned to more normal levels. Unlike Zcytor17 expression, OSMRbeta levels were the highest in the control animals and levels actually decreased in all three DSS treated groups.

TABLE 12

| IBD Model | Description | SAC Day | Zcytor17 | OSMRbeta |
|---|---|---|---|---|
| Group 1 | Normal Control | 14 | + | ++ |
| Group 2 | DSS-Treated 2 days | 2 | ++ | + |
| Group 3 | DSS-Treated 7 days | 7 | +++ | + |
| Group 4 | DSS-Treated 7 days | 14 | + | + |

Example 28

Human Zcytor17lig Tissue Distribution Expression Based on RT-PCR Analysis of Multiple Tissue First-Strand cDNAs Gene expression of the zcytor17lig was examined using commercially available normalized multiple tissue first-strand cDNA panels (OriGene Technologies, Inc. Rockville, Md.; BD Biosciences Clontech, Palo Alto, Calif.). These included the OriGene "Human Tissue Rapid-Scan™ Panel" (Cat. #CHSCA-101, containing 22 different tissues, bone marrow, and plasma blood leucocytes) and the BD Biosciences Clontech "Human Blood Fractions MTC™ Panel" (Cat. #K1428-1, containing 9 different blood fractions).

PCR reactions were set up using the zcytor17lig specific oligo primers ZC41,458 (SEQ ID NO:60), and ZC41,457

(SEQ ID NO:61), which yield a 139 bp product, and ZC41, 459 (SEQ ID NO: 62), and ZC41,460 (SEQ ID NO:63), which yield a 92 bp product, Qiagen HotStarTaq DNA polymerase and buffer (Qiagen, Inc., Valencia, Calif.), dH$_2$O, and RediLoad™ dye (Research Genetics, Inc., Huntville, Ala.). The PCR cycler conditions were as follows: an initial 1 cycle 15 minute denaturation at 95° C., 35 cycles of a 45 second denaturation at 95° C., 1 minute annealing at 53° C. or 56° C. and 1 minute and 15 seconds extension at 72° C., followed by a final 1 cycle extension of 7 minutes at 72° C. The reactions were separated by electrophoresis on a 2% agarose gel (EM Science, Gibbstown, N.J.) and visualized by staining with ethidium bromide.

A DNA fragment of the correct size was observed in the following human adult tissues using the OriGene "Human Tissue Rapid-Scan™ Panel": testis, plasma blood leucocytes (PBL), and bone marrow.

A DNA fragment of the correct size was observed in the following human blood fractions using the BD Biosciences Clontech "Human Blood Fractions MTC™ Panel": activated mononuclear cells (B- & T-cells and monocytes), activated CD8+ cells (T-suppressor/cytotoxic), activated CD4+ cells (T-helper/inducer) and faintly in resting CD8+ cells.

Example 29

Cloning the Human Oncostatin M Receptor

The OncostatinM beta receptor (OSMRbeta) is a type I cytokine receptor with structural similarity to IL12R-B2. ZcytoR17 has structural similarity to IL12R-B1. The OSMRbeta and zcytor17 were tested to see whether they could interact as subunits in a cytokine signaling complex, and whether together they could act as a signaling receptor, or soluble receptor antagonist, for zcytor17lig.

To isolate OSMRbeta, oligonucleotide PCR primers ZC39982 (SEQ ID NO:64) and ZC39983 (SEQ ID NO:65) were designed to amplify the full length coding region of the human OncostatinM beta cDNA sequence (SEQ ID NO:6) (Genbank Accession No. U60805; Mosley B, *JBC Volume* 271, Number 50, Issue of Dec. 20, 1996 pp. 32635-32643).

PCR reactions were run on an array of cDNA library templates using a robust polymerase, Advantage II (Clonetech, Palo Alto, Calif.), in order to identify a source of the cDNA. The template DNA used was from amplified cDNA plasmid libraries each containing 5 million independent cDNA clones. Reactions were assembled as per manufacturer's instructions using 400 fmol/µl of each oligonucleotide and 2-20 ng/µl purified plasmid library DNA as template. The cDNA libraries were derived from the following human tissues and cell lines: fetal brain, prostate smooth muscle, bone marrow, RPMI1588, thyroid, WI-38, testis, stimulated peripheral blood mononuclear cells, stimulated CD3+ cells, THP-1, activated tonsil, HACAT and fetal liver. Reactions were performed on a thermocycler machine using the following conditions: 30 cycles of 95° C. for 20 seconds, 68° C. for 3 minutes. At the conclusion of 30 cycles an additional single extension cycle of 8 minutes at 68° C. was run. PCR products were visualized by TAE agarose, gel electrophoresis in the presence of ethidium bromide followed by UV illumination. The most abundant product was found to be from a prostate smooth muscle cDNA library. The PCR reaction using prostate smooth muscle template and oligonucleotides ZC39982 (SEQ ID NO:64) and ZC39983 (SEQ ID NO:65) was repeated using a less robust but higher fidelity thermostable DNA polymerase "turboPFu", (Stratagene, La Jolla, Calif.). Thirty amplification cycles were run with the following conditions: denaturing at 94° C., 30 seconds, annealing at 63° C. 45 seconds, extension at 72° C. 3.5 minutes. A single band product was gel purified on a 0.8% TAE, agarose gel.

This DNA was then amplified again using primers ZC39980 (SEQ ID NO:66) and ZC39981 (SEQ ID NO:67) designed to include restriction enzyme recognition sequences to allow the cloning of this cDNA into a mammalian expression vector.

The PCR reaction was performed using "TurboPfu" and the purified PCR product for 15 cycles of: 95° C. 1 minute, 64° C. 1 minute 20 seconds, 72° C. 4.5 minutes. The PCR reaction was then digested with EcoR1 and Xho1 (Invitrogen, Carlsbad, Calif.) and gel purified as described above. A mammalian expression vector, pZ7NX, was prepared by digesting with EcoR1 and Xho1 and the PCR product was ligated to this vector and electroporated into *E. coli* DH10b cells. Several bacterial colonies were isolated and sequenced. One clone was correct with the exception of a single non-conservative mutation. In order to change this base to match the expected sequence, an oligonucleotide spanning mutation and a neighboring Pst1 restriction site was used in a PCR reaction with "TurboPfu" using the pZP7Nx-h. OncostatinM R plasmid previously sequenced as a template. The PCR amplified DNA was digested with Pst1 and Xho1 and cloned back into the pZP7Nx-h OncostatinM R plasmid in place of the Pst1/Xho1 fragment containing the offending mutation. This new plasmid was sequenced over the recently amplified Pst1 to Xho1 region to confirm the correction and make sure no other errors were created in the amplification process. This analysis confirmed sequence that matched the expected sequence over the coding region. The sequence is shown in SEQ ID NO:6, and corresponding amino acid sequence shown in SEQ ID NO:7.

Example 30

Constructs for Generating a Human Zcytor17/OncostatinM Receptor (OSMRbeta) Heterodimer A system for construction, expression and purification of such soluble heterodimeric receptors is known in the art, and has been adapted to the receptor pair, human oncostatin M receptor (OSMRbeta) and human zcytor17. For this construct, the polynucleotide for the soluble receptor for OSMRbeta is shown in SEQ ID NO:68 and corresponding polypeptide is shown in SEQ ID NO:69; and the polynucleotide for the soluble receptor for human zcytor17 is shown in SEQ ID NO:70 and corresponding polypeptide is shown in SEQ ID NO:71.

To construct a cell line expressing a secreted soluble hzcytor17/human OSMRbeta heterodimer, a construct was made so that the resulting heterodimeric soluble receptor comprises the extracellular domain of human OSMRbeta fused to the heavy chain of IgG gamma1 (Fc4) (SEQ ID NO:37) with a Glu-Glu tag (SEQ ID NO:35) at the C-terminus; while the extracellular domain of zcytoR17 is fused to Fc4 (SEQ ID NO:37) with a His tag (SEQ ID NO:72) at the C-terminus. For both of the hzcytor17 and human OSMRbeta arms of the heterodimer a Gly-Ser spacer of 12 amino acids (SEQ ID NO:73) was engineered between the extracellular portion of the receptor and the N-terminus of Fc4.

A. Construction of Human Soluble OSMRbeta/Fc4-CEE

For construction of the human soluble OSMRbeta/Fc4-CEE portion of the heterodimer the extracellular portion of human OSMRbeta was isolated using PCR with oligos ZC14063 (SEQ ID NO:48) and ZC41557 (SEQ ID NO:74) under PCR reaction conditions as follows: 30 cycles of 95° C.

for 60 sec., 57° C. for 30 sec., and 72° C. for 100 sec.; and 72° C. for 7 min. PCR products were purified using QIAquick PCR Purification Kit (Qiagen), digested with EcoR1 and BglII (Boerhinger-Mannheim), separated by gel electrophoresis and purified using a QIAquick gel extraction kit (Qiagen).

The expression cassette, plasmid backbone and Fc4-Glu-Glu tag portion of the chimera were contained within a previously made in house plasmid vector. The plasmid vector was digested with EcoR1 and BamH1 (Boerhinger-Mannheim), separated by gel electrophoresis and purified using a QIAquick gel extraction kit (Qiagen). The digested and purified fragments of human OSMRbeta and Fc4-cEE containing plasmid were ligated together using T4 DNA Ligase (Life Technologies, Bethesda, Md.) using standard ligation methods. Minipreps of the resulting ligation were screened for an EcoRI/Sma1 insert of the correct size (772 bp) for the soluble OSMRbeta and positive minipreps were sequenced to confirm accuracy of the PCR reaction. This new plasmid construction is termed pZP9-ONCOMR-Fc4CEE.

B. Construction of Human Soluble Zcytor17/Fc4-CHIS

For construction of the hzcytor17/Fc4-CHIS portion of the heterodimer, the extracellular portion of human zcytor17 was isolated by digestion of a plasmid previously containing Zcytor17-Fc4 soluble receptor. The plasmid was first digested with Sal1 (New England Biolabs, Beverly, Mass.) after which the reaction was serially phenol chloroform extracted and ethanol precipitated. The digested DNA was then treated with T4 DNA Polymerase (Boerhinger-Mannheim), to fill in the 5' overhangs created by the Sal1 digestion, leaving the DNA ends blunt, after which the reaction was serially phenol chloroform extracted and ethanol precipitated. The blunted DNA was then further digested with BglII to cut at the 3' end.), separated by gel electrophoresis and purified using a QIAquick gel extraction kit (Qiagen) as per manufacturer's instruction. The resulting DNA fragment containing the sequence coding for the extracellular domain of zcytoR17 was ligated into an Fc4-CHIS tag containing mammalian expression vector prepared as follows.

The expression cassette, plasmid backbone and Fc4-CHIS tag portion of the chimera were contained within a previously made in house plasmid vector. This plasmid vector was digested with EcoR1 (Boerhinger-Mannheim) after which the reaction was serially phenol chloroform extracted and ethanol precipitated. The digested DNA was then treated with T4 DNA Polymerase (Boerhinger-Mannheim), to fill in the 5' overhangs created by the EcoR1 digestion, leaving the DNA ends blunt, after which the reaction was serially phenol chloroform extracted and ethanol precipitated. The blunted DNA was then further digested with BamH1 (Boerhinger-Mannheim) to cut at the 3' end, separated by gel electrophoresis and purified using a QIAquick gel extraction kit (Qiagen). The digested and purified fragments of human zcytor17 and Fc4-CHIS containing plasmid were ligated together using T4 DNA Ligase (Life Technologies, Bethesda, Md.) using standard ligation methods.

Minipreps of the resulting ligation were screened by PCR using the zcytor17 specific sense primer ZC29180 (SEQ ID NO:22) and the Fc4 specific antisense primer ZC29232 (SEQ ID NO:75) with the following PCR reaction conditions: 30 cycles of 94° C. for 60 sec., 68° C. for 150 sec; and 72° C. for 7 min. An expected product size of 848 bp confirmed the correct assembly of the plasmid termed pZEM228 hzcytor17/Fc4HIS.

A second zcytor17-Fc4 construction was created for use in generating homodimer protein from COS cells. Briefly the coding region for the full fusion protein was isolated by digestion of a plasmid previously containing Zcytor17-Fc4 soluble receptor with Sal1 (Boerhinger-Mannheim). The reaction was serially phenol chloroform extracted and ethanol precipitated. The digested DNA was then treated with T4 DNA Polymerase (Boerhinger-Mannheim), to fill in the 5' overhangs created by the EcoR1 digestion, leaving the DNA ends blunt, after which the reaction was serially phenol chloroform extracted and ethanol precipitated. The blunted DNA was then further digested with Not1 (Boerhinger-Mannheim) to cut at the 3' end, separated by gel electrophoresis and purified using a QIAquick gel extraction kit (Qiagen). A mammalian expression vector containing a CMV driven expression cassette was digested to generate compatible ends and the 2 fragments were ligated together. Minipreps of the resulting ligation were screened by PCR using the vector specific sense primer ZC14063 (SEQ ID NO:48) and the zcytor17 specific antisense primer ZC27899 (SEQ ID NO:19) with the following PCR reaction conditions: 30 cycles of 94° C. for 30 sec., 64° C. for 30 sec; 70° C. for 90 sec; and 72° C. for 7 min. An expected product size of approximately 1000 bp confirmed the correct assembly of the plasmid termed pZP7NX-hzcytor17-Fc4. This plasmid was subsequently transfected into COS cells using Lipofectamine (Gibco/BRL), as per manufacturer's instructions. The cells were conditioned for 60 hours in DMEM+5% FBS (Gibco/BRL) after which the protein was purified over a protein G-sepharose 4B chromatography column and made available for in vitro bioassays, for example, such as those described herein.

C. Generating a Human Zcytor17/OncostatinM Receptor (OSMRbeta)

About 16 µg each of the pZP9-ONCOMR-Fc4CEE and pZEM228 hzcytor17/Fc4HIS were co-transfected into BHK-570 (ATCC No. CRL-10314) cells using lipofectamine (Gibco/BRL), as per manufacturer's instructions. The transfected cells were selected for 10 days in DMEM+5% FBS (Gibco/BRL) containing 0.5 mg/ml G418 (Gibco/BRL) and 250 nM methyltrexate (MTX) (Sigma, St. Louis, Mo.) for 10 days.

The resulting pool of doubly-selected cells was used to generate the heterodimeric protein. Three cell Factories (Nunc, Denmark) of this pool were used to generate 10 L of serum free conditioned medium. This conditioned media was passed over a 1 ml protein-A column and eluted in (10) 750 microliter fractions. Four of these fractions found to have the highest concentration were pooled and dialyzed (10 kD MW cutoff) against PBS. The desired heterodimeric soluble zcytor17/OSMRbeta protein complex was isolated from other media components by passing the pool over a Nickel column and washing the column with various concentrations of Imidazole. The soluble zcytor17/OSMRbeta protein eluted at intermediate concentrations of Imidazole, while hzcytor17/Fc4HIS homodimer eluted at higher concentrations of Imidazole.

Example 31

Tissue Distribution of Human Zcytor17 in Tissue Panels Using Northern Blot and PCR A. Human Zcytor17 Tissue Distribution Using Northern Blot Human Multiple Tissue Northern Blots (Human 12-lane MTN Blot I and II, and Human Immune System MTN Blot II; Human Endocrine MTN, Human Fetal MTN Blot II, Human Multiple Tissue Array) (Clontech) as well as in house blots containing various tissues were probed to determine the tissue distribution of human zcytor17 expression. The in-house prepared blots included the following tissue and cell line mRNA:

SK-Hep-1 cells, THP1 cells, Adrenal gland (Clontech); Kidney (Clontech), Liver (Clontech and Invitrogen); Spinal cord (Clontech), Testis (Clontech), Human CD4+ T-cells, Human CD8+ T-cells, Human CD19+ T-cells, human mixed lymphocyte reaction (MLR), THP1 cell line (ATCC No. TIB-202), U937 cell line, p388D1 mouse lymphoblast cell line (ATCC No. CCL-46) with or without stimulation by Ionomycin; and WI-38 human embryonic lung cell line (ATCC No. CRL-2221) with or without stimulation by Ionomycin.

An approximately 500 bp PCR derived probe for zcytor17 (SE ID NO:4) was amplified using oligonucleotides ZC28, 575 (SEQ ID NO:77) and ZC27,899 (SEQ ID NO:19) as primers. The PCR amplification was carried out as follows: 30 cycles of 94° C. for 1 minute, 65° C. for 1 minute, and 72° C. for 1 minute; followed by 1 cycle at 72° C. for 7 minutes. The PCR product was visualized by agarose gel electrophoresis and the approximately 500 bp PCR product was gel purified as described herein. The probe was radioactively labeled using the PRIME IT II™ Random Primer Labeling Kit (Stratagene) according to the manufacturer's instructions. The probe was purified using a NUCTRAP™ push column (Stratagene). EXPRESSHYB™ (Clontech) solution was used for the prehybridization and as a hybridizing solution for the Northern blots. Prehybridization was carried out at 68° C. for 2 hours. Hybridization took place overnight at 68° C. with about $1.5 \times 10^6$ cpm/ml of labeled probe. The blots were washed three times at room temperature in 2×SSC, 0.05% SDS, followed by 1 wash for 10 minutes in 2×SSC, 0.1% SDS at 50° C. Several faint bands were seen after several days exposure. An approximately 9 kb transcript was seen in trachea, skeletal muscle and thymus; an approximately 2 kb transcript was seen in PBL, HPV, U937 and THP-1 cells; and about a 1.2 kb transcript was seen in placenta, bone marrow and thyroid, and HPV and U937 cells. In all the tissues listed above, the signal intensity was faint. There appeared to be little expression in most normal tissues, suggesting that zcytor17 expression may be dependent on activation of the cell or tissues in which it is expressed.

B. Tissue Distribution in Tissue Panels Using PCR

A panel of cDNAs from human tissues was screened for zcytor17 expression using PCR. The panel was made in-house and contained 94 marathon cDNA and cDNA samples from various normal and cancerous human tissues and cell lines as shown below in Table 13. The cDNAs came from in-house libraries or marathon cDNAs from in-house RNA preps, Clontech RNA, or Invitrogen RNA. The marathon cDNAs were made using the marathon-Ready™ kit (Clontech, Palo Alto, Calif.) and QC tested with clathrin primers ZC21195 (SEQ ID NO:78) and ZC21196 (SEQ ID NO:79) and then diluted based on the intensity of the clathrin band. To assure quality of the panel samples, three tests for quality control (QC) were run: (1) To assess the RNA quality used for the libraries, the in-house cDNAs were tested for average insert size by PCR with vector oligos that were specific for the vector sequences for an individual cDNA library; (2) Standardization of the concentration of the cDNA in panel samples was achieved using standard PCR methods to amplify full length alpha tubulin or G3PDH cDNA using a 5' vector oligo ZC14,063 (SEQ ID NO:48) and 3' alpha tubulin specific oligo primer ZC17,574 (SEQ ID NO:49) or 3' G3PDH specific oligo primer ZC17,600 (SEQ ID NO:50); and (3) a sample was sent to sequencing to check for possible ribosomal or mitochondrial DNA contamination. The panel was set up in a 96-well format that included a human genomic DNA (Clontech, Palo Alto, Calif.) positive control sample. Each well contained approximately 0.2-100 pg/μl of cDNA. The PCR reactions were set up using oligos ZC26,358 (SEQ ID NO:80) and ZC26,359 (SEQ ID NO:81), TaKaRa Ex Taq™ (TAKARA Shuzo Co LTD, Biomedicals Group, Japan), and Rediload dye (Research Genetics, Inc., Huntsville, Ala.). The amplification was carried out as follows: 1 cycle at 94° C. for 2 minutes, 35 cycles of 94° C. for 30 seconds, 66.3° C. for 30 seconds and 72° C. for 30 seconds, followed by 1 cycle at 72° C. for 5 minutes. About 10 μl of the PCR reaction product was subjected to standard agarose gel electrophoresis using a 4% agarose gel. The correct predicted DNA fragment size was observed in lymph node, prostate, thyroid, HPV (prostate epithelia), HPVS (prostate epithelia, selected), lung tumor, uterus tumor reactions, along with the genomic DNA reaction.

The DNA fragment for prostate tissue (2 samples), HPV (prostate epithelia), HPVS (prostate epithelia, selected), and genomic were excised and purified using a Gel Extraction Kit (Qiagen, Chatsworth, Calif.) according to manufacturer's instructions. Fragments were confirmed by sequencing to show that they were indeed zcytor17.

TABLE 13

| Tissue/Cell line | #samples |
| --- | --- |
| Adrenal gland | 1 |
| Bladder | 1 |
| Bone Marrow | 1 |
| Brain | 1 |
| Cervix | 1 |
| Colon | 1 |
| Fetal brain | 1 |
| Fetal heart | 1 |
| Fetal kidney | 1 |
| Fetal liver | 1 |
| Fetal lung | 1 |
| Fetal muscle | 1 |
| Fetal skin | 1 |
| Heart | 2 |
| K562 (ATCC # CCL-243) | 1 |
| Kidney | 1 |
| Liver | 1 |
| Lung | 1 |
| Lymph node | 1 |
| Melanoma | 1 |
| Pancreas | 1 |
| Pituitary | 1 |
| Placenta | 1 |
| Prostate | 1 |
| Rectum | 1 |
| Salivary Gland | 1 |
| Skeletal muscle | 1 |
| Small intestine | 1 |
| Spinal cord | 1 |
| Spleen | 1 |
| Stomach | 1 |
| Testis | 2 |
| Thymus | 1 |
| Thyroid | 1 |
| Trachea | 1 |
| Uterus | 1 |
| Esophagus tumor | 1 |
| Gastric tumor | 1 |
| Kidney tumor | 1 |
| Liver tumor | 1 |
| Lung tumor | 1 |
| Ovarian tumor | 1 |
| Rectal tumor | 1 |
| Uterus tumor | 1 |
| Bone marrow | 3 |
| Fetal brain | 3 |
| Islet | 2 |
| Prostate | 3 |
| RPMI #1788 (ATCC # CCL-156) | 2 |
| Testis | 4 |
| Thyroid | 2 |
| WI38 (ATCC # CCL-75 | 2 |
| ARIP (ATCC # CRL-1674 - rat) | 1 |

TABLE 13-continued

| Tissue/Cell line | #samples |
| --- | --- |
| HaCat - human keratinocytes | 1 |
| HPV (ATCC # CRL-2221) | 1 |
| Adrenal gland | 1 |
| Prostate SM | 2 |
| CD3+ selected PBMC's Ionomycin + PMA stimulated | 1 |
| HPVS (ATCC # CRL-2221) - selected | 1 |
| Heart | 1 |
| Pituitary | 1 |
| Placenta | 2 |
| Salivary gland | 1 |
| HL60 (ATCC # CCL-240) | 3 |
| Platelet | 1 |
| HBL-100 | 1 |
| Renal mesangial | 1 |
| T-cell | 1 |
| Neutrophil | 1 |
| MPC | 1 |
| Hut-102 (ATCC # TIB-162) | 1 |
| Endothelial | 1 |
| HepG2 (ATCC # HB-8065) | 1 |
| Fibroblast | 1 |
| E. Histo | 1 |

C. Expression Analysis of zcytoR17 by PCR and Northern

Annotation of the cell types and growth conditions that affect expression of the receptor is a useful means of elucidating its function and predicting a source of ligand. To that end a wide variety of tissue and cell types were surveyed by PCR. The thermostable polymerase Advantage II™ (Clontech, La Jolla, Calif.) was used with the oligonucleotide primers ZC29,180 (SEQ ID NO:22) and ZC29,179 (SEQ ID NO:82) and 1-10 ng of the various cDNA templates listed below for 30 amplification cycles of (94° C., 30 sec.; 66° C., 20 sec.; 68° C., 1 min. 30 sec.). Following this, 20% of each reaction was run out on 0.8% agarose, TAE/ethidium bromide gels and visualized with UV light. Samples were then scored on the basis of band intensity. See Table 14 below.

TABLE 14

| Cells and Conditions | Score 0-5 |
| --- | --- |
| Hel stimulated with PMA | 0 |
| U937 | 3 |
| MCF-7 | 0 |
| HuH7 | 1 |
| Human follicle | 0 |
| HT-29 | 0 |
| HEPG2 | 0 |
| HepG2 stimulated with IL6 | 0 |
| Human dermal endothelial | 0 |
| Human venous endothelial | 0 |
| Human CD4+ | 0 |
| BEWO | 0 |
| Human CD19+ | 1 |
| Human PBMC stimulated with PHA, PMA, Ionomycin, IL2, IL4, TNFα 24 hours | 0 |
| Human PBMC stimulated with LPS, PWM, IFNγ, TNFα, 24 hours | 0 |
| Human PBMC all of the above conditions for 48 hours | 4 |
| HUVEC p.2 | 4 |
| RPMI1788 | 0 |
| TF1 | 0 |
| Monkey spleen T cells stimulated with PMA, Ionomycin | 0 |
| Human prostate epithelia HPV transformed | 5 |
| Human tonsils, inflamed | 0 |
| HACAT | 0 |
| Human chondrocyte | 1 |
| Human synoviacyte | 1 |
| THP1 | 5 |
| REH | 0 |

Of the strong positive PCR signals, two were from the human monocyte cell lines U937 and THP1.

These two cell lines along with a prostate epithelia line were selected for further analysis by Northern blot. Previous attempts at visualizing a transcript by northern analysis using mRNA from various tissues yielded weak and diffuse signals in the surprisingly large size range of 7-10 kb making this data difficult to interpret. A denaturing formaldehyde/MOPS/0.8% agarose gel was prepared (RNA Methodologies, Farrell, R E Academic Press) and 2 μg of polyA+ mRNA was run for each sample along side an RNA ladder (Life Technologies, Bethesda, Md.). The gel was then transferred to Hybond nylon (Amersham, Buckinghamshire, UK), UV crosslinked, and hybridized in ExpressHyb solution (Clontech, LaJolla, Calif.) at 68° C. overnight using a probe to human zcytoR17 generated by PCR with the oligos ZC28,575 (SEQ ID NO:77), and ZC27,899 (SEQ ID NO:19) and labeled with a Megaprime $^{32}$P kit (Amersham). The northern blot was subsequently washed with 0.2×SSC+0.1% SDS at 65 C for 15 minutes and exposed to film for 7 days with intensifying screens. A prominent 8 kb band was seen in both the prostate epithelia and U937 lanes while a fainter band was present in the THP1 lane.

To optimize the cDNA used as a hybridization probe, four different regions of the full-length human zcytoR17 sequence were amplified by PCR, labeled and hybridized as described above to southern blots containing genomic and amplified cDNA library DNA. The four probes, herein designated probes A-D, were amplified using the following primer pairs: (A) ZC28,575 (SEQ ID NO:77), ZC27,899 (SEQ ID NO:19); (B) ZC27,895 (SEQ ID NO:20), ZC28,917 (SEQ ID NO:83); (C) ZC28,916 (SEQ ID NO:84), ZC28,918 (SEQ ID NO:85); and (D) ZC28,916 (SEQ ID NO:84), ZC29,122 (SEQ ID NO:21). Human genomic DNA along with amplified cDNA libraries demonstrated to contain zcytor17 by PCR were digested with EcoR1 and Xho1 to liberate inserts and run out on duplicate TAE/0.8% agarose gels, denatured with 0.5M NaOH, 1.5 M NaCl, blotted to Hybond, UV crosslinked and each hybridized with a distinct probe. Probe B was found to have the least nonspecific binding and strongest signal. Thus, Probe B was used for all subsequent hybridizations.

Given that the THP1 cells are an excellent model of circulating monocytes and expressed zcytor17 at low levels we treated them with a variety of compounds in an effort to increase expression of zcytoR17. The cells were grown to a density of 2e5/ml, washed and resuspended in various stimulating media, grown for four or thirty hours, and harvested for RNA preparations. Each media was supplemented with one of the following drugs or pairs of cytokines: LPS 2 ug/ml (Sigma Chemicals, St. Louis, Mo.), hTNFα 2 ng/ml (R&D Systems, Minneapolis, Minn.), hGM-CSF 2 ng/ml (R&D Systems, Minneapolis, Minn.), hIFNγ 50 ng/ml (R&D Systems, Minneapolis, Minn.), hMCSF 1 ng/ml (R&D Systems, Minneapolis, Minn.), hIL6 1 ng/ml (R&D Systems, Minneapolis, Minn.), hIL1β 2 ng/ml (R&D Systems, Minneapolis, Minn.), hIFNγ 50 ng/ml+hIL4 0.5 ng/ml (R&D Systems, Minneapolis, Minn.), hIFNγ 50 ng/ml+hIL10 1 ng/ml (R&D Systems, Minneapolis, Minn.), PMA 10 ng/ml (Calbiochem, San Diego, Calif.) and an untreated control. At the end of the culture period Total RNA was prepared using an RNAeasy Midi-kit (Qiagen, Valencia, Calif.). Poly A+ RNA was selected from the total RNA using an MPG kit (CPG, Lincoln Park, N.J.). Two micrograms of polyA+ RNA from each condition was run on formaldehyde/MOPS/agarose gels, transferred to nylon and UV crosslinked as described above. These northern blots were then hybridized, as above, to probe B at 68° C. overnight, washed at high stringency with 0.2×

SSC, 0.1% SDS at 65 C, exposed to film overnight then exposed to phosphor screens for signal quantitation. A dominant 8 kb mRNA as well a relatively weaker 2.8 kb band were seen in all lanes. A 20-fold increase in zcytor17 mRNA was seen in RNA from cells treated with hIFNγ for 30 hours, this effect was slightly muted with simultaneous treatment with IL4. Minor 3 fold increases in mRNA were seen in RNA from cells treated with LPS, TNFα and GM-CSF while MCSF, IL6, and IL1β had no effect on zcytor17 mRNA levels. Taken together this data suggests a role for the zcytor17 receptor and its ligand in monocyte macrophage biology and by extension any number of disease processes in which these cells participate.

Example 32

Tissue Distribution of Human Zcytor17 in Tissue Panels Using Northern Blot and PCR A human zcytor17lig cDNA fragment was obtained using PCR with gene specific primers: Sense primer ZC41438 (SEQ ID NO:93) and antisense primer ZC41437 (SEQ ID NO:94) and template human zcytor17lig cDNA (SEQ ID NO:90) This fragment was purified using standard methods and about 25 ng labeled with $^{32}P$ alpha dCTP using the Prime-It RmT random primer labeling kit (Stratagene) and hybridized in Ultrahyb, (Ambion) and used to expose Biomax film/intensifying screens per the manufacturer's recommendations in each case. New, previously unused blots Including the Clontech Human 12 lane MTN, the human brain MTN II, and the human brain MTN blot IV, the human immune system MTN II, and the human MTE array II, from Clontech were hybridized overnight at 42° C. per the Ambion ultrahyb method. Non-specific radioactive counts were washed off using 0.1 SSC/0.5% SDS at 55° C. The positive blots included the human 12 lane MTN (Clontech). Of the 12 tissues examined, only placenta was positive for an approximately 1.2 KB transcript.

Example 33

Construction of Mammalian Expression Vectors that Express Human Zcytor17lig-CEE

A. Construction of zCytor17Lig-CEE/pZMP21

An expression plasmid containing all or part of a polynucleotide encoding zCytor17Lig-CEE (SEQ ID NO:95) was constructed via homologous recombination. The plasmid was called zCytor17Lig-CEE/pZMP21.

The construction of zCytor17Lig-CEE/pZMP21 was accomplished by generating a zCytor17Lig-CEE fragment using PCR amplification. The DNA template used for the production of the zCytor17Lig-CEE fragment was zCytor17Lig/pZP7nx. The primers used for the production of the zCytor17Lig-CEE fragment were: (1) ZC41,607 (SEQ ID NO:97) (sense sequence), which includes from the 5' to the 3' end: 28 bp of the vector flanking sequence (5' of the insert) and 21 bp corresponding to the 5' sequence of zCytor17Lig; and (2) ZC41,605 (SEQ ID NO:98) (anti-sense sequence), which includes from the 5' to the 3' end: 37 bp of the vector flanking sequence (3' of the insert), 3 bp of the stop codon, 21 bp encoding a C-terminal EE tag, and 21 bp corresponding to the 3' end of zCytor17Lig sequence. The fragment resulting from the above PCR amplification is a copy of the template zCytor17Lig with the addition of a C-terminal EE tag, yielding a final product zCytor17Lig-CEE.

PCR reactions were run as follows: To a 100 μl final volume was added: 10 μl of 10× Taq Polymerase Reaction Buffer with 15 mM MgCl (Gibco), 1 μl of Taq DNA Polymerase (5 units/μl, Gibco), 3 μl of 10 mM dNTPs, 78 μl dH₂O, 3 μl of a 20 pmol/μl stock of primer ZC41,607 (SEQ ID NO:97) 3 μl of a 20 pmol/μl stock of primer ZC41,605 (SEQ ID NO:98), and 41 of a 0.13 μg/μl stock of zCytor17lig template DNA. A volume equal to 50 μl of mineral oil was added to the mixture. The reaction was heated to 94° C. for 5 minutes, followed by 35 cycles at 94° C. for 1 minute; 55° C. for 2 minutes; 72° C. for 3 minutes; followed by a 10 minute extension at 72° C. and held at 4° C. until the reaction was collected.

The plasmid pZMP21 was restriction digested with BglII enzyme, cleaned with a QiaQuick PCR Purification Kit (Qiagen) using a microcentrifuge protocol, and used for recombination with the PCR fragment. Plasmid pZMP21 was constructed from pZMP20 which was constructed from pZP9 (deposited at the American Type Culture Collection, 10801 University Boulevard, Manassas, Va. 20110-2209, and is designated No. 98668) with the yeast genetic elements from pRS316 (deposited at the American Type Culture Collection, 10801 University Boulevard, Manassas, Va. 20110-2209, and designated No. 77145), an IRES element from poliovirus, and the extracellular domain of CD8, truncated at the carboxyl terminal end of the transmembrane domain. PZMP21 is a mammalian expression vector containing an expression cassette having the MPSV promoter, immunoglobulin signal peptide intron, multiple restriction sites for insertion of coding sequences, a stop codon and a human growth hormone terminator. The plasmid also has an *E. coli* origin of replication, a mammalian selectable marker expression unit having an SV40 promoter, enhancer and origin of replication, a DHFR gene, the SV40 terminator, as well as the URA3 and CEN-ARS sequences required for selection and replication in *S. cerevisiae*.

Fifty microliters of competent yeast cells (*S. cerevisiae*) were independently combined with 100 ng of cut plasmid, 5 μl of previously described PCR mixture, and transferred to a 0.2 cm electroporation cuvette. The yeast/DNA mixture was electropulsed at 0.75 kV (5 kV/cm), ∞ ohms, 25 μF. Each cuvette had 600 μl of 1.2 M sorbitol added, and the yeast was plated in one 100 μl aliquot and one 300 μl aliquot onto two URA-D plates and incubated at 30° C. After about 72 hours, the Ura+ yeast transformants from a single plate were resuspended in 1 ml H₂O and spun briefly to pellet the yeast cells. The cell pellet was resuspended in 500 μl of lysis buffer (2% Triton X-100, 1% SDS, 100 mM NaCl, 10 mM Tris, pH 8.0, 1 mM EDTA). The 500 μl of the lysis mixture was added to an Eppendorf tube containing 300 μl acid washed 600 μm glass beads and 300 μl phenol-chloroform, vortexed for 1 minute intervals two or three times, followed by a 5 minute spin in a Eppendorf centrifuge at maximum speed. Three hundred microliters of the aqueous phase was transferred to a fresh tube, and the DNA precipitated with 600 μl 100% ethanol (EtOH), followed by centrifugation for 10 minutes at 4° C. The DNA pellet was then washed with 500 μl 70% EtOH, followed by centrifugation for 1 minute at 4° C. The DNA pellet was resuspended in 30 μl H₂O.

Transformation of electrocompetent *E. coli* cells (MC1061) was done with 5 μl of the yeast DNA prep and 50 μl of MC1061 cells. The cells were electropulsed at 2.0 kV, 25 μF and 400 ohms (Ω). Following electroporation, 600 μl SOC (2% Bacto' Tryptone (Difco, Detroit, Mich.), 0.5% yeast extract (Difco), 10 mM NaCl, 2.5 mM KCl, 10 mM MgCl₂, 10 mM MgSO₄, 20 mM glucose) was added. The electroporated *E. coli* cells were plated in a 200 μl and a 50 μl aliquot on two LB AMP plates (LB broth (Lennox), 1.8% Bacto Agar (Difco), 100 mg/L Ampicillin). The plates were incubated upside down for about 24 hours at 37° C. Three Ampicillin-resistant colonies were selected at random and submitted for sequence analysis of the insert. Large-scale plasmid DNA was isolated from a sequence-confirmed clone using the Qiagen Maxi kit (Qiagen) according to manufacturer's instructions.

B. Construction of Mouse zCytor17Lig(m)-CEE/pZMP21

An expression plasmid containing the entire polynucleotide encoding murine zCytor17Lig-CEE (SEQ ID NO:104 and SEQ ID NO:105) was also constructed via homologous recombination using the method described in Example 33A above. The primers used were: (1) ZC41643 (SEQ ID NO:106) (forward, 5' to 3' sense) having a 28 bp vector overlap 5' of the insertion point; 21 bp of the 5' end of zcytor17lig(m) and (2) ZC41641 (SEQ ID NO:107) (reverse, 5' to 3' anti-sense) having a 37 bp vector overlap 3' of the insertion point; 3 bp stop codon; 21 bp C-terminal EE tag; 24 bp of the 3' end of zCytor17Lig(m)-CEE. The plasmid was called zcytor17lig(m)-CEE/pZMP21. The polynucleotide sequence of zcytor17lig(m)-CEE is shown in SEQ ID NO:104, and corresponding polypeptide sequence is shown in SEQ ID NO:105.

Example 34

Transfection and Expression of Zcytor17lig-CEE Polypeptides

A. Expression of Human ZCytor17Lig-CEE/pZMP21 in 293T Cells

ZCytor17Lig-CEE was expressed transiently in 293T cells (Stanford University School of Medicine, Stanford, Calif.; ATCC No. SD-3515) to generate initial purified protein. The day before the transfection, 293T cells were seeded at $6.5 \times 10^4$ cells/cm$^2$ in 30 T162 culture flasks with a total volume of 30 ml of culture media (SL7V4+5% FBS+1% Pen/Strep) per flask. The cells were allowed to incubate for 24 hours at 37° C.

A DNA/Liposome mixture was prepared as follows: Two 50 ml conical tubes were filled with 25 mLs of transfection media (SL7V4+1% Pen/Strep) and 1.13 mg of zCytor17Lig-CEE/pZMP21 (Example 33) was added to each. A separate set of two 50 ml conical tubes were filled with 22 ml of transfection media (above) and 3 ml of liposomes (Lipofectamine, Gibco) was added to each. For each set of tubes, one tube of DNA was added to one tube of liposomes and the DNA/liposome mix was incubated for 30 minutes. The two 50 ml conical tubes containing the DNA/liposome mixtures were pooled (about 100 ml) and 300 ml of transfection media was added.

The 30 flasks of the 293T cells were decanted, washed 1× with about 15 ml of PBS, and 12.5 ml of the diluted DNA/liposome mixture was added to each flask. The flasks were incubated for 3 hours at 37° C. After the incubation period, 25 ml of culture media (above) were added to each T162 flask. The transfection media was harvested after approximately 96 hours and was used for protein purification (Example 35).

B. Expression of Mouse ZCytor17Lig-CEE(m)/pZMP21 in 293T Cells

Mouse zCytor17Lig(m)-CEE was expressed transiently in 293T cells as described in Example 34A and cultured media was used for protein purification (Example 35).

Example 35

Purification of Zcytor17lig-CEE from 293T Cells

Unless otherwise noted, all operations were carried out at 4° C. The following procedure was used for purifying both mouse and human Zcytor17lig containing C-terminal Glu-Glu (EE) tags (SEQ ID NO:103). Conditioned media from 293T cells expressing Zcytor17lig-CEE (Example 34) was purified. Total target protein concentrations of the conditioned media were determined via SDS-PAGE and Western blot analysis with the anti-EE antibody.

A 5.5 ml column of anti-EE Poros 50 A (PE BioSystems, Framingham, Mass.) (prepared as described below) was poured in a Waters AP-1, 1 cm×7 cm glass column (Waters, Milford, Mass.). The column was flow packed and equilibrated on a BioCad Sprint (PE BioSystems, Framingham, Mass.) with phosphate buffered saline (PBS) pH 7.4. The conditioned media was adjusted with NaCl to 0.3 M and the pH adjusted to 7.2. The conditioned media was then loaded on the column overnight with about 3 ml/minute flow rate. The column was washed with 10 column volumes (CVs) of PBS pH 7.4, and again washed with 3 CVs 5× Sigma PBS pH 7.4. It was step eluted with 0.5 M Acetate, 0.5 M NaCl, pH 2.5 at 3 ml/minute. The fraction tubes contained 1 ml Tris base (no pH adjustment) to neutralize the elution immediately. The column was again washed for 2 CVs with 5× Sigma PBS, pH 7.4 to neutralize the column and then equilibrated in PBS (pH 7.4). Two ml fractions were collected over the entire elution chromatography and absorbance at 280 and 215 nM were monitored; the pass through and wash pools were also saved and analyzed. The 5×PBS and the acid elution peak fractions were analyzed for the target protein via SDS-PAGE Silver staining and Western Blotting with the primary antibody anti-EE and secondary antibody, anti mouse-HRP conjugated. The acid elution fractions of interest were pooled and concentrated from 38 ml to 0.8 ml using a 5000 Dalton molecular weight cutoff membrane spin concentrator (Millipore, Bedford, Mass.) according to the manufacturer's instructions.

To separate Zcytor17lig-CEE from aggregated material and any other contaminating co-purifying proteins, the pooled concentrated fractions were subjected to size exclusion chromatography on a 1.6×60 cm (120 ml) Superdex 75 (Pharmacia, Piscataway, N.J.) column equilibrated and loaded in PBS at a flow rate of 1.0 ml/min using a BioCad Sprint. Three milliliter fractions were collected across the entire chromatography and the absorbance at 280 and 215 nM were monitored. The peak fractions were characterized via SDS-PAGE Silver staining, and only the most pure fractions were pooled. This material represented purified Zcytor17lig-CEE protein.

On Western blotted, Coomassie Blue and Silver stained SDS-PAGE gels, the Zcytor17lig-CEE was one major band. The protein concentration of the purified material was performed by BCA analysis (Pierce, Rockford, Ill.) and the protein was aliquoted, and stored at −80° C. according to standard procedures.

To prepare PorosA50 anti-EE, a 65 ml bed volume of Poros A50 (PE Biosystems) was washed with 100 ml of water and then 0.1 M triethanolamine, pH 8.2 (TEA, ICN, Aurora, Ohio), 1 M Na$_2$S0$_4$, pH 8.8 containing 0.02% sodium azide using a vacuum flask filter unit. The EE monoclonal antibody solution, at a concentration of 2 mg/ml in a volume of 300 ml, was mixed with the washed resin in a volume of 250 ml. After an overnight incubation at room temperature, the unbound antibody was removed by washing the resin with 5 volumes of 200 mM TEA, 1 M Na$_2$S0$_4$, pH 8.8 containing 0.02% sodium azide as described above. The resin was resuspended in 2 volumes of TEA, 1 M Na$_2$S0$_4$, pH 8.8 containing 0.02% sodium azide and transferred to a suitable container. Three ml of 25 mg/ml (68 mM) Disuccinimidyl suberate (in DMSO supplied by Pierce, Rockford, Ill.) is added and the solution is incubated for three hours at room temperature. Nonspecific sites on the resin were then blocked by incubating for 10 min at room temperature with 5 volumes of 20 mM ethanolamine (Sigma, St. Louis, Mo.) in 200 mM TEA, pH 8.8 using the vacuum flask filter unit. The resin is washed with PBS, pH 7.4, followed by 0.1 M Glycine, pH 3 and then neutralized with 10×PBS. After washing with distilled water, the final coupled anti-EE Poros-A 50 resin was stored at 4° C. in 20% Ethanol.

Example 36

N-Terminal Sequencing of Human and Mouse Zcytor17lig

A. N-Terminal Sequencing of Human Zcytor17lig

Standard automated N-terminal polypeptide sequencing (Edman degradation) was performed using reagents from Applied Biosystems. N-terminal sequence analysis was performed on a Model 494 Protein Sequencer System (Applied Biosystems, Inc., Foster City, Calif.). Data analysis was performed with Model 610A Data Analysis System for Protein Sequencing, version 2.1a (Applied Biosystems).

A purified human zcytor17lig-CEE sample (Example 35) was supplied. The sample was loaded onto a prepared glass fiber filter for n-terminal sequencing. The glass fiber filter was prepared by precycling it with Biobrene™.

N-terminal sequence analysis of the secreted human zcytor17lig polypeptide did not verify the predicted cleavage site of the signal sequence but resulted in a mature start at residue 27(Leu) in SEQ ID NO:2 of the human zcytor17lig precursor sequence.

B. N-Terminal Sequencing of Human Zcytor17lig

Standard automated N-terminal polypeptide sequencing (Edman degradation) was performed using reagents from Applied Biosystems. N-terminal sequence analysis was performed on a Model 494 Protein Sequencer System (Applied Biosystems, Inc., Foster City, Calif.). Data analysis was performed with Model 610A Data Analysis System for Protein Sequencing, version 2.1a (Applied Biosystems).

A purified mouse zcytor17lig-CEE sample was supplied as captured on Protein G Sepharose/anti-EE beads (Example 35). The beads were placed in reducing SDS PAGE sample buffer and on a boiling water bath before running on SDS PAGE, using a Novex SDS PAGE system (4-12% Bis-Tris MES NuPAGE; Invitrogen) as per manufacturer's instructions. The gel was electrotransferred to a Novex PVDF membrane (Invitrogen), and Coomassie blue stained (Sigma, St. Louis, Mo.) using standard methods. Corresponding anti-EE Western blots were performed to identify the zcytor17lig band for N-terminal protein sequencing. The mouse anti-EE IgG HRP conjugated antibody used was produced in house.

N-terminal sequence analysis of the secreted mouse zcytor17lig polypeptide verified the predicted cleavage site of the signal sequence resulting in a mature start at 31 (Ala) in reference to SEQ ID NO:11 and SEQ ID NO:91 of the mouse zcytor17lig precursor sequence.

Example 37

Cos Cell Binding Assay

A binding assay was used to test the binding of the zcytor17lig to receptors comprising zcytor17 receptor, such as the zcytor17 receptor or receptor heterodimers and trimers comprising zcytor17 receptor (e.g., zcytor17/OSMR, zcytor17/WSX-1, or zcytor17/OSMR/WSX-1, or other Class I cytokine receptor subunits). Zcytor17 receptor plasmid DNA was transfected into COS cells and transfected COS cells were used to assess binding of the zcytor17lig to receptors comprising zcytor17 receptor as described below.

A. COS Cell Transfections

The COS cell transfection was performed as follows: Mix 800 ng receptor plasmid DNA in the following combinations: pZp7pX/zcytor17 alone; pZp7Z/WSX-1 alone; pZp7NX/OSMR alone; pZp7pX/zcytor17+pZp7NX/OSMR; pZp7pX/zcytor17+pZp7Z/WSX-1; pZp7NX/OSMR+pZp7Z/WSX-1; pZp7pX/zcytor17+pZp7NX/OSMR+pZp7Z/WSX-1) and 4 ul Lipofectamine™ in 80 μl serum free DMEM media (55 mg sodium pyruvate, 146 mg L-glutamine, 5 mg transferrin, 2.5 mg insulin, 1 μg selenium and 5 mg fetuin in 500 ml DMEM), incubate at room temperature for 30 minutes and then add 320 μl serum free DMEM media. Add this 400 ul mixture onto $2 \times 10^5$ COS cells/well plated on 12-well tissue culture plate (fibronectin-coated) and incubate for 5 hours at 37° C. Add 500 ul 20% FBS DMEM media (100 ml FBS, 55 mg sodium pyruvate and 146 mg L-glutamine in 500 ml DMEM) and incubate overnight.

B. Binding Assay

The binding assay was performed as follows: media was rinsed off cells with PBS+0.1% BSA, and then cells were blocked for 60 minutes with the same solution. The cells were then incubated for 1 hour in PBS+0.1% BSA with 1.0 μg/ml zcytor17ligCEE purified protein. Cells were then washed with PBS+0.1% BSA and incubated for another hour with 1:1000 diluted mouse anti-GluGlu antibody. Again cells were washed with PBS+0.1% BSA, then incubated for 1 hour with 1:200 diluted goat anti-mouse-HRP conjugated antibody.

Positive binding was detected with fluorescein tyramide reagent diluted 1:50 in dilution buffer (NEN kit) and incubated for 4-6 minutes, and washed with PBS+0.1% BSA. Cells were fixed for 15 minutes with 1.8% Formaldehyde in PBS, then washed with PBS+0.1% BSA. Cells were preserved with Vectashield Mounting Media (Vector Labs Burlingame, Calif.) diluted 1:5 in PBS. Cells were visualized using a FITC filter on fluorescent microscope.

Positive binding was detected for cells transfected with zcytor17 only, zcytor17+OSMRbeta, zcytor17+WSX-1, and zcytor17+OSMRbeta+WSX-1. No binding was detected for cells transfected with WSX-1+OSMRbeta, with OSMRbeta only, or with WSX-1 only.

Example 38

Mouse Zcytor17lig Activates Mouse Zcytor17/OSMRbeta Receptor-in Luciferase Assay A. Cloning of Full-Length Mouse Zcytor17 and Mouse OSMRbeta for Expression A mouse testes cDNA library was screened for a full-length clone of mouse zcytoR17. The library was plated at 65,500 cfu/plate on 24 LB+Amp plates. Filter lifts were prepared using Hybond N (Amersham-Pharmacia Biotech, Inc., Piscataway, N.J.) on a total of approximately 1.6 million colonies. The filters were marked with a hot needle for orientation and then denatured for 6 minutes in 0.5 M NaOH and 1.5 M Tris-HCl, pH 7.2. The filters were then neutralized in 1.5 M NaCl and 0.5 M Tris-HCl, pH 7.2 for 6 minutes. The DNA was affixed to the filters using a UV crosslinker (Stratalinker®, Stratagene, La Jolla, Calif.) at 1200 joules. The filters were then left to dry overnight at room temperature.

The next day, the filters were pre-washed at 65° C. in pre-wash buffer consisting of 0.25×SSC, 0.25% SDS and 1 mM EDTA. Cell debris was manually removed using Kimwipes® (Kimberly-Clark) and the solution was changed 3 times over a period of 1 hour. Filters were air dried and stored at room temperature until needed. The filters were then prehybridized for approximately 3 hours at 63° C. in 20 ml of ExpressHyb™ Hybridization Solution (Clontech, Palo Alto, Calif.).

Probe B (Example 31) was generated by PCR from human zcytoR17 template using oligonucleotide primers ZC27,895 (SEQ ID NO:20) and ZC28,917 (SEQ ID NO:83) and was radioactively labeled with $^{32}$P using a commercially available kit (Megaprime DNA Labeling System; Amersham Pharmacia Biotech, Piscataway, N.J.) according to the manufacturer's instructions. The probe was purified using a Stratagene™ push column (NucTrap® column; Stratagene, La Jolla, Calif.). The probe was denatured at 100° C. for 15 min and added to ExpressHyb™. Filters were hybridized in 15 ml hybridizing solution containing $1.6 \times 10^6$ cpm/ml of probe at 63° C. overnight. Filters were washed at 55° C. in 2×SSC, 0.1% SDS and 1 mM EDTA and exposed to X-ray film at −80° C. for 4½ days. Thirteen positives were picked from the plates as plugs and placed in 1 ml LB+amp in 1.7 ml tubes. Tubes were placed at 4° C. overnight. These 13 positives were subjected to two further rounds of purification. The tertiary plates were outgrown at 37° C. after filter lifts were taken and single colonies were picked and sent to sequencing. Three of these were determined to contain sequence of the mouse ortholog of zcytoR17.

In addition, a PCR product was generated using CTLL-2 cDNA as a template and oligonucleotides ZC38,239 (SEQ ID NO:123) and ZC38,245 (SEQ ID NO:124) as primers. CTLL-2 is a mouse cytotoxic T lymphocyte cell line (ATCC No. TIB-214). This PCR reaction was run as follows: 1 cycle at 95° C. for 1 minute, 30 cycles at 95° C. for 15 seconds, 68° C. for 3 minutes, then 68° C. for 10 minutes; 4° C. soak. The PCR reaction used approximately 0.5 ng of cDNA, 20 pmoles of each oligonucleotide, and 1 µl of Advantage II polymerase mix (ClonTech). About 6% of the PCR product was used as a template in a new PCR reaction, as above, except with oligonucleotides ZC38,239 (SEQ ID NO:123) and ZC38,238 (SEQ ID NO:125). This PCR reaction was run as follows: 30 cycles at 94° C. for 45 seconds, 65° C. for 45 seconds, 72° C. for 1 minute, then 72° C. for 7 minutes; 10° C. soak. Most of the PCR reaction was loaded on a 1.0% agarose gel and the predominant band at approximately 360 bp was excised, the DNA fragment was eluted, and DNA sequencing was performed.

The sequence of the mouse zcytor17 polynucleotide is shown in SEQ ID NO:126 and the corresponding amino acid sequence shown in SEQ ID NO:127. In addition, a truncated soluble form of the mouse zcytor17 polynucleotide is shown in SEQ ID NO:128 and the corresponding amino acid sequence shown in SEQ ID NO:129.

To obtain a full-length mouse OSMRbeta cDNA, 5' and 3' PCR products were isolated and joined using an internal BamHI site. The PCR primers were designed using the nucleotide sequence SEQ ID NO:134 and include EcoRI and XbaI restriction sites for cloning purposes. The genomic mouse OSMRbeta nucleic acid sequence is shown in SEQ ID NO:134, wherein the coding sequence encompasses residues 780 to 3692 encoding a mouse OSMRbeta 970 amino acid polypeptide, which is shown in SEQ ID NO:135. A degenerate nucleic acid sequence which encodes the polypeptide of SEQ ID NO:135 is shown in SEQ ID NO:136.

A 5' PCR product was generated using an in-house 3T3-L1 (differentiated mouse adipocyte) cDNA library as a template and oligonucleotides ZC41,764 (SEQ ID NO:130) and ZC41,598 (SEQ ID NO:131) as primers. This 5' PCR reaction was run as follows: 30 cycles at 95° C. for 45 seconds, 55° C. for 45 seconds, 72° C. for 1 minute 30 seconds, then 72° C. for 7 minutes; 4° C. soak. The PCR reaction used approximately 3 µg of plasmid prepared from the cDNA library, 20 pmoles of each oligonucleotide, and five units of Pwo DNA polymerase (Roche). About 90% of the 5' PCR product was digested with EcoRI and BamHI and gel purified on a 1.0% agarose gel. The approximately 1446 bp band was excised and used for ligation (see below).

A 3' PCR product was generated using a mouse placenta in-house cDNA library as a template and oligonucleotides ZC41,948 (SEQ ID NO:132) and ZC41,766 (SEQ ID NO:133) as primers. This 3' PCR reaction was run as follows: 30 cycles at 95° C. for 45 seconds, 55° C. for 45 seconds, 72° C. for 1 minute 30 seconds, then 72° C. for 7 minutes; 4° C. soak. The PCR reaction used approximately 3 µg of plasmid prepared from the cDNA library, 20 pmoles of each oligonucleotide, and five units of Pwo DNA polymerase (Roche). About 90% of the 3' PCR product was digested with BamHI and XbaI and gel purified on a 1.0% agarose gel. The approximately 2200 bp band was excised and used for ligation along with the 5' PCR product (described above) to the expression vector pZP-5Z digested with EcoRI and XbaI. The three-part ligation was performed with the 5' EcoRI to BamHI fragment above, the 3' BamHI to XbaI fragment, and the expression vector pZP-5Z digested with EcoRI and XbaI. This generated a pZP-5Z plasmid containing a full-length cDNA for mouse OSMRbeta (nucleotides 780 to 3692 of SEQ ID NO:134), designated pZP-5Z/OSMRbeta. The full length mouse OSMRbeta cDNA in pZP5Z/OSMRbeta has two amino acid insertions from SEQ ID NO:135. There is a duplication of amino acid Glycine at position 370 and a duplication of amino acid Glutamic Acid at position 526. Plasmid pZP-5Z is a mammalian expression vector containing an expression cassette having the CMV promoter, multiple restriction sites for insertion of coding sequences, and a human growth hormone terminator. The plasmid also has an *E. coli* origin of replication, a mammalian selectable marker expression unit having an SV40 promoter, enhancer and origin of replication, a zeocin resistance gene and the SV40 terminator.

The resulting transformants were sequenced to confirm the mouse OSMRbeta cDNA sequence.

B. Construction of BaF3/KZ134/Zcytor17m, BaF3/KZ134/Zcytor17 m/OSMRbetam, BHK/KZ134/Zcytor17m, and BHK/KZ134/Zcytor17 m/OSMRbetam Cell Lines Stable BaF3/KZ134 and BHK/KZ134 cell lines (Example 20) were transfected with an expression plasmid encoding full-length mouse zcytor17, pZP-7P/zcytor17m (Example 38A), to create BaF3/KZ134/zcytor17m and BHK/KZ134/zcytor17m cells, respectively. The mouse OSMRbeta expression plasmid, pZP-5Z/OSMRbetam (Example 38A), was then transfected into these cells to create BaF3/KZ134/zcytor17 m/OSMRbetam and BHK/KZ134/zcytor17 m/OSMRbetam cell lines, respectively. Methods were as described in Example 4 with the exception that Baf3/KZ134/zcytor17m and BHK/KZ134/zcytor17m were selected with, in addition to Geneticin, 2 ug/ml puromycin while Baf3/KZ134/zcytor17 m/OSMRbetam and BHK/KZ134/zcytor17 m/OSMRbetam were selected with, in addition to Geneticin, 2 ug/ml puromycin and 200 ug/ml zeocin.

Clones were diluted, plated and selected using standard techniques. Clones were screened by luciferase assay (see Example 20, above) using the mouse zcytor17lig conditioned media or purified mouse zcytor17lig protein (Example 35) as an inducer. Clones with the highest luciferase response (via STAT luciferase) and the lowest background were selected. Stable transfectant cell lines were selected.

C. Mouse Zcytor17lig Activates Mouse Zcytor17 Receptor in BaF3/KZ134/Zcytor17m/OSMRbetam or BHK/KZ134/Zcytor17 m/OSMRbetam Luciferase Assay Cell lines were plated for luciferase assays as described in Example 20 above. STAT activation of the BaF3/KZ134/Zcytor17m, BaF3/KZ134/zcytor17 m/OSMRbetam, BHK/KZ134/zcytor17m, or BHK/KZ134/zcytor17 m/OSMRbetam cells was assessed using (1) conditioned media from BHK570 cells transfected with the human zcytor17lig (Example 7), (2) conditioned media from BHK570 cells transfected with the mouse zcytor17lig (Example 18), (3) purified mouse and human zcytor17lig (Example 35), and (4) mIL-3 free media to measure media-only control response. Luciferase assays were performed as described in Example 20.

The results of this assay confirm the STAT reporter response of the BaF3/KZ134/zcytor17 m/OSMRbetam and BHK/KZ134/zcytor17 m/OSMRbetam cells to the mouse zcytor17lig when compared to either the BaF3/KZ134/zcytor17m cells, the BHK/KZ134/zcytor17m cells or the untransfected BaF3/KZ134 or BHK/KZ134 control cells, and show that the response is mediated through the mouse zcytor17/OSMRbeta receptors. The results also show that the human zcytor17lig does not activate the STAT reporter assay through the mouse receptor complex.

Example 39

Human Zcytor17 Ligand Binding to Zcytor17 and Zcytor17/OSMRbeta by Flow Cytometry The biotinylation of human zcytor17L was done as follows: 1000 μL of zcytor17 at 5.26 mg/mL was combined with 30 μL of 10 mg/mL EZ-link Sulfo-NHS-LC-biotin (Pierce, Rockford, Ill.) dissolved in ddH$_2$O. This solution was incubated on a rocker for 30 minutes at room temperature. After biotinylation the solution was dialyzed in PBS using a Slide-A-Lyzer dialysis cassette.

To test the binding properties of human zcytor17 ligand to different receptor combinations both BHK and BAF3 cells were transfected with expression plasmids using standard techniques well-known in the art. These plasmids were transfected into both cell lines in the following combinations: zcytor17 alone, OSMRbeta alone, and both zcytor17 and OSMRbeta. Transfection was performed as detailed above. Untransfected BHK and BAF3 cells were used as controls. Cells were stained by FACS as follows: 2E5 cells were stained with either: 2.0 μg/mL, 100 ng/mL, 10 ng/mL, L0ng/mL, 100 pg/mL, 10 pg/mL, 1.0 pg/mL of biotinylated zcytor17L or left unstained for 30 minutes on ice in FACS buffer (PBS+2% BSA+2% NHS (Gemini)+2% NGS). Cells were washed 1.5 times and then stained with SA-PE (Jackson Immuno Laboratories) at 1:250 for 30 minutes on ice. Cells were then washed 1.5 times with FACS buffer and resuspended in FACS buffer and analyzed by FACS on a BD FACSCaliber using CellQuest software (Becton Dickinson, Mountain View, Calif.).

Both BHK and BAF3 cells showed that zcytor17 ligand bound to both zcytor17 alone and in combination with OSMRbeta with the binding to the zcytor17/OSMRbeta heterodimer being slightly stronger. No binding was seen in either cell lines expressing OSMRbeta alone. The zcytor17 ligand bound in a concentration dependent manner. The mean fluorescent intensity (MFI) values for the BHK binding are shown below in Table 15.

TABLE 15

| zcytor17 μg/mL | 2.0 | 0.100 | 0.010 | 0.001 | 0.0001 | 0.00001 | 0.000001 | 0.0 |
|---|---|---|---|---|---|---|---|---|
| BHK C17 + OSMRbeta | 3780 | 2126 | 328 | 53 | 17 | 15 | 14 | 13 |
| BHK-C17 | 3032 | 1600 | 244 | 39 | 16 | 15 | 14 | 15 |
| BHK-OSMRbeta | 13 | X | X | X | X | X | X | 0 |
| BHK-WT | 15 | 14 | 13 | X | X | X | X | 13 |

| zcytor17 μg/mL | 10.0 | 3.33 | 1.11 | 0.37 | 0.12 | 0.04 | 0.00 |
|---|---|---|---|---|---|---|---|
| BAF3-C17 + OSMRbeta | 531 | 508 | 489 | 441 | 364 | 247 | 7 |
| BAF3-OSMRbeta | 6 | 5 | 5 | 5 | 5 | 5 | 11 |
| BAF3-WT | 13 | 13 | 12 | 12 | 12 | 12 | 13 |

| zcytor17 ng/mL | 100.0 | 10.0 | 1.0 | 0.0 |
|---|---|---|---|---|
| BAF3-C17 | 347 | 72 | 17 | 7 |

Example 40

Gene Expression Array Analysis of Human Zcytor17lig Treated Cells

RNA was isolated from human zcytor17lig treated A549 cells, zcytor17lig treated SK-LU-1 cells, and untreated control cells using a RNeasy Midi Kit (Qiagen, Valencia, Calif.) according to the manufactures instructions.

Gene expression profiling of the cells treated with zcytor17lig and the respective control cells was carried out using GEArray Q series cDNA expression arrays (SuperArray Inc., Bethesda, Md.). The Q Series cDNA expression arrays contain up to 96 cDNA fragments associated with a specific biological pathway, or genes with similar functions or structural features. Comparison of arrays from treated and control cells allows for a determination of the up and down regulation of specific genes. Probe labeling, hybridization and detection were carried out according to the manufactures instructions. Chemiluminescent signal detection and data acquisition was carried out on a Lumi-Imager workstation (Roche, Indianapolis, Ind.). The resulting image data was analyzed using ImageQuant 5.2 (Amersham Biosciences, Inc., Piscataway, N.J.) and GEArray Analyzer 1.2 (SuperArray Inc., Bethesda, Md.) software.

Analysis of the results from the Human Interleukin and Receptor Q series HS-014N arrays, showed, after normalization, an approximate 4.7 fold increase of IL13RA2 signal in the zcytor17lig treated human SK-LU-1 cells and an approximate 2.2 fold increase of the IL13RA2 signal in the zcytor17lig treated human A549 cells.

These results indicate that zcytor17lig significantly up regulated

IL13RA2 in the SK-LU-1 and A549 cells. Both of these are established cell lines derived from human lung carcinomas (Blobel et al., *Virchows Arch B Cell Pathol Incl Mol Pathol.*, 1984; 45(4):407-29). More specifically, A549 is characterized as a human pulmonary epithelial cell line (Lin, et al., *J Pharm Pharmacol.*, 2002 September; 54(9):1271-8; Martinez et al., *Toxicol Sci.*, 2002 October; 69(2):409-23).

Interleukin-13 (IL13), a cytokine secreted by activated T lymphocytes, has been demonstrated to be both necessary and sufficient for the expression of allergic asthma and for use in experimental models of asthma, which include airway hyperresponsiveness, eosinophil recruitment, and mucus overproduction (Wills-Karp et al., *Science*, 1998; 282:2258-2261). It has been shown, that selective neutralization of IL13 will ameliorate the asthma phenotype (Grunig et al., *Science*, 1998; 282:2261-2263). It has also been reported that IL13 is involved in the up regulation of mucin gene MUC8 expression in human nasal polyp epithelium and cultured nasal epithelium (Kimm et al., *Acta Otolaryngol.*, 2002; September; 122(6):638-643; Seong et al., *Acta Otolaryngol.*, 2002; June; 122(4):401-407). MUC8, a major airway mucin glycoprotein, is implicated as playing a role in the pathogenesis of mucus hypersecretion in chronic sinusitis with polps (Seong et al., *Acta Otolaryngol.*, 2002; June; 122(4):401-407).

Functionally, IL13 signals through a receptor complex consisting of the interleukin-13 receptor alpha-1 chain (IL13RA1) and IL-4 receptor alpha (IL4RA) (Daines and Hershey, *J Biol Chem.*, 2002; 22(12):10387-10393). It has also been shown, that the interleukin-13 receptor alpha-2 (IL13RA2) binds IL13 with high affinity, but by itself (Daines and Hershey, *J Biol Chem.*, 2002; 22(12):10387-10393). This receptor lacks, however, the cytoplasmic domain necessary for signaling and, therefore, is considered to be a decoy receptor. It has been shown that IL13RA2 is predominately an intracellular molecule that can be quickly mobilized from intracellular stores and surface expressed following cellular treatment with interferon (IFN)-gamma. The surface expression of IL13RA2 after IFN-gamma treatment does not involve protein synthesis and results in diminished IL13 signaling (Daines and Hershey, *J Biol Chem.*, 2002; 22(12): 10387-10393).

The results of the gene expression array analysis for zcytor17lig indicate the action of zcytor17lig to be novel to that of IFN-gamma in that the zcytor17lig treatment of lung epithelial derived cell lines resulted in a significant increase of IL13RA2 gene expression. It is conceivable, therefore, that zcytor17lig treatment would be beneficial in cases where long-term up regulation of IL13RA2 expression and down regulation of IL13 is desired such as in asthma, airway hyperactivity (AHR), and mucin regulation, including chronic sinusitis with polps.

Example 41

Murine Zcytor17lig Transgenic Mice

To evaluate the in vivo effects of zcytor17lig overexpression, multiple founders of transgenic mice expressing the murine form of the gene were generated, driven by two different promoters: the lymphocyte-specific promoter Eµ/lck, and the ubiquitous promoter, EF1α (Example 22). Serum protein levels range from approximately 20-300 ng/ml. The Eµ/lck promoter generated mice with higher levels of serum protein than those in the EF1α-zcytor17lig transgenic mice.

The zcytor17lig transgenic mice developed a skin phenotype around 4-8 weeks of age. The fur of the transgenic mice became "ruffled," with obvious piloerection and mild to severe hair loss, usually on their backs, sides of the torso, and around their eyes. This phenotype was consistently found in mice with detectable levels of zcytor17lig protein in their serum. Among the founders, 100% incidence rate among the mice expressing the Eµ/lck-driven gene, and a 50% incidence in the EF1α-zcytor17lig transgenic mice was noted, correlating well with the relative levels of zcytor17lig that was detected in their serum. The transgenic skin appeared to be pruritic, as evidenced by the scratching behavior of the mice, sometimes excessive enough to induce excoriation and lesions of the skin, which usually became infected (with at least *Staphylococcus aureus*). The mice were originally identified with metal ear tags, but in most cases, the ear tags were forcibly removed by the mice themselves. This often resulted in severe damage to the external ear. These wounded ears often did not heal properly, as reflected in the presence of long-lasting pustules and crusting, and a seeping, expanding wound would that developed in many of the animals, behind and between their ears. Some of the transgenic mice also developed scabby wounds on their shoulders and neck. Skin lesions were observed in a subset of the animals, generally evolving on areas of skin where hair loss had already been apparent, and were often exacerbated by the scratching behavior of the mice.

RealTime quantitative RT-PCR was used to detect zcytor17lig RNA transcripts in transgenic (but not non-transgenic) skin samples, with the Eµ/lck transgenic skin expressing more zcytor17lig RNA than skin from EF1α-zcytor17lig transgenic mice. The genes encoding the zcytor17 receptor subunits, zcytor17 and OSM-Rbeta, were expressed in the skin of both non-transgenic and zcytor17lig-transgenic mice.

An examination of the lymphoid tissues from a subset of the Eµ/lck-transgenic founders by flow cytometry revealed a significant increase in the proportion of activated T cells in the spleen and lymph nodes of these mice. Two of the four mice analyzed had severely enlarged cervical lymph nodes, possibly due to the presence of lesions on their necks. A subtle increase in spleen weight and a slight increase in monocytes and neutrophils circulating in the blood of the transgenic mice was observed. There was no increase in a variety of cytokines tested, nor were there changes in the circulating serum amyloid A levels in these mice. The effects on the immune cells in the transgenic mice may be a direct or an indirect result of zcytor17lig, or are secondary effects of the skin lesions.

Histopathology was performed on many tissues other than skin, including liver, thymus, spleen, kidney, and testes, and no significant abnormalities in these organs were noted. Analysis of the transgenic skin, however, did reveal a number of alterations, which varied greatly depending upon the source and location of skin (e.g., normal, hairless, or lesional). In many cases, the ears of the transgenic mice had a thickened epidermis as compared to the non-transgenic controls (e.g., approximately 4 layers versus 2 layers), and the underlying tissues contained low to moderate numbers of inflammatory cells, which were primarily mononuclear with occasional neutrophils. The epidermis over the abdomen appeared multifocally slightly thicker in the transgenic, but there was no apparent increase in inflammatory cells in the underlying dermis or subcutis. In the hairless portions of skin from these mice, there were dilated hair follicles that contained some debris but no hair shafts (e.g., the hairs fell out by the roots). In the lesioned areas, there was severe thickening of the epidermis (acanthosis), increased keratin on the surface of the skin (hyperkeratosis), scattered ulcers of varying size and significant numbers of inflammatory cells in the dermis (mainly neutrophils, with varying numbers of macrophages and lymphocytes). The dermis also contained numerous mast cells bordering the lesions. Some of the hair shafts in the lesioned areas of the transgenic skin were in the active stage (anagen), in contrast to many of the hair shafts in "normal" areas which were in the involuting (catagen) to inactive (telogen) stage.

The phenotype of the zcytor17lig transgenic mice strongly resembles that of atopic dermatitis (AD) patients, and mouse models of AD. AD is a common chronic inflammatory disease that is characterized by hyperactivated cytokines of the helper T cell subset 2 (Th2). Zcytor17lig is preferentially expressed by Th2 vs. Th1 cells, which lends further credence to this comparison. Although the exact etiology of AD is unknown, multiple factors have been implicated, including hyperactive Th2 immune responses, autoimmunity, infection, allergens, and genetic predisposition. Key features of the disease include xerosis (dryness of the skin), pruritus (itchiness of the skin), conjunctivitis, inflammatory skin lesions, *Staphylococcus aureus* infection, elevated blood eosinophilia, elevation of serum IgE and IgG1, and chronic dermatitis with T cell, mast cell, macrophage and eosinophil infiltration. Colonization or infection with *S. aureus* has been recognized to exacerbate AD and perpetuate chronicity of this skin disease.

AD is often found in patients with asthma and allergic rhinitis, and is frequently the initial manifestation of allergic disease. About 20% of the population in Western countries suffer from these allergic diseases, and the incidence of AD in developed countries is rising for unknown reasons. AD typically begins in childhood and can often persist through adolescence into adulthood. Current treatments for AD include topical corticosteroids, oral cyclosporin A, non-corticosteroid immunosuppressants such as tacrolimus (FK506 in ointment form), and interferon-gamma. Despite the variety of treatments for AD, many patients' symptoms do not improve, or they have adverse reactions to medications, requiring the search for other, more effective therapeutic agents.

Epithelial cells, which express the heterodimeric receptor for zcytor17lig (zcytoR17 and OSM-Rbeta), are located at the sites (e.g., skin, gut, lung, etc.) of allergen entry into the body and interact closely with dendritic cells (professional antigen presenting cells) in situ. Dendritic cells play an important role in the pathogenesis of allergic diseases, and it is possible that zcytor17lig can interact with its receptor on epithelial cells in the skin and lung and influence immune responses in these organs. Zcytor17lig and its receptor(s) may therefore contribute to the pathogenesis of allergic diseases such as AD and asthma. Furthermore, the phenotype of the zcytor17lig transgenic mice suggests that this ligand may play a role in wound healing, since the mice seem unable to repair damage to their ears, and often bear long-lasting lesions on their backs and sides. An antagonist of zcytor17lig might therefore represent a viable therapeutic for these and other indications.

Example 42

Luciferase Assay on Human Transformed Epithelial Cell Lines Via Transient Infection with an Adenoviral STAT/SRE Reporter Gene A wide variety of human transformed epithelial cell lines (see Table 16 below) were seeded in 96-well flat-bottom plates at 10,000 cell/well in regular growth media as specified for each cell type. The following day, the cells were infected with an adenovirus reporter construct, KZ136, at a multiplicity of infection of 5000. The KZ136 reporter contains the STAT elements in addition to a serum response element. The total volume was 100 ul/well using DMEM supplemented with 2 mM L-glutamine (GibcoBRL), 1 mM Sodium Pyruvate (GibcoBRL) and 1× Insulin-Transferrin-Selenium supplement (GibcoBRL) (hereinafter referred to as serum-free media). Cells were cultured overnight.

The following day, the media was removed and replaced with 100 μl of induction media. The induction media was human zcytor17 ligand diluted in serum-free media at 100 ng/ml, 50 ng/ml, 25 ng/ml, 12.5 ng/ml, 6.25 ng/ml, 3.125 ng/ml and 1.56 ng/ml. A positive control of 20% FBS was used to validate the assay and to ensure the infection by adenovirus was successful. The cells were induced for 5 hours at which time the media was aspirated. The cells were then washed in 50 μl/well of PBS, and subsequently lysed in 30 μl/well of 1× cell lysis buffer (Promega). After a 10-minute incubation at room temperature, 25 μl/well of lysate was transferred to opaque white 96-well plates. The plates were then read on the Luminometer using 5-second integration with 40 μl/well injection of luciferase substrate (Promega).

The results revealed the ability of multiple epithelial cell lines to respond to zcytor17 ligand as shown in Table 16 below.

TABLE 16

| Cell Line | Species | Tissue | Morphology | Disease | Fold Induction |
| --- | --- | --- | --- | --- | --- |
| A549 | Human | Lung | Epithelial | Carcinoma | 2x |
| Sk-Lu-1 | Human | Lung | Epithelial | Adenocarcinoma | 6x |
| WI-38 | Human | Embryonic Lung | Fibroblast | | Negative |
| MRC-5 | Human | Lung | Fibroblast | | Negative |
| DU 145 | Human | Prostate | Epithelial | Carcinoma | 10x |
| PZ-HPV-7 | Human | Prostate | Epithelial | Transformed with HPV | 5x |
| PC-3 | Human | Prostate | Epithelial | Adenocarcinoma | Negative |
| U2OS | Human | Bone | Epithelial | Osteosarcoma | 15.5x |
| SaOS2 | Human | Bone | Epithelial | Osteosarcoma | 22x |
| MG-63 | Human | Bone | Fibroblast | Osteosarcoma | Negative |
| 143B | Human | Bone | Fibroblast | Osteosarcoma | 3.5x |
| HOS | Human | Bone | Fibroblast and Epithelial | | 8x |
| TRBMeC | Human | Vascular Bone Marrow | Epithelial | | 2x |
| HT144 | Human | Skin | Fibroblast | Melanoma | 5x |
| C32 | Human | Skin | | Melanoma | Negative |
| Sk-Mel-2 | Human | Skin | Polygonal | Melanoma | 2.7x |

TABLE 16-continued

| Cell Line | Species | Tissue | Morphology | Disease | Fold Induction |
|---|---|---|---|---|---|
| WM-115 | Human | Skin | Epithelial | Melanoma | 2x |
| HCT-116 | Human | Colon | Epithelial | Carcinoma | Negative |
| HT-29 | Human | Colon | Epithelial | Carcinoma | Negative |
| CaCo2 | Human | Colon | Epithelial | Adenocarcinoma | 3x |
| HBL-100 | Human | Breast | Epithelial | | 1.5x |
| ME-180 | Human | Cervix | Epithelial | Carcinoma | Negative |
| HeLa 299 | Human | Cervix | Epithelial | Adenocarcinoma | Negative |
| SK-N-SH | Human | Brain | Epithelial | Neuroblastoma | Negative |
| U138 MG | Human | Brain | Polygonal | Glioblastoma | Negative |
| HepG2 | Human | Liver | Epithelial | Carcinoma | Negative |
| Chang liver | Human | Liver | Epithelial | | Negative |
| Sk-Hep-1 | Human | Liver | Epithelial | Adenocarcinoma | 4x |
| Int 407 | Human | Intestine | Epithelial | | Negative |
| 3a-Sub E | Human | Placenta | | | Negative |

Example 43

Cytokine Production by Human Epithelial Cell Lines Cultured with Human Zcytor17 Ligand Human disease-state epithelial cell lines (A549, human lung epithelial carcinoma; SkLu1, human lung epithelial adenocarcinoma; DU145, human prostate epithelial carcinoma; PZ-HPV-7, human prostate epithelial HPV transformed; U20S, human bone epithelial osteosarcoma) were screened for cytokine production in response to zcytor17 ligand in vitro. These cell lines have both zcytor17 and OSMR-beta, identified by RT-PCR, and respond to human zcytor17 ligand when assayed with the adenoviral luciferase reporter construct, KZ136 (Example 42). Cytokine production by these cell lines was determined in response to human zcytor17 ligand in a series of three experiments.

A. Cytokine Production by Human Disease-State Epithelial Cell Lines Cultured with Human Zcytor17lig Cells were plated at a density of $4.5 \times 10^5$ cells per well in a 6 well plate (Costar) and cultured in respective growth media. The cells were cultured with test reagents; 100 ng/mL zcytor17 ligand, 10 ng/mL Interferon gamma (IFN gamma) (R&D Systems, Minneapolis, Minn.), 10 ng/mL Tumor Necrosis Factor alpha (TNF alpha) (R&D Systems, Minneapolis, Minn.), 10 ng/mL IL-1beta (R&D Systems, Minneapolis, Minn.) or 100 ug/mL Lipopolysaccharide (LPS) (Sigma). Supernatants were harvested at 24 and 48 hours and assayed for cytokines; GM-CSF (Granulocyte-Macrophage Colony-Stimulating Factor), IL-1b, IL-6, IL-8, MCP-1 (Macrophage Chemoattractant Protein-1) and TNFa. Multiplex Antibody Bead kits from BioSource International (Camarillo, Calif.) were used to measure cytokines in samples. Assays were read on a Luminex-100 instrument (Luminex, Austin, Tex.) and data was analyzed using MasterPlex software (MiraiBio, Alameda, Calif.). Cytokine production (pg/mL) for each cell line in the 24-hour samples is shown below in Table 17.

TABLE 17

| | A549 | SkLu1 | DU145 | U2OS | PZ-HPV-7 |
|---|---|---|---|---|---|
| GM-CSF pg/mL | | | | | |
| zcytor17L | 18.80 | 10.26 | 16.19 | 13.26 | 14.10 |
| IFN-g | 16.19 | 13.36 | 11.56 | 16.26 | 11.81 |
| IL-1b | 104.60 | 126.44 | 76.77 | 338.25 | 27.32 |
| TNFa | 106.67 | 33.20 | 58.50 | 107.09 | 33.79 |
| LPS | 17.64 | 10.62 | 11.81 | 25.47 | 18.34 |
| control | 14.81 | 8.56 | 13.26 | 21.67 | 13.96 |
| IL-1b pg/mL | | | | | |
| zcytor17L | 26.90 | 30.17 | 28.77 | 29.07 | 28.00 |
| IFN-g | 29.07 | 35.33 | 21.96 | 26.90 | 26.73 |
| IL-1b | 1332.88 | 1256.17 | 979.02 | 1107.35 | 998.60 |
| TNFa | 31.11 | 33.28 | 35.33 | 31.24 | 25.66 |
| LPS | 33.28 | 28.77 | 29.07 | 31.11 | 31.24 |
| control | 28.77 | 28.77 | 26.73 | 31.24 | 29.07 |
| IL-6 pg/mL | | | | | |
| zcytor17L | 20.09 | 26.89 | 193.05 | 19.37 | 17.30 |
| IFN-g | 17.52 | 33.64 | 217.58 | 27.02 | 17.63 |
| IL-1b | 175.44 | 5920.19 | 2375.29 | 304.08 | 18.44 |
| TNFa | 354.16 | 1002.51 | 1612.17 | 103.58 | 18.33 |
| LPS | 18.06 | 35.65 | 162.18 | 22.42 | 17.30 |
| control | 17.63 | 27.80 | 71.23 | 19.32 | 17.19 |
| IL-8 pg/mL | | | | | |
| zcytor17L | 86.33 | 150.81 | 150.61 | 45.92 | 6.81 |
| IFN-g | 24.07 | 72.82 | 163.31 | 81.78 | 1.35 |
| IL-1b | 1726.24 | 4083.12 | 4407.79 | 5308.83 | 124.17 |
| TNFa | 3068.68 | 3811.75 | 2539.39 | 3324.02 | 69.65 |
| LPS | 20.28 | 167.13 | 230.39 | 115.08 | 7.95 |
| control | 14.92 | 109.78 | 107.27 | 93.44 | 9.49 |
| MCP-1 pg/mL | | | | | |
| zcytor17L | 8.97 | 187.29 | 26.84 | 105.15 | 7.20 |
| IFN-g | 7.30 | 267.99 | 17.05 | 88.68 | 7.71 |
| IL-1b | 8.11 | 8039.84 | 88.78 | 3723.81 | 4.70 |
| TNFa | 8.50 | 7100.37 | 153.26 | 3826.80 | 2.80 |
| LPS | 9.40 | 185.83 | 22.65 | 61.62 | 5.61 |
| control | 8.16 | 167.93 | 13.68 | 47.78 | 5.61 |
| TNFa pg/mL | | | | | |
| zcytor17L | 16.23 | 17.52 | 16.67 | 15.80 | 17.09 |
| IFN-g | 15.80 | 17.09 | 15.80 | 16.65 | 15.80 |
| IL-1b | 16.66 | 17.09 | 15.80 | 17.95 | 16.23 |
| TNFa | 1639.92 | 1648.83 | 2975.07 | 1348.33 | 3554.82 |
| LPS | 16.87 | 15.80 | 15.37 | 17.09 | 17.52 |
| control | 16.23 | 15.80 | 15.80 | 17.09 | 16.66 |

All cell lines tested produced GM-CSF and IL-8 in response to stimulation with control cytokines IL-1b and TNFa. Most cell lines produced IL-6 and MCP-1 in response to IL-1b and TNFa stimulation. Zcytor17 ligand stimulated IL-6 production in the DU145 cell line compared to control (193 pg/mL vs. 71 pg/mL). Zcytor17 ligand stimulated 3 of 5 cell lines to produce IL-8 with the greatest effect seen in A549 cells (5 fold), and reduced IL-8 production in U20S cells by 2 fold. There was a slight effect on MCP-1 production by DU145 and U20S cells when cultured with zcytor17 ligand.

B. Cytokine Production by Normal Human Epithelial Cell Lines Cultured with Human Zcytor17lig In addition to the human epithelial cell lines, normal human bronchial epithelial cells (NHBE, Clonetics) were also tested. Cells were plated at a density of $1\times10^5$ cells per well in a 24 well plate and cultured with test reagents; 1000 ng/mL, 100 ng/mL and 10 ng/mL zcytor17 ligand (A760F), 10 ng/mL TNFa, 10 ng/mL OSM, 10 ng/mL IFNa, 10 ng/mL TGFb or 10 ng/mL Lymphotactin. Supernatants were harvested at 24 and 48 hours and assayed for cytokines; IL-6, IL-8, MCP-1, MIP-1a, RANTES and Eotaxin. Cytokines were assayed as previously described. Cytokine production (pg/mL) for each cell line in the 48-hour samples is shown below in Table 18.

TABLE 18

|  | A549 | DU145 | SkLu1 | U2OS | NHBE |
| --- | --- | --- | --- | --- | --- |
| IL-6 pg/ml | | | | | |
| r17L 1000 ng/ml | 24.5 | 56.3 | 32.1 | 25.2 | 64.5 |
| r17IL 100 ng/ml | 25.0 | 65.0 | 31.0 | 25.4 | 50.2 |
| r17L 10 ng/ml | 24.8 | 51.8 | 30.2 | 25.3 | 54.3 |
| TNFa | 272.9 | 355.4 | 437.5 | 36.1 | 299.3 |
| OSM | 26.4 | 73.5 | 112.4 | 25.6 | 80.4 |
| IFNa | 24.6 | 109.3 | 33.7 | 26.4 | 52.4 |
| TGFb | 24.4 | 102.6 | 42.7 | 27.8 | 268.9 |
| control | 24.5 | 36.3 | 29.9 | 25.2 | 47.9 |
| IL-8 pg/ml | | | | | |
| r17L 1000 ng/ml | 35.0 | 243.3 | 45.6 | 18.6 | 402.0 |
| r17IL 100 ng/ml | 31.0 | 290.7 | 40.1 | 21.3 | 296.0 |
| r17L 10 ng/ml | 30.4 | 240.4 | 33.4 | 18.9 | 361.8 |
| TNFa | 2809.3 | 2520.9 | 1385.2 | 784.9 | 1486.3 |
| OSM | 37.8 | 60.6 | 68.0 | 22.5 | 494.6 |
| IFNa | 18.9 | 315.3 | 39.5 | 33.1 | 231.6 |
| TGFb | 9.9 | 77.5 | 19.6 | 88.9 | 246.9 |
| control | 10.9 | 238.0 | 38.0 | 39.7 | 315.8 |
| MCP-1 pg/ml | | | | | |
| r17L 1000 ng/ml | nd | nd | 149.1 | 81.0 | nd |
| r17IL 100 ng/ml | nd | nd | 130.6 | 81.9 | nd |
| r17L 10 ng/ml | nd | nd | 111.7 | 49.1 | nd |
| TNFa | nd | 22.1 | 2862.6 | 1104.7 | nd |
| OSM | nd | 17.2 | 448.2 | 85.8 | nd |
| IFNa | nd | nd | 131.7 | 10.5 | nd |
| TGFb | nd | 1.7 | 54.5 | 27.6 | nd |
| control | nd | nd | 113.0 | 1.7 | nd | nd = not detected

DU145 cells produced IL-6 in response to zcytor17 ligand, repeating the previous results in Example 43A. However, only A549 and U20S had similar IL-8 responses as seen Example 43A. SkLu1 and U2OS cells both produced MCP-1 in response to zcytor17 ligand. Cytokine production by NHBE cells was marginal compared to controls.

C. Cytokine Production by Human Disease-State Epithelial Cell Lines Co-Cultured with Human Zcytor17lig and IFN Gamma Cells were plated at a density of $2\times10^5$ cells per well in 24 well plate and co-cultured with 10 ng/mL IFN gamma+/− zcytor17 ligand at 100 ng/mL, 10 ng/mL or 1 ng/mL. Supernatants were collected at 24 and 48 hours and assayed for IL-8 and MCP-1 as described above. Cytokine production (pg/mL) for each cell line in the 24-hour samples is shown below in Table 19.

TABLE 19

|  |  | IL-8 pg/ml | MCP-1 pg/ml |
| --- | --- | --- | --- |
| A549 | 10 ng/mL IFNg + 100 ng/mL r17L | 86.7 | nd |
|  | 10 ng/mL IFNg + 10 ng/mL r17L | 75.1 | nd |
|  | 10 ng/mL IFNg + 1 ng/mL r17L | 63.6 | nd |
|  | 10 ng/mL IFNg | 35.4 | nd |
|  | control | 36.6 | nd |
| DU145 | 10 ng/mL IFNg + 100 ng/mL r17L | 102.3 | nd |
|  | 10 ng/mL IFNg + 10 ng/mL r17L | 92.9 | nd |
|  | 10 ng/mL IFNg + 1 ng/mL r17L | 79.9 | nd |
|  | 10 ng/mL IFNg | 70.7 | nd |
|  | control | 79.4 | nd |
| SkLu1 | 10 ng/mL IFNg + 100 ng/mL r17L | 152.2 | 604.9 |
|  | 10 ng/mL IFNg + 10 ng/mL r17L | 194.4 | 870.7 |
|  | 10 ng/mL IFNg + 1 ng/mL r17L | 138.7 | 585.4 |
|  | 10 ng/mL IFNg | 170.8 | 652.6 |
|  | control | 203.0 | 292.3 |
| U2OS | 10 ng/mL IFNg + 100 ng/mL r17L | 106.8 | 357.0 |
|  | 10 ng/mL IFNg + 10 ng/mL r17L | 108.2 | 347.7 |
|  | 10 ng/mL IFNg + 1 ng/mL r17L | 109.9 | 293.3 |
|  | 10 ng/mL IFNg | 118.8 | 159.8 |
|  | control | 146.8 | 7.0 |

A549 cells produced IL-8 in response to zcytor17 ligand, however there was no effect of co-culturing cells with the addition of IFN gamma. U2OS cells made 20 fold more MCP-1 when cultured with IFNg and 50 fold more MCP-1 when cultured with IFN gamma+zcytor17 ligand.

Example 44

Zcytor17lig Effects on $^3$H-TdR Incorporation in DU145 Prostate Epithelial Carcinoma Cells Cells were seeded in 96-well tissue clusters (Falcon) at a density of 25,000/well in MEM (Life Technologies) growth medium supplemented with glutamine, pyruvate, non-essential amino acids (Life Technologies) and 10% fetal bovine serum (Hyclone). At confluence (24 hours later), cells were switched to growth arrest media by substituting 0.1% BSA (Life Technologies) for serum. After 48 hours to achieve cell synchronization, the growth-arrest medium was replaced with fresh medium. Then, human recombinant zcytor17lig (test reagent) was added at various concentrations (from 0.24 to 60 ng/mL) (see Table 16 below), to test for the effect of the protein on basal DNA replication. Some wells received 2.5% FBS (Hyclone) in addition to zcytor17Ligand, in order to test effect of the protein on elevated levels of TdR incorporation. FBS 10% and 20 ng/ml Platelet Derived Growth Factor-BB (PDGF-BB) (R&D) were used as positive control.

Eighteen hours following addition of zcytor17Ligand and the rest of the test reagents, cells were pulsed with 250 nCi/mL [$^3$H]-thymidine (NEN) for 4 hours. Following the 4-hour pulse, media were discarded and 100 µL trypsin solution (Life Technologies) was added in each well to dislodge the cells. The radioactivity incorporated by DU145 was determined by harvesting the cells with a Packard Filtermate 196 cell harvester and by counting the incorporated label using a Packard TopCount NXT microplate scintillation counter.

As can be seen in Table 20 below, zcytor17lig induced thymidine incorporation in quiescent cells (in 0.1% BSA) in a concentration-dependent manner. This effect reached 2.5-fold of the BSA control at the highest concentration used, 60 ng/mL. In addition, this effect of zcytor17lig was also detectable when the baseline incorporation was elevated by the addition of 2.5% FBS (in this series as potent a mitogen as 10% FBS). These results therefore indicate that under both basal and stimulated conditions zcytor17lig can act as a mitogenic factor for the DU145 carcinoma cells.

Table 16 shows the effects of zcytor17lig on thymidine incorporation by DU145 cells. Results are expressed in cpm/well and numbers are the mean±st.dev of triplicate wells.

TABLE 20

|  | 0.1% BSA | 2.5% FBS |
|---|---|---|
| BSA Control | 1139 ± 336 | 4228 ± 600 |
| Zcytor17lig (0.24 ng/mL) | 1430 ± 136 | 4894 ± 1037 |
| Zcytor17lig (0.74 ng/mL) | 1657 ± 32 | 5038 ± 810 |
| Zcytor17lig (2.22 ng/mL) | 1646 ± 57 | 5162 ± 808 |
| Zcytor17lig (6.67 ng/mL) | 2226 ± 189 | 6385 ± 1613 |
| Zcytor17lig (20 ng/mL) | 2168 ± 108 | 5880 ± 1085 |
| Zcytor17lig (60 ng/mL) | 2512 ± 111 | 6165 ± 417 |
| PDGF-BB (20 ng/mL) | 4094 ± 202 | 5927 ± 360 |

Example 45

Expression of Huzcytor17Ligand in *E. coli*

A. Construction of Expression Vector pRPS01 that Expresses Huzcytor17Lig/MBP-6H Fusion Polypeptide An expression plasmid containing a polynucleotide encoding a huzcytor17lig fused C-terminally to Maltose Binding Protein (MBP) was constructed via homologous recombination. The fusion polypeptide contains an N-terminal approximately 388 amino acid MBP portion fused to the huzcytor17Lig described herein. A fragment of huzcytor17lig cDNA was isolated using the PCR method as described herein. Two primers were used in the production of the zcytor17lig fragment in a standard PCR reaction: (1) one containing 40 bp of the vector flanking sequence and 20 bp corresponding to the amino terminus of the huzcytor17lig, and (2) another containing 40 bp of the 3' end corresponding to the flanking vector sequence and 20 bp corresponding to the carboxyl terminus of the huzcytor17lig. Two microliters of the 100 µl PCR reaction was run on a 1.0% agarose gel with 1×TBE buffer for analysis, and the expected molecular weight fragment was observed. The remaining PCR reaction was combined with the second PCR tube and precipitated with 400 µl of absolute ethanol. The precipitated DNA was used for recombination into the Sma1 cut recipient vector pTAP98 to produce the construct encoding the MBP-huzcytor17lig fusion, as described below.

The vector pTAP98 was constructed using yeast homologous recombination. One hundred nanograms of EcoR1 cut pMAL-c2 was recombined with 11 µg Pvu1 cut pRS316, 1 µg linker, and 1 µg Sca1/EcoR1 cut pRS316 were combined in a PCR reaction. PCR products were concentrated via 100% ethanol precipitation. The competent yeast cell (*S. cerevisiae*) strain, SF838-9Dα, was combined with 10 µl of a mixture containing approximately 1 µg of the huzcytor17lig PCR product (above) and 100 ng of Sma1 digested pTAP98 vector, and electroporated at 0.75 kV, 25 µF and ∞ ohms. The resulting reaction mixture was plated onto URA-D plates and incubated at 30° C.

After 48 hours, the Ura+ yeast transformants from a single plate were selected. DNA was isolated and transformed into electrocompetent *E. coli* cells (e.g., MC1061, Casadaban et. al. *J. Mol. Biol.* 138, 179-207). The resulting *E. coli* cells were plated on MM/CA+AMP 100 mg/L plates (Pryor and Leiting, *Protein Expression and Purification* 10:309-319, 1997) using standard procedures. Four individual clones were harvested from the plates and inoculated into MM/CA with 100 µg/ml Ampicillin for two hours at 37° C. One milliliter of each of the culture was induced with 1 mM IPTG. Approximately 2-4 hours later, 250 µl of each induced culture was mixed with 250 µl acid washed glass beads and 250 µl Thorner buffer with 5% βME and dye (8M urea, 100 mM Tris pH7.0, 10% glycerol, 2 mM EDTA, 5% SDS). Samples were vortexed for one minute and heated to 65° C. for 10 minutes. Twenty microliters of each sample was loaded per lane on a 4%-12% PAGE gel (NOVEX). Gels were run in 1×MES buffer. The positive clones were designated pRPS01 and subjected to sequence analysis.

One microliter of sequencing DNA was used to transform electrocompetent *E. coli* cell strain MC1061. The cells were electropulsed at 2.0 kV, 25 µF and 400 ohms. Following electroporation, cells were rescued 0.6 ml SOC and grown on LB+Amp plates at 37° C. overnight, with 100 mg/L Ampicillin. Four cultures were induced with ITPG and screened for positives as described above. The positive clones were expanded for protein purification of the huzcytor17lig/MBP-6H fusion protein using standard techniques.

B. Purification of Huzcytor17Lig/MBP-6H from *E. coli* Fermentation

Unless otherwise noted, all operations were carried out at 4° C. The following procedure was used to purify recombinant huzcytor17Lig/MBP-6H polypeptide. *E. coli* cells containing the pRPS01 construct and expressing huzcytor17Lig/MBP-6H, were constructed using standard molecular biology methods and cultured in 50.0 g/L SuperBroth II (12 g/L Casien, 24 g/L Yeast Extract, 11.4 g/L di-potassium phosphate, 1.7 g/L Mono-potassium phosphate; Becton Dickenson, Cockeysville, Md.), 5 g/L glycerol and 5 mL/L 1M Magnesium Sulfate. Twenty grams of cells were harvested and frozen for protein purification.

The thawed cells were resuspended in 500 mL Amylose Equilibration buffer (20 mM Tris, 100 mM NaCl, pH 8.0). A French Press cell breaking system (Constant Systems Ltd., Warwick, UK) with a temperature setting of −7° C. to −10° C. and 30K PSI was used to lyse the cells. The resuspended cells were assayed for breakage by $A_{600}$ readings before and after cycling through the French Press. The processed cell suspension was pelleted at 10,000 G for 30 minutes to remove the cellular debris and the supernatant was harvested for protein purification.

A 25 ml column of Amylose resin (New England Biolabs, Beverly, Mass.) (prepared as described below) was poured into a Bio-Rad, 2.5 cm D×10 cm H glass column. The column was packed and equilibrated by gravity with 10 column volumes (CVs) of Amylose Equilibration buffer. The processed cell supernatant was batch loaded to the Amylose resin overnight, with rocking. The resin was returned to the Bio-Rad column and washed with 10 CV's of Amylose Equilibration buffer by gravity. The column was eluted with ~2 CV of Amylose Elution buffer (Amylose Equilibration buffer+10 mM Maltose, Fluka Biochemical, Switzerland) by gravity. Ten 5 mL fractions were collected over the elution profile and assayed for Absorbance at 280 and 320 nM. The Amylose resin was regenerated with 1 CV of distilled $H_2O$, 5 CVs of 0.1% (w/v) SDS (Sigma), 5 CVs of distilled $H_2O$, 5 CVs of Amylose Equilibration buffer and finally 1 CV of Amylose Storage buffer (Amylose Equilibration buffer+0.02% Sodium Azide). The regenerated column was stored at 4° C.

Elution profile fractions of interest were pooled and dialyzed in a 10K dialysis chamber (Slide-A-Lyzer, Pierce Immunochemicals) against 4×4 L PBS pH 7.4 (Sigma) over an 8 hour time period to remove low molecular weight contaminants, buffer exchange and desalt. Following dialysis, the material harvested represented the purified huzcytor17Lig/MBP-6H polypeptide. The purified huzcytor17Lig/MBP-6H polypeptide was filter sterilized and analyzed via SDS-PAGE Coomassie staining for an appropriate molecular weight product. The concentration of the huzcytor17Lig/MBP-6H polypeptide was determined by BCA analysis to be 1.28 mg/mL.

Example 46

Human Zcytor17lig Polyclonal Antibody

A. Preparation and Purification

Polyclonal antibodies were prepared by immunizing 2 female New Zealand white rabbits with the purified recombinant protein hzcytor17L/MBP-6H (Example 45). The rabbits were each given an initial intraperitoneal (IP) injection of 200 µg of purified protein in Complete Freund's Adjuvant followed by booster IP injections of 100 µg protein in Incomplete Freund's Adjuvant every three weeks. Seven to ten days after the administration of the second booster injection (3 total injections), the animals were bled and the serum was collected. The animals were then boosted and bled every three weeks.

The hzcytor17L/MBP-6H specific rabbit serum was pre-adsorbed of anti-MBP antibodies using a CNBr-SEPHAROSE 4B protein column (Pharmacia LKB) that was prepared using 10 mg of non-specific purified recombinant MBP-fusion protein per gram of CNBr-SEPHAROSE. The hzcytor17L/MBP-6H-specific polyclonal antibodies were affinity purified from the pre-adsorbed rabbit serum using a CNBr-SEPHAROSE 4B protein column (Pharmacia LKB) that was prepared using 10 mg of the specific antigen purified recombinant protein hzcytor17L/MBP-6H. Following purification, the polyclonal antibodies were dialyzed with 4 changes of 20 times the antibody volume of PBS over a time period of at least 8 hours. Hzcytor17-Ligand-specific antibodies were characterized by ELISA using 500 ng/ml of the purified recombinant proteins hzcytor17L/MBP-6H or hzcytor17L-CEE produced in a baculovirus expression system as antibody targets. The lower limit of detection (LLD) of the rabbit anti-hzcytor17L/MBP-6H affinity purified antibody is 100 pg/ml on its specific purified recombinant antigen hzcytor17L/MBP-6H and 500 pg/ml on purified recombinant hzcytor17L-CEE produced in a baculovirus expression system.

B. SDS-PAGE and Western Blotting Analysis of Rabbit Anti-Human ZcytoR17lig MBP-6H Antibody Rabbit Anti-human ZcytoR17lig MBP-6H antibody was tested by SDS-PAGE (NuPage 4-12%, Invitrogen, Carlsbad, Calif.) with coomassie staining method and Western blotting using goat anti-rabbit IgG-HRP. Human and mouse zcytor17lig purified protein (200-25 ng) was electrophoresed using an Invitrogen Novex's Xcell II mini-cell, and transferred to nitrocellulose (0.2 mm; Invitrogen, Carlsbad, Calif.) at room temperature using Novex's Xcell blot module with stirring according to directions provided in the instrument manual. The transfer was run at 300 mA for one hour in a buffer containing 25 mM Tris base, 200 mM glycine, and 20% methanol. The filter was then blocked with Western A buffer (in house, 50 mM Tris, pH 7.4, 5 mM EDTA, pH 8.0, 0.05% Igepal CA-630, 150 mM NaCl, and 0.25% gelatin) overnight with gentle rocking at 4° C. The nitrocellulose was quickly rinsed, then the rabbit anti-human zcytoR17 µg MBP-6H (1:1000) was added in Western A buffer. The blot was incubated for 1.5 hours at room temperature with gentle rocking. The blot was rinsed 3 times for 5 minutes each in Western A, then goat anti-rabbit IgG HRP antibody (1:5000) was added in Western A buffer. The blot was incubated for 1 hour at room temperature with gentle rocking. The blot was rinsed 3 times for 5 minutes each in Western A, then quickly rinsed in $H_2O$. The blot was developed using commercially available chemiluminescent substrate reagents (ECLWestern blotting detection reagents 1 and 2 mixed 1:1; reagents obtained from Amersham Pharmacia Biotech, Buckinghamshire, England) and the blot was exposed to x-ray film for up to 5 minutes.

The purified human zcytor17lig appeared as a large band at about 30 kDa and a smaller band at about 20 kDa under reduced conditions. The mouse zcytor17lig was not detected by the rabbit anti-human zcytor17lig antibody.

Example 47

Zcytor17lig Effects on U937 Monocyte Adhesion to Transformed Bone Marrow Endothelial Cell (TRBMEC) Monolayer Transformed Bone Marrow Endothelial Cells (TRBMEC) were seeded in 96-well tissue clusters (Falcon) at a density of 25,000/well in medium M131 (Cascade Biologics) supplemented with Microvascular Growth Supplement (MVGS) (Cascade Biologics). At confluence (24 hours later), cells were switched to M199 (Gibco-Life Technologies) supplemented with 1% Fetal Bovine Serum (Hyclone). Human recombinant zcytor17lig (test reagent) was added at various concentrations (from 0.4 to 10 ng/mL) (see Table 21 below), to test for the effect of the protein on immune cell-endothelial cell interactions resulting in adhesion. Some wells received 0.3 ng/ml Tumor Necrosis Factor (TNFalpha R&D Systems), a known pro-inflammatory cytokine, in addition to zcytor17lig, to test an effect of the protein on endothelial cells under inflammatory conditions. TNFalpha at 0.3 ng/ml alone was used as positive control and the concentration used represents approximately 70% of the maximal TNFalpha effect in this system, i.e., it does not induce maximal adherence of U937 cells (a human monocyte-like cell line) to the endothelium. For this reason, this setup can detect both upregulation and downregulation of the TNFalpha effects. Basal levels of adhesion both with and without TNFalpha were used as baseline to assess effect of test reagents.

After overnight incubation of the endothelial cells with the test reagents (zcytor17ligand±TNFalpha), U937 cells, stained with 5 µM Calcein-AM fluorescent marker (Molecular Probes), the cells were suspended in RPMI 1640 (no phenol-red) supplemented with 1% FBS and plated at 100,000 cells/well on the rinsed TRBMEC monolayer. Fluorescence levels at excitation/emission wavelengths of 485/538 nm (Molecular Devices micro-plate reader, CytoFluor application) were measured 30 minutes later, before and after rinsing the well three times with warm RPMI 1640 (no phenol-red), to remove non-adherent U937. Pre-rinse (total) and post-rinse (adherence-specific) fluorescence levels were used to determine percent adherence (net adherent/net total× 100=% adherence).

As can be seen in Table 21 below, zcytor17lig when added alone affected the basal adherence of U937 cells to the endothelial monolayers at the concentration range used (less than 2-fold increases, p<0.01 by ANOVA test). By itself, the positive control, 0.3 ng/mL TNFalpha, increased the adherence of U937 cells from a basal 5.8% to 35% (6-fold). In the presence of TNFalpha, zcytor17lig synergized with TNFalpha and further enhanced U937 adhesion in a concentration-dependent manner between 0.4 and 10 ng/mL (p<0.01 by ANOVA test). At 10 ng/mL, zcytor17lig enhanced the effect of TNFalpha by 62%. These results indicate that zcytor17lig may by itself be a pro-inflammatory agent. Zcytor17lig was able to synergize with sub-maximal concentrations of TNFalpha to increase monocyte adherence to endothelial cells. These results also show that endothelial cells, especially when exposed to pro-inflammatory cytokines such as TNFalpha, are a likely target tissue of zcytor17lig action. The consequence of zcytor17ligand on endothelial cells may be to heighten monocyte or macrophage adhesion to a site of proinflammatory activity. Activated monocytes and macrophages are important in many inflammatory diseases. Therefore inhibition of monocyte/macrophage adhesions may provide a therapeutic rationale for zcytor17ligand antagonists. This data would support the use of zcytor17 ligand antagonists for treatment lung diseases, vascular diseases, autoimmunity, tumor metastasis, disease involving allergic reactions, wound healing and diseases of the skin including contact, allergic or non-allergic dermatistic or psoriasis and inflammatory bowel disease. Table 21 shows the effects of zcytor17lig on U937 monocyte adhesion to TRBMEC endothelial monolayers. Results are expressed in percent adhesion and numbers are the mean±st.dev of triplicate wells.

TABLE 21

|  | Basal | 0.3 ng/mL TNFalpha |
|---|---|---|
| Basal | 5.8 ± 1.2 | 35 ± 5.5 |
| zcytor17lig 0.4 ng/mL | 9 ± 0.7 | 44.7 ± 2.5 |
| zcytor17lig 1.1 ng/mL | 10.4 ± 0.8 | 45.2 ± 0.6 |
| zcytor17lig 3.3 ng/mL | 7.9 ± 1.7 | 51.1 ± 4 |
| zcytor17lig 10 ng/mL | 9.5 ± 0.5 | 56.6 ± 3.9 |

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An isolated heterodimeric cytokine receptor comprising:
   a) a first polypeptide comprising amino acid residues 33-532 of SEQ ID NO:5; and
   b) a second polypeptide comprising amino acid residues 28-739 of SEQ ID NO:7,
   wherein the first polypeptide and the second polypeptide form a heterodimeric cytokine receptor, and
   wherein the heterodimeric cytokine receptor is capable of binding a ligand polypeptide comprising amino acid residues 27-164 of SEQ ID NO:2.

2. The isolated heterodimeric cytokine receptor of claim 1, wherein the first polypeptide comprises amino acid residues 33-662 of SEQ ID NO:5.

3. The isolated heterodimeric cytokine receptor of claim 1, wherein the second polypeptide comprises amino acid residues 28-979 of SEQ ID NO:7.

4. The isolated heterodimeric cytokine receptor of claim 1, wherein the heterodimeric cytokine receptor further comprises an affinity tag or cytotoxic molecule.

5. The isolated heterodimeric cytokine receptor of claim 4, wherein the affinity tag polyhistidine, protein A, glutathione S transferase, Glu-Glu, substance P, Flag™ peptide, streptavidin binding peptide, or immunoglobulin Fc polypeptide.

6. The isolated heterodimeric cytokine receptor of claim 4, wherein the cytotoxic molecule is a toxin or radionuclide.

* * * * *

UNITED STATES PATENT AND TRADEMARK OFFICE
CERTIFICATE OF CORRECTION

| | |
|---|---|
| PATENT NO. | : 9,212,213 B2 |
| APPLICATION NO. | : 14/138199 |
| DATED | : December 15, 2015 |
| INVENTOR(S) | : Sprecher et al. |

Page 1 of 1

It is certified that error appears in the above-identified patent and that said Letters Patent is hereby corrected as shown below:

On the Title page:

Related U.S. Application data (60)

Column 1, line 9:

After October 25, 2006, now abandoned, delete "and" and insert -- which is --, therefor.

In the Claims:

Claim 5, column 351, line 61:

Before "polyhistidine," insert -- is --.

Signed and Sealed this
Sixteenth Day of August, 2016

Michelle K. Lee
*Director of the United States Patent and Trademark Office*

SEQUENCE LISTING

<160> NUMBER OF SEQ ID NOS: 183

<210> SEQ ID NO 1
<211> LENGTH: 904
<212> TYPE: DNA
<213> ORGANISM: Homo sapiens
<220> FEATURE:
<221> NAME/KEY: CDS
<222> LOCATION: (28)...(519)

<400> SEQUENCE: 1

```
ctgaagctgg ccttgctctc tctcgcc atg gcc tct cac tca ggc ccc tcg acg      54
                                Met Ala Ser His Ser Gly Pro Ser Thr
                                 1               5 tct gtg ctc ttt ctg ttc tgc tgc ctg gga ggc tgg ctg gcc tcc cac      102
Ser Val Leu Phe Leu Phe Cys Cys Leu Gly Gly Trp Leu Ala Ser His
 10                  15                  20                  25 acg ttg ccc gtc cgt tta cta cga cca agt gat gat gta cag aaa ata      150
Thr Leu Pro Val Arg Leu Leu Arg Pro Ser Asp Asp Val Gln Lys Ile
                 30                  35                  40 gtc gag gaa tta cag tcc ctc tcg aag atg ctt ttg aaa gat gtg gag      198
Val Glu Glu Leu Gln Ser Leu Ser Lys Met Leu Leu Lys Asp Val Glu
             45                  50                  55 gaa gag aag ggc gtg ctc gtg tcc cag aat tac acg ctg ccg tgt ctc      246
Glu Glu Lys Gly Val Leu Val Ser Gln Asn Tyr Thr Leu Pro Cys Leu
         60                  65                  70 agc cct gac gcc cag ccg cca aac aac atc cac agc cca gcc atc cgg      294
Ser Pro Asp Ala Gln Pro Pro Asn Asn Ile His Ser Pro Ala Ile Arg
     75                  80                  85 gca tat ctc aag aca atc aga cag cta gac aac aaa tct gtt att gat      342
Ala Tyr Leu Lys Thr Ile Arg Gln Leu Asp Asn Lys Ser Val Ile Asp
 90                  95                 100                 105 gag atc ata gag cac ctc gac aaa ctc ata ttt caa gat gca cca gaa      390
Glu Ile Ile Glu His Leu Asp Lys Leu Ile Phe Gln Asp Ala Pro Glu
                110                 115                 120 aca aac att tct gtg cca aca gac acc cat gaa tgt aaa cgc ttc atc      438
Thr Asn Ile Ser Val Pro Thr Asp Thr His Glu Cys Lys Arg Phe Ile
            125                 130                 135 ctg act att tct caa cag ttt tca gag tgc atg gac ctc gca cta aaa      486
Leu Thr Ile Ser Gln Gln Phe Ser Glu Cys Met Asp Leu Ala Leu Lys
        140                 145                 150 tca ttg acc tct gga gcc caa cag gcc act taaggccatc tcttcctttc        539
Ser Leu Thr Ser Gly Ala Gln Gln Ala Thr Thr
    155                 160
```

```
ggattggcag gaacttaagg agccttaaaa agatgaccga cagctaagtg tgggaactct      599
gccgtgattc cttaagtaca ttttccaat gaataatctc agggacccct catatgggct       659
agtcccggga gggctgagat gtgaatttgt gaattacctt gaaaaacatt aggttattgt      719
tattagtctt ggtattatg gaatgctttt cttctgcagg cttaagtctt acttattata       779
ccctcgtgag ggtgggaggt ggcagctatg ttaatttatt gatatttatt gtactaagag      839
ttgtcaatgc tccctggggg agccctcgga atctatttaa taaattatat tgaattttc       899 tcata                                                                  904
```

<210> SEQ ID NO 2
<211> LENGTH: 164
<212> TYPE: PRT
<213> ORGANISM: Homo sapiens

<400> SEQUENCE: 2

```
Met Ala Ser His Ser Gly Pro Ser Thr Ser Val Leu Phe Leu Phe Cys
  1               5                  10                  15

Cys Leu Gly Gly Trp Leu Ala Ser His Thr Leu Pro Val Arg Leu Leu
             20                  25                  30

Arg Pro Ser Asp Asp Val Gln Lys Ile Val Glu Glu Leu Gln Ser Leu
         35                  40                  45

Ser Lys Met Leu Leu Lys Asp Val Glu Glu Lys Gly Val Leu Val
     50                  55                  60

Ser Gln Asn Tyr Thr Leu Pro Cys Leu Ser Pro Asp Ala Gln Pro Pro
 65                  70                  75                  80

Asn Asn Ile His Ser Pro Ala Ile Arg Ala Tyr Leu Lys Thr Ile Arg
                 85                  90                  95

Gln Leu Asp Asn Lys Ser Val Ile Asp Glu Ile Ile Glu His Leu Asp
            100                 105                 110

Lys Leu Ile Phe Gln Asp Ala Pro Glu Thr Asn Ile Ser Val Pro Thr
        115                 120                 125

Asp Thr His Glu Cys Lys Arg Phe Ile Leu Thr Ile Ser Gln Gln Phe
    130                 135                 140

Ser Glu Cys Met Asp Leu Ala Leu Lys Ser Leu Thr Ser Gly Ala Gln
145                 150                 155                 160

Gln Ala Thr Thr
```

<210> SEQ ID NO 3
<211> LENGTH: 492
<212> TYPE: DNA
<213> ORGANISM: Artificial Sequence
<220> FEATURE:
<223> OTHER INFORMATION: human zcytor17lig degenerate polynucleotide of
      SEQ ID NO:2
<220> FEATURE:
<221> NAME/KEY: misc_feature
<222> LOCATION: (1)...(492)
<223> OTHER INFORMATION: n = A,T,C or G

<400> SEQUENCE: 3

```
atggcnwsnc aywsnggncc nwsnacnwsn gtnytnttyy tnttytgytg yytnggnggn       60
tggytngcnw sncayacnyt nccngtnmgn ytnytnmgnc cnwsngayga ygtncaraar      120
athgtngarg arytncarws nytnwsnaar atggtnytna argaygtnga rgargaraar     180
ggngtnytng tnwsncaraa ytayacnytn ccntgyytnw snccngaygc ncarccnccn     240
aayaayathc aywsnccngc nathmgngcn tayytnaara cnathmgnca rytngayaay    300
```

```
aarwsngtna thgaygarat hathgarcay ytngayaary tnathttyca rgaygcnccn      360
garacnaaya thwsngtncc nacngayacn caygartgya armgnttyat hytnacnath      420
wsncarcart tywsngartg yatggayytn gcnytnaarw snytnacnws nggngcncar      480
cargcnacna cn                                                         492
```

```
<210> SEQ ID NO 4
<211> LENGTH: 2903
<212> TYPE: DNA
<213> ORGANISM: Homo sapiens
<220> FEATURE:
<221> NAME/KEY: CDS
<222> LOCATION: (497)...(2482)

<400> SEQUENCE: 4
```

```
tgaaaagaca tgtgtgtgca gtatgaaaat tgagacagga aggcagagtg tcagcttgtt      60
ccacctcagc tgggaatgtg catcaggcaa ctcaagtttt tcaccacggc atgtgtctgt     120
gaatgtccgc aaaacattag tttcactctt gtcgccaggt ggagtacaa tggcacgatc     180 ttggctcact gcaacctctg cctcccgggt tcaagcgatt ctcctgcctc agcctcccga    240
gtagctggga ttacagttaa caataatgca atccatttcc cagcataagt gggtaagtgc    300
cactttgact tgggctgggc ttaaaagcac aagaaaagct cgcagacaat cagagtggaa    360
acactcccac atcttagtgt ggataaaatta agtccagat tgttcttcct gtcctgactt    420
gtgctgtggg aggtggagtt gcctttgatg caaatccttt gagccagcag aacatctgtg    480
gaacatcccc tgatac atg aag ctc tct ccc cag cct tca tgt gtt aac ctg    532
                   Met Lys Leu Ser Pro Gln Pro Ser Cys Val Asn Leu
                    1               5                  10 ggg atg atg tgg acc tgg gca ctg tgg atg ctc cct tca ctc tgc aaa     580
Gly Met Met Trp Thr Trp Ala Leu Trp Met Leu Pro Ser Leu Cys Lys
         15                  20                  25 ttc agc ctg gca gct ctg cca gct aag cct gag aac att tcc tgt gtc     628
Phe Ser Leu Ala Ala Leu Pro Ala Lys Pro Glu Asn Ile Ser Cys Val
     30                  35                  40 tac tac tat agg aaa aat tta acc tgc act tgg agt cca gga aag gaa     676
Tyr Tyr Tyr Arg Lys Asn Leu Thr Cys Thr Trp Ser Pro Gly Lys Glu
 45                  50                  55                  60 acc agt tat acc cag tac aca gtt aag aga act tac gct ttt gga gaa     724
Thr Ser Tyr Thr Gln Tyr Thr Val Lys Arg Thr Tyr Ala Phe Gly Glu
                 65                  70                  75 aaa cat gat aat tgt aca acc aat agt tct aca agt gaa aat cgt gct     772
Lys His Asp Asn Cys Thr Thr Asn Ser Ser Thr Ser Glu Asn Arg Ala
             80                  85                  90 tcg tgc tct ttt ttc ctt cca aga ata acg atc cca gat aat tat acc     820
Ser Cys Ser Phe Phe Leu Pro Arg Ile Thr Ile Pro Asp Asn Tyr Thr
         95                  100                 105 att gag gtg gaa gct gaa aat gga gat ggt gta att aaa tct cat atg     868
Ile Glu Val Glu Ala Glu Asn Gly Asp Gly Val Ile Lys Ser His Met
     110                 115                 120 aca tac tgg aga tta gag aac ata gcg aaa act gaa cca cct aag att     916
Thr Tyr Trp Arg Leu Glu Asn Ile Ala Lys Thr Glu Pro Pro Lys Ile
125                 130                 135                 140 ttc cgt gtg aaa cca gtt ttg ggc atc aaa cga atg att caa att gaa     964
Phe Arg Val Lys Pro Val Leu Gly Ile Lys Arg Met Ile Gln Ile Glu
                 145                 150                 155 tgg ata aag cct gag ttg gcg cct gtt tca tct gat tta aaa tac aca    1012
Trp Ile Lys Pro Glu Leu Ala Pro Val Ser Ser Asp Leu Lys Tyr Thr
             160                 165                 170
```

```
ctt cga ttc agg aca gtc aac agt acc agc tgg atg gaa gtc aac ttc      1060
Leu Arg Phe Arg Thr Val Asn Ser Thr Ser Trp Met Glu Val Asn Phe
        175                 180                 185 gct aag aac cgt aag gat aaa aac caa acg tac aac ctc acg ggg ctg      1108
Ala Lys Asn Arg Lys Asp Lys Asn Gln Thr Tyr Asn Leu Thr Gly Leu
190                 195                 200 cag cct ttt aca gaa tat gtc ata gct ctg cga tgt gcg gtc aag gag      1156
Gln Pro Phe Thr Glu Tyr Val Ile Ala Leu Arg Cys Ala Val Lys Glu
205                 210                 215                 220 tca aag ttc tgg agt gac tgg agc caa gaa aaa atg gga atg act gag      1204
Ser Lys Phe Trp Ser Asp Trp Ser Gln Glu Lys Met Gly Met Thr Glu
                225                 230                 235 gaa gaa gct cca tgt ggc ctg gaa ctg tgg aga gtc ctg aaa cca gct      1252
Glu Glu Ala Pro Cys Gly Leu Glu Leu Trp Arg Val Leu Lys Pro Ala
            240                 245                 250 gag gcg gat gga aga agg cca gtg cgg ttg tta tgg aag aag gca aga      1300
Glu Ala Asp Gly Arg Arg Pro Val Arg Leu Leu Trp Lys Lys Ala Arg
        255                 260                 265 gga gcc cca gtc cta gag aaa aca ctt ggc tac aac ata tgg tac tat      1348
Gly Ala Pro Val Leu Glu Lys Thr Leu Gly Tyr Asn Ile Trp Tyr Tyr
    270                 275                 280 cca gaa agc aac act aac ctc aca gaa aca atg aac act act aac cag      1396
Pro Glu Ser Asn Thr Asn Leu Thr Glu Thr Met Asn Thr Thr Asn Gln
285                 290                 295                 300 cag ctt gaa ctg cat ctg gga ggc gag agc ttt tgg gtg tct atg att      1444
Gln Leu Glu Leu His Leu Gly Gly Glu Ser Phe Trp Val Ser Met Ile
                305                 310                 315 tct tat aat tct ctt ggg aag tct cca gtg gcc acc ctg agg att cca      1492
Ser Tyr Asn Ser Leu Gly Lys Ser Pro Val Ala Thr Leu Arg Ile Pro
            320                 325                 330 gct att caa gaa aaa tca ttt cag tgc att gag gtc atg cag gcc tgc      1540
Ala Ile Gln Glu Lys Ser Phe Gln Cys Ile Glu Val Met Gln Ala Cys
        335                 340                 345 gtt gct gag gac cag cta gtg gtg aag tgg caa agc tct gct cta gac      1588
Val Ala Glu Asp Gln Leu Val Val Lys Trp Gln Ser Ser Ala Leu Asp
    350                 355                 360 gtg aac act tgg atg att gaa tgg ttt ccg gat gtg gac tca gag ccc      1636
Val Asn Thr Trp Met Ile Glu Trp Phe Pro Asp Val Asp Ser Glu Pro
365                 370                 375                 380 acc acc ctt tcc tgg gaa tct gtg tct cag gcc acg aac tgg acg atc      1684
Thr Thr Leu Ser Trp Glu Ser Val Ser Gln Ala Thr Asn Trp Thr Ile
                385                 390                 395 cag caa gat aaa tta aaa cct ttc tgg tgc tat aac atc tct gtg tat      1732
Gln Gln Asp Lys Leu Lys Pro Phe Trp Cys Tyr Asn Ile Ser Val Tyr
            400                 405                 410 cca atg ttg cat gac aaa gtt ggc gag cca tat tcc atc cag gct tat      1780
Pro Met Leu His Asp Lys Val Gly Glu Pro Tyr Ser Ile Gln Ala Tyr
        415                 420                 425 gcc aaa gaa ggc gtt cca tca gaa ggt cct gag acc aag gtg gag aac      1828
Ala Lys Glu Gly Val Pro Ser Glu Gly Pro Glu Thr Lys Val Glu Asn
    430                 435                 440 att ggc gtg aag acg gtc acg atc aca tgg aaa gag att ccc aag agt      1876
Ile Gly Val Lys Thr Val Thr Ile Thr Trp Lys Glu Ile Pro Lys Ser
445                 450                 455                 460 gag aga aag ggt atc atc tgc aac tac acc atc ttt tac caa gct gaa      1924
Glu Arg Lys Gly Ile Ile Cys Asn Tyr Thr Ile Phe Tyr Gln Ala Glu
                465                 470                 475 ggt gga aaa gga ttc tcc aag aca gtc aat tcc agc atc ttg cag tac      1972
Gly Gly Lys Gly Phe Ser Lys Thr Val Asn Ser Ser Ile Leu Gln Tyr
```

|  |  |  |  | 480 |  |  |  | 485 |  |  |  | 490 |  |  |  |  |
|---|---|---|---|---|---|---|---|---|---|---|---|---|---|---|---|---|

```
ggc ctg gag tcc ctg aaa cga aag acc tct tac att gtt cag gtc atg      2020
Gly Leu Glu Ser Leu Lys Arg Lys Thr Ser Tyr Ile Val Gln Val Met
            495                 500                 505 gcc agc acc agt gct ggg gga acc aac ggg acc agc ata aat ttc aag      2068
Ala Ser Thr Ser Ala Gly Gly Thr Asn Gly Thr Ser Ile Asn Phe Lys
510                 515                 520 aca ttg tca ttc agt gtc ttt gag att atc ctc ata act tct ctg att      2116
Thr Leu Ser Phe Ser Val Phe Glu Ile Ile Leu Ile Thr Ser Leu Ile
525                 530                 535                 540 ggt gga ggc ctt ctt att ctc att atc ctg aca gtg gca tat ggt ctc      2164
Gly Gly Gly Leu Leu Ile Leu Ile Ile Leu Thr Val Ala Tyr Gly Leu
                545                 550                 555 aaa aaa ccc aac aaa ttg act cat ctg tgt tgg ccc acc gtt ccc aac      2212
Lys Lys Pro Asn Lys Leu Thr His Leu Cys Trp Pro Thr Val Pro Asn
            560                 565                 570 cct gct gaa agt agt ata gcc aca tgg cat gga gat gat ttc aag gat      2260
Pro Ala Glu Ser Ser Ile Ala Thr Trp His Gly Asp Asp Phe Lys Asp
        575                 580                 585 aag cta aac ctg aag gag tct gat gac tct gtg aac aca gaa gac agg      2308
Lys Leu Asn Leu Lys Glu Ser Asp Asp Ser Val Asn Thr Glu Asp Arg
    590                 595                 600 atc tta aaa cca tgt tcc acc ccc agt gac aag ttg gtg att gac aag      2356
Ile Leu Lys Pro Cys Ser Thr Pro Ser Asp Lys Leu Val Ile Asp Lys
605                 610                 615                 620 ttg gtg gtg aac ttt ggg aat gtt ctg caa gaa att ttc aca gat gaa      2404
Leu Val Val Asn Phe Gly Asn Val Leu Gln Glu Ile Phe Thr Asp Glu
                625                 630                 635 gcc aga acg ggt cag gaa aac aat tta gga ggg gaa aag aat ggg act      2452
Ala Arg Thr Gly Gln Glu Asn Asn Leu Gly Gly Glu Lys Asn Gly Thr
            640                 645                 650 aga att ctg tct tcc tgc cca act tca ata taagtgtgga ctaaaatgcg       2502
Arg Ile Leu Ser Ser Cys Pro Thr Ser Ile
        655                 660 agaaaggtgt cctgtggtct atgcaaatta gaaaggacat gcagagtttt ccaactagga    2562
agactgaatc tgtggcccca agagaaccat ctctgaagac tgggtatgtg gtctttccca    2622
cacatggacc acctacggat gcaatctgta atgcatgtgc atgagaagtc tgttattaag    2682
tagagtgtga aaacatggtt atggtaatag gaacagcttt taaatgcttt tgtatttgg     2742 gcctttcata caaaaaagcc ataataccat tttcatgtaa tgctatactt ctatactatt    2802
ttcatgtaat actatacttc tatactattt tcatgtaata ctatacttct atactatttt   2862
catgtaatac tatacttcta tattaaagtt ttacccactc a                        2903
```

<210> SEQ ID NO 5
<211> LENGTH: 662
<212> TYPE: PRT
<213> ORGANISM: Homo sapiens

<400> SEQUENCE: 5

```
Met Lys Leu Ser Pro Gln Pro Ser Cys Val Asn Leu Gly Met Met Trp
 1               5                  10                  15

Thr Trp Ala Leu Trp Met Leu Pro Ser Leu Cys Lys Phe Ser Leu Ala
            20                  25                  30

Ala Leu Pro Ala Lys Pro Glu Asn Ile Ser Cys Val Tyr Tyr Tyr Arg
        35                  40                  45

Lys Asn Leu Thr Cys Thr Trp Ser Pro Gly Lys Glu Thr Ser Tyr Thr
    50                  55                  60
```

```
Gln Tyr Thr Val Lys Arg Thr Tyr Ala Phe Gly Lys His Asp Asn
 65                  70                  75                  80

Cys Thr Thr Asn Ser Ser Thr Ser Glu Asn Arg Ala Ser Cys Ser Phe
                 85                  90                  95

Phe Leu Pro Arg Ile Thr Ile Pro Asp Asn Tyr Thr Ile Glu Val Glu
            100                 105                 110

Ala Glu Asn Gly Asp Gly Val Ile Lys Ser His Met Thr Tyr Trp Arg
            115                 120                 125

Leu Glu Asn Ile Ala Lys Thr Glu Pro Pro Lys Ile Phe Arg Val Lys
130                 135                 140

Pro Val Leu Gly Ile Lys Arg Met Ile Gln Ile Glu Trp Ile Lys Pro
145                 150                 155                 160

Glu Leu Ala Pro Val Ser Ser Asp Leu Lys Tyr Thr Leu Arg Phe Arg
                165                 170                 175

Thr Val Asn Ser Thr Ser Trp Met Glu Val Asn Phe Ala Lys Asn Arg
            180                 185                 190

Lys Asp Lys Asn Gln Thr Tyr Asn Leu Thr Gly Leu Gln Pro Phe Thr
            195                 200                 205

Glu Tyr Val Ile Ala Leu Arg Cys Ala Val Lys Glu Ser Lys Phe Trp
210                 215                 220

Ser Asp Trp Ser Gln Glu Lys Met Gly Met Thr Glu Glu Ala Pro
225                 230                 235                 240

Cys Gly Leu Glu Leu Trp Arg Val Leu Lys Pro Ala Glu Ala Asp Gly
                245                 250                 255

Arg Arg Pro Val Arg Leu Leu Trp Lys Lys Ala Arg Gly Ala Pro Val
            260                 265                 270

Leu Glu Lys Thr Leu Gly Tyr Asn Ile Trp Tyr Tyr Pro Glu Ser Asn
            275                 280                 285

Thr Asn Leu Thr Glu Thr Met Asn Thr Thr Asn Gln Gln Leu Glu Leu
290                 295                 300

His Leu Gly Gly Glu Ser Phe Trp Val Ser Met Ile Ser Tyr Asn Ser
305                 310                 315                 320

Leu Gly Lys Ser Pro Val Ala Thr Leu Arg Ile Pro Ala Ile Gln Glu
                325                 330                 335

Lys Ser Phe Gln Cys Ile Glu Val Met Gln Ala Cys Val Ala Glu Asp
            340                 345                 350

Gln Leu Val Val Lys Trp Gln Ser Ser Ala Leu Asp Val Asn Thr Trp
            355                 360                 365

Met Ile Glu Trp Phe Pro Asp Val Asp Ser Glu Pro Thr Thr Leu Ser
370                 375                 380

Trp Glu Ser Val Ser Gln Ala Thr Asn Trp Thr Ile Gln Gln Asp Lys
385                 390                 395                 400

Leu Lys Pro Phe Trp Cys Tyr Asn Ile Ser Val Tyr Pro Met Leu His
                405                 410                 415

Asp Lys Val Gly Glu Pro Tyr Ser Ile Gln Ala Tyr Ala Lys Glu Gly
            420                 425                 430

Val Pro Ser Glu Gly Pro Glu Thr Lys Val Glu Asn Ile Gly Val Lys
            435                 440                 445

Thr Val Thr Ile Thr Trp Lys Glu Ile Pro Lys Ser Glu Arg Lys Gly
450                 455                 460

Ile Ile Cys Asn Tyr Thr Ile Phe Tyr Gln Ala Glu Gly Gly Lys Gly
465                 470                 475                 480
```

```
Phe Ser Lys Thr Val Asn Ser Ser Ile Leu Gln Tyr Gly Leu Glu Ser
            485                 490                 495

Leu Lys Arg Lys Thr Ser Tyr Ile Val Gln Val Met Ala Ser Thr Ser
            500                 505                 510

Ala Gly Gly Thr Asn Gly Thr Ser Ile Asn Phe Lys Thr Leu Ser Phe
            515                 520                 525

Ser Val Phe Glu Ile Ile Leu Ile Thr Ser Leu Ile Gly Gly Gly Leu
530                 535                 540

Leu Ile Leu Ile Ile Leu Thr Val Ala Tyr Gly Leu Lys Lys Pro Asn
545                 550                 555                 560

Lys Leu Thr His Leu Cys Trp Pro Thr Val Pro Asn Pro Ala Glu Ser
            565                 570                 575

Ser Ile Ala Thr Trp His Gly Asp Asp Phe Lys Asp Lys Leu Asn Leu
            580                 585                 590

Lys Glu Ser Asp Asp Ser Val Asn Thr Glu Asp Arg Ile Leu Lys Pro
            595                 600                 605

Cys Ser Thr Pro Ser Asp Lys Leu Val Ile Asp Lys Leu Val Val Asn
610                 615                 620

Phe Gly Asn Val Leu Gln Glu Ile Phe Thr Asp Glu Ala Arg Thr Gly
625                 630                 635                 640

Gln Glu Asn Asn Leu Gly Gly Glu Lys Asn Gly Thr Arg Ile Leu Ser
            645                 650                 655

Ser Cys Pro Thr Ser Ile
            660

<210> SEQ ID NO 6
<211> LENGTH: 4171
<212> TYPE: DNA
<213> ORGANISM: Homo sapiens
<220> FEATURE:
<221> NAME/KEY: CDS
<222> LOCATION: (368)...(3304)

<400> SEQUENCE: 6
gggccgcctc tgcacgtccg ccccggagcc cgcacccgcg ccccacgcgc cgccgaggac      60
tcggcccggc tcgtggagcc cttcgcccgc ggcgtgagta ccccgacc gcccgtcccc     120 gctctgctcg cgccctgccg ctgcgccgcc ctcggtggct tttccgacgg gcgagccccg     180
tgctgtgcgg gaaagaatcc gacaacttcg cagcccatcc cggctggacg cgaccgggag     240
tgcagcagcc cgttcccctc ctcggtgccg cctctgccca gcgtttgctt ggctgggcta     300
ccacctgcgc tcgacggcg ctcggagggt cctcgcccc ggcctgccta cctgaaaacc     360 agaactg atg gct cta ttt gca gtc ttt cag aca aca ttc ttc tta aca      409
        Met Ala Leu Phe Ala Val Phe Gln Thr Thr Phe Phe Leu Thr
        1               5                   10 ttg ctg tcc ttg agg act tac cag agt gaa gtc ttg gct gaa cgt tta     457
Leu Leu Ser Leu Arg Thr Tyr Gln Ser Glu Val Leu Ala Glu Arg Leu
15                  20                  25                  30 cca ttg act cct gta tca ctt aaa gtt tcc acc aat tct acg cgt cag     505
Pro Leu Thr Pro Val Ser Leu Lys Val Ser Thr Asn Ser Thr Arg Gln
                35                  40                  45 agt ttg cac tta caa tgg act gtc cac aac ctt cct tat cat cag gaa     553
Ser Leu His Leu Gln Trp Thr Val His Asn Leu Pro Tyr His Gln Glu
            50                  55                  60 ttg aaa atg gta ttt cag atc cag atc agt agg att gaa aca tcc aat     601
Leu Lys Met Val Phe Gln Ile Gln Ile Ser Arg Ile Glu Thr Ser Asn
65                  70                  75
```

```
gtc atc tgg gtg ggg aat tac agc acc act gtg aag tgg aac cag gtt    649
Val Ile Trp Val Gly Asn Tyr Ser Thr Thr Val Lys Trp Asn Gln Val
         80                  85                  90 ctg cat tgg agc tgg gaa tct gag ctc cct ttg gaa tgt gcc aca cac    697
Leu His Trp Ser Trp Glu Ser Glu Leu Pro Leu Glu Cys Ala Thr His
 95                 100                 105                 110 ttt gta aga ata aag agt ttg gtg gac gat gcc aag ttc cct gag cca    745
Phe Val Arg Ile Lys Ser Leu Val Asp Asp Ala Lys Phe Pro Glu Pro
                115                 120                 125 aat ttc tgg agc aac tgg agt tcc tgg gag gaa gtc agt gta caa gat    793
Asn Phe Trp Ser Asn Trp Ser Ser Trp Glu Glu Val Ser Val Gln Asp
            130                 135                 140 tct act gga cag gat ata ttg ttc gtt ttc cct aaa gat aag ctg gtg    841
Ser Thr Gly Gln Asp Ile Leu Phe Val Phe Pro Lys Asp Lys Leu Val
        145                 150                 155 gaa ggc acc aat gtt acc att tgt tac gtt tct agg aac att caa        889
Glu Gly Thr Asn Val Thr Ile Cys Tyr Val Ser Arg Asn Ile Gln
160                 165                 170 aat aat gta tcc tgt tat ttg gaa ggg aaa cag att cat gga gaa caa    937
Asn Asn Val Ser Cys Tyr Leu Glu Gly Lys Gln Ile His Gly Glu Gln
175                 180                 185                 190 ctt gat cca cat gta act gca ttc aac ttg aat agt gtg cct ttc att    985
Leu Asp Pro His Val Thr Ala Phe Asn Leu Asn Ser Val Pro Phe Ile
                195                 200                 205 agg aat aaa ggg aca aat atc tat tgt gag gca agt caa gga aat gtc   1033
Arg Asn Lys Gly Thr Asn Ile Tyr Cys Glu Ala Ser Gln Gly Asn Val
            210                 215                 220 agt gaa ggc atg aaa ggc atc gtt ctt ttt gtc tca aaa gta ctt gag   1081
Ser Glu Gly Met Lys Gly Ile Val Leu Phe Val Ser Lys Val Leu Glu
        225                 230                 235 gag ccc aag gac ttt tct tgt gaa acc gag gac ttc aag act ttg cac   1129
Glu Pro Lys Asp Phe Ser Cys Glu Thr Glu Asp Phe Lys Thr Leu His
    240                 245                 250 tgt act tgg gat cct ggg acg gac act gcc ttg ggg tgg tct aaa caa   1177
Cys Thr Trp Asp Pro Gly Thr Asp Thr Ala Leu Gly Trp Ser Lys Gln
255                 260                 265                 270 cct tcc caa agc tac act tta ttt gaa tca ttt tct ggg gaa aag aaa   1225
Pro Ser Gln Ser Tyr Thr Leu Phe Glu Ser Phe Ser Gly Glu Lys Lys
                275                 280                 285 ctt tgt aca cac aaa aac tgg tgt aat tgg caa ata act caa gac tca   1273
Leu Cys Thr His Lys Asn Trp Cys Asn Trp Gln Ile Thr Gln Asp Ser
            290                 295                 300 caa gaa acc tat aac ttc aca ctc ata gct gaa aat tac tta agg aag   1321
Gln Glu Thr Tyr Asn Phe Thr Leu Ile Ala Glu Asn Tyr Leu Arg Lys
        305                 310                 315 aga agt gtc aat atc ctt ttt aac ctg act cat cga gtt tat tta atg   1369
Arg Ser Val Asn Ile Leu Phe Asn Leu Thr His Arg Val Tyr Leu Met
    320                 325                 330 aat cct ttt agt gtc aac ttt gaa aat gta aat gcc aca aat gcc atc   1417
Asn Pro Phe Ser Val Asn Phe Glu Asn Val Asn Ala Thr Asn Ala Ile
335                 340                 345                 350 atg acc tgg aag gtg cac tcc ata agg aat aat ttc aca tat ttg tgt   1465
Met Thr Trp Lys Val His Ser Ile Arg Asn Asn Phe Thr Tyr Leu Cys
                355                 360                 365 cag att gaa ctc cat ggt gaa gga aaa atg atg caa tac aat gtt tcc   1513
Gln Ile Glu Leu His Gly Glu Gly Lys Met Met Gln Tyr Asn Val Ser
            370                 375                 380 atc aag gtg aac ggt gag tac ttc tta agt gaa ctg gaa cct gcc aca   1561
Ile Lys Val Asn Gly Glu Tyr Phe Leu Ser Glu Leu Glu Pro Ala Thr
        385                 390                 395
```

```
gag tac atg gcg cga gta cgg tgt gct gat gcc agc cac ttc tgg aaa    1609
Glu Tyr Met Ala Arg Val Arg Cys Ala Asp Ala Ser His Phe Trp Lys
    400                 405                 410 tgg agt gaa tgg agt ggt cag aac ttc acc aca ctt gaa gct gct ccc    1657
Trp Ser Glu Trp Ser Gly Gln Asn Phe Thr Thr Leu Glu Ala Ala Pro
415                 420                 425                 430 tca gag gcc cct gat gtc tgg aga att gtg agc ttg gag cca gga aat    1705
Ser Glu Ala Pro Asp Val Trp Arg Ile Val Ser Leu Glu Pro Gly Asn
                435                 440                 445 cat act gtg acc tta ttc tgg aag cca tta tca aaa ctg cat gcc aat    1753
His Thr Val Thr Leu Phe Trp Lys Pro Leu Ser Lys Leu His Ala Asn
            450                 455                 460 gga aag atc ctg ttc tat aat gta gtt gta gaa aac cta gac aaa cca    1801
Gly Lys Ile Leu Phe Tyr Asn Val Val Val Glu Asn Leu Asp Lys Pro
        465                 470                 475 tcc agt tca gag ctc cat tcc att cca gca cca gcc aac agc aca aaa    1849
Ser Ser Ser Glu Leu His Ser Ile Pro Ala Pro Ala Asn Ser Thr Lys
    480                 485                 490 cta atc ctt gac agg tgt tcc tac caa atc tgc gtc ata gcc aac aac    1897
Leu Ile Leu Asp Arg Cys Ser Tyr Gln Ile Cys Val Ile Ala Asn Asn
495                 500                 505                 510 agt gtg ggt gct tct cct gct tct gta ata gtc atc tct gca gac ccc    1945
Ser Val Gly Ala Ser Pro Ala Ser Val Ile Val Ile Ser Ala Asp Pro
                515                 520                 525 gaa aac aaa gag gtt gag gaa gaa aga att gca ggc aca gag ggt gga    1993
Glu Asn Lys Glu Val Glu Glu Glu Arg Ile Ala Gly Thr Glu Gly Gly
            530                 535                 540 ttc tct ctg tct tgg aaa ccc caa cct gga gat gtt ata ggc tat gtt    2041
Phe Ser Leu Ser Trp Lys Pro Gln Pro Gly Asp Val Ile Gly Tyr Val
        545                 550                 555 gtg gac tgg tgt gac cat acc cag gat gtg ctc ggt gat ttc cag tgg    2089
Val Asp Trp Cys Asp His Thr Gln Asp Val Leu Gly Asp Phe Gln Trp
    560                 565                 570 aag aat gta ggt ccc aat acc aca agc aca gtc att agc aca gat gct    2137
Lys Asn Val Gly Pro Asn Thr Thr Ser Thr Val Ile Ser Thr Asp Ala
575                 580                 585                 590 ttt agg cca gga gtt cga tat gac ttc aga att tat ggg tta tct aca    2185
Phe Arg Pro Gly Val Arg Tyr Asp Phe Arg Ile Tyr Gly Leu Ser Thr
                595                 600                 605 aaa agg att gct tgt tta tta gag aaa aaa aca gga tac tct cag gaa    2233
Lys Arg Ile Ala Cys Leu Leu Glu Lys Lys Thr Gly Tyr Ser Gln Glu
            610                 615                 620 ctt gct cct tca gac aac cct cac gtg ctg gtg gat aca ttg aca tcc    2281
Leu Ala Pro Ser Asp Asn Pro His Val Leu Val Asp Thr Leu Thr Ser
        625                 630                 635 cac tcc ttc act ctg agt tgg aaa gat tac tct act gaa tct caa cct    2329
His Ser Phe Thr Leu Ser Trp Lys Asp Tyr Ser Thr Glu Ser Gln Pro
    640                 645                 650 ggt ttt ata caa ggg tac cat gtc tat ctg aaa tcc aag gcg agg cag    2377
Gly Phe Ile Gln Gly Tyr His Val Tyr Leu Lys Ser Lys Ala Arg Gln
655                 660                 665                 670 tgc cac cca cga ttt gaa aag gca gtt ctt tca gat ggt tca gaa tgt    2425
Cys His Pro Arg Phe Glu Lys Ala Val Leu Ser Asp Gly Ser Glu Cys
                675                 680                 685 tgc aaa tac aaa att gac aac ccg gaa gaa aag gca ttg att gtg gac    2473
Cys Lys Tyr Lys Ile Asp Asn Pro Glu Glu Lys Ala Leu Ile Val Asp
            690                 695                 700 aac cta aag cca gaa tcc ttc tat gag ttt ttc atc act cca ttc act    2521
Asn Leu Lys Pro Glu Ser Phe Tyr Glu Phe Phe Ile Thr Pro Phe Thr
```

```
                 705                 710                 715
agt gct ggt gaa ggc ccc agt gct acg ttc acg aag gtc acg act ccg    2569
Ser Ala Gly Glu Gly Pro Ser Ala Thr Phe Thr Lys Val Thr Thr Pro
720                 725                 730 gat gaa cac tcc tcg atg ctg att cat atc cta ctg ccc atg gtt ttc    2617
Asp Glu His Ser Ser Met Leu Ile His Ile Leu Leu Pro Met Val Phe
735                 740                 745                 750 tgc gtc ttg ctc atc atg gtc atg tgc tac ttg aaa agt cag tgg atc    2665
Cys Val Leu Leu Ile Met Val Met Cys Tyr Leu Lys Ser Gln Trp Ile
                755                 760                 765 aag gag acc tgt tat cct gac atc cct gac cct tac aag agc agc atc    2713
Lys Glu Thr Cys Tyr Pro Asp Ile Pro Asp Pro Tyr Lys Ser Ser Ile
            770                 775                 780 ctg tca tta ata aaa ttc aag gag aac cct cac cta ata ata atg aat    2761
Leu Ser Leu Ile Lys Phe Lys Glu Asn Pro His Leu Ile Ile Met Asn
785                 790                 795 gtc agt gac tgt atc cca gat gct att gaa gtt gta agc aag cca gaa    2809
Val Ser Asp Cys Ile Pro Asp Ala Ile Glu Val Val Ser Lys Pro Glu
800                 805                 810 ggg aca aag ata cag ttc cta ggc act agg aag tca ctc aca gaa acc    2857
Gly Thr Lys Ile Gln Phe Leu Gly Thr Arg Lys Ser Leu Thr Glu Thr
815                 820                 825                 830 gag ttg act aag cct aac tac ctt tat ctc ctt cca aca gaa aag aat    2905
Glu Leu Thr Lys Pro Asn Tyr Leu Tyr Leu Leu Pro Thr Glu Lys Asn
                835                 840                 845 cac tct ggc cct ggc ccc tgc atc tgt ttt gag aac ttg acc tat aac    2953
His Ser Gly Pro Gly Pro Cys Ile Cys Phe Glu Asn Leu Thr Tyr Asn
            850                 855                 860 cag gca gct tct gac tct ggc tct tgt ggc cat gtt cca gta tcc cca    3001
Gln Ala Ala Ser Asp Ser Gly Ser Cys Gly His Val Pro Val Ser Pro
865                 870                 875 aaa gcc cca agt atg ctg gga cta atg acc tca cct gaa aat gta cta    3049
Lys Ala Pro Ser Met Leu Gly Leu Met Thr Ser Pro Glu Asn Val Leu
880                 885                 890 aag gca cta gaa aaa aac tac atg aac tcc ctg gga gaa atc cca gct    3097
Lys Ala Leu Glu Lys Asn Tyr Met Asn Ser Leu Gly Glu Ile Pro Ala
895                 900                 905                 910 gga gaa aca agt ttg aat tat gtg tcc cag ttg gct tca ccc atg ttt    3145
Gly Glu Thr Ser Leu Asn Tyr Val Ser Gln Leu Ala Ser Pro Met Phe
                915                 920                 925 gga gac aag gac agt ctc cca aca aac cca gta gag gca cca cac tgt    3193
Gly Asp Lys Asp Ser Leu Pro Thr Asn Pro Val Glu Ala Pro His Cys
            930                 935                 940 tca gag tat aaa atg caa atg gca gtc tcc ctg cgt ctt gcc ttg cct    3241
Ser Glu Tyr Lys Met Gln Met Ala Val Ser Leu Arg Leu Ala Leu Pro
945                 950                 955 ccc ccg acc gag aat agc agc ctc tcc tca att acc ctt tta gat cca    3289
Pro Pro Thr Glu Asn Ser Ser Leu Ser Ser Ile Thr Leu Leu Asp Pro
960                 965                 970 ggt gaa cac tac tgc taaccagcat gccgatttca taccttatgc tacacagaca    3344
Gly Glu His Tyr Cys
975 ttaagaagag cagagctggc accctgtcat caccagtggc cttggtcctt aatcccagta   3404 caatttgcag gtctggttta tataagacca ctacagtctg gctaggttaa aggccagagg   3464 ctatggaact taacactccc cattggagca agcttgccct agagacggca ggatcatggg   3524 agcatgctta ccttctgctg tttgttccag gctcaccttt agaacaggag acttgagctt   3584 gacctaagga tatgcattaa ccactctaca gactcccact cagtactgta cagggtggct   3644
```

-continued

```
gtggtcctag aagttcagtt tttactgagg aaatatttcc attaacagca attattatat    3704
tgaaggcttt aataaaggcc acaggagaca ttactatagc atagattgtc aaatgtaaat    3764
ttactgagcg tgttttataa aaaactcaca ggtgtttgag gccaaaacag attttagact    3824
taccttgaac ggataagaat ctatagttca ctgacacagt aaaattaact ctgtgggtgg    3884 gggcggggg catagctcta atctaatata taaaatgtgt gatgaatcaa caagatttcc     3944
acaattcttc tgtcaagctt actacagtga aagaatggga ttggcaagta acttctgact    4004
tactgtcagt tgtacttctg ctccatagac atcagtattc tgccatcatt tttgatgact    4064
acctcagaac ataaaaagga acgtatatca cataattcca gtcacagttt ttggttcctc    4124 tttctttca agaactatat ataaatgacc tgttttcacg cggccgc                   4171
```

<210> SEQ ID NO 7
<211> LENGTH: 979
<212> TYPE: PRT
<213> ORGANISM: Homo sapiens

<400> SEQUENCE: 7

Met Ala Leu Phe Ala Val Phe Gln Thr Thr Phe Phe Leu Thr Leu Leu
1               5                   10                  15

Ser Leu Arg Thr Tyr Gln Ser Glu Val Leu Ala Glu Arg Leu Pro Leu
            20                  25                  30

Thr Pro Val Ser Leu Lys Val Ser Thr Asn Ser Thr Arg Gln Ser Leu
        35                  40                  45

His Leu Gln Trp Thr Val His Asn Leu Pro Tyr His Gln Glu Leu Lys
    50                  55                  60

Met Val Phe Gln Ile Gln Ile Ser Arg Ile Glu Thr Ser Asn Val Ile
65                  70                  75                  80

Trp Val Gly Asn Tyr Ser Thr Thr Val Lys Trp Asn Gln Val Leu His
                85                  90                  95

Trp Ser Trp Glu Ser Glu Leu Pro Leu Glu Cys Ala Thr His Phe Val
            100                 105                 110

Arg Ile Lys Ser Leu Val Asp Asp Ala Lys Phe Pro Glu Pro Asn Phe
        115                 120                 125

Trp Ser Asn Trp Ser Ser Trp Glu Glu Val Ser Val Gln Asp Ser Thr
    130                 135                 140

Gly Gln Asp Ile Leu Phe Val Phe Pro Lys Asp Lys Leu Val Glu Glu
145                 150                 155                 160

Gly Thr Asn Val Thr Ile Cys Tyr Val Ser Arg Asn Ile Gln Asn Asn
                165                 170                 175

Val Ser Cys Tyr Leu Glu Gly Lys Gln Ile His Gly Glu Gln Leu Asp
            180                 185                 190

Pro His Val Thr Ala Phe Asn Leu Asn Ser Val Pro Phe Ile Arg Asn
        195                 200                 205

Lys Gly Thr Asn Ile Tyr Cys Glu Ala Ser Gln Gly Asn Val Ser Glu
    210                 215                 220

Gly Met Lys Gly Ile Val Leu Phe Val Ser Lys Val Leu Glu Glu Pro
225                 230                 235                 240

Lys Asp Phe Ser Cys Glu Thr Glu Asp Phe Lys Thr Leu His Cys Thr
                245                 250                 255

Trp Asp Pro Gly Thr Asp Thr Ala Leu Gly Trp Ser Lys Gln Pro Ser
            260                 265                 270

Gln Ser Tyr Thr Leu Phe Glu Ser Phe Ser Gly Glu Lys Lys Leu Cys

-continued

```
                275                 280                 285
Thr His Lys Asn Trp Cys Asn Trp Gln Ile Thr Gln Asp Ser Gln Glu
290                 295                 300

Thr Tyr Asn Phe Thr Leu Ile Ala Glu Asn Tyr Leu Arg Lys Arg Ser
305                 310                 315                 320

Val Asn Ile Leu Phe Asn Leu Thr His Arg Val Tyr Leu Met Asn Pro
                325                 330                 335

Phe Ser Val Asn Phe Glu Asn Val Asn Ala Thr Asn Ala Ile Met Thr
                340                 345                 350

Trp Lys Val His Ser Ile Arg Asn Asn Phe Thr Tyr Leu Cys Gln Ile
                355                 360                 365

Glu Leu His Gly Glu Gly Lys Met Met Gln Tyr Asn Val Ser Ile Lys
370                 375                 380

Val Asn Gly Glu Tyr Phe Leu Ser Glu Leu Glu Pro Ala Thr Glu Tyr
385                 390                 395                 400

Met Ala Arg Val Arg Cys Ala Asp Ala Ser His Phe Trp Lys Trp Ser
                405                 410                 415

Glu Trp Ser Gly Gln Asn Phe Thr Thr Leu Glu Ala Ala Pro Ser Glu
                420                 425                 430

Ala Pro Asp Val Trp Arg Ile Val Ser Leu Glu Pro Gly Asn His Thr
                435                 440                 445

Val Thr Leu Phe Trp Lys Pro Leu Ser Lys Leu His Ala Asn Gly Lys
450                 455                 460

Ile Leu Phe Tyr Asn Val Val Glu Asn Leu Asp Lys Pro Ser Ser
465                 470                 475                 480

Ser Glu Leu His Ser Ile Pro Ala Pro Ala Asn Ser Thr Lys Leu Ile
                485                 490                 495

Leu Asp Arg Cys Ser Tyr Gln Ile Cys Val Ile Ala Asn Asn Ser Val
                500                 505                 510

Gly Ala Ser Pro Ala Ser Val Ile Val Ile Ser Ala Asp Pro Glu Asn
                515                 520                 525

Lys Glu Val Glu Glu Glu Arg Ile Ala Gly Thr Glu Gly Gly Phe Ser
530                 535                 540

Leu Ser Trp Lys Pro Gln Pro Gly Asp Val Ile Gly Tyr Val Val Asp
545                 550                 555                 560

Trp Cys Asp His Thr Gln Asp Val Leu Gly Asp Phe Gln Trp Lys Asn
                565                 570                 575

Val Gly Pro Asn Thr Thr Ser Thr Val Ile Ser Thr Asp Ala Phe Arg
                580                 585                 590

Pro Gly Val Arg Tyr Asp Phe Arg Ile Tyr Gly Leu Ser Thr Lys Arg
                595                 600                 605

Ile Ala Cys Leu Leu Glu Lys Lys Thr Gly Tyr Ser Gln Glu Leu Ala
610                 615                 620

Pro Ser Asp Asn Pro His Val Leu Val Asp Thr Leu Thr Ser His Ser
625                 630                 635                 640

Phe Thr Leu Ser Trp Lys Asp Tyr Ser Thr Glu Ser Gln Pro Gly Phe
                645                 650                 655

Ile Gln Gly Tyr His Val Tyr Leu Lys Ser Lys Ala Arg Gln Cys His
                660                 665                 670

Pro Arg Phe Glu Lys Ala Val Leu Ser Asp Gly Ser Glu Cys Cys Lys
                675                 680                 685

Tyr Lys Ile Asp Asn Pro Glu Glu Lys Ala Leu Ile Val Asp Asn Leu
690                 695                 700
```

-continued

```
Lys Pro Glu Ser Phe Tyr Glu Phe Ile Thr Pro Phe Thr Ser Ala
705                 710                 715                 720

Gly Glu Gly Pro Ser Ala Thr Phe Thr Lys Val Thr Pro Asp Glu
            725                 730                 735

His Ser Ser Met Leu Ile His Ile Leu Leu Pro Met Val Phe Cys Val
        740                 745                 750

Leu Leu Ile Met Val Met Cys Tyr Leu Lys Ser Gln Trp Ile Lys Glu
    755                 760                 765

Thr Cys Tyr Pro Asp Ile Pro Asp Pro Tyr Lys Ser Ser Ile Leu Ser
770                 775                 780

Leu Ile Lys Phe Lys Glu Asn Pro His Leu Ile Ile Met Asn Val Ser
785                 790                 795                 800

Asp Cys Ile Pro Asp Ala Ile Glu Val Val Ser Lys Pro Glu Gly Thr
            805                 810                 815

Lys Ile Gln Phe Leu Gly Thr Arg Lys Ser Leu Thr Glu Thr Glu Leu
        820                 825                 830

Thr Lys Pro Asn Tyr Leu Tyr Leu Leu Pro Thr Glu Lys Asn His Ser
    835                 840                 845

Gly Pro Gly Pro Cys Ile Cys Phe Glu Asn Leu Thr Tyr Asn Gln Ala
850                 855                 860

Ala Ser Asp Ser Gly Ser Cys Gly His Val Pro Val Ser Pro Lys Ala
865                 870                 875                 880

Pro Ser Met Leu Gly Leu Met Thr Ser Pro Glu Asn Val Leu Lys Ala
            885                 890                 895

Leu Glu Lys Asn Tyr Met Asn Ser Leu Gly Glu Ile Pro Ala Gly Glu
        900                 905                 910

Thr Ser Leu Asn Tyr Val Ser Gln Leu Ala Ser Pro Met Phe Gly Asp
    915                 920                 925

Lys Asp Ser Leu Pro Thr Asn Pro Val Glu Ala Pro His Cys Ser Glu
930                 935                 940

Tyr Lys Met Gln Met Ala Val Ser Leu Arg Leu Ala Leu Pro Pro Pro
945                 950                 955                 960

Thr Glu Asn Ser Ser Leu Ser Ser Ile Thr Leu Leu Asp Pro Gly Glu
            965                 970                 975

His Tyr Cys

<210> SEQ ID NO 8
<211> LENGTH: 2657
<212> TYPE: DNA
<213> ORGANISM: Homo sapiens
<220> FEATURE:
<221> NAME/KEY: CDS
<222> LOCATION: (133)...(2040)

<400> SEQUENCE: 8
cggaggcggc ctgccggggt ggttcggctt cccgttgccg cctcgggcgc tgtacccaga      60
gctcgaagag gagcagcgcg gccgcgcgga cccggcaagg ctgggccgga ctcggggctc     120
ccgagggacg cc atg cgg gga ggc agg ggc gcc cct ttc tgg ctg tgg ccg    171
              Met Arg Gly Gly Arg Gly Ala Pro Phe Trp Leu Trp Pro
                1               5                   10 ctg ccc aag ctg gcg ctg ctg cct ctg ttg tgg gtg ctt ttc cag cgg      219
Leu Pro Lys Leu Ala Leu Leu Pro Leu Leu Trp Val Leu Phe Gln Arg
     15                  20                  25 acg cgt ccc cag ggc agc gcc ggg cca ctg cag tgc tac gga gtt gga      267
Thr Arg Pro Gln Gly Ser Ala Gly Pro Leu Gln Cys Tyr Gly Val Gly
```

```
                 30                  35                  40                  45 ccc ttg ggc gac ttg aac tgc tcg tgg gag cct ctt ggg gac ctg gga        315
Pro Leu Gly Asp Leu Asn Cys Ser Trp Glu Pro Leu Gly Asp Leu Gly
             50                  55                  60 gcc ccc tcc gag tta cac ctc cag agc caa aag tac cgt tcc aac aaa        363
Ala Pro Ser Glu Leu His Leu Gln Ser Gln Lys Tyr Arg Ser Asn Lys
         65                  70                  75 acc cag act gtg gca gtg gca gcc gga cgg agc tgg gtg gcc att cct        411
Thr Gln Thr Val Ala Val Ala Ala Gly Arg Ser Trp Val Ala Ile Pro
     80                  85                  90 cgg gaa cag ctc acc atg tct gac aaa ctc ctt gtc tgg ggc act aag        459
Arg Glu Gln Leu Thr Met Ser Asp Lys Leu Leu Val Trp Gly Thr Lys
 95                 100                 105 gca ggc cag cct ctc tgg ccc ccc gtc ttc gtg aac cta gaa acc caa        507
Ala Gly Gln Pro Leu Trp Pro Pro Val Phe Val Asn Leu Glu Thr Gln
110                 115                 120                 125 atg aag cca aac gcc ccc cgg ctg ggc cct gac gtg gac ttt tcc gag        555
Met Lys Pro Asn Ala Pro Arg Leu Gly Pro Asp Val Asp Phe Ser Glu
                130                 135                 140 gat gac ccc ctg gag gcc act gtc cat tgg gcc cca cct aca tgg cca        603
Asp Asp Pro Leu Glu Ala Thr Val His Trp Ala Pro Pro Thr Trp Pro
            145                 150                 155 tct cat aaa gtt ctg atc tgc cag ttc cac tac cga aga tgt cag gag        651
Ser His Lys Val Leu Ile Cys Gln Phe His Tyr Arg Arg Cys Gln Glu
        160                 165                 170 gcg gcc tgg acc ctg ctg gaa ccg gag ctg aag acc ata ccc ctg acc        699
Ala Ala Trp Thr Leu Leu Glu Pro Glu Leu Lys Thr Ile Pro Leu Thr
    175                 180                 185 cct gtt gag atc caa gat ttg gag cta gcc act ggc tac aaa gtg tat        747
Pro Val Glu Ile Gln Asp Leu Glu Leu Ala Thr Gly Tyr Lys Val Tyr
190                 195                 200                 205 ggc cgc tgc cgg atg gag aaa gaa gag gat ttg tgg ggc gag tgg agc        795
Gly Arg Cys Arg Met Glu Lys Glu Glu Asp Leu Trp Gly Glu Trp Ser
                210                 215                 220 ccc att ttg tcc ttc cag aca ccg cct tct gct cca aaa gat gtg tgg        843
Pro Ile Leu Ser Phe Gln Thr Pro Pro Ser Ala Pro Lys Asp Val Trp
            225                 230                 235 gta tca ggg aac ctc tgt ggg acg cct gga gga gag gaa cct ttg ctt        891
Val Ser Gly Asn Leu Cys Gly Thr Pro Gly Gly Glu Glu Pro Leu Leu
        240                 245                 250 cta tgg aag gcc cca ggg ccc tgt gtg cag gtg agc tac aaa gtc tgg        939
Leu Trp Lys Ala Pro Gly Pro Cys Val Gln Val Ser Tyr Lys Val Trp
    255                 260                 265 ttc tgg gtt gga ggt cgt gag ctg agt cca gaa gga att acc tgc tgc        987
Phe Trp Val Gly Gly Arg Glu Leu Ser Pro Glu Gly Ile Thr Cys Cys
270                 275                 280                 285 tgc tcc cta att ccc agt ggg gcg gag tgg gcc agg gtg tcc gct gtc        1035
Cys Ser Leu Ile Pro Ser Gly Ala Glu Trp Ala Arg Val Ser Ala Val
                290                 295                 300 aac gcc aca agc tgg gag cct ctc acc aac ctc tct ttg gtc tgc ttg        1083
Asn Ala Thr Ser Trp Glu Pro Leu Thr Asn Leu Ser Leu Val Cys Leu
            305                 310                 315 gat tca gcc tct gcc ccc gtt agc gtg gca gtc agc agc atc gct ggg        1131
Asp Ser Ala Ser Ala Pro Arg Ser Val Ala Val Ser Ser Ile Ala Gly
        320                 325                 330 agc acg gag cta ctg gtg acc tgg caa ccg ggg cct ggg gaa cca ctg        1179
Ser Thr Glu Leu Leu Val Thr Trp Gln Pro Gly Pro Gly Glu Pro Leu
    335                 340                 345 gag cat gta gtg gac tgg gct cga gat ggg gac ccc ctg gag aaa ctc        1227
```

```
Glu His Val Val Asp Trp Ala Arg Asp Gly Asp Pro Leu Glu Lys Leu
350             355                 360                 365 aac tgg gtc cgg ctt ccc cct ggg aac ctc agt gct ctg tta cca ggg        1275
Asn Trp Val Arg Leu Pro Pro Gly Asn Leu Ser Ala Leu Leu Pro Gly
            370                 375                 380 aat ttc act gtc ggg gtc ccc tat cga atc act gtg acc gca gtc tct        1323
Asn Phe Thr Val Gly Val Pro Tyr Arg Ile Thr Val Thr Ala Val Ser
        385                 390                 395 gct tca ggc ttg gcc tct gca tcc tcc gtc tgg ggg ttc agg gag gaa        1371
Ala Ser Gly Leu Ala Ser Ala Ser Ser Val Trp Gly Phe Arg Glu Glu
    400                 405                 410 tta gca ccc cta gtg ggg cca acg ctt tgg cga ctc caa gat gcc cct        1419
Leu Ala Pro Leu Val Gly Pro Thr Leu Trp Arg Leu Gln Asp Ala Pro
415                 420                 425 cca ggg acc ccc gcc ata gcg tgg gga gag gtc cca agg cac cag ctt        1467
Pro Gly Thr Pro Ala Ile Ala Trp Gly Glu Val Pro Arg His Gln Leu
430                 435                 440                 445 cga ggc cac ctc acc cac tac acc ttg tgt gca cag agt gga acc agc        1515
Arg Gly His Leu Thr His Tyr Thr Leu Cys Ala Gln Ser Gly Thr Ser
            450                 455                 460 ccc tcc gtc tgc atg aat gtg agt ggc aac aca cag agt gtc acc ctg        1563
Pro Ser Val Cys Met Asn Val Ser Gly Asn Thr Gln Ser Val Thr Leu
                465                 470                 475 cct gac ctt cct tgg ggt ccc tgt gag ctg tgg gtg aca gca tct acc        1611
Pro Asp Leu Pro Trp Gly Pro Cys Glu Leu Trp Val Thr Ala Ser Thr
            480                 485                 490 atc gct gga cag ggc cct cct ggt ccc atc ctc cgg ctt cat cta cca        1659
Ile Ala Gly Gln Gly Pro Pro Gly Pro Ile Leu Arg Leu His Leu Pro
495                 500                 505 gat aac acc ctg agg tgg aaa gtt ctg cca ggc atc cta ttc ttg tgg        1707
Asp Asn Thr Leu Arg Trp Lys Val Leu Pro Gly Ile Leu Phe Leu Trp
510                 515                 520                 525 ggc ttg ttc ctg ttg ggg tgt ggc ctg agc ctg gcc acc tct gga agg        1755
Gly Leu Phe Leu Leu Gly Cys Gly Leu Ser Leu Ala Thr Ser Gly Arg
                530                 535                 540 tgc tac cac cta agg cac aaa gtg ctg ccc cgc tgg gtc tgg gag aaa        1803
Cys Tyr His Leu Arg His Lys Val Leu Pro Arg Trp Val Trp Glu Lys
            545                 550                 555 gtt cct gat cct gcc aac agc agt tca ggc cag ccc cac atg gag caa        1851
Val Pro Asp Pro Ala Asn Ser Ser Ser Gly Gln Pro His Met Glu Gln
            560                 565                 570 gta cct gag gcc cag ccc ctt ggg gac ttg ccc atc ctg gaa gtg gag        1899
Val Pro Glu Ala Gln Pro Leu Gly Asp Leu Pro Ile Leu Glu Val Glu
575                 580                 585 gag atg gag ccc ccg ccg gtt atg gag tcc tcc cag ccc gcc cag gcc        1947
Glu Met Glu Pro Pro Pro Val Met Glu Ser Ser Gln Pro Ala Gln Ala
590                 595                 600                 605 acc gcc ccg ctt gac tct ggg tat gag aag cac ttc ctg ccc aca cct        1995
Thr Ala Pro Leu Asp Ser Gly Tyr Glu Lys His Phe Leu Pro Thr Pro
            610                 615                 620 gag gag ctg ggc ctt ctg ggg ccc ccc agg cca cag gtt ctg gcc              2040
Glu Glu Leu Gly Leu Leu Gly Pro Pro Arg Pro Gln Val Leu Ala
                625                 630                 635 tgaaccacac gtctggctgg gggctgccag ccaggctaga gggatgctca tgcaggttgc        2100
accccagtcc tggattagcc ctcttgatgg atgaagacac tgaggactca gagaggctga        2160
gtcacttacc tgaggacacc cagccaggca gagctgggat tgaaggaccc ctatagaaa         2220 gggcttggcc cccatgggga agacacggat ggaaggtgga gcaaaggaaa atacatgaaa        2280
```

```
ttgagagtgg cagctgcctg ccaaaatctg ttccgctgta acagaactga atttggaccc    2340
cagcacagtg gctcacgcct gtaatcccag cactttggca ggccaaggtg aaggatcac     2400 ttagagctag gagtttgaga ccagcctggg caatatagca agaccctca ctacaaaaat     2460 aaaacatcaa aaacaaaaac aattagctgg gcatgatggc acacacctgt agtccgagcc    2520
acttgggagg ctgaggtggg aggatcggtt gagcccagga gttcgaagct gcagggacct    2580
ctgattgcac cactgcactc caggctgggt aacagaatga gaccttatct caaaaataaa    2640
caaactaata aaaagca                                                   2657

<210> SEQ ID NO 9
<211> LENGTH: 636
<212> TYPE: PRT
<213> ORGANISM: Homo sapiens

<400> SEQUENCE: 9

Met Arg Gly Gly Arg Gly Ala Pro Phe Trp Leu Trp Pro Leu Pro Lys
1               5                   10                  15

Leu Ala Leu Leu Pro Leu Leu Trp Val Leu Phe Gln Arg Thr Arg Pro
            20                  25                  30

Gln Gly Ser Ala Gly Pro Leu Gln Cys Tyr Gly Val Gly Pro Leu Gly
        35                  40                  45

Asp Leu Asn Cys Ser Trp Glu Pro Leu Gly Asp Leu Gly Ala Pro Ser
    50                  55                  60

Glu Leu His Leu Gln Ser Gln Lys Tyr Arg Ser Asn Lys Thr Gln Thr
65                  70                  75                  80

Val Ala Val Ala Ala Gly Arg Ser Trp Val Ala Ile Pro Arg Glu Gln
                85                  90                  95

Leu Thr Met Ser Asp Lys Leu Leu Val Trp Gly Thr Lys Ala Gly Gln
            100                 105                 110

Pro Leu Trp Pro Pro Val Phe Val Asn Leu Glu Thr Gln Met Lys Pro
        115                 120                 125

Asn Ala Pro Arg Leu Gly Pro Asp Val Asp Phe Ser Glu Asp Asp Pro
    130                 135                 140

Leu Glu Ala Thr Val His Trp Ala Pro Thr Trp Pro Ser His Lys
145                 150                 155                 160

Val Leu Ile Cys Gln Phe His Tyr Arg Arg Cys Gln Glu Ala Ala Trp
                165                 170                 175

Thr Leu Leu Glu Pro Glu Leu Lys Thr Ile Pro Leu Thr Pro Val Glu
            180                 185                 190

Ile Gln Asp Leu Glu Leu Ala Thr Gly Tyr Lys Val Tyr Gly Arg Cys
        195                 200                 205

Arg Met Glu Lys Glu Glu Asp Leu Trp Gly Glu Trp Ser Pro Ile Leu
    210                 215                 220

Ser Phe Gln Thr Pro Pro Ser Ala Pro Lys Asp Val Trp Val Ser Gly
225                 230                 235                 240

Asn Leu Cys Gly Thr Pro Gly Gly Glu Glu Pro Leu Leu Leu Trp Lys
                245                 250                 255

Ala Pro Gly Pro Cys Val Gln Val Ser Tyr Lys Val Trp Phe Trp Val
            260                 265                 270

Gly Gly Arg Glu Leu Ser Pro Glu Gly Ile Thr Cys Cys Cys Ser Leu
        275                 280                 285

Ile Pro Ser Gly Ala Glu Trp Ala Arg Val Ser Ala Val Asn Ala Thr
    290                 295                 300
```

Ser Trp Glu Pro Leu Thr Asn Leu Ser Leu Val Cys Leu Asp Ser Ala
305                 310                 315                 320

Ser Ala Pro Arg Ser Val Ala Val Ser Ser Ile Ala Gly Ser Thr Glu
            325                 330                 335

Leu Leu Val Thr Trp Gln Pro Gly Pro Gly Glu Pro Leu Glu His Val
            340                 345                 350

Val Asp Trp Ala Arg Asp Gly Asp Pro Leu Glu Lys Leu Asn Trp Val
            355                 360                 365

Arg Leu Pro Pro Gly Asn Leu Ser Ala Leu Leu Pro Gly Asn Phe Thr
            370                 375                 380

Val Gly Val Pro Tyr Arg Ile Thr Val Thr Ala Val Ser Ala Ser Gly
385                 390                 395                 400

Leu Ala Ser Ala Ser Ser Val Trp Gly Phe Arg Glu Glu Leu Ala Pro
                405                 410                 415

Leu Val Gly Pro Thr Leu Trp Arg Leu Gln Asp Ala Pro Pro Gly Thr
            420                 425                 430

Pro Ala Ile Ala Trp Gly Glu Val Pro Arg His Gln Leu Arg Gly His
            435                 440                 445

Leu Thr His Tyr Thr Leu Cys Ala Gln Ser Gly Thr Ser Pro Ser Val
450                 455                 460

Cys Met Asn Val Ser Gly Asn Thr Gln Ser Val Thr Leu Pro Asp Leu
465                 470                 475                 480

Pro Trp Gly Pro Cys Glu Leu Trp Val Thr Ala Ser Thr Ile Ala Gly
                485                 490                 495

Gln Gly Pro Pro Gly Pro Ile Leu Arg Leu His Leu Pro Asp Asn Thr
            500                 505                 510

Leu Arg Trp Lys Val Leu Pro Gly Ile Leu Phe Leu Trp Gly Leu Phe
            515                 520                 525

Leu Leu Gly Cys Gly Leu Ser Leu Ala Thr Ser Gly Arg Cys Tyr His
            530                 535                 540

Leu Arg His Lys Val Leu Pro Arg Trp Val Trp Glu Lys Val Pro Asp
545                 550                 555                 560

Pro Ala Asn Ser Ser Ser Gly Gln Pro His Met Glu Gln Val Pro Glu
                565                 570                 575

Ala Gln Pro Leu Gly Asp Leu Pro Ile Leu Glu Val Glu Glu Met Glu
            580                 585                 590

Pro Pro Pro Val Met Glu Ser Ser Gln Pro Ala Gln Ala Thr Ala Pro
            595                 600                 605

Leu Asp Ser Gly Tyr Glu Lys His Phe Leu Pro Thr Pro Glu Glu Leu
            610                 615                 620

Gly Leu Leu Gly Pro Pro Arg Pro Gln Val Leu Ala
625                 630                 635

<210> SEQ ID NO 10
<211> LENGTH: 755
<212> TYPE: DNA
<213> ORGANISM: Mus musculus
<220> FEATURE:
<221> NAME/KEY: CDS
<222> LOCATION: (1)...(489)

<400> SEQUENCE: 10 atg atc ttc cac aca gga aca acg aag cct acc ctg gtg ctg ctt tgc    48
Met Ile Phe His Thr Gly Thr Thr Lys Pro Thr Leu Val Leu Leu Cys
1               5                   10                  15 tgt ata gga acc tgg ctg gcc acc tgc agc ttg tcc ttc ggt gcc cca    96

```
                Cys Ile Gly Thr Trp Leu Ala Thr Cys Ser Leu Ser Phe Gly Ala Pro
                                20                  25                  30 ata tcg aag gaa gac tta aga act aca att gac ctc ttg aaa caa gag          144
Ile Ser Lys Glu Asp Leu Arg Thr Thr Ile Asp Leu Leu Lys Gln Glu
         35                  40                  45 tct cag gat ctt tat aac aac tat agc ata aag cag gca tct ggg atg          192
Ser Gln Asp Leu Tyr Asn Asn Tyr Ser Ile Lys Gln Ala Ser Gly Met
 50                  55                  60 tca gca gac gaa tca ata cag ctg ccg tgt ttc agc ctg gac cgg gaa          240
Ser Ala Asp Glu Ser Ile Gln Leu Pro Cys Phe Ser Leu Asp Arg Glu
 65                  70                  75                  80 gca tta acc aac atc tcg gtc atc ata gca cat ctg gag aaa gtc aaa          288
Ala Leu Thr Asn Ile Ser Val Ile Ile Ala His Leu Glu Lys Val Lys
                 85                  90                  95 gtg ttg agc gag aac aca gta gat act tct tgg gta ata aga tgg cta          336
Val Leu Ser Glu Asn Thr Val Asp Thr Ser Trp Val Ile Arg Trp Leu
                100                 105                 110 aca aac atc agc tgt ttc aac cca ctg aat tta aac att tct gtg cct          384
Thr Asn Ile Ser Cys Phe Asn Pro Leu Asn Leu Asn Ile Ser Val Pro
            115                 120                 125 gga aat act gat gaa tcc tat gat tgt aaa gtg ttc gtg ctt acg gtt          432
Gly Asn Thr Asp Glu Ser Tyr Asp Cys Lys Val Phe Val Leu Thr Val
130                 135                 140 tta aag cag ttc tca aac tgc atg gca gaa ctg cag gct aag gac aat          480
Leu Lys Gln Phe Ser Asn Cys Met Ala Glu Leu Gln Ala Lys Asp Asn
145                 150                 155                 160 act aca tgc tgagtgatgg ggggggggg ggtgcagtgt cctcagcagt                   529
Thr Thr Cys gcctgtcctt cgagggctga gcttgcaacc caggacttaa ctccaaaggg actgtgcggt        589
cattactagt catgttattt atgttttat tttgtccact gaaatcttgt tctgctaccc         649
tgtagggact ggaagtggca gctatattta tttatttatg tactgagttt gttaacgctc        709
catggaggag ccttcagagt ctatttaata aattatattg acatga                      755

<210> SEQ ID NO 11
<211> LENGTH: 163
<212> TYPE: PRT
<213> ORGANISM: Mus musculus

<400> SEQUENCE: 11

Met Ile Phe His Thr Gly Thr Thr Lys Pro Thr Leu Val Leu Leu Cys
 1               5                  10                  15

Cys Ile Gly Thr Trp Leu Ala Thr Cys Ser Leu Ser Phe Gly Ala Pro
                20                  25                  30

Ile Ser Lys Glu Asp Leu Arg Thr Thr Ile Asp Leu Leu Lys Gln Glu
         35                  40                  45

Ser Gln Asp Leu Tyr Asn Asn Tyr Ser Ile Lys Gln Ala Ser Gly Met
 50                  55                  60

Ser Ala Asp Glu Ser Ile Gln Leu Pro Cys Phe Ser Leu Asp Arg Glu
 65                  70                  75                  80

Ala Leu Thr Asn Ile Ser Val Ile Ile Ala His Leu Glu Lys Val Lys
                 85                  90                  95

Val Leu Ser Glu Asn Thr Val Asp Thr Ser Trp Val Ile Arg Trp Leu
                100                 105                 110

Thr Asn Ile Ser Cys Phe Asn Pro Leu Asn Leu Asn Ile Ser Val Pro
            115                 120                 125

Gly Asn Thr Asp Glu Ser Tyr Asp Cys Lys Val Phe Val Leu Thr Val
```

Leu Lys Gln Phe Ser Asn Cys Met Ala Glu Leu Gln Ala Lys Asp Asn
145                 150                 155                 160

Thr Thr Cys

<210> SEQ ID NO 12
<211> LENGTH: 489
<212> TYPE: DNA
<213> ORGANISM: Artificial Sequence
<220> FEATURE:
<223> OTHER INFORMATION: mouse zcytor17lig degenerate polynucleotide of
      SEQ ID NO:11
<220> FEATURE:
<221> NAME/KEY: misc_feature
<222> LOCATION: (1)...(489)
<223> OTHER INFORMATION: n = A,T,C or G

<400> SEQUENCE: 12
atgathttyc ayacnggnac nacnaarccn acnytngtny tnytntgytg yathggnacn        60
tggytngcna cntgywsnyt nwsnttyggn gcnccnathw snaargarga yytnmgnacn       120
acnathgayy tnytnaarca rgarwsncar gayytntaya ayaaytayws nathaarcar       180
gcnwsnggna tgwsngcnga ygarwsnath carytnccnt gyttywsnyt ngaymgngar       240
gcnytnacna ayathwsngt nathathgcn cayytngara argtnaargt nytnwsngar       300
aayacngtng yacnwsntng ggtnathmgn tggytnacna ayathwsngt yttyaayccn       360
ytnaayytna ayathwsngt nccnggnaay acngaygarw sntaygaytg yaargtntty       420
gtnytnacng tnytnaarca rttywsnaay tgyatggcng arytncargc naargayaay       480 acnacntgy                                                              489

<210> SEQ ID NO 13
<211> LENGTH: 21
<212> TYPE: DNA
<213> ORGANISM: Artificial Sequence
<220> FEATURE:
<223> OTHER INFORMATION: Oligonucleotide primer ZC6673

<400> SEQUENCE: 13
gcgcaaggtg ccgttcacag c                                                 21

<210> SEQ ID NO 14
<211> LENGTH: 36
<212> TYPE: DNA
<213> ORGANISM: Artificial Sequence
<220> FEATURE:
<223> OTHER INFORMATION: Oligonucleotide primer ZC29082

<400> SEQUENCE: 14
caatttgttg ggttttttta gcagcagtag gcccag                                 36

<210> SEQ ID NO 15
<211> LENGTH: 36
<212> TYPE: DNA
<213> ORGANISM: Artificial Sequence
<220> FEATURE:
<223> OTHER INFORMATION: Oligonucleotide primer ZC29083

<400> SEQUENCE: 15
ctgggcctac tgctgctaaa aaacccaac aaattg                                  36

<210> SEQ ID NO 16
<211> LENGTH: 36

```
<212> TYPE: DNA
<213> ORGANISM: Artificial Sequence
<220> FEATURE:
<223> OTHER INFORMATION: Oligonucleotide primer ZC29145

<400> SEQUENCE: 16
gcgtctagag ggttatattg aagttgggca ggaaga                                    36

<210> SEQ ID NO 17
<211> LENGTH: 8
<212> TYPE: PRT
<213> ORGANISM: Artificial Sequence
<220> FEATURE:
<223> OTHER INFORMATION: Gly-Ser Modified Glu-Glu (CEE) peptide tag

<400> SEQUENCE: 17

Gly Ser Glu Tyr Met Pro Met Glu
 1               5

<210> SEQ ID NO 18
<211> LENGTH: 33
<212> TYPE: DNA
<213> ORGANISM: Artificial Sequence
<220> FEATURE:
<223> OTHER INFORMATION: Oligonucleotide primer ZC29359

<400> SEQUENCE: 18
gcgggatcca tgaagctctc tccccagcct tca                                       33

<210> SEQ ID NO 19
<211> LENGTH: 23
<212> TYPE: DNA
<213> ORGANISM: Artificial Sequence
<220> FEATURE:
<223> OTHER INFORMATION: Oligonucleotide primer ZC27899

<400> SEQUENCE: 19
ccagaacttt gactccttga ccg                                                  23

<210> SEQ ID NO 20
<211> LENGTH: 23
<212> TYPE: DNA
<213> ORGANISM: Artificial Sequence
<220> FEATURE:
<223> OTHER INFORMATION: Oligonucleotide primer ZC27895

<400> SEQUENCE: 20
gaagtcaact tcgctaagaa ccg                                                  23

<210> SEQ ID NO 21
<211> LENGTH: 34
<212> TYPE: DNA
<213> ORGANISM: Artificial Sequence
<220> FEATURE:
<223> OTHER INFORMATION: Oligonucleotide primer ZC29122

<400> SEQUENCE: 21
ccgctcgagt tatattgaag ttgggcagga agac                                      34

<210> SEQ ID NO 22
<211> LENGTH: 22
<212> TYPE: DNA
<213> ORGANISM: Artificial Sequence
<220> FEATURE:
<223> OTHER INFORMATION: Oligonucleotide primer ZC29180

<400> SEQUENCE: 22
```

```
cctggagtcc ctgaaacgaa ag                                            22

<210> SEQ ID NO 23
<211> LENGTH: 34
<212> TYPE: DNA
<213> ORGANISM: Artificial Sequence
<220> FEATURE:
<223> OTHER INFORMATION: Oligonucleotide primer ZC29122

<400> SEQUENCE: 23
ccgctcgagt tatattgaag ttgggcagga agac                               34

<210> SEQ ID NO 24
<211> LENGTH: 20
<212> TYPE: DNA
<213> ORGANISM: Artificial Sequence
<220> FEATURE:
<223> OTHER INFORMATION: Oligonucleotide primer ZC9791

<400> SEQUENCE: 24
cgttccaaca aaacccagac                                               20

<210> SEQ ID NO 25
<211> LENGTH: 19
<212> TYPE: DNA
<213> ORGANISM: Artificial Sequence
<220> FEATURE:
<223> OTHER INFORMATION: Oligonucleotide primer ZC9793

<400> SEQUENCE: 25
tggcgttgac agcggacac                                                19

<210> SEQ ID NO 26
<211> LENGTH: 20
<212> TYPE: DNA
<213> ORGANISM: Artificial Sequence
<220> FEATURE:
<223> OTHER INFORMATION: Oligonucleotide primer ZC40109

<400> SEQUENCE: 26
ccattccagc accagccaac                                               20

<210> SEQ ID NO 27
<211> LENGTH: 22
<212> TYPE: DNA
<213> ORGANISM: Artificial Sequence
<220> FEATURE:
<223> OTHER INFORMATION: Oligonucleotide primer ZC40112

<400> SEQUENCE: 27
tacaacttca atagcatctg gg                                            22

<210> SEQ ID NO 28
<211> LENGTH: 40
<212> TYPE: DNA
<213> ORGANISM: Artificial Sequence
<220> FEATURE:
<223> OTHER INFORMATION: Oligonucleotide primer ZC13946

<400> SEQUENCE: 28
ccctgcagtg atcaacatgg ccaagttgac cagtgccgtt                         40

<210> SEQ ID NO 29
<211> LENGTH: 45
<212> TYPE: DNA
```

```
<213> ORGANISM: Artificial Sequence
<220> FEATURE:
<223> OTHER INFORMATION: Oligonucleotide primer ZC13945

<400> SEQUENCE: 29
gcccatggac tagtttcgaa aggtcgagtg tcagtcctgc tcctc         45

<210> SEQ ID NO 30
<211> LENGTH: 34
<212> TYPE: DNA
<213> ORGANISM: Artificial Sequence
<220> FEATURE:
<223> OTHER INFORMATION: Oligonucleotide primer ZC18698

<400> SEQUENCE: 30
tttttttctc gagactttt tttttttttt tttt                      34

<210> SEQ ID NO 31
<220> FEATURE:
<223> OTHER INFORMATION: Skipped Sequence

<400> SEQUENCE: 31

000

<210> SEQ ID NO 32
<211> LENGTH: 10
<212> TYPE: PRT
<213> ORGANISM: Artificial Sequence
<220> FEATURE:
<223> OTHER INFORMATION: Glu-Glu (CEE) peptide tag with Gly-Ser residue
      pair

<400> SEQUENCE: 32

Gly Ser Gly Gly Glu Tyr Met Pro Met Glu
 1               5                  10

<210> SEQ ID NO 33
<211> LENGTH: 33
<212> TYPE: DNA
<213> ORGANISM: Artificial Sequence
<220> FEATURE:
<223> OTHER INFORMATION: Oligonucleotide primer ZC29451

<400> SEQUENCE: 33
ccggaattcc cctgatacat gaagctctct ccc                      33

<210> SEQ ID NO 34
<211> LENGTH: 33
<212> TYPE: DNA
<213> ORGANISM: Artificial Sequence
<220> FEATURE:
<223> OTHER INFORMATION: Oligonucleotide primer ZC29124

<400> SEQUENCE: 34
cgcggatccc tcaaagacac tgaatgacaa tgt                      33

<210> SEQ ID NO 35
<211> LENGTH: 6
<212> TYPE: PRT
<213> ORGANISM: Artificial Sequence
<220> FEATURE:
<223> OTHER INFORMATION: Glu-Glu (CEE) peptide tag without Gly-Ser
      residue pair

<400> SEQUENCE: 35

Glu Tyr Met Pro Met Glu
```

<210> SEQ ID NO 36
<211> LENGTH: 8
<212> TYPE: PRT
<213> ORGANISM: Artificial Sequence
<220> FEATURE:
<223> OTHER INFORMATION: C-terminal FLAG peptide sequence

<400> SEQUENCE: 36

Asp Tyr Lys Asp Asp Asp Asp Lys
 1               5

<210> SEQ ID NO 37
<211> LENGTH: 684
<212> TYPE: DNA
<213> ORGANISM: Homo sapiens

<400> SEQUENCE: 37
tcagacaaaa ctcacacatg cccaccgtgc ccagcacctg aagccgaggg ggcaccgtca      60
gtcttcctct tccccccaaa acccaaggac accctcatga tctcccggac ccctgaggtc     120
acatgcgtgg tggtggacgt gagccacgaa gaccctgagg tcaagttcaa ctggtacgtg     180
gacggcgtgg aggtgcataa tgccaagaca aagccgcggg aggagcagta caacagcacg     240
taccgtgtgg tcagcgtcct caccgtcctg caccaggact ggctgaatgg caaggagtac     300
aagtgcaagg tctccaacaa agccctccca tcctccatcg agaaaaccat ctccaaagcc     360
aaagggcagc cccgagaacc acaggtgtac accctgcccc catcccggga tgagctgacc     420
aagaaccagg tcagcctgac ctgcctggtc aaaggcttct atcccagcga catcgccgtg     480
gagtgggaga gcaatgggca gccggagaac aactacaaga ccacgcctcc cgtgctggac     540
tccgacggct ccttcttcct ctacagcaag ctcaccgtgg acaagagcag gtggcagcag     600
gggaacgtct tctcatgctc cgtgatgcat gaggctctgc acaaccacta cacgcagaag     660
agcctctccc tgtctccggg taaa                                            684

<210> SEQ ID NO 38
<211> LENGTH: 2295
<212> TYPE: DNA
<213> ORGANISM: Artificial Sequence
<220> FEATURE:
<223> OTHER INFORMATION: human zcytor17-Fc4 fusion polynucleotide
<220> FEATURE:
<221> NAME/KEY: CDS
<222> LOCATION: (1)...(2295)

<400> SEQUENCE: 38 atg aag ctc tct ccc cag cct tca tgt gtt aac ctg ggg atg atg tgg        48
Met Lys Leu Ser Pro Gln Pro Ser Cys Val Asn Leu Gly Met Met Trp
 1               5                  10                  15 acc tgg gca ctg tgg atg ctc cct tca ctc tgc aaa ttc agc ctg gca        96
Thr Trp Ala Leu Trp Met Leu Pro Ser Leu Cys Lys Phe Ser Leu Ala
             20                  25                  30 gct ctg cca gct aag cct gag aac att tcc tgt gtc tac tac tat agg       144
Ala Leu Pro Ala Lys Pro Glu Asn Ile Ser Cys Val Tyr Tyr Tyr Arg
         35                  40                  45 aaa aat tta acc tgc act tgg agt cca gga aag gaa acc agt tat acc       192
Lys Asn Leu Thr Cys Thr Trp Ser Pro Gly Lys Glu Thr Ser Tyr Thr
     50                  55                  60 cag tac aca gtt aag aga act tac gct ttt gga gaa aaa cat gat aat       240
Gln Tyr Thr Val Lys Arg Thr Tyr Ala Phe Gly Glu Lys His Asp Asn
 65                  70                  75                  80

```
tgt aca acc aat agt tct aca agt gaa aat cgt gct tcg tgc tct ttt    288
Cys Thr Thr Asn Ser Ser Thr Ser Glu Asn Arg Ala Ser Cys Ser Phe
                85                  90                  95 ttc ctt cca aga ata acg atc cca gat aat tat acc att gag gtg gaa    336
Phe Leu Pro Arg Ile Thr Ile Pro Asp Asn Tyr Thr Ile Glu Val Glu
            100                 105                 110 gct gaa aat gga gat ggt gta att aaa tct cat atg aca tac tgg aga    384
Ala Glu Asn Gly Asp Gly Val Ile Lys Ser His Met Thr Tyr Trp Arg
        115                 120                 125 tta gag aac ata gcg aaa act gaa cca cct aag att ttc cgt gtg aaa    432
Leu Glu Asn Ile Ala Lys Thr Glu Pro Pro Lys Ile Phe Arg Val Lys
    130                 135                 140 cca gtt ttg ggc atc aaa cga atg att caa att gaa tgg ata aag cct    480
Pro Val Leu Gly Ile Lys Arg Met Ile Gln Ile Glu Trp Ile Lys Pro
145                 150                 155                 160 gag ttg gcg cct gtt tca tct gat tta aaa tac aca ctt cga ttc agg    528
Glu Leu Ala Pro Val Ser Ser Asp Leu Lys Tyr Thr Leu Arg Phe Arg
                165                 170                 175 aca gtc aac agt acc agc tgg atg gaa gtc aac ttc gct aag aac cgt    576
Thr Val Asn Ser Thr Ser Trp Met Glu Val Asn Phe Ala Lys Asn Arg
            180                 185                 190 aag gat aaa aac caa acg tac aac ctc acg ggg ctg cag cct ttt aca    624
Lys Asp Lys Asn Gln Thr Tyr Asn Leu Thr Gly Leu Gln Pro Phe Thr
        195                 200                 205 gaa tat gtc ata gct ctg cga tgt gcg gtc aag gag tca aag ttc tgg    672
Glu Tyr Val Ile Ala Leu Arg Cys Ala Val Lys Glu Ser Lys Phe Trp
    210                 215                 220 agt gac tgg agc caa gaa aaa atg gga atg act gag gaa gaa gct cca    720
Ser Asp Trp Ser Gln Glu Lys Met Gly Met Thr Glu Glu Glu Ala Pro
225                 230                 235                 240 tgt ggc ctg gaa ctg tgg aga gtc ctg aaa cca gct gag gcg gat gga    768
Cys Gly Leu Glu Leu Trp Arg Val Leu Lys Pro Ala Glu Ala Asp Gly
                245                 250                 255 aga agg cca gtg cgg ttg tta tgg aag aag gca aga gga gcc cca gtc    816
Arg Arg Pro Val Arg Leu Leu Trp Lys Lys Ala Arg Gly Ala Pro Val
            260                 265                 270 cta gag aaa aca ctt ggc tac aac ata tgg tac tat cca gaa agc aac    864
Leu Glu Lys Thr Leu Gly Tyr Asn Ile Trp Tyr Tyr Pro Glu Ser Asn
        275                 280                 285 act aac ctc aca gaa aca atg aac act act aac cag cag ctt gaa ctg    912
Thr Asn Leu Thr Glu Thr Met Asn Thr Thr Asn Gln Gln Leu Glu Leu
    290                 295                 300 cat ctg gga ggc gag agc ttt tgg gtg tct atg att tct tat aat tct    960
His Leu Gly Gly Glu Ser Phe Trp Val Ser Met Ile Ser Tyr Asn Ser
305                 310                 315                 320 ctt ggg aag tct cca gtg gcc acc ctg agg att cca gct att caa gaa   1008
Leu Gly Lys Ser Pro Val Ala Thr Leu Arg Ile Pro Ala Ile Gln Glu
                325                 330                 335 aaa tca ttt cag tgc att gag gtc atg cag gcc tgc gtt gct gag gac   1056
Lys Ser Phe Gln Cys Ile Glu Val Met Gln Ala Cys Val Ala Glu Asp
            340                 345                 350 cag cta gtg gtg aag tgg caa agc tct gct cta gac gtg aac act tgg   1104
Gln Leu Val Val Lys Trp Gln Ser Ser Ala Leu Asp Val Asn Thr Trp
        355                 360                 365 atg att gaa tgg ttt ccg gat gtg gac tca gag ccc acc acc ctt tcc   1152
Met Ile Glu Trp Phe Pro Asp Val Asp Ser Glu Pro Thr Thr Leu Ser
    370                 375                 380 tgg gaa tct gtg tct cag gcc acg aac tgg acg atc cag caa gat aaa   1200
Trp Glu Ser Val Ser Gln Ala Thr Asn Trp Thr Ile Gln Gln Asp Lys
```

|   |   |   |   |   |   |   |   |   |   |   |   |   |   |   |   |
|---|---|---|---|---|---|---|---|---|---|---|---|---|---|---|---|
| 385 |   |   |   |   | 390 |   |   |   |   | 395 |   |   |   |   | 400 |

| tta | aaa | ccc | ttc | tgg | tgc | tat | aac | atc | tct | gtg | tat | cca | atg | ttg | cat | 1248 |
|---|---|---|---|---|---|---|---|---|---|---|---|---|---|---|---|---|
| Leu | Lys | Pro | Phe | Trp | Cys | Tyr | Asn | Ile | Ser | Val | Tyr | Pro | Met | Leu | His | |
|   |   |   |   | 405 |   |   |   |   | 410 |   |   |   |   | 415 |   | |

| gac | aaa | gtt | ggc | gag | cca | tat | tcc | atc | cag | gct | tat | gcc | aaa | gaa | ggc | 1296 |
|---|---|---|---|---|---|---|---|---|---|---|---|---|---|---|---|---|
| Asp | Lys | Val | Gly | Glu | Pro | Tyr | Ser | Ile | Gln | Ala | Tyr | Ala | Lys | Glu | Gly | |
|   |   |   | 420 |   |   |   |   | 425 |   |   |   |   | 430 |   |   | |

| gtt | cca | tca | gaa | ggt | cct | gag | acc | aag | gtg | gag | aac | att | ggc | gtg | aag | 1344 |
|---|---|---|---|---|---|---|---|---|---|---|---|---|---|---|---|---|
| Val | Pro | Ser | Glu | Gly | Pro | Glu | Thr | Lys | Val | Glu | Asn | Ile | Gly | Val | Lys | |
|   |   | 435 |   |   |   |   | 440 |   |   |   |   | 445 |   |   |   | |

| acg | gtc | acg | atc | aca | tgg | aaa | gag | att | ccc | aag | agt | gag | aga | aag | ggt | 1392 |
|---|---|---|---|---|---|---|---|---|---|---|---|---|---|---|---|---|
| Thr | Val | Thr | Ile | Thr | Trp | Lys | Glu | Ile | Pro | Lys | Ser | Glu | Arg | Lys | Gly | |
|   |   | 450 |   |   |   |   | 455 |   |   |   |   | 460 |   |   |   | |

| atc | atc | tgc | aac | tac | acc | atc | ttt | tac | caa | gct | gaa | ggt | gga | aaa | gga | 1440 |
|---|---|---|---|---|---|---|---|---|---|---|---|---|---|---|---|---|
| Ile | Ile | Cys | Asn | Tyr | Thr | Ile | Phe | Tyr | Gln | Ala | Glu | Gly | Gly | Lys | Gly | |
| 465 |   |   |   |   | 470 |   |   |   |   | 475 |   |   |   |   | 480 | |

| ttc | tcc | aag | aca | gtc | aat | tcc | agc | atc | ttg | cag | tac | ggc | ctg | gag | tcc | 1488 |
|---|---|---|---|---|---|---|---|---|---|---|---|---|---|---|---|---|
| Phe | Ser | Lys | Thr | Val | Asn | Ser | Ser | Ile | Leu | Gln | Tyr | Gly | Leu | Glu | Ser | |
|   |   |   |   | 485 |   |   |   |   | 490 |   |   |   |   | 495 |   | |

| ctg | aaa | cga | aag | acc | tct | tac | att | gtt | cag | gtc | atg | gcc | agc | acc | agt | 1536 |
|---|---|---|---|---|---|---|---|---|---|---|---|---|---|---|---|---|
| Leu | Lys | Arg | Lys | Thr | Ser | Tyr | Ile | Val | Gln | Val | Met | Ala | Ser | Thr | Ser | |
|   |   |   | 500 |   |   |   |   | 505 |   |   |   |   | 510 |   |   | |

| gct | ggg | gga | acc | aac | ggg | acc | agc | ata | aat | ttc | aag | aca | ttg | tca | ttc | 1584 |
|---|---|---|---|---|---|---|---|---|---|---|---|---|---|---|---|---|
| Ala | Gly | Gly | Thr | Asn | Gly | Thr | Ser | Ile | Asn | Phe | Lys | Thr | Leu | Ser | Phe | |
|   |   |   | 515 |   |   |   |   | 520 |   |   |   |   | 525 |   |   | |

| agt | gtc | ttt | gag | gag | ccc | aga | tct | tca | gac | aaa | act | cac | aca | tgc | cca | 1632 |
|---|---|---|---|---|---|---|---|---|---|---|---|---|---|---|---|---|
| Ser | Val | Phe | Glu | Glu | Pro | Arg | Ser | Ser | Asp | Lys | Thr | His | Thr | Cys | Pro | |
|   |   | 530 |   |   |   |   | 535 |   |   |   |   | 540 |   |   |   | |

| ccg | tgc | cca | gca | cct | gaa | gcc | gag | ggg | gca | ccg | tca | gtc | ttc | ctc | ttc | 1680 |
|---|---|---|---|---|---|---|---|---|---|---|---|---|---|---|---|---|
| Pro | Cys | Pro | Ala | Pro | Glu | Ala | Glu | Gly | Ala | Pro | Ser | Val | Phe | Leu | Phe | |
| 545 |   |   |   |   | 550 |   |   |   |   | 555 |   |   |   |   | 560 | |

| ccc | cca | aaa | ccc | aag | gac | acc | ctc | atg | atc | tcc | cgg | acc | cct | gag | gtc | 1728 |
|---|---|---|---|---|---|---|---|---|---|---|---|---|---|---|---|---|
| Pro | Pro | Lys | Pro | Lys | Asp | Thr | Leu | Met | Ile | Ser | Arg | Thr | Pro | Glu | Val | |
|   |   |   |   | 565 |   |   |   |   | 570 |   |   |   |   | 575 |   | |

| aca | tgc | gtg | gtg | gtg | gac | gtg | agc | cac | gaa | gac | cct | gag | gtc | aag | ttc | 1776 |
|---|---|---|---|---|---|---|---|---|---|---|---|---|---|---|---|---|
| Thr | Cys | Val | Val | Val | Asp | Val | Ser | His | Glu | Asp | Pro | Glu | Val | Lys | Phe | |
|   |   |   |   | 580 |   |   |   |   | 585 |   |   |   |   | 590 |   | |

| aac | tgg | tac | gtg | gac | ggc | gtg | gag | gtg | cat | aat | gcc | aag | aca | aag | ccg | 1824 |
|---|---|---|---|---|---|---|---|---|---|---|---|---|---|---|---|---|
| Asn | Trp | Tyr | Val | Asp | Gly | Val | Glu | Val | His | Asn | Ala | Lys | Thr | Lys | Pro | |
|   |   |   | 595 |   |   |   |   | 600 |   |   |   |   | 605 |   |   | |

| cgg | gag | gag | cag | tac | aac | agc | acg | tac | cgt | gtg | gtc | agc | gtc | ctc | acc | 1872 |
|---|---|---|---|---|---|---|---|---|---|---|---|---|---|---|---|---|
| Arg | Glu | Glu | Gln | Tyr | Asn | Ser | Thr | Tyr | Arg | Val | Val | Ser | Val | Leu | Thr | |
|   |   | 610 |   |   |   |   | 615 |   |   |   |   | 620 |   |   |   | |

| gtc | ctg | cac | cag | gac | tgg | ctg | aat | ggc | aag | gag | tac | aag | tgc | aag | gtc | 1920 |
|---|---|---|---|---|---|---|---|---|---|---|---|---|---|---|---|---|
| Val | Leu | His | Gln | Asp | Trp | Leu | Asn | Gly | Lys | Glu | Tyr | Lys | Cys | Lys | Val | |
| 625 |   |   |   |   | 630 |   |   |   |   | 635 |   |   |   |   | 640 | |

| tcc | aac | aaa | gcc | ctc | cca | tcc | tcc | atc | gag | aaa | acc | atc | tcc | aaa | gcc | 1968 |
|---|---|---|---|---|---|---|---|---|---|---|---|---|---|---|---|---|
| Ser | Asn | Lys | Ala | Leu | Pro | Ser | Ser | Ile | Glu | Lys | Thr | Ile | Ser | Lys | Ala | |
|   |   |   |   | 645 |   |   |   |   | 650 |   |   |   |   | 655 |   | |

| aaa | ggg | cag | ccc | cga | gaa | cca | cag | gtg | tac | acc | ctg | ccc | cca | tcc | cgg | 2016 |
|---|---|---|---|---|---|---|---|---|---|---|---|---|---|---|---|---|
| Lys | Gly | Gln | Pro | Arg | Glu | Pro | Gln | Val | Tyr | Thr | Leu | Pro | Pro | Ser | Arg | |
|   |   |   | 660 |   |   |   |   | 665 |   |   |   |   | 670 |   |   | |

| gat | gag | ctg | acc | aag | aac | cag | gtc | agc | ctg | acc | tgc | ctg | gtc | aaa | ggc | 2064 |
|---|---|---|---|---|---|---|---|---|---|---|---|---|---|---|---|---|
| Asp | Glu | Leu | Thr | Lys | Asn | Gln | Val | Ser | Leu | Thr | Cys | Leu | Val | Lys | Gly | |
|   |   |   | 675 |   |   |   |   | 680 |   |   |   |   | 685 |   |   | |

| ttc | tat | ccc | agc | gac | atc | gcc | gtg | gag | tgg | gag | agc | aat | ggg | cag | ccg | 2112 |
|---|---|---|---|---|---|---|---|---|---|---|---|---|---|---|---|---|
| Phe | Tyr | Pro | Ser | Asp | Ile | Ala | Val | Glu | Trp | Glu | Ser | Asn | Gly | Gln | Pro | |
|   |   | 690 |   |   |   |   | 695 |   |   |   |   | 700 |   |   |   | |

| gag | aac | aac | tac | aag | acc | acg | cct | ccc | gtg | ctg | gac | tcc | gac | ggc | tcc | 2160 |

```
Glu Asn Asn Tyr Lys Thr Thr Pro Val Leu Asp Ser Asp Gly Ser
705                 710                 715                 720 ttc ttc ctc tac agc aag ctc acc gtg gac aag agc agg tgg cag cag      2208
Phe Phe Leu Tyr Ser Lys Leu Thr Val Asp Lys Ser Arg Trp Gln Gln
                725                 730                 735 ggg aac gtc ttc tca tgc tcc gtg atg cat gag gct ctg cac aac cac      2256
Gly Asn Val Phe Ser Cys Ser Val Met His Glu Ala Leu His Asn His
            740                 745                 750 tac acg cag aag agc ctc tcc ctg tct ccg ggt aaa taa                   2295
Tyr Thr Gln Lys Ser Leu Ser Leu Ser Pro Gly Lys *
            755                 760

<210> SEQ ID NO 39
<211> LENGTH: 764
<212> TYPE: PRT
<213> ORGANISM: Artificial Sequence
<220> FEATURE:
<223> OTHER INFORMATION: human zcytor17-Fc4 fusion polypeptide

<400> SEQUENCE: 39

Met Lys Leu Ser Pro Gln Pro Ser Cys Val Asn Leu Gly Met Met Trp
1               5                   10                  15

Thr Trp Ala Leu Trp Met Leu Pro Ser Leu Cys Lys Phe Ser Leu Ala
            20                  25                  30

Ala Leu Pro Ala Lys Pro Glu Asn Ile Ser Cys Val Tyr Tyr Tyr Arg
        35                  40                  45

Lys Asn Leu Thr Cys Thr Trp Ser Pro Gly Lys Glu Thr Ser Tyr Thr
    50                  55                  60

Gln Tyr Thr Val Lys Arg Thr Tyr Ala Phe Gly Glu Lys His Asp Asn
65                  70                  75                  80

Cys Thr Thr Asn Ser Ser Thr Ser Glu Asn Arg Ala Ser Cys Ser Phe
                85                  90                  95

Phe Leu Pro Arg Ile Thr Ile Pro Asp Asn Tyr Thr Ile Glu Val Glu
            100                 105                 110

Ala Glu Asn Gly Asp Gly Val Ile Lys Ser His Met Thr Tyr Trp Arg
        115                 120                 125

Leu Glu Asn Ile Ala Lys Thr Glu Pro Pro Lys Ile Phe Arg Val Lys
    130                 135                 140

Pro Val Leu Gly Ile Lys Arg Met Ile Gln Ile Glu Trp Ile Lys Pro
145                 150                 155                 160

Glu Leu Ala Pro Val Ser Ser Asp Leu Lys Tyr Thr Leu Arg Phe Arg
                165                 170                 175

Thr Val Asn Ser Thr Ser Trp Met Glu Val Asn Phe Ala Lys Asn Arg
            180                 185                 190

Lys Asp Lys Asn Gln Thr Tyr Asn Leu Thr Gly Leu Gln Pro Phe Thr
        195                 200                 205

Glu Tyr Val Ile Ala Leu Arg Cys Ala Val Lys Glu Ser Lys Phe Trp
    210                 215                 220

Ser Asp Trp Ser Gln Glu Lys Met Gly Met Thr Glu Glu Ala Pro
225                 230                 235                 240

Cys Gly Leu Glu Leu Trp Arg Val Leu Lys Pro Ala Glu Ala Asp Gly
                245                 250                 255

Arg Arg Pro Val Arg Leu Leu Trp Lys Lys Ala Arg Gly Ala Pro Val
            260                 265                 270

Leu Glu Lys Thr Leu Gly Tyr Asn Ile Trp Tyr Tyr Pro Glu Ser Asn
        275                 280                 285
```

```
Thr Asn Leu Thr Glu Thr Met Asn Thr Thr Asn Gln Gln Leu Glu Leu
    290                 295                 300

His Leu Gly Gly Glu Ser Phe Trp Val Ser Met Ile Ser Tyr Asn Ser
305                 310                 315                 320

Leu Gly Lys Ser Pro Val Ala Thr Leu Arg Ile Pro Ala Ile Gln Glu
                325                 330                 335

Lys Ser Phe Gln Cys Ile Glu Val Met Gln Ala Cys Val Ala Glu Asp
                340                 345                 350

Gln Leu Val Val Lys Trp Gln Ser Ala Leu Asp Val Asn Thr Trp
            355                 360                 365

Met Ile Glu Trp Phe Pro Asp Val Asp Ser Gly Pro Thr Thr Leu Ser
370                 375                 380

Trp Glu Ser Val Ser Gln Ala Thr Asn Trp Thr Ile Gln Gln Asp Lys
385                 390                 395                 400

Leu Lys Pro Phe Trp Cys Tyr Asn Ile Ser Val Tyr Pro Met Leu His
                405                 410                 415

Asp Lys Val Gly Glu Pro Tyr Ser Ile Gln Ala Tyr Ala Lys Glu Gly
                420                 425                 430

Val Pro Ser Glu Gly Pro Glu Thr Lys Val Glu Asn Ile Gly Val Lys
            435                 440                 445

Thr Val Thr Ile Thr Trp Lys Glu Ile Pro Lys Ser Glu Arg Lys Gly
        450                 455                 460

Ile Ile Cys Asn Tyr Thr Ile Phe Tyr Gln Ala Glu Gly Gly Lys Gly
465                 470                 475                 480

Phe Ser Lys Thr Val Asn Ser Ser Ile Leu Gln Tyr Gly Leu Glu Ser
                485                 490                 495

Leu Lys Arg Lys Thr Ser Tyr Ile Val Gln Val Met Ala Ser Thr Ser
            500                 505                 510

Ala Gly Gly Thr Asn Gly Thr Ser Ile Asn Phe Lys Thr Leu Ser Phe
        515                 520                 525

Ser Val Phe Glu Glu Pro Arg Ser Ser Asp Lys Thr His Thr Cys Pro
530                 535                 540

Pro Cys Pro Ala Pro Glu Ala Glu Gly Ala Pro Ser Val Phe Leu Phe
545                 550                 555                 560

Pro Pro Lys Pro Lys Asp Thr Leu Met Ile Ser Arg Thr Pro Glu Val
                565                 570                 575

Thr Cys Val Val Val Asp Val Ser His Glu Asp Pro Glu Val Lys Phe
                580                 585                 590

Asn Trp Tyr Val Asp Gly Val Glu Val His Asn Ala Lys Thr Lys Pro
            595                 600                 605

Arg Glu Glu Gln Tyr Asn Ser Thr Tyr Arg Val Val Ser Val Leu Thr
610                 615                 620

Val Leu His Gln Asp Trp Leu Asn Gly Lys Glu Tyr Lys Cys Lys Val
625                 630                 635                 640

Ser Asn Lys Ala Leu Pro Ser Ser Ile Glu Lys Thr Ile Ser Lys Ala
                645                 650                 655

Lys Gly Gln Pro Arg Glu Pro Gln Val Tyr Thr Leu Pro Pro Ser Arg
                660                 665                 670

Asp Glu Leu Thr Lys Asn Gln Val Ser Leu Thr Cys Leu Val Lys Gly
            675                 680                 685

Phe Tyr Pro Ser Asp Ile Ala Val Glu Trp Glu Ser Asn Gly Gln Pro
        690                 695                 700

Glu Asn Asn Tyr Lys Thr Thr Pro Pro Val Leu Asp Ser Asp Gly Ser
```

```
                705                 710                 715                 720
            Phe Phe Leu Tyr Ser Lys Leu Thr Val Asp Lys Ser Arg Trp Gln Gln
                            725                 730                 735
            Gly Asn Val Phe Ser Cys Ser Val Met His Glu Ala Leu His Asn His
                            740                 745                 750
            Tyr Thr Gln Lys Ser Leu Ser Leu Ser Pro Gly Lys
                            755                 760
```

```
<210> SEQ ID NO 40
<211> LENGTH: 34
<212> TYPE: DNA
<213> ORGANISM: Artificial Sequence
<220> FEATURE:
<223> OTHER INFORMATION: Oligonucleotide primer ZC29157

<400> SEQUENCE: 40
ctagtatggc cggccatgaa gctctctccc cagc                                    34

<210> SEQ ID NO 41
<211> LENGTH: 41
<212> TYPE: DNA
<213> ORGANISM: Artificial Sequence
<220> FEATURE:
<223> OTHER INFORMATION: Oligonucleotide primer ZC29150

<400> SEQUENCE: 41
gtctgaagat ctgggctcct caaagacact gaatgacaat g                            41

<210> SEQ ID NO 42
<211> LENGTH: 21
<212> TYPE: DNA
<213> ORGANISM: Artificial Sequence
<220> FEATURE:
<223> OTHER INFORMATION: Oligonucleotide primer ZC41458

<400> SEQUENCE: 42
tggacctcgc actaaaatca t                                                  21

<210> SEQ ID NO 43
<211> LENGTH: 22
<212> TYPE: DNA
<213> ORGANISM: Artificial Sequence
<220> FEATURE:
<223> OTHER INFORMATION: Oligonucleotide primer ZC41457

<400> SEQUENCE: 43
aatcacggca gagttcccac ac                                                 22

<210> SEQ ID NO 44
<211> LENGTH: 100
<212> TYPE: DNA
<213> ORGANISM: Artificial Sequence
<220> FEATURE:
<223> OTHER INFORMATION: Oligonucleotide primer ZC12749

<400> SEQUENCE: 44
gtaccttccc gtaaatccct ccccttcccg gaattacacc cgcgtatttc ccagaaaagg        60
aactgtagat ttctaggaat tcaatccttg gccacgcgtc                             100

<210> SEQ ID NO 45
<211> LENGTH: 100
<212> TYPE: DNA
<213> ORGANISM: Artificial Sequence
<220> FEATURE:
```

```
<223> OTHER INFORMATION: Oligonucleotide primer ZC12748

<400> SEQUENCE: 45
tcgagacgcg tggccaagga ttgaattcct agaaatctac agttcctttt ctgggaaata    60
cgcgggtgta attccgggaa ggggagggat ttacgggaag                          100

<210> SEQ ID NO 46
<211> LENGTH: 20
<212> TYPE: DNA
<213> ORGANISM: Artificial Sequence
<220> FEATURE:
<223> OTHER INFORMATION: Oligonucleotide primer ZC10651

<400> SEQUENCE: 46
agcttttctg cagcagctct                                                 20

<210> SEQ ID NO 47
<211> LENGTH: 23
<212> TYPE: DNA
<213> ORGANISM: Artificial Sequence
<220> FEATURE:
<223> OTHER INFORMATION: Oligonucleotide primer ZC10565

<400> SEQUENCE: 47
tttgcagaaa aggttgcaaa tgc                                             23

<210> SEQ ID NO 48
<211> LENGTH: 25
<212> TYPE: DNA
<213> ORGANISM: Artificial Sequence
<220> FEATURE:
<223> OTHER INFORMATION: Oligonucleotide primer ZC14063

<400> SEQUENCE: 48
caccagacat aatagctgac agact                                           25

<210> SEQ ID NO 49
<211> LENGTH: 21
<212> TYPE: DNA
<213> ORGANISM: Artificial Sequence
<220> FEATURE:
<223> OTHER INFORMATION: Oligonucleotide primer ZC17574

<400> SEQUENCE: 49
ggtrttgctc agcatgcaca c                                               21

<210> SEQ ID NO 50
<211> LENGTH: 24
<212> TYPE: DNA
<213> ORGANISM: Artificial Sequence
<220> FEATURE:
<223> OTHER INFORMATION: Oligonucleotide primer ZC17600

<400> SEQUENCE: 50
catgtaggcc atgaggtcca ccac                                            24

<210> SEQ ID NO 51
<211> LENGTH: 21
<212> TYPE: DNA
<213> ORGANISM: Artificial Sequence
<220> FEATURE:
<223> OTHER INFORMATION: Oligonucleotide primer ZC38065

<400> SEQUENCE: 51
ctttcctggg aatctgtgtc t                                               21
```

<210> SEQ ID NO 52
<211> LENGTH: 18
<212> TYPE: DNA
<213> ORGANISM: Artificial Sequence
<220> FEATURE:
<223> OTHER INFORMATION: Oligonucleotide primer ZC38068

<400> SEQUENCE: 52
cctccagctc tggtgctg                                             18

<210> SEQ ID NO 53
<211> LENGTH: 24
<212> TYPE: DNA
<213> ORGANISM: Artificial Sequence
<220> FEATURE:
<223> OTHER INFORMATION: Oligonucleotide primer ZC37877

<400> SEQUENCE: 53
caaaaaaccc aacaaattga ctca                                      24

<210> SEQ ID NO 54
<211> LENGTH: 25
<212> TYPE: DNA
<213> ORGANISM: Artificial Sequence
<220> FEATURE:
<223> OTHER INFORMATION: Oligonucleotide primer ZC37876

<400> SEQUENCE: 54
catgtggcta tactactttc agcag                                     25

<210> SEQ ID NO 55
<211> LENGTH: 22
<212> TYPE: DNA
<213> ORGANISM: Artificial Sequence
<220> FEATURE:
<223> OTHER INFORMATION: zcytor17 receptor TaqManr probe

<400> SEQUENCE: 55
ctgtgttggc ccaccgttcc ca                                        22

<210> SEQ ID NO 56
<211> LENGTH: 20
<212> TYPE: DNA
<213> ORGANISM: Artificial Sequence
<220> FEATURE:
<223> OTHER INFORMATION: rRNA forward primer

<400> SEQUENCE: 56
cggctaccac atccaaggaa                                           20

<210> SEQ ID NO 57
<211> LENGTH: 18
<212> TYPE: DNA
<213> ORGANISM: Artificial Sequence
<220> FEATURE:
<223> OTHER INFORMATION: the rRNA reverse primer

<400> SEQUENCE: 57
gctggaatta ccgcggct                                             18

<210> SEQ ID NO 58
<211> LENGTH: 22
<212> TYPE: DNA
<213> ORGANISM: Artificial Sequence
<220> FEATURE:

<223> OTHER INFORMATION: rRNA TaqManr probe

<400> SEQUENCE: 58
tgctggcacc agacttgccc tc                                          22

<210> SEQ ID NO 59
<220> FEATURE:
<223> OTHER INFORMATION: Skipped Sequence

<400> SEQUENCE: 59

000

<210> SEQ ID NO 60
<211> LENGTH: 21
<212> TYPE: DNA
<213> ORGANISM: Artificial Sequence
<220> FEATURE:
<223> OTHER INFORMATION: Oligonucleotide primer ZC41458

<400> SEQUENCE: 60
tggacctcgc actaaaatca t                                           21

<210> SEQ ID NO 61
<211> LENGTH: 22
<212> TYPE: DNA
<213> ORGANISM: Artificial Sequence
<220> FEATURE:
<223> OTHER INFORMATION: Oligonucleotide primer ZC41457

<400> SEQUENCE: 61
aatcacggca gagttcccac ac                                          22

<210> SEQ ID NO 62
<211> LENGTH: 19
<212> TYPE: DNA
<213> ORGANISM: Artificial Sequence
<220> FEATURE:
<223> OTHER INFORMATION: Oligonucleotide primer ZC41459

<400> SEQUENCE: 62
agaagggcgt gctcgtgtc                                              19

<210> SEQ ID NO 63
<211> LENGTH: 18
<212> TYPE: DNA
<213> ORGANISM: Artificial Sequence
<220> FEATURE:
<223> OTHER INFORMATION: Oligonucleotide primer ZC41460

<400> SEQUENCE: 63
ccggatggct gggctgtg                                               18

<210> SEQ ID NO 64
<211> LENGTH: 25
<212> TYPE: DNA
<213> ORGANISM: Artificial Sequence
<220> FEATURE:
<223> OTHER INFORMATION: Oligonucleotide primer ZC39982

<400> SEQUENCE: 64
aatgtctgtg tagcataagg tatga                                       25

<210> SEQ ID NO 65
<211> LENGTH: 22
<212> TYPE: DNA

```
<213> ORGANISM: Artificial Sequence
<220> FEATURE:
<223> OTHER INFORMATION: Oligonucleotide primer ZC39983

<400> SEQUENCE: 65
cctgcctacc tgaaaaccag aa                                              22

<210> SEQ ID NO 66
<211> LENGTH: 36
<212> TYPE: DNA
<213> ORGANISM: Artificial Sequence
<220> FEATURE:
<223> OTHER INFORMATION: Oligonucleotide primer ZC39980

<400> SEQUENCE: 66
tttgaattcg ccaccatggc tctatttgca gtcttt                               36

<210> SEQ ID NO 67
<211> LENGTH: 28
<212> TYPE: DNA
<213> ORGANISM: Artificial Sequence
<220> FEATURE:
<223> OTHER INFORMATION: Oligonucleotide primer ZC39981

<400> SEQUENCE: 67
ctgtctcgag tgctggttag cagtgttc                                        28

<210> SEQ ID NO 68
<211> LENGTH: 2217
<212> TYPE: DNA
<213> ORGANISM: Homo sapiens
<220> FEATURE:
<221> NAME/KEY: CDS
<222> LOCATION: (1)...(2217)

<400> SEQUENCE: 68 atg gct cta ttt gca gtc ttt cag aca aca ttc ttc tta aca ttg ctg      48
Met Ala Leu Phe Ala Val Phe Gln Thr Thr Phe Phe Leu Thr Leu Leu
 1               5                  10                  15 tcc ttg agg act tac cag agt gaa gtc ttg gct gaa cgt tta cca ttg      96
Ser Leu Arg Thr Tyr Gln Ser Glu Val Leu Ala Glu Arg Leu Pro Leu
            20                  25                  30 act cct gta tca ctt aaa gtt tcc acc aat tct acg cgt cag agt ttg     144
Thr Pro Val Ser Leu Lys Val Ser Thr Asn Ser Thr Arg Gln Ser Leu
        35                  40                  45 cac tta caa tgg act gtc cac aac ctt cct tat cat cag gaa ttg aaa     192
His Leu Gln Trp Thr Val His Asn Leu Pro Tyr His Gln Glu Leu Lys
    50                  55                  60 atg gta ttt cag atc cag atc agt agg att gaa aca tcc aat gtc atc     240
Met Val Phe Gln Ile Gln Ile Ser Arg Ile Glu Thr Ser Asn Val Ile
65                  70                  75                  80 tgg gtg ggg aat tac agc acc act gtg aag tgg aac cag gtt ctg cat     288
Trp Val Gly Asn Tyr Ser Thr Thr Val Lys Trp Asn Gln Val Leu His
                85                  90                  95 tgg agc tgg gaa tct gag ctc cct ttg gaa tgt gcc aca cac ttt gta     336
Trp Ser Trp Glu Ser Glu Leu Pro Leu Glu Cys Ala Thr His Phe Val
           100                 105                 110 aga ata aag agt ttg gtg gac gat gcc aag ttc cct gag cca aat ttc     384
Arg Ile Lys Ser Leu Val Asp Asp Ala Lys Phe Pro Glu Pro Asn Phe
       115                 120                 125 tgg agc aac tgg agt tcc tgg gag gaa gtc agt gta caa gat tct act     432
Trp Ser Asn Trp Ser Ser Trp Glu Glu Val Ser Val Gln Asp Ser Thr
   130                 135                 140
```

```
gga cag gat ata ttg ttc gtt ttc cct aaa gat aag ctg gtg gaa gaa       480
Gly Gln Asp Ile Leu Phe Val Phe Pro Lys Asp Lys Leu Val Glu Glu
145                 150                 155                 160 ggc acc aat gtt acc att tgt tac gtt tct agg aac att caa aat aat       528
Gly Thr Asn Val Thr Ile Cys Tyr Val Ser Arg Asn Ile Gln Asn Asn
                165                 170                 175 gta tcc tgt tat ttg gaa ggg aaa cag att cat gga gaa caa ctt gat       576
Val Ser Cys Tyr Leu Glu Gly Lys Gln Ile His Gly Glu Gln Leu Asp
            180                 185                 190 cca cat gta act gca ttc aac ttg aat agt gtg cct ttc att agg aat       624
Pro His Val Thr Ala Phe Asn Leu Asn Ser Val Pro Phe Ile Arg Asn
        195                 200                 205 aaa ggg aca aat atc tat tgt gag gca agt caa gga aat gtc agt gaa       672
Lys Gly Thr Asn Ile Tyr Cys Glu Ala Ser Gln Gly Asn Val Ser Glu
    210                 215                 220 ggc atg aaa ggc atc gtt ctt ttt gtc tca aaa gta ctt gag gag ccc       720
Gly Met Lys Gly Ile Val Leu Phe Val Ser Lys Val Leu Glu Glu Pro
225                 230                 235                 240 aag gac ttt tct tgt gaa acc gag gac ttc aag act ttg cac tgt act       768
Lys Asp Phe Ser Cys Glu Thr Glu Asp Phe Lys Thr Leu His Cys Thr
                245                 250                 255 tgg gat cct ggg acg gac act gcc ttg ggg tgg tct aaa caa cct tcc       816
Trp Asp Pro Gly Thr Asp Thr Ala Leu Gly Trp Ser Lys Gln Pro Ser
            260                 265                 270 caa agc tac act tta ttt gaa tca ttt tct ggg gaa aag aaa ctt tgt       864
Gln Ser Tyr Thr Leu Phe Glu Ser Phe Ser Gly Glu Lys Lys Leu Cys
        275                 280                 285 aca cac aaa aac tgg tgt aat tgg caa ata act caa gac tca caa gaa       912
Thr His Lys Asn Trp Cys Asn Trp Gln Ile Thr Gln Asp Ser Gln Glu
    290                 295                 300 acc tat aac ttc aca ctc ata gct gaa aat tac tta agg aag aga agt       960
Thr Tyr Asn Phe Thr Leu Ile Ala Glu Asn Tyr Leu Arg Lys Arg Ser
305                 310                 315                 320 gtc aat atc ctt ttt aac ctg act cat cga gtt tat tta atg aat cct      1008
Val Asn Ile Leu Phe Asn Leu Thr His Arg Val Tyr Leu Met Asn Pro
                325                 330                 335 ttt agt gtc aac ttt gaa aat gta aat gcc aca aat gcc atc atg acc      1056
Phe Ser Val Asn Phe Glu Asn Val Asn Ala Thr Asn Ala Ile Met Thr
            340                 345                 350 tgg aag gtg cac tcc ata agg aat aat ttc aca tat ttg tgt cag att      1104
Trp Lys Val His Ser Ile Arg Asn Asn Phe Thr Tyr Leu Cys Gln Ile
        355                 360                 365 gaa ctc cat ggt gaa gga aaa atg atg caa tac aat gtt tcc atc aag      1152
Glu Leu His Gly Glu Gly Lys Met Met Gln Tyr Asn Val Ser Ile Lys
    370                 375                 380 gtg aac ggt gag tac ttc tta agt gaa ctg gaa cct gcc aca gag tac      1200
Val Asn Gly Glu Tyr Phe Leu Ser Glu Leu Glu Pro Ala Thr Glu Tyr
385                 390                 395                 400 atg gcg cga gta cgg tgt gct gat gcc agc cac ttc tgg aaa tgg agt      1248
Met Ala Arg Val Arg Cys Ala Asp Ala Ser His Phe Trp Lys Trp Ser
                405                 410                 415 gaa tgg agt ggt cag aac ttc acc aca ctt gaa gct gct ccc tca gag      1296
Glu Trp Ser Gly Gln Asn Phe Thr Thr Leu Glu Ala Ala Pro Ser Glu
            420                 425                 430 gcc cct gat gtc tgg aga att gtg agc ttg gag cca gga aat cat act      1344
Ala Pro Asp Val Trp Arg Ile Val Ser Leu Glu Pro Gly Asn His Thr
        435                 440                 445 gtg acc tta ttc tgg aag cca tta tca aaa ctg cat gcc aat gga aag      1392
Val Thr Leu Phe Trp Lys Pro Leu Ser Lys Leu His Ala Asn Gly Lys
    450                 455                 460
```

```
atc ctg ttc tat aat gta gtt gta gaa aac cta gac aaa cca tcc agt     1440
Ile Leu Phe Tyr Asn Val Val Val Glu Asn Leu Asp Lys Pro Ser Ser
465                 470                 475                 480 tca gag ctc cat tcc att cca gca cca gcc aac agc aca aaa cta atc     1488
Ser Glu Leu His Ser Ile Pro Ala Pro Ala Asn Ser Thr Lys Leu Ile
                485                 490                 495 ctt gac agg tgt tcc tac caa atc tgc gtc ata gcc aac aac agt gtg     1536
Leu Asp Arg Cys Ser Tyr Gln Ile Cys Val Ile Ala Asn Asn Ser Val
            500                 505                 510 ggt gct tct cct gct tct gta ata gtc atc tct gca gac ccc gaa aac     1584
Gly Ala Ser Pro Ala Ser Val Ile Val Ile Ser Ala Asp Pro Glu Asn
        515                 520                 525 aaa gag gtt gag gaa gaa aga att gca ggc aca gag ggt gga ttc tct     1632
Lys Glu Val Glu Glu Glu Arg Ile Ala Gly Thr Glu Gly Gly Phe Ser
    530                 535                 540 ctg tct tgg aaa ccc caa cct gga gat gtt ata ggc tat gtt gtg gac     1680
Leu Ser Trp Lys Pro Gln Pro Gly Asp Val Ile Gly Tyr Val Val Asp
545                 550                 555                 560 tgg tgt gac cat acc cag gat gtg ctc ggt gat ttc cag tgg aag aat     1728
Trp Cys Asp His Thr Gln Asp Val Leu Gly Asp Phe Gln Trp Lys Asn
                565                 570                 575 gta ggt ccc aat acc aca agc aca gtc att agc aca gat gct ttt agg     1776
Val Gly Pro Asn Thr Thr Ser Thr Val Ile Ser Thr Asp Ala Phe Arg
            580                 585                 590 cca gga gtt cga tat gac ttc aga att tat ggg tta tct aca aaa agg     1824
Pro Gly Val Arg Tyr Asp Phe Arg Ile Tyr Gly Leu Ser Thr Lys Arg
        595                 600                 605 att gct tgt tta tta gag aaa aaa aca gga tac tct cag gaa ctt gct     1872
Ile Ala Cys Leu Leu Glu Lys Lys Thr Gly Tyr Ser Gln Glu Leu Ala
    610                 615                 620 cct tca gac aac cct cac gtg ctg gtg gat aca ttg aca tcc cac tcc     1920
Pro Ser Asp Asn Pro His Val Leu Val Asp Thr Leu Thr Ser His Ser
625                 630                 635                 640 ttc act ctg agt tgg aaa gat tac tct act gaa tct caa cct ggt ttt     1968
Phe Thr Leu Ser Trp Lys Asp Tyr Ser Thr Glu Ser Gln Pro Gly Phe
                645                 650                 655 ata caa ggg tac cat gtc tat ctg aaa tcc aag gcg agg cag tgc cac     2016
Ile Gln Gly Tyr His Val Tyr Leu Lys Ser Lys Ala Arg Gln Cys His
            660                 665                 670 cca cga ttt gaa aag gca gtt ctt tca gat ggt tca gaa tgt tgc aaa     2064
Pro Arg Phe Glu Lys Ala Val Leu Ser Asp Gly Ser Glu Cys Cys Lys
        675                 680                 685 tac aaa att gac aac ccg gaa gaa aag gca ttg att gtg gac aac cta     2112
Tyr Lys Ile Asp Asn Pro Glu Glu Lys Ala Leu Ile Val Asp Asn Leu
    690                 695                 700 aag cca gaa tcc ttc tat gag ttt ttc atc act cca ttc act agt gct     2160
Lys Pro Glu Ser Phe Tyr Glu Phe Phe Ile Thr Pro Phe Thr Ser Ala
705                 710                 715                 720 ggt gaa ggc ccc agt gct acg ttc acg aag gtc acg act ccg gat gaa     2208
Gly Glu Gly Pro Ser Ala Thr Phe Thr Lys Val Thr Thr Pro Asp Glu
                725                 730                 735 cac tcc tcg                                                         2217
His Ser Ser <210> SEQ ID NO 69
<211> LENGTH: 739
<212> TYPE: PRT
<213> ORGANISM: Homo sapiens

<400> SEQUENCE: 69
```

```
Met Ala Leu Phe Ala Val Phe Gln Thr Thr Phe Phe Leu Thr Leu Leu
  1               5                  10                  15

Ser Leu Arg Thr Tyr Gln Ser Glu Val Leu Ala Glu Arg Leu Pro Leu
             20                  25                  30

Thr Pro Val Ser Leu Lys Val Ser Thr Asn Ser Thr Arg Gln Ser Leu
             35                  40                  45

His Leu Gln Trp Thr Val His Asn Leu Pro Tyr His Gln Glu Leu Lys
 50                  55                  60

Met Val Phe Gln Ile Gln Ile Ser Arg Ile Glu Thr Ser Asn Val Ile
 65                  70                  75                  80

Trp Val Gly Asn Tyr Ser Thr Thr Val Lys Trp Asn Gln Val Leu His
                 85                  90                  95

Trp Ser Trp Glu Ser Glu Leu Pro Leu Glu Cys Ala Thr His Phe Val
                100                 105                 110

Arg Ile Lys Ser Leu Val Asp Asp Ala Lys Phe Pro Glu Pro Asn Phe
            115                 120                 125

Trp Ser Asn Trp Ser Ser Trp Glu Glu Val Ser Val Gln Asp Ser Thr
            130                 135                 140

Gly Gln Asp Ile Leu Phe Val Phe Pro Lys Asp Lys Leu Val Glu Glu
145                 150                 155                 160

Gly Thr Asn Val Thr Ile Cys Tyr Val Ser Arg Asn Ile Gln Asn Asn
                165                 170                 175

Val Ser Cys Tyr Leu Glu Gly Lys Gln Ile His Gly Glu Gln Leu Asp
            180                 185                 190

Pro His Val Thr Ala Phe Asn Leu Asn Ser Val Pro Phe Ile Arg Asn
            195                 200                 205

Lys Gly Thr Asn Ile Tyr Cys Glu Ala Ser Gln Gly Asn Val Ser Glu
210                 215                 220

Gly Met Lys Gly Ile Val Leu Phe Val Ser Lys Val Leu Glu Glu Pro
225                 230                 235                 240

Lys Asp Phe Ser Cys Glu Thr Glu Asp Phe Lys Thr Leu His Cys Thr
                245                 250                 255

Trp Asp Pro Gly Thr Asp Thr Ala Leu Gly Trp Ser Lys Gln Pro Ser
            260                 265                 270

Gln Ser Tyr Thr Leu Phe Glu Ser Phe Ser Gly Glu Lys Lys Leu Cys
            275                 280                 285

Thr His Lys Asn Trp Cys Asn Trp Gln Ile Thr Gln Asp Ser Gln Glu
            290                 295                 300

Thr Tyr Asn Phe Thr Leu Ile Ala Glu Asn Tyr Leu Arg Lys Arg Ser
305                 310                 315                 320

Val Asn Ile Leu Phe Asn Leu Thr His Arg Val Tyr Leu Met Asn Pro
                325                 330                 335

Phe Ser Val Asn Phe Glu Asn Val Asn Ala Thr Asn Ala Ile Met Thr
            340                 345                 350

Trp Lys Val His Ser Ile Arg Asn Asn Phe Thr Tyr Leu Cys Gln Ile
            355                 360                 365

Glu Leu His Gly Glu Gly Lys Met Met Gln Tyr Asn Val Ser Ile Lys
370                 375                 380

Val Asn Gly Glu Tyr Phe Leu Ser Glu Leu Glu Pro Ala Thr Glu Tyr
385                 390                 395                 400

Met Ala Arg Val Arg Cys Ala Asp Ala Ser His Phe Trp Lys Trp Ser
                405                 410                 415
```

```
Glu Trp Ser Gly Gln Asn Phe Thr Thr Leu Ala Ala Pro Ser Glu
            420                 425                 430

Ala Pro Asp Val Trp Arg Ile Val Ser Leu Glu Pro Gly Asn His Thr
        435                 440                 445

Val Thr Leu Phe Trp Lys Pro Leu Ser Lys Leu His Ala Asn Gly Lys
    450                 455                 460

Ile Leu Phe Tyr Asn Val Val Glu Asn Leu Asp Lys Pro Ser Ser
465                 470                 475                 480

Ser Glu Leu His Ser Ile Pro Ala Pro Ala Asn Ser Thr Lys Leu Ile
                485                 490                 495

Leu Asp Arg Cys Ser Tyr Gln Ile Cys Val Ile Ala Asn Asn Ser Val
            500                 505                 510

Gly Ala Ser Pro Ala Ser Val Ile Val Ile Ser Ala Asp Pro Glu Asn
        515                 520                 525

Lys Glu Val Glu Glu Glu Arg Ile Ala Gly Thr Glu Gly Gly Phe Ser
    530                 535                 540

Leu Ser Trp Lys Pro Gln Pro Gly Asp Val Ile Gly Tyr Val Val Asp
545                 550                 555                 560

Trp Cys Asp His Thr Gln Asp Val Leu Gly Asp Phe Gln Trp Lys Asn
                565                 570                 575

Val Gly Pro Asn Thr Thr Ser Thr Val Ile Ser Thr Asp Ala Phe Arg
            580                 585                 590

Pro Gly Val Arg Tyr Asp Phe Arg Ile Tyr Gly Leu Ser Thr Lys Arg
        595                 600                 605

Ile Ala Cys Leu Leu Glu Lys Lys Thr Gly Tyr Ser Gln Glu Leu Ala
610                 615                 620

Pro Ser Asp Asn Pro His Val Leu Val Asp Thr Leu Thr Ser His Ser
625                 630                 635                 640

Phe Thr Leu Ser Trp Lys Asp Tyr Ser Thr Glu Ser Gln Pro Gly Phe
                645                 650                 655

Ile Gln Gly Tyr His Val Tyr Leu Lys Ser Lys Ala Arg Gln Cys His
            660                 665                 670

Pro Arg Phe Glu Lys Ala Val Leu Ser Asp Gly Ser Glu Cys Cys Lys
        675                 680                 685

Tyr Lys Ile Asp Asn Pro Glu Glu Lys Ala Leu Ile Val Asp Asn Leu
690                 695                 700

Lys Pro Glu Ser Phe Tyr Glu Phe Phe Ile Thr Pro Phe Thr Ser Ala
705                 710                 715                 720

Gly Glu Gly Pro Ser Ala Thr Phe Thr Lys Val Thr Thr Pro Asp Glu
                725                 730                 735

His Ser Ser

<210> SEQ ID NO 70
<211> LENGTH: 1557
<212> TYPE: DNA
<213> ORGANISM: Homo sapiens
<220> FEATURE:
<221> NAME/KEY: CDS
<222> LOCATION: (1)...(1557)

<400> SEQUENCE: 70 atg atg tgg acc tgg gca ctg tgg atg ctc ccc tca ctc tgc aaa ttc      48
Met Met Trp Thr Trp Ala Leu Trp Met Leu Pro Ser Leu Cys Lys Phe
  1               5                  10                  15 agc ctg gca gct ctg cca gct aag cct gag aac att tcc tgt gtc tac      96
Ser Leu Ala Ala Leu Pro Ala Lys Pro Glu Asn Ile Ser Cys Val Tyr
```

```
                    20                  25                  30
tac tat agg aaa aat tta acc tgc act tgg agt cca gga aag gaa acc    144
Tyr Tyr Arg Lys Asn Leu Thr Cys Thr Trp Ser Pro Gly Lys Glu Thr
         35                  40                  45 agt tat acc cag tac aca gtt aag aga act tac gct ttt gga gaa aaa    192
Ser Tyr Thr Gln Tyr Thr Val Lys Arg Thr Tyr Ala Phe Gly Glu Lys
 50                  55                  60 cat gat aat tgt aca acc aat agt tct aca agt gaa aat cgt gct tcg    240
His Asp Asn Cys Thr Thr Asn Ser Ser Thr Ser Glu Asn Arg Ala Ser
 65                  70                  75                  80 tgc tct ttt ttc ctt cca aga ata acg atc cca gat aat tat acc att    288
Cys Ser Phe Phe Leu Pro Arg Ile Thr Ile Pro Asp Asn Tyr Thr Ile
             85                  90                  95 gag gtg gaa gct gaa aat gga gat ggt gta att aaa tct cat atg aca    336
Glu Val Glu Ala Glu Asn Gly Asp Gly Val Ile Lys Ser His Met Thr
        100                 105                 110 tac tgg aga tta gag aac ata gcg aaa act gaa cca cct aag att ttc    384
Tyr Trp Arg Leu Glu Asn Ile Ala Lys Thr Glu Pro Pro Lys Ile Phe
            115                 120                 125 cgt gtg aaa cca gtt ttg ggc atc aaa cga atg att caa att gaa tgg    432
Arg Val Lys Pro Val Leu Gly Ile Lys Arg Met Ile Gln Ile Glu Trp
130                 135                 140 ata aag cct gag ttg gcg cct gtt tca tct gat tta aaa tac aca ctt    480
Ile Lys Pro Glu Leu Ala Pro Val Ser Ser Asp Leu Lys Tyr Thr Leu
145                 150                 155                 160 cga ttc agg aca gtc aac agt acc agc tgg atg gaa gtc aac ttc gct    528
Arg Phe Arg Thr Val Asn Ser Thr Ser Trp Met Glu Val Asn Phe Ala
                165                 170                 175 aag aac cgt aag gat aaa aac caa acg tac aac ctc acg ggg ctg cag    576
Lys Asn Arg Lys Asp Lys Asn Gln Thr Tyr Asn Leu Thr Gly Leu Gln
            180                 185                 190 cct ttt aca gaa tat gtc ata gct ctg cga tgt gcg gtc aag gag tca    624
Pro Phe Thr Glu Tyr Val Ile Ala Leu Arg Cys Ala Val Lys Glu Ser
        195                 200                 205 aag ttc tgg agt gac tgg agc caa gaa aaa atg gga atg act gag gaa    672
Lys Phe Trp Ser Asp Trp Ser Gln Glu Lys Met Gly Met Thr Glu Glu
    210                 215                 220 gaa gct cca tgt ggc ctg gaa ctg tgg aga gtc ctg aaa cca gct gag    720
Glu Ala Pro Cys Gly Leu Glu Leu Trp Arg Val Leu Lys Pro Ala Glu
225                 230                 235                 240 gcg gat gga aga agg cca gtg cgg ttg tta tgg aag aag gca aga gga    768
Ala Asp Gly Arg Arg Pro Val Arg Leu Leu Trp Lys Lys Ala Arg Gly
                245                 250                 255 gcc cca gtc cta gag aaa aca ctt ggc tac aac ata tgg tac tat cca    816
Ala Pro Val Leu Glu Lys Thr Leu Gly Tyr Asn Ile Trp Tyr Tyr Pro
            260                 265                 270 gaa agc aac act aac ctc aca gaa aca atg aac act act aac cag cag    864
Glu Ser Asn Thr Asn Leu Thr Glu Thr Met Asn Thr Thr Asn Gln Gln
        275                 280                 285 ctt gaa ctg cat ctg gga ggc gag agc ttt tgg gtg tct atg att tct    912
Leu Glu Leu His Leu Gly Gly Glu Ser Phe Trp Val Ser Met Ile Ser
    290                 295                 300 tat aat tct ctt ggg aag tct cca gtg gcc acc ctg agg att cca gct    960
Tyr Asn Ser Leu Gly Lys Ser Pro Val Ala Thr Leu Arg Ile Pro Ala
305                 310                 315                 320 att caa gaa aaa tca ttt cag tgc att gag gtc atg cag gcc tgc gtt   1008
Ile Gln Glu Lys Ser Phe Gln Cys Ile Glu Val Met Gln Ala Cys Val
                325                 330                 335 gct gag gac cag cta gtg gtg aag tgg caa agc tct gct cta gac gtg   1056
```

```
Ala Glu Asp Gln Leu Val Val Lys Trp Gln Ser Ser Ala Leu Asp Val
            340                 345                 350 aac act tgg atg att gaa tgg ttt ccg gat gtg gac tca gag ccc acc    1104
Asn Thr Trp Met Ile Glu Trp Phe Pro Asp Val Asp Ser Glu Pro Thr
        355                 360                 365 acc ctt tcc tgg gaa tct gtg tct cag gcc acg aac tgg acg atc cag    1152
Thr Leu Ser Trp Glu Ser Val Ser Gln Ala Thr Asn Trp Thr Ile Gln
    370                 375                 380 caa gat aaa tta aaa cct ttc tgg tgc tat aac atc tct gtg tat cca    1200
Gln Asp Lys Leu Lys Pro Phe Trp Cys Tyr Asn Ile Ser Val Tyr Pro
385                 390                 395                 400 atg ttg cat gac aaa gtt ggc gag cca tat tcc atc cag gct tat gcc    1248
Met Leu His Asp Lys Val Gly Glu Pro Tyr Ser Ile Gln Ala Tyr Ala
                405                 410                 415 aaa gaa ggc gtt cca tca gaa ggt cct gag acc aag gtg gag aac att    1296
Lys Glu Gly Val Pro Ser Glu Gly Pro Glu Thr Lys Val Glu Asn Ile
            420                 425                 430 ggc gtg aag acg gtc acg atc aca tgg aaa gag att ccc aag agt gag    1344
Gly Val Lys Thr Val Thr Ile Thr Trp Lys Glu Ile Pro Lys Ser Glu
        435                 440                 445 aga aag ggt atc atc tgc aac tac acc atc ttt tac caa gct gaa ggt    1392
Arg Lys Gly Ile Ile Cys Asn Tyr Thr Ile Phe Tyr Gln Ala Glu Gly
    450                 455                 460 gga aaa gga ttc tcc aag aca gtc aat tcc agc atc ttg cag tac ggc    1440
Gly Lys Gly Phe Ser Lys Thr Val Asn Ser Ser Ile Leu Gln Tyr Gly
465                 470                 475                 480 ctg gag tcc ctg aaa cga aag acc tct tac att gtt cag gtc atg gcc    1488
Leu Glu Ser Leu Lys Arg Lys Thr Ser Tyr Ile Val Gln Val Met Ala
                485                 490                 495 agc acc agt gct ggg gga acc aac ggg acc agc ata aat ttc aag aca    1536
Ser Thr Ser Ala Gly Gly Thr Asn Gly Thr Ser Ile Asn Phe Lys Thr
            500                 505                 510 ttg tca ttc agt gtc ttt gag                                        1557
Leu Ser Phe Ser Val Phe Glu
        515

<210> SEQ ID NO 71
<211> LENGTH: 519
<212> TYPE: PRT
<213> ORGANISM: Homo sapiens

<400> SEQUENCE: 71

Met Met Trp Thr Trp Ala Leu Trp Met Leu Pro Ser Leu Cys Lys Phe
1               5                   10                  15

Ser Leu Ala Ala Leu Pro Ala Lys Pro Glu Asn Ile Ser Cys Val Tyr
            20                  25                  30

Tyr Tyr Arg Lys Asn Leu Thr Cys Thr Trp Ser Pro Gly Lys Glu Thr
        35                  40                  45

Ser Tyr Thr Gln Tyr Thr Val Lys Arg Thr Tyr Ala Phe Gly Glu Lys
    50                  55                  60

His Asp Asn Cys Thr Thr Asn Ser Ser Thr Ser Glu Asn Arg Ala Ser
65                  70                  75                  80

Cys Ser Phe Phe Leu Pro Arg Ile Thr Ile Pro Asp Asn Tyr Thr Ile
                85                  90                  95

Glu Val Glu Ala Glu Asn Gly Asp Gly Val Ile Lys Ser His Met Thr
            100                 105                 110

Tyr Trp Arg Leu Glu Asn Ile Ala Lys Thr Glu Pro Pro Lys Ile Phe
        115                 120                 125
```

```
Arg Val Lys Pro Val Leu Gly Ile Lys Arg Met Ile Gln Ile Glu Trp
130                 135                 140

Ile Lys Pro Glu Leu Ala Pro Val Ser Ser Asp Leu Lys Tyr Thr Leu
145                 150                 155                 160

Arg Phe Arg Thr Val Asn Ser Thr Ser Trp Met Glu Val Asn Phe Ala
            165                 170                 175

Lys Asn Arg Lys Asp Lys Asn Gln Thr Tyr Asn Leu Thr Gly Leu Gln
            180                 185                 190

Pro Phe Thr Glu Tyr Val Ile Ala Leu Arg Cys Ala Val Lys Glu Ser
            195                 200                 205

Lys Phe Trp Ser Asp Trp Ser Gln Glu Lys Met Gly Met Thr Glu Glu
210                 215                 220

Glu Ala Pro Cys Gly Leu Glu Leu Trp Arg Val Leu Lys Pro Ala Glu
225                 230                 235                 240

Ala Asp Gly Arg Arg Pro Val Arg Leu Leu Trp Lys Lys Ala Arg Gly
                245                 250                 255

Ala Pro Val Leu Glu Lys Thr Leu Gly Tyr Asn Ile Trp Tyr Tyr Pro
            260                 265                 270

Glu Ser Asn Thr Asn Leu Thr Glu Thr Met Asn Thr Thr Asn Gln Gln
            275                 280                 285

Leu Glu Leu His Leu Gly Gly Glu Ser Phe Trp Val Ser Met Ile Ser
290                 295                 300

Tyr Asn Ser Leu Gly Lys Ser Pro Val Ala Thr Leu Arg Ile Pro Ala
305                 310                 315                 320

Ile Gln Glu Lys Ser Phe Gln Cys Ile Glu Val Met Gln Ala Cys Val
                325                 330                 335

Ala Glu Asp Gln Leu Val Val Lys Trp Gln Ser Ser Ala Leu Asp Val
            340                 345                 350

Asn Thr Trp Met Ile Glu Trp Phe Pro Asp Val Asp Ser Glu Pro Thr
            355                 360                 365

Thr Leu Ser Trp Glu Ser Val Ser Gln Ala Thr Asn Trp Thr Ile Gln
370                 375                 380

Gln Asp Lys Leu Lys Pro Phe Trp Cys Tyr Asn Ile Ser Val Tyr Pro
385                 390                 395                 400

Met Leu His Asp Lys Val Gly Glu Pro Tyr Ser Ile Gln Ala Tyr Ala
            405                 410                 415

Lys Glu Gly Val Pro Ser Glu Gly Pro Glu Thr Lys Val Glu Asn Ile
            420                 425                 430

Gly Val Lys Thr Val Thr Ile Thr Trp Lys Glu Ile Pro Lys Ser Glu
            435                 440                 445

Arg Lys Gly Ile Ile Cys Asn Tyr Thr Ile Phe Tyr Gln Ala Glu Gly
450                 455                 460

Gly Lys Gly Phe Ser Lys Thr Val Asn Ser Ser Ile Leu Gln Tyr Gly
465                 470                 475                 480

Leu Glu Ser Leu Lys Arg Lys Thr Ser Tyr Ile Val Gln Val Met Ala
            485                 490                 495

Ser Thr Ser Ala Gly Gly Thr Asn Gly Thr Ser Ile Asn Phe Lys Thr
            500                 505                 510

Leu Ser Phe Ser Val Phe Glu
            515
```

<210> SEQ ID NO 72
<211> LENGTH: 10
<212> TYPE: PRT

```
<213> ORGANISM: Artificial Sequence
<220> FEATURE:
<223> OTHER INFORMATION: C-Terminal His peptide tag

<400> SEQUENCE: 72

Gly Ser Gly Gly His His His His His His
 1               5                  10

<210> SEQ ID NO 73
<211> LENGTH: 12
<212> TYPE: PRT
<213> ORGANISM: Artificial Sequence
<220> FEATURE:
<223> OTHER INFORMATION: Gly-Ser spacer of 12 amino acids

<400> SEQUENCE: 73

Gly Ser Gly Ser Gly Ser Gly Ser Glu Pro Arg Ser
 1               5                  10

<210> SEQ ID NO 74
<211> LENGTH: 31
<212> TYPE: DNA
<213> ORGANISM: Artificial Sequence
<220> FEATURE:
<223> OTHER INFORMATION: Oligonucleotide primer ZC41557

<400> SEQUENCE: 74
ttatagatct cgaggagtgt tcatccggag t                              31

<210> SEQ ID NO 75
<211> LENGTH: 65
<212> TYPE: DNA
<213> ORGANISM: Artificial Sequence
<220> FEATURE:
<223> OTHER INFORMATION: Oligonucleotide primer ZC29232

<400> SEQUENCE: 75
cgactgactc gagtcagtga tggtgatggt gatggccacc tgatccttta cccggagaca    60
gggag                                                                65

<210> SEQ ID NO 76
<211> LENGTH: 3196
<212> TYPE: DNA
<213> ORGANISM: Mus musculus

<400> SEQUENCE: 76
tgtatgtctg cacagtttgt gtatgcctgg tgcccacaga ggctcgagag tgtcagattc     60
cccccaaaac tggagttaca gttttgagcc gccccatgct tgatagcaat caaacctggg   120
tcctctgaaa gagcatccag tgcatgtaac cactgaacca tctctccaaa ccatgaacat   180
cactttaatt ttttttaata gttaaaggat attttgattc taaagatgta aagaacgtc    240 tcacctattt tgaaatttgg taataaatgt ttcttcaaag cttaaaaaaa ttagttcagg   300
tttttttttt ttttcagtca gtgatttgct aagctgccca aactggctta gaatttgtga   360
ccctcttgtc tcagcatact gagtgttaag attacaagtg cacccctac ccagttccca    420 taattaactg atccacccc accccatcc accccactc ccattgcctg ggcaagtaac      480
tcttgagccc cattctggtt ctagagtctg aagtcacaaa ggtgcaggtg agaacgcaag   540
gacaagggca ggccctggag cacagatgcc ttctccttat gccttccctg tgttcactag   600
agccatcccc ctgcctccgg aattcccaca gatggatcgc tctgtggctt cttaaaactt   660
ccctgcaggg cactgaccct cagcccctct aagtcacttc ttccccagtg attgtacttt   720
```

| | |
|---|---|
| tcaatcgggc ttcaaacttt cctctcatta aatcagcaag cactttccaa gaaaagagag | 780 |
| atgctcaaga tgccttcctg tgtggtatgt gtatgcgttt gtgtgtgtgc acgcatgtgt | 840 |
| gtgcatgtga ctcaatcttc tgccttgcct tgagggtaac ctcagcattt ccttccagcc | 900 |
| ctgctttccc caggccgagc cgaggctggc aaccttttga aaatgttttc tggagaaaag | 960 |
| ctgagcaatg gttttgccat gggcgggcct ttgatctgct tcctcatgac aacccttttat | 1020 |
| atattgcctg gtggccatgg cgaacacacc aggctccaga gaccacaggc aaagcgggcc | 1080 |
| ttcctcactc tcttaccgtc gccatgatct tccacacagg taccgctggc tccacacgca | 1140 |
| gctcagcatg gcttcagctc catggctctt atcatgttag gggaaggagc cgggaatggc | 1200 |
| tgcctcaggt ggttgctgga cagaggctgt tgtaactgaa gctgggatgg cagggcat | 1260 |
| ctgacctatc agctccatgg tatccttctt tttctccagg aacaacgaag cctaccctgg | 1320 |
| tgctgctttg ctgtatagga acctggctgg ccacctgcag cttgtccttc ggtgcccaa | 1380 |
| tatcgaagga agacttaaga actacaattg acctcttgaa acaagagtct caggatcttt | 1440 |
| ataacaacta tgtaagtgcc cttgagattg ttttttctta accatttctt taaaatgtct | 1500 |
| tattttgcta tctaagcaca gctatccttt ctcgatataa agccagctat ggaagccaga | 1560 |
| gaggcatggg gaaacattgg aattcggttg gggtgaaatg tttccaaggg ggtaaatgca | 1620 |
| ctagcagaag aggcagaggc agactggtcc agggactgaa accttggcag cttacgaaac | 1680 |
| actacaggat gtatgctccc tgaattcttt atctcaaatc cacccggctc acagtcccta | 1740 |
| ctaaacgagc attcttgctg aaagggcatc cttagagaag gccagcttg attcaggaat | 1800 |
| ccccccaagag caatgagagc cagtttcagc agccaaagat gtcctagtgg aagcagggtg | 1860 |
| tgaggatctt cctttgggtc tccgttgact aactaggcaa ctgtctgtgt gttcttggag | 1920 |
| catcctggag ggccctctgc ctggccagag cctggcacag gtacagcaca ggacccagaa | 1980 |
| agtgtgaata cttcatttcc ttgggaccgc ttagataact tcagttgaag caagtaacag | 2040 |
| ggaaactgat ggagacacag ataacctccc tgcccctctc acttcagtca ctgagcctcc | 2100 |
| gagaacaggt tgcagatggc tagggggcagc ctcagccaga taggcggagg cagactgggt | 2160 |
| agaagcatcc ttaggaacca cggccaacct gggtgggtat gccatgtctt ctagctcata | 2220 |
| agccaactag accttcgatt cctgtagaca cagagttagt gatggcccaa gcttcagaag | 2280 |
| gttgttgtac caattagata aggtctgagg caggctagac acagaggaag ccctggaaat | 2340 |
| gagctgttct gagctgtagg gttgttacaa atgtcttcct tacaatattt caaacctcct | 2400 |
| cttctacag agcataaagc aggcatctgg gatgtcagca gacgaatcaa tacagctgcc | 2460 |
| gtgtttcagc ctggaccggg aagcattaac caacatctcg gtcatcatag cacatctgga | 2520 |
| gaaagtcaaa gtgttgagcg agaacacagt agatacttct tgggtgataa gatggctaac | 2580 |
| aaacatcagc tgtttcaacc cactgaattt aaacatttct gtgcctggaa atactgatga | 2640 |
| atcctatgat tgtaaagtgt tcgtgcttac ggttttaaag cagttctcaa actgcatggc | 2700 |
| agaactgcag gctaaggaca atactacatg ctgagtgatg gggggggggg ggtgcagtgt | 2760 |
| cctcagcagt gcctgtcctt cgagggctga gcttgcaacc caggacttaa ctccaaaggg | 2820 |
| actgtgcggt cattactagt catgttattt atgttttat tttgtccact gaaatcttgt | 2880 |
| tctgctaccc tgtagggact ggaagtggca gctatattta tttatttatg tactgagttt | 2940 |
| gttaacgctc catggaggag ccttcagagt ctatttaata aattatattg acatgatcac | 3000 |
| ataatcagtt ttggaatttg tgatgggtt gaaatcaaag attaggaatg ttctggaaat | 3060 |

```
agtttatgct accctctccc tccattagac agactcatga gcaaataatc ccagcagcat      3120
cacgtgcatg ataaacatct ttgttccagg tcataagtac aatcactgtc cttttggtat      3180
gtaggctgga aactaa                                                     3196
```

<210> SEQ ID NO 77
<211> LENGTH: 24
<212> TYPE: DNA
<213> ORGANISM: Artificial Sequence
<220> FEATURE:
<223> OTHER INFORMATION: Oligonucleotide primer ZC28575

<400> SEQUENCE: 77

```
ccaggaaagg aaaccagtta tacc                                              24
```

<210> SEQ ID NO 78
<211> LENGTH: 23
<212> TYPE: DNA
<213> ORGANISM: Artificial Sequence
<220> FEATURE:
<223> OTHER INFORMATION: Oligonucleotide primer ZC21195

<400> SEQUENCE: 78

```
gaggagacca taacccccga cag                                               23
```

<210> SEQ ID NO 79
<211> LENGTH: 23
<212> TYPE: DNA
<213> ORGANISM: Artificial Sequence
<220> FEATURE:
<223> OTHER INFORMATION: Oligonucleotide primer ZC21196

<400> SEQUENCE: 79

```
catagctccc accacacgat ttt                                               23
```

<210> SEQ ID NO 80
<211> LENGTH: 25
<212> TYPE: DNA
<213> ORGANISM: Artificial Sequence
<220> FEATURE:
<223> OTHER INFORMATION: Oligonucleotide primer ZC26358

<400> SEQUENCE: 80

```
aaaaccaaac gtacaacctc acggg                                             25
```

<210> SEQ ID NO 81
<211> LENGTH: 25
<212> TYPE: DNA
<213> ORGANISM: Artificial Sequence
<220> FEATURE:
<223> OTHER INFORMATION: Oligonucleotide primer ZC26359

<400> SEQUENCE: 81

```
gagcagccat acaccagagc agaca                                             25
```

<210> SEQ ID NO 82
<211> LENGTH: 19
<212> TYPE: DNA
<213> ORGANISM: Artificial Sequence
<220> FEATURE:
<223> OTHER INFORMATION: Oligonucleotide primer ZC29179

<400> SEQUENCE: 82

```
gcagggttgg gaacggtgg                                                    19
```

```
<210> SEQ ID NO 83
<211> LENGTH: 20
<212> TYPE: DNA
<213> ORGANISM: Artificial Sequence
<220> FEATURE:
<223> OTHER INFORMATION: Oligonucleotide primer ZC28917

<400> SEQUENCE: 83
tgcaagatgc tggaattgac                                               20

<210> SEQ ID NO 84
<211> LENGTH: 20
<212> TYPE: DNA
<213> ORGANISM: Artificial Sequence
<220> FEATURE:
<223> OTHER INFORMATION: Oligonucleotide primer ZC28916

<400> SEQUENCE: 84
agtcaattcc agcatcttgc                                               20

<210> SEQ ID NO 85
<211> LENGTH: 20
<212> TYPE: DNA
<213> ORGANISM: Artificial Sequence
<220> FEATURE:
<223> OTHER INFORMATION: Oligonucleotide primer ZC28918

<400> SEQUENCE: 85
tcacagagtc atcagactcc                                               20

<210> SEQ ID NO 86
<211> LENGTH: 18
<212> TYPE: DNA
<213> ORGANISM: Artificial Sequence
<220> FEATURE:
<223> OTHER INFORMATION: Oligonucleotide primer ZC41498

<400> SEQUENCE: 86
ggctccagag accacagg                                                 18

<210> SEQ ID NO 87
<211> LENGTH: 22
<212> TYPE: DNA
<213> ORGANISM: Artificial Sequence
<220> FEATURE:
<223> OTHER INFORMATION: Oligonucleotide primer ZC41496

<400> SEQUENCE: 87
atgactagta atgaccgcac ag                                            22

<210> SEQ ID NO 88
<211> LENGTH: 39
<212> TYPE: DNA
<213> ORGANISM: Artificial Sequence
<220> FEATURE:
<223> OTHER INFORMATION: Oligonucleotide primer ZC41583

<400> SEQUENCE: 88
cgtacgggcc ggccaccatg atcttccaca caggaacaa                          39

<210> SEQ ID NO 89
<211> LENGTH: 36
<212> TYPE: DNA
<213> ORGANISM: Artificial Sequence
<220> FEATURE:
<223> OTHER INFORMATION: Oligonucleotide primer ZC41584
```

```
<400> SEQUENCE: 89
tgacgaggcg cgcctcagca tgtagtattg tcctta                              36

<210> SEQ ID NO 90
<211> LENGTH: 650
<212> TYPE: DNA
<213> ORGANISM: Mus musculus
<220> FEATURE:
<221> NAME/KEY: CDS
<222> LOCATION: (53)...(542)

<400> SEQUENCE: 90
ggctccagag accacaggca aagcgggcct tcctcactct cttaccgtcg cc atg atc    58
                                                         Met Ile
                                                           1 ttc cac aca gga aca acg aag cct acc ctg gtg ctg ctt tgc tgt ata    106
Phe His Thr Gly Thr Thr Lys Pro Thr Leu Val Leu Leu Cys Cys Ile
      5                  10                  15 gga acc tgg ctg gcc acc tgc agc ttg tcc ttc ggt gcc cca ata tcg    154
Gly Thr Trp Leu Ala Thr Cys Ser Leu Ser Phe Gly Ala Pro Ile Ser
 20                  25                  30 aag gaa gac tta aga act aca att gac ctc ttg aaa caa gag tct cag    202
Lys Glu Asp Leu Arg Thr Thr Ile Asp Leu Leu Lys Gln Glu Ser Gln
 35                  40                  45                  50 gat ctt tat aac aac tat agc ata aag cag gca tct ggg atg tca gca    250
Asp Leu Tyr Asn Asn Tyr Ser Ile Lys Gln Ala Ser Gly Met Ser Ala
              55                  60                  65 gac gaa tca ata cag ctg ccg tgt ttc agc ctg gac cgg gaa gca tta    298
Asp Glu Ser Ile Gln Leu Pro Cys Phe Ser Leu Asp Arg Glu Ala Leu
         70                  75                  80 acc aac atc tcg gtc atc ata gca cat ctg gag aaa gtc aaa gtg ttg    346
Thr Asn Ile Ser Val Ile Ile Ala His Leu Glu Lys Val Lys Val Leu
     85                  90                  95 agc gag aac aca gta gat act tct tgg gtg ata aga tgg cta aca aac    394
Ser Glu Asn Thr Val Asp Thr Ser Trp Val Ile Arg Trp Leu Thr Asn
100                 105                 110 atc agc tgt ttc aac cca ctg aat tta aac att tct gtg cct gga aat    442
Ile Ser Cys Phe Asn Pro Leu Asn Leu Asn Ile Ser Val Pro Gly Asn
115                 120                 125                 130 act gat gaa tcc tat gat tgt aaa gtg ttc gtg ctt acg gtt tta aag    490
Thr Asp Glu Ser Tyr Asp Cys Lys Val Phe Val Leu Thr Val Leu Lys
                135                 140                 145 cag ttc tca aac tgc atg gca gaa ctg cag gct aag gac aat act aca    538
Gln Phe Ser Asn Cys Met Ala Glu Leu Gln Ala Lys Asp Asn Thr Thr
            150                 155                 160 tgc t gagtgatggg gggggggtgc agtgtcctca gcagtgcctg tccttcgagg        592
Cys gctgagcttg caacccagga cttaactcca aagggactgt gcggtcatta ctagtcat    650

<210> SEQ ID NO 91
<211> LENGTH: 163
<212> TYPE: PRT
<213> ORGANISM: Mus musculus

<400> SEQUENCE: 91

Met Ile Phe His Thr Gly Thr Thr Lys Pro Thr Leu Val Leu Leu Cys
  1               5                  10                  15

Cys Ile Gly Thr Trp Leu Ala Thr Cys Ser Leu Ser Phe Gly Ala Pro
             20                  25                  30

Ile Ser Lys Glu Asp Leu Arg Thr Thr Ile Asp Leu Leu Lys Gln Glu
```

```
                    35                  40                  45
Ser Gln Asp Leu Tyr Asn Asn Tyr Ser Ile Lys Gln Ala Ser Gly Met
         50                  55                  60

Ser Ala Asp Glu Ser Ile Gln Leu Pro Cys Phe Ser Leu Asp Arg Glu
 65                  70                  75                  80

Ala Leu Thr Asn Ile Ser Val Ile Ile Ala His Leu Glu Lys Val Lys
                 85                  90                  95

Val Leu Ser Glu Asn Thr Val Asp Thr Ser Trp Val Ile Arg Trp Leu
            100                 105                 110

Thr Asn Ile Ser Cys Phe Asn Pro Leu Asn Leu Asn Ile Ser Val Pro
        115                 120                 125

Gly Asn Thr Asp Glu Ser Tyr Asp Cys Lys Val Phe Val Leu Thr Val
    130                 135                 140

Leu Lys Gln Phe Ser Asn Cys Met Ala Glu Leu Gln Ala Lys Asp Asn
145                 150                 155                 160

Thr Thr Cys

<210> SEQ ID NO 92
<211> LENGTH: 511
<212> TYPE: DNA
<213> ORGANISM: Artificial Sequence
<220> FEATURE:
<223> OTHER INFORMATION: Cloned murine cDNA sequence (SEQ ID NO:90)
      w/FseI and AscI restriction sites and a partial Kozak
      sequence to the mcytor17lig open reading frame and
      termination codon

<400> SEQUENCE: 92
ggccggccac catgatcttc cacacaggaa caacgaagcc taccctggtg ctgctttgct      60
gtataggaac ctggctggcc acctgcagct tgtccttcgg tgccccaata tcgaaggaag     120
acttaagaac tacaattgac ctcttgaaac aagagtctca ggatctttat aacaactata     180
gcataaagca ggcatctggg atgtcagcag acgaatcaat acagctgccg tgtttcagcc     240
tggaccggga agcattaacc aacatctcgg tcatcatagc acatctggag aaagtcaaag     300
tgttgagcga gaacacagta gatacttctt gggtgataag atggctaaca acatcagct     360 gtttcaaccc actgaattta aacatttctg tgcctggaaa tactgatgaa tcctatgatt     420
gtaaagtgtt cgtgcttacg gttttaaagc agttctcaaa ctgcatggca gaactgcagg     480
ctaaggacaa tactacatgc tgaggcgcgc c                                    511

<210> SEQ ID NO 93
<211> LENGTH: 21
<212> TYPE: DNA
<213> ORGANISM: Artificial Sequence
<220> FEATURE:
<223> OTHER INFORMATION: Oligonucleotide primer ZC41438

<400> SEQUENCE: 93
gccatggcct ctcactcagg c                                                21

<210> SEQ ID NO 94
<211> LENGTH: 24
<212> TYPE: DNA
<213> ORGANISM: Artificial Sequence
<220> FEATURE:
<223> OTHER INFORMATION: Oligonucleotide primer ZC41437

<400> SEQUENCE: 94
ccagggagca ttgacaactc ttag                                             24
```

```
<210> SEQ ID NO 95
<211> LENGTH: 516
<212> TYPE: DNA
<213> ORGANISM: Artificial Sequence
<220> FEATURE:
<223> OTHER INFORMATION: human zCytor17Lig-CEE polynucleotide
<220> FEATURE:
<221> NAME/KEY: CDS
<222> LOCATION: (1)...(516)

<400> SEQUENCE: 95 atg gcc tct cac tca ggc ccc tcg acg tct gtg ctc ttt ctg ttc tgc      48
Met Ala Ser His Ser Gly Pro Ser Thr Ser Val Leu Phe Leu Phe Cys
 1               5                  10                  15 tgc ctg gga ggc tgg ctg gcc tcc cac acg ttg ccc gtc cgt tta cta      96
Cys Leu Gly Gly Trp Leu Ala Ser His Thr Leu Pro Val Arg Leu Leu
            20                  25                  30 cga cca agt gat gat gta cag aaa ata gtc gag gaa tta cag tcc ctc     144
Arg Pro Ser Asp Asp Val Gln Lys Ile Val Glu Glu Leu Gln Ser Leu
        35                  40                  45 tcg aag atg ctt ttg aaa gat gtg gag gaa gag aag ggc gtg ctc gtg     192
Ser Lys Met Leu Leu Lys Asp Val Glu Glu Glu Lys Gly Val Leu Val
    50                  55                  60 tcc cag aat tac acg ctg ccg tgt ctc agc cct gac gcc cag ccg cca     240
Ser Gln Asn Tyr Thr Leu Pro Cys Leu Ser Pro Asp Ala Gln Pro Pro
65                  70                  75                  80 aac aac atc cac agc cca gcc atc cgg gca tat ctc aag aca atc aga     288
Asn Asn Ile His Ser Pro Ala Ile Arg Ala Tyr Leu Lys Thr Ile Arg
                85                  90                  95 cag cta gac aac aaa tct gtt att gat gag atc ata gag cac ctc gac     336
Gln Leu Asp Asn Lys Ser Val Ile Asp Glu Ile Ile Glu His Leu Asp
            100                 105                 110 aaa ctc ata ttt caa gat gca cca gaa aca aac att tct gtg cca aca     384
Lys Leu Ile Phe Gln Asp Ala Pro Glu Thr Asn Ile Ser Val Pro Thr
        115                 120                 125 gac acc cat gaa tgt aaa cgc ttc atc ctg act att tct caa cag ttt     432
Asp Thr His Glu Cys Lys Arg Phe Ile Leu Thr Ile Ser Gln Gln Phe
    130                 135                 140 tca gag tgc atg gac ctc gca cta aaa tca ttg acc tct gga gcc caa     480
Ser Glu Cys Met Asp Leu Ala Leu Lys Ser Leu Thr Ser Gly Ala Gln
145                 150                 155                 160 cag gcc acc act gaa gaa tac atg ccg atg gaa taa                      516
Gln Ala Thr Thr Glu Glu Tyr Met Pro Met Glu *
                165                 170

<210> SEQ ID NO 96
<211> LENGTH: 171
<212> TYPE: PRT
<213> ORGANISM: Artificial Sequence
<220> FEATURE:
<223> OTHER INFORMATION: human zCytor17Lig-CEE polypeptide

<400> SEQUENCE: 96

Met Ala Ser His Ser Gly Pro Ser Thr Ser Val Leu Phe Leu Phe Cys
 1               5                  10                  15

Cys Leu Gly Gly Trp Leu Ala Ser His Thr Leu Pro Val Arg Leu Leu
            20                  25                  30

Arg Pro Ser Asp Asp Val Gln Lys Ile Val Glu Glu Leu Gln Ser Leu
        35                  40                  45

Ser Lys Met Leu Leu Lys Asp Val Glu Glu Glu Lys Gly Val Leu Val
    50                  55                  60
```

```
Ser Gln Asn Tyr Thr Leu Pro Cys Leu Ser Pro Asp Ala Gln Pro Pro
 65                  70                  75                  80

Asn Asn Ile His Ser Pro Ala Ile Arg Ala Tyr Leu Lys Thr Ile Arg
                 85                  90                  95

Gln Leu Asp Asn Lys Ser Val Ile Asp Glu Ile Ile Glu His Leu Asp
            100                 105                 110

Lys Leu Ile Phe Gln Asp Ala Pro Glu Thr Asn Ile Ser Val Pro Thr
        115                 120                 125

Asp Thr His Glu Cys Lys Arg Phe Ile Leu Thr Ile Ser Gln Gln Phe
    130                 135                 140

Ser Glu Cys Met Asp Leu Ala Leu Lys Ser Leu Thr Ser Gly Ala Gln
145                 150                 155                 160

Gln Ala Thr Thr Glu Glu Tyr Met Pro Met Glu
                165                 170

<210> SEQ ID NO 97
<211> LENGTH: 49
<212> TYPE: DNA
<213> ORGANISM: Artificial Sequence
<220> FEATURE:
<223> OTHER INFORMATION: Oligonucleotide primer ZC41607

<400> SEQUENCE: 97
tccagggaat tcatataggc cggccaccat ggcctctcac tcaggcccc            49

<210> SEQ ID NO 98
<211> LENGTH: 82
<212> TYPE: DNA
<213> ORGANISM: Artificial Sequence
<220> FEATURE:
<223> OTHER INFORMATION: Oligonucleotide primer ZC41605

<400> SEQUENCE: 98 caacccccaga gctgttttaa ggcgcgcctc tagattatta ttccatcggc atgtattctt    60
cagtggtggc ctgttgggct cc                                             82

<210> SEQ ID NO 99
<211> LENGTH: 629
<212> TYPE: DNA
<213> ORGANISM: Mus musculus
<220> FEATURE:
<221> NAME/KEY: CDS
<222> LOCATION: (28)...(528)

<400> SEQUENCE: 99
aaccccttgg aggaccagaa cgagaca atg gtt ctt gcc agc tct acc acc agc     54
                                Met Val Leu Ala Ser Ser Thr Thr Ser
                                  1               5 atc cac acc atg ctg ctc ctg ctc ctg atg ctc ttc cac ctg gga ctc     102
Ile His Thr Met Leu Leu Leu Leu Leu Met Leu Phe His Leu Gly Leu
 10                  15                  20                  25 caa gct tca atc agt ggc cgg gat acc cac cgt tta acc aga acg ttg     150
Gln Ala Ser Ile Ser Gly Arg Asp Thr His Arg Leu Thr Arg Thr Leu
                 30                  35                  40 aat tgc agc tct att gtc aag gag att ata ggg aag ctc cca gaa cct     198
Asn Cys Ser Ser Ile Val Lys Glu Ile Ile Gly Lys Leu Pro Glu Pro
             45                  50                  55 gaa ctc aaa act gat gat gaa gga ccc tct ctg agg aat aag agc ttt     246
Glu Leu Lys Thr Asp Asp Glu Gly Pro Ser Leu Arg Asn Lys Ser Phe
         60                  65                  70
```

```
cgg aga gta aac ctg tcc aaa ttc gtg gaa agc caa gga gaa gtg gat       294
Arg Arg Val Asn Leu Ser Lys Phe Val Glu Ser Gln Gly Glu Val Asp
         75                  80                  85 cct gag gac aga tac gtt atc aag tcc aat ctt cag aaa ctt aac tgt       342
Pro Glu Asp Arg Tyr Val Ile Lys Ser Asn Leu Gln Lys Leu Asn Cys
 90                  95                 100                 105 tgc ctg cct aca tct gcg aat gac tct gcg ctg cca ggg gtc ttc att       390
Cys Leu Pro Thr Ser Ala Asn Asp Ser Ala Leu Pro Gly Val Phe Ile
             110                 115                 120 cga gat ctg gat gac ttt cgg aag aaa ctg aga ttc tac atg gtc cac       438
Arg Asp Leu Asp Asp Phe Arg Lys Lys Leu Arg Phe Tyr Met Val His
         125                 130                 135 ctt aac gat ctg gag aca gtg cta acc tct aga cca cct cag ccc gca       486
Leu Asn Asp Leu Glu Thr Val Leu Thr Ser Arg Pro Pro Gln Pro Ala
             140                 145                 150 tct ggc tcc gtc tct cct aac cgt gga acc gtg gaa tgt taa              528
Ser Gly Ser Val Ser Pro Asn Arg Gly Thr Val Glu Cys  *
155                 160                 165 aacagcaggc agagcaccta aagtctgaat gttcctcatg cccatggtc aaaaggattt      588 tacattcctt tatgccatca aatgtcttat caatttatct a                        629

<210> SEQ ID NO 100
<211> LENGTH: 166
<212> TYPE: PRT
<213> ORGANISM: Mus musculus

<400> SEQUENCE: 100

Met Val Leu Ala Ser Ser Thr Thr Ser Ile His Thr Met Leu Leu Leu
 1               5                  10                  15

Leu Leu Met Leu Phe His Leu Gly Leu Gln Ala Ser Ile Ser Gly Arg
             20                  25                  30

Asp Thr His Arg Leu Thr Arg Thr Leu Asn Cys Ser Ser Ile Val Lys
         35                  40                  45

Glu Ile Ile Gly Lys Leu Pro Glu Pro Glu Leu Lys Thr Asp Asp Glu
 50                  55                  60

Gly Pro Ser Leu Arg Asn Lys Ser Phe Arg Arg Val Asn Leu Ser Lys
65                  70                  75                  80

Phe Val Glu Ser Gln Gly Glu Val Asp Pro Glu Asp Arg Tyr Val Ile
                 85                  90                  95

Lys Ser Asn Leu Gln Lys Leu Asn Cys Cys Leu Pro Thr Ser Ala Asn
            100                 105                 110

Asp Ser Ala Leu Pro Gly Val Phe Ile Arg Asp Leu Asp Asp Phe Arg
        115                 120                 125

Lys Lys Leu Arg Phe Tyr Met Val His Leu Asn Asp Leu Glu Thr Val
    130                 135                 140

Leu Thr Ser Arg Pro Pro Gln Pro Ala Ser Gly Ser Val Ser Pro Asn
145                 150                 155                 160

Arg Gly Thr Val Glu Cys
                165

<210> SEQ ID NO 101
<211> LENGTH: 674
<212> TYPE: DNA
<213> ORGANISM: Homo sapiens
<220> FEATURE:
<221> NAME/KEY: CDS
<222> LOCATION: (10)...(464)

<400> SEQUENCE: 101
```

```
gatccaaac atg agc cgc ctg ccc gtc ctg ctc ctg ctc caa ctc ctg gtc      51
            Met Ser Arg Leu Pro Val Leu Leu Leu Gln Leu Leu Val
              1               5                  10 cgc ccc gga ctc caa gct ccc atg acc cag aca acg tcc ttg aag aca        99
Arg Pro Gly Leu Gln Ala Pro Met Thr Gln Thr Thr Ser Leu Lys Thr
 15              20                  25                  30 agc tgg gtt aac tgc tct aac atg atc gat gaa att ata aca cac tta       147
Ser Trp Val Asn Cys Ser Asn Met Ile Asp Glu Ile Ile Thr His Leu
                 35                  40                  45 aag cag cca cct ttg cct ttg ctg gac ttc aac aac ctc aat ggg gaa       195
Lys Gln Pro Pro Leu Pro Leu Leu Asp Phe Asn Asn Leu Asn Gly Glu
                 50                  55                  60 gac caa gac att ctg atg gaa aat aac ctt cga agg cca aac ctg gag       243
Asp Gln Asp Ile Leu Met Glu Asn Asn Leu Arg Arg Pro Asn Leu Glu
 65                  70                  75 gca ttc aac agg gct gtc aag agt tta cag aac gca tca gca att gag       291
Ala Phe Asn Arg Ala Val Lys Ser Leu Gln Asn Ala Ser Ala Ile Glu
     80                  85                  90 agc att ctt aaa aat ctc ctg cca tgt ctg ccc ctg gcc acg gcc gca       339
Ser Ile Leu Lys Asn Leu Leu Pro Cys Leu Pro Leu Ala Thr Ala Ala
 95                 100                 105                 110 ccc acg cga cat cca atc cat atc aag gac ggt gac tgg aat gaa ttc       387
Pro Thr Arg His Pro Ile His Ile Lys Asp Gly Asp Trp Asn Glu Phe
                115                 120                 125 cgg agg aaa ctg acg ttc tat ctg aaa acc ctt gag aat gcg cag gct       435
Arg Arg Lys Leu Thr Phe Tyr Leu Lys Thr Leu Glu Asn Ala Gln Ala
                130                 135                 140 caa cag acg act ttg agc ctc gcg atc tt ttagtccaac gtccagctcg          484
Gln Gln Thr Thr Leu Ser Leu Ala Ile
                145                 150 ttctctgggc cttctcacca cagcgcctcg ggacatcaaa aacagcagaa cttctgaaac      544
ctctgggtca tctctcacac attccaggac cagaagcatt tcaccttttc ctgcggcatc     604
agatgaattg ttaattatct aatttctgaa atgtgcagct cccatttggc cttgtgcggt     664
tgtgttctca                                                             674

<210> SEQ ID NO 102
<211> LENGTH: 151
<212> TYPE: PRT
<213> ORGANISM: Homo sapiens

<400> SEQUENCE: 102

Met Ser Arg Leu Pro Val Leu Leu Leu Gln Leu Leu Val Arg Pro
 1               5                  10                  15

Gly Leu Gln Ala Pro Met Thr Gln Thr Thr Ser Leu Lys Thr Ser Trp
             20                  25                  30

Val Asn Cys Ser Asn Met Ile Asp Glu Ile Ile Thr His Leu Lys Gln
         35                  40                  45

Pro Pro Leu Pro Leu Leu Asp Phe Asn Asn Leu Asn Gly Glu Asp Gln
     50                  55                  60

Asp Ile Leu Met Glu Asn Asn Leu Arg Arg Pro Asn Leu Glu Ala Phe
 65                  70                  75                  80

Asn Arg Ala Val Lys Ser Leu Gln Asn Ala Ser Ala Ile Glu Ser Ile
                 85                  90                  95

Leu Lys Asn Leu Leu Pro Cys Leu Pro Leu Ala Thr Ala Ala Pro Thr
            100                 105                 110

Arg His Pro Ile His Ile Lys Asp Gly Asp Trp Asn Glu Phe Arg Arg
```

```
                115                 120                 125
Lys Leu Thr Phe Tyr Leu Lys Thr Leu Glu Asn Ala Gln Ala Gln Gln
            130                 135                 140

Thr Thr Leu Ser Leu Ala Ile
145             150
```

<210> SEQ ID NO 103
<211> LENGTH: 7
<212> TYPE: PRT
<213> ORGANISM: Artificial Sequence
<220> FEATURE:
<223> OTHER INFORMATION: Alternative Glu-Glu (CEE) peptide tag without
      Gly-Ser residue pair

<400> SEQUENCE: 103

```
Glu Glu Tyr Met Pro Met Glu
 1               5
```

<210> SEQ ID NO 104
<211> LENGTH: 513
<212> TYPE: DNA
<213> ORGANISM: Artificial Sequence
<220> FEATURE:
<223> OTHER INFORMATION: Mouse zCytor17Lig(m)-CEE polynucleotide
<220> FEATURE:
<221> NAME/KEY: CDS
<222> LOCATION: (1)...(513)

<400> SEQUENCE: 104

```
atg atc ttc cac aca gga aca acg aag cct acc ctg gtg ctg ctt tgc      48
Met Ile Phe His Thr Gly Thr Thr Lys Pro Thr Leu Val Leu Leu Cys
 1               5                  10                  15 tgt ata gga acc tgg ctg gcc acc tgc agc ttg tcc ttc ggt gcc cca      96
Cys Ile Gly Thr Trp Leu Ala Thr Cys Ser Leu Ser Phe Gly Ala Pro
            20                  25                  30 ata tcg aag gaa gac tta aga act aca att gac ctc ttg aaa caa gag     144
Ile Ser Lys Glu Asp Leu Arg Thr Thr Ile Asp Leu Leu Lys Gln Glu
        35                  40                  45 tct cag gat ctt tat aac aac tat agc ata aag cag gca tct ggg atg     192
Ser Gln Asp Leu Tyr Asn Asn Tyr Ser Ile Lys Gln Ala Ser Gly Met
    50                  55                  60 tca gca gac gaa tca ata cag ctg ccg tgt ttc agc ctg gac cgg gaa     240
Ser Ala Asp Glu Ser Ile Gln Leu Pro Cys Phe Ser Leu Asp Arg Glu
65                  70                  75                  80 gca tta acc aac atc tcg gtc atc ata gca cat ctg gag aaa gtc aaa     288
Ala Leu Thr Asn Ile Ser Val Ile Ile Ala His Leu Glu Lys Val Lys
                85                  90                  95 gtg ttg agc gag aac aca gta gat act tct tgg gtg ata aga tgg cta     336
Val Leu Ser Glu Asn Thr Val Asp Thr Ser Trp Val Ile Arg Trp Leu
            100                 105                 110 aca aac atc agc tgt ttc aac cca ctg aat tta aac att tct gtg cct     384
Thr Asn Ile Ser Cys Phe Asn Pro Leu Asn Leu Asn Ile Ser Val Pro
        115                 120                 125 gga aat act gat gaa tcc tat gat tgt aaa gtg ttc gtg ctt acg gtt     432
Gly Asn Thr Asp Glu Ser Tyr Asp Cys Lys Val Phe Val Leu Thr Val
    130                 135                 140 tta aag cag ttc tca aac tgc atg gca gaa ctg cag gct aag gac aat     480
Leu Lys Gln Phe Ser Asn Cys Met Ala Glu Leu Gln Ala Lys Asp Asn
145                 150                 155                 160 act aca tgc gaa gaa tac atg ccg atg gaa tga                          513
Thr Thr Cys Glu Glu Tyr Met Pro Met Glu *
                165                 170
```

<210> SEQ ID NO 105
<211> LENGTH: 170
<212> TYPE: PRT
<213> ORGANISM: Artificial Sequence
<220> FEATURE:
<223> OTHER INFORMATION: Mouse zCytor17Lig(m)-CEE polypeptide

<400> SEQUENCE: 105

```
Met Ile Phe His Thr Gly Thr Thr Lys Pro Thr Leu Val Leu Leu Cys
 1               5                  10                  15

Cys Ile Gly Thr Trp Leu Ala Thr Cys Ser Leu Ser Phe Gly Ala Pro
             20                  25                  30

Ile Ser Lys Glu Asp Leu Arg Thr Thr Ile Asp Leu Leu Lys Gln Glu
         35                  40                  45

Ser Gln Asp Leu Tyr Asn Asn Tyr Ser Ile Lys Gln Ala Ser Gly Met
 50                  55                  60

Ser Ala Asp Glu Ser Ile Gln Leu Pro Cys Phe Ser Leu Asp Arg Glu
 65                  70                  75                  80

Ala Leu Thr Asn Ile Ser Val Ile Ile Ala His Leu Glu Lys Val Lys
                 85                  90                  95

Val Leu Ser Glu Asn Thr Val Asp Thr Ser Trp Val Ile Arg Trp Leu
            100                 105                 110

Thr Asn Ile Ser Cys Phe Asn Pro Leu Asn Leu Asn Ile Ser Val Pro
        115                 120                 125

Gly Asn Thr Asp Glu Ser Tyr Asp Cys Lys Val Phe Val Leu Thr Val
130                 135                 140

Leu Lys Gln Phe Ser Asn Cys Met Ala Glu Leu Gln Ala Lys Asp Asn
145                 150                 155                 160

Thr Thr Cys Glu Glu Tyr Met Pro Met Glu
                165                 170
```

<210> SEQ ID NO 106
<211> LENGTH: 49
<212> TYPE: DNA
<213> ORGANISM: Artificial Sequence
<220> FEATURE:
<223> OTHER INFORMATION: Oligonucleotide primer ZC41643

<400> SEQUENCE: 106
tccagggaat tcatataggc cggccaccat gatcttccac acaggaaca          49

<210> SEQ ID NO 107
<211> LENGTH: 85
<212> TYPE: DNA
<213> ORGANISM: Artificial Sequence
<220> FEATURE:
<223> OTHER INFORMATION: Oligonucleotide primer ZC41641

<400> SEQUENCE: 107 caacccccaga gctgttttaa ggcgcgcctc tagattatca ttccatcggc atgtattctt     60
cgcatgtagt attgtcctta gcctg                                           85

<210> SEQ ID NO 108
<211> LENGTH: 2529
<212> TYPE: DNA
<213> ORGANISM: Homo sapiens
<220> FEATURE:
<221> NAME/KEY: CDS
<222> LOCATION: (162)...(2108)

<400> SEQUENCE: 108

-continued

```
tgtgtgtgca gtatgaaaat tgagacagga aggcagagtg tcagcttgtt ccacctcagc    60
tgggaatgtg catcaggcaa ctcaagtttt tcaccacggc atgtgtctgt gaatgtccgc   120
aaaacattct ctctccccag ccttcatgtg ttaacctggg g atg atg tgg acc tgg   176
                                             Met Met Trp Thr Trp
                                               1               5 gca ctg tgg atg ctc ccc tca ctc tgc aaa ttc agc ctg gca gct ctg    224
Ala Leu Trp Met Leu Pro Ser Leu Cys Lys Phe Ser Leu Ala Ala Leu
             10                  15                  20 cca gct aag cct gag aac att tcc tgt gtc tac tac tat agg aaa aat    272
Pro Ala Lys Pro Glu Asn Ile Ser Cys Val Tyr Tyr Tyr Arg Lys Asn
         25                  30                  35 tta acc tgc act tgg agt cca gga aag gaa acc agt tat acc cag tac    320
Leu Thr Cys Thr Trp Ser Pro Gly Lys Glu Thr Ser Tyr Thr Gln Tyr
     40                  45                  50 aca gtt aag aga act tac gct ttt gga gaa aaa cat gat aat tgt aca    368
Thr Val Lys Arg Thr Tyr Ala Phe Gly Glu Lys His Asp Asn Cys Thr
 55                  60                  65 acc aat agt tct aca agt gaa aat cgt gct tcg tgc tct ttt ttc ctt    416
Thr Asn Ser Ser Thr Ser Glu Asn Arg Ala Ser Cys Ser Phe Phe Leu
 70                  75                  80                  85 cca aga ata acg atc cca gat aat tat acc att gag gtg gaa gct gaa    464
Pro Arg Ile Thr Ile Pro Asp Asn Tyr Thr Ile Glu Val Glu Ala Glu
             90                  95                 100 aat gga gat ggt gta att aaa tct cat atg aca tac tgg aga tta gag    512
Asn Gly Asp Gly Val Ile Lys Ser His Met Thr Tyr Trp Arg Leu Glu
        105                 110                 115 aac ata gcg aaa act gaa cca cct aag att ttc cgt gtg aaa cca gtt    560
Asn Ile Ala Lys Thr Glu Pro Pro Lys Ile Phe Arg Val Lys Pro Val
    120                 125                 130 ttg ggc atc aaa cga atg att caa att gaa tgg ata aag cct gag ttg    608
Leu Gly Ile Lys Arg Met Ile Gln Ile Glu Trp Ile Lys Pro Glu Leu
135                 140                 145 gcg cct gtt tca tct gat tta aaa tac aca ctt cga ttc agg aca gtc    656
Ala Pro Val Ser Ser Asp Leu Lys Tyr Thr Leu Arg Phe Arg Thr Val
150                 155                 160                 165 aac agt acc agc tgg atg gaa gtc aac ttc gct aag aac cgt aag gat    704
Asn Ser Thr Ser Trp Met Glu Val Asn Phe Ala Lys Asn Arg Lys Asp
            170                 175                 180 aaa aac caa acg tac aac ctc acg ggg ctg cag cct ttt aca gaa tat    752
Lys Asn Gln Thr Tyr Asn Leu Thr Gly Leu Gln Pro Phe Thr Glu Tyr
        185                 190                 195 gtc ata gct ctg cga tgt gcg gtc aag gag tca aag ttc tgg agt gac    800
Val Ile Ala Leu Arg Cys Ala Val Lys Glu Ser Lys Phe Trp Ser Asp
    200                 205                 210 tgg agc caa gaa aaa atg gga atg act gag gaa gaa gct cca tgt ggc    848
Trp Ser Gln Glu Lys Met Gly Met Thr Glu Glu Glu Ala Pro Cys Gly
215                 220                 225 ctg gaa ctg tgg aga gtc ctg aaa cca gct gag gcg gat gga aga agg    896
Leu Glu Leu Trp Arg Val Leu Lys Pro Ala Glu Ala Asp Gly Arg Arg
230                 235                 240                 245 cca gtg cgg ttg tta tgg aag aag gca aga gga gcc cca gtc cta gag    944
Pro Val Arg Leu Leu Trp Lys Lys Ala Arg Gly Ala Pro Val Leu Glu
            250                 255                 260 aaa aca ctt ggc tac aac ata tgg tac tat cca gaa agc aac act aac    992
Lys Thr Leu Gly Tyr Asn Ile Trp Tyr Tyr Pro Glu Ser Asn Thr Asn
        265                 270                 275 ctc aca gaa aca atg aac act act aac cag cag ctt gaa ctg cat ctg   1040
Leu Thr Glu Thr Met Asn Thr Thr Asn Gln Gln Leu Glu Leu His Leu
```

-continued

```
            280                 285                 290
gga ggc gag agc ttt tgg gtg tct atg att tct tat aat tct ctt ggg    1088
Gly Gly Glu Ser Phe Trp Val Ser Met Ile Ser Tyr Asn Ser Leu Gly
295                 300                 305 aag tct cca gtg gcc acc ctg agg att cca gct att caa gaa aaa tca    1136
Lys Ser Pro Val Ala Thr Leu Arg Ile Pro Ala Ile Gln Glu Lys Ser
310                 315                 320                 325 ttt cag tgc att gag gtc atg cag gcc tgc gtt gct gag gac cag cta    1184
Phe Gln Cys Ile Glu Val Met Gln Ala Cys Val Ala Glu Asp Gln Leu
            330                 335                 340 gtg gtg aag tgg caa agc tct gct cta gac gtg aac act tgg atg att    1232
Val Val Lys Trp Gln Ser Ser Ala Leu Asp Val Asn Thr Trp Met Ile
345                 350                 355 gaa tgg ttt ccg gat gtg gac tca gag ccc acc acc ctt tcc tgg gaa    1280
Glu Trp Phe Pro Asp Val Asp Ser Glu Pro Thr Thr Leu Ser Trp Glu
            360                 365                 370 tct gtg tct cag gcc acg aac tgg acg atc cag caa gat aaa tta aaa    1328
Ser Val Ser Gln Ala Thr Asn Trp Thr Ile Gln Gln Asp Lys Leu Lys
375                 380                 385 cct ttc tgg tgc tat aac atc tct gtg tat cca atg ttg cat gac aaa    1376
Pro Phe Trp Cys Tyr Asn Ile Ser Val Tyr Pro Met Leu His Asp Lys
390                 395                 400                 405 gtt ggc gag cca tat tcc atc cag gct tat gcc aaa gaa ggc gtt cca    1424
Val Gly Glu Pro Tyr Ser Ile Gln Ala Tyr Ala Lys Glu Gly Val Pro
            410                 415                 420 tca gaa ggt cct gag acc aag gtg gag aac att ggc gtg aag acg gtc    1472
Ser Glu Gly Pro Glu Thr Lys Val Glu Asn Ile Gly Val Lys Thr Val
425                 430                 435 acg atc aca tgg aaa gag att ccc aag agt gag aga aag ggt atc atc    1520
Thr Ile Thr Trp Lys Glu Ile Pro Lys Ser Glu Arg Lys Gly Ile Ile
            440                 445                 450 tgc aac tac acc atc ttt tac caa gct gaa ggt gga aaa gga ttc tcc    1568
Cys Asn Tyr Thr Ile Phe Tyr Gln Ala Glu Gly Gly Lys Gly Phe Ser
455                 460                 465 aag aca gtc aat tcc agc atc ttg cag tac ggc ctg gag tcc ctg aaa    1616
Lys Thr Val Asn Ser Ser Ile Leu Gln Tyr Gly Leu Glu Ser Leu Lys
470                 475                 480                 485 cga aag acc tct tac att gtt cag gtc atg gcc agc acc agt gct ggg    1664
Arg Lys Thr Ser Tyr Ile Val Gln Val Met Ala Ser Thr Ser Ala Gly
            490                 495                 500 gga acc aac ggg acc agc ata aat ttc aag aca ttg tca ttc agt gtc    1712
Gly Thr Asn Gly Thr Ser Ile Asn Phe Lys Thr Leu Ser Phe Ser Val
505                 510                 515 ttt gag att atc ctc ata act tct ctg att ggt gga ggc ctt ctt att    1760
Phe Glu Ile Ile Leu Ile Thr Ser Leu Ile Gly Gly Gly Leu Leu Ile
            520                 525                 530 ctc att atc ctg aca gtg gca tat ggt ctc aaa aaa ccc aac aaa ttg    1808
Leu Ile Ile Leu Thr Val Ala Tyr Gly Leu Lys Lys Pro Asn Lys Leu
535                 540                 545 act cat ctg tgt tgg ccc acc gtt ccc aac cct gct gaa agt agt ata    1856
Thr His Leu Cys Trp Pro Thr Val Pro Asn Pro Ala Glu Ser Ser Ile
550                 555                 560                 565 gcc aca tgg cat gga gat gat ttc aag gat aag cta aac ctg aag gag    1904
Ala Thr Trp His Gly Asp Asp Phe Lys Asp Lys Leu Asn Leu Lys Glu
            570                 575                 580 tct gat gac tct gtg aac aca gaa gac agg atc tta aaa cca tgt tcc    1952
Ser Asp Asp Ser Val Asn Thr Glu Asp Arg Ile Leu Lys Pro Cys Ser
585                 590                 595 acc ccc agt gac aag ttg gtg att gac aag ttg gtg gtg aac ttt ggg    2000
```

```
                Thr Pro Ser Asp Lys Leu Val Ile Asp Lys Leu Val Asn Phe Gly
                    600             605             610 aat gtt ctg caa gaa att ttc aca gat gaa gcc aga acg ggt cag gaa    2048
Asn Val Leu Gln Glu Ile Phe Thr Asp Glu Ala Arg Thr Gly Gln Glu
    615                 620                 625 aac aat tta gga ggg gaa aag aat ggg act aga att ctg tct tcc tgc    2096
Asn Asn Leu Gly Gly Glu Lys Asn Gly Thr Arg Ile Leu Ser Ser Cys
630                 635                 640                 645 cca act tca ata taagtgtgga ctaaaatgcg agaaaggtgt cctgtggtct        2148
Pro Thr Ser Ile atgcaaatta gaaggacat gcagagtttt ccaactagga agactgaatc tgtggcccca   2208
agagaaccat ctctgaagac tgggtatgtg gtctttttcca cacatggacc acctacggat 2268 gcaatctgta atgcatgtgc atgagaagtc tgttattaag tagagtgtga aaacatggtt  2328
atggtaatag gaacagcttt taaaatgctt ttgtatttgg gcctttcata caaaaaagcc  2388
ataataccat tttcatgtaa tgctatactt ctatactatt ttcatgtaat actatacttc  2448
tatactattt tcatgtaata ctatacttct atactatttt catgtaatac tacttcta    2508 tattaaagtt ttacccactc a                                             2529
```

<210> SEQ ID NO 109  
<211> LENGTH: 649  
<212> TYPE: PRT  
<213> ORGANISM: Homo sapiens

<400> SEQUENCE: 109

```
Met Met Trp Thr Trp Ala Leu Trp Met Leu Pro Ser Leu Cys Lys Phe
 1               5                  10                  15

Ser Leu Ala Ala Leu Pro Ala Lys Pro Glu Asn Ile Ser Cys Val Tyr
            20                  25                  30

Tyr Tyr Arg Lys Asn Leu Thr Cys Thr Trp Ser Pro Gly Lys Glu Thr
        35                  40                  45

Ser Tyr Thr Gln Tyr Thr Val Lys Arg Thr Tyr Ala Phe Gly Glu Lys
    50                  55                  60

His Asp Asn Cys Thr Thr Asn Ser Ser Thr Ser Glu Asn Arg Ala Ser
65                  70                  75                  80

Cys Ser Phe Phe Leu Pro Arg Ile Thr Ile Pro Asp Asn Tyr Thr Ile
                85                  90                  95

Glu Val Glu Ala Glu Asn Gly Asp Gly Val Ile Lys Ser His Met Thr
            100                 105                 110

Tyr Trp Arg Leu Glu Asn Ile Ala Lys Thr Glu Pro Pro Lys Ile Phe
        115                 120                 125

Arg Val Lys Pro Val Leu Gly Ile Lys Arg Met Ile Gln Ile Glu Trp
    130                 135                 140

Ile Lys Pro Glu Leu Ala Pro Val Ser Ser Asp Leu Lys Tyr Thr Leu
145                 150                 155                 160

Arg Phe Arg Thr Val Asn Ser Thr Ser Trp Met Glu Val Asn Phe Ala
                165                 170                 175

Lys Asn Arg Lys Asp Lys Asn Gln Thr Tyr Asn Leu Thr Gly Leu Gln
            180                 185                 190

Pro Phe Thr Glu Tyr Val Ile Ala Leu Arg Cys Ala Val Lys Glu Ser
        195                 200                 205

Lys Phe Trp Ser Asp Trp Ser Gln Glu Lys Met Gly Met Thr Glu Glu
    210                 215                 220

Glu Ala Pro Cys Gly Leu Glu Leu Trp Arg Val Leu Lys Pro Ala Glu
```

```
            225                 230                 235                 240
Ala Asp Gly Arg Arg Pro Val Arg Leu Leu Trp Lys Lys Ala Arg Gly
                    245                 250                 255
Ala Pro Val Leu Glu Lys Thr Leu Gly Tyr Asn Ile Trp Tyr Tyr Pro
                260                 265                 270
Glu Ser Asn Thr Asn Leu Thr Glu Thr Met Asn Thr Thr Asn Gln Gln
            275                 280                 285
Leu Glu Leu His Leu Gly Gly Glu Ser Phe Trp Val Ser Met Ile Ser
        290                 295                 300
Tyr Asn Ser Leu Gly Lys Ser Pro Val Ala Thr Leu Arg Ile Pro Ala
305                 310                 315                 320
Ile Gln Glu Lys Ser Phe Gln Cys Ile Glu Val Met Gln Ala Cys Val
                    325                 330                 335
Ala Glu Asp Gln Leu Val Val Lys Trp Gln Ser Ser Ala Leu Asp Val
                340                 345                 350
Asn Thr Trp Met Ile Glu Trp Phe Pro Asp Val Asp Ser Glu Pro Thr
            355                 360                 365
Thr Leu Ser Trp Glu Ser Val Ser Gln Ala Thr Asn Trp Thr Ile Gln
        370                 375                 380
Gln Asp Lys Leu Lys Pro Phe Trp Cys Tyr Asn Ile Ser Val Tyr Pro
385                 390                 395                 400
Met Leu His Asp Lys Val Gly Glu Pro Tyr Ser Ile Gln Ala Tyr Ala
                    405                 410                 415
Lys Glu Gly Val Pro Ser Glu Gly Pro Glu Thr Lys Val Glu Asn Ile
                420                 425                 430
Gly Val Lys Thr Val Thr Ile Thr Trp Lys Glu Ile Pro Lys Ser Glu
            435                 440                 445
Arg Lys Gly Ile Ile Cys Asn Tyr Thr Ile Phe Tyr Gln Ala Glu Gly
        450                 455                 460
Gly Lys Gly Phe Ser Lys Thr Val Asn Ser Ser Ile Leu Gln Tyr Gly
465                 470                 475                 480
Leu Glu Ser Leu Lys Arg Lys Thr Ser Tyr Ile Val Gln Val Met Ala
                    485                 490                 495
Ser Thr Ser Ala Gly Gly Thr Asn Gly Thr Ser Ile Asn Phe Lys Thr
                500                 505                 510
Leu Ser Phe Ser Val Phe Glu Ile Ile Leu Ile Thr Ser Leu Ile Gly
            515                 520                 525
Gly Gly Leu Leu Ile Leu Ile Ile Leu Thr Val Ala Tyr Gly Leu Lys
        530                 535                 540
Lys Pro Asn Lys Leu Thr His Leu Cys Trp Pro Thr Val Pro Asn Pro
545                 550                 555                 560
Ala Glu Ser Ser Ile Ala Thr Trp His Gly Asp Asp Phe Lys Asp Lys
                    565                 570                 575
Leu Asn Leu Lys Glu Ser Asp Asp Ser Val Asn Thr Glu Asp Arg Ile
                580                 585                 590
Leu Lys Pro Cys Ser Thr Pro Ser Asp Lys Leu Val Ile Asp Lys Leu
            595                 600                 605
Val Val Asn Phe Gly Asn Val Leu Gln Glu Ile Phe Thr Asp Glu Ala
        610                 615                 620
Arg Thr Gly Gln Glu Asn Asn Leu Gly Gly Glu Lys Asn Gly Thr Arg
625                 630                 635                 640
Ile Leu Ser Ser Cys Pro Thr Ser Ile
                645
```

```
<210> SEQ ID NO 110
<211> LENGTH: 2402
<212> TYPE: DNA
<213> ORGANISM: Homo sapiens
<220> FEATURE:
<221> NAME/KEY: CDS
<222> LOCATION: (171)...(2366)

<400> SEQUENCE: 110
ggcacgaggt gtgtgtgcag tatgaaaatt gagacaggaa ggcagagtgt cagcttgttc      60
cacctcagct gggaatgtgc atcaggcaac tcaagttttt caccacggca tgtgtctgtg     120
aatgtccgca aaacattctc tctccccagc cttcatgtgt taacctgggg atg atg       176
                                                         Met Met
                                                           1 tgg acc tgg gca ctg tgg atg ctc ccc tca ctc tgc aaa ttc agc ctg      224
Trp Thr Trp Ala Leu Trp Met Leu Pro Ser Leu Cys Lys Phe Ser Leu
      5                  10                  15 gca gct ctg cca gct aag cct gag aac att tcc tgt gtc tac tac tat      272
Ala Ala Leu Pro Ala Lys Pro Glu Asn Ile Ser Cys Val Tyr Tyr Tyr
 20                  25                  30 agg aaa aat tta acc tgc act tgg agt cca gga aag gaa acc agt tat      320
Arg Lys Asn Leu Thr Cys Thr Trp Ser Pro Gly Lys Glu Thr Ser Tyr
 35                  40                  45                  50 acc cag tac aca gtt aag aga act tac gct ttt gga gaa aaa cat gat      368
Thr Gln Tyr Thr Val Lys Arg Thr Tyr Ala Phe Gly Glu Lys His Asp
                 55                  60                  65 aat tgt aca acc aat agt tct aca agt gaa aat cgt gct tcg tgc tct      416
Asn Cys Thr Thr Asn Ser Ser Thr Ser Glu Asn Arg Ala Ser Cys Ser
             70                  75                  80 ttt ttc ctt cca aga ata acg atc cca gat aat tat acc att gag gtg      464
Phe Phe Leu Pro Arg Ile Thr Ile Pro Asp Asn Tyr Thr Ile Glu Val
         85                  90                  95 gaa gct gaa aat gga gat ggt gta att aaa tct cat atg aca tac tgg      512
Glu Ala Glu Asn Gly Asp Gly Val Ile Lys Ser His Met Thr Tyr Trp
    100                 105                 110 aga tta gag aac ata gcg aaa act gaa cca cct aag att ttc cgt gtg      560
Arg Leu Glu Asn Ile Ala Lys Thr Glu Pro Pro Lys Ile Phe Arg Val
115                 120                 125                 130 aaa cca gtt ttg ggc atc aaa cga atg att caa att gaa tgg ata aag      608
Lys Pro Val Leu Gly Ile Lys Arg Met Ile Gln Ile Glu Trp Ile Lys
                135                 140                 145 cct gag ttg gcg cct gtt tca tct gat tta aaa tac aca ctt cga ttc      656
Pro Glu Leu Ala Pro Val Ser Ser Asp Leu Lys Tyr Thr Leu Arg Phe
            150                 155                 160 agg aca gtc aac agt acc agc tgg atg gaa gtc aac ttc gct aag aac      704
Arg Thr Val Asn Ser Thr Ser Trp Met Glu Val Asn Phe Ala Lys Asn
        165                 170                 175 cgt aag gat aaa aac caa acg tac aac ctc acg ggg ctg cag cct ttt      752
Arg Lys Asp Lys Asn Gln Thr Tyr Asn Leu Thr Gly Leu Gln Pro Phe
    180                 185                 190 aca gaa tat gtc ata gct ctg cga tgt gcg gtc aag gag tca aag ttc      800
Thr Glu Tyr Val Ile Ala Leu Arg Cys Ala Val Lys Glu Ser Lys Phe
195                 200                 205                 210 tgg agt gac tgg agc caa gaa aaa atg gga atg act gag gaa gaa gct      848
Trp Ser Asp Trp Ser Gln Glu Lys Met Gly Met Thr Glu Glu Glu Ala
                215                 220                 225 cca tgt ggc ctg gaa ctg tgg aga gtc ctg aaa cca gct gag gcg gat      896
Pro Cys Gly Leu Glu Leu Trp Arg Val Leu Lys Pro Ala Glu Ala Asp
            230                 235                 240
```

```
gga aga agg cca gtg cgg ttg tta tgg aag aag gca aga gga gcc cca      944
Gly Arg Arg Pro Val Arg Leu Leu Trp Lys Lys Ala Arg Gly Ala Pro
        245                 250                 255 gtc cta gag aaa aca ctt ggc tac aac ata tgg tac tat cca gaa agc      992
Val Leu Glu Lys Thr Leu Gly Tyr Asn Ile Trp Tyr Tyr Pro Glu Ser
    260                 265                 270 aac act aac ctc aca gaa aca atg aac act act aac cag cag ctt gaa     1040
Asn Thr Asn Leu Thr Glu Thr Met Asn Thr Thr Asn Gln Gln Leu Glu
275                 280                 285                 290 ctg cat ctg gga ggc gag agc ttt tgg gtg tct atg att tct tat aat     1088
Leu His Leu Gly Gly Glu Ser Phe Trp Val Ser Met Ile Ser Tyr Asn
                295                 300                 305 tct ctt ggg aag tct cca gtg gcc acc ctg agg att cca gct att caa     1136
Ser Leu Gly Lys Ser Pro Val Ala Thr Leu Arg Ile Pro Ala Ile Gln
            310                 315                 320 gaa aaa tca ttt cag tgc att gag gtc atg cag gcc tgc gtt gct gag     1184
Glu Lys Ser Phe Gln Cys Ile Glu Val Met Gln Ala Cys Val Ala Glu
        325                 330                 335 gac cag cta gtg gtg aag tgg caa agc tct gct cta gac gtg aac act     1232
Asp Gln Leu Val Val Lys Trp Gln Ser Ser Ala Leu Asp Val Asn Thr
    340                 345                 350 tgg atg att gaa tgg ttt ccg gat gtg gac tca gag ccc acc acc ctt     1280
Trp Met Ile Glu Trp Phe Pro Asp Val Asp Ser Glu Pro Thr Thr Leu
355                 360                 365                 370 tcc tgg gaa tct gtg tct cag gcc acg aac tgg acg atc cag caa gat     1328
Ser Trp Glu Ser Val Ser Gln Ala Thr Asn Trp Thr Ile Gln Gln Asp
                375                 380                 385 aaa tta aaa cct ttc tgg tgc tat aac atc tct gtg tat cca atg ttg     1376
Lys Leu Lys Pro Phe Trp Cys Tyr Asn Ile Ser Val Tyr Pro Met Leu
            390                 395                 400 cat gac aaa gtt ggc gag cca tat tcc atc cag gct tat gcc aaa gaa     1424
His Asp Lys Val Gly Glu Pro Tyr Ser Ile Gln Ala Tyr Ala Lys Glu
        405                 410                 415 ggc gtt cca tca gaa ggt cct gag acc aag gtg gag aac att ggc gtg     1472
Gly Val Pro Ser Glu Gly Pro Glu Thr Lys Val Glu Asn Ile Gly Val
    420                 425                 430 aag acg gtc acg atc aca tgg aaa gag att ccc aag agt gag aga aag     1520
Lys Thr Val Thr Ile Thr Trp Lys Glu Ile Pro Lys Ser Glu Arg Lys
435                 440                 445                 450 ggt atc atc tgc aac tac acc atc ttt tac caa gct gaa ggt gga aaa     1568
Gly Ile Ile Cys Asn Tyr Thr Ile Phe Tyr Gln Ala Glu Gly Gly Lys
                455                 460                 465 gga ttc tcc aag aca gtc aat tcc agc atc ttg cag tac ggc ctg gag     1616
Gly Phe Ser Lys Thr Val Asn Ser Ser Ile Leu Gln Tyr Gly Leu Glu
            470                 475                 480 tcc ctg aaa cga aag acc tct tac att gtt cag gtc atg gcc agc acc     1664
Ser Leu Lys Arg Lys Thr Ser Tyr Ile Val Gln Val Met Ala Ser Thr
        485                 490                 495 agt gct ggg gga acc aac ggg acc agc ata aat ttc aag aca ttg tca     1712
Ser Ala Gly Gly Thr Asn Gly Thr Ser Ile Asn Phe Lys Thr Leu Ser
    500                 505                 510 ttc agt gtc ttt gag att atc ctc ata act tct ctg att ggt gga ggc     1760
Phe Ser Val Phe Glu Ile Ile Leu Ile Thr Ser Leu Ile Gly Gly Gly
515                 520                 525                 530 ctt ctt att ctc att atc ctg aca gtg gca tat ggt ctc aaa aaa ccc     1808
Leu Leu Ile Leu Ile Ile Leu Thr Val Ala Tyr Gly Leu Lys Lys Pro
                535                 540                 545 aac aaa ttg act cat ctg tgt ggg ccc acc gtt ccc aac cct gct gaa     1856
Asn Lys Leu Thr His Leu Cys Trp Pro Thr Val Pro Asn Pro Ala Glu
```

-continued

```
                    550                 555                 560
agt agt ata gcc aca tgg cat gga gat gat ttc aag gat aag cta aac      1904
Ser Ser Ile Ala Thr Trp His Gly Asp Asp Phe Lys Asp Lys Leu Asn
            565                 570                 575 ctg aag gag tct gat gac tct gtg aac aca gaa gac agg atc tta aaa      1952
Leu Lys Glu Ser Asp Asp Ser Val Asn Thr Glu Asp Arg Ile Leu Lys
        580                 585                 590 cca tgt tcc acc ccc agt gac aag ttg gtg att gac aag ttg gtg gtg      2000
Pro Cys Ser Thr Pro Ser Asp Lys Leu Val Ile Asp Lys Leu Val Val
595                 600                 605                 610 aac ttt ggg aat gtt ctg caa gaa att ttc aca gat gaa gcc aga acg      2048
Asn Phe Gly Asn Val Leu Gln Glu Ile Phe Thr Asp Glu Ala Arg Thr
                615                 620                 625 ggt cag gaa aac aat tta gga ggg gaa aag aat ggg tat gtg acc tgc      2096
Gly Gln Glu Asn Asn Leu Gly Gly Glu Lys Asn Gly Tyr Val Thr Cys
            630                 635                 640 ccc ttc agg cct gat tgt ccc ctg ggg aaa agt ttt gag gag ctc cca      2144
Pro Phe Arg Pro Asp Cys Pro Leu Gly Lys Ser Phe Glu Glu Leu Pro
        645                 650                 655 gtt tca cct gag att ccg ccc aga aaa tcc caa tac cta cgt tcg agg      2192
Val Ser Pro Glu Ile Pro Pro Arg Lys Ser Gln Tyr Leu Arg Ser Arg
660                 665                 670 atg cca gag ggg acc cgc cca gaa gcc aaa gag cag ctt ctc ttt tct      2240
Met Pro Glu Gly Thr Arg Pro Glu Ala Lys Glu Gln Leu Leu Phe Ser
675                 680                 685                 690 ggt caa agt tta gta cca gat cat ctg tgt gag gaa gga gcc cca aat      2288
Gly Gln Ser Leu Val Pro Asp His Leu Cys Glu Glu Gly Ala Pro Asn
                695                 700                 705 cca tat ttg aaa aat tca gtg aca gcc agg gaa ttt ctt gtg tct gaa      2336
Pro Tyr Leu Lys Asn Ser Val Thr Ala Arg Glu Phe Leu Val Ser Glu
            710                 715                 720 aaa ctt cca gag cac acc aag gga gaa gtc taaatgcgac catagcatga       2386
Lys Leu Pro Glu His Thr Lys Gly Glu Val
        725                 730 gaccctcggg gcctca                                                    2402

<210> SEQ ID NO 111
<211> LENGTH: 732
<212> TYPE: PRT
<213> ORGANISM: Homo sapiens

<400> SEQUENCE: 111

Met Met Trp Thr Trp Ala Leu Trp Met Leu Pro Ser Leu Cys Lys Phe
1               5                   10                  15

Ser Leu Ala Ala Leu Pro Ala Lys Pro Glu Asn Ile Ser Cys Val Tyr
            20                  25                  30

Tyr Tyr Arg Lys Asn Leu Thr Cys Thr Trp Ser Pro Gly Lys Glu Thr
        35                  40                  45

Ser Tyr Thr Gln Tyr Thr Val Lys Arg Thr Tyr Ala Phe Gly Glu Lys
    50                  55                  60

His Asp Asn Cys Thr Thr Asn Ser Ser Thr Ser Glu Asn Arg Ala Ser
65                  70                  75                  80

Cys Ser Phe Phe Leu Pro Arg Ile Thr Ile Pro Asp Asn Tyr Thr Ile
                85                  90                  95

Glu Val Glu Ala Glu Asn Gly Asp Gly Val Ile Lys Ser His Met Thr
            100                 105                 110

Tyr Trp Arg Leu Glu Asn Ile Ala Lys Thr Glu Pro Pro Lys Ile Phe
        115                 120                 125
```

```
Arg Val Lys Pro Val Leu Gly Ile Lys Arg Met Ile Gln Ile Glu Trp
130                 135                 140

Ile Lys Pro Glu Leu Ala Pro Val Ser Ser Asp Leu Lys Tyr Thr Leu
145                 150                 155                 160

Arg Phe Arg Thr Val Asn Ser Thr Ser Trp Met Glu Val Asn Phe Ala
                165                 170                 175

Lys Asn Arg Lys Asp Lys Asn Gln Thr Tyr Asn Leu Thr Gly Leu Gln
            180                 185                 190

Pro Phe Thr Glu Tyr Val Ile Ala Leu Arg Cys Ala Val Lys Glu Ser
        195                 200                 205

Lys Phe Trp Ser Asp Trp Ser Gln Glu Lys Met Gly Met Thr Glu Glu
    210                 215                 220

Glu Ala Pro Cys Gly Leu Glu Leu Trp Arg Val Leu Lys Pro Ala Glu
225                 230                 235                 240

Ala Asp Gly Arg Arg Pro Val Arg Leu Leu Trp Lys Lys Ala Arg Gly
                245                 250                 255

Ala Pro Val Leu Glu Lys Thr Leu Gly Tyr Asn Ile Trp Tyr Tyr Pro
            260                 265                 270

Glu Ser Asn Thr Asn Leu Thr Glu Thr Met Asn Thr Thr Asn Gln Gln
        275                 280                 285

Leu Glu Leu His Leu Gly Gly Glu Ser Phe Trp Val Ser Met Ile Ser
    290                 295                 300

Tyr Asn Ser Leu Gly Lys Ser Pro Val Ala Thr Leu Arg Ile Pro Ala
305                 310                 315                 320

Ile Gln Glu Lys Ser Phe Gln Cys Ile Glu Val Met Gln Ala Cys Val
                325                 330                 335

Ala Glu Asp Gln Leu Val Val Lys Trp Gln Ser Ser Ala Leu Asp Val
            340                 345                 350

Asn Thr Trp Met Ile Glu Trp Phe Pro Asp Val Asp Ser Glu Pro Thr
        355                 360                 365

Thr Leu Ser Trp Glu Ser Val Ser Gln Ala Thr Asn Trp Thr Ile Gln
    370                 375                 380

Gln Asp Lys Leu Lys Pro Phe Trp Cys Tyr Asn Ile Ser Val Tyr Pro
385                 390                 395                 400

Met Leu His Asp Lys Val Gly Glu Pro Tyr Ser Ile Gln Ala Tyr Ala
                405                 410                 415

Lys Glu Gly Val Pro Ser Glu Gly Pro Glu Thr Lys Val Glu Asn Ile
            420                 425                 430

Gly Val Lys Thr Val Thr Ile Thr Trp Lys Glu Ile Pro Lys Ser Glu
        435                 440                 445

Arg Lys Gly Ile Ile Cys Asn Tyr Thr Ile Phe Tyr Gln Ala Glu Gly
    450                 455                 460

Gly Lys Gly Phe Ser Lys Thr Val Asn Ser Ser Ile Leu Gln Tyr Gly
465                 470                 475                 480

Leu Glu Ser Leu Lys Arg Lys Thr Ser Tyr Ile Val Gln Val Met Ala
                485                 490                 495

Ser Thr Ser Ala Gly Gly Thr Asn Gly Thr Ser Ile Asn Phe Lys Thr
            500                 505                 510

Leu Ser Phe Ser Val Phe Glu Ile Ile Leu Ile Thr Ser Leu Ile Gly
        515                 520                 525

Gly Gly Leu Leu Ile Leu Ile Ile Leu Thr Val Ala Tyr Gly Leu Lys
    530                 535                 540
```

```
Lys Pro Asn Lys Leu Thr His Leu Cys Trp Pro Thr Val Pro Asn Pro
545                 550                 555                 560

Ala Glu Ser Ser Ile Ala Thr Trp His Gly Asp Asp Phe Lys Asp Lys
                565                 570                 575

Leu Asn Leu Lys Glu Ser Asp Ser Val Asn Thr Glu Asp Arg Ile
            580                 585                 590

Leu Lys Pro Cys Ser Thr Pro Ser Asp Lys Leu Val Ile Asp Lys Leu
        595                 600                 605

Val Val Asn Phe Gly Asn Val Leu Gln Glu Ile Phe Thr Asp Glu Ala
        610                 615                 620

Arg Thr Gly Gln Glu Asn Asn Leu Gly Gly Glu Lys Asn Gly Tyr Val
625                 630                 635                 640

Thr Cys Pro Phe Arg Pro Asp Cys Pro Leu Gly Lys Ser Phe Glu Glu
                645                 650                 655

Leu Pro Val Ser Pro Glu Ile Pro Pro Arg Lys Ser Gln Tyr Leu Arg
            660                 665                 670

Ser Arg Met Pro Glu Gly Thr Arg Pro Glu Ala Lys Glu Gln Leu Leu
            675                 680                 685

Phe Ser Gly Gln Ser Leu Val Pro Asp His Leu Cys Glu Glu Gly Ala
690                 695                 700

Pro Asn Pro Tyr Leu Lys Asn Ser Val Thr Ala Arg Glu Phe Leu Val
705                 710                 715                 720

Ser Glu Lys Leu Pro Glu His Thr Lys Gly Glu Val
            725                 730

<210> SEQ ID NO 112
<211> LENGTH: 1299
<212> TYPE: DNA
<213> ORGANISM: Homo sapiens
<220> FEATURE:
<221> NAME/KEY: CDS
<222> LOCATION: (162)...(1133)

<400> SEQUENCE: 112
tgtgtgtgca gtatgaaaat tgagacagga aggcagagtg tcagcttgtt ccacctcagc    60
tgggaatgtg catcaggcaa ctcaagtttt tcaccacggc atgtgtctgt gaatgtccgc   120
aaaacattct ctctccccag ccttcatgtg ttaacctggg g atg atg tgg acc tgg   176
                                            Met Met Trp Thr Trp
                                              1               5 gca ctg tgg atg ctc ccc tca ctc tgc aaa ttc agc ctg gca gct ctg    224
Ala Leu Trp Met Leu Pro Ser Leu Cys Lys Phe Ser Leu Ala Ala Leu
             10                  15                  20 cca gct aag cct gag aac att tcc tgt gtc tac tac tat agg aaa aat    272
Pro Ala Lys Pro Glu Asn Ile Ser Cys Val Tyr Tyr Tyr Arg Lys Asn
         25                  30                  35 tta acc tgc act tgg agt cca gga aag gaa acc agt tat acc cag tac    320
Leu Thr Cys Thr Trp Ser Pro Gly Lys Glu Thr Ser Tyr Thr Gln Tyr
     40                  45                  50 aca gtt aag aga act tac gct ttt gga gaa aaa cat gat aat tgt aca    368
Thr Val Lys Arg Thr Tyr Ala Phe Gly Glu Lys His Asp Asn Cys Thr
 55                  60                  65 acc aat agt tct aca agt gaa aat cgt gct tcg tgc tct ttt ttc ctt    416
Thr Asn Ser Ser Thr Ser Glu Asn Arg Ala Ser Cys Ser Phe Phe Leu
 70                  75                  80                  85 cca aga ata acg atc cca gat aat tat acc att gag gtg gaa gct gaa    464
Pro Arg Ile Thr Ile Pro Asp Asn Tyr Thr Ile Glu Val Glu Ala Glu
         90                  95                 100
```

```
aat gga gat ggt gta att aaa tct cat atg aca tac tgg aga tta gag       512
Asn Gly Asp Gly Val Ile Lys Ser His Met Thr Tyr Trp Arg Leu Glu
            105                 110                 115 aac ata gcg aaa act gaa cca cct aag att ttc cgt gtg aaa cca gtt       560
Asn Ile Ala Lys Thr Glu Pro Pro Lys Ile Phe Arg Val Lys Pro Val
            120                 125                 130 ttg ggc atc aaa cga atg att caa att gaa tgg ata aag cct gag ttg       608
Leu Gly Ile Lys Arg Met Ile Gln Ile Glu Trp Ile Lys Pro Glu Leu
            135                 140                 145 gcg cct gtt tca tct gat tta aaa tac aca ctt cga ttc agg aca gtc       656
Ala Pro Val Ser Ser Asp Leu Lys Tyr Thr Leu Arg Phe Arg Thr Val
150                 155                 160                 165 aac agt acc agc tgg atg gaa gtc aac ttc gct aag aac cgt aag gat       704
Asn Ser Thr Ser Trp Met Glu Val Asn Phe Ala Lys Asn Arg Lys Asp
            170                 175                 180 aaa aac caa acg tac aac ctc acg ggg ctg cag cct ttt aca gaa tat       752
Lys Asn Gln Thr Tyr Asn Leu Thr Gly Leu Gln Pro Phe Thr Glu Tyr
            185                 190                 195 gtc ata gct ctg cga tgt gcg gtc aag gag tca aag ttc tgg agt gac       800
Val Ile Ala Leu Arg Cys Ala Val Lys Glu Ser Lys Phe Trp Ser Asp
            200                 205                 210 tgg agc caa gaa aaa atg gga atg act gag gaa gaa gct cca tgt ggc       848
Trp Ser Gln Glu Lys Met Gly Met Thr Glu Glu Glu Ala Pro Cys Gly
215                 220                 225 ctg gaa ctg tgg aga gtc ctg aaa cca gct gag gcg gat gga aga agg       896
Leu Glu Leu Trp Arg Val Leu Lys Pro Ala Glu Ala Asp Gly Arg Arg
230                 235                 240                 245 cca gtg cgg ttg tta tgg aag aag gca aga gga gcc cca gtc cta gag       944
Pro Val Arg Leu Leu Trp Lys Lys Ala Arg Gly Ala Pro Val Leu Glu
            250                 255                 260 aaa aca ctt ggc tac aac ata tgg tac tat cca gaa agc aac act aac       992
Lys Thr Leu Gly Tyr Asn Ile Trp Tyr Tyr Pro Glu Ser Asn Thr Asn
            265                 270                 275 ctc aca gaa aca atg aac act act aac cag cag ctt gaa ctg cat ctg      1040
Leu Thr Glu Thr Met Asn Thr Thr Asn Gln Gln Leu Glu Leu His Leu
            280                 285                 290 gga ggc gag agc ttt tgg gtg tct atg att tct tat aat tct ctt ggg      1088
Gly Gly Glu Ser Phe Trp Val Ser Met Ile Ser Tyr Asn Ser Leu Gly
295                 300                 305 aag tct cca gtg gcc acc ctg agg att cca gct att caa gaa aaa          1133
Lys Ser Pro Val Ala Thr Leu Arg Ile Pro Ala Ile Gln Glu Lys
310                 315                 320 tagaaacttt acagatgcta gtcccagaca taaaagaaaa taatgttctg gatgtgcacg    1193
atggctcacg cctgtaatcc cagcactttg aggccaagac gggtggatcg ctgagttcag    1253
gagttcaaga caagtccagg caacatagtg aaaccttgtt tctaca                   1299
```

<210> SEQ ID NO 113
<211> LENGTH: 324
<212> TYPE: PRT
<213> ORGANISM: Homo sapiens

<400> SEQUENCE: 113

```
Met Met Trp Thr Trp Ala Leu Trp Met Leu Pro Ser Leu Cys Lys Phe
1               5                   10                  15

Ser Leu Ala Ala Leu Pro Ala Lys Pro Glu Asn Ile Ser Cys Val Tyr
            20                  25                  30

Tyr Tyr Arg Lys Asn Leu Thr Cys Thr Trp Ser Pro Gly Lys Glu Thr
        35                  40                  45
```

```
Ser Tyr Thr Gln Tyr Thr Val Lys Arg Thr Tyr Ala Phe Gly Glu Lys
 50                  55                  60
His Asp Asn Cys Thr Thr Asn Ser Ser Thr Ser Glu Asn Arg Ala Ser
 65                  70                  75                  80
Cys Ser Phe Phe Leu Pro Arg Ile Thr Ile Pro Asp Asn Tyr Thr Ile
                 85                  90                  95
Glu Val Glu Ala Glu Asn Gly Asp Gly Val Ile Lys Ser His Met Thr
            100                 105                 110
Tyr Trp Arg Leu Glu Asn Ile Ala Lys Thr Pro Pro Lys Ile Phe
        115                 120                 125
Arg Val Lys Pro Val Leu Gly Ile Lys Arg Met Ile Gln Ile Glu Trp
130                 135                 140
Ile Lys Pro Glu Leu Ala Pro Val Ser Ser Asp Leu Lys Tyr Thr Leu
145                 150                 155                 160
Arg Phe Arg Thr Val Asn Ser Thr Ser Trp Met Glu Val Asn Phe Ala
                165                 170                 175
Lys Asn Arg Lys Asp Lys Asn Gln Thr Tyr Asn Leu Thr Gly Leu Gln
            180                 185                 190
Pro Phe Thr Glu Tyr Val Ile Ala Leu Arg Cys Ala Val Lys Glu Ser
        195                 200                 205
Lys Phe Trp Ser Asp Trp Ser Gln Glu Lys Met Gly Met Thr Glu Glu
210                 215                 220
Glu Ala Pro Cys Gly Leu Glu Leu Trp Arg Val Leu Lys Pro Ala Glu
225                 230                 235                 240
Ala Asp Gly Arg Arg Pro Val Arg Leu Leu Trp Lys Lys Ala Arg Gly
                245                 250                 255
Ala Pro Val Leu Glu Lys Thr Leu Gly Tyr Asn Ile Trp Tyr Tyr Pro
            260                 265                 270
Glu Ser Asn Thr Asn Leu Thr Glu Thr Met Asn Thr Thr Asn Gln Gln
        275                 280                 285
Leu Glu Leu His Leu Gly Gly Ser Phe Trp Val Ser Met Ile Ser
290                 295                 300
Tyr Asn Ser Leu Gly Lys Ser Pro Val Ala Thr Leu Arg Ile Pro Ala
305                 310                 315                 320
Ile Gln Glu Lys

<210> SEQ ID NO 114
<211> LENGTH: 1476
<212> TYPE: DNA
<213> ORGANISM: Homo sapiens
<220> FEATURE:
<221> NAME/KEY: CDS
<222> LOCATION: (162)...(878)

<400> SEQUENCE: 114
tgtgtgtgca gtatgaaaat tgagacagga aggcagagtg tcagcttgtt ccacctcagc    60
tgggaatgtg catcaggcaa ctcaagtttt tcaccacggc atgtgtctgt gaatgtccgc   120
aaaacattct ctctccccag ccttcatgtg ttaacctggg g atg atg tgg acc tgg   176
                                            Met Met Trp Thr Trp
                                              1               5 gca ctg tgg atg ctc ccc tca ctc tgc aaa ttc agc ctg gca gct ctg   224
Ala Leu Trp Met Leu Pro Ser Leu Cys Lys Phe Ser Leu Ala Ala Leu
                 10                  15                  20 cca gct aag cct gag aac att tcc tgt gtc tac tac tat agg aaa aat   272
Pro Ala Lys Pro Glu Asn Ile Ser Cys Val Tyr Tyr Tyr Arg Lys Asn
            25                  30                  35
```

| | | |
|---|---|---|
| tta acc tgc act tgg agt cca gga aag gaa acc agt tat acc cag tac<br>Leu Thr Cys Thr Trp Ser Pro Gly Lys Glu Thr Ser Tyr Thr Gln Tyr<br>          40                        45                      50 | 320 | |
| aca gtt aag aga act tac gct ttt gga gaa aaa cat gat aat tgt aca<br>Thr Val Lys Arg Thr Tyr Ala Phe Gly Glu Lys His Asp Asn Cys Thr<br>    55                        60                        65 | 368 | |
| acc aat agt tct aca agt gaa aat cgt gct tcg tgc tct ttt ttc ctt<br>Thr Asn Ser Ser Thr Ser Glu Asn Arg Ala Ser Cys Ser Phe Phe Leu<br>70                        75                        80                  85 | 416 | |
| cca aga ata acg atc cca gat aat tat acc att gag gtg gaa gct gaa<br>Pro Arg Ile Thr Ile Pro Asp Asn Tyr Thr Ile Glu Val Glu Ala Glu<br>                        90                        95                    100 | 464 | |
| aat gga gat ggt gta att aaa tct cat atg aca tac tgg aga tta gag<br>Asn Gly Asp Gly Val Ile Lys Ser His Met Thr Tyr Trp Arg Leu Glu<br>                  105                      110                    115 | 512 | |
| aac ata gcg aaa act gaa cca cct aag att ttc cgt gtg aaa cca gtt<br>Asn Ile Ala Lys Thr Glu Pro Pro Lys Ile Phe Arg Val Lys Pro Val<br>        120                      125                      130 | 560 | |
| ttg ggc atc aaa cga atg att caa att gaa tgg ata aag cct gag ttg<br>Leu Gly Ile Lys Arg Met Ile Gln Ile Glu Trp Ile Lys Pro Glu Leu<br>    135                        140                        145 | 608 | |
| gcg cct gtt tca tct gat tta aaa tac aca ctt cga ttc agg aca gtc<br>Ala Pro Val Ser Ser Asp Leu Lys Tyr Thr Leu Arg Phe Arg Thr Val<br>150                        155                        160                  165 | 656 | |
| aac agt acc agc tgg atg gaa gtc aac ttc gct aag aac cgt aag gat<br>Asn Ser Thr Ser Trp Met Glu Val Asn Phe Ala Lys Asn Arg Lys Asp<br>                170                      175                    180 | 704 | |
| aaa aac caa acg tac aac ctc acg ggg ctg cag cct ttt aca gaa tat<br>Lys Asn Gln Thr Tyr Asn Leu Thr Gly Leu Gln Pro Phe Thr Glu Tyr<br>        185                      190                      195 | 752 | |
| gtc ata gct ctg cga tgt gcg gtc aag gag tca aag ttc tgg agt gac<br>Val Ile Ala Leu Arg Cys Ala Val Lys Glu Ser Lys Phe Trp Ser Asp<br>    200                        205                        210 | 800 | |
| tgg agc caa gaa aaa atg gga atg act gag gaa gaa ggc aag cta ctc<br>Trp Ser Gln Glu Lys Met Gly Met Thr Glu Glu Glu Gly Lys Leu Leu<br>215                        220                        225 | 848 | |
| cct gcg att ccc gtc ctg tct gct ctg gtg tagggctgct ttgggctaga<br>Pro Ala Ile Pro Val Leu Ser Ala Leu Val<br>230                        235 | 898 | |
| cttggtgggg tttgtcacca cctggttggg aatcatggaa tctcatgacc ccaggggccc | 958 | |
| cctgtaccat cgagagtgag cctgcacaac tttgtgcccc aaaggcaaag gatcacattt | 1018 | |
| taatactcat gaggttctta tactatacat gaaagggtat catatcattt gttttgtttt | 1078 | |
| gttttgtttt tgagatggag tcttactctg tcacccagga tggagtgcag tgatgtgatc | 1138 | |
| tcggctcact gccaccacca cctcccgagt tcaagcaatt cttgtgcctc agcctcccaa | 1198 | |
| gtagctggga ttacaggggc ccacgaccat gcccggttga ttttgtatt tttagtagag | 1258 | |
| aagggatatc accatgttgg ctaggctagt cttgaactcc tgacctcagg taatctgccc | 1318 | |
| accttgacct cccaaagtgt tgggattaca ggcgtgagcc actgtgcccc gccagtatca | 1378 | |
| tatcatctga aggtatcctg tgataaatta aagatacata ttgtgaatcc tggagctact | 1438 | |
| actcaaaaaa taaataaagg tgtaactaat acaattta | 1476 | |

<210> SEQ ID NO 115
<211> LENGTH: 239
<212> TYPE: PRT
<213> ORGANISM: Homo sapiens

```
<400> SEQUENCE: 115

Met Met Trp Thr Trp Ala Leu Trp Met Leu Pro Ser Leu Cys Lys Phe
  1               5                  10                  15

Ser Leu Ala Ala Leu Pro Ala Lys Pro Glu Asn Ile Ser Cys Val Tyr
             20                  25                  30

Tyr Tyr Arg Lys Asn Leu Thr Cys Thr Trp Ser Pro Gly Lys Glu Thr
         35                  40                  45

Ser Tyr Thr Gln Tyr Thr Val Lys Arg Thr Tyr Ala Phe Gly Glu Lys
 50                  55                  60

His Asp Asn Cys Thr Thr Asn Ser Ser Thr Ser Glu Asn Arg Ala Ser
 65                  70                  75                  80

Cys Ser Phe Phe Leu Pro Arg Ile Thr Ile Pro Asp Asn Tyr Thr Ile
                 85                  90                  95

Glu Val Glu Ala Glu Asn Gly Asp Gly Val Ile Lys Ser His Met Thr
            100                 105                 110

Tyr Trp Arg Leu Glu Asn Ile Ala Lys Thr Glu Pro Pro Lys Ile Phe
        115                 120                 125

Arg Val Lys Pro Val Leu Gly Ile Lys Arg Met Ile Gln Ile Glu Trp
130                 135                 140

Ile Lys Pro Glu Leu Ala Pro Val Ser Ser Asp Leu Lys Tyr Thr Leu
145                 150                 155                 160

Arg Phe Arg Thr Val Asn Ser Thr Ser Trp Met Glu Val Asn Phe Ala
                165                 170                 175

Lys Asn Arg Lys Asp Lys Asn Gln Thr Tyr Asn Leu Thr Gly Leu Gln
            180                 185                 190

Pro Phe Thr Glu Tyr Val Ile Ala Leu Arg Cys Ala Val Lys Glu Ser
        195                 200                 205

Lys Phe Trp Ser Asp Trp Ser Gln Glu Lys Met Gly Met Thr Glu Glu
    210                 215                 220

Glu Gly Lys Leu Leu Pro Ala Ile Pro Val Leu Ser Ala Leu Val
225                 230                 235

<210> SEQ ID NO 116
<211> LENGTH: 2748
<212> TYPE: DNA
<213> ORGANISM: Mus musculus
<220> FEATURE:
<221> NAME/KEY: CDS
<222> LOCATION: (237)...(2222)

<400> SEQUENCE: 116 gatgggccc tgaatgttga tctgacagaa ttccagacca acctggtggt tattgtcctt    60
ttcatctggt catgctgaat atactctcaa gatgtgctgg agaaggtgct gctgtccggg   120
ctctcagaga aggcagtgct ggaggcgttc ctggcccggg tctcctccta ctgttcctgg   180
tagcccagcc ttctcggggt ggaaggagaa gctggccagg tgagctctga ggaagc atg   239
                                                              Met
                                                                1 ctg agc agc cag aag gga tcc tgc agc cag gaa cca ggg gca gcc cac   287
Leu Ser Ser Gln Lys Gly Ser Cys Ser Gln Glu Pro Gly Ala Ala His
         5                  10                  15 gtc cag cct ctg ggt gtg aac gct gga ata atg tgg acc ttg gca ctg   335
Val Gln Pro Leu Gly Val Asn Ala Gly Ile Met Trp Thr Leu Ala Leu
     20                  25                  30 tgg gca ttc tct ttc ctc tgc aaa ttc agc ctg gca gtc ctg ccg act   383
Trp Ala Phe Ser Phe Leu Cys Lys Phe Ser Leu Ala Val Leu Pro Thr
 35                  40                  45
```

```
aag cca gag aac att tcc tgc gtc ttt tac ttc gac aga aat ctg act    431
Lys Pro Glu Asn Ile Ser Cys Val Phe Tyr Phe Asp Arg Asn Leu Thr
 50              55                  60                  65 tgc act tgg aga cca gag aag gaa acc aat gat acc agc tac att gtg    479
Cys Thr Trp Arg Pro Glu Lys Glu Thr Asn Asp Thr Ser Tyr Ile Val
             70                  75                  80 act ttg act tac tcc tat gga aaa agc aat tat agt gac aat gct aca    527
Thr Leu Thr Tyr Ser Tyr Gly Lys Ser Asn Tyr Ser Asp Asn Ala Thr
                 85                  90                  95 gag gct tca tat tct ttt ccc cgt tcc tgt gca atg ccc cca gac atc    575
Glu Ala Ser Tyr Ser Phe Pro Arg Ser Cys Ala Met Pro Pro Asp Ile
            100                 105                 110 tgc agt gtt gaa gta caa gct caa aat gga gat ggt aaa gtt aaa tct    623
Cys Ser Val Glu Val Gln Ala Gln Asn Gly Asp Gly Lys Val Lys Ser
        115                 120                 125 gac atc aca tat tgg cat tta atc tcc ata gca aaa acc gaa cca cct    671
Asp Ile Thr Tyr Trp His Leu Ile Ser Ile Ala Lys Thr Glu Pro Pro
130                 135                 140                 145 ata att tta agt gtg aat cca att tgt aat aga atg ttc cag ata caa    719
Ile Ile Leu Ser Val Asn Pro Ile Cys Asn Arg Met Phe Gln Ile Gln
                150                 155                 160 tgg aaa ccg cgt gaa aag act cgt ggg ttt cct tta gta tgc atg ctt    767
Trp Lys Pro Arg Glu Lys Thr Arg Gly Phe Pro Leu Val Cys Met Leu
            165                 170                 175 cgg ttc aga act gtc aac agt agc cgc tgg acg gaa gtc aat ttt gaa    815
Arg Phe Arg Thr Val Asn Ser Ser Arg Trp Thr Glu Val Asn Phe Glu
        180                 185                 190 aac tgt aaa cag gtc tgc aac ctc aca gga ctt cag gct ttc aca gaa    863
Asn Cys Lys Gln Val Cys Asn Leu Thr Gly Leu Gln Ala Phe Thr Glu
195                 200                 205 tat gtc ctg gct cta cga ttc agg ttc aat gac tca aga tat tgg agc    911
Tyr Val Leu Ala Leu Arg Phe Arg Phe Asn Asp Ser Arg Tyr Trp Ser
210                 215                 220                 225 aag tgg agc aaa gaa gaa acc aga gtg act atg gag gaa gtt cca cat    959
Lys Trp Ser Lys Glu Glu Thr Arg Val Thr Met Glu Glu Val Pro His
                230                 235                 240 gtc ctg gac ctg tgg aga att ctg gaa cca gca gac atg aac gga gac   1007
Val Leu Asp Leu Trp Arg Ile Leu Glu Pro Ala Asp Met Asn Gly Asp
            245                 250                 255 agg aag gtg cga ttg ctg tgg aag aag gca aga gga gcc ccc gtc ttg   1055
Arg Lys Val Arg Leu Leu Trp Lys Lys Ala Arg Gly Ala Pro Val Leu
        260                 265                 270 gag aaa aca ttt ggc tac cac ata cag tac ttt gca gag aac agc act   1103
Glu Lys Thr Phe Gly Tyr His Ile Gln Tyr Phe Ala Glu Asn Ser Thr
275                 280                 285 aac ctc aca gag ata aac aac atc acc acc cag cag tat gaa ctg ctt   1151
Asn Leu Thr Glu Ile Asn Asn Ile Thr Thr Gln Gln Tyr Glu Leu Leu
290                 295                 300                 305 ctg atg agc cag gca cac tct gtg tcc gtg act tct ttt aat tct ctt   1199
Leu Met Ser Gln Ala His Ser Val Ser Val Thr Ser Phe Asn Ser Leu
                310                 315                 320 ggc aag tcc caa gag acc atc ctg agg atc cca gat gtc cat gag aag   1247
Gly Lys Ser Gln Glu Thr Ile Leu Arg Ile Pro Asp Val His Glu Lys
            325                 330                 335 acc ttc cag tac att aag agc atg cag gcc tac ata gcc gag ccc ctg   1295
Thr Phe Gln Tyr Ile Lys Ser Met Gln Ala Tyr Ile Ala Glu Pro Leu
        340                 345                 350 ttg gtg gtg aac tgg caa agc tcc att cct gcg gtg gac act tgg ata   1343
Leu Val Val Asn Trp Gln Ser Ser Ile Pro Ala Val Asp Thr Trp Ile
```

```
                      355                 360                 365
gtg gag tgg ctc cca gaa gct gcc atg tcg aag ttc cct gcc ctt tcc    1391
Val Glu Trp Leu Pro Glu Ala Ala Met Ser Lys Phe Pro Ala Leu Ser
370                 375                 380                 385 tgg gaa tct gtg tct cag gtc acg aac tgg acc atc gag caa gat aaa    1439
Trp Glu Ser Val Ser Gln Val Thr Asn Trp Thr Ile Glu Gln Asp Lys
                390                 395                 400 cta aaa cct ttc aca tgc tat aat ata tca gtg tat cca gtg ttg gga    1487
Leu Lys Pro Phe Thr Cys Tyr Asn Ile Ser Val Tyr Pro Val Leu Gly
            405                 410                 415 cac cga gtt gga gag ccg tat tca atc caa gct tat gcc aaa gaa gga    1535
His Arg Val Gly Glu Pro Tyr Ser Ile Gln Ala Tyr Ala Lys Glu Gly
        420                 425                 430 act cca tta aaa ggt cct gag acc agg gtg gag aac atc ggt ctg agg    1583
Thr Pro Leu Lys Gly Pro Glu Thr Arg Val Glu Asn Ile Gly Leu Arg
    435                 440                 445 aca gcc acg atc aca tgg aag gag att cct aag agt gct agg aat gga    1631
Thr Ala Thr Ile Thr Trp Lys Glu Ile Pro Lys Ser Ala Arg Asn Gly
450                 455                 460                 465 ttt atc aac aat tac act gta ttt tac caa gct gaa ggt gga aaa gaa    1679
Phe Ile Asn Asn Tyr Thr Val Phe Tyr Gln Ala Glu Gly Gly Lys Glu
                470                 475                 480 ctc tcc aag act gtt aac tct cat gcc ctg cag tgt gac ctg gag tct    1727
Leu Ser Lys Thr Val Asn Ser His Ala Leu Gln Cys Asp Leu Glu Ser
            485                 490                 495 ctg aca cga agg acc tct tat act gtt tgg gtc atg gcc agc acc aga    1775
Leu Thr Arg Arg Thr Ser Tyr Thr Val Trp Val Met Ala Ser Thr Arg
        500                 505                 510 gct gga ggt acc aac ggg gtg aga ata aac ttc aag aca ttg tca atc    1823
Ala Gly Gly Thr Asn Gly Val Arg Ile Asn Phe Lys Thr Leu Ser Ile
    515                 520                 525 agt gtg ttt gaa att gtc ctt cta aca tct cta gtt gga gga ggc ctt    1871
Ser Val Phe Glu Ile Val Leu Leu Thr Ser Leu Val Gly Gly Gly Leu
530                 535                 540                 545 ctt cta ctt agc atc aaa aca gtg act ttt ggc ctc aga aag cca aac    1919
Leu Leu Leu Ser Ile Lys Thr Val Thr Phe Gly Leu Arg Lys Pro Asn
                550                 555                 560 cgg ttg act ccc ctg tgt tgt cct gat gtt ccc aac cct gct gaa agt    1967
Arg Leu Thr Pro Leu Cys Cys Pro Asp Val Pro Asn Pro Ala Glu Ser
            565                 570                 575 agt tta gcc aca tgg ctc gga gat ggt ttc aag aag tca aat atg aag    2015
Ser Leu Ala Thr Trp Leu Gly Asp Gly Phe Lys Lys Ser Asn Met Lys
        580                 585                 590 gag act gga aac tct ggg aac aca gaa gac gtg gtc cta aaa cca tgt    2063
Glu Thr Gly Asn Ser Gly Asn Thr Glu Asp Val Val Leu Lys Pro Cys
    595                 600                 605 ccc gtc ccc gcg gat ctc att gac aag ctg gta gtg aac ttt gag aat    2111
Pro Val Pro Ala Asp Leu Ile Asp Lys Leu Val Val Asn Phe Glu Asn
610                 615                 620                 625 ttt ctg gaa gta gtt ttg aca gag gaa gct gga aag ggt cag gcg agc    2159
Phe Leu Glu Val Val Leu Thr Glu Glu Ala Gly Lys Gly Gln Ala Ser
                630                 635                 640 att ttg gga gga gaa gcg aat gag tat atc tta tcc cag gaa cca agc    2207
Ile Leu Gly Gly Glu Ala Asn Glu Tyr Ile Leu Ser Gln Glu Pro Ser
            645                 650                 655 tgt cct ggc cat tgc tgaagctacc ctcagggtcc aggacagctg tcttgttggc    2262
Cys Pro Gly His Cys
        660 acttgactct ggcaggaacc tgatctctac ttttcttctc cctgtctccg gacactttct    2322
```

```
ctccttcatg cagagaccag gactagagcg gattcctcat ggtttgccag gctcctcagt    2382
ccttgctcgg gctcaggatc ttcaacaatg cccttctctgg gacactccat catccactta   2442
tatttatttt ttgcaacatt gtggattgaa cccagggact tgtttatgcg cgcaacttca    2502
gtaactgtgg cagagactta ggaatggaga tctgacccct tgcagaaggt ttctggacat    2562
ccgtccctgt gtgagcctca gacagcattg tctttacttt gaatcagctt ccaagttaat    2622
aaaagaaaaa cagagaggtg cataacagc tcctgcttcc tgacctgctt gagttccagt     2682
tctgacttcc tttggtgatg aacagcaatg tgggaagtgt aagctgaata aacccttttcc  2742 tcccca                                                               2748
```

<210> SEQ ID NO 117
<211> LENGTH: 662
<212> TYPE: PRT
<213> ORGANISM: Mus musculus

<400> SEQUENCE: 117

```
Met Leu Ser Ser Gln Lys Gly Ser Cys Ser Gln Glu Pro Gly Ala Ala
1               5                   10                  15

His Val Gln Pro Leu Gly Val Asn Ala Gly Ile Met Trp Thr Leu Ala
            20                  25                  30

Leu Trp Ala Phe Ser Phe Leu Cys Lys Phe Ser Leu Ala Val Leu Pro
        35                  40                  45

Thr Lys Pro Glu Asn Ile Ser Cys Val Phe Tyr Phe Asp Arg Asn Leu
    50                  55                  60

Thr Cys Thr Trp Arg Pro Lys Glu Thr Asn Asp Thr Ser Tyr Ile
65                  70                  75                  80

Val Thr Leu Thr Tyr Ser Tyr Gly Lys Ser Asn Tyr Ser Asp Asn Ala
                85                  90                  95

Thr Glu Ala Ser Tyr Ser Phe Pro Arg Ser Cys Ala Met Pro Pro Asp
            100                 105                 110

Ile Cys Ser Val Glu Val Gln Ala Gln Asn Gly Asp Gly Lys Val Lys
        115                 120                 125

Ser Asp Ile Thr Tyr Trp His Leu Ile Ser Ile Ala Lys Thr Glu Pro
    130                 135                 140

Pro Ile Ile Leu Ser Val Asn Pro Ile Cys Asn Arg Met Phe Gln Ile
145                 150                 155                 160

Gln Trp Lys Pro Arg Glu Lys Thr Arg Gly Phe Pro Leu Val Cys Met
                165                 170                 175

Leu Arg Phe Arg Thr Val Asn Ser Ser Arg Trp Thr Glu Val Asn Phe
            180                 185                 190

Glu Asn Cys Lys Gln Val Cys Asn Leu Thr Gly Leu Gln Ala Phe Thr
        195                 200                 205

Glu Tyr Val Leu Ala Leu Arg Phe Arg Phe Asn Asp Ser Arg Tyr Trp
    210                 215                 220

Ser Lys Trp Ser Lys Glu Thr Arg Val Thr Met Glu Glu Val Pro
225                 230                 235                 240

His Val Leu Asp Leu Trp Arg Ile Leu Glu Pro Ala Asp Met Asn Gly
                245                 250                 255

Asp Arg Lys Val Arg Leu Leu Trp Lys Lys Ala Arg Gly Ala Pro Val
            260                 265                 270

Leu Glu Lys Thr Phe Gly Tyr His Ile Gln Tyr Phe Ala Glu Asn Ser
        275                 280                 285
```

```
Thr Asn Leu Thr Glu Ile Asn Asn Ile Thr Thr Gln Gln Tyr Glu Leu
    290                 295                 300

Leu Leu Met Ser Gln Ala His Ser Val Ser Val Thr Ser Phe Asn Ser
305                 310                 315                 320

Leu Gly Lys Ser Gln Glu Thr Ile Leu Arg Ile Pro Asp Val His Glu
                325                 330                 335

Lys Thr Phe Gln Tyr Ile Lys Ser Met Gln Ala Tyr Ile Ala Glu Pro
            340                 345                 350

Leu Leu Val Val Asn Trp Gln Ser Ser Ile Pro Ala Val Asp Thr Trp
        355                 360                 365

Ile Val Glu Trp Leu Pro Glu Ala Ala Met Ser Lys Phe Pro Ala Leu
    370                 375                 380

Ser Trp Glu Ser Val Ser Gln Val Thr Asn Trp Thr Ile Glu Gln Asp
385                 390                 395                 400

Lys Leu Lys Pro Phe Thr Cys Tyr Asn Ile Ser Val Tyr Pro Val Leu
                405                 410                 415

Gly His Arg Val Gly Glu Pro Tyr Ser Ile Gln Ala Tyr Ala Lys Glu
            420                 425                 430

Gly Thr Pro Leu Lys Gly Pro Glu Thr Arg Val Glu Asn Ile Gly Leu
        435                 440                 445

Arg Thr Ala Thr Ile Thr Trp Lys Glu Ile Pro Lys Ser Ala Arg Asn
    450                 455                 460

Gly Phe Ile Asn Asn Tyr Thr Val Phe Tyr Gln Ala Glu Gly Gly Lys
465                 470                 475                 480

Glu Leu Ser Lys Thr Val Asn Ser His Ala Leu Gln Cys Asp Leu Glu
                485                 490                 495

Ser Leu Thr Arg Arg Thr Ser Tyr Thr Val Trp Val Met Ala Ser Thr
            500                 505                 510

Arg Ala Gly Gly Thr Asn Gly Val Arg Ile Asn Phe Lys Thr Leu Ser
        515                 520                 525

Ile Ser Val Phe Glu Ile Val Leu Leu Thr Ser Leu Val Gly Gly Gly
    530                 535                 540

Leu Leu Leu Leu Ser Ile Lys Thr Val Thr Phe Gly Leu Arg Lys Pro
545                 550                 555                 560

Asn Arg Leu Thr Pro Leu Cys Cys Pro Asp Val Pro Asn Pro Ala Glu
                565                 570                 575

Ser Ser Leu Ala Thr Trp Leu Gly Asp Gly Phe Lys Lys Ser Asn Met
            580                 585                 590

Lys Glu Thr Gly Asn Ser Gly Asn Thr Glu Asp Val Val Leu Lys Pro
        595                 600                 605

Cys Pro Val Pro Ala Asp Leu Ile Asp Lys Leu Val Val Asn Phe Glu
    610                 615                 620

Asn Phe Leu Glu Val Val Leu Thr Glu Glu Ala Gly Lys Gly Gln Ala
625                 630                 635                 640

Ser Ile Leu Gly Gly Glu Ala Asn Glu Tyr Ile Leu Ser Gln Glu Pro
                645                 650                 655

Ser Cys Pro Gly His Cys
            660

<210> SEQ ID NO 118
<211> LENGTH: 2728
<212> TYPE: DNA
<213> ORGANISM: Mus musculus
<220> FEATURE:
<221> NAME/KEY: CDS
```

<222> LOCATION: (237)...(1877)

<400> SEQUENCE: 118

| | |
|---|---|
| gatgggccc tgaatgttga tctgacagaa ttccagacca acctggtggt tattgtcctt | 60 |
| ttcatctggt catgctgaat atactctcaa gatgtgctgg agaaggtgct gctgtccggg | 120 |
| ctctcagaga aggcagtgct ggaggcgttc ctggcccggg tctcctccta ctgttcctgg | 180 |
| tagcccagcc ttctcggggt ggaaggagaa gctggccagg tgagctctga ggaagc atg | 239 |
| | Met |
| | 1 |

| | |
|---|---|
| ctg agc agc cag aag gga tcc tgc agc cag gaa cca ggg gca gcc cac | 287 |
| Leu Ser Ser Gln Lys Gly Ser Cys Ser Gln Glu Pro Gly Ala Ala His | |
| 5                 10                  15 | |
| gtc cag cct ctg ggt gtg aac gct gga ata atg tgg acc ttg gca ctg | 335 |
| Val Gln Pro Leu Gly Val Asn Ala Gly Ile Met Trp Thr Leu Ala Leu | |
| 20                  25                  30 | |
| tgg gca ttc tct ttc ctc tgc aaa ttc agc ctg gca gtc ctg ccg act | 383 |
| Trp Ala Phe Ser Phe Leu Cys Lys Phe Ser Leu Ala Val Leu Pro Thr | |
| 35                  40                  45 | |
| aag cca gag aac att tcc tgc gtc ttt tac ttc gac aga aat ctg act | 431 |
| Lys Pro Glu Asn Ile Ser Cys Val Phe Tyr Phe Asp Arg Asn Leu Thr | |
| 50                  55                  60                  65 | |
| tgc act tgg aga cca gag aag gaa acc aat gat acc agc tac att gtg | 479 |
| Cys Thr Trp Arg Pro Glu Lys Glu Thr Asn Asp Thr Ser Tyr Ile Val | |
| 70                  75                  80 | |
| act ttg act tac tcc tat gga aaa agc aat tat agt gac aat gct aca | 527 |
| Thr Leu Thr Tyr Ser Tyr Gly Lys Ser Asn Tyr Ser Asp Asn Ala Thr | |
| 85                  90                  95 | |
| gag gct tca tat tct ttt ccc cgt tcc tgt gca atg ccc cca gac atc | 575 |
| Glu Ala Ser Tyr Ser Phe Pro Arg Ser Cys Ala Met Pro Pro Asp Ile | |
| 100                 105                 110 | |
| tgc agt gtt gaa gta caa gct caa aat gga gat ggt aaa gtt aaa tct | 623 |
| Cys Ser Val Glu Val Gln Ala Gln Asn Gly Asp Gly Lys Val Lys Ser | |
| 115                 120                 125 | |
| gac atc aca tat tgg cat tta atc tcc ata gca aaa acc gaa cca cct | 671 |
| Asp Ile Thr Tyr Trp His Leu Ile Ser Ile Ala Lys Thr Glu Pro Pro | |
| 130                 135                 140                 145 | |
| ata att tta agt gtg aat cca att tgt aat aga atg ttc cag ata caa | 719 |
| Ile Ile Leu Ser Val Asn Pro Ile Cys Asn Arg Met Phe Gln Ile Gln | |
| 150                 155                 160 | |
| tgg aaa ccg cgt gaa aag act cgt ggg ttt cct tta gta tgc atg ctt | 767 |
| Trp Lys Pro Arg Glu Lys Thr Arg Gly Phe Pro Leu Val Cys Met Leu | |
| 165                 170                 175 | |
| cgg ttc aga act gtc aac agt agc cgc tgg acg gaa gtc aat ttt gaa | 815 |
| Arg Phe Arg Thr Val Asn Ser Ser Arg Trp Thr Glu Val Asn Phe Glu | |
| 180                 185                 190 | |
| aac tgt aaa cag gtc tgc aac ctc aca gga ctt cag gct ttc aca gaa | 863 |
| Asn Cys Lys Gln Val Cys Asn Leu Thr Gly Leu Gln Ala Phe Thr Glu | |
| 195                 200                 205 | |
| tat gtc ctg gct cta cga ttc agg ttc aat gac tca aga tat tgg agc | 911 |
| Tyr Val Leu Ala Leu Arg Phe Arg Phe Asn Asp Ser Arg Tyr Trp Ser | |
| 210                 215                 220                 225 | |
| aag tgg agc aaa gaa gaa acc aga gtg act atg gag gaa gtt cca cat | 959 |
| Lys Trp Ser Lys Glu Glu Thr Arg Val Thr Met Glu Glu Val Pro His | |
| 230                 235                 240 | |
| gtc ctg gac ctg tgg aga att ctg gaa cca gca gac atg aac gga gac | 1007 |
| Val Leu Asp Leu Trp Arg Ile Leu Glu Pro Ala Asp Met Asn Gly Asp | |
| 245                 250                 255 | |
| agg aag gtg cga ttg ctg tgg aag aag gca aga gga gcc ccc gtc ttg | 1055 |

```
                Arg Lys Val Arg Leu Leu Trp Lys Lys Ala Arg Gly Ala Pro Val Leu
                            260                 265                 270 gag aaa aca ttt ggc tac cac ata cag tac ttt gca gag aac agc act       1103
Glu Lys Thr Phe Gly Tyr His Ile Gln Tyr Phe Ala Glu Asn Ser Thr
275                 280                 285 aac ctc aca gag ata aac aac atc acc acc cag cag tat gaa ctg ctt       1151
Asn Leu Thr Glu Ile Asn Asn Ile Thr Thr Gln Gln Tyr Glu Leu Leu
290                 295                 300                 305 ctg atg agc cag gca cac tct gtg tcc gtg act tct ttt aat tct ctt       1199
Leu Met Ser Gln Ala His Ser Val Ser Val Thr Ser Phe Asn Ser Leu
                310                 315                 320 ggc aag tcc caa gag acc atc ctg agg atc cca gat gtc cat gag aag       1247
Gly Lys Ser Gln Glu Thr Ile Leu Arg Ile Pro Asp Val His Glu Lys
            325                 330                 335 acc ttc cag tac att aag agc atg cag gcc tac ata gcc gag ccc ctg       1295
Thr Phe Gln Tyr Ile Lys Ser Met Gln Ala Tyr Ile Ala Glu Pro Leu
        340                 345                 350 ttg gtg gtg aac tgg caa agc tcc att cct gcg gtg gac act tgg ata       1343
Leu Val Val Asn Trp Gln Ser Ser Ile Pro Ala Val Asp Thr Trp Ile
355                 360                 365 gtg gag tgg ctc cca gaa gct gcc atg tcg aag ttc cct gcc ctt tcc       1391
Val Glu Trp Leu Pro Glu Ala Ala Met Ser Lys Phe Pro Ala Leu Ser
370                 375                 380                 385 tgg gaa tct gtg tct cag gtc acg aac tgg acc atc gag caa gat aaa       1439
Trp Glu Ser Val Ser Gln Val Thr Asn Trp Thr Ile Glu Gln Asp Lys
                390                 395                 400 cta aaa cct ttc aca tgc tat aat ata tca gtg tat cca gtg ttg gga       1487
Leu Lys Pro Phe Thr Cys Tyr Asn Ile Ser Val Tyr Pro Val Leu Gly
            405                 410                 415 cac cga gtt gga gag ccg tat tca atc caa gct tat gcc aaa gaa gga       1535
His Arg Val Gly Glu Pro Tyr Ser Ile Gln Ala Tyr Ala Lys Glu Gly
        420                 425                 430 act cca tta aaa ggt cct gag acc agg gtg gag aac atc ggt ctg agg       1583
Thr Pro Leu Lys Gly Pro Glu Thr Arg Val Glu Asn Ile Gly Leu Arg
435                 440                 445 aca gcc acg atc aca tgg aag gag att cct aag agt gct agg aat gga       1631
Thr Ala Thr Ile Thr Trp Lys Glu Ile Pro Lys Ser Ala Arg Asn Gly
450                 455                 460                 465 ttt atc aac aat tac act gta ttt tac caa gct gaa ggt gga aaa gaa       1679
Phe Ile Asn Asn Tyr Thr Val Phe Tyr Gln Ala Glu Gly Gly Lys Glu
                470                 475                 480 ctc tcc aag act gtt aac tct cat gcc ctg cag tgt gac ctg gag tct       1727
Leu Ser Lys Thr Val Asn Ser His Ala Leu Gln Cys Asp Leu Glu Ser
            485                 490                 495 ctg aca cga agg acc tct tat act gtt tgg gtc atg gcc agc acc aga       1775
Leu Thr Arg Arg Thr Ser Tyr Thr Val Trp Val Met Ala Ser Thr Arg
        500                 505                 510 gct gga ggt acc aac ggg gtg aga ata aac ttc aag aca ttg tca atc       1823
Ala Gly Gly Thr Asn Gly Val Arg Ile Asn Phe Lys Thr Leu Ser Ile
515                 520                 525 agt gag tac tgg ctt cag gcc tca ttc tgg agt tta ctt cgg gtt gga       1871
Ser Glu Tyr Trp Leu Gln Ala Ser Phe Trp Ser Leu Leu Arg Val Gly
530                 535                 540                 545 aat gtt tgacaggagc aaggagagcc agcagagggc agcagagcat ggcttctcct        1927
Asn Val gctctctctg gctcactcac ctcccaggag ttactgagga ctggcaaag ggagggctga      1987 gttagaccaa caggccattt tgatccttgc tggtaagcag ccacaaataa tcttaagatg     2047
aagcaagcaa catccacttc agcctcagcc acgtcaaagg ctgttgcctg agctcacact     2107
```

```
ggccagttcc taaatgtcag gagttgtgca atagaacctg ggaaggaaca actggttgat    2167
cagaggtcac tgacaaggga cttaatgtta ccatctgcgg tggggctttt gtttcgtttt    2227
gtttgtttgt tatgtgtatt caacttatca gcttttacgt tgaaaacatg aaaagcaaga    2287
caaatttgtt agatatcaca tataatgtga aatataatag tttaataatt gagtaggaaa    2347
gctgagggca tgtaatagac agagggaaaa gaagaggaaa gccagtctgg tctacaaagt    2407
gagttccagg acagccaggg ctacatggag aaaccctgtc tcaatcaatc aatcaatcaa    2467
tcaatcagtc aatcaatcaa aattcaagca gcattgacaa gttttgcaat aactactata    2527
aaccaaaaaa gtcatcttga tgtatctcag aagccccttg ttatttatgt tcctgaagac    2587
taaagtagac cgtggctctg agaaccatga gcaagataac acgttctgtc ctgcagccta    2647
acaatgcctt cttggtattc ttttttgatac aacttctaaa ataacttttt tttaaaaaaa    2707
ataaaaatca tgttacagct a                                              2728
```

<210> SEQ ID NO 119
<211> LENGTH: 547
<212> TYPE: PRT
<213> ORGANISM: Mus musculus

<400> SEQUENCE: 119

Met Leu Ser Ser Gln Lys Gly Ser Cys Ser Gln Glu Pro Gly Ala Ala
1               5                   10                  15

His Val Gln Pro Leu Gly Val Asn Ala Gly Ile Met Trp Thr Leu Ala
            20                  25                  30

Leu Trp Ala Phe Ser Phe Leu Cys Lys Phe Ser Leu Ala Val Leu Pro
        35                  40                  45

Thr Lys Pro Glu Asn Ile Ser Cys Val Phe Tyr Phe Asp Arg Asn Leu
    50                  55                  60

Thr Cys Thr Trp Arg Pro Glu Lys Glu Thr Asn Asp Thr Ser Tyr Ile
65                  70                  75                  80

Val Thr Leu Thr Tyr Ser Tyr Gly Lys Ser Asn Tyr Ser Asp Asn Ala
                85                  90                  95

Thr Glu Ala Ser Tyr Ser Phe Pro Arg Ser Cys Ala Met Pro Pro Asp
            100                 105                 110

Ile Cys Ser Val Glu Val Gln Ala Gln Asn Gly Asp Gly Lys Val Lys
        115                 120                 125

Ser Asp Ile Thr Tyr Trp His Leu Ile Ser Ile Ala Lys Thr Glu Pro
    130                 135                 140

Pro Ile Ile Leu Ser Val Asn Pro Ile Cys Asn Arg Met Phe Gln Ile
145                 150                 155                 160

Gln Trp Lys Pro Arg Glu Lys Thr Arg Gly Phe Pro Leu Val Cys Met
                165                 170                 175

Leu Arg Phe Arg Thr Val Asn Ser Ser Arg Trp Thr Glu Val Asn Phe
            180                 185                 190

Glu Asn Cys Lys Gln Val Cys Asn Leu Thr Gly Leu Gln Ala Phe Thr
        195                 200                 205

Glu Tyr Val Leu Ala Leu Arg Phe Arg Phe Asn Asp Ser Arg Tyr Trp
    210                 215                 220

Ser Lys Trp Ser Lys Glu Glu Thr Arg Val Thr Met Glu Glu Val Pro
225                 230                 235                 240

His Val Leu Asp Leu Trp Arg Ile Leu Glu Pro Ala Asp Met Asn Gly
                245                 250                 255

```
Asp Arg Lys Val Arg Leu Leu Trp Lys Lys Ala Arg Gly Ala Pro Val
            260                 265                 270

Leu Glu Lys Thr Phe Gly Tyr His Ile Gln Tyr Phe Ala Glu Asn Ser
        275                 280                 285

Thr Asn Leu Thr Glu Ile Asn Asn Ile Thr Thr Gln Gln Tyr Glu Leu
    290                 295                 300

Leu Leu Met Ser Gln Ala His Ser Val Ser Val Thr Ser Phe Asn Ser
305                 310                 315                 320

Leu Gly Lys Ser Gln Glu Thr Ile Leu Arg Ile Pro Asp Val His Glu
                325                 330                 335

Lys Thr Phe Gln Tyr Ile Lys Ser Met Gln Ala Tyr Ile Ala Glu Pro
            340                 345                 350

Leu Leu Val Val Asn Trp Gln Ser Ser Ile Pro Ala Val Asp Thr Trp
        355                 360                 365

Ile Val Glu Trp Leu Pro Glu Ala Ala Met Ser Lys Phe Pro Ala Leu
    370                 375                 380

Ser Trp Glu Ser Val Ser Gln Val Thr Asn Trp Thr Ile Glu Gln Asp
385                 390                 395                 400

Lys Leu Lys Pro Phe Thr Cys Tyr Asn Ile Ser Val Tyr Pro Val Leu
                405                 410                 415

Gly His Arg Val Gly Glu Pro Tyr Ser Ile Gln Ala Tyr Ala Lys Glu
            420                 425                 430

Gly Thr Pro Leu Lys Gly Pro Glu Thr Arg Val Glu Asn Ile Gly Leu
        435                 440                 445

Arg Thr Ala Thr Ile Thr Trp Lys Glu Ile Pro Lys Ser Ala Arg Asn
    450                 455                 460

Gly Phe Ile Asn Asn Tyr Thr Val Phe Tyr Gln Ala Glu Gly Gly Lys
465                 470                 475                 480

Glu Leu Ser Lys Thr Val Asn Ser His Ala Leu Gln Cys Asp Leu Glu
                485                 490                 495

Ser Leu Thr Arg Arg Thr Ser Tyr Thr Val Trp Val Met Ala Ser Thr
            500                 505                 510

Arg Ala Gly Gly Thr Asn Gly Val Arg Ile Asn Phe Lys Thr Leu Ser
        515                 520                 525

Ile Ser Glu Tyr Trp Leu Gln Ala Ser Phe Trp Ser Leu Leu Arg Val
    530                 535                 540

Gly Asn Val
545

<210> SEQ ID NO 120
<211> LENGTH: 2196
<212> TYPE: DNA
<213> ORGANISM: Artificial Sequence
<220> FEATURE:
<223> OTHER INFORMATION: Degenerate polynucleotide of SEQ ID NO:111
<220> FEATURE:
<221> NAME/KEY: misc_feature
<222> LOCATION: (1)...(2196)
<223> OTHER INFORMATION: n = A, T, C or G

<400> SEQUENCE: 120
atgatgtgga cntgggcnyt ntggatgytn ccnwsnytnt gyaarttyws nytngcngcn      60
ytnccngcna arccngaraa yathwsntgy gtntaytayt aymgnaaraa yytnacntgy     120
acntggwsnc cnggnaarga racnwsntay acncartaya cngtnaarmg nacntaygcn     180
ttyggngara arcaygayaa ytgyacnacn aaywsnwsna cnwsngaraa ymgngcnwsn     240
```

-continued

```
tgywsnttyt tyytnccnmg nathacnath ccngayaayt ayacnathga rgtngargcn    300
garaayggng ayggngtnat haarwsncay atgacntayt ggmgnytnga raayathgcn    360
aaracngarc cnccnaarat httymgngtn aarccngtny tnggnathaa rmgnatgath    420
carathgart ggathaarcc ngarytngcn ccngtnwsnw sngayytnaa rtayacnytn    480
mgnttymgna cngtnaayws nacnwsntgg atggargtna ayttygcnaa raaymgnaar    540
gayaaraayc aracntayaa yytnacnggn ytncarccnt tyacngarta ygtnathgcn    600
ytnmgntgyg cngtnaarga rwsnaartty tggwsngayt ggwsncarga raaratgggn    660
atgacngarg argargcncc ntgyggnytn garytntggm gngtnytnaa rccngcngar    720
gcngayggnm gnmgnccngt nmgnytnytn tggaaraarg cnmgnggngc nccngtnytn    780
garaaracny tnggntayaa yathtggtay tayccngarw snaayacnaa yytnacngar    840
acnatgaaya cnacnaayca rcarytngar ytncayytng gnggngarws nttytgggtn    900
wsnatgathw sntayaayws nytnggnaar wsnccngtng cnacnytnmg nathccngcn    960
athcargara arwsnttyca rtgyathgar gtnatgcarg cntgygtngc ngargaycar   1020
ytngtngtna artggcarws nwsngcnytn gaygtnaaya cntggatgat hgartggtty   1080
ccngaygtng aywsngarcc nacnacnytn wsntgggarw sngtnwsnca rgcnacnaay   1140
tggacnathc arcargayaa rytnaarccn ttytggtgyt ayaayathws ngtntayccn   1200
atgytncayg ayaargtngg ngarccntay wsnathcarg cntaygcnaa rgarggngtn   1260
ccnwsngarg gnccngarac naargtngar aayathggng tnaaracngt nacnathacn   1320
tggaargara thccnaarws ngarmgnaar ggnathatht gyaaytayac nathttytay   1380
cargcngarg gnggnaargg nttywsnaar acngtnaayw snwsnathyt ncartayggn   1440
ytngarwsny tnaarmgnaa racnwsntay athgtncarg tnatggcnws nacnwsngcn   1500
ggnggnacna ayggnacnws nathaaytty aaracnytnw snttywsngt nttygarath   1560
athytnatha cnwsnytnat hggnggnggn ytnytnathy tnathathyt nacngtngcn   1620
tayggnytna araarccnaa yaarytnacn cayytntgyt ggccnacngt nccnaayccn   1680
gcngarwsnw snathgcnac ntggcayggn gaygayttya argayaaryt naayytnaar   1740
garwsngayg aywsngtnaa yacngargay mgnathytna arccntgyws nacnccnwsn   1800
gayaarytng tnathgayaa rytngtngtn aayttyggna aygtnytnca rgarathtty   1860
acngaygarg cnmgnacngg ncargaraay aayytnggng gngaraaraa yggntaygtn   1920
acntgyccnt tymgnccnga ytgyccnytn ggnaarwsnt tygargaryt nccngtnwsn   1980
ccngarathc cnccnmgnaa rwsncartay ytnmgnwsnm gnatgccnga rggnacnmgn   2040
ccngargcna argarcaryt nytnttywsn ggncarwsny tngtnccnga ycayytntgy   2100
gargarggng cnccnaaycc ntayytnaar aaywsngtna cngcnmgnga rttyytngtn   2160
wsngaraary tnccngarca yacnaarggn gargtn                             2196
```

<210> SEQ ID NO 121
<211> LENGTH: 1947
<212> TYPE: DNA
<213> ORGANISM: Artificial Sequence
<220> FEATURE:
<223> OTHER INFORMATION: Degenerate polynucleotide of SEQ ID NO:109
<220> FEATURE:
<221> NAME/KEY: misc_feature
<222> LOCATION: (1)...(1947)
<223> OTHER INFORMATION: n = A, G, C or G

<400> SEQUENCE: 121

```
atgatgtgga cntgggcnyt ntggatgytn ccnwsnytnt gyaarttyws nytngcngcn      60
ytnccngcna arccngaraa yathw

<400> SEQUENCE: 122

```
atgaarytnw snccncarcc nwsntgygtn aayytnggna tgatgtggac ntgggcnytn     60
tggatgytnc cnwsnytntg yaarttywsn ytngcngcny tnccngcnaa rccngaraay    120
athwsntgyg tntaytayta ymgnaaraay ytnacntgya cntggwsncc nggnaargar    180
acnwsntaya cncartayac ngtnaarmgn acntaygcnt tyggngaraa rcaygayaay    240
tgyacnacna aywsnwsnac nwsngaraay mgngcnwsnt gywsnttytt yytnccnmgn    300
athacnathc cngayaayta yacnathgar gtngargcng araayggnga yggngtnath    360
aarwsncaya tgacntaytg gmgnytngar aayathgcna aracngarcc nccnaarath    420
ttymgngtna arccngtnyt nggnathaar mgnatgathc arathgartg gathaarccn    480
garytngcnc cngtnwsnws ngayytnaar tayacnytnm gnttymgnac ngtnaaywsn    540
acnwsntgga tggargtnaa yttygcnaar aaymgnaarg ayaaraayca racntayaay    600
ytnacnggny tncarccntt yacngartay gtnathgcny tnmgntgygc ngtnaargar    660
wsnaarttyt ggwsngaytg gwsncargar aaratgggna tgacngarga rgargcnccn    720
tgyggnytng arytntggmg ngtnytnaar ccngcngarg cngayggnmg nmgnccngtn    780
mgnytnytnt ggaaraargc nmgnggngcn ccngtnytng araaracnyt nggntayaay    840
athtggtayt ayccngarws naayacnaay ytnacngara cnatgaayac nacnaaycar    900
carytngary tncayytngg nggngarwsn ttytgggtnw snatgathws ntayaaywsn    960
ytnggnaarw snccngtngc nacnytnmgn athccngcna thcargaraa rwsnttycar   1020
tgyathgarg tnatgcargc ntgygtngcn gargaycary tngtngtnaa rtggcarwsn   1080
wsngcnytng aygtnaayac ntggatgath gartggttyc cngaygtnga ywsngarccn   1140
acnacnytnw sntgggarws ngtnwsncar gcnacnaayt ggacnathca rcargayaar   1200
ytnaarccnt tytggtgyta yaayathwsn gtntayccna tgytncayga yaargtnggn   1260
garccntayw snathcargc ntaygcnaar garggngtnc cnwsngargg nccngaracn   1320
aargtngara ayathggngt naaracngtn acnathacnt ggaargarat hccnaarwsn   1380
garmgnaarg gnathathtg yaaytayacn athttytayc argcngargg nggnaarggn   1440
ttywsnaara cngtnaayws nwsnathytn cartayggny tngarwsnyt naarmgnaar   1500
acnwsntaya thgtncargt natggcnwsn acnwsngcng gnggnacnaa yggnacnwsn   1560
athaayttya aracnytnws nttywsngtn ttygaratha thytnathac nwsnytnath   1620
ggnggnggny tnytnathyt nathathytn acngtngcnt ayggnytnaa raarccnaay   1680
aarytnacnc ayytntgytg gccnacngtn ccnaayccng cngarwsnws nathgcnacn   1740
tggcayggng aygayttyaa rgayaarytn aayytnaarg arwsngayga ywsngtnaay   1800
acngargaym gnathytnaa rccntgywsn acnccnwsng ayaarytngt nathgayaar   1860
ytngtngtna ayttyggnaa ygtnytncar garathttya cngaygargc nmgnacnggn   1920
cargaraaya ayytnggngg ngaraaraay ggnacnmgna thytnwsnws ntgyccnacn   1980
wsnath                                                              1986
```

<210> SEQ ID NO 123
<211> LENGTH: 19
<212> TYPE: DNA
<213> ORGANISM: Artificial Sequence
<220> FEATURE:
<223> OTHER INFORMATION: Oligonucleotide primer ZC38,239

<400> SEQUENCE: 123

```
gccgactaag ccagagaac                                                    19

<210> SEQ ID NO 124
<211> LENGTH: 20
<212> TYPE: DNA
<213> ORGANISM: Artificial Sequence
<220> FEATURE:
<223> OTHER INFORMATION: Oligonucleotide primer ZC38,245

<400> SEQUENCE: 124
ctgttgacag ttctgaaccg                                                   20

<210> SEQ ID NO 125
<211> LENGTH: 20
<212> TYPE: DNA
<213> ORGANISM: Artificial Sequence
<220> FEATURE:
<223> OTHER INFORMATION: Oligonucleotide primer ZC38,238

<400> SEQUENCE: 125
cgcggtttcc attgtatctg                                                   20

<210> SEQ ID NO 126
<211> LENGTH: 2748
<212> TYPE: DNA
<213> ORGANISM: Mus musculus
<220> FEATURE:
<221> NAME/KEY: CDS
<222> LOCATION: (237)...(2222)

<400> SEQUENCE: 126 gatgggccc tgaatgttga tctgacagaa ttccagacca acctggtggt tattgtcctt       60
ttcatctggt catgctgaat atactctcaa gatgtgctgg agaaggtgct gctgtccggg     120
ctctcagaga aggcagtgct ggaggcgttc ctggcccggg tctcctccta ctgttcctgg     180
tagcccagcc ttctcggggt ggaaggagaa gctggccagg tgagctctga ggaagc atg    239
                                                                Met
                                                                 1 ctg agc agc cag aag gga tcc tgc agc cag gaa cca ggg gca gcc cac       287
Leu Ser Ser Gln Lys Gly Ser Cys Ser Gln Glu Pro Gly Ala Ala His
         5                  10                  15 gtc cag cct ctg ggt gtg aac gct gga ata atg tgg acc ttg gca ctg       335
Val Gln Pro Leu Gly Val Asn Ala Gly Ile Met Trp Thr Leu Ala Leu
     20                  25                  30 tgg gca ttc tct ttc ctc tgc aaa ttc agc ctg gca gtc ctg ccg act       383
Trp Ala Phe Ser Phe Leu Cys Lys Phe Ser Leu Ala Val Leu Pro Thr
 35                  40                  45 aag cca gag aac att tcc tgc gtc ttt tac ttc gac aga aat ctg act       431
Lys Pro Glu Asn Ile Ser Cys Val Phe Tyr Phe Asp Arg Asn Leu Thr
 50                  55                  60                  65 tgc act tgg aga cca gag aag gaa acc aat gat acc agc tac att gtg       479
Cys Thr Trp Arg Pro Glu Lys Glu Thr Asn Asp Thr Ser Tyr Ile Val
                 70                  75                  80 act ttg act tac tcc tat gga aaa agc aat tat agt gac aat gct aca       527
Thr Leu Thr Tyr Ser Tyr Gly Lys Ser Asn Tyr Ser Asp Asn Ala Thr
             85                  90                  95 gag gct tca tat tct ttt ccc cgt tcc tgt gca atg ccc cca gac atc       575
Glu Ala Ser Tyr Ser Phe Pro Arg Ser Cys Ala Met Pro Pro Asp Ile
        100                 105                 110 tgc agt gtt gaa gta caa gct caa aat gga gat ggt aaa gtt aaa tct       623
Cys Ser Val Glu Val Gln Ala Gln Asn Gly Asp Gly Lys Val Lys Ser
    115                 120                 125
```

```
gac atc aca tat tgg cat tta atc tcc ata gca aaa acc gaa cca cct    671
Asp Ile Thr Tyr Trp His Leu Ile Ser Ile Ala Lys Thr Glu Pro Pro
130             135                 140                 145 ata att tta agt gtg aat cca att tgt aat aga atg ttc cag ata caa    719
Ile Ile Leu Ser Val Asn Pro Ile Cys Asn Arg Met Phe Gln Ile Gln
            150                 155                 160 tgg aaa ccg cgt gaa aag act cgt ggg ttt cct tta gta tgc atg ctt    767
Trp Lys Pro Arg Glu Lys Thr Arg Gly Phe Pro Leu Val Cys Met Leu
        165                 170                 175 cgg ttc aga act gtc aac agt agc cgc tgg acg gaa gtc aat ttt gaa    815
Arg Phe Arg Thr Val Asn Ser Ser Arg Trp Thr Glu Val Asn Phe Glu
    180                 185                 190 aac tgt aaa cag gtc tgc aac ctc aca gga ctt cag gct ttc aca gaa    863
Asn Cys Lys Gln Val Cys Asn Leu Thr Gly Leu Gln Ala Phe Thr Glu
195                 200                 205 tat gtc ctg gct cta cga ttc agg ttc aat gac tca aga tat tgg agc    911
Tyr Val Leu Ala Leu Arg Phe Arg Phe Asn Asp Ser Arg Tyr Trp Ser
210                 215                 220                 225 aag tgg agc aaa gaa gaa acc aga gtg act atg gag gaa gtt cca cat    959
Lys Trp Ser Lys Glu Glu Thr Arg Val Thr Met Glu Glu Val Pro His
                230                 235                 240 gtc ctg gac ctg tgg aga att ctg gaa cca gca gac atg aac gga gac    1007
Val Leu Asp Leu Trp Arg Ile Leu Glu Pro Ala Asp Met Asn Gly Asp
            245                 250                 255 agg aag gtg cga ttg ctg tgg aag aag gca aga gga gcc ccc gtc ttg    1055
Arg Lys Val Arg Leu Leu Trp Lys Lys Ala Arg Gly Ala Pro Val Leu
        260                 265                 270 gag aaa aca ttt ggc tac cac ata cag tac ttt gca gag aac agc act    1103
Glu Lys Thr Phe Gly Tyr His Ile Gln Tyr Phe Ala Glu Asn Ser Thr
    275                 280                 285 aac ctc aca gag ata aac aac atc acc acc cag cag tat gaa ctg ctt    1151
Asn Leu Thr Glu Ile Asn Asn Ile Thr Thr Gln Gln Tyr Glu Leu Leu
290                 295                 300                 305 ctg atg agc cag gca cac tct gtg tcc gtg act tct ttt aat tct ctt    1199
Leu Met Ser Gln Ala His Ser Val Ser Val Thr Ser Phe Asn Ser Leu
                310                 315                 320 ggc aag tcc caa gag acc atc ctg agg atc cca gat gtc cat gag aag    1247
Gly Lys Ser Gln Glu Thr Ile Leu Arg Ile Pro Asp Val His Glu Lys
            325                 330                 335 acc ttc cag tac att aag agc atg cag gcc tac ata gcc gag ccc ctg    1295
Thr Phe Gln Tyr Ile Lys Ser Met Gln Ala Tyr Ile Ala Glu Pro Leu
        340                 345                 350 ttg gtg gtg aac tgg caa agc tcc att cct gcg gtg gac act tgg ata    1343
Leu Val Val Asn Trp Gln Ser Ser Ile Pro Ala Val Asp Thr Trp Ile
    355                 360                 365 gtg gag tgg ctc cca gaa gct gcc atg tcg aag ttc cct gcc ctt tcc    1391
Val Glu Trp Leu Pro Glu Ala Ala Met Ser Lys Phe Pro Ala Leu Ser
370                 375                 380                 385 tgg gaa tct gtg tct cag gtc acg aac tgg acc atc gag caa gat aaa    1439
Trp Glu Ser Val Ser Gln Val Thr Asn Trp Thr Ile Glu Gln Asp Lys
                390                 395                 400 cta aaa cct ttc aca tgc tat aat ata tca gtg tat cca gtg ttg gga    1487
Leu Lys Pro Phe Thr Cys Tyr Asn Ile Ser Val Tyr Pro Val Leu Gly
            405                 410                 415 cac cga gtt gga gag ccg tat tca atc caa gct tat gcc aaa gaa gga    1535
His Arg Val Gly Glu Pro Tyr Ser Ile Gln Ala Tyr Ala Lys Glu Gly
        420                 425                 430 act cca tta aaa ggt cct gag acc agg gtg gag aac atc ggt ctg agg    1583
Thr Pro Leu Lys Gly Pro Glu Thr Arg Val Glu Asn Ile Gly Leu Arg
```

```
                435                 440                 445
aca gcc acg atc aca tgg aag gag att cct aag agt gct agg aat gga    1631
Thr Ala Thr Ile Thr Trp Lys Glu Ile Pro Lys Ser Ala Arg Asn Gly
450                 455                 460                 465 ttt atc aac aat tac act gta ttt tac caa gct gaa ggt gga aaa gaa    1679
Phe Ile Asn Asn Tyr Thr Val Phe Tyr Gln Ala Glu Gly Gly Lys Glu
                470                 475                 480 ctc tcc aag act gtt aac tct cat gcc ctg cag tgt gac ctg gag tct    1727
Leu Ser Lys Thr Val Asn Ser His Ala Leu Gln Cys Asp Leu Glu Ser
            485                 490                 495 ctg aca cga agg acc tct tat act gtt tgg gtc atg gcc agc acc aga    1775
Leu Thr Arg Arg Thr Ser Tyr Thr Val Trp Val Met Ala Ser Thr Arg
        500                 505                 510 gct gga ggt acc aac ggg gtg aga ata aac ttc aag aca ttg tca atc    1823
Ala Gly Gly Thr Asn Gly Val Arg Ile Asn Phe Lys Thr Leu Ser Ile
    515                 520                 525 agt gtg ttt gaa att gtc ctt cta aca tct cta gtt gga gga ggc ctt    1871
Ser Val Phe Glu Ile Val Leu Leu Thr Ser Leu Val Gly Gly Gly Leu
530                 535                 540                 545 ctt cta ctt agc atc aaa aca gtg act ttt ggc ctc aga aag cca aac    1919
Leu Leu Leu Ser Ile Lys Thr Val Thr Phe Gly Leu Arg Lys Pro Asn
                550                 555                 560 cgg ttg act ccc ctg tgt tgt cct gat gtt ccc aac cct gct gaa agt    1967
Arg Leu Thr Pro Leu Cys Cys Pro Asp Val Pro Asn Pro Ala Glu Ser
            565                 570                 575 agt tta gcc aca tgg ctc gga gat ggt ttc aag aag tca aat atg aag    2015
Ser Leu Ala Thr Trp Leu Gly Asp Gly Phe Lys Lys Ser Asn Met Lys
        580                 585                 590 gag act gga aac tct ggg aac aca gaa gac gtg gtc cta aaa cca tgt    2063
Glu Thr Gly Asn Ser Gly Asn Thr Glu Asp Val Val Leu Lys Pro Cys
    595                 600                 605 ccc gtc ccc gcg gat ctc att gac aag ctg gta gtg aac ttt gag aat    2111
Pro Val Pro Ala Asp Leu Ile Asp Lys Leu Val Val Asn Phe Glu Asn
610                 615                 620                 625 ttt ctg gaa gta gtt ttg aca gag gaa gct gga aag ggt cag gcg agc    2159
Phe Leu Glu Val Val Leu Thr Glu Glu Ala Gly Lys Gly Gln Ala Ser
                630                 635                 640 att ttg gga gga gaa gcg aat gag tat atc tta tcc cag gaa cca agc    2207
Ile Leu Gly Gly Glu Ala Asn Glu Tyr Ile Leu Ser Gln Glu Pro Ser
            645                 650                 655 tgt cct ggc cat tgc tgaagctacc ctcagggtcc aggacagctg tcttgttggc    2262
Cys Pro Gly His Cys
            660 acttgactct ggcaggaacc tgatctctac ttttcttctc cctgtctccg gacactttct    2322 ctccttcatg cagagaccag gactagagcg gattcctcat ggtttgccag gctcctcagt    2382 ccttgctcgg gctcaggatc ttcaacaatg ccctttctgg gacactccat catccactta    2442 tatttatttt ttgcaacatt gtggattgaa cccagggact tgtttatgcg cgcaacttca    2502 gtaactgtgg cagagactta ggaatggaga tctgacccct tgcagaaggt ttctggacat    2562 ccgtccctgt gtgagcctca gacagcattg tctttacttt gaatcagctt ccaagttaat    2622 aaaagaaaaa cagagaggtg gcataacagc tcctgcttcc tgacctgctt gagttccagt    2682 tctgacttcc tttggtgatg aacagcaatg tgggaagtgt aagctgaata aacccttttcc    2742 tcccca                                                                2748

<210> SEQ ID NO 127
<211> LENGTH: 662
```

<212> TYPE: PRT
<213> ORGANISM: Mus musculus

<400> SEQUENCE: 127

```
Met Leu Ser Ser Gln Lys Gly Ser Cys Ser Gln Glu Pro Gly Ala Ala
 1               5                  10                  15

His Val Gln Pro Leu Gly Val Asn Ala Gly Ile Met Trp Thr Leu Ala
             20                  25                  30

Leu Trp Ala Phe Ser Phe Leu Cys Lys Phe Ser Leu Ala Val Leu Pro
         35                  40                  45

Thr Lys Pro Glu Asn Ile Ser Cys Val Phe Tyr Phe Asp Arg Asn Leu
     50                  55                  60

Thr Cys Thr Trp Arg Pro Glu Lys Glu Thr Asn Asp Thr Ser Tyr Ile
 65                  70                  75                  80

Val Thr Leu Thr Tyr Ser Tyr Gly Lys Ser Asn Tyr Ser Asp Asn Ala
                 85                  90                  95

Thr Glu Ala Ser Tyr Ser Phe Pro Arg Ser Cys Ala Met Pro Pro Asp
            100                 105                 110

Ile Cys Ser Val Glu Val Gln Ala Gln Asn Gly Asp Gly Lys Val Lys
        115                 120                 125

Ser Asp Ile Thr Tyr Trp His Leu Ile Ser Ile Ala Lys Thr Glu Pro
    130                 135                 140

Pro Ile Ile Leu Ser Val Asn Pro Ile Cys Asn Arg Met Phe Gln Ile
145                 150                 155                 160

Gln Trp Lys Pro Arg Glu Lys Thr Arg Gly Phe Pro Leu Val Cys Met
                165                 170                 175

Leu Arg Phe Arg Thr Val Asn Ser Ser Arg Trp Thr Glu Val Asn Phe
            180                 185                 190

Glu Asn Cys Lys Gln Val Cys Asn Leu Thr Gly Leu Gln Ala Phe Thr
        195                 200                 205

Glu Tyr Val Leu Ala Leu Arg Phe Arg Phe Asn Asp Ser Arg Tyr Trp
    210                 215                 220

Ser Lys Trp Ser Lys Glu Glu Thr Arg Val Thr Met Glu Glu Val Pro
225                 230                 235                 240

His Val Leu Asp Leu Trp Arg Ile Leu Glu Pro Ala Asp Met Asn Gly
                245                 250                 255

Asp Arg Lys Val Arg Leu Leu Trp Lys Lys Ala Arg Gly Ala Pro Val
            260                 265                 270

Leu Glu Lys Thr Phe Gly Tyr His Ile Gln Tyr Phe Ala Glu Asn Ser
        275                 280                 285

Thr Asn Leu Thr Glu Ile Asn Asn Ile Thr Thr Gln Gln Tyr Glu Leu
    290                 295                 300

Leu Leu Met Ser Gln Ala His Ser Val Ser Thr Ser Phe Asn Ser
305                 310                 315                 320

Leu Gly Lys Ser Gln Glu Thr Ile Leu Arg Ile Pro Asp Val His Glu
                325                 330                 335

Lys Thr Phe Gln Tyr Ile Lys Ser Met Gln Ala Tyr Ile Ala Glu Pro
            340                 345                 350

Leu Leu Val Val Asn Trp Gln Ser Ser Ile Pro Ala Val Asp Thr Trp
        355                 360                 365

Ile Val Glu Trp Leu Pro Glu Ala Ala Met Ser Lys Phe Pro Ala Leu
    370                 375                 380

Ser Trp Glu Ser Val Ser Gln Val Thr Asn Trp Thr Ile Glu Gln Asp
385                 390                 395                 400
```

```
Lys Leu Lys Pro Phe Thr Cys Tyr Asn Ile Ser Val Tyr Pro Val Leu
            405                 410                 415

Gly His Arg Val Gly Glu Pro Tyr Ser Ile Gln Ala Tyr Ala Lys Glu
        420                 425                 430

Gly Thr Pro Leu Lys Gly Pro Glu Thr Arg Val Glu Asn Ile Gly Leu
    435                 440                 445

Arg Thr Ala Thr Ile Thr Trp Lys Glu Ile Pro Lys Ser Ala Arg Asn
450                 455                 460

Gly Phe Ile Asn Asn Tyr Thr Val Phe Tyr Gln Ala Glu Gly Gly Lys
465                 470                 475                 480

Glu Leu Ser Lys Thr Val Asn Ser His Ala Leu Gln Cys Asp Leu Glu
            485                 490                 495

Ser Leu Thr Arg Arg Thr Ser Tyr Thr Val Trp Val Met Ala Ser Thr
        500                 505                 510

Arg Ala Gly Gly Thr Asn Gly Val Arg Ile Asn Phe Lys Thr Leu Ser
    515                 520                 525

Ile Ser Val Phe Glu Ile Val Leu Leu Thr Ser Leu Val Gly Gly Gly
530                 535                 540

Leu Leu Leu Leu Ser Ile Lys Thr Val Thr Phe Gly Leu Arg Lys Pro
545                 550                 555                 560

Asn Arg Leu Thr Pro Leu Cys Cys Pro Asp Val Pro Asn Pro Ala Glu
            565                 570                 575

Ser Ser Leu Ala Thr Trp Leu Gly Asp Gly Phe Lys Lys Ser Asn Met
        580                 585                 590

Lys Glu Thr Gly Asn Ser Gly Asn Thr Glu Asp Val Val Leu Lys Pro
    595                 600                 605

Cys Pro Val Pro Ala Asp Leu Ile Asp Lys Leu Val Val Asn Phe Glu
610                 615                 620

Asn Phe Leu Glu Val Val Leu Thr Glu Glu Ala Gly Lys Gly Gln Ala
625                 630                 635                 640

Ser Ile Leu Gly Gly Glu Ala Asn Glu Tyr Ile Leu Ser Gln Glu Pro
            645                 650                 655

Ser Cys Pro Gly His Cys
        660

<210> SEQ ID NO 128
<211> LENGTH: 2728
<212> TYPE: DNA
<213> ORGANISM: Mus musculus
<220> FEATURE:
<221> NAME/KEY: CDS
<222> LOCATION: (237)...(1877)

<400> SEQUENCE: 128
gatgggaccc tgaatgttga tctgacagaa ttccagacca acctggtggt tattgtcctt        60
ttcatctggt catgctgaat atactctcaa gatgtgctgg agaaggtgct gctgtccggg       120
ctctcagaga aggcagtgct ggaggcgttc ctggcccggg tctcctccta ctgttcctgg       180
tagcccagcc ttctcggggt ggaaggagaa gctggccagg tgagctctga ggaagc atg      239
                                                               Met
                                                                 1 ctg agc agc cag aag gga tcc tgc agc cag gaa cca ggg gca gcc cac         287
Leu Ser Ser Gln Lys Gly Ser Cys Ser Gln Glu Pro Gly Ala Ala His
          5                  10                  15 gtc cag cct ctg ggt gtg aac gct gga ata atg tgg acc ttg gca ctg         335
Val Gln Pro Leu Gly Val Asn Ala Gly Ile Met Trp Thr Leu Ala Leu
```

-continued

```
                    20                  25                  30
tgg gca ttc tct ttc ctc tgc aaa ttc agc ctg gca gtc ctg ccg act      383
Trp Ala Phe Ser Phe Leu Cys Lys Phe Ser Leu Ala Val Leu Pro Thr
 35                  40                  45 aag cca gag aac att tcc tgc gtc ttt tac ttc gac aga aat ctg act      431
Lys Pro Glu Asn Ile Ser Cys Val Phe Tyr Phe Asp Arg Asn Leu Thr
 50                  55                  60                  65 tgc act tgg aga cca gag aag gaa acc aat gat acc agc tac att gtg      479
Cys Thr Trp Arg Pro Glu Lys Glu Thr Asn Asp Thr Ser Tyr Ile Val
                 70                  75                  80 act ttg act tac tcc tat gga aaa agc aat tat agt gac aat gct aca      527
Thr Leu Thr Tyr Ser Tyr Gly Lys Ser Asn Tyr Ser Asp Asn Ala Thr
                     85                  90                  95 gag gct tca tat tct ttt ccc cgt tcc tgt gca atg ccc cca gac atc      575
Glu Ala Ser Tyr Ser Phe Pro Arg Ser Cys Ala Met Pro Pro Asp Ile
                100                 105                 110 tgc agt gtt gaa gta caa gct caa aat gga gat ggt aaa gtt aaa tct      623
Cys Ser Val Glu Val Gln Ala Gln Asn Gly Asp Gly Lys Val Lys Ser
115                 120                 125 gac atc aca tat tgg cat tta atc tcc ata gca aaa acc gaa cca cct      671
Asp Ile Thr Tyr Trp His Leu Ile Ser Ile Ala Lys Thr Glu Pro Pro
130                 135                 140                 145 ata att tta agt gtg aat cca att tgt aat aga atg ttc cag ata caa      719
Ile Ile Leu Ser Val Asn Pro Ile Cys Asn Arg Met Phe Gln Ile Gln
                    150                 155                 160 tgg aaa ccg cgt gaa aag act cgt ggg ttt cct tta gta tgc atg ctt      767
Trp Lys Pro Arg Glu Lys Thr Arg Gly Phe Pro Leu Val Cys Met Leu
                165                 170                 175 cgg ttc aga act gtc aac agt agc cgc tgg acg gaa gtc aat ttt gaa      815
Arg Phe Arg Thr Val Asn Ser Ser Arg Trp Thr Glu Val Asn Phe Glu
            180                 185                 190 aac tgt aaa cag gtc tgc aac ctc aca gga ctt cag gct ttc aca gaa      863
Asn Cys Lys Gln Val Cys Asn Leu Thr Gly Leu Gln Ala Phe Thr Glu
195                 200                 205 tat gtc ctg gct cta cga ttc agg ttc aat gac tca aga tat tgg agc      911
Tyr Val Leu Ala Leu Arg Phe Arg Phe Asn Asp Ser Arg Tyr Trp Ser
210                 215                 220                 225 aag tgg agc aaa gaa gaa acc aga gtg act atg gag gaa gtt cca cat      959
Lys Trp Ser Lys Glu Glu Thr Arg Val Thr Met Glu Glu Val Pro His
                    230                 235                 240 gtc ctg gac ctg tgg aga att ctg gaa cca gca gac atg aac gga gac     1007
Val Leu Asp Leu Trp Arg Ile Leu Glu Pro Ala Asp Met Asn Gly Asp
                245                 250                 255 agg aag gtg cga ttg ctg tgg aag aag gca aga gga gcc ccc gtc ttg     1055
Arg Lys Val Arg Leu Leu Trp Lys Lys Ala Arg Gly Ala Pro Val Leu
            260                 265                 270 gag aaa aca ttt ggc tac cac ata cag tac ttt gca gag aac agc act     1103
Glu Lys Thr Phe Gly Tyr His Ile Gln Tyr Phe Ala Glu Asn Ser Thr
275                 280                 285 aac ctc aca gag ata aac aac atc acc acc cag cag tat gaa ctg ctt     1151
Asn Leu Thr Glu Ile Asn Asn Ile Thr Thr Gln Gln Tyr Glu Leu Leu
290                 295                 300                 305 ctg atg agc cag gca cac tct gtg tcc gtg act tct ttt aat tct ctt     1199
Leu Met Ser Gln Ala His Ser Val Ser Val Thr Ser Phe Asn Ser Leu
                    310                 315                 320 ggc aag tcc caa gag acc atc ctg agg atc cca gat gtc cat gag aag     1247
Gly Lys Ser Gln Glu Thr Ile Leu Arg Ile Pro Asp Val His Glu Lys
                325                 330                 335 acc ttc cag tac att aag agc atg cag gcc tac ata gcc gag ccc ctg     1295
```

```
                Thr Phe Gln Tyr Ile Lys Ser Met Gln Ala Tyr Ile Ala Glu Pro Leu
                                340                 345                 350 ttg gtg gtg aac tgg caa agc tcc att cct gcg gtg gac act tgg ata        1343
Leu Val Val Asn Trp Gln Ser Ser Ile Pro Ala Val Asp Thr Trp Ile
            355                 360                 365 gtg gag tgg ctc cca gaa gct gcc atg tcg aag ttc cct gcc ctt tcc        1391
Val Glu Trp Leu Pro Glu Ala Ala Met Ser Lys Phe Pro Ala Leu Ser
370                 375                 380                 385 tgg gaa tct gtg tct cag gtc acg aac tgg acc atc gag caa gat aaa        1439
Trp Glu Ser Val Ser Gln Val Thr Asn Trp Thr Ile Glu Gln Asp Lys
                390                 395                 400 cta aaa cct ttc aca tgc tat aat ata tca gtg tat cca gtg ttg gga        1487
Leu Lys Pro Phe Thr Cys Tyr Asn Ile Ser Val Tyr Pro Val Leu Gly
            405                 410                 415 cac cga gtt gga gag ccg tat tca atc caa gct tat gcc aaa gaa gga        1535
His Arg Val Gly Glu Pro Tyr Ser Ile Gln Ala Tyr Ala Lys Glu Gly
420                 425                 430 act cca tta aaa ggt cct gag acc agg gtg gag aac atc ggt ctg agg        1583
Thr Pro Leu Lys Gly Pro Glu Thr Arg Val Glu Asn Ile Gly Leu Arg
                435                 440                 445 aca gcc acg atc aca tgg aag gag att cct aag agt gct agg aat gga        1631
Thr Ala Thr Ile Thr Trp Lys Glu Ile Pro Lys Ser Ala Arg Asn Gly
450                 455                 460                 465 ttt atc aac aat tac act gta ttt tac caa gct gaa ggt gga aaa gaa        1679
Phe Ile Asn Asn Tyr Thr Val Phe Tyr Gln Ala Glu Gly Gly Lys Glu
                470                 475                 480 ctc tcc aag act gtt aac tct cat gcc ctg cag tgt gac ctg gag tct        1727
Leu Ser Lys Thr Val Asn Ser His Ala Leu Gln Cys Asp Leu Glu Ser
            485                 490                 495 ctg aca cga agg acc tct tat act gtt tgg gtc atg gcc agc acc aga        1775
Leu Thr Arg Arg Thr Ser Tyr Thr Val Trp Val Met Ala Ser Thr Arg
500                 505                 510 gct gga ggt acc aac ggg gtg aga ata aac ttc aag aca ttg tca atc        1823
Ala Gly Gly Thr Asn Gly Val Arg Ile Asn Phe Lys Thr Leu Ser Ile
                515                 520                 525 agt gag tac tgg ctt cag gcc tca ttc tgg agt tta ctt cgg gtt gga        1871
Ser Glu Tyr Trp Leu Gln Ala Ser Phe Trp Ser Leu Leu Arg Val Gly
530                 535                 540                 545 aat gtt tgacaggagc aaggagagcc agcagagggc agcagagcat ggcttctcct         1927
Asn Val gctctctctg gctcactcac ctcccaggag ttactgagga gctggcaaag ggagggctga      1987
gttagaccaa caggccattt tgatccttgc tggtaagcag ccacaaataa tcttaagatg      2047
aagcaagcaa catccacttc agcctcagcc acgtcaaagg ctgttgcctg agctcacact      2107
ggccagttcc taaatgtcag gagttgtgca atagaacctg ggaaggaaca actggttgat      2167
cagaggtcac tgacaaggga cttaatgtta ccatctgcgg tggggctttt gtttcgtttt      2227
gtttgtttgt tatgtgtatt caacttatca gcttttacgt tgaaaacatg aaaagcaaga      2287
caaatttgtt agatatcaca tataatgtga aatataatag tttaataatt gagtaggaaa      2347
gctgagggca tgtaatagac agagggaaaa gaagaggaaa gccagtctgg tctacaaagt      2407
gagttccagg acagccaggg ctacatggag aaaccctgtc tcaatcaatc aatcaatcaa      2467
tcaatcagtc aatcaatcaa aattcaagca gcattgacaa gttttgcaat aactactata      2527
aaccaaaaaa gtcatcttga tgtatctcag aagccccttg ttatttatgt tcctgaagac      2587
taaagtagac cgtggctctg agaaccatga gcaagataac acgttctgtc ctgcagccta      2647
acaatgcctt cttggtattc tttttgatac aacttctaaa ataactttt tttaaaaaaa       2707
```
ataaaaatca tgttacagct a 2728

<210> SEQ ID NO 129
<211> LENGTH: 547
<212> TYPE: PRT
<213> ORGANISM: Mus musculus

<400> SEQUENCE: 129

| Met | Leu | Ser | Ser | Gln | Lys | Gly | Ser | Cys | Ser | Gln | Glu | Pro | Gly | Ala | Ala |
|---|---|---|---|---|---|---|---|---|---|---|---|---|---|---|---|
| 1 | | | | 5 | | | | | 10 | | | | | 15 | |

| His | Val | Gln | Pro | Leu | Gly | Val | Asn | Ala | Gly | Ile | Met | Trp | Thr | Leu | Ala |
| | | | 20 | | | | | 25 | | | | | 30 | | |

| Leu | Trp | Ala | Phe | Ser | Phe | Leu | Cys | Lys | Phe | Ser | Leu | Ala | Val | Leu | Pro |
| | | | 35 | | | | 40 | | | | | 45 | | | |

| Thr | Lys | Pro | Glu | Asn | Ile | Ser | Cys | Val | Phe | Tyr | Phe | Asp | Arg | Asn | Leu |
| | 50 | | | | | 55 | | | | | 60 | | | | |

| Thr | Cys | Thr | Trp | Arg | Pro | Glu | Lys | Glu | Thr | Asn | Asp | Thr | Ser | Tyr | Ile |
| 65 | | | | | 70 | | | | | 75 | | | | | 80 |

| Val | Thr | Leu | Thr | Tyr | Ser | Tyr | Gly | Lys | Ser | Asn | Tyr | Ser | Asp | Asn | Ala |
| | | | | 85 | | | | | 90 | | | | | 95 | |

| Thr | Glu | Ala | Ser | Tyr | Ser | Phe | Pro | Arg | Ser | Cys | Ala | Met | Pro | Pro | Asp |
| | | | 100 | | | | | 105 | | | | | 110 | | |

| Ile | Cys | Ser | Val | Glu | Val | Gln | Ala | Gln | Asn | Gly | Asp | Gly | Lys | Val | Lys |
| | | 115 | | | | | 120 | | | | | 125 | | | |

| Ser | Asp | Ile | Thr | Tyr | Trp | His | Leu | Ile | Ser | Ile | Ala | Lys | Thr | Glu | Pro |
| | 130 | | | | | 135 | | | | | 140 | | | | |

| Pro | Ile | Ile | Leu | Ser | Val | Asn | Pro | Ile | Cys | Asn | Arg | Met | Phe | Gln | Ile |
| 145 | | | | | 150 | | | | | 155 | | | | | 160 |

| Gln | Trp | Lys | Pro | Arg | Glu | Lys | Thr | Arg | Gly | Phe | Pro | Leu | Val | Cys | Met |
| | | | | 165 | | | | | 170 | | | | | 175 | |

| Leu | Arg | Phe | Arg | Thr | Val | Asn | Ser | Ser | Arg | Trp | Thr | Glu | Val | Asn | Phe |
| | | | 180 | | | | | 185 | | | | | 190 | | |

| Glu | Asn | Cys | Lys | Gln | Val | Cys | Asn | Leu | Thr | Gly | Leu | Gln | Ala | Phe | Thr |
| | | 195 | | | | | 200 | | | | | 205 | | | |

| Glu | Tyr | Val | Leu | Ala | Leu | Arg | Phe | Arg | Phe | Asn | Asp | Ser | Arg | Tyr | Trp |
| | 210 | | | | | 215 | | | | | 220 | | | | |

| Ser | Lys | Trp | Ser | Lys | Glu | Glu | Thr | Arg | Val | Thr | Met | Glu | Glu | Val | Pro |
| 225 | | | | | 230 | | | | | 235 | | | | | 240 |

| His | Val | Leu | Asp | Leu | Trp | Arg | Ile | Leu | Glu | Pro | Ala | Asp | Met | Asn | Gly |
| | | | | 245 | | | | | 250 | | | | | 255 | |

| Asp | Arg | Lys | Val | Arg | Leu | Leu | Trp | Lys | Lys | Ala | Arg | Gly | Ala | Pro | Val |
| | | | 260 | | | | | 265 | | | | | 270 | | |

| Leu | Glu | Lys | Thr | Phe | Gly | Tyr | His | Ile | Gln | Tyr | Phe | Ala | Glu | Asn | Ser |
| | | 275 | | | | | 280 | | | | | 285 | | | |

| Thr | Asn | Leu | Thr | Glu | Ile | Asn | Asn | Ile | Thr | Thr | Gln | Gln | Tyr | Glu | Leu |
| | 290 | | | | | 295 | | | | | 300 | | | | |

| Leu | Leu | Met | Ser | Gln | Ala | His | Ser | Val | Ser | Val | Thr | Ser | Phe | Asn | Ser |
| 305 | | | | | 310 | | | | | 315 | | | | | 320 |

| Leu | Gly | Lys | Ser | Gln | Glu | Thr | Ile | Leu | Arg | Ile | Pro | Asp | Val | His | Glu |
| | | | | 325 | | | | | 330 | | | | | 335 | |

| Lys | Thr | Phe | Gln | Tyr | Ile | Lys | Ser | Met | Gln | Ala | Tyr | Ile | Ala | Glu | Pro |
| | | | 340 | | | | | 345 | | | | | 350 | | |

| Leu | Leu | Val | Val | Asn | Trp | Gln | Ser | Ser | Ile | Pro | Ala | Val | Asp | Thr | Trp |
| | | 355 | | | | | 360 | | | | | 365 | | | |

```
Ile Val Glu Trp Leu Pro Glu Ala Ala Met Ser Lys Phe Pro Ala Leu
    370                 375                 380

Ser Trp Glu Ser Val Ser Gln Val Thr Asn Trp Thr Ile Glu Gln Asp
385                 390                 395                 400

Lys Leu Lys Pro Phe Thr Cys Tyr Asn Ile Ser Val Tyr Pro Val Leu
                405                 410                 415

Gly His Arg Val Gly Glu Pro Tyr Ser Ile Gln Ala Tyr Ala Lys Glu
            420                 425                 430

Gly Thr Pro Leu Lys Gly Pro Glu Thr Arg Val Glu Asn Ile Gly Leu
        435                 440                 445

Arg Thr Ala Thr Ile Thr Trp Lys Glu Ile Pro Lys Ser Ala Arg Asn
    450                 455                 460

Gly Phe Ile Asn Asn Tyr Thr Val Phe Tyr Gln Ala Glu Gly Gly Lys
465                 470                 475                 480

Glu Leu Ser Lys Thr Val Asn Ser His Ala Leu Gln Cys Asp Leu Glu
                485                 490                 495

Ser Leu Thr Arg Arg Thr Ser Tyr Thr Val Trp Val Met Ala Ser Thr
            500                 505                 510

Arg Ala Gly Gly Thr Asn Gly Val Arg Ile Asn Phe Lys Thr Leu Ser
        515                 520                 525

Ile Ser Glu Tyr Trp Leu Gln Ala Ser Phe Trp Ser Leu Leu Arg Val
    530                 535                 540

Gly Asn Val
545

<210> SEQ ID NO 130
<211> LENGTH: 30
<212> TYPE: DNA
<213> ORGANISM: Artificial Sequence
<220> FEATURE:
<223> OTHER INFORMATION: Oligonucleotide primer ZC41,764

<400> SEQUENCE: 130
atcgaattca gaccaatggc tttctctgtg                                    30

<210> SEQ ID NO 131
<211> LENGTH: 24
<212> TYPE: DNA
<213> ORGANISM: Artificial Sequence
<220> FEATURE:
<223> OTHER INFORMATION: Oligonucleotide primer ZC41,598

<400> SEQUENCE: 131
acagtagtgt tctgactcag ttgg                                          24

<210> SEQ ID NO 132
<211> LENGTH: 21
<212> TYPE: DNA
<213> ORGANISM: Artificial Sequence
<220> FEATURE:
<223> OTHER INFORMATION: Oligonucleotide primer ZC41,948

<400> SEQUENCE: 132
ggtactgttc tctttgtctc g                                             21

<210> SEQ ID NO 133
<211> LENGTH: 27
<212> TYPE: DNA
<213> ORGANISM: Artificial Sequence
<220> FEATURE:
```

-continued

<223> OTHER INFORMATION: Oligonucleotide primer ZC41,766

<400> SEQUENCE: 133
atctctagat gtttactgtt caccttg    27

<210> SEQ ID NO 134
<211> LENGTH: 4026
<212> TYPE: DNA
<213> ORGANISM: Mus musculus
<220> FEATURE:
<221> NAME/KEY: CDS
<222> LOCATION: (780)...(3692)

<400> SEQUENCE: 134

```
ctgtggacat tttaccatgc agccataaag agaggtcaaa aatgtctttc aagtgcccgg    60
ttagtaaaga tctgatggcg ttctaaggag agaaaggaac ttggatcttc gtggacaaag   120
aattcaggtc tgtagctgaa ggaggcgtgg ccacacaggg cgtttccagg tcctgtagag   180
gaagcacagt tcatagatct ctgttctaac acgtctgtct tgctctgaac gccgaaagtc   240
aactcgatca caagtttgat ccaacagttt gacatttcag gtaattttca gacggagcgc   300
tggggttgga tctcccaagc aacacaattg gctctgtgca ggacacctgg cacggggcac   360
tgggtcgcag ctcgtcccct ctccctccag gaacaacgat gctcaaggac cagcttttcc   420
tcccaggcct ctcccacttc ccttctcacc ggtgctgccc gccggtccc gggaaccgcg    480 cccgtcgcag ggtcccgatc gttcccccta catcccttgg gaccaggagc aaattcctgt   540
gggtcccagg agtgccaaaa gtgctcagcg agacgggaaa ttgcaacagt acttggccct   600
tcggccctcc cccggcgctt tcccgtaact cccgcccctg gacacttgtc ccgtagttga   660
ttcatagctg gggcgcgggg ccgcctccac acgcctggac agacgtccgc gcccgttccc   720
ctgtgaggcc gaggaccggc aaggctccgg agcaggtcgc caggcgggta atcagacca    779
```

```
atg gct ttc tct gtg gtc ctt cat cca gcc ttc ctc ctg gca gtg ctg    827
Met Ala Phe Ser Val Val Leu His Pro Ala Phe Leu Leu Ala Val Leu
  1               5                  10                  15 tcc ctg agg gca tcc cga agc gaa gtc ttg gag gag cct tta cca ttg    875
Ser Leu Arg Ala Ser Arg Ser Glu Val Leu Glu Glu Pro Leu Pro Leu
             20                  25                  30 act cct gag ata cat aaa gtt tct ttt caa ttg aaa ctt caa gaa gtg    923
Thr Pro Glu Ile His Lys Val Ser Phe Gln Leu Lys Leu Gln Glu Val
         35                  40                  45 aat tta gaa tgg act gtc cca gcc ctt act cat gaa gaa tta aac atg    971
Asn Leu Glu Trp Thr Val Pro Ala Leu Thr His Glu Glu Leu Asn Met
     50                  55                  60 ata ttt cag ata gag atc agt aga ctg aac ata tcc aac acc atc tgg   1019
Ile Phe Gln Ile Glu Ile Ser Arg Leu Asn Ile Ser Asn Thr Ile Trp
 65                  70                  75                  80 gtg gag aat tat agc acc act gtg aag cgt gaa gaa gct gtg cgt tgg   1067
Val Glu Asn Tyr Ser Thr Thr Val Lys Arg Glu Glu Ala Val Arg Trp
                 85                  90                  95 aac tgg acg tct gat atc cct ttg gag tgt gtc aaa cat ttc ata aga   1115
Asn Trp Thr Ser Asp Ile Pro Leu Glu Cys Val Lys His Phe Ile Arg
            100                 105                 110 atc agg gct ctg gta gat gac acc aag tcc ctt cca cag agt tcc tgg   1163
Ile Arg Ala Leu Val Asp Asp Thr Lys Ser Leu Pro Gln Ser Ser Trp
        115                 120                 125 ggc aac tgg agt tcc tgg aaa gaa gtt aat gca aag gtt tcc gtt gaa   1211
Gly Asn Trp Ser Ser Trp Lys Glu Val Asn Ala Lys Val Ser Val Glu
    130                 135                 140
```

```
cct gat aaa tca tta ata ttt cct aaa gac aaa gtg ttg gaa gaa ggc    1259
Pro Asp Lys Ser Leu Ile Phe Pro Lys Asp Lys Val Leu Glu Glu Gly
145                 150                 155                 160 tcc aat gtc acc atc tgt ctg atg tat ggg cag aat gta tat aat gta    1307
Ser Asn Val Thr Ile Cys Leu Met Tyr Gly Gln Asn Val Tyr Asn Val
                165                 170                 175 tcc tgt aag ttg caa gat gag cca atc cat gga gaa caa ctt gat tcc    1355
Ser Cys Lys Leu Gln Asp Glu Pro Ile His Gly Glu Gln Leu Asp Ser
            180                 185                 190 cac gtg tca tta tta aaa ttg aac aat gta gtt ttc ctt agt gac aca    1403
His Val Ser Leu Leu Lys Leu Asn Asn Val Val Phe Leu Ser Asp Thr
        195                 200                 205 ggg aca aac atc aat tgt caa gcc acg aag ggt cct aaa aga ata ttt    1451
Gly Thr Asn Ile Asn Cys Gln Ala Thr Lys Gly Pro Lys Arg Ile Phe
    210                 215                 220 ggt act gtt ctc ttt gtc tcg aaa gtg ctc gag gaa cct aag aat gtt    1499
Gly Thr Val Leu Phe Val Ser Lys Val Leu Glu Glu Pro Lys Asn Val
225                 230                 235                 240 tcc tgt gaa acc cga gac ttt aag act ttg gac tgt tca tgg gaa cct    1547
Ser Cys Glu Thr Arg Asp Phe Lys Thr Leu Asp Cys Ser Trp Glu Pro
                245                 250                 255 ggg gta gat acg act ttg act tgg cgt aaa caa aga ttc caa aac tac    1595
Gly Val Asp Thr Thr Leu Thr Trp Arg Lys Gln Arg Phe Gln Asn Tyr
            260                 265                 270 act tta tgt gaa tcg ttc tct aag aga tgt gag gtt tct aac tac agg    1643
Thr Leu Cys Glu Ser Phe Ser Lys Arg Cys Glu Val Ser Asn Tyr Arg
        275                 280                 285 aac tcc tat acc tgg caa atc act gaa ggc tca cag gaa atg tat aac    1691
Asn Ser Tyr Thr Trp Gln Ile Thr Glu Gly Ser Gln Glu Met Tyr Asn
    290                 295                 300 ttt act ctc aca gct gaa aac caa cta agg aaa aga agt gtc aac att    1739
Phe Thr Leu Thr Ala Glu Asn Gln Leu Arg Lys Arg Ser Val Asn Ile
305                 310                 315                 320 aat ttt aac ctg acc cat aga gtt cat cca aag gct ccg cag gac gtc    1787
Asn Phe Asn Leu Thr His Arg Val His Pro Lys Ala Pro Gln Asp Val
                325                 330                 335 acc ctt aaa att ata ggt gct aca aaa gcc aac atg act tgg aag gtt    1835
Thr Leu Lys Ile Ile Gly Ala Thr Lys Ala Asn Met Thr Trp Lys Val
            340                 345                 350 cac tcc cat gga aac aac tac aca ctt ttg tgt cag gtt aaa ctc caa    1883
His Ser His Gly Asn Asn Tyr Thr Leu Leu Cys Gln Val Lys Leu Gln
        355                 360                 365 tat gga gaa gtg att cat gag cac aat gtt tct gtc cac atg agc gca    1931
Tyr Gly Glu Val Ile His Glu His Asn Val Ser Val His Met Ser Ala
    370                 375                 380 aac tac ctc ttc agt gat ctg gat cca gac aca aag tac aag gct ttt    1979
Asn Tyr Leu Phe Ser Asp Leu Asp Pro Asp Thr Lys Tyr Lys Ala Phe
385                 390                 395                 400 gtg cgc tgt gca agt gcc aac cac ttc tgg aaa tgg agc gac tgg acc    2027
Val Arg Cys Ala Ser Ala Asn His Phe Trp Lys Trp Ser Asp Trp Thr
                405                 410                 415 caa aaa gag ttc agc aca ccc gag act gct ccc tca cag gct ctt gat    2075
Gln Lys Glu Phe Ser Thr Pro Glu Thr Ala Pro Ser Gln Ala Leu Asp
            420                 425                 430 gta tgg aga caa gtg tgg tcg gag aat gga aga cgc att gtg act tta    2123
Val Trp Arg Gln Val Trp Ser Glu Asn Gly Arg Arg Ile Val Thr Leu
        435                 440                 445 ttc tgg aag cca cta tta aaa tca cag gcc aat ggc aaa atc ata tcc    2171
Phe Trp Lys Pro Leu Leu Lys Ser Gln Ala Asn Gly Lys Ile Ile Ser
    450                 455                 460
```

-continued

```
tat aat ata gtt gta gaa aat gaa gcc aaa cca act gag tca gaa cac    2219
Tyr Asn Ile Val Val Glu Asn Glu Ala Lys Pro Thr Glu Ser Glu His
465             470                 475                 480 tac tgt gtc tgg gca cca gcc ctc agc aca aac ctg agc ctt gac ctg    2267
Tyr Cys Val Trp Ala Pro Ala Leu Ser Thr Asn Leu Ser Leu Asp Leu
                485                 490                 495 caa cct tac aag att cgc atc aca gcc aac aac agc atg ggg gca tct    2315
Gln Pro Tyr Lys Ile Arg Ile Thr Ala Asn Asn Ser Met Gly Ala Ser
            500                 505                 510 cct gag tcc ttg atg gtc ctt tct aat gat tct gga cac gag gtc aag    2363
Pro Glu Ser Leu Met Val Leu Ser Asn Asp Ser Gly His Glu Val Lys
        515                 520                 525 gaa aag aca att aaa ggt ata aag gat gca ttc aat att tct tgg gag    2411
Glu Lys Thr Ile Lys Gly Ile Lys Asp Ala Phe Asn Ile Ser Trp Glu
530                 535                 540 ccc gta tct gga gac acg atg ggc tat gtt gtg gac tgg tgt gca cat    2459
Pro Val Ser Gly Asp Thr Met Gly Tyr Val Val Asp Trp Cys Ala His
545                 550                 555                 560 tcc cag gac caa cgc tgt gat ttg cag tgg aag aac ctt ggt ccc aat    2507
Ser Gln Asp Gln Arg Cys Asp Leu Gln Trp Lys Asn Leu Gly Pro Asn
                565                 570                 575 acc aca agc acc acc atc acc tca gat gat ttt aaa cca ggc gtc cgt    2555
Thr Thr Ser Thr Thr Ile Thr Ser Asp Asp Phe Lys Pro Gly Val Arg
            580                 585                 590 tac aac ttc aga att ttt gaa agg tct gtg gaa cac aaa gct cgg tta    2603
Tyr Asn Phe Arg Ile Phe Glu Arg Ser Val Glu His Lys Ala Arg Leu
        595                 600                 605 gta gag aaa caa aga gga tac acc cag gaa ctg gct cct ttg gtg aat    2651
Val Glu Lys Gln Arg Gly Tyr Thr Gln Glu Leu Ala Pro Leu Val Asn
610                 615                 620 cca aaa gtg gag att cct tac tcg acc cct aac tcc ttc gtt cta aga    2699
Pro Lys Val Glu Ile Pro Tyr Ser Thr Pro Asn Ser Phe Val Leu Arg
625                 630                 635                 640 tgg cca gat tat gac agc gac ttc cag gct ggt ttt ata aaa ggg tac    2747
Trp Pro Asp Tyr Asp Ser Asp Phe Gln Ala Gly Phe Ile Lys Gly Tyr
                645                 650                 655 ctc gtg tat gtg aaa tcc aag gag atg cag tgc aac caa ccc tgg gaa    2795
Leu Val Tyr Val Lys Ser Lys Glu Met Gln Cys Asn Gln Pro Trp Glu
            660                 665                 670 agg acc ctc ctt cca gat aat tca gtc ctc tgt aaa tac gac atc aat    2843
Arg Thr Leu Leu Pro Asp Asn Ser Val Leu Cys Lys Tyr Asp Ile Asn
        675                 680                 685 ggc tca gag aca aag aca ctc acc gtg gaa aac ctt cag cca gag tcc    2891
Gly Ser Glu Thr Lys Thr Leu Thr Val Glu Asn Leu Gln Pro Glu Ser
690                 695                 700 ctc tat gag ttt ttc gtc act ccg tac acc agc gct ggc cca gga ccc    2939
Leu Tyr Glu Phe Phe Val Thr Pro Tyr Thr Ser Ala Gly Pro Gly Pro
705                 710                 715                 720 aat gaa acg ttc aca aag gtc aca act cca gat gca cgc tcc cac atg    2987
Asn Glu Thr Phe Thr Lys Val Thr Thr Pro Asp Ala Arg Ser His Met
                725                 730                 735 ctg ctg cag atc ata cta ccc atg acc ctc tgc gtc ttg ctc agc atc    3035
Leu Leu Gln Ile Ile Leu Pro Met Thr Leu Cys Val Leu Leu Ser Ile
            740                 745                 750 att gtc tgc tac tgg aaa agt cag tgg gtg aag gag aag tgc tac cct    3083
Ile Val Cys Tyr Trp Lys Ser Gln Trp Val Lys Glu Lys Cys Tyr Pro
        755                 760                 765 gac att ccc aat ccg tac aag agc agc att ctg tca ctc ata aaa tcc    3131
Asp Ile Pro Asn Pro Tyr Lys Ser Ser Ile Leu Ser Leu Ile Lys Ser
```

```
                770                 775                 780
aag aag aat cct cac tta ata atg aat gtc aaa gac tgc att cca gat     3179
Lys Lys Asn Pro His Leu Ile Met Asn Val Lys Asp Cys Ile Pro Asp
785                 790                 795                 800 gtc ctt gaa gtg ata aac aaa gca gaa ggc agc aag aca cag tgt gta     3227
Val Leu Glu Val Ile Asn Lys Ala Glu Gly Ser Lys Thr Gln Cys Val
                805                 810                 815 ggc tct ggg aaa ctt cac att gaa gat gta ccc act aag ccg cca atc     3275
Gly Ser Gly Lys Leu His Ile Glu Asp Val Pro Thr Lys Pro Pro Ile
            820                 825                 830 gtg cca aca gaa aag gat tcc tca ggg cct gtg ccc tgc atc ttc ttt     3323
Val Pro Thr Glu Lys Asp Ser Ser Gly Pro Val Pro Cys Ile Phe Phe
        835                 840                 845 gag aat ttt act tac gat cag tca gct ttt gac tct ggt tcc cat ggc     3371
Glu Asn Phe Thr Tyr Asp Gln Ser Ala Phe Asp Ser Gly Ser His Gly
    850                 855                 860 ctc att cca ggt ccc cta aaa gac aca gca cac caa ctt gga cta ttg     3419
Leu Ile Pro Gly Pro Leu Lys Asp Thr Ala His Gln Leu Gly Leu Leu
865                 870                 875                 880 gct cca cct aac aag ttc cag aac gta tta aaa aat gac tac atg aag     3467
Ala Pro Pro Asn Lys Phe Gln Asn Val Leu Lys Asn Asp Tyr Met Lys
                885                 890                 895 ccc ctg gtc gaa agt cca act gaa gaa act agc ttg att tat gtg tca     3515
Pro Leu Val Glu Ser Pro Thr Glu Glu Thr Ser Leu Ile Tyr Val Ser
            900                 905                 910 cag ctg gct tca ccc atg tgc gga gac aag gac acg ctt gcc aca gaa     3563
Gln Leu Ala Ser Pro Met Cys Gly Asp Lys Asp Thr Leu Ala Thr Glu
        915                 920                 925 cca ccc gtg cca gtg cat ggt tca gag tat aaa agg caa atg gta gtt     3611
Pro Pro Val Pro Val His Gly Ser Glu Tyr Lys Arg Gln Met Val Val
    930                 935                 940 ccc ggg agc ctc gca tca cct tct ctg aag gag gat aac agc ttg acc     3659
Pro Gly Ser Leu Ala Ser Pro Ser Leu Lys Glu Asp Asn Ser Leu Thr
945                 950                 955                 960 tca acg gtc ctc tta ggc caa ggt gaa cag taa acaccacgca gcacaaataa   3712
Ser Thr Val Leu Leu Gly Gln Gly Glu Gln  *
                965                 970 atgcactcca cacactatag gcactttggg agatgtagct gttaccatgc caacaccacg   3772
tgccctggtt ggttccaggg gtgggggttg aggggagact cattatctgc agtgctgatt   3832
tatcaacgat cactacagac caacagactt aaggaccata taatatggtg ttcaccctga   3892
aggcgttccc tagaaatggc agatccgaga gcatgctgac cttgctatta tttggtccag   3952
gctcacccct attgcagtag cttgacatag ggtgtacacc agtcatttcg cagagcctac   4012
ctactcaaaa ctac                                                     4026
```

<210> SEQ ID NO 135
<211> LENGTH: 970
<212> TYPE: PRT
<213> ORGANISM: Mus musculus

<400> SEQUENCE: 135

```
Met Ala Phe Ser Val Val Leu His Pro Ala Phe Leu Leu Ala Val Leu
1               5                   10                  15

Ser Leu Arg Ala Ser Arg Ser Glu Val Leu Glu Glu Pro Leu Pro Leu
            20                  25                  30

Thr Pro Glu Ile His Lys Val Ser Phe Gln Leu Lys Leu Gln Glu Val
        35                  40                  45
```

-continued

```
Asn Leu Glu Trp Thr Val Pro Ala Leu Thr His Glu Leu Asn Met
    50                  55                  60
Ile Phe Gln Ile Glu Ile Ser Arg Leu Asn Ile Ser Asn Thr Ile Trp
65                  70                  75                  80
Val Glu Asn Tyr Ser Thr Thr Val Lys Arg Glu Glu Ala Val Arg Trp
                85                  90                  95
Asn Trp Thr Ser Asp Ile Pro Leu Glu Cys Val Lys His Phe Ile Arg
            100                 105                 110
Ile Arg Ala Leu Val Asp Asp Thr Lys Ser Leu Pro Gln Ser Ser Trp
        115                 120                 125
Gly Asn Trp Ser Ser Trp Lys Glu Val Asn Ala Lys Val Ser Val Glu
    130                 135                 140
Pro Asp Lys Ser Leu Ile Phe Pro Lys Asp Lys Val Leu Glu Glu Gly
145                 150                 155                 160
Ser Asn Val Thr Ile Cys Leu Met Tyr Gly Gln Asn Val Tyr Asn Val
                165                 170                 175
Ser Cys Lys Leu Gln Asp Glu Pro Ile His Gly Glu Gln Leu Asp Ser
            180                 185                 190
His Val Ser Leu Leu Lys Leu Asn Asn Val Val Phe Leu Ser Asp Thr
        195                 200                 205
Gly Thr Asn Ile Asn Cys Gln Ala Thr Lys Gly Pro Lys Arg Ile Phe
    210                 215                 220
Gly Thr Val Leu Phe Val Ser Lys Val Leu Glu Pro Lys Asn Val
225                 230                 235                 240
Ser Cys Glu Thr Arg Asp Phe Lys Thr Leu Asp Cys Ser Trp Glu Pro
                245                 250                 255
Gly Val Asp Thr Thr Leu Thr Trp Arg Lys Gln Arg Phe Gln Asn Tyr
            260                 265                 270
Thr Leu Cys Glu Ser Phe Ser Lys Arg Cys Glu Val Ser Asn Tyr Arg
        275                 280                 285
Asn Ser Tyr Thr Trp Gln Ile Thr Glu Gly Ser Gln Glu Met Tyr Asn
    290                 295                 300
Phe Thr Leu Thr Ala Glu Asn Gln Leu Arg Lys Arg Ser Val Asn Ile
305                 310                 315                 320
Asn Phe Asn Leu Thr His Arg Val His Pro Lys Ala Pro Gln Asp Val
                325                 330                 335
Thr Leu Lys Ile Ile Gly Ala Thr Lys Ala Asn Met Thr Trp Lys Val
            340                 345                 350
His Ser His Gly Asn Asn Tyr Thr Leu Leu Cys Gln Val Lys Leu Gln
        355                 360                 365
Tyr Gly Glu Val Ile His Glu His Asn Val Ser Val His Met Ser Ala
    370                 375                 380
Asn Tyr Leu Phe Ser Asp Leu Asp Pro Asp Thr Lys Tyr Lys Ala Phe
385                 390                 395                 400
Val Arg Cys Ala Ser Ala Asn His Phe Trp Lys Trp Ser Asp Trp Thr
                405                 410                 415
Gln Lys Glu Phe Ser Thr Pro Glu Thr Ala Pro Ser Gln Ala Leu Asp
            420                 425                 430
Val Trp Arg Gln Val Trp Ser Glu Asn Gly Arg Arg Ile Val Thr Leu
        435                 440                 445
Phe Trp Lys Pro Leu Leu Lys Ser Gln Ala Asn Gly Lys Ile Ile Ser
    450                 455                 460
Tyr Asn Ile Val Val Glu Asn Glu Ala Lys Pro Thr Glu Ser Glu His
```

-continued

```
            465                 470                 475                 480
        Tyr Cys Val Trp Ala Pro Ala Leu Ser Thr Asn Leu Ser Leu Asp Leu
                            485                 490                 495
        Gln Pro Tyr Lys Ile Arg Ile Thr Ala Asn Asn Ser Met Gly Ala Ser
                            500                 505                 510
        Pro Glu Ser Leu Met Val Leu Ser Asn Asp Ser Gly His Glu Val Lys
                            515                 520                 525
        Glu Lys Thr Ile Lys Gly Ile Lys Asp Ala Phe Asn Ile Ser Trp Glu
                            530                 535                 540
        Pro Val Ser Gly Asp Thr Met Gly Tyr Val Val Asp Trp Cys Ala His
        545                 550                 555                 560
        Ser Gln Asp Gln Arg Cys Asp Leu Gln Trp Lys Asn Leu Gly Pro Asn
                            565                 570                 575
        Thr Thr Ser Thr Thr Ile Thr Ser Asp Asp Phe Lys Pro Gly Val Arg
                            580                 585                 590
        Tyr Asn Phe Arg Ile Phe Glu Arg Ser Val Glu His Lys Ala Arg Leu
                            595                 600                 605
        Val Glu Lys Gln Arg Gly Tyr Thr Gln Glu Leu Ala Pro Leu Val Asn
                            610                 615                 620
        Pro Lys Val Glu Ile Pro Tyr Ser Thr Pro Asn Ser Phe Val Leu Arg
        625                 630                 635                 640
        Trp Pro Asp Tyr Asp Ser Asp Phe Gln Ala Gly Phe Ile Lys Gly Tyr
                            645                 650                 655
        Leu Val Tyr Val Lys Ser Lys Glu Met Gln Cys Asn Gln Pro Trp Glu
                            660                 665                 670
        Arg Thr Leu Leu Pro Asp Asn Ser Val Leu Cys Lys Tyr Asp Ile Asn
                            675                 680                 685
        Gly Ser Glu Thr Lys Thr Leu Thr Val Glu Asn Leu Gln Pro Glu Ser
                            690                 695                 700
        Leu Tyr Glu Phe Phe Val Thr Pro Tyr Thr Ser Ala Gly Pro Gly Pro
        705                 710                 715                 720
        Asn Glu Thr Phe Thr Lys Val Thr Thr Pro Asp Ala Arg Ser His Met
                            725                 730                 735
        Leu Leu Gln Ile Ile Leu Pro Met Thr Leu Cys Val Leu Leu Ser Ile
                            740                 745                 750
        Ile Val Cys Tyr Trp Lys Ser Gln Trp Val Lys Glu Lys Cys Tyr Pro
                            755                 760                 765
        Asp Ile Pro Asn Pro Tyr Lys Ser Ser Ile Leu Ser Leu Ile Lys Ser
                            770                 775                 780
        Lys Lys Asn Pro His Leu Ile Met Asn Val Lys Asp Cys Ile Pro Asp
        785                 790                 795                 800
        Val Leu Glu Val Ile Asn Lys Ala Glu Gly Ser Lys Thr Gln Cys Val
                            805                 810                 815
        Gly Ser Gly Lys Leu His Ile Glu Asp Val Pro Thr Lys Pro Pro Ile
                            820                 825                 830
        Val Pro Thr Glu Lys Asp Ser Ser Gly Pro Val Pro Cys Ile Phe Phe
                            835                 840                 845
        Glu Asn Phe Thr Tyr Asp Gln Ser Ala Phe Asp Ser Gly Ser His Gly
                            850                 855                 860
        Leu Ile Pro Gly Pro Leu Lys Asp Thr Ala His Gln Leu Gly Leu Leu
        865                 870                 875                 880
        Ala Pro Pro Asn Lys Phe Gln Asn Val Leu Lys Asn Asp Tyr Met Lys
                            885                 890                 895
```

```
Pro Leu Val Glu Ser Pro Thr Glu Glu Thr Ser Leu Ile Tyr Val Ser
            900                 905                 910

Gln Leu Ala Ser Pro Met Cys Gly Asp Lys Asp Thr Leu Ala Thr Glu
        915                 920                 925

Pro Pro Val Pro Val His Gly Ser Glu Tyr Lys Arg Gln Met Val Val
    930                 935                 940

Pro Gly Ser Leu Ala Ser Pro Ser Leu Lys Glu Asp Asn Ser Leu Thr
945                 950                 955                 960

Ser Thr Val Leu Leu Gly Gln Gly Glu Gln
                965                 970

<210> SEQ ID NO 136
<211> LENGTH: 2910
<212> TYPE: DNA
<213> ORGANISM: Artificial Sequence
<220> FEATURE:
<223> OTHER INFORMATION: Degenerate polynucleotide sequence encoding the
      polypeptide of SEQ ID NO:135.
<220> FEATURE:
<221> NAME/KEY: misc_feature
<222> LOCATION: (1)...(2910)
<223> OTHER INFORMATION: n = A, T, G, or C

<400> SEQUENCE: 136
atggcnttyw sngtngtnyt ncayccngcn ttyytnytng cngtnytnws nytnmgngcn    60
wsnmgnwsng argtnytnga rgarccnytn ccnytnacnc cngarathca yaargtnwsn   120
ttycarytna arytncarga rgtnaayytn gartggacng tnccngcnyt nacncaygar   180
garytnaaya tgathttyca rathgarath wsnmgnytna ayathwsnaa yacnathtgg   240
gtngaraayt aywsnacnac ngtnaarmgn gargargcng tnmgntggaa ytggacnwsn   300
gayathccny tngartgygt naarcaytty athmgnathm gngcnytngt ngaygayacn   360
aarwsnytnc cncarwsnws ntggggnaay tggwsnwsnt ggaargargt naaygcnaar   420
gtnwsngtng arccngayaa rwsnytnath ttyccnaarg ayaargtnyt ngargarggn   480
wsnaaygtna cnathtgyyt natgtayggn caraaygtnt ayaaygtnws ntgyaarytn   540
cargaygarc cnathcaygg ngarcarytn gaywsncayg tnwsnytnyt naarytnaay   600
aaygtngtnt tyytnwsnga yacnggnacn aayathaayt gycargcnac naarggnccn   660
aarmgnatht tyggnacngt nytnttygtn wsnaargtny tngargarcc naaraaygtn   720
wsntgygara cnmgngaytt yaaracnytn gaytgywsnt gggarccngg ngtngayacn   780
acnytnacnt ggmgnaarca rmgnttycar aaytayacny tntgygarws nttywsnaar   840
mgntgygarg tnwsnaayta ymgnaaywsn tayacntggc arathacnga rggnwsncar   900
garatgtaya ayttyacnyt nacngcngar aaycarytnm gnaarmgnws ngtnaayath   960
aayttyaayy tnacncaymg ngtncayccn aargcnccnc argaygtnac nytnaarath  1020
athggngcna cnaargcnaa yatgacntgg aargtncayw sncayggnaa yaaytayacn  1080
ytnytntgyc argtnaaryt ncartayggn gargtnathc aygarcayaa ygtnwsngtn  1140
cayatgwsng cnaaytayyt nttywsngay ytngayccng ayacnaarta yaargcntty  1200
gtnmgntgyg cnwsngcnaa ycayttytgg aartggwsng aytggacnca raargartty  1260
wsnacnccng aracngcncc nwsncargcn ytngaygtnt ggmgncargt ntggwsngar  1320
aayggnmgnm gnathgtnac nytnttytgg aarccnytny tnaarwsnca rgcnaayggn  1380
aarathathw sntayaayat hgtngtngar aaygargcna arccnacnga rwsngarcay  1440
```
taytgygtnt gggcnccngc nytnwsnacn aayytnwsny tngayytnca rccntayaar 1500
athmgnatha cngcnaayaa ywsnatgggn gcnwsnccng arwsnytnat ggtnytnwsn 1560
aaygaywsng gncaygargt naargaraar acnathaarg gnathaarga ygcnttyaay 1620
athwsntggg arccngtnws nggngayacn atgggntayg tngtngaytg gtgygcncay 1680
wsncargayc armgntgyga yytncartgg aaraayytng gnccnaayac nacnwsnacn 1740
acnathacnw sngaygaytt yaarccnggn gtnmgntaya ayttymgnat httygarmgn 1800
wsngtngarc ayaargcnmg nytngtngar aarcarmgng gntayacnca rgarytngcn 1860
ccnytngtna ayccnaargt ngarathccn taywsnacnc cnaaywsntt ygtnytnmgn 1920
tggccngayt aygaywsnga yttycargcn ggnttyatha arggntayyt ngtntaygtn 1980
aarwsnaarg aratgcartg yaaycarccn tgggarmgna cnytnytncc ngayaaywsn 2040
gtnytntgya artaygayat haayggnwsn garacnaara cnytnacngt ngaraayytn 2100
carccngarw snytntayga rttyttygtn acnccntaya cnwsngcngg nccnggnccn 2160
aaygaracnt tyacnaargt nacnacnccn gaygcnmgnw sncayatgyt nytncarath 2220
athytnccna tgacnytntg ygtnytnytn wsnathathg tntgytaytg gaarwsncar 2280
tgggtnaarg araartgyta yccngayath ccnaayccnt ayaarwsnws nathytnwsn 2340
ytnathaarw snaaraaraa yccncayytn athatgaayg tnaargaytg yathccngay 2400
gtnytngarg tnathaayaa rgcngarggn wsnaaracnc artgygtngg nwsnggnaar 2460
ytncayathg argaygtncc nacnaarccn ccnathgtnc cnacngaraa rgaywsnwsn 2520
ggnccngtnc cntgyathtt yttygaraay ttyacntayg aycarwsngc nttygaywsn 2580
ggnwsncayg gnytnathcc nggnccnytn aargayacng cncaycaryt nggnytnytn 2640
gcnccnccna ayaarttyca raaygtnytn aaraaygayt ayatgaarcc nytngtngar 2700
wsnccnacng argaracnws nytnathtay gtnwsncary tngcnwsncc natgtgyggn 2760
gayaargaya cnytngcnac ngarccnccn gtnccngtnc ayggnwsnga rtayaarmgn 2820
caratggtng tnccnggnws nytngcnwsn ccnwsnytna argargayaa ywsnytnacn 2880
wsnacngtny tnytnggnca rggngarcar 2910

<210> SEQ ID NO 137
<211> LENGTH: 24
<212> TYPE: DNA
<213> ORGANISM: Artificial Sequence
<220> FEATURE:
<223> OTHER INFORMATION: Primer ZC43891

<400> SEQUENCE: 137
gggcagtagg atatgaatca gcat 24

<210> SEQ ID NO 138
<211> LENGTH: 19
<212> TYPE: DNA
<213> ORGANISM: Artificial Sequence
<220> FEATURE:
<223> OTHER INFORMATION: Primer ZC43900

<400> SEQUENCE: 138
gaaggcccca gtgctacgt 19

<210> SEQ ID NO 139
<211> LENGTH: 24
<212> TYPE: DNA
<213> ORGANISM: Artificial Sequence

```
<220> FEATURE:
<223> OTHER INFORMATION: OSMRbeta probe ZC43896

<400> SEQUENCE: 139
tcatccggag tcgtgacctt cgtg                                              24

<210> SEQ ID NO 140
<211> LENGTH: 20
<212> TYPE: DNA
<213> ORGANISM: Artificial Sequence
<220> FEATURE:
<223> OTHER INFORMATION: Primer ZC43280

<400> SEQUENCE: 140
gagcacgccc ttctcttcct                                                   20

<210> SEQ ID NO 141
<211> LENGTH: 20
<212> TYPE: DNA
<213> ORGANISM: Artificial Sequence
<220> FEATURE:
<223> OTHER INFORMATION: Primer ZC43281

<400> SEQUENCE: 141
cgttgcccgt ccgtttacta                                                   20

<210> SEQ ID NO 142
<211> LENGTH: 40
<212> TYPE: DNA
<213> ORGANISM: Artificial Sequence
<220> FEATURE:
<223> OTHER INFORMATION: zcytor17lig probe ZC43275

<400> SEQUENCE: 142
ctgtaattcc tcgactattt tctgtacatc atcacttggt                             40

<210> SEQ ID NO 143
<211> LENGTH: 22
<212> TYPE: DNA
<213> ORGANISM: Artificial Sequence
<220> FEATURE:
<223> OTHER INFORMATION: Primer ZC40574

<400> SEQUENCE: 143
ctcatttgga attttgccga tt                                                22

<210> SEQ ID NO 144
<211> LENGTH: 22
<212> TYPE: DNA
<213> ORGANISM: Artificial Sequence
<220> FEATURE:
<223> OTHER INFORMATION: Primer ZC40575

<400> SEQUENCE: 144
ccgagtgaag atccccttttt ta                                               22

<210> SEQ ID NO 145
<211> LENGTH: 26
<212> TYPE: DNA
<213> ORGANISM: Artificial Sequence
<220> FEATURE:
<223> OTHER INFORMATION: GUS probe ZC43017

<400> SEQUENCE: 145
tgaacagtca ccgacgagag tgctgg                                            26
```

```
<210> SEQ ID NO 146
<211> LENGTH: 24
<212> TYPE: DNA
<213> ORGANISM: Artificial Sequence
<220> FEATURE:
<223> OTHER INFORMATION: Primer ZC28480

<400> SEQUENCE: 146
cgattcagga cagtcaacag tacc                                              24

<210> SEQ ID NO 147
<211> LENGTH: 21
<212> TYPE: DNA
<213> ORGANISM: Artificial Sequence
<220> FEATURE:
<223> OTHER INFORMATION: Primer ZC41653

<400> SEQUENCE: 147
ccttcgtgaa cgtagcactg g                                                 21

<210> SEQ ID NO 148
<211> LENGTH: 19
<212> TYPE: DNA
<213> ORGANISM: Artificial Sequence
<220> FEATURE:
<223> OTHER INFORMATION: Primer ZC41655

<400> SEQUENCE: 148
ctgaaatcca aggcgaggc                                                    19

<210> SEQ ID NO 149
<211> LENGTH: 20
<212> TYPE: DNA
<213> ORGANISM: Artificial Sequence
<220> FEATURE:
<223> OTHER INFORMATION: Primer ZC41703

<400> SEQUENCE: 149
tgaagctggc cttgctctct                                                   20

<210> SEQ ID NO 150
<211> LENGTH: 19
<212> TYPE: DNA
<213> ORGANISM: Artificial Sequence
<220> FEATURE:
<223> OTHER INFORMATION: Primer ZC41704

<400> SEQUENCE: 150
gagatatgcc cggatggct                                                    19

<210> SEQ ID NO 151
<211> LENGTH: 24
<212> TYPE: DNA
<213> ORGANISM: Artificial Sequence
<220> FEATURE:
<223> OTHER INFORMATION: Primer ZC43272

<400> SEQUENCE: 151
gctggtatca ttggtttcct tctc                                              24

<210> SEQ ID NO 152
<211> LENGTH: 24
<212> TYPE: DNA
<213> ORGANISM: Artificial Sequence
<220> FEATURE:
<223> OTHER INFORMATION: Primer ZC43273
```

```
<400> SEQUENCE: 152
cattctcttt cctctgcaaa ttca                                          24

<210> SEQ ID NO 153
<211> LENGTH: 34
<212> TYPE: DNA
<213> ORGANISM: Artificial Sequence
<220> FEATURE:
<223> OTHER INFORMATION: zcytor17 probe ZC43478

<400> SEQUENCE: 153
tagagaacat ttcctgcgtc ttttacttcg acag                               34

<210> SEQ ID NO 154
<211> LENGTH: 30
<212> TYPE: DNA
<213> ORGANISM: Artificial Sequence
<220> FEATURE:
<223> OTHER INFORMATION: Primer ZC43278

<400> SEQUENCE: 154
aaacaagagt ctcaggatct ttataacaac                                    30

<210> SEQ ID NO 155
<211> LENGTH: 21
<212> TYPE: DNA
<213> ORGANISM: Artificial Sequence
<220> FEATURE:
<223> OTHER INFORMATION: Primer ZC43279

<400> SEQUENCE: 155
acggcagctg tattgattcg t                                             21

<210> SEQ ID NO 156
<211> LENGTH: 26
<212> TYPE: DNA
<213> ORGANISM: Artificial Sequence
<220> FEATURE:
<223> OTHER INFORMATION: zcytor17lig probe ZC43276

<400> SEQUENCE: 156
taaagcaggc atctgggatg tcagca                                        26

<210> SEQ ID NO 157
<211> LENGTH: 33
<212> TYPE: DNA
<213> ORGANISM: Artificial Sequence
<220> FEATURE:
<223> OTHER INFORMATION: Primer ZC43045

<400> SEQUENCE: 157
aaacatgata tttcagatag agatcagtag act                                33

<210> SEQ ID NO 158
<211> LENGTH: 26
<212> TYPE: DNA
<213> ORGANISM: Artificial Sequence
<220> FEATURE:
<223> OTHER INFORMATION: Primer ZC43046

<400> SEQUENCE: 158
cttatgaaat gtttgacaca ctccaa                                        26

<210> SEQ ID NO 159
```

```
<211> LENGTH: 29
<212> TYPE: DNA
<213> ORGANISM: Artificial Sequence
<220> FEATURE:
<223> OTHER INFORMATION: OSMRbeta probe ZC43141

<400> SEQUENCE: 159
ctgtgcgttg gaactggacg tctgatatc                                  29

<210> SEQ ID NO 160
<211> LENGTH: 21
<212> TYPE: DNA
<213> ORGANISM: Artificial Sequence
<220> FEATURE:
<223> OTHER INFORMATION: Primer ZC43004

<400> SEQUENCE: 160
gaaacccgcc gcatattact t                                          21

<210> SEQ ID NO 161
<211> LENGTH: 19
<212> TYPE: DNA
<213> ORGANISM: Artificial Sequence
<220> FEATURE:
<223> OTHER INFORMATION: Primer ZC43005

<400> SEQUENCE: 161
tggcgttgct cacaaaggt                                             19

<210> SEQ ID NO 162
<211> LENGTH: 24
<212> TYPE: DNA
<213> ORGANISM: Artificial Sequence
<220> FEATURE:
<223> OTHER INFORMATION: Murine GUS probe ZC43018

<400> SEQUENCE: 162
acccacacca aagccctgga cctc                                       24

<210> SEQ ID NO 163
<211> LENGTH: 23
<212> TYPE: DNA
<213> ORGANISM: Artificial Sequence
<220> FEATURE:
<223> OTHER INFORMATION: Primer ZC40269

<400> SEQUENCE: 163
gccagtttca cacactcctc ttt                                        23

<210> SEQ ID NO 164
<211> LENGTH: 26
<212> TYPE: DNA
<213> ORGANISM: Artificial Sequence
<220> FEATURE:
<223> OTHER INFORMATION: Primer ZC40268

<400> SEQUENCE: 164
gcagctattg cactagtcat tttctt                                     26

<210> SEQ ID NO 165
<211> LENGTH: 29
<212> TYPE: DNA
<213> ORGANISM: Artificial Sequence
<220> FEATURE:
<223> OTHER INFORMATION: Transferrin receptor probe ZC40298

<400> SEQUENCE: 165
```

```
cccaggtagc cactcatgaa tccaatcaa                                         29
```

<210> SEQ ID NO 166
<211> LENGTH: 20
<212> TYPE: DNA
<213> ORGANISM: Artificial Sequence
<220> FEATURE:
<223> OTHER INFORMATION: Primer ZC43140

<400> SEQUENCE: 166

```
ttcttccaca gcaatcgcac                                                   20
```

<210> SEQ ID NO 167
<211> LENGTH: 21
<212> TYPE: DNA
<213> ORGANISM: Artificial Sequence
<220> FEATURE:
<223> OTHER INFORMATION: Primer ZC43139

<400> SEQUENCE: 167

```
atgcatgctt cggttcagaa c                                                 21
```

<210> SEQ ID NO 168
<211> LENGTH: 24
<212> TYPE: DNA
<213> ORGANISM: Artificial Sequence
<220> FEATURE:
<223> OTHER INFORMATION: Primer ZC41608

<400> SEQUENCE: 168

```
gcagacaatg atgctgagca agac                                              24
```

<210> SEQ ID NO 169
<211> LENGTH: 24
<212> TYPE: DNA
<213> ORGANISM: Artificial Sequence
<220> FEATURE:
<223> OTHER INFORMATION: Primer ZC41609

<400> SEQUENCE: 169

```
caacgctgtg atttgcagtg gaag                                              24
```

<210> SEQ ID NO 170
<211> LENGTH: 18
<212> TYPE: DNA
<213> ORGANISM: Artificial Sequence
<220> FEATURE:
<223> OTHER INFORMATION: Primer ZC41502

<400> SEQUENCE: 170

```
agcgggcctt cctcactc                                                     18
```

<210> SEQ ID NO 171
<211> LENGTH: 24
<212> TYPE: DNA
<213> ORGANISM: Artificial Sequence
<220> FEATURE:
<223> OTHER INFORMATION: Primer ZC41500

<400> SEQUENCE: 171

```
ggacaaaata aaacataaa taac                                               24
```

<210> SEQ ID NO 172
<211> LENGTH: 40
<212> TYPE: DNA

```
<213> ORGANISM: Artificial Sequence
<220> FEATURE:
<223> OTHER INFORMATION: Linker

<400> SEQUENCE: 172
tgtcgatgaa gccctgaaag acgcgcagac taattcgagc                                40

<210> SEQ ID NO 173
<211> LENGTH: 60
<212> TYPE: DNA
<213> ORGANISM: Artificial Sequence
<220> FEATURE:
<223> OTHER INFORMATION: Linker

<400> SEQUENCE: 173
acgcgcagac taattcgagc tcccaccatc accatcacca cgcgaattcg gtaccgctgg         60

<210> SEQ ID NO 174
<211> LENGTH: 60
<212> TYPE: DNA
<213> ORGANISM: Artificial Sequence
<220> FEATURE:
<223> OTHER INFORMATION: Linker

<400> SEQUENCE: 174
actcactata gggcgaattg cccgggggat ccacgcggaa ccagcggtac cgaattcgcg         60

<210> SEQ ID NO 175
<211> LENGTH: 42
<212> TYPE: DNA
<213> ORGANISM: Artificial Sequence
<220> FEATURE:
<223> OTHER INFORMATION: Linker

<400> SEQUENCE: 175
acggccagtg aattgtaata cgactcacta tagggcgaat tg                           42

<210> SEQ ID NO 176
<211> LENGTH: 825
<212> TYPE: DNA
<213> ORGANISM: Homo sapiens
<220> FEATURE:
<221> NAME/KEY: CDS
<222> LOCATION: (48)...(518)

<400> SEQUENCE: 176
```

| | | | | | | | | | | | |
|---|---|---|---|---|---|---|---|---|---|---|---|
| atcactctct ttaatcacta ctcacattaa cctcaactcc tgccaca | atg<br>Met<br>1 | tac<br>Tyr | agg<br>Arg | | | | | | | | 56 |

```
atg caa ctc ctg tct tgc att gca cta att ctt gca ctt gtc aca aac        104
Met Gln Leu Leu Ser Cys Ile Ala Leu Ile Leu Ala Leu Val Thr Asn
    5                   10                  15 agt gca cct act tca agt tcg aca aag aaa aca aag aaa aca cag cta        152
Ser Ala Pro Thr Ser Ser Ser Thr Lys Lys Thr Lys Lys Thr Gln Leu
 20                  25                  30                  35 caa ctg gag cat tta ctg ctg gat tta cag atg att tgt aat gga att        200
Gln Leu Glu His Leu Leu Leu Asp Leu Gln Met Ile Leu Asn Gly Ile
                40                  45                  50 aat aat tac aag aat ccc aaa ctc acc agg atg ctc aca ttt aag ttt        248
Asn Asn Tyr Lys Asn Pro Lys Leu Thr Arg Met Leu Thr Phe Lys Phe
            55                  60                  65 tac atg ccc aag aag gcc aca gaa ctg aaa cag ctt cag tgt cta gaa        296
Tyr Met Pro Lys Lys Ala Thr Glu Leu Lys Gln Leu Gln Cys Leu Glu
        70                  75                  80
```

```
gaa gaa ctc aaa cct ctg gag gaa gtg ctg aat tta gct caa agc aaa      344
Glu Glu Leu Lys Pro Leu Glu Glu Val Leu Asn Leu Ala Gln Ser Lys
     85                  90                  95 aac ttt cac tta aga ccc agg gac tta atc agc aat atc aac gta ata      392
Asn Phe His Leu Arg Pro Arg Asp Leu Ile Ser Asn Ile Asn Val Ile
100             105                 110                 115 gtt ctg gaa cta aag gga tct gaa aca aca ttc atg tgt gaa tat gca      440
Val Leu Glu Leu Lys Gly Ser Glu Thr Thr Phe Met Cys Glu Tyr Ala
             120                 125                 130 gat gag aca gca acc att gta gaa ttt ctg aac aga tgg att acc ttt      488
Asp Glu Thr Ala Thr Ile Val Glu Phe Leu Asn Arg Trp Ile Thr Phe
                 135                 140                 145 tgt caa agc atc atc tca aca cta act tga taattaagtg cttcccactt        538
Cys Gln Ser Ile Ile Ser Thr Leu Thr  *
                 150                 155 aaaacatatc aggccttcta tttatttatt taaatattta aatttatat ttattgttga     598 atgtatggtt gctacctatt gtaactatta ttcttaatct taaaactata aatatggatc    658
ttttatgatt cttttttgtaa gccctagggg ctctaaaatg gtttaccttaa tttatcccaa  718 aaatattttat tattatgttg aatgttaaat atagtatcta tgtagattgg ttagtaaaac   778
tatttaataa atttgataaa tataaaaaaa aaaaacaaaa aaaaaaa                  825
```

<210> SEQ ID NO 177
<211> LENGTH: 156
<212> TYPE: PRT
<213> ORGANISM: Homo sapiens

<400> SEQUENCE: 177

```
Met Tyr Arg Met Gln Leu Leu Ser Cys Ile Ala Leu Ile Leu Ala Leu
 1               5                  10                  15

Val Thr Asn Ser Ala Pro Thr Ser Ser Ser Thr Lys Lys Thr Lys Lys
             20                  25                  30

Thr Gln Leu Gln Leu Glu His Leu Leu Leu Asp Leu Gln Met Ile Leu
         35                  40                  45

Asn Gly Ile Asn Asn Tyr Lys Asn Pro Lys Leu Thr Arg Met Leu Thr
 50                  55                  60

Phe Lys Phe Tyr Met Pro Lys Lys Ala Thr Glu Leu Lys Gln Leu Gln
 65                  70                  75                  80

Cys Leu Glu Glu Glu Leu Lys Pro Leu Glu Glu Val Leu Asn Leu Ala
             85                  90                  95

Gln Ser Lys Asn Phe His Leu Arg Pro Arg Asp Leu Ile Ser Asn Ile
            100                 105                 110

Asn Val Ile Val Leu Glu Leu Lys Gly Ser Glu Thr Thr Phe Met Cys
        115                 120                 125

Glu Tyr Ala Asp Glu Thr Ala Thr Ile Val Glu Phe Leu Asn Arg Trp
    130                 135                 140

Ile Thr Phe Cys Gln Ser Ile Ile Ser Thr Leu Thr
145                 150                 155
```

<210> SEQ ID NO 178
<211> LENGTH: 614
<212> TYPE: DNA
<213> ORGANISM: Homo sapiens
<220> FEATURE:
<221> NAME/KEY: CDS
<222> LOCATION: (64)...(525)

<400> SEQUENCE: 178

```
gatcgttagc ttctcctgat aaactaattg cctcacattg tcactgcaaa tcgacaccta      60 tta atg ggt ctc acc tcc caa ctg ctt ccc cct ctg ttc ttc ctg cta     108
    Met Gly Leu Thr Ser Gln Leu Leu Pro Pro Leu Phe Phe Leu Leu
    1               5                   10                  15 gca tgt gcc ggc aac ttt gtc cac gga cac aag tgc gat atc acc tta     156
Ala Cys Ala Gly Asn Phe Val His Gly His Lys Cys Asp Ile Thr Leu
                20                  25                  30 cag gag atc atc aaa act ttg aac agc ctc aca gag cag aag act ctg     204
Gln Glu Ile Ile Lys Thr Leu Asn Ser Leu Thr Glu Gln Lys Thr Leu
            35                  40                  45 tgc acc gag ttg acc gta aca gac atc ttt gct gcc tcc aag aac aca     252
Cys Thr Glu Leu Thr Val Thr Asp Ile Phe Ala Ala Ser Lys Asn Thr
        50                  55                  60 act gag aag gaa acc ttc tgc agg gct gcg act gtg ctc cgg cag ttc     300
Thr Glu Lys Glu Thr Phe Cys Arg Ala Ala Thr Val Leu Arg Gln Phe
65                  70                  75 tac agc cac cat gag aag gac act cgc tgc ctg ggt gcg act gca cag     348
Tyr Ser His His Glu Lys Asp Thr Arg Cys Leu Gly Ala Thr Ala Gln
80                  85                  90                  95 cag ttc cac agg cac aag cag ctg atc cga ttc ctg aaa cgg ctc gac     396
Gln Phe His Arg His Lys Gln Leu Ile Arg Phe Leu Lys Arg Leu Asp
                100                 105                 110 agg aac ctc tgg ggc ctg gcg ggc ttg aat tcc tgt cct gtg aag gaa     444
Arg Asn Leu Trp Gly Leu Ala Gly Leu Asn Ser Cys Pro Val Lys Glu
            115                 120                 125 gcc aac cag agt acg ttg gaa aac ttc ttg gaa agg cta aag acg atc     492
Ala Asn Gln Ser Thr Leu Glu Asn Phe Leu Glu Arg Leu Lys Thr Ile
        130                 135                 140 atg aga gag aaa tat tca aag tgt tcg agc tga atattttaat ttatgagttt   545
Met Arg Glu Lys Tyr Ser Lys Cys Ser Ser *
145                 150 ttgatagctt tattttttaa gtatttatat atttataact catcataaaa taaagtatat    605
atagaatct                                                            614

<210> SEQ ID NO 179
<211> LENGTH: 153
<212> TYPE: PRT
<213> ORGANISM: Homo sapiens

<400> SEQUENCE: 179

Met Gly Leu Thr Ser Gln Leu Leu Pro Pro Leu Phe Phe Leu Leu Ala
1               5                   10                  15

Cys Ala Gly Asn Phe Val His Gly His Lys Cys Asp Ile Thr Leu Gln
            20                  25                  30

Glu Ile Ile Lys Thr Leu Asn Ser Leu Thr Glu Gln Lys Thr Leu Cys
        35                  40                  45

Thr Glu Leu Thr Val Thr Asp Ile Phe Ala Ala Ser Lys Asn Thr Thr
    50                  55                  60

Glu Lys Glu Thr Phe Cys Arg Ala Ala Thr Val Leu Arg Gln Phe Tyr
65                  70                  75                  80

Ser His His Glu Lys Asp Thr Arg Cys Leu Gly Ala Thr Ala Gln Gln
                85                  90                  95

Phe His Arg His Lys Gln Leu Ile Arg Phe Leu Lys Arg Leu Asp Arg
            100                 105                 110

Asn Leu Trp Gly Leu Ala Gly Leu Asn Ser Cys Pro Val Lys Glu Ala
        115                 120                 125

Asn Gln Ser Thr Leu Glu Asn Phe Leu Glu Arg Leu Lys Thr Ile Met
```

Arg Glu Lys Tyr Ser Lys Cys Ser Ser
145             150

<210> SEQ ID NO 180
<211> LENGTH: 756
<212> TYPE: DNA
<213> ORGANISM: Homo sapiens
<220> FEATURE:
<221> NAME/KEY: CDS
<222> LOCATION: (9)...(443)

<400> SEQUENCE: 180

```
gctggagg atg tgg ctg cag agc ctg ctg ctc ttg ggc act gtg gcc tgc        50
         Met Trp Leu Gln Ser Leu Leu Leu Leu Gly Thr Val Ala Cys
          1               5                  10 agc atc tct gca ccc gcc cgc tcg ccc agc ccc agc acg cag ccc tgg         98
Ser Ile Ser Ala Pro Ala Arg Ser Pro Ser Pro Ser Thr Gln Pro Trp
 15              20                  25                  30 gag cat gtg aat gcc atc cag gag gcc cgg cgt ctc ctg aac ctg agt        146
Glu His Val Asn Ala Ile Gln Glu Ala Arg Arg Leu Leu Asn Leu Ser
                 35                  40                  45 aga gac act gct gct gag atg aat gaa aca gta gaa gtc atc tca gaa        194
Arg Asp Thr Ala Ala Glu Met Asn Glu Thr Val Glu Val Ile Ser Glu
             50                  55                  60 atg ttt gac ctc cag gag ccg acc tgc cta cag acc cgc ctg gag ctg        242
Met Phe Asp Leu Gln Glu Pro Thr Cys Leu Gln Thr Arg Leu Glu Leu
         65                  70                  75 tac aag cag ggc ctg cgg ggc agc ctc acc aag ctc aag ggc ccc ttg        290
Tyr Lys Gln Gly Leu Arg Gly Ser Leu Thr Lys Leu Lys Gly Pro Leu
     80                  85                  90 acc atg atg gcc agc cac tac aag cag cac tgc cct cca acc ccg gaa        338
Thr Met Met Ala Ser His Tyr Lys Gln His Cys Pro Pro Thr Pro Glu
 95                 100                 105                 110 act tcc tgt gca acc cag act atc acc ttt gaa agt ttc aaa gag aac        386
Thr Ser Cys Ala Thr Gln Thr Ile Thr Phe Glu Ser Phe Lys Glu Asn
                115                 120                 125 ctg aag gac ttt ctg ctt gtc atc ccc ttt gac tgc tgg gag cca gtc        434
Leu Lys Asp Phe Leu Leu Val Ile Pro Phe Asp Cys Trp Glu Pro Val
            130                 135                 140 cag gag tga gaccggccag atgaggctgg ccaagccggg gagctgctct              483
Gln Glu * ctcatgaaac aagagctaga aactcaggat ggtcatcttg gagggaccaa ggggtgggcc      543
acagccatgg tggagtggc ctggacctgc cctgggccac actgaccctg atacaggcat       603
ggcagaagaa tgggaatatt ttatactgac agaaatcagt aatatttata tatttatatt      663
tttaaaatat ttatttattt atttatttaa gttcatattc catatttatt caagatgttt      723
taccgtaata attattatta aaaatatgct tct                                   756
```

<210> SEQ ID NO 181
<211> LENGTH: 144
<212> TYPE: PRT
<213> ORGANISM: Homo sapiens

<400> SEQUENCE: 181

Met Trp Leu Gln Ser Leu Leu Leu Leu Gly Thr Val Ala Cys Ser Ile
 1               5                  10                  15

Ser Ala Pro Ala Arg Ser Pro Ser Pro Ser Thr Gln Pro Trp Glu His
                 20                  25                  30

```
Val Asn Ala Ile Gln Glu Ala Arg Arg Leu Leu Asn Leu Ser Arg Asp
        35                  40                  45

Thr Ala Ala Glu Met Asn Glu Thr Val Glu Val Ile Ser Glu Met Phe
 50                  55                  60

Asp Leu Gln Glu Pro Thr Cys Leu Gln Thr Arg Leu Glu Leu Tyr Lys
 65                  70                  75                  80

Gln Gly Leu Arg Gly Ser Leu Thr Lys Leu Lys Gly Pro Leu Thr Met
                 85                  90                  95

Met Ala Ser His Tyr Lys Gln His Cys Pro Pro Thr Pro Glu Thr Ser
                100                 105                 110

Cys Ala Thr Gln Thr Ile Thr Phe Glu Ser Phe Lys Glu Asn Leu Lys
        115                 120                 125

Asp Phe Leu Leu Val Ile Pro Phe Asp Cys Trp Glu Pro Val Gln Glu
        130                 135                 140

<210> SEQ ID NO 182
<211> LENGTH: 60
<212> TYPE: DNA
<213> ORGANISM: Homo sapiens
<220> FEATURE:
<221> NAME/KEY: CDS
<222> LOCATION: (1)...(60)
<220> FEATURE:
<221> NAME/KEY: misc_feature
<222> LOCATION: (25)...(30)
<223> OTHER INFORMATION: n = A, T, G or C

<400> SEQUENCE: 182 gcc aca gaa ctg aaa cag ctt cag nnn nnn gaa gaa gaa ctc aaa cct      48
Ala Thr Glu Leu Lys Gln Leu Gln Xaa Xaa Glu Glu Glu Leu Lys Pro
 1               5                  10                  15 ctg gag gaa gtg                                                      60
Leu Glu Glu Val
            20

<210> SEQ ID NO 183
<211> LENGTH: 20
<212> TYPE: PRT
<213> ORGANISM: Homo sapiens
<220> FEATURE:
<221> NAME/KEY: VARIANT
<222> LOCATION: (9)...(10)
<223> OTHER INFORMATION: Any amino acid

<400> SEQUENCE: 183

Ala Thr Glu Leu Lys Gln Leu Gln Xaa Xaa Glu Glu Glu Leu Lys Pro
 1               5                  10                  15

Leu Glu Glu Val
            20
```